(12) United States Patent
Medrano et al.

(10) Patent No.: US 8,551,703 B2
(45) Date of Patent: Oct. 8, 2013

(54) SNPS ASSOCIATED WITH FATTY ACID COMPOSITION OF BOVINE MEAT AND MILK

(75) Inventors: Juan F. Medrano, Vacaville, CA (US); Gonzalo Rincon, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 304 days.

(21) Appl. No.: 12/666,249

(22) PCT Filed: Jul. 3, 2008

(86) PCT No.: PCT/US2008/069235
§ 371 (c)(1),
(2), (4) Date: Apr. 8, 2010

(87) PCT Pub. No.: WO2009/009439
PCT Pub. Date: Jan. 15, 2009

(65) Prior Publication Data
US 2011/0045469 A1 Feb. 24, 2011

Related U.S. Application Data

(60) Provisional application No. 61/047,650, filed on Apr. 24, 2008, provisional application No. 60/958,597, filed on Jul. 6, 2007.

(51) Int. Cl.
*C12Q 1/68* (2006.01)
(52) U.S. Cl.
USPC .............................................. 435/6.11; 435/6
(58) Field of Classification Search
None
See application file for complete search history.

(56) References Cited

U.S. PATENT DOCUMENTS

| 7,972,790 B2 | 7/2011 | Medrano |
| 2007/0077558 A1 | 4/2007 | Tsuji et al. |
| 2008/0010696 A1 | 1/2008 | Tsuji et al. |

OTHER PUBLICATIONS

Morris et al. Mamm Genome. Jan. 2007; 18(1)64-74. Epub Jan. 22, 2007.*
NIH News Advisory, 2004 Release: Bovine Genome Assembled (accessed from http://www.genome.gov/pfv.cfm?pageID=12512900 on Jan. 10, 2013), 2 pages.*
GenBank record having accession AC222185.1. Obtained from http://www.ncbi.nlm.nih.gov/nuccore/ac222185[Jan. 10, 2013 1:06:19 PM], 39 pages.*
GenBank record having accession AC170624.3. Obtained from http://www.ncbi.nlm.nih.gov/nuccore/AC170624[Jan. 11, 2013 3:42:17 PM], 50 pages.*
GenBank record having Accession AC165666.2. Obtained from http://www.ncbi.nlm.nih.gov/nuccore/AC165666[Jan. 11, 2013 3:42:44 PM], 53 pages.*
International Search Report from PCT/US2008/069235, mailed Dec. 24, 2008 (4 pages).
Hoashi et al.; Gentoype of bovine sterol regulatory element binding protein-1 (SREBP-1) is associated with fatty acid composition in Japanese Black cattle; *Mamm. Genome*; 18(12): 880-886 (2007).
Lee et al.; "Confirming single nucleotide polymorphisms from expressed sequence tag datasets derived from three cattle cDNA libraries"; *J. Biochem. Mol. Biol.*; 39(2): 183-188 (2006).
Lee et al.; "Identification of differentially expressed genes related to intramuscular fat development in the early and late fattening stages of hanwoo steers"; *J. Biochem. Mol. Biol.*; 40(5): 757-764 (2007).
Sasazaki et al.; "Development of breed identification markers derived from AFLP in beef cattle"; *Meat Science*. 67(2): 275-280 (2004).
Sasazaki et al.; "Development of DNA markers for discrimination between domestic and imported beef"; 77(2): 161-166 (2007).
Rincon, et al, "Polymorphisms in genes in the SREBP1 signalling pathway and SCD are associated with milk fatty acid composition in Holstein cattle," Journal of Dairy Research (2012) 79 66-75.

* cited by examiner

*Primary Examiner* — Juliet Switzer
(74) *Attorney, Agent, or Firm* — Jennifer L. Wahlsten; Weaver Austin Villeneuve & Sampson LLP

(57) ABSTRACT

The present invention provides compositions and methods for genotyping bovines including dairy cows and beef cattle More particularly, the invention is directed to single nucleotide polymorphisms in Stearoyl-CoA-Desaturase 5 (SCD5) Sterol regulatory element-binding protein-1 (SREBP1). SREBP cleavage-activating protein (SCAP), Insulin induced protein 1 (INS1G1). Insulin induced protein 2 (INS1G2) and Signal recognition particle receptor (SRPR) associated with fatty acid composition of bovine meat and milk.

11 Claims, 74 Drawing Sheets

Bovine SREBP1 Gene

```
   1 ATTAGTATCT CAGTCCACCT TATTAGGACC CTCCCTTGGC ACCTAGTCT GCCCCCAACC CACAGGACCC AGGGTCCTGG TCCAGCTCTC TCCCAGTCT
 101 AGCTGTCTCC TCTGACCTGC GCCAAGGGGT GGCAAGGGGT CCCGGATCGG GTCCGGAAGAC AAGCACAGAC TGCCCCTACC TCATCCCAAGC TGCCTCTGGG
 201 ACGGGCTCCA GTCCTGGTAC AGCCTCCAGG GCTTGTGCTG GTGAGAGGCG AAACCCGGG TGCAGAGCC AGCCCACCCT CAGGAGCCGG
 301 ACTGGGCCCA GCCCTCTGT CAGTCCCACA GCTGGATCTG GGAGGAAAAC GGCCACCGTT ACTAACGTCC AGAGTAAGTC ATTCTAGCCT CTTCCAGACT
 401 CTTCAGAAGA CTAACCCCCA GCCCTCTGT CAGTCCCACA CTTATCTCAC AACCTAAGGA GGAGGCACAC AGCAGGTCTT GGACTAGTCT ATGCGGAGAC ACCATCAAGC
 501 CCCGTTACAG CTGAGGAAAC TGCGGAACAG TGTGGTGAGG CCCAAGTTG CCCCAAGTTC AGCGACATCT GGGACGCACAC CAAACCGGGG GCCTCCACTG GCCCAAATC
 601 TCAGAATGAA GTTTGTCGGG TCACTTCTTG CCCCAAGTTC AGCGACATCT GATGGAACGG CCAGATCGGG CCGAGTCAGG GTCCTCAGG GTCCTCAGG
 701 AGAAGCCGGG GCCTGGGAGC CCGCAGCAG GATGGAGCAA ACTGAGCCAA GCTCCGCCCG CCCCCCAGAA CCGCGCCCGG GAACCCAGTT TCCGAGGAAC
 801 TTGGCCGGA CCGTCCACCC GGGGCGGGG CTCCCAGCAG GGGAGCGCAA ACTGAGCCAA GCTGGCACTC CCCCGCAGCCC CGGGGCCCC CGAGAGGAGG TGACTGCGCC
 901 TTTTCTCGGG CCTGGGCAC CACCCAGTTC CGGAACGGGG GCGAACGGCG GGAAGGGCCTG GGGGACCTC CGGGGACCTC
                                                                              E1
1001 ATGGACCAGC CACCCTTCAA CGAGGCTGG TTGGAGCTGG CGCTGGCGA CTGGACGCGG CGCTGCTGAC CGACATAGAA GGTGCGTCAG
                                                                                          SNP_1199
1101 GGCCACTGGG CTCCGGCGAC GGGCGGCGC CGCGGAGGGC GTCGGGCGCC CTGGACGCCGG GGCCGCGGC GGCCGCGCGC TCTGTGCGGA GCGCTCCCCG TCTCTGCCCC
1201 GAGGGCTGCC GGCCTGCGG TCCTGTCCCC GCGGAGCTGC CCGTGCCCGC TGGGTCCTGT AGGAGGCTGT GCGCTGAGCA CGTGCGCCTC GGGCGCCCCC
                                                                                          E2
1301 GGCCCCGCAC CCGGGGGCAC CGAGTCCTCA GTCGGCGAGGC GCGGTTGGCG AGAGCGCGGG ACCCGCGGTC CGCCCGCGCC CGGTCCCCGC GGCCCTTGAC
1401 GTCAGGAGGA GGTTACTTCC GGTCCGTTCC TCCGGCCGGA GAGTTCAGCT CGGCGCCGC GCTCCTCGC ATGGCGCGCG CGGTCCCCCG GACCCTGACA
1501 GACCAGGCCG CCGTTCTCCT GCCTATCCGT TCCTCAGCCT CGGTATCCGT CGGCACACG TTTATCGAGC GTCTACTGAA AGTTCTAGCC ACCAGAGGTT
1601 CACAGACCTG GCTCCCCCT GCACAAACC CACCTAAGGA AACCCATAAA CAGGATACTA TATCTGTGT GGAGCTGTGT CAGGGTGACT
1701 GCTTCGGGTA GGCGGGTGG GTTGGAACCTG AGCTCAGCCC TGAGAAGGAT GTCTTCCCG CAGAGGGCAC GGCGAGAGT TGGAGGGGCA CAGGTGAGAC
1801 TGGGCAGATG GGTGGAAGAG GACTTGGCAG GGAAAGGCGG GCGGGCTCTC TTACCACCT AGAACACTG CTCTGGTTGT TCTACAAGA
1901 GGGTGTTGGG GCCGAAGCTG CAGCGGGCG GCTCGGCGC CGGAGCACAG AGCACATTCC AGCCTCGGA GTTGCCCCTCC GAGGTTCCTA
2001 TGGAGTTTCA GCCACGTTGG CTACCTTGCA AATGACACA ACAGACCCA AACCTCCCAC AGCCTGGATG GACTCATCCA
2101 TGGAGCTCC CTGGAGGGGA GTTGAGAGGA ACTGAGCTC GGGGAAAACA CCCCTCTTTG GATGGCTCTC TGGGAACCCA GCTGGATAGG CCCAGAGTT
2201 GCCAGGTCC CTGGAGGGGA GTTGAGAGGA AATGACACAG GCGTTGACTC GGAGTGAGA GCTGAACTGG ATCCAGAGG CAGTGGGATG TTAAGTGACT
2301 TGTCCAGGT CACACAGCAG AGCATGGTAG GACTCAGGGA GGACTCAGGA CAAACCCAGG GCTGCTCTA GTGGAGTGG GTCGAAACGG TCACAGGTCA
2401 GTGTGTATGT GTGTGACACT GTATCCTAGC CATGAGAGCT GGACTCATGA TGACTCAGCTT GACGGAAGAC CAGGAGCCCC GAGTGCCTGG GCCTGGGCAT
2501 CACGGTCACC TCATCCTAGC CAGACTCCGT CATGTGACCA CAGGAGCCCCC AAGTCCTCTG GGCATGCCCC CCACTGCACC GCACTGGCT ACAACTCTGG
2601 GTCGCTGCCTCC TTGCCTCAGT ATGCCGTGGA CCTCCCCTC TCCCCACTGT CTCCCTAGAT CCCGTTGCCA CCCCCTTCCA TGGAGGACGC TCGGGTCGG
2701 GTAGATCCAC TTGCCACCCC ATGCCGTGGA CCTCCCTATC TCCCACTGGT TCATTCACTG GTGGAAGCAA ACTCTGCCT GGGCTCAGGA TGTCACTCGT CAGGTGCTGG
2801 GATTGTCTTG CAAGGCGGTG CCCTAAAA TCAACCACAG GCTGGGACC TCCAGTGCATA GTGGAAGTC ACTCTGGCT CTTCGAAGTG CAGTGTCTG
2901 GTGGGCCTGG ACCCTAAA TCAACCACAG GCTGGGACC AGTCCAGT TGCCCAGGT CCCAGTCCCAG GGCAACCTG CCCCAGG
3001 CCTTCCTA CAGTCTCTCA TGCCCAGGT CCCCCTCG ATGCCCCT CTTAGAAC CTTACAGG AAGCCAAGA TGCTTCAGG CTGTCAGTG
3101 GCCACAGAC ATGCCCGCT AGCCTGCTCTC CCCAAGAATAC CCCAAGATAC ACACTCTGCC CATCCCCTCT CTTAGAAC AGTCCCTTG TCTTTGAGAC CTGTCAGTG
3201 GGCCCGGGCCC GTGAGGCCC GGTGAGTCCT GCTGAGTCCT GCCCCTCCAG ACACTCTGCC TGCCTGGGG TCCCCTCTC TGGCTGCC ATCTGCCCA
3301 TCGAGGGTC CTGAGGGAG GGTGAGTCCT AGGCCTCTCC CCTGGACAT GGCCCGACAT GGCCCCTGCC TGCCTGGGG TCTCCTGCT TGCCGTCC ATCTGCCCCA
3401 GCCAGAGCC AGCCCTGCTCTC AGTCCCTAA CCACCATGGC TGGCACCTGCAGG TGGCCAGTGGC TGCAGTGGC TGCAGTGGC AGCCTCAAGT CTGTCAGGTG
3501 GGTGGCAGGA AGCAGAGGCC CTCCGGGTGT GGCTGTGTAC TTGCAGTGGC TTGCAGTGCC AGCTGGGGTG AGGCCATAGG TGGGCTGCCC
```

```
                                                                                           E10
12201 ~~~~~~~~~~ CGGTCCCAAGG CGCAGCATGC TGGGTGCTGA GGGCAAGAGT AGGGTGGTAG GAGGGGGGCT CTCGCAGAGG TGGATCTTGT CCTGTGGGCT TGGGGTCTG
                                                                                                              E11
12301 AATTCCTGG GTGCCCAGCC TCTGTGTCCC CAGCTTCTGT ~~~~~~~~~~ ~~~~~~~~~~ ATGGTCCTGG CTGGGCCCCA TGCCTGCTGC CCCACTGGT CTGGCTCATG
                                                                                 E11
12401 AATGGGCTGC TGGTGCTCTT CTCCTTGGKA CTTCTCTTTG TCTATGGAGA ACCAGTCACT CGGCCCCACT CATGCCCCGC CGTGCACTTC TGGAGGCATC
12501 GCAAGCAGGC TGACCTGGAC CTGGCCAGGG TAAGTGCCCA GACCCTGGGG GATGGGATCC GGCAAGGCTG GGACCCCGAG CAGTCTCTGG GAAGGTCTG
12601 GGCATACCGT GGACCTCCCC TGTTCTTCCC ACTCCTGACT ACCCCTCCGA CTCCTGTGGA GTTTCTTACC TGAAAAACCCC GCCAGCCTGC GGTGCTGGGA TGGTGTGGTC
                                                                                                                        E12
12701 CTCACGGGAG GCCCAAGGTG GAGGAGTAGC ACAGCCCCAC GTTTCTTACC TGAAAACCCC TCACCCCCAG GGGGACTTTG CCCAGGCTGC CCAGCAGCTG
                                                E12
12801 TGGCTGGCCC TGCGGGCCTT GGGCCCGCCT CTGCCCACCT CCCACCCACT CTGGGCTGCC AGCCTGCTCT CGAGCCTCAT CCGCCACCTG CTGCAACGTC
                                                                                           E12
12901 TCTGGGTGGG CCGCTGGCTG GCCGGCTGGG CAGGGCCCT ACGGAGGGAC AGGGCCCTAC AGGCAGATGC TGGCACCAGT GCCGGTGACG CAGCCCTCGT
13001 CTACCACAAG CTGACCAGC TGCACACCAT GGGTATGCGA GGCCCCGGG GTCCTGCTGC CTCCACACCA CTCCTTGGCCT CACGCCTCT
                                                    E13
13101 TATCTTCCAG GAAGTACTC AGGTGGGCAC CTCGCTGCTG CCAACCTGGC ACTGAGTGCC CTGAACCTGG CCAGTGCGC TGGAGATGCT GTGTCCGTGG
13201 CCACGCTGGC TGAGATCTAC GTGGCCGCCC CACTCAGGGT CAAGGCCAGT CTTGCAGTTT TCTGACAGTG AGTAGGTGGT GACCAGTGGG
                                                                         SNP_12504
13301 CGGCTCGTCG GTAGCTGAGG GCTAGCACAGA AAGGCACGTG GTTATCGGC CGGGCTGGG CCTCCCGTGG TCTCGGCCAG CGTTCACTTT GACGGCCCT
                                                    E14
13401 TCCTTCCCCA ACAGGCGCTT TTCCTGAGCA GTGCTCGCCA GGCTGCCTG GCACAGAGCG GCTCAGTGCC CCTTGCCATG CAGTGGCTCT GCCACCCTGT
                                                                           E14
13501 GGGCCACCGT TCTTCGTGG ATGCAAACTG GGCCCTGTGC AGCGCCCCGA GGGGACAGCTT GTACAGCGTG GCTGGGAACC CAGGTGCCTT CTCTCCCTGG
13601 GCCCTTCCCC GTGCCACCC CTTTCCCAC AGCTGGCCGC CTCCTCTGTC CCCGGTTCCC ATTCCTCATG CCTTCCCTG GTCAGTCTCT TGTCCCCTGC
13701 CTCTCTGCTG TCCCGGCCA CCCTGGCCT CTGCCCGCC ATCTGGTGTG GCTATGGGGA TGTGCAGATG CCTGGGTCTG TCTCAGGGG
13801 GCTCTTTCAG AGCAAACAG GAGCACGGGG CAGGGCGGG CGGGCTGAT TCAAGAGGTC CATCACCATG CACCAGGAGA CAGCTGCGGG GTCGGAAG
```

Fig. 1E

```
13901  GGCGTGCATC CCAGGTGGGT TATCCTGTCC ACAGGTGGAC GGAGTGTTTA TCCACCAGCT TTCAATTGTC TCAGAGCCAG GCCCTCCCGT GCCCAGAAAA
                                                                                                              E15

14001  GATCCCTAGT GCAGGGAGGT GCCTGTGCAC AGGAGGGGTG GGGCCATTCT CGCCCCACT  CTGCCCACT  CTTCTCCACA GTGGATCCCC TGGCCCAGGT

14101  GACTCAACTG TTCCGGCGAAC ACTCTTGGA  GCGACCACTG AATTGCGTGG CCCAGTCCT  CCCAGTCCT  GGATCAGCCG AGGGGGACAA GTGAGTGTCT
14201  CTGTGCACCT CAGCAGGCCA GAGCCCCTG  TTCACTGGAG GCCAGCTG   CCCTAGTG   GCCACTGTG  GCCTTAGTTG CATTCGGTT  CCTCTCTGGC
                                                                                  SNP_13508

14301  CCTCAGTTTC CCACCGGCCC AGCACGAGGG GATGCAGGCT CTTGGAGGAG CCAAGAGGCC AGGCTTGCT  GTGTGCAGAG GTGAGGACCC CTGCCAGCCA
                                                                                                    SNP_13636
                                                                     E16

14401  TCCTGACCGC CCGTCCCTC  CTGCCACACAGG GAGTTCTCAG ATGCCCTGG  GTACCTGCAG CTGCTGAACA GCTGTTCGGA CGTGGCCGGA GCTCTTACCT
                       E16

14501  GCAGCTTCTC CATCAGGCTG AGCATGGCTG CCACCCCGG   TGAGCCCCC  ACCTGTGACG CCCTCAGCCC CAGCGCCAAG CAGCTCAGCT TCGGGTGCAG
                                                                                                              E17

14601  TCTGGGTGAG TTTCTGCCCT CTGTGCCCCC TTTGCAGGCA CAGACCCGGT GGCCAAGTGG TGGGCCCTC  TGACCAGCTGT GGTGACCCAC TGGCTTCGGC
                                          E17

14701  GGGATGAGGA GGCAGCCGAG AGGCTGTACC CATTGGTACC TCTGCACTCC TTCAAGGCGG CCCCGGACCAT TCTAGGCCGC GGGAAGGCTG AGTCTGGCCC
14801  CCCCAACCCT GCCCCAGCT  TGTTCTATG  TCCTTGGGGT CTCACCATGC TCTTCCCATG AAGCCAGAAC CAGGGCAGAG GGAGGTCCAA CCATGACACT
                                                          E18

14901  TCTGCCCTTGG CCCCAACAGG AAACCCTAC  CCAGGGGCGGC TCTGCACTCC TTCAAGGCGG CCCGGACCAT TCTAGGCCGC GGGAAGGCTG AGTCTGGCCC

15001  AGCCAGCCTG GCAATGTGTG AGAAGGCCAG TGGGTACCTG CAGGACAGCC ACCAGGTGAC AGCTCCATTG ACAAGGTAAG GGCTGGGGCC
15101  AGGGGCCTGG CCTGTCTCAG GGGCCTTGGC CTTTCCACTC CCCCCTTGGG CTGCAGGAGA CTGCAGGGTC AGCCCAACAG CACAGGACGG
15201  GGACCCAGC  CGGCCTTGCC TTCTGGCTAA GGCTGGGTC  GCCGCCAGG  CAGGGGAGAA TGGCTGCTCC CTCTGGGCTC AATGTTGCCC TCCTAGGAGG AGGGTGGGGT
15301  GAACATGTGG CAGGGCCCTC CTGGAGGCT  GCCCAGCAGG CGGGTGGGGG CCGGTGGGGG CATGGGGCCC TGGAGAGCGG CGGCCCCGC  GGTGCATTGC TGTTGCATTG
15401  CATGTGTGAG GCAGCTGCAG TGCCTCGGCA GTGCAGCCCG GAGCCGGCC  GAGCCGGCCC GGGCCCCTA  GCCTTCTCTC CCACAGCCAG AGGCCTGAC
                                                                    E19

15501  CCCTGCCCTG CCCTACCCAC CAGGCCTCCC AGGGGGGCC  GCTCCTGTGT TGTGGCGCG  GACCTGCTCC TTGTGGCGCG CACCAGCCTC TGGCAGCCGC AGAAGCTGCC
                                                             E19

15601  GGCACCCACC CAGGCCTCCG AGGTGGGGCC CAGGCCCTCTG CCCCTCGAGCT TCGTGGTTTC CAGAGGGACC TGAGTGGCCT GAGCCGTCTG

15701  GCACAGAATG TTCGGCCTGC CATGCCGGAGG GTGAGTGCCC ACAGAGTCCT GACTTGCGAT GGGGACAGAAC ATGAGGTGTC TGAAGGGAGT TGAAGGGAGT GGGGCCTGAC
```

Fig. 1F

```
                                                                                                              E20
15801  CTGAACCTCT  CCTGGTCCT  CCTGCCCAGG  TATTCCTACA  TGAAGCCACT  GCCCGACTGA  TGGCAGGCGC  CAGCCCAGCC  CCGACACACC  AGCTTCTGGA
                                E20

15901  TCCAGCCCTG  AGGAGGAGGG  TGGCCCCCTG  CCCGGGACTT  CCAGGTGGCC  GCTGACTCGG  GGCCTAACCT  GCCCTAGGCC  GTGGGAAGGG  GCTGCCCCAG  GTGGGAAGGG  GCTGGCCCAG  GTGGAAGGCT  GCAGAGGGAG
16001  ACCATAAGAC  ACACAGGAGC  CTCGGGACTT  CCAGGTGGCC  TTGACCTGCG  GGCCTACCCA  GGCCCGCTCC  GATGTCACGT  GTGACTCGGG  CCTTTGTGGA  GCACTGGCTC
16101  TGTCTCCCAG  GGGAAGAAGC  GGAAGGGACC  AAGCTGCATG  GCAGCCCAAA  ACCAAAGGCG  TGGGGGCGCA  GGCTGGACCA  GGCGACAGGG  GCGGGGCCGG

16201  GGGCTGAGCC  CCAGCCTGGC  CCACCCTGGG  GCAGCCCCCG  CCCCCTGACGT  GCTCCCGTGT  GCGTCGGCAG  GTCGGGTGCC  GGCGGAACTG  GAGTCCCCGC  CCACGAGGCG
                                                                         E21

16301  GGACCAGGCC  GAGGGCTTTGC  TGCTGGCCTG  TGCTGGCCTG  CCGCCCGGCT  TTGCTACCTG  CCGCCCGGCT  TCCTATCGGC  GCCCGGGCAG  CCGGTGGGCA  TGCTGGGCGA  GGCGGCGCGC
                                                           E21

16401  ACGCTGGAGA  AGCTCGGTGA  CCCCGGCTG  GCTCATGCGC  GTCAGCAGACT  CCGAGAGCGA  CCGAGAGCGA  GCTCATGCGC  CTGGGCGGTG  GGACCACTGT  GACCTCCAGC  TAGACTCCTG
16501  CCGGCGGGCC  TGCCCTAGAG  TGCCCAGAG  CCCGGTCTCC  GTATCAGCGG  CCGAGAGCGA  GCCCCAGTGG  CGCCCAGTGG  CGCCCAGTCC  CGCCCAGTCC  ACAGACTCCG  TGGCCCCTGG
16601  GCGGCTGGAG  ACCCTCAGAG  ACGTCTGCTC  TTGACCTGCG  GGCCTACCCA  GGCCCGCTCC  GCACTCGGCG  GCACTCGGCG  CGGGTGGGCG  AGGATAGTGC  TGGCCCCTGG
16701  TGGCCGGCTG  GGGAATTACC  GGGGCCCTGC  GCCCCGCGCCG  GATGTCACGT  GCCCCAGTG  ACACCGCTCC  TGGGTGTCAT  GGGCCCCCAG  TCCGCAGCTC
16801  TCCCCCTCCC  TCCAGAGAGA  AGAGAGGGGT  GCATTCCACC  GAACCGAGGG  ACCCTACCCC  CTGTGCCTCC  CTCCATCTA  GGGAGACCTG  TGCATAGTGT
16901  AGATCCGAGT  GCACCAGCT  CTCGCCTCC  AAGGCTCAGG  CCTTACTTTG  CCTTTTGCAG  ACTTTATTTT  CATAGGTTGA  GAAGTTTGT  ACAGAGAATA
17001  AAAAATGAAA  TTATTATAA  TCTGGGTTTT  GCTCCTTTGG  GGAGAGGCTA  CCCAGAGGGG  ATTCTTTGGG  CCTTCTGTCC  CTCTAGGACC  CAGGCAAAGG
17101  CTTCTTGTTG  CCACCTGCCC  TTCTGTGTTT  GGGAGGCCTG  GCTTTATTCC  CTCCAGCTGA  CTGGGCCCT  GGCGCGCGCT  CTCATCTCCT  AACCCTTAGG
17201  GCCCTGTGTG  TCTCAGCTTT  TCCCCTCCC  AGCTTCTGCC  CCCTTTAGGT  CCCTTTAGGT  CCAGGAATGA  TATGTTCTTG  GGAATCTGTG  GTGACGGGAG
17301  GAACTACAAC  CTGGCTCTC  CTCTGTGTCT  GGGTGTGTCA  CTGGCCTAAC  CCCTGTCCCC  TCATCTGAGG  CCACACAGCT  GTGGCAGGGC  AGCAGGGGCT
17401  TCTCTCCCTG  ACAGGACATT  CCTGTCCCAG  AGCCCGCCCC  TAAAGCCTGG  ACCCTCTCCC  AGGAAAATCT  GGTCAGAATC  CACGGGCTGC  AGA
```

Fig. 1G

Bovine SCAP Gene

```
   1  AATTCTAGAT CTCTGGGGCT TTCTGTTAGA ATTTTATATT CTGATTTTTT GCGGTGTAAG TTTCTCTGTT GGGAAGCAAG GCACAGACAA AACAGAGATT
 101  TAATTGGAAG GATATGGGAT GGCCGGAAGG AAGACCTAAT GAGTCTTCAG GTGTCAGAAG CAAAGTCCAG AGAGACAGAC AGCCAGATGA GTGGAGCTG CTGGAGCTCA
 201  GGGACGATTC AGTACCGCCA TGTCCAGTTT TGCTTCTTTT TGTTCAGAAG T CTTGTGCAGA AAGCTAGTGT CTGAGTCGC GCTGGGCGCT ATGACCAGCC TGATGGGGGT CAGGAGAGG
 301  ACCTTAACTG ACAGTCCATA CAGGGCCCTC TGGGCCACAT CAACGGGGA CTGAACCTCA CAAGACAGAC GTCCCTCAAA GTCCCAGTGC AATTTGTTTT ATGTCAGGGG
 401  CAGGAGCAGA AGGGGCCCTC TGCCCACACA TCGTGTGTT TACGTTGAGG GCTGACCTCA CTGAACGTTC AATCACTCGT TGTGCAAGAA GGAGGGTTTC TGAGGGGTCA
 501  CCTAGGCTTT TTGGTGTTTT GTTTTCCA AGGATTTCTC TTGGCTCTGC CTTGCACAA TATGAGAACA AGAACAGGGG CAGAAAGTCC CCTTTTAAG ACAGTGCTTA GTGCAGCTGA
 601  GTCCTGAAG GTTTACACAG GATGCTCTC CTGTGCCACA TATGAGAACA AGAACAGGGG ATGCCCTCTC GAGGAGTGG CCTTTTAAG ACAGTGCTTA ATGTGGAAGA
 701  AGGTGCTGTC GATTACACAG GCATGCTCTC CTGTGCCACA TATGAGAACA AGCCCTCTC GGTTAGACTT ATTTGGACAC TGCCACAGT CACTAGGAGC TGACCAAGAT
 801  TGGTTACTA TTTGTTACTA GAATTAGAGG GGCAGTTTTT TGGTTTCTTT GGTTAGACTT ATTTGGACAC TGCCACAGT CACTAGGAGC ATCCCCCTGG
 901  TATGCACGTG TGTATATGCA TGTGGTGGGCT CGACGTTTTG TGCCCTTAC TGCCCTTAC ATCCCGGCA CTCCCCTGG
1001  GTGCCCTAGT GTTCACAGCC AGGGATTCTT TGCTAATTTG CTTTTCTCCC TTCTTGCAA GTCTCTGCAG ATGGTGTACA TTGTCACTTC CATCCAGCGT
                                                                                           E1

1101  GTGCCAGGCT GATCCATGGT CACTTTCCGG GATGGCAGCA AGGTGACTTC AGCTGACGAT GACCCTGACT GAAAAGCTGC GTCAGAAGAT ATCCCAGGCC
                                                 E1

1201  TTCTACAACC ATGGGCTGTT CTGTCGCTCC TACCCGCTCC CCATCATTCT CTTCACGGGG CTCTGCATCT TAGCCTGCTG GTATGTTCC AAGTTGCCCT
1301  GTATTGCGTG GGCCAGTCGA CCTCCTAACC CTGACTGTTG TGTAGCCCTT GGACTGGGGTC ATTTTACACA GTGGAACTTG AGGCTCATCC CGGCCACCA
1401  GCGGAAGCT CTAGTCCTGG GGTGCAAGCC ACTGCACTAG ATTGCACTAG AACGGGCCTA AACAGAAAAG TCGCGGTCGT ATTTAGTAAG TCGCCAGATT TGTTCATATT ATTGAGAATT
1501  TCTCAAAATA ACGTTGACAT GTTCGAAGA AACTGCAAGA TGAATAAAAG TGTGATCTTT TAATTTCCT TGCGCTCCTA GGTAGCTTCC TTTTCGTATC
1601  TGGTTAAGAG CAGGAGCAT CCTCGTCATTG GGAGAACAGT CACTCAACA ATTCTGGA TGCAGGCT GTTGCAGGCT AATCCAGGA GTCTGCGGC TAGGGTTTC
1701  TACATAGGGG CCTCGCATTG CCTCGCGGG GATCTTTGT TGCATGGACT CTCTAGTGAT GTGTGGGCCC AGTACTGCA GTGTGCGGGC TCTCTGGTTG
1801  TTGGACTTAG TGTGCTTCCA GTARGTGGGG TCTTAGGTCC TGGACCAGGG ATCATACCGG TGTCTCTGC ATTGCAAGGT GGATTCTAA CCACTGGATC
1901  ACCAGGCACC TCCTCTTCCA GTCATTTCT TGTGTTTCTG GGGAGCTCC GTTGGTCCCT GGGCTGCCA CACTCACCAG GCCTGATGT
2001  TGTCCCCCCC TCTCTCCATC TCTGTTGTGC TGTCCCAGCG AAGACACTG TAGAAGCACA GGCTGATGT
2101  AAGGTGATAA CCAGGGCTC CCTTTGGCTT GCAAACACTG AGCGACTCC GTGTCCCTG GAATTCTGAT TTCAGATTGT
2201  ATTGCACATC TAATGTTTAT AGAAGTTTAG ATTGCTGTGC AGTGCTCTGA ATGGTCTCGT TGTTATGAT CCCAAGTTCT CCCTTAATTA GGACAAGGAA
2301  AGATGAGCAT ATTCTGAGA GGGCGCTTCA GGTTTAAGC TTGCCTAGTC TACACACCA ATGAGCAGCT CCTCTAAAAT CCTTGGAAA TGGTCCAGTT
2401  ATATTTCCAT TAACCARAG GGAGGATGGA GGTTTAAGGC TGCCTAGTC CTGGTTCA GTGTATTTGT TTAAACTTT TTAATTTGC AGATCCAGGC CAGGGATCCT
2501  GGTCCTGCA CTAGCCTGG TGTGTCCCC CCTCTTGTCA GAAACCAGG GTTAAGC CTGGTTCA AGAATTCCA TCCCTTAAG TTGTACAGA TAAGATGCTT
2601  GTGGCTTTA CCTCACATG ATGAATTAGG AGTTGCCTA GAAACCAGG CTTGGTTGT CTGCTATTCT ACATCCTCAC ACATCCGTC CCAGAATCC AGGTCTGCGC
2701  TTTGAGAATC ATCCTTTTCT AGGTCCTGCT CATCTGCAG CTCTAGCTCC GCTCTAGCTCT GCTCTAGCTGT CTCTAGATCT
2801  CTGCCGGCT CTACCCCAGA GTTCCTGTCT GTCTTGAAAA GTCTCAGCGT AAAGAATGC TTATTCTGAC TTCTGGAAGC CCAGGGGTC TACATGCTGA
2901  GAACACTAGA CTGTGCCT GCCTTCCGTC GCCTCTGTA GGGTGGGG GTGCCAAGCT ACCCTGTCCT CAGCTGTCCT ACATCCTCAC TTGTGTGATA GCTAGTTGTG GGGACACTCC
3001  TGGCGTTAT TGCTCCTGCA GCCGCTAGG TAAATCTATA AGGATGTTC TTCTGCAAT CACCCTGTCT ACATCCTCAC TTGTGTGATA GCTAGTTGTG ATCTCCTTC
3101  GCACAGGACA GCTCTAGTAA CAGAAAGAA CAGAACAGCT TCAGCAGTA ACCCTAGGTT TTCTGCCAAC TGGGATTTAT AGGATTGAAA AGTATGGAA GCTAGTGTG GGGCACTCC
3201  CACAAGGACA GTCTCAGTG GCGCGTAGG GCCAGCTG GCCAGCTG GATAGGGC GTGCAGAGTT ACCTGCAC TCACCTTGCAC TTGGCAGCCA GCTACTGTG ATCACACATG CTCAAGGTGA
3301  ACAGGGACTG TGCCCATCGC TGGATTTTAT ATAGGGGCC TCAGTGATGGGATTT AAACTGTG CTAAGCCTCT TAGGCAC TTGGCAGCCA AGTATGGAA CAGTCGTGA GATGCCTGAA TGTTCCAA
3401  CAAATGTCC GGCCGTAGG ATAAGTGTAG GGAAAGAGAG GCAAGAGG CAAAGTGTG CTAAGCACG CTAATTGAAT CTTTTCAAA AGAAATAGAG GAATGGGAAT
3501  ATTTGAATCC GGCCGTAGG ATAGCAGAG GGAAAGAGAG GAAAGAAGA CAATGTGCC CTAATGTG ATCACTGAA AGAAATAGAG GAATGGGAAT
3601  GGAAAGGTAT GCTCACCTGA ATGCAGAGTT CCAGAGAATA GCAGGAAGGC ACAAGAAGGC CTTTTCAAA AGAAATAGAG GAATGGGAAT
```

```
                                                                                                          E4
28701   CACCAGGCAC CTGGGAGCTT CACGGGCGGG GCTGTGTGGG GCCGGCAGAG TCGGCAGGGC CTCGTCCTGT CCCCCGCACA GCTCCGGGAC CAGGAGGCCTG
28801   GAGGACTGT GCCTGCAGGT GACTGACCTG CTGCCAGGCC TCAGGAAGCT CCCGAACCTC CTGCCCGAGC ATGGATGCCT GCTGCTCTC CCCGGAACT
                                                          E4
28901   TCTGGCAGAA TGACAGGGAG CGCTTCCACG CAGATCCCGA CATCATCACAG ACCATCCACC AGCACGAGCC CAAAACCCTG CAGACCTCGG CCACACTCAA
        E4
29001   AGGTGCCCGG GCAGTCCCTT GAGAGCCATC GGGGCCTGT CAGTCACCAC ATCCTCTTTG GAGGCTGCTC TGGCAGATCT GGGGTTGCCC TGAGTTTCTC
                                                                                                                  E5
29101   AGGGTTGGGT AGAAAGGGGT CCTTGGTATC TCTAGGTAGC TGCCGGTCCT TTGTCAGCAC CTGTTGCCCT CTGTCTGCAG AACCTGCTGT TGGCGTCCCT
29201   GGGAAGTACA GCGGGGTGAG CCTGTACACC AGGAAGCGGC TGGTCTTCC CACCATCACC CTGGTCTTCC AGCACTACCA CCCCAAGTAA GGCTGGCCTG
29301   CGGCACAGCA GGCAGCTTTT CCATTTGGAG TGTCACCAGT GCCCCGGGA GCTTGGAGTT CTCAGGCTT TCAGGCCTT GTTCATGTCC CTCAGGGTGC
29401   TGTCTGCTCA CGCTTGAGGG GGGCCACCTG ACACGTGACT AAGAACAATG GGGAAGGCAG GCTGGCAAG CTCAGGGTCC TGTGCCCC ATGGTCTCTC
29501   TGGAGCCTG GGTGCCGTC CCCAGCTGT CGCCTTCCACG GACTCCATGT GGGGGAGAG CTTGGAGAG GGCGGAGAGG GGGGCGAGGG CACCAGGGG
29601   GCCCCGATG GCCTGTTCTG GCCTGTGCC GGCTGTGGC AGTCAGAGGG CAGTGATGAG GGGTTCTGA GGGGTCCAGG GACACGTCCA CCAACCCCT
29701   CAAGACTGGA GGGAAGGTTA GACACGGCA ATTGCCTTG TCCCCGGAC AGAGAGGGAC AGGCCATCTC
                                       E6
29801   CCACCCCCA CCCAGGTTCC TGGGCAGGCT GGGGGCCCGC CTGATGCTCC TGCACCCCAG AGCCTCAGAG CAGAGAGCCT GGTCCATGTG
29901   CACTTCAAGG AGGAGATTGG CATCGCTGAG CTCAGCTTCC CCCAGGCT TAGGCAACT CCTCCCTGC CCCGGGCAG AGATGTAGAA TGTGCCAGCT
30001   CACAGAGGCC AGGGCTTTCT CCCAGCTAAT TGGGCGTTT TCCAGGTAAG GCCCCCAG ATCCCCCAG GTCCTCCCA CTACTCACAG ACTCCCTCC TGGGAAGGTT
30101   GGTCACCGAA GCTGCGGCTT CATCCCCCAG CGGGCCTGA GGGTACACAT TCTCTGGGAA AACCAGGCC TTCTCTTCCT CGAATGTCAG GCACACCCCC TCCCACCTCC
30201   TTCAAGGACA CTGTGCCCTG AGACTGGGAA GGGTACACAT TCTCTGGGAA AACCAGGCC TTCTCTTCCT CGAATGTCAG GCACACCCCC TCCCACCTCC
                                                                                                          E7
30301   CAGGATACAG GGCCAGTGA GCCAGCTCT GGGGAGAGGC TGCCCCCTGATG TATTCTTTGC CCTCCAGGCA AGATCGACAT GGTCAAGTCC AAGTGGGGCC
30401   TGGCTCTGGC TGCCCTCGTC ACGTGCTCA GCTGCCTGCT CATGTCTGTG GGGCTCTGCA CACTCTTCCG CCTGACACCC ACGCTCAATG GCGGGTAGGT
30501   CCCAGCAGGC TCCCCTGGGG GGCAGGGTGG GCCAGCATCA CGGAGCCTG TGCACCCTG GGTGCTTGC CTGCCCTGCC CTCGACACTT GCTGTTACCC
30601   TATATTTCA CATGGTAATT TTGACACTTA AGAGGATGT GTTTTACTT TTTTGAGTTA CCTGAGTTAC GATCATACAT ATTTATATAC AAACCGTATG
30701   TATATTACA TATAATACAT CCATAGGTGT GTGATGTGT GTGTATATTC ATGTTATGT TGGGTGTAT AGTATTTATA TGTGTGTATG
30801   TAIGTGTTTA CGCATATGTA TGGGAATGTA CTGTGTGCT CTGTGTGTCT GAGGTGTAT AGATGTGTGA ATTGTGTTG TTCGTTGCTG AGTTGTGTCT
30901   GACTCTGCAA CCCATGGAC TGCAGCACGC CGGGTCCC TGTCCTTCAC AGTTGCTCA AACTCGTGTC CACTGAGTCG GTGATGCCAT
```

```
34101  TAGGGAGGGC TTTTGGAGTA CTGCAGGCTG TTTGGGCATC AGTGCCAGGG GGAGGGAGGG AGTGCTGCT  CCCCTCATGG GCATCCTCCT
34201  TGGTGGCTCC TGGATGTCAA AGTTCCAGCA TCTCTCTCCC CTGCTGTGCC TCGCAAGAAA CTGCCCTGCA GGTCCAGCTGT TTGGGGTGCA
34301  GTGGTCAGGG CCCATGAGGC TCCCAGGGCC GGCTGCGGCC ACAGCAGGCA GGGAACTGGT TCTCCAGTGC TGGGCCCTGA GGTCAGTGTC CTCTCATTGC
                                                                              E10
34401  CTTTTTTCCA CGAGTTCTGT CTTTTTGCCC TCGTCGGCCT GGTGTCTGAC TTTTTCCTTC AGATGTCTGT TTTTCACCACT GTCCTGTCCA TTGACATTCG
         E10
34501  CCGGATGGAG GTAGGAGTGG ACCATGGGGG CCCCTAACCA CCTCCTCCTC AGCCCTGGCT GTGCTCAGGG GTCTCTGGGC AAGAGAGGGC AGACCTAGGG
                                                                                                            E11
34601  CAGGGCCGCA GCCCCAAGTG GGAGCTTCTG GACGCGCGCT CCAGGCCCTG ACGTTTGAG CGGCGGACCT GAACAAGCGG CTGCCCCCTG
                 E11
34701  AGGCCTGCCT GCCCCAGCC AAGCCGGTGG GGCGGCCAAC AGGCTGGGCC ATCCATGCCC CTGTGGGGCC CACACCATCA CACTGCAGCC
34801  GTCCTCCTTC CGGCAACCTGC GTCTCCCCAA GCGGCTGCGT TCCTGGCCCG AACCCGCCTG GCACAGCGCC TCATCATGGT ACCTGCCACC
34901  CCCACCCCCA GCCCCGCACT CACAGTCCTC TTGCCCGTTG CATTCTCTTT TGGGGTGAGA AGCCTGGTGC CTGCCCTGGG CTGCAAGCCT AGCTTTGGGA
35001  AGCTTCCCCT TCTCCCCTCC TGCCCAGACC TTGTGCTTTC TGGGGTGAGA AGCCTGTCTC TGGAGAAGCA GCTGGTGTCA TCAGGGGGAG GAGTCTGCCC
35101  ACAGTGACCA GGACGGATGC TCTGGGATGG AACCAGCTGG TTCCCCAAGT CAGGGTCAG GCAGGAAGCA CCGTGGTGTC CTGGCTGCCC AGACCGAAGA
35201  AGGAGCAAGG TTGGCTGAAG TCAGTGCCTG TGAGCTGA AGGGAGCAGT AGGGTCAGTT GGCCCTGTGTC GTGCCTTCGC CAGGAGCAGC TGGGCCCTGC
35301  GGCTATGCTG ACCATGGGGG CCCCAGCTGA GGAGCGAGTG AGGGCAGGTT AGGGTGGGAA AGTTCTGTAT CAAACCCAGG GTGCCTTTCT CTATTTCGCC CAGGAGTCTC
35401  AAACCCGAGC ATGGAAAGGG AGCTTGGTCC GTCCAGGGGG GGGAGTTGGT CTTAGTCATA GAGGACTTGA GGCAGAAGGG AAGGACAGGT GGCCTGTGTC
35501  CTCTCCTTAC CCTCTGGGCT GCCGCTTTCC AGCGTGAGGG CCGAGTGTAC AGCGGGGTGAA TCCTCCCTGG GGTCCTGCTG AGCCCCCACT
                                                                         E12
35601  CCCCTCTGCA GGCTGGCACG GTGGTGTGGA TCGGCATCCT TGTGTACACG GACCCAGCTG GCTGCGCAC CTACCTGGCC GCCCAGGTAA CGGAGCAGAG
35701  CCCGCTGGGC GAGGGTGCCC TGGCTCCCTCT GCCTGTGCCC AGTGGTGTGC TGCCTGCCAG CCACCCGGAT CCTGCCTTTT CCATCTTCCC GCCGGATGCC
35801  TCCAAGTTAC CCGAGAACCA GACGTTGCCA GGGGAGCCGC CTGAGCCCGC GGGTCTCGCC GAGGGGGTCC ATGACAGCCC GGCCCCCAGAG GTCACCTGGG
35901  GGCCCGAGGA CGGAGGAGTC TGGAGGAAAC TGTCCTTCCG CCACTGGCGCC ACGCCTTTCA CATCACACTG GCCAAGAGT GGGGGGCTG
36001  AGCTGGGTCC GCGTCGTGT CTGTCCGTGT CAGCTGCACTG CAGCTGCTGT GGAAGCAGTG TTCTCAGTAG CCAACAACTG GACGAGGGA TTTGAATTCT GAATTTTCTT
36101  TGAAATAAAC ACCATCAGG TTGTGGGGTA ATCCACACCT CACTTCCCCG AACTCTGCCA CCAACACTG GAATTGGTGA CCCCGCTCTG TGAGGTCATA GGTCGCTGTC
36201  AGCTACTTAG CCAAAATGAG AGCTGGAGCC AGCTGGAGCG CACTGGAGGG GGGGAGGACA GAATTGCTGTG CACAGGGGACA GTGATTGCTA GGTGGTGGA GTCTCTGACA
36301  GGGCAAGGTT GGGGGCCCCA AGCTGCCAG AGCTGGAGCC GGGACCCTA CCCACTGGGAA GACTGTCTTC GGAGGATGTT CTTGAGCTT GGCAGAGCAG GCCAGGTCCC
```

Fig. 2J

```
                                                                                                          E13
36401  ATGGGGAGAG TAGAGGGGGC CCTGGGCAGC AGCAGGCCCT CCGAGGGCGT CTCCGCTGAG GCTGAGCGCT GCCCGGCTCA GGTACGTCAG CCTGCTGCCT
                                                                  E13
36501  GTCATCCCCG TCACGCTCCG CCTGAACCCG CGGGAGGCTC TGGAGGGCCG GCAGGCCGCA GACCCCTCAG GACGGCCGCA GCGCCTGGCC CCCGCCCTGG CCCGGGCAGG
36601  GTGGGCTCTG GGAGGCCGGC CCCAAGGGGC CAGGCACGGC GCAGGCGCAG AGAGACCTCA CCCTGTACAA GTAAGGCCCA ACTTGGCCTG TGAGTCGGGG GTGGGGCGGC
                                                                                            E14
36701  CGGCGGGGTC GCGGGGCCGG GGCAGGCTCT ACCAGGCTCT GCCCGATGCA GGGTGGCGGC ACTTGGCCTG GCCTCAGGCA TCGTGCTTGT GCTGTGCTG
                                                    E14
36801  CTCTGCCTGT ACCGTGTGCT CTGCCCCGCG AACTACGGGC AGCCCGGCGC GGGGCCCGGC CGGGGGCCGG GGGGGGAGCT GCCCTGCCAC GATTATGGCT
36901  ACGCGCCCCC CGAGACGGGA ATTGTGCCCC TGGTGCTGCG CGGGCACCTC ATGGTGAGTG GATGGGGCCC AGCTGTTGCC GGGCCGAGCC GGGCGGGC
                                                                                        E15
37001  CAGTGCCCAT GTGCATGCCG CGCTCCCGCA GGACATCGAG GCGACGGGAT GCTACTGGTG CTGCCCTTGG CCGNCCCCTC CNTTNNNNNN NNNNNNCCCC
37101  TGGGACGCGC AGACCGGAGA CTGCCTCACC CGCATCCCGC ACCCGGGTAG GTGCTCCGCG CTGCCCTTGG CCGNCCCCTC CNTTNNNNNN NNNNNNCCCC
                                                                  E16
37201  TAGCAGGCAG CGGCGGGACA GCGGHTGTTGG CCTTGGGCTG GAGACTCAGG AGAACCTGGGA ACGGCTGTCG GACGGCGGGA AGGGTGGCCC GGAGGAGCCT
                                                        E16
37301  GGGGACAGCC CTCCGCTGCG GCACCGGCCC CGGGGGCCCTC CACCCCCTGC CCTCTTTGGG GACCAGCCAG ACCTCACCTG CTTGATTGAC ACCAACTTTT
                                                        E16
37401  CAGCGCGGCC ACAGCTCCCC GAGCCGGCTC AGCCCGAGCC CCGGTACCGG GCGGGCCGCC GTGCTCAAGA CTCCGCAGGC TACGACTTCA GCCGCCTGGT
                                                    E16
37501  GCCAGCCGCTG TACCAGGACG CCGGACATGCC TCCCGTGCAC ACCGCAGCCC TGCCCCACC CTCTCCCCGG CCCACGTTCC CCCTGCCCC TGAGGACCAG
37601  GCTGGCCTTTC CTCCCGAGAA GAGCTCCCCG TCCCTCGCCT GGCCCCCCAG CCGATGGA GTCTGGACTT TCCATCTGGA GTCGGACTT TCAGCGGCAGC CTCATCCTGG
                                                        E16
37701  TGGGGCGGAG CAGTGGCCGG CTGGAGGTGG GCAGCGGGGAG GCAGGGGGGT CGTGGGTGTT CCCAGTTACA GCCCTCTGGGC
```

```
                                                                                                    E21
        ACTCCTGCAG ACCATGGTGC TGCCAGCGGG AGGCCAAGAC GGGGCCCATCT GCCTGTGGGA CGTGCTGACC GGGCAGCCGGG TCAGCCACAT GTTCGCTCAC
40401                                                                 E21
        CGTGGGGATG TCACCTCCCT CACCTGCACC ACCTCGTGCG TCATCAGCAG TGGCCTGGAC GACCTCATCA GCATCTGGGA CGGCAGCACG GGCATCAAGC
40501            E21                                                                                           E22
        TCTACTCCAT CCAGCAGTA GGGCTGGGGG CCACGGGGCC TCTGGCTGTC GGGAACGGGCT CCAGACCCCG AGCCGTCTT GTCCCTTGTCT CCAGGACCTG
40601                                                                      E22
        GGCTGTGGCG CGAGCCTGGG TGTCATCTCA GACAACCTGC TGGTGACCGG CGGCCAGGGC TGTGTTTCCT TTTGGGACCT GAACTACGGG GACCTGTTAC
40701                                                         E22
        AGACAGTCTA CCTGGGCAAG AACAGCGAGG CCCAGCCGGC CGGCCAGATC CTGGTGCTGG ACAACGCTGC CATTGCTCTG GGGAGCTCAG
40801                                                            E22
        CCTGGTGTAC GTGCCCTCTG TGCTGGAGAA GCTGGACTGA GGTGGGGCCT TCCCCACCCC TCTGGCTGGG GCGCTCGGTT GGCAACGCAT GGGACCTGGA
40901                                           E22
        CGGGGGGAGT GCTGAGTCTT GGGAAAGCTG CTTCTGACTG TCCTGTCCTG CCTCATGACT GTAATATTAA ATGTTTTTTT AAATGACATC AGCCAGGGGC
41001   CTTTTGAGCC ACTTGGTGTC TTCCCTTGGA CGGGCTCTGC CATCACTCAC ACCCTCCGGT TGCAACCCTG GGGTTTAAAC CCTTGCTCA
41101   ACCTCAAAA CGGCTTCCCT GGCCAGGAAA ACCCCAATTG GGCCAATTTA AAAAAATTTT GGGGGGGGGG GGGGGGGGGC AAACCCCGGG
41201   GGGCCCCCCC CCCCTCCTTA AAAACCCCC TCCCCTTTTT GTTAAAAATA AAAGCAGGGG GGGGGCCGG GGAGAGAAT
41301
```

Fig. 2M

Bovine INSIG1 Gene

```
   1 CGGGCAGCCC GCAGCGGGGC GCCCCTCGGC CAGGTACGCG GGGCGCGCCG AGGGCGCGCG GGTGGGGGCT CCAAGGCGGG ATGTCCGGGT
 101 GCCAGCCCCT CCACTCCAGA GCCTCCCTTC TAGGCCGCTT CCCTTTGGGG GACTCTCGGG CCTGGGCCCC AGCCCTGACC TCCTGCGCGG
 201 GGGCCCCAGC ACCCGACCCC CCTGCCGGTG GTCGGGAGGA CCCCAGGAAC TTGTCCTGGG ACAACCTGCC CCAGGTCCTG CCTGGCTGAG
 301 TCCATCTCCT CCGACTGGGA AAACTTCTGG ACTGGACGGG AGGCCTTCTG TGGAGGGCGG TCGTGGGCGG AGCGCAACGC
 401 TCAGATGCAC CTAACCTGCC TGCCCTGGAA AGCATGTCGT GCATCTCGCT TTCCTGGACC GGCCGGGAGT GTGGGCAGGA TGCCTGCAGC TCCTGCAGCT
 501 CCTGCCCGGT GTGACTAAGT CCCGGGAGGC CTTGGGGGTT TTCCTGGACC TGCCGGTGGT GAACCAGAGC AGAGCCCTCC TTGAGTGGGC CTCCCTGGTC
                                                                                                    E1
 601 CTGACCTCCT TTGAAGTGA ACTTGATCTG GGTTCCACCT CCAAGCCCCC TTTTCGTTCT AGGAAAGCCT GCAGGCGGGT GGCTCATGCC CAGACTGGAC
                                                                        E1
 701 GACCACCTCT GGAGAGTCC CTGTCCCAAG GGCACGAAGC ACAGAAGCCA CCCGAGGGCC AGCGCCAGAG GGTGGTGCGC CAAAGCGGGA GAGATGATCA
                                             E1
 801 ACTCCTCGGG GTCAGGCCCC TCTCTGCTGG CAGCCCATGG TGCCCTGGGC ACTGACCCCG CTCACGGGCC TCAGAGCGCT GGTGTAGGGG GCCAGGGCAG
 901 CAGGAGCCAC GTCAACAGCT GGCATCACCA CTTGGTGCAG AGGAGCCTGG TGCTGTTCTC GGTGGGGTG GTCCTGGCCT CCTCCTGCAG
1001 GTCCAGAGGA ACGTCACCCT GTTCCCGGAC GAGGTCATCG GTGTCAGTAC CCACCATCTT CTCCTCCCCG TGGTGGGTTC CTCCGTGCTG GCGGTGAGT
1101 AGACACTGGA GATGTCTGTT GGGTTGTGG AAACTTCTGG GGGAGGCCAG CCCTCTCAAGA CTGTTTATTT GAGAATGAAA CCATCCACAG TGCCTCTCCA
1201 GTGACGGTAT CTAGAGGAGA AGGGGCCAGA GGCAGGAGCC CAGATGCCAG GACTCTGGAT GCTGAGGGGC GTTGAGCGGC GGGCACTGA TTGGCTGTTC
1301 CTGCCCCGTG CCAGGCTGAC CGAGGCCCTT CGAGGGTCAG GAACTGCCGA CCTCTGGCCT GATCTGGCGT GTGGACAGT GTTGAGGCGG TACCCGAGC AAGCGCGCC
1401 ATTGGCCAAC ACCGGAACTC GTGAGCGAG GAACTGCCGA GTCATCGCT CCTTTTCAG GTCATCGCT CCTTTTCAG GTTGAAGTGC TGAACGTCC CCGAAACAA ACCATCACGT
1501 GGGCCAGTGG GCAGAGCTGC CCCAGTGGCT TCTTGCACTT AAAACAAGTG TCTTATTCAG AGTTTAGCTT TGGCGTACC TGAACGTCCG CTTTCCCCTG CCCCTCCA
1561 AAAAAAACA CCGGGGTCCC TGGATGAAGG AAAACAAGTG TCTTATTCAG AGTTTAGCTT TTGACTCTT TGGCCAARGA CAAACCTGA CCCAGAGTCT
1701 GCAGTCTTAA CAGACTGACTA GGATGACTA TACCCTGTGAG TGGCCTAAGG TGGCCCTAAGG GGCCAGAGG TGGTCGTCTG GGTAGTTTTA CTGAATTGAT CTCAGCCCAG
1801 TAGGCGCTT AGGACTTCTC TGGTCACCCA GCGTTTGCCG TGCCCTAAGG TCTGCCGGTG GTTGAAGTGC AGCGAGCAGC CTGCCCCTGG CGGCGTCCT
1901 GGGCTAGGGG GCACGACAGG TGTGCGACCTG CGCAGCTCCA CAAGGGGCCA CCCTCCGGCCA CGGCGAGTGG GGTTGGCATT TATGGACTGT TTGATATGTT GGGTGTGTCC
2001 TGGTCCTTAC GAGACTCTGC GAACGCTGCC TCGTCAGCAG CCCCCTTAG CCCTCCTCCA GGCCCAAGGCA TGGAGTGGGG ACCCTCAGGG GAGGGGTGCT GTGGGAGAA
2101 CCTGCACTGG GAACGCTGCC GTCCTGCACC AGGTCGGCTC CTGCTCTGTT TTCTAAGCCC CCTCTCAAGA CCCTTTTGGG AGTGTGCAC TTCCGTCTTC
2201 GGTTCGCACC ATTCCATAT GATCCATAT GATACAGTAG TTTTTTGAC TGAAACAGTA GATCTCAAAA CCGTCCAAGA ATTGGGTTTA GGCTTTATTT GTAACAGAAG CTTCAAGGAA
2301 ATTCCATAT GATACAGTAG TTTTTTGAC TGAAACAGTA GATCTCAAAA CCGTCCAAGA ATTGGGTTTA GGCTTTATTT GTAACAGAAG CTTCAAGGAA
2401 TTCCAGGAT ATCTGTACGT GATGTCTGGT TTAAGATATA GGCTTCACTG CTTTTTTAA GCCAATCACTG CTTGCACTG AGGAGCATAA CCATAGTACA TTTTCACCTA
2501 CTCAATCTG AAAGTAACG TTAAGATATA GTGACTTAAG TGATAGACT GTTTGGGTTC CTGGTCAGG CATTTTTCAA GACTCCAGAA TTATGGGAAT TCCCTGGCGG
2601 CCCCTCAAAAA AAGCTCAAA ATCAGAACTG GATAAAATGT ATTAGAAAT CTGGTCAGG TGGGCGGTTCC AACTAAGATC CAACAATCA TGCCATCGGG GTCCCACCC
2701 GTTTGGTGGGA TGAACTCTCA CCTTCTCCGTG GACACCAGG TAATTAAACC ATGACTCTCA ACCTCCGTA AGCCTCGGTA CCGCTGCCAC CCTGCTCGTC CTGCCCTCT
2801 CCAGCCACCA GCAGGAGTGC CGCGGGGCTT CCCATGTGGA TAATTAAACC ATGACTCTCA TCCCTTCTAT AGGTCAAGCC AAACAACCC AGTTTATTT
                                                                        E3
3001 AAAATTGTAC AAAATGATGT GGGTTTTTG GTTTGTATTC AAGGAGAACA AAGTGTAACA TTAGTTTAAA AATAAAAGAT GTAAAGTTAG TTTAAATATC
                E2
```

```
10231 TTTGAGATG GGGGTTGGAG CCCAGAGGC TGAGCGCCTG GCGTCTGGTG CAGAGCGGGC TGGCCCTTGT GGCTCGCTCA GCCTCTCAGC AGGGGTCAGG
10301 GTGGACACGC AGGGACCCCG GCTCTGGCAG GAGGCAGGGG GCTCTCCCTCA AGGCCAGGCC TGAACTCAGG AAGGTCAGCC TCTGGTCTCG GACCTGCTGC
10401 TCCAGTGGGG TGTCCATCCT CGGTCGAGGG CCACCAGGCC AGGGCCACA ACCGGCCACA AGTGTGGGGT GCCCTCTCTG GGTATCTGTG CTGTCCGGCG
10501 ACGAGACGTG CATAGACACA GCTTCTGGGC AGCAGTACCA CCTCCTGTCC TGCCTGCTAC ACCCCGCCCC TGCCTGAGCG GGACAGACCA GGTCTGCTGA
10601 GATGTGGGCT CCCAGTCAG GGCTCCGAGG GCATCGCTGT GGGGCCGGGG GAGCCGTGTC GCTGCTCCGT GATCTGGTC TCCACCCTCG CCTCTGCCGC
10701 AAAGGGATTC TTCATTCTC ACTTGTAGG GTCCGCTTAA ATTGTAAGT AAAACACGCA CACATACAGC GCTAACATGC TTTTTTTCT CTCTTCTCTC
                                        E7

10801 ACATAGGGTG TCCCGAAAAA GCCACACAGT GATTGAATCC TCAGGCGCAC GGATCCTGAA GAGTGGCAAG GTTTGGGGAG AAAGTCCCGG ATACTGGGTA
10901 CTGACCAGAC TATCTCTTTT CCTCAGTAAC CTCTCAGAT GGGCCTGACT GTACCAGTCA CTCCTGCAAA ACACTTCACC TGTTTCAGAG CAGCCAGCG
11001 GTGGATGGGC GCTGGTGGTG GACGGTGCC CCTGCCCGGC TCCGTGCGG GCACCACGAG CAGGCCGGCG GGGCACCGGG CCCCGAGGAC TCAGTTCTC
11101 GTGTTATTAA ATGCCAAGTT GCCATATTG CTAGCCTCGA GACTGCCAGC TCTGGTTCCG TGTCAGCGCC CGGGGACGG CTTGGTGTG
11201 CTTACAAAGA TGAAGTGTGG TGAGACAGGA ATATCACTCA TCCAAAAGAT TTTAAAAATA GGGCTGTGTT ATGAAAAAAG AAAAGGCGGG GGTGGCAGCA
                              SNP_12052

11301 ACCGCAGGGT CGGCCGTGCC CCCAGCCGGC CACGGCGTGG CTCTAGGT GCTACGCAGA CAATCCTGCA GACGAGGCAG TGAGTGGGAC
11401 GTTGTGGCTC TGGGCTGCAA TGGGTTGGAC TTTCCACCCT GGTGTTCACG GAATCCGCAC CGTCTGGAAT GGGCGCCCG TCGGCCACAC GTCTCCGTCT
11501 TGGGCCAAAC CTTGCCTTT CTTTGCTACT CGGAAGAAGA GACGGCTTT TCCCCACAGC CCTATGGGAT CTGCAATCTG TGATTGCCTT GTAAAAGAA
11601 GAGTGCGCAC GTCACTGCAT CACATTCGGT GTCTCTAAAC CCTCAAAGGA CGGCGTGAGC ACAGTGTACT CACTCAATGG CACAGCCCAC GTTGGGCCCG
11701 GTGTGCCAGT CCTGGCCCT CGACTTCAAG TGCAATGTAT AGGAACACCA ATCTGAGCCT TGTATTCTCT TTAAATATT ATTATTATTT TTTTAAACGT
11801 GTGAGATGCT AAAGAGGGTT CTCCATTTCA GTGGTG
```

Fig. 3D

Bovine INSIG2 Gene

```
   1 ACAGTCCATG GGGTGCAAAA AGTTGGACAT GACTGAGCAT AGTTGGACAT GCATGAGCAT TCTTAAAACT CACTTCTTGG TACAAAGGAA AGACCACTTT GGTTGGCAAG
 101 GGCAGGGAGT GATGGTGAGT GAATACCTAG AGTGACTTAG TCCTTCTTA CGGTTCCTGC TCTAGGTTTT AGGAATCAGA CGCCCTGTGC CTCGAACTCC TTAGAATCTA
 201 GCCCAGAGGT TATTCTTTGT TTTCTTAGCT TCCTTTCTTA CGGTTCCTGC TCCAGTCTAT TCACAATAGC TCTCATGATT GCAACAAAGG TGGACTGGGT
 301 GACGGCAGGG GTGGCTCACA ACTCTGGACC TGGGGACAGA GGGTCAGGTC TGATTTCTAT GCTTGATGTA GGTCGTAGTG AATGGCTGCT GGTCTCTTTT
 401 TTATAGGGCA CTTTTGTGCA GAAATTCACA TGTTAAGCA TTAAACATTA AAAGAGTCAT TTTATTCCCC GCTCGAGATT TATGGAGATG AAAATTCCTG AGCATGTCAC
 501 ATTTGATTGA GAACAGTAAA ACACTTACAG TCAGAGAATG CCGATTTTCT GTAAAGTTCT GTAAAGTGTA TTTCTCCAAC AGTAAAAGTG TGTGAATCTC CAAGCCCTTC
 601 AGTTCATGGG GCTTGGAGAT AAGCAAGGTC ACTAGTTCTG TCCTAGTAAA TATAAATTTA CCACTTCATG TTTTATTACA ATATGCATAT CCTGACCTGC
 701 TTTTTTCACT GATGTGGGGC AAGCAAGGTC ACTAGTTCTG TCCTAGTAAA TATAAATTTA CCACTTCATG TTTTATTACA ATATGCATAT AAAAGTCTT
 801 TTTAGGTCTT CTTATTCCAT AAGTAACTAA TTTAAATAGA CATGTAAACT TGTCATTTCA TTATTTGTTC TTTAAAATGA ACTAGTATTG AAATCAGGAA
 901 AACTCTAGTC ATTTATTAGG CATACATTGA TTGCTTTTTT CTTATCTCTT GCAGGATTTC TGGTAGGTCC TGTTTTAGGA CGAGATGCAG TACTGTTGAA
1001 ACGCAGTCT GCTTTCGTTC ATACAATCAG CTTTTCAGC TGGGAAACCC TTCTTCTC CTTTTTTT TTTTGCCAA CTTACTGAAC TTATGAAACC

1101 ATGGCAGAAAG GAGAGACAGA GTCACCTGGG CCCAAAAAGC GTGGTCCATA TATCTCATCT GTCACTAGCC GGAGTGTGAA CTTGATGATT CGAGGAGTAG
                                                     E1

1201 TGCTGTTTTT TATTGGACTA TTTCTTGCAT TAGTGTAAA TTTACTTCAG ATTCAGAGAA ATGTGACACT CTTTCCACCT GATGTGATTG CAAGCATCTT
               E1

1301 TTCTTCAGCA TGGTGGGTAC CGCCATGAGC TGGCACAGCA TCAGGTATGT GTAGTTTAAA TCAGGTATGT GAAGGCTGTT TCTGTAATGC AAAAGACATT AGGATAAATG ACTATGGCTG
1401 TTTTTCGGGA AATATTTGAA AAAGTCAGCT CTACTGGGTT CTAGTTTAA AACATTCTG CTGCTAAGTC CAGGGCCTAC TGGACCTGTT TGGACCCTGT TTAAGTGATC AGTTTAATGA GTTTAGACAG
1501 ATCATACATT CATGTAACCA CCCCCACAGT TCAGCTATAG ACAGTTGATC CTTGAACAGC GGCGAACTGT AAAGTTACAG GCCATTTTC ACTTATACAG AGGGTTGGTG CCCTTAAGCG
1601 AGCCCATCAG GCTCACACGT CCTCCGACGT CCTCAGGGAA GTGGGTTGCC ACAAGTGTGA ACAAGGTAGC ATGGGGTAGG GGTTATGT GTGGGGTTGT TTTTTTTAA ATGTGTATCA CACAGTCTGA
1701 AGTCGCTCAG TCGTGTCCGA CTCTTATCGA CCCAGGGAAC TGGAGCCTAC CAGGGCCTCA GTCCATGGGT GTCCGACTC ATTCCTTCT CCAATGCATG AAAGTCAAAA GTGAAAGTGA
1801 GCCATTACCT CTGCAATGG AACATTCTG CTGCTGTTCG TGCTAAGTTG CTTCAGTCGT GTCCGACTGT GGGCGACCCC ATAGACGGAA CAAGAGTACT GGAGTGGGGT
1901 CTCCCCGTC CCTGGGATTC TCCAGGCAAG AACTCTGGAG TGCGTTGCCA TTTCCTTCTC CAGTGCATGA AAGTCAAAAG CCCTCTAAAT TCTCTGTGC GCACACCAGG
2001 CGTGTCCTAC TCTTAGCGAC CCTTAGCGAC GCAGCCTACC AGKCTCCTCC GCCCATGGGA TTTTCCAGGC ATTTCTAGTA CCCTCTAAAT AGAGTCTTA TCTCTGTGC
2101 CCTTTCCAG CCTACCACA CCCTCAGGCT GAATCTGGAT TATTTCACC TCTCTAGAA AACAGTCTT GATTCTCCTG AGGATGAGGC TTTAACCTC TTAATTTGT
2201 TCTGATTTCT ATGTGACTGA CCCATATGAC CTTTAAAAAT TTTGAAATTA TTTTGATGAC ACTGGTTTTA AGGTTTTGAT GTATGTATC GTCCAGTTTT TAAAGTAAAT
2301 TCTTTCCTCA ACCACCTCA TATAAATTTA CCTTGAACAGC ACAAGTGTGA ACAAGTTAT GCTTTTTTAA ATGTGTATCA ACACGTCTGA
2401 GAAAACTTGA AAATGGAAG ACAGTTGATC CTTGAACAGC GTATACAGAG GGCGAACTGT AAAGTTACAG GCCATTTTC ACTTATACAG AGGGTTGGTG CCCTTAAGCG
2501 GCTTGGTTGA ATCTGCAGGT ACTATAATTT TATACAATT AGAGAAGTAA ATACTGTATT GATGCTGCAC AAGAGAAATC ATTTTTAT TGGCTTTC TCTCTTTATAT CTTGTTTTA
2601 TCAATGTTGT CAAGGGGTTG ACTATAATTT AATTCTTAAA AGAGAAGTAA ATACTGTATT GATGCTGCAC CAGTACCGTG TTCAGCATGG TGGAGATAT TCATGGGCAA
2701 GATATATTT CAGAATAATA AATGGTCAGA AATACGCATT GAAGAAAGCC ACATGGGGTAG GCCAAGGGTG GCTGCTGCTA TTCTCTGAGA TTTATATACT AATAGATTAT
2801 TGTATATTGG ATAAGGTGGG CCATTACGAC GAGCATCGCAC GATGCGCCGAC TTCTCTGAGA TTTATATACT AATAGATTAT
2901 ACTACTTTAT GTAATAAAGT AATAGATGTA GAAGAAAGCC ACATGGGGTAG GCCAAGGGTG GCTGCTGCTA TTCTCTGAGA TTTATATACT AATAGATTAT
3001 TATATACTA CCTTTCAATA TAATGTAGAT CATTTACTA ATCCCATTGC GTGGATGGAA TTAATTCTC TGTATGCTGA AGGAGTTAGG TGTGAGATAT TTTTAAAATG
3101 CTATTGCAGT ACTATTGGAA CATTTACCTA AAGAGACTT TATTGTTTT TCTTTATTTC GTAATCTTCA CAGTACTACC TTTCCCCAGG GCTGCTGCTA TTCTCTGAGA TTTTCAGGACT TAGAAGAGTG
3201 AGACAAGGA AAAAAGCATA TTCCCAACAA AGGAGCAGCG GGGGAGGAAA ACCCTTGTT TATTGAGTGT TGGTCTGTCC CTTAATCACA GGGATCTGTA
```

```
7601  TCAGGAGTGC CGAGGCAGAG AGTCCTGTTC TGATTTCTTG GGACAGTCCT TGAAACCTAG TGTGACTACA CTGGCCTTGC TTCCTCACAC CTCTGATTTC
7701  ATGGGAGAGT ATGGGAGTAA CTCATGTTTC ACGGATACAC ATAATATAAT GTAATGCAAA AAGTTTGTTC AGGTTTTCTG TAACATGTA
7801  TGGGAGGAAC TCGAATGAACT TTTTGGCCGA CCCAATGTAA CATAACATAT GATGAACAAG CTGAAAAGAA AGAACTAGGA CAAAAGCCA ATAGTATTT
7901  AGGCCATTGA TTCTTGAACG AGGGGTCTTG AGGGTCTTG AGATTCAGTA GATCCGGGGA GAGATCCGGGGA GAGATCCGGA
8001  ACTTTTGCTT CTAACAAGTC TGCAGGTGGC GCTGGTGCTG TTGGTTCAGG GTCTGAGTGT CACCAGTGAG TGTTTGGCTG AGACCTAGG TCTTCCAGTA
8101  TGTGAGAGAG AGGGGCTAAT AAAGGGCTGG CCCTTAGGG CCACTCAGG CATGAGACGC AGTTGCAAAG AGTTGCAATT AGACCTTAGG AAGGTCAGA
8201  AAAGTTTGG ATTTATAACA TTTCAGATTC CAAGGCAAAT TCCTCCAGA TACTATTTGA ACACTTGACT CAAAATGACT ACATTTTAC AAGGTCAGA
8301  GAACCGTGGG CTTACAGGCA AAGGGCTTCT TTTGACTATT AAATCTTCCA AATTCTGTAA TATTTTAAAA AATTGAGTTG ATTACAGTG TTGTTTTAGT
8401  AATTCCAGCA TACGGACAAA TAACCAACAG TCTTTGTGAT CCCGCCTCC TTCCTCTTCA CCAACTTATC CTCTGTGGCA CATGGGCTGC AGGGCTCTTG
8501  AAGGAAGTGC CCACATCTTC TAGATTCAAC AGAAAGGGAA CAGAACAGAA GGGAAAGCCT AGATTTCTTG CATTTCACAG GTACTGCCTA TTTTCCTCCA
8601  GCATCCTTCC TGCCTTCAGT TAGTTTCACT TAGACCATTC TGAAGTTCTG CCAAAGCCT GTTGATTTAC AAAATATAGT ACAAGTACTA
8701  TAAAAGTTCAT AGCAGATTCAA TAACAACCAG TAATCTTGCC TATGCAAGA AGGCTGCAGT CCATGGGGTC GCTAAGAGTC
8801  GGACACGACT GAGGGACTTC ACTTCCACTT TTCACTTTCA TGCACTGGAG TGCACTGGAG CTTAGCAGCA CTTAGCAGCA CAACCCACTC CAGTGTCTTT GCCTGGACAA TCCCAGGGAC
8901  GGGGGAGGCT GGTGGCCTGC CGACTATGGG GTCGCACAGA GTTTAGTCGT TCAGTTGTGT GCAGCAGCAG GCAGCAGCAG GCATGCAGCC ATGCCAGGCT
9001  GCATGTTTCC TCTCTCCTGT TGCACCTGC TATCTATTCA GTTTAGTCGT TCAGTTGTGT GTGACCCCAT GTGACCCCAT ATCCATCCT CTTCTCCTAC
9101  TCCCTGTCTA TCACCAACTC CCAGAGCTTG CTCAAACTCA GTCCGATGA GTTGGTGATG CCATCCAACC CAAAAGATTG GAGTTTCAGC GTCCTTCCAA
9201  GCTCAATCTT AGGGTCTTT AGGGTCTTT CTAATGAGTC AGTTCGATGC AGTCAGGTGGC ATCAGGGTGGC GAGTTCAGG TTCAGCATCA GTCCTTCCAA
9301  TGAATATTG GGGTTGATTT CCTTTAGGAT TGTCTGGTTT GATCTCCTTG CAGTCCATGG GACTCTCACC AGTCTTCACC AGGATCACAG TTTGAAACA
9401  TCAGTTCTCA GCCTTCCATC TTGCCCCCAGG CCAAATGTGT CCATTGCTGA AGTAGAATCA GGATTCTCTG GTGCTCTTT GGTGGCTAGA ACCCAGCCTA
9501  TGGGAGGAAG CTGAGGCATG GCAGAGGGTGG ATAAGGCCAGT CTGGCAGGAG CTTGGGTCAG GAGAGACAGG GTTTGAACC TGCTGGTCCA CCAGTCAAAT
9601  TCTGCCCAAT CCTGTGAGCT GCCAAGGAT TCAAATGAC CTGTCAGACA CTGGGTAGCC TGAATCCACA CCTTGCATGG TCCTAACCTC TTTGTTGAGT
9701  TGTCTTCTT TTTTTCGTC AAATCCCTAA TATTGTTGAG GAGTCCTGC AATGCGTGGC CATGGACTGC TGTTTCACCT CCGGGTTTT TTGGTGAAA
9801  GTGAAAGTGA AATGGCTCAG TCGTGTCCGA CTCCTTGCGA CTCCTTGCGA AAAATGATA GATCCGTACT TCTTCGCTCAT AGCCTACAGG GTCCTCCATC CACAGGATTG
9901  TCCAGGCAAG AGTACTGGAG TGGGTTGCCA TGGGTTGCCA TTTTCCTCTC CAGGGGATCT TTAGCTGCTC TCAATTACCC TGGTCCTGAT ACTGCCTTG CTTTGGTTTG
10001 TACCCTCTGA GCCACCAGGG AAGCCCACAG ACCCTCAACTT CTAAAAGAG CAATGTGAAT GATCCGTACT AGCCTACAGT GTCCTCAGTC ACCAACTCCA CTCTCCTCCC
10101 GGATAAATAA ACATCTCCAG TTGGCACAGA AGCTGCCCT TCTCACCTGT AAAATGATA GATCCGTACT GAGGTTGTGA GAAATAAATT CGATAATAGG
10201 TGTAAATTAC TTGGCACAGA CATTTGAGCC ACCAGAAATT TTGCAGCACA ATCAGTTCTA CAATGCTGGC ATACAACGTG TGGTCCTGAT ACTGCCTTC TTTTCTTTAG
10301 TAGAAGGAAA AAAGGCCCTC TTGCAGCACA ATCAGTTCTA CAATGCTGGC ATACAACGTG GCCCTGTTCC TCCTCCCTCC GAAAAGATGG CTTGGTTTG
10401 GGAAACAAGG GTTCTTCTC AAAGTCTCCA AAGTCTCCA TCACTATTTT GTAAATAAGT ATCTTTTGT TCAGCTGGAC GTCTCTAGTG TCTCTTTGG GGTTTTTGA
10501 TCCCCTTTT CTCTAAAAAG TCACTATTT GTTTAAAACA GGGGTTAATC ATTTCCCTAA ATGTCCTTAGG TCTCAGTGT TTTCTTTGG CTTCTTGAGT
10601 GGAGCGCCAGG TTGCAGTCGC AAAAAACAAG ACTTTAATGT TCAAAATACT AAAACATCA AAAAACATCA ATGAGACTTT TCTTTAAAGT CTGTAATCC CAGCCATTG
10701 CATCTTTTA AAAAAACAAA AAAAAACAAA AAAAAACAAA AGCCTACTAAAG CAAAACACC AAAACCCAG AAAACCCGGG AGAATGGAGC GTGGCTTCAT
10801 TTGCAACTCT TCCATTTTA AGTATTAAATA TAGGTTGAGA TTAACATTAT TAACTTGGTT CTTTTTTCT GTCAAGGTCA CTGCCAACTG CACTGTGATC
10901 AGTCCAACA AGTATTAAATA AGTATTAAATA CAGGGTAGGAAC CAGGGCATGAG AGTCCCAGC CTGCCTCTTGG GGCCAAGTCTC TTTCCAGTGT GAGAGCCTTG
11001 CTAAATGTA AAGTCCTGCA CAGGGGCCT GAAACCTCCTT TAAAGCATCAG GGGAATGGAAG AAGTTGGAGC AGTTCTCTCT ACTGCTTCTA AAATCCGAAT
11101 GCTCCCTGGT CTGCTGAGCTG ATCAGGAATT TTGCAGCACA ATCAGTTCTA CAATGCTGGC ATACAACGTG GCCCTGTTCC TCCTCCCTCC GAAAAGATGG CTTGGTTTG
11201 CGGGAGCCTC ATCAGGAATT TCAACAGGGT TCTCAGGGCT TAAGCATGG GCAAATGGC AAAGTGGAGC AGTTGCTCT ATAATGCCA TCTTAAAAG CCGGTGATAA
11301 AAACATCAT GACCTTCTT GACCTTCTT GTGTAACATT TAGTCTCCAT TAGTTCCTGA CAGTGTGTGG TGACTCTTG GTAGAAAATT CTTTAAAAAG CCGGTGATAA
11401 ATTACACAA GGTGACACA ATGGTGAAGT GTTAGTTTAG GGCCAGTCC CCTCCCCCA TGACCCCATG TGACCTCTGG GTTGACCCC CACCAGGCTC ATTACAGGCA
11501 GAATTCTCC AGGCAAGAAA TGGGGTGTGG GTAGCCATTC CCTTCCCCA CAACTCAGGG GGCCTCTGC TATTGCTGGC TATTTGATG CCTGCTTGC
11601 GATTATTTAC CATTTTGACC GCCAGAAATT TCTATAAAA CGGCCTACTA CAGGGGAGCC AGGGCTCTCTT AGAGACTT GGTTCAATC CAGTGTCTCT CCCAGGTTGG
11701 TCGGTGTCA GTCTCCCCAT CCCTCGCTG TGCCTGAGCG GCCATCTTGG GCATTATTGAGACG CATCCTGGGG CACCAGAATTT AGCGGTTCGA GTCTAGTGT
11801 CTGAATCAA AGCCTAGCCG CCCGCCCGG AGGGTAGCAC GCCCCTAGCA GATCAATTGC TAAAGAACTT GACCCCTTTGC AGTAGAATGC ACAGGTCAG
11901 CAGGGTCACT TCCAGCCTGG AGGTGAGGTGA CAAAAACTGA GTGGAGCTGG AACAAGTCGA TAAAGAATTC GACCCCTTTGC AGTAGAATGC ACAGGTCAG
```

```
47201 GTAGGGTGCT TAATCTGGTA GCTGTGCATA GGATTGAAGG AGGGAAGAAA GAGCCAGAAA GGTTGAATGG AAAACTGATT GAAGGGTTGG ATGGTGGTTG
47301 AGGAAATGGA AAGAGGAATG CTTGGGTGCA TGGATGGACT GAATGGAATG GAAGAGGGA CCCAGAGGGA TCATAACTTT ACTGAGAAGG AATAGACTGT AACTGATTGG
47401 ATACAGCAGA ACAGGTGAGG GGAACTGTAA TGTTTGAGCT TGGTGAGTA GCAAAGCAGT CCACACTGTG AAAGAAAGGG TGCTTATGAA ACCTTGTGTT
47501 AATCAAAAAA CACAAGAGGA AAATTCTTGC CTTTAAGTAA CTCACAGGCA AGTACGAGGA GACCACTGTG ATTAGAGATG CCAGGACAGA AGCATGTGGA
47601 GAGTCCAGGG AAGGGCTCAC AGGAAGGAGT GGTCCTCCAT TCTGGGGAAG CAGAGTTGAC TCAGGAAGAG GTTTATAAGA GATGCCCTTG AACTGAATGC
47701 TGAGGGACAG CTTATTTGAG TGTGTCATT GATGTGACTT GGAGGTGA AACAGAACAT CTAAGTGGAA GCATTCATTC GTTCCATTCA
47801 TTGTTACAGA GGGACTTCTG TGTGAGTCTG CCCTTGGGCA GGAATGAACA GATGAAGCAA CACCGTGGAG CTCGCCCC GAACTCCCCG TCCAGTGCGG
47901 GGAGGAACAT TCACTGTATC CTTCAAAGGT CTGTTTAGAC AACCATGTGC TGCGGGGGC ACTGGATCAC AGGAGTGAAC AGAACGGACC
48001 AGATTCCTCC TCTCACAGAG CCCATCTGCT AGTTAAGAAC TTCTCACCA ACAGCCACAA TTAACGCTAGC TAACAAAGCA CAGCTTGAAG GGGACTCCAA
48101 AGGATGCAAA GAAAAGGAGT GAATTCT CGCAGACCA GTCAGCACC CAGCAGTGTC AGGGTATGAG GGCCACCTGG TGAGTGGTTT CATTACCTC
48201 GCTTGGAGCC AGCGTCTGT TCGTAGGGCG CGGAGAATGA GTGAGAATGA GCTGGCTCTG AGGGATGAAG TCCAGTGTTG TATGTCCCCC CTGATTGTGA
48301 GATGAGAGGC TTGTTCCTTT GAGAAGCGAC CTTTGTCGCT GGCAGTGCG CAGGCGCTGG GTGTTTGTG CACCACGCGG GTGCACCACC
48401 ACCATGGAA AGTGTGTTCA TGACTCTGCC GTCCAATAC CCCTGGCACT GACACCAACG TCTGTCACAA GACCCAAGGC TCATGTCTG GTGACAGAGT
48501 GCTCTCTGGA GACTGGATCT TATGGCGATG ATGTAATCC CACCTCCCAT TTATAGGTTA AAGTCTTAAC CTCTGAACC TCAGAAGGTG GCTGTGTTTG
48601 AGATAGGTCT TTACAAGTA ATCAAACTAA AATGAAGTCA TTAGCTATGG TTTTTCCATC CATGTACGGA TGTGAGAGTT GGACTGGCTG AGCACTGAAG
48701 AATTGATGCC GGTCGCCCAC TGCTAGGGAA GCTCCTGAG AGTCCCTTGG ACAGCAAGAA GATCAAACCA AGGAAATCA ACCCTAAATA
48801 TTCATTGGAA GGATTCTGC TGACTCTGCA CTTTGTGGGT GTCCAATAC TTTGGCCACG TGAATGAAG AGTCGACTCA TTGGGAAAGA CCCTGATGCT GGGAAAGACT
48901 GAAGGCAGAA GGAGAGAGAA TGGCCCCTG CGACAGAGA TGAGATGGTT GGATGGCATC AGTCCAGCA ACCTAAGCGA AGTGAGCAG TCAGACTGAA GACAGAGAGT
49001 CAGGGAAGGC TGGGCCTCTG AAAGACGAAA GCTCGGCCCA GATGTCCTCA CAGCGAGATC CCAGTGAAG ATGAAGGCCAG AGTCGAGGAG TGATGCCACC TCAGACTGAA
49101 ATGTCCTTAT GGTCGCCAC AAACCAGTTT CTTCACCC GCCGCTGACT TGGAGGGAGC GTGAGCCCGA TGAAGCTCCT CAGCAGGTCT CACACCTTGA
49201 GAACATCAGA AGCTCTTGT ATCTTCACCC GCCGCTGACT TGGAGGGAGC GTGAGCCCGA TGAAGCTCCT CGTAGACTCA CACACCTTGA
49301 TTTCATTGGA GGATTCTGC TGACTCTGCA AAACCAGTTT ATGGCCCCTG CGCCCATACT GGAAATCGT GTTTCCTTG CAGGCTTGA CACAGAGAGT
49401 CAGGCTTTCA GGGAAGCTG GGGCGCCCTG GGGCCGTGA CCAACGTGAA ATGGCCCTTC CCATAT ACTG AGGGCCTTTC CCTTTCTCT CAGGCTTGA TTGTTATTT
49501 GAGTCTCAGT CAGAAGCTTT GCTCTGACTG AGCTCCTTCA GAGAATGTGT TGGCAGCTGT CCTTTAGGAT GACTGGTT GATCCTGCAG TCCAAGAGGC
49601 TTTGGGATT GTGCTGGTG CTCAAGATAC CAGTCGTATC AGCAAATGC TCTCCTGGAC AGTGGTAGA TCCAGTCAG TCCAAGTTAG CAAAGAAAA
49701 TCTCAAGAGT CTTCTCCAGT GCCTAACTAC AGCAGAACCT CAGGATTTC TCCGTTATGT AGCATTTAA TGAACTCAGA TCCAGTCCT GGCATGACTG
49801 AATTCATAC ATGCTTGTG CGCGCTGACT GCCCGTTCGG CTGCTGGGGC AGAGTTTTGA GGAGGTGTA AGGAAGTTAT ATTGGTTAAG AAGTCCTCT
49901 CCAGGAAATC ATTTCTAATC ATCTTCACCC ACCCATTGT AGAGTTTTGA CTCTGGGGAA GGCTTCCCTG CAGTTAGCA TCCAGGGAC TCTGCTGCA
50001 GGACAAAGTA TGGATCTGT ACCCCTGGGT TGGAAGATC GAGCCCACTC GAGCTATCT CAGTATCTT ACCTGGGAG GTAAATCTGC AGAGGAGTCT
50101 ACGGAGGAGA CCTGAGTCA AATCCATGGG GTCGGGAGA ACTGAGTGAG TAACACTCCA GCTCTGAGA GTTAATCTGC ACTAGCAGGA
50201 GGCAGCCTGC CATCCAGGG ATCCGCTCCC TGCCACCACC GTCGGAGATG TAACACTCACT GTTGCTCCCC AGGATGGTTC CCTGGCCTCC
50301 TCACAGCAGG GTCTTCCACC TGCTGGGAA TGCTGCCATG GAGAGGGAAG ACCTGCCAGG GCATCGAGTC GCATCATCTC CGCTCACTT TGGAAGCT
50401 CAGAAGCAGC CAAATGAACA TCATATCCAA GATTATGTCA CACCCTGGA TGCCTATAAA CCCTGCCAGG TGCCCAGC GGTGGCCATC ACCAGCAGA
50501 TTTTAAATTT GCATTCTATT GCTATTTGTT CTTCCAAATA CGTCTGTGAA CCGCGCCAGA GTTCAGCATC AGCTATGAAGC CGTTTACAG ATGGGCCTTC ACAAGGTCAA
50601 AGACTCTGTG TTAAATAAC CTTGTTGTT CTCCACAATA CGTCTGTCA CGCGCTGGGG TGCCCCTGC TCCTGGATAA AGGCTTCC TGGCAGCT GGAAGGTCAA
50701 TGCAGGATA AATATATTAG AGTCGTAAAG TGCCAGTAAA TGCTGTATAT GTGGCCCSC ACTCTAGTT CACACATGTCA TGGATGTGTT GGGAGATCT TGGAAGGAC
50801 TTTTGGGTCTG AATATATTAG AGTCGTAAAG AGAGTTTGCC CATGAGGTT CAGGGATTC TGTTCTATC ACTCTAGTT CACACATGT TGGCAGGTT AACACACGG
50901 AGCTTTGGAA ACCCAGAGGA AGACTTTGCC CAAGGGGTTGG CATGAGGTTC TCCAGGCAAG AATACTGGAG TCACATTG AACACACGG
51001 TGTAGCCCCT AGCTACAGG CACCCTCTATC TCCAGGATTC TGCAGGCAAG AATACTGCAG TCACATTG AACACACGG
51101 TTGAACCTGT GTCTCCTGCG TTGGCAGGTG GGTTTCTATCC AGGCGCCTCT ATCCACCAGGA TTCTCCAGCC AAGTACTACTG TTCCTTCTCC
51201 AGGGAGATC CCCTGGCCGG GAATTCGAACC GAGCTGGAGA ACTTTGCAT GCCAAATCA AGGAATACTG GTTCTGGGAG TCTGAAGTCT TTGAAGTCT
51301 AGGGGAAGC CAGGGAAGT ACCAAGTCG GAGATGAAGG GAGCCGCGCA AGGAAATCTCT AGGAAATCA AGGCTCGCAG GATTCTGAAG ACATCACCGG
51401 ACCTCAGAGT AGCAGCCCAC AGCAGGCCAC CAGGCGCCA AGGAGCCAT AGGCTGGCAT ATGCCCAGAGC CAAGACGGGC GGTGAACAGC
51501 ACGTCAGAGT GCAAGCGACAG ACCAGACTGACCAGGCCAC CAGGCGCCA AGGAGCCAT AGGCTGGCAT ATGCCCCAGAGC CAAGACGGGC GGTGAACAGC
```

```
56001 GACCCTACTT CCGCGAGTTC CTGGGGAGCC AGAGGTTCTG TCCTTCCAGC AGGCTTCTGG AAAGGCTGGT CCTCAGACTG TGCTCTGAGC AGCAAGGCG
56101 GGGATAGTCT TCAAGATCTT TGCACGCTCG ATATTCTACA CTTCCTTAAT TATTTCTCCG GCAGGGAGAG GGCAGGGAGT GAGTCAAAGA GACATTATTT
56201 TAATGGTGTA GTGGGAGTAA GTTCCCGTTC ATCACTGGAG CGAAATGATG TCTATGGGAA AATGTGACAG TATTTGGCCG GTAGGGTTCA GTTGTATCT
56301 GATTCAATA TTGAACTCGG TTTAATTAGG GAGAAAAAGG CCTGTCTATC CATCTGTATC TCCATGCGTG TTGGATGTG GTAGCCCGAT TGTGTGTG
56401 ATAGAGAGAG AGAGAAATAG AACTTGCATA CGTGACATGT TGTGTTCAGT CCTGTCTGAC CCTTTGCCAC CCCATGGACT GTAGCCCGAT TCTTTGCAGT
56501 CCCATAGACT GTAGCCGCC AGGCTCTCT GTCCATGGAG TCTTCCAAGT CAAGAATGCT GGAGCGGGTT GCCATTCCT TCTCCAGGAG ATCTTCCTGA
56601 CCAGGGATC GAACCACATC TCCTCTGTTT CCTGCATTGG AAGGTGGATT CTGTACCACT GAGCCATCCG GAAGGCCTGA GAAATACAGA GACAATGAAA
56701 GGGGCAATG AGTGAATGTA TGAGTGTTGC TAGGGTGAAT GTTCTGAATA AATGAATTTT AAGAGGGCAT GTGTAGCTTC TCCAGGCCA
56801 GTTGTGGTGA GGAGACTAGA GAAGAGGGC AGGTTTTATT CAGGTGGGAT TGAAGGTGGA CTAGAGCAGT CTAGAGGGCA GGAGACTCCA
56901 TCTCCTCAGC ACTGTCTCAT CCTAGGTCTT AGCAGCTCTT TGCTTAATTT ATTCCTGAAA TTCTAGAGAC AGCTTTGGGC TTATCAGAAC TTCCCATCAT
57001 TTGAACCTAG GAGTAGACGT GAGATTGTGC CTTTCTTGT CAGAAAATT CAGCTGGCTG CTTTCAAAAG GCTCTCTCCT TGTATCTCCC CAGCCCTTCA
57101 GCCTAACCAT GAGCCACGGA CACTAFCTTG AAATGTGAAG ACTTAGTCCA ATATAAATAT ATATTTTAAA GTGAAGGTCA GCCTTAGAGA
57201 TGTTGCCTGC ATTTTTGCCT TCTGCTTTTC CTCACTTGA TAGAAGTACG GATTCCTATA CATGAATGAA TTCCCCCCGG TTTAAATTA TATTTAATTC
57301 AGATTAAACA CTTCAGACTT TGTGATAGTG GTTCTGCCCA CATAATTIATG AGGATTTGTT TIGCTTTTAGC ACAGGTATCA TGCAGCCAG TATTTCTTGC
57401 TAGAATTCAC AATTCAGACT TCCTATTTC AGAGATTTCT CCAATTGTG GTTAAAGGGA GAAGAATGTT TITTGTGATAA AGATATTTTC
57501 CAGTCTTTAA AAAGGCAATT TATCTTCTC CGTGACATCA TTTTCATCCC CTCCCCTCA TAAGAAGGAT TCCTCATTAC CTCACTTTAC ACATCTGTCT
57601 AATGGGAGTA CCAGTTCTAC CCCTCGTCTT GTGCGATCA GCTGAGGTAA AGTCCTTGAC AGCAAGGCTA AGCATCAAG TATTAGTCAC ATCTATTCCT
57701 CCCCTTTCCT TTCCTCCAAT TCTTATTCT TCCTCTGCCT CAAATGCATT AGTCCCTGGC CTCCTTGGCA CTTTGATCAG TCGTTAGGTC ATTCAAGAAA
57801 CATTCTCCAA GCACTTATGA GACCGGCCTT GTCCAAGCA CCCAGAATGG AGCAGGCACA CTCCTCGT CCTCAAGGAG GACATAGAAG GAGGTGACCA
57901 GGATATTAAA TACAGAGAA TTACAGAGGC AATCATGGAT TATAAAGAAG GGGCACCTAA CTCAGCCTGG CTGAGGATGG AAGGAGGTGG CCCGGGTGTT
58001 TGGGAAGCC TTACAGAGAA GAATGATAAG TGAGAGTTAG TGGGAACTAG CGAACAGGGA AGTGAAAGAA CACCTGATTT CCGCAAACTG AAATAGTTC
58101 CCATGGTTCT TGTGGGGACC AAGGAATCAA CCTGAAGCT CCCTGAAGGT TAGGATTGAG TTTAGGGCT CCCCAGTGG CTCAGTGGTA AAGAATCTGC
58201 TGCCAATGC AGGAGACTGG GGTTCCATGC CTTGCTGCAC AAGATCCCT AGGATGGGA ATGCAACCC GCAGCCCAC ACTTCAGTAT TCTTCCGTGG GAAATCGAT
58301 CTGCTGCTGC CGCTCGCTGC AACCTGGCAA TCGCTCAGT CGTGTGCGAC TGTGTGCGAC CATGACTGAG TGCACACAGG GGCATATCCA ACTGAGTTTG TGTCCAGGC
58401 AAGAACACTG GAGTGGGTTG TCTCTGCCC CCATTTCCTT GTAATGCA GGAAAGTGAA AGTGAAGTCG CTCAGTCGTG AGGACCCCA TGGACTGCAG
58501 CCTCCCAGGC TCTCGTGCC ACCATCGA GTGTAGCTCC AAGGAGAGA GTATTGGAGT GGGGTGCCAT TATTATTGGC AGAATATCAG ACAAATAAGG
58601 ACTAGTATTC TTTACTCAA CCTGTGCTAA TAGTATTGGC CCTGACCTTC AAATGCCTT TAGAGTTTA GCCATTGGAC CTTAGGGGC CCAGGATTGA ACCTGGGAGA
58701 GGTTGCAGGA GGTTAGGCA AACTCATGC ATGTTATGTA GGTTAGAAA TCAATAGGTT TAGAGTTTTA GCAACCAGCA TGAAGTAGAA GTCCCAGRA TGCCTTGTTT TACTGAGGCT
58801 CAGGTTCCAA GCCATATTTC GCCTATTGGA GTACACTGA CTGTATACTG CGTGTCCACC CCCAGGAAA GCAGGCCAGA TATTTCCCT TGTTCCTAA CTTCAGTTGA TTCCTCAGG
58901 CTGCTGCTGC GTGAAATTGA AAATCAGTTC AAAACAGTTC AGAGTCGGTG CCTAGACTCA GCGAGAAAGT GCATCACGGA TTAGCAGTGC CCCTGCTGGT CTCACAGCAG
59001 AAGAACACTG GACTGGATTG CCAACGGCC TGTGCATTTG CCCTCCTTGT TGAAGGCTCT ATACAGAGTTA AAAGTAGTTG CTAGGGCCTT CCCTGGTGGT CCATCATTTA
59101 CTCCCCAGGC CAGGTGGCAC AGTGGCTAAG AACCCACCTG TGCCTAAAAG CAATGCAGGA AGCCACAGGA GCTGCAGGTT CCATATTTGG GGTCAAGAAG ATCCCCTGGG
59201 ACTAGTATTC GCTAGCAAGC CCAGTATTCT TGCCTGAAGA ATCCGATAAA CAAGATTGAG TGTGGGCGC CAGGGAGACG GGTCACATGA AGTTGCATA
59301 GACCGAAGCA ACTTACCATG CACACACCAT GCACACACAC ACATAGATAT TTACATGTAT ATGTACACAT ACATACACAC ATACTACAC ATACTTCATT
59401 GTAGTTTTCA TTAATAAGAA ACCTCATTAT AACAAAGAAT TTAAATGCT AGAGATATAG CTTAAAACAT CTAAAACAT TTCAGCCTGT TAAATAGTTT
59501 GGAAAGATAC TTTTAGGCT CATCAGTTG ATTTCCATTT AGAAAGGAA AGATTACAAA GTGTCACTTG ATTAACCCAT GTGCTCTGAG ACAGACATTT
59601 GTATTAATAA CTTGAAATTT TCATGTATTA GGAAGCTACT AGAGTCGGTG AGACGACTG CAATGGCACC CCACTCCAGT ACTCTTGCCT GGAATATCCC
60001 ATGGATGGAG CAGCCTGGTG TCCTCGGGTG GGCCTGGGTG CATGCGGGG CTGGAGTCG GACAGGAGGA GACACGACTG AGCGAGTTCA CTTCACTTT GGATTCACAG
60101 AGGAAATGGC AACCCACTCC AGTGTTCTTG CCTGGGCAAT GTGGGTTGCC GTGGGTTGCC GTGGGTTGCC AGCGAGCCTG TCGCACAGAG TCGGACACGA
```

```
1.21301  AAATATAGCA  GAGGCTTTTT  ATAAAATCTT  ACCCTCTCTTG  TACCACAGAT  GTATTCTTAA  GCATTTCAAG  GTGATTAAAT  TTTGTAAGCA  AATAATGACA
1.21401  GACTTTCAAG  GCATACAGAG  AGTTTTTATT  GAAAGAAACA  CTTGGTAAAG  TTGAGGGTAT  TTTTTGCAAAC  AAATAGCCAC  CAGATTTTA   CCGATACATG
1.21501  TGAATTGGC   TCCACACCTC  TATTGAAAGA  TATTTTAAGA  TGAATATTAA  AATGAATACC  TCTATTTTTA  GATGAATTTC  ACATGCAGTT  CTGTCCATTT
1.21601  GGAAATCTGTC TTGAAACATA  TTTTCAAGCT  AAATGTTTCT  TTCTCCCTTC  TTTCACACC   TAAGATGTTT  AAAAGTGCAG  AGACAGGGCA  TCTTAAGAGT
1.21701  ATTCTGTCCC  TACCCCTCTCT TCACCTCTCT  CCCCACCTCC  ACTCCGCCCC  GCCAGTCTTT  TCTGAAACCA  CAAAAGTTTG  AAGCTGAGGG  ACATTAAAAA
1.21801  CTAAGTCCTA  TACCCCTTTCT AACAACTGAA  AAGTGCTGAG  TCCGTCAGTT  CCGTCCGACT  GTGTCCAACC  TCTTGCAACC  CTGTGGATGG  GGCTCCTCTG
1.21901  TCCATGGGGA  TCTCGAAGGC  AAGAGCACTG  GGGTGGGGTG  CCATGTCCTC  CAACACTGGA  AAAATGAAGG  GCCAAATATC  ATACTTATTT  TTGTTTATTT
1.22001  TTTCCACATT  TTCTCCAAAA  AATGCTGGTG  GGCGTTGAAG  GAGACTGTGT  CATGGTGCAA  GTCCCTTACA  AGCCTTTTCT  CTCTGTACCT  GCCACCAAGC
1.22101  GTTGGGGGG   AGCCACCAGG  TTGTCACCGC  TCATTCTTCA  TTCCACTCGT  TTCCACTAAA  ACGCTTTTCT  GTTGCTGTT   TCTAGGTTTC  CCAACCCACT
1.22201  GATTATTTTG  CATCGTGTGT  GATTTCTCTC  CCCTCAATGA  TCATTTGCAT  TTTGCCTAAA  TCAAATCTCA  TTGTGATAAT  TTCTCTTCCT  ATTTCTAACC
1.22301  TCTTTAGAGTC CATTCTGTGTT ATTTCTCTGTT CCCTCAATGA  TGTCTGCAGC  ACCCCCTAAT  TTGGCACCCA  CCAAAAATGT  TATTAAATGT  GTACGCTTG
1.22401  TTCCTAGTCA  TTAATGTCGTT CTGTAAATAA  AGCTAGAGCT  AACAGCTAGT  CCTTTAGCTG  CATCCCCCAC  AGAGCTCTTG  CCGATCCCCA  TCACAGGAAT
1.22501  GCTGTTTTC   ATCTCGTT    CTTGTTTTTAT TATGCTTTAT  TAAGCTCCAG  AGTTACAATA  CTTTCAATC   ATACTCTTCT  AGTGCCAAAC  AAATTTATAG
1.22601  GTTTCAAGGA  TGCTGGTTTTA TATGCTTTAT  TTTTCGCCTT  TTTTCAAGG   CAAACACATT  TGATTACCCT  TTATCTCTC   CTATTTATTC  TTTAGAGCTT
1.22701  TTTCATATGC  CGGAGGAAAT  TTTTCCAGTT  AATTCTCTTT  GAATTTAAAG  GTGCATAAAC  CATTATGCGC  TGGTGAAGAA  CACAGGCTAT  TGGCCTTGTT
1.22801  TTTATGTAAA  TCTGCTAGTT  AATTCTCTTT  CTAGAGCAGG  GAATTTAAAG  GTGCATAAAC  ATCCAGATGA  ATCCAGACTCT AATTGCTTGA  AAGCTGCAAA
1.22901  CATGAGAAAC  TTATGATCTG  CTAGAGCAGG  CTAGATTCAT  GTATAATGAA  GAAGGACTCT  CAGAAGGAAA  TTTTTGAGCT  GAAAACTCAA  AAGGTGAAAA
1.23001  CTGACTCTTA  GGGGTGCAAA  AATAGAAGTA  TGGGTTAGGG  TATTAGGATA  ATTTGAGCAA  CAAGGGCACC  ACTCTTTGCCT GGAAAATCCC  ATGGACAGAG
1.23101  GGATTTGCAT  TGGCAAGGAA  GAAGGGGAAG  AATGGAAAC   ATTTGAGCAA  GACACGACTG  ATCGACTTCA  TCACTTTCAT  GCATTGGAGA  AGGAAATGGC
1.23201  GAGCCTGGTG  GGCTGGTCTC  CATGGGGTTG  CCAAGAGTCG  CGAAGAGTG   GTGGCCTGTGG TCACACAGG   TCAGCAAGG   TGAGGACGAG  TTGAAGCAAC
1.23301  AACCCACTVG  AGTCTTCTTG  TCTGGAGAAG  CGAAGAACCG  ACTTCTCAG   GGTAAAGAAC  CTAACTTTCA  AAGGAGAGAT  TAAGAGAGGT  AGATTTGATC
1.23401  CTAGCAGCAG  CAGACGAAGG  AGAGAGAAGG  ACTTCTCAG   TGGCTGCTAG  TGTGGGAGAT  CTGGGTTCAA  TCTCTGGGTT  GGAAGATCC   CCTGGAGAAG
1.23501  CCTGGGTTGG  GCTTCTCTTG  TGGCTCCAGT  ATTCTGGCCT  GGAGAATATC  ATGGGCCTCT  CCATGGGAAT  CTGGACAACT  GAGAGACTTT  CACTTCACTC
1.23601  GAAAGGTAC   CCAGTCCAGT  ATTCTGGCCT  GGAGAATATC  ATGGGCCTCT  ATGGGCCTGT  GAAAAGAGTC  AGGCACAGAG  GACTCAGGAG  TGCTGACCAT
1.23701  ACTTGGGAA   GATCCCTGG   AGCAGAAGTG  GACAGAAGTG  ACCTAGCACA  TCTAGTATTT  TTGGCTGGAA  AACTTCACG   AATGATTGTA  ACATACTGCA
1.23801  AGCCTGGTCT  AGTGCTGACAT GATCGACAT   AAAACTGGCG  TGGCCATG    CAGATGTACG  TGGCCATGA   ACATACTGTA  TGGCGTCCT   GAGTAGTAGA
1.23901  ACATGGCTCT  GATTGCCTTT  GAATCAAAGT  TCATCCCTCA  CCAATATTTT  TCCTGTCCCC  GAATCCCACT  CTCTCCTAGT  CACCAGATGT  GTCTGAGGCA
1.24001  TCTTAAAACC  AGTGTGCCTT  AGTCCCCAA   TCATCCCTCA  CCAATATTTT  CCCCATATTT  TAGCCCATCT  TGTATCTGC   AGAAATCTGG  ATGTCTTTCCA
1.24101  TCATTTCTCT  AGTCCGGAC   TACCTGCAAA  ACCAAAGAAAG AATATTTGAA  CGTGTCTTCC  CCTCCAGCA   GTCCCTTGA   TTGTATCTGC  TTTTCAC
1.24201  TCTCTAGTCT  TAGCCTGGAC  ACTCCTCTCAC AAGAAAAGAA  AATATTTTGAA TGACTCAGG   GAGAGACTCA  GAGTGAAATC  AGCCACACAG  AACTTACTGA
1.24301  AAATGGAAACC ACTCCTTCAC  AAGAAAAGAA  ACCAGTGCCT  TTCCACGA    GAGATGTGCA  GAGAGACTCA  AGTGAAATC   TCATGACATA  GATAGCCTGG
1.24401  TATGGTCAG   CTATTACATA  CCAGTGCTT   CTAGTCTAAA  CCTGGTTTT   CTAGACAGTC  CCTTGACAGTC CAAGGGATC   ACTCATTGA   ATGCTGGAA
1.24501  AAAGACACCA  CTTTGCTGGC  AAAGGTCCGT  TTGTAGTCGT  CGAGAAGACT  CTTGACAGTC  CCTTGACAGT  AGAGACTG    GCAAACCTTG  ATGCTGGAA
1.24601  AAAGAGTTGA  TGCTTTTGAA  TTGTAGTCGT  GATGGGAGG   AATACTTTGG  AATACTTTGG  CCATCTGATG  GAAAGAGCTG  GCAAACCTTG  ATGCTGGAA
1.24701  TCTAGCTCT   TGGAAGGACT  GATGGGAGG   AGCGGGAGCA  GAGGATGGAT  TGGTGGATG   GCATCAACCGT CTCAAGCCTG  GCAAGATGA   GTCCCTACT
1.24801  AGATTGAGAG  AGCGGGAGGA  AGCGGGGACA  AATATTTGAA  TGTGGCAGCA  GACACGACTT  AGTAACTTAT  TCAAAAAACA  ATGCAAGGGA  AAGCCTCTC
1.24901  AAGGACAGGG  AAGCCTGATG  TACTGAAGTC  ACAAGCAGGA  CAAAGGGTCA  GACACGACTT  AGTAACTTAT  GGAGTTCCA   CAATCCCCTC  AGTTTAATAA
1.25001  GTATGGCCAC  CCCTACTTCA  TATGCCAGGC  TTACTCTTAC  AGTTTTATA   TAAAGGTAC   AAATCAGAAC  CTTTGCCTGC  CTATCTGTGG  GTTCACCAGC
1.25101  TTTCTAGAA   CACTCACAG   ACTCAGAA    AGCGCTATAC  TTACTCTTAC  TCGCCTTCC   TCACAAGCTC  AGGCGCTCA   CATGTTACCA  AGCTCGATCT
1.25201  ACAGTGGAGA  CTCTGGAGG   ATTCATCATG  CAGCATCATG  TCCCCATCC   AGCTTTTAT   TACAAAGGCT  GGGTGATTA   AATCTGGAA   GATAGCCTGG
1.25301  CAGGAGTTTC  CTCGAACCT   CTCTGAACAC  AGCGGGGAGA  AGCTTTTACT  GGAGTTTCAT  GGGATTGTAA  AATCCTTGC   CATGTTACCA  AGCTGATCT
1.25401  AATGGAAACC  ACTCCTCCCA  TCTCCTCCA   AAGTCCAGCC  AACTCCAGCC  AGCTCGACTT  CTTTCGGGTG  ACCAGCCCCA  ATCCTGAAGC  TATGCAGTGG
1.25501  CCAGTCCCT   GTCATCTAAT  AATTCTCTCA  AAGTCACTTC  AAGTCACTTC  AATCATGCAT  TATGATTCAG  ACATAAAAGA  ATGCAAGGGA  AAGCCCCTCC
1.25601  TTGTATCACA  ATACTTCTCA  GATCCCCATCT AATTCTCTCA  TACACCACCTCT TTGCACCACTTC GAAATTCCAA  CCCACGAGAC  AGCTCTCGC   TCTCTTAACT  CCTGGACTGT  TATATCTTTA  GCCAACTCCT
```

Fig. 5CC

```
125701  TTCCTCTCCC  TGAGACAATT  CCTTCTCTCC  TATTTCAGTC  CTGCTCTACC  TCCCCCAGCC  TTAAGAATATA  TGTCCAGTAC  AATGGACATG  AACTTGGGCA
125801  AACTTTGGGA  GATGGTGAGG  GACAGGGAGG  CCTGGCAAGC  TGCAGTCCAT  GGGGTCGCAA  AGAGTCGGAC  ACCACTGGGC  GACTGAACAA  CAACAACAAG
125901  ATTATCTGAT  TAGAAAGCCT  TTGCCTGTCT  CAATGTCATC  CTTTTATCTC  TCCATACTTA  TCTGCTTCAT  GGGACTAATT  CCAATCTGAA  ATGATTCAT
126001  TTATGTTTAT  GCCTCCATAA  AATGTAAACA  GCCTTGATTG  TCTTGTCCT  TCTTTATCTT  CTAGCACATA  GGGACTACTT  CCAACATTCA  GTAAATATTT  ATCAACTAA
126101  AGCAAGTGGG  AAAGTGGGAA  AGATAATAAT  CAGGCTATTT  GAAGCTATTC  GATTGCTAAG  AAGAAGTCTT  TAGGCTTGAT  GAGAAAAGTG  ATATGGTGAA
126201  GTTGTCAGAT  CACAAGCAAG  GGCCCTTCCA  AGAATGATAG  CAGGCCTATT  GAATGAGTA  TGTGAAGTCT  GATCACAGTT  TATCAATTGT  ATTGTGGAAG  GGAAAGGACT
126301  AGAGGCAGGG  GGCCCTTCCA  GGAGCTGAGG  GAAGTCGAAC  AGAGTCGGAA  GAAGTCGGAA  CAAGGGTGGT  GGAGTACCAAC  TGGAGTCAAC  GGGAAAACT  GAGGTTTTTA
126401  AGAAAGATGC  CCTTGACATT  TTTTTCTTTT  AGGTTTAACT  GTTTATTTTG  AAATAATTTC  AAACTGACAA  AAAAGTTGCA  AAAACATTAT  GAAGGACTCC
126501  TGTGTACCTG  TCACTCATTG  TTAARATGTT  CAACTCATG  CCTCTTCATC  CTTTATTATT  CTCTTCTTT  GTGTGTAGAG  TATGCATTCT  TTTGTGTAT
126601  TTTTTCATGA  ATCCTTTGCA  AATAAGCTAT  AATGTTGATA  CAGTACTGTA  CCTCAGGTCC  CCTAAACACT  TTAGTGTGCA  TTTCCTAATG  GGAAAGACAA  TTCACAGTGA
126701  CACAATGCTT  GTACCAACGC  CAGGGAATT  AATGTTGATA  CAGTACTGTG  TGGTCTTTGA  CAGTACTGTA  ACCAGCTCAA  GATCCTGCAT  AACAGTGAGT
126801  TGACCTGTCC  CTTTASTCCT  TTTTATTGG  AATAGTTCCT  TGGTCTTTGA  AGTAGACAT  TTTTGAAGTA  TGCATGCCAA  TTATTTTGCA  CAATACTCCT
126901  CATTTTGGT  TTGCTCAAGT  ATCACTTGT  CATATTATTC  ATGGATGAA  CTTCACTCAG  ATGGGCACT  ATGCTCAAGG  ATGCTACATT  AATGATCTTG  TGTCCTAGCA  TTACTATGTT
127001  GGCCATGAT  ATCACTTGT  CTTTASTCCT  TTCTCATAA  CATATTATTC  ATGGATGAA  CTTCACTCAG  TAGCTAAGG  TAGTGTCCAC  CAAGGTAAGA  TTTTAGCACA
127101  TCCATTGGTA  ATTAATGTGT  AATTTATGCT  GAGATCTGTT  GAGCGAATCG  CATAAATCGC  AATATGTTT  TTATTTTAAT  CAACCTTTTG  ATTTTAGTAA  TTTTAGCACA
127201  CATGGTGAG  TCTTGCTGA  TATTTATTGT  GGGTTCATGG  GCCAAGACAC  CTGCAAAATG  GTCATTTTTC  TAGCTCCATT  CAATTTTCTA  CATTTGTGG  TTGACATTTT
127301  ACTTCTTAAT  TATTTATTGT  GGGTTCATGG  GCTCCTGGT  TATTAATCCA  TCCCGTTAG  TGTTCATTCTT  AACACACCCA  CATTATTCAT  CAGAGTACCC
127401  CAGTGTGTTC  AATGGGAGCA  CTCCAGATGG  GCTCCTGGT  CCTTTTGACA  GGTCCCCATC  GTATTTTGGA  GCAATTCCTT  ACTTCTCCT  GTAACAAAT
127501  ATACCAAGTT  CCTCTGCTGC  TTTCCTGCC  TTCCTGCC  CACCAGCCAT  TACACTGAAG  AGTTCTGATT  CCTTTGCAGT  GGGAAATGTA  TTTAAAACC
127601  GAGATCTGGG  AGTGAGCTGT  ATCTGTGGTG  ACTGAGCTGT  CCAAAATCGC  CATTGTTTC  CTTTCCCTGA  GTTTTGACTC  ATTGASTGAG  AGAGATCTAG
127701  GTTAGGAGAC  TAAACAGTGG  TCACCTCACA  CACCAAAATC  CAGGCTCTC  CAAACTGAA  AGATTCACAG  AAGGCAAACG  AGTGAACCAA  GGTGCTGTG
127801  CTAAGTCTGA  CTCTTTGCGA  CCGCATGGAC  TGTAGCCCAC  CAGGCCCAC  TGTCCATGCC  CCTTTATGTT  ATTCTCTAGC  CAAGAATCCT  GGAGTGGGTT  TCCATGCCCC
127901  CCTCCAGGG  ATCTTCCCAA  CCCAGGGATG  CAACCCAGT  CCTTATTTTT  GCCTTTATGG  CAGGCGAGTT  CTTTACCATT  GAGTACCCAG  ACAAGTTAC
128001  CAGAGGACTA  CCCCAAGCCA  TCTTAAAAAT  GTGTCTTAAA  AATATCTTAC  ACAAATATAT  TCTTTGTCTA  AGAATTTAAG  TAGTGGAGGA  ATAAAAGAAA
128101  ACATGACTCA  CCCCTCCAGT  CTTTACGTTT  TGTCAGCAAA  CACTTTTTAA  ATGCTAAAAC  ATGTAAAAC  TGGTTTTTCA  ATGTTCACCG  GTTCCGAAA  CTTCCCACCG
128201  CCCAGACTGG  GGTGGGACT  TGTTCTGCG  AAGCTGCCAT  TACTGACCTG  GTATCAACTG  TTGCCAGTG  ACGCCAGGCC  TTCTTGGGGA  CCTTCTTACA
128301  GATTGTCAGT  GTTAACTGGA  GGGAAATCAA  TACTGACCTG  GGACACAGAG  ATAAAGTCTG  TTTCGAATGA  ACCGAACCTC  CTTCACTGTT  TGAATAGCGC  AGTGTTGTCA
128401  TCTGAACTGG  GGGAGATGAG  ATTCAGACTT  TTTCTCAGAC  AGGATGCCGT  TACTCACAAA  AGTCTCACAT  CCCTGAAGAG  TGGGCGCCAC  AGCCGTCTTT  AACTTGCCAG
128501  CTGTGTTCA  CCCCTTGATA  AAATGACTCC  CCTGGTTCT  CAGAAGTGTA  CGAAGGTGTA  TTACGAACAA  AGCTCACAT  TACCTGGGG  TGTGTTTTGA
128601  TCAAACTGG  ACATGTTGCC  TTTTGTTTT  CCTGGTTCT  TGTAGCAGC  TGCACAATTG  GTCTCAGCAG  TGGACAGCC  AAGTGGAAT  TACCTGGGG  GCAAGCATCT
128701  GACCACCTGG  TAGAGCTTT  CCCTAGGCGG  AAAGCCAGCC  AGTCGATGCA  GTCTCAGCAG  CCACCTGAAG  TGGACAGCC  ACACGGGTGT  CTGGTCAAAA  GCAAGCATCT
128801  GTTTGCAGTA  CCCTCAGTGG  AATGGATACG  TGTATATGTA  TGGCTAAGTC  CCTTTGCTGT  GGGACAAGCC  GTTCATGCAC  GTCGGCCGCC  GGATGGCGGG  GGTGCTGCAG
128901  TTTGGGGAG  AAAAATGATTC  TGGTCTTGA  TCTGTTGACT  ATTTAGAGAG  TTAGACTGAA  CAGTCTGTT  GTTCATCGC  GTCACTCCA  TACAAATGA
129001  AAAGTTAAAA  AAAAATGATTC  CCCTAGTGCC  ATTTAGAGAG  TTAGACTCCA  AAGCTCCTCGG  CACTCTCGC  AGGAGATTGG  TAACCAGAGA  CAAATGAGGT
129101  GGGGCCACTT  CTAGGGAGAA  TCTCTTTTCTA  GCTTATCTC  TTGATTACTC  AAGTCCCGA  TTGATTACTC  CGTCTAAATA  CATATTTTA  AAAGTTAAAA  GTTCTGATTC
129201  AGCAAGTTCT  TCCTAATCTG  CTTCAGTAGA  GTCTCAGCAG  TTGATTACTC  AAGCACGGA  TTGATTACTC  AGGAGATTGG  CATATTTTTA  TCAAGATC  TATCACATAC
129301  TTGATCACAG  GATCAATTTC  CATTTCTACA  GTCCCTGTAC  GGACCCGGTT  GGACCCGGTT  AGGGACATTA  AGTGACGTGA  TCTATGATGG  TAGCAAGTAA  GGACCCAGGG
129401  TGGTTTTCAG  CGAGGCACT  AATGGATACG  TTGAGTTGGG  ATAGGTTGAT  CAGTGCTCAT  AAGAATAGAG  ATCAAAGAAG  CGTGGTATAA  ACATGCATCA
129501  CTGACTGCCT  TGTTACCTCT  GTATTATTGC  CTCATCATTT  TTTCTACATT  TTCTAACA  AAAATGTAGA  GGCAGAAGCT  GATTGTTTG  ATTCAGGCAT  GTCATCCACT
129601  AAAAATACTT  TGTTACCCTC  ATATTACACG  ATTATTTTA  GATTATTTA  AAAATGTACA  AAAATACAACA  AAATACAACA  AAAGTTAAAA  GTCATCCACT
129701  GCCCACTTT  CTAGGGAGAA  CTAGGAGAA  CAGCTATAAA  TAGATGACA  TATACTTCTA  TGTTTCTCA  GCTTAAAT  CATATTTTTA  TCAAGATC  ATTCATTCCT
129801  GCGTTCACGC  ACATGTTGCC  TCTTTGTGT  CTGACTCTT  GCGACCCTAT  GGACTGCAGC  CCACCGTCAGC  TCTCGTCCA  TGGGATTCTC  TAGCAAGAA  CACTGGAGTG
129901  GCGCACCATT  CCCTCCTGCA  CCAATCAGT  GGGGATCTC  GCCATTCATCA  GGCAAAACC  GTCACCGGG  TCTCCTGC  CATCCCTGC  GGATTCTTA  CTGTGAGCC
130001  ACCAGGGAAG  CCCAATACAG  GCATTCATCA  GCATTCATCA  CTCTCATCAG  TACTTTTCCA  TACTTTTCCT  TACTTTCCT  CTCACCCTC  CATGCAATA  CTGCAGTATC
```

```
177201  AGATCCCAGT CTGAGGGCAG GAGAAGATGA AATAGACATT CAATGAGTGT GTCTGGAAAA CAGGGGGCAA TTCCTCCTCC AAGGCTTGAA GGGAATGAAA
177301  GAAAGTGAAT TCGCTCAGTC ATGTCCAGCA TGCATCCGAC TTTTTCAACC TCATGGACTG TAGCCTACCA AGCTCCTCTG CCCTGGGATT TTCCAGGCAA TAATACTGGA
177401  GTGGATTGCC ATTTCCTTCT TAAGGGACTG GCTGGATGCA ACTCACATGG AGGAGGACCA TCTACTTTAC TGACTCCATT GCTTCAAATG CTAATCTCAT
177501  CCAGAAACAC CTTCACAGAC ACCCAGAAAT AAGGGTTAAT CTGCGCACTC CATCCATCCT TGGGGAGTGG TAGCTTAACA GGTTTCTTTT ACCATCACAG AGGAAGAAAG
177601  TAGGACTGGA AGGATGGGGG GATGGATGGG GCTCAACATC CTGAGAGCCA TTAACTTGGA TACTTTAAAT GGGTGAATTG TAGGTAGTGA AAACGTTGTA AAGATCGTTG
177701  TGGGGATGCC TGCACAACTC TGCAAATATA TGCTGAAAAC ACCCGGGGG TCACTTACTT ATGGGCAGTA AGGGAGGAAA AGTTACTCAC TGCCAAGGGA AGAGTAATAT
177801  TGACAAAAAT GAAAAAAGAT GTGAGACTCC TCCTGAAAAC ACCCGGGGGG TCACTTACTT ATGGGCAGTA AGGGAGGAAA AGTTACTCAC TGCCAAGGGA AGAGTAATAT
177901  ATAGGAAGAT TTTGGATATT TAAAGATCCA ACTCCTTAAT TCACTTACTT ATGGGCAGTA AGGGAGGAAA AGTTACTCAC TGCCAAGGGA AGAGTAATAT
178001  TTTAATCCCT TCACTGACCA GAGGCTATTT TTCTTTCGTC AACATACATC AAAATGACTA TCTCTTATCA TCTCTTCCGA GCTTTGCCT ATCATTTGTC
178101  CTCTAAAGTC ATGGGAGCAT GTCACCAGTT CATGGGAAAA TTCATCTTGA GACTTTATGC TGATAACTTT ATTGTTATTT TTCTGTTCCT ATCATTTGTC
178201  TAGCCAATTC AGTGAATGCT GCCTAAGGGC AGACGGCAAG TACAGTAAGT CCCCTACATA CGAACACGTT CGATTCTGAG ACCAAGTTCG GAAGTCCGT
178301  TTGTTCAGAA ATCCAACAAA GTTAGCCTAG GTAGCCCATCT AACACAATTG GCTATATAAT ACTGACTGT AATAGGTCTC TAATACTTTT CACAGATA
178401  ATACATACAT AAAAAGCAAA CAAAAAAATAA ACCATCTCTA ATCTTACAGT CCAGTACCTT GAAATGCATG CACAGTACAA CCAGTACAAA ACAACACGTC
178501  TTTGCAGGTT TGTACATAGG GGACTTTCTG TAAGTTTTTT GTACCCCATG GAGCCTAACA CAGGGTCTTG CAATCTCGTG GCATTTCAAA GCTCTGCAGA
                                                                                                          Exon_5
178601  GAGGTGCCGA TAGTGTTATT TCAAGCCTTC TTTGTCTTCC AGGTGAAGGT TTCCATAACT ACCATCACAC CTTTCCCTTT GACTACTCTG CGAGTGAATT
                                                         Exon_5
178701  TGGCTTAAAT TTCAACCCAA CCACCTGGTT CATTGACTTC ATGTGACTTGGC TGGGGCTAGC CACTGACCGC AAACGGGCAA CCAAGCAGAT GATCGAAGCC
                                                         Exon_5
178801  CGGAAAGCCC GGACTCGAGA CGGCAGCGCC TGACTCTGGA TCCTCCATCT GCGCCCGCTG TCAACGACGC CTCGTTCAT GGCCTTTGTT ACTACACTTC
                                                         Exon_5
178901  TCTTGTTCAT TGGATCGTGG GAGGGGGCGC AAGCTGGGGA GAGAACAGAA TCCACGCAGT TTGGGGGTTT TTTCGTTGG TCTCAAAATA ATGTCAAGAT
                                                         Exon_5
179001  ACAAACTATC AATGAAAAGA ATTTTTAAA AGTCAGTGTA ACTATGCTTT AACACTAGAA CGCGGACATG TGATTAATC TCTGTAGCTA CAACATGTCA
                                                         Exon_5
179101  TTCAAACATA CATCGTCATG TGCTGGTACT TGTACGTGAT GTTAACCCTG ACAGGATGAA GGAATTTCAT ATTCTTTCAG TGTGATTCAG GAGAGCCTTT
                                                         Exon_5
179201  GTTTTCTGTT TTAAACCCAA CCTTATTTTT AAACAGACTA TCTGAAGGAG CAGAGAGGCA GGGTGGAAGA CAAAAGAGAG TCTAAGTAGT AAGGAAAGAA
                                                         Exon_5
179301  TGTTTCTGCT TTGTAAATTAT TGTGCTGTGTG TGTTGTGTT TTAAGTAAG AAAATTGAAA ATGTTAAAAA ATGAGAATAC AGGAAATGGC TCTCTTATTT
                                                         Exon_5
        SNP_179412
        ~
179401  TTTTGCCCTG TTTCCAGCTT GTTAATGTTC CGCTTTTCTT GCTTCAAGGG GTCTGTTCAC TGCTCAGCTA GTTTGTGTC CTGAGCTGTC CGTCCAGCTG
```

Fig. 5PP

```
                                                Exon_5
179501  ACCCTATAAT CAGTGCCTGT TTTAAGTGTT TGATTTTGTT CTCTTTGCTA TTGTCGTTTT AAGGTGTAGA ACTCAGAAGT GCCAGACATC AAGTGAAGCT
                                                       Exon_5
179601  CAAAGGAAGC TCTCATTTCA ATGTTTAGAC ACCTAATTTA TATTCTAATT GATCCTTAGCC ACTGTGTGCAT ACTGGTGCAT GTACTTTACC TACTCCTGCT AAATAAGCAT
                                                         Exon_5
179701  ATTAATTTTC CACACCAGT CATCAGATCT GAATAACCAA CAGTTATCTA GAACTCAGTG TCTACAAATG TTTCACCTGC ATGCGGCCTT CATTGATTTT
                                       Exon_5
179801  GCAGCAAGAC ATAAAGTGAT CATTATGTAG CCTCTGGATT TTAAAAAAAT CTGTGTGTTA AGTTGCCTTG TAAAGAGCAT GTCGATTAA TGGGACAGCG
                                                Exon_5
179901  TGCCCTTTGT GTTAGATGTT AGAGCAAAAG AGAGCCTTAT AGTTTGGCAT CAGAGCACTT CGAAGATAGT GCTGCAAAGA TAGGAAGAG TAGGATTTAA
                                   Exon_5
180001  TTTTACATTT TTGAAAGAAG TGACGCCCGT AGGAAATGTC ATAATAAAGT TCTTCATCCA GCAGGTGTTT AACGGTGTTA TTTTGCCATT AATATGTGTA
             Exon_5
180101  AACTATGAGT GATCACACAATA AATGATTATG AATTCGTTGG TGTTCCTGAC TGATACTTAA ACCCAGTTTG AATGTCCCTC AAGGGTGCCT TATGCTTTGT
180201  GATGACCACA TAATGCACAT TTGATTTGGG CTCTGGGCTA ACAACAGCCC CTAAGATGGG ACCTCCCTA TCCCATCAGT CTTACGCATA ACCAGAGGGA
180301  AAATCAGCAG GTTTTATTTG GACTGTAGAG CAGCAGTCCC CAACCTTTGG CACCGGGGAC TGGTTTTGTG AAAGACGTT TTTTCACAGA CTTGGGGGGG
180401  GGGTGTGTTT TGGGGGGGT GCTTTCGGAA TGATTCAAAT GCATTACAAT TATTGTGCAC TTTATTGCAT CAGCTCTACC TCAGGTCATC AGGCATTAGA
180501  TCCCGAGTTT GGGGACCCCT GCTGCCCAG TGGTCTCACT TCTCACTCAG CAACACCTCT GCTTGTACTG CTTCGAGCTG ACACGTGGAA ACCCAACTCC
180601  TACATGTCAT CAAAACATCA TGAAGCATCC ACTCTCTGC CTTCCTCCCC ACAGCCCTGC GTGGGGC AGATGGACTC AACTCTCACT CCAGCCTGC CTCTCAGCTC
180701  TGCCCCATGC CATGCTCCTC ACTCTCTGCC CATCTTTTGC CCCAAAGCAG TGCCCTGGCC CCCAAAGCAG ACGACTCTA AAGTCCTGTC AAGTCCTAG CCTGCCTGCA GTTGAGTGGG
180801  AGGCCAGCTC TCGGTGGGGG CCAGACTGGA TTTCATTCCT AAGCCAAGAC GAATCTATAT AGGCACTGAA GTTCAGCTGC TTTGTACCCT AAAGATATGT TGCTAAGACC
180901  TTGAATGCAG TGTTGGTAGA ATGTAGATAT AGTCCAAGAC GAATCTATAT CTGATTGGCC ATATTTCTGT GAACTTTTGA
181001  CCCCTCAAAG TACTAAACTT ATTTGCTTGT CTATTAATAG AAAAGATTAC ACTTGGAATC TTTGTAATCT TCTCACAAAA GGAAGCTGTT TCACAGCTAA
181101  TCCAAGTAAA TCCAGAACCT CTGGATTTAC ACTC
```

Fig. 5QQ

Bovine SRPR Gene

| | | | | | | | | |
|---|---|---|---|---|---|---|---|---|
| 1 | CAAGGCTGAT | CTCAGTTCCC | AGCCGTTCCA | TGTATGCTCA | CCAACACTAC | CTACTGGCAG | TGCAGGACAT | CGTCCTAGTT | GGCTTCTCTT | CAGTTTTCAA |
| 101 | CTGGTCTACG | AAGCCTTCCC | TCTCCAGCTA | CACCTCAGAC | ACCTCCAGGA | CGTGTATCGA | ATCCTCCTC | TTCTTTCCTC | CTCACGGCCA | CAAAACAGCA |
| 201 | TCCTGCGTGC | AAGCACGACT | TCATTAATTT | CGTTGCAACC | AAAGAATCAG | CCCGGCTGCA | ATTTTGGTGG | CAAACTCAGG | CACAGAATCA | TCTGGGATAT |
| 301 | GTCACCTGAG | AAAGGCAACT | CTGGGATCCA | TACCCCTGTC | CAGGGCTCTAC | AAGCTCCGGC | AGGCAAGGTT | ACCCCTACT | CCGAGGGACC | CACTGTCTTC |
| 401 | CCAGGGCCTC | CTTGGATTCT | GAGTCCTGAA | GGTCACAAGG | CTGGAGACTG | GGGACACCGA | CGAACCACGA | TACCCTCCGC | TGCCCTCAAC | TTTACCCAGA |
| 501 | GTAGAGCCTC | TTCTGTATGT | GCCTAGCCCC | CGTCCGGAGA | GGCACGGGCC | CAGGCGGAGC | CGCAGCGCCC | TCCGAAGCAT | GGCCCTGCTG | TTCCTGGCCG |
| 601 | CTACCAGACC | ACCACCTGGC | CCCCCCCCCC | TCCCAGCCTG | CAGTCACTAC | TACGCCACCC | CAGTCCTTCA | TTCGACCACT | CCCATTGCCA | CCCACCCCAC |
| 701 | GGGGTCCTGC | CTCGGCCCCC | AGCACCATAGG | CGGTCGGTCC | CTCCCAGAGC | ATGCTGAGAG | GCCGGCCGAG | GCCCGCCCCC | ACCCTCCATT |
| 801 | GGCCAGCTGG | GCGTCTACGT | CAGTCCTGCG | CGGAGCCGGG | GAGGGATCCG | GGCGGCGCTG | AGCGGAAGTG | CGGCTGCGCC | GGTTCCGGG |
| 901 | GCCGCTGGTG | TGACGTGTCC | CGCGCTTGGC | GCAGCCAGGAA | GCAGCGGCGA | TCGAGGCCTG | AGTTCCGGC | GCCGGCCCCG | GTCCTTTCC | CGCTGCCGCC |
| | | | E1 | | | | | | | |
| 1001 | ATGCTCGACT | TCTTCACCAT | TTTTTCCAAA | GGCTGGCTCC | TTCTCTGGTG | CTTTCAGGGC | GTGAAGCGACT | CATGCACCGG | GCCTGTTAAC | GGGTTAATTC |
| 1101 | GTTCCGTGCT | GCTGCAGGTA | CCGCCCCGG | CCCACCTCTC | CCCACTCAA | CTGGGCCACT | ACTCTGGTAG | CTCCCAGTT | CCGCTGAGG | CCCTTGAC | TGATCCGGG |
| 1201 | CCTCCCTCTC | ACCCTGTCTG | CCCACCTCAA | GCTTCTAGC | CGCTGTAGC | GATCGGTAG | CCTCCCTTCC | CAGACCATCC | CGGCTTGCTT |
| 1301 | TGATGTCCCC | TCCCCCTCC | GCTTCTCGGG | ACTCTGGCAG | AACGTCTTT | TCCATTGAGA | AAGAAGTGTA | GGCTGCCGGT | AAACCTGATT | GTTTACATGA |
| 1401 | TTCTGTTGTC | GCAAAGGCTG | GATGAGATAA | AGATGAGAA | TCCCACCTT | CCCCTCCTTC | CCCACCCC | CCAGCTGGGT | GTCTACACTT | TTCTCCCAGG | TCTAATGCTG |
| 1501 | GGACTCTCT | CGCTGGCACA | TGTCGGTCC | TCCCACCTG | GAGATGTCT | GGTTCCTTCC | CGAAGGTAGT | GCTGGAGGGG | CCCAGCTCCA |
| 1601 | GAGAGCAGTG | CCCTGAATCT | TTTGGCCCTG | GAGACAGGT | TTGAGTTTAG | GGGAATGTTAG | E2 | | | |
| 1701 | GGTGTTTGAG | GGGACAGTCT | CAATTCTGAG | ATACACTCTT | TTTCCAGGAG | AGAGGAGTA | ACAACTCCTT | CACCCATGAG | GCACTCACTC | TCAAGTATAA |
| 1801 | ACTGGACAAC | CAGTTTGAGT | TGGTGTTTGT | GGTAAGTGAG | GGTATTTAG | AGGGGTAACG | ATTACACTGA | CAGGCAGTCC | TGATGATTCA | GAAAATCCTG |
| 1901 | ATTAATTGCG | CCCAGTGTCT | ACGATGAAGT | AACTGAGAAA | ACAAGGAGGG | TGGAGGGAA | AAGGGAAGCC | GCTCTTGGGC | CCAGTCAGAG | GGCTTGGCTG |
| 2001 | CTCCTCAGGT | CAGGGAAACC | GGCAGGGCC | TGAGCAGTC | CCTGGAGGCC | TGGGTCAAGT | TGGCTTCCCT | CTGTTCTGGG | CCGGCATGTA | AGCAGATCTG |
| | | | E3 | | | | | | | |
| 2101 | CTGGCTCTGT | TCCTTTCCCT | GAAACAGGTAG | GTTTTCAGAA | GATCCTAACA | CTGACGTATG | TGGACAAGTT | GATAGAGAC | GTCACCGGC | TGTTTCGAGA |
| 2201 | CAAGTACCGC | ACTGAGATCC | AACAGCAGAG | TGGCCTAAGT | CTATTGAAAT | TCTTCCGA | AGCACTTTCA | TTTCCAGAAT | GACTTTCTGC | GGCTCCTTCG | GTGAGGGCC |
| 2301 | TCCCCTACCC | AAAATCAATT | TCTGAGACT | GATGAGTTCC | TTTCCTTCCC | AAGGCAGCAT | AGTACACTGT | GGTTGAAAG | CTTCCTGAAAG | GGCTTGGCTG | GTTGGCTTCC |
| 2401 | CAGTTCTGAT | GGCCTGCTCA | GTGTGAGGGC | CCTTCCCTG | GATTTAGACT | GTCAACCTTT | TCTCTTTGGG | GGCTCAGATG | GGCTCAGATG | GTAAAGAATA |
| 2501 | CCTCCAATCT | GGGAAACCCA | GGTTTGATCC | CTGCCTTGGG | AAGATCCCCT | GGAAGAGGAA | CGTTCAACCC | ACTCTAGAAT | TCTTGACTCG | AGAATCCAAT |
| | | | | | | | | E4 | | |
| 2601 | CCTGGCCCAC | CAGGCTCCTC | TGTCCATAGA | ATCCAGAGT | CAGACACGAC | TGAAGCGACT | TAGTATGAAC | TTTTCTCTTT | AGTGAAGCAG | AGGAGAGCAG |

Fig. 6A

```
2701                 TAAGATCCGT GCTCCCACTA CCATGAAGAA ATTTGAAGAT TCTGAGAAGG CGAAGAAACC TGTGAGATCC ATGATTGAGA CACGGGTGA AAAGCCTAAG
                                                          E4

2801  GAAAAAGCCA AGAATAACAA AAAAAACAAG GGGGCCAAGA GTTCATTCAG GGACATCAAG GTTTGAACTT GGACATCAGA GGGCATGAGA CGTTGTTCAG GTGGCACTGA
2901  AGCGGGTCCC TGTCCTTCCC TCTGTCGTCG TTTGCCTCCC TGGCTCAGGT GCCCACCACC CTGATTATTG TCCCCAATGT CGGTGATCCC CCAGGTGTTT
                                                                                       SNP_3064                            E5

3001  CTTCACAGTT TTCTCTGAAT GATCTGGGAG GGTTTTCCCC ATTTGTCTAT TTTGTTGGAA TTCGGTCTTT TTTTTTTCAG TGAGTTTTCT CCTTGACAGG
                                                              E5

3101  TTCTGATGGC CCTCTGGCTA CTAGCAAAGC AGCCCCTCCA GAAAAGTCAG GTCTCCCAGT AGGACCTGAG AACGGGGAGG AACTTTCCAA AGAGGAGCAG

3201  ATCCGGAAGA AGCGGGAAGA GTTCATTCAG AAGCATGGGA GGGGTATGGA GAAGTCCAGG TGAGCAGCCC AGCTTTGCCC TCAGCTTTTG CTATCCAGAC
                                                                                                                      E6

3301  ACGTTAGGGG TGAGGGAGTC CTTGCTCTCG AGGTGGATGC TGCCTCTCCT GCTGCTCCAC CATAACCCTC TCTACTGTAA CCCTTCACAC CAAGTCCAGT

3401  AAGTCAGATG CTCCCAAGGA GAAAGGCAAA AAGGCACCCC GGGTGTGGGC ACTGGGAGGC TCTGCTAACA AGGAAGTTCT GGACTACAGC ACTCCCACCA
                         E6

3501  CCAACGGAGC CCCCGAAGCG GCCCCGCCTG AGGACATCAA CTTGGTAAGA GGTAGCAGGG GCCAGAGTGA GGGTTAATGG TAATAAGCAG CAGGGGGAAG
3601  GAGAGATGAG GAGGGCAGTC CCCTTCATTG CTTGGAGCCA GAGGGTGGGT TACATTTGA GCTTCTGGAG GCTTCGGAG AGAGCAGTGT GGGACAGGGT
                                                                                                     E7

3701  CACTCCAGGC TTCCCTCCCC ACCAGCTCAT GGTTTCCTGA TCCCTTCTTC CTCTCCCCAC ACCCTCCAGA TTCGAGGGAC TGGGCCTGGG AGGCAGCTTC

3801  AGGATCTGGA CTGCAGCAGC TCAGATGATG AAGGAGCTGC TCAGAACTGC ACCAAACCTA GGTACGGGAT TTGGTGGCGG GTGGTGGGTA TGGCTCCAAA
                                                                                                                       E8

3901  GGCACAGGAC TTGCTGGCTG CCTGCTGGCT TTCTGTGCAT CTGTGGTTTT CTGTGCCTGC AGTGCTACCA AGGGGACTCT GGGTGGCATG TTTGGGATGC

4001                                TCAAGGGCCT TGTGGGTTCC AAGAGCTTGA CATGGAATCT GTGCTGGACA AGATGCGTGA TCATCTCATT GGTGAGTCAG GACAGGCAG
                                                                                             SNP_4150

4101                                ACTCGGTGTT TGGGCTGTTT GATAGTGGGG TAGAAGGGCT GTACCGTGGG GGTCGTTCAC TCCTGCCAGG GCATTCACCC CACGTTTGTC CCCCCTCCTT
```

Fig. 6B

```
4201  AGCTAAGAAT GTGGCAGCAG ACATTGCAGT CCAGCTCTGT GAATCCGTGG CCAACAAGTT GGAAGGGAAG GTGATGGGGA CGTTCAGCAG TAAGTATCTC
4301  CCCAGACCTA GAACTGCTTG GGTGGAGGTT ATGAAGTCAC TCTTGCAGAT ATTAGATGCG TGACTTTTGA CAAACTGTAA TCTCTAAATC TATGTGTTT
4401  CACTTAGAGT TCAGGTGTTC ATGACATCTA ACTTAAGAAG ATTTGAATCA ATTACTTGTC AGGTGCTTAG GGCTGTCAGA TATGGTGTGG ATTCCTGGGC
                                                                                                              E10
4501  AGGATCCTAG TTCCCTTTAG CTCAGCAAGA TGCCAGGTGT TCGGAGCACC TGACTTGGGC TTCATGGGTA CCCCACCCCC AGCGGTGACT
                E10
4601  TCCACGGTCA AGCAAGCTCT GCAGGAGTCC TTGGTGCAGA TTCTACAGCC GCAGCGCCGC GTAGACATGC TCCGGGACAT CATGGATGCC CAGCGTCATC
                                        E10
4701  AGCGCCCGTA CGTGGTCACT TTCTGTGGTG TGAACGGCGT GGGGAAGTCT ACCAACCTTG CCAAGTGTGG TGCTGTTCAC CAGGCTGAGT CTGACATTGT
                                                                                  E11
4801  TTCTGCTGCT TTTTCCGTCT CTGCCACTGT GGGGCTGGCT GACAGTTCTG CCCTCTTTTGC AGATCTCCTT CTGGCTGTTA GAGAACGGCT TCAGTGTCCT
                                                    E11
4901  CATCGCTGCC TGCGACACAT TTCGTGCCGG GGCTGTGGAA CAGCTGCGCA CGCACACCCG GCGTCTGCAGC GCCCTGCACC CCCCGAGAA GCACGCGGC
5001  CGGACCATGG TGCAGCTGTT CGAGAAGGGC TACGCCAAGG ATGCTGCTGG CATTGCCATG GAGGCCATTG CCTTTGGTAC AAGTGTGGG
5101  CTTGTGCGGG CCCCTCTGCT CCGGGGCTTC TCTTGGAACT TGCAGAGGAC CAGGGTTACC CTACCACCAA CTTTCTGCTC AGTAGCAGCT CAGAATAGT
5201  GATGTGCCAT GCCATGCTCC CCCGGGTGTG ACTTTGGGGT GACGTGTAGT TGCAGGCAAA CCTCATATAT TCGTTTTGTT ACCTCAATAT TTGGTCACCT TTATCCTCCT
5301  GCTAGGGCTT CCCGGGTGTG GCTCAGTGGT AAAGAATCTG CCTGCCAATG CAGGAGACAA AATAGATACA GGTTCCAGCC CTGGGTCGGG AAGATCCCCT
5401  GCAGGAGGAA ATGGAACCCA CTTGCCTGCC CTCCAGTATT CTTGCCTGCT ACAGAGGAGC CTGGCGGCT ACAGTCCACA GAGTTGCAGA GAGTCAGCA
5501  CACTCAGTGT ACACACACAC CAGACTTCTA CCACCTGCTC TCCTTTCCCT AAATATGCTT CATGACAGCG TGTGGAAACT GTTTCTTTACA TCACCTTCTA ACTTGATTCG
5601  AACCTAAGGA AATAAACAGG CAGACTTCTA ATAGGGCCAG TTTAGGACCT GTTGAGAGGA AGCTGGAAAT GAGTGTTAAC AGTCCAGGAG TTTTGAGTTG
5701  ACCACTTTTT TCTTTCTAAG ACGTAACCAA GGCTTTGATG TGGTGCTGGT GGACACAGCT GGCCGCCATGC TCCCCTGATG ACTGCCCTGG
                                                        E12
5801  CCAAGCTCAT CACTGTCAAC ACACCTGACC TGGTGCTGTT TGTGGGGGAG GCCTTAGTAG GCAACGAGGC CGTGGACCAG CTGGTGAGGG CTCGGGCTG
                                                                                                E13
5901  GTTCCTCTTCC CAACCTCAGC TCTGGCCAGT TAGGTATGTT ATATTTATAT CATGTTTCTC CTTTCAGGTC AAGTTCAACA GAGCCTTGGC TGACCATTCT
6001  ATGGCCCAGA CACCCCGGCT TATTGATGCC ATTGTCCTTA CCAAATTTGA TACCATTGAT GACAAGGTAA ACATGGCGCA GACAGGGCAG AGTGGGACCA
6101  GGAAGGGAGT CACTGTCCTT GGCTGTCCTT CACAGGGGAG CGGAGCCCTCC CGTCGCTGAG GGAGTGCAAA GGCAGGGTCC AGAAATGACT GGGTATCCTG TCTCTGCCTC
6201  AAGTGGGAGC T
```

Fig. 6C

SNPS ASSOCIATED WITH FATTY ACID COMPOSITION OF BOVINE MEAT AND MILK

This application is the U.S. National Stage entry under §371 of International Application No. PCT/US2008/069235, filed Jul. 3, 2008, which claims the benefit of U.S. Provisional Application No. 60/958,597, filed on Jul. 6, 2007, and U.S. Provisional Application No. 61/047,650, filed on Apr. 24, 2008, the disclosures of each are hereby incorporated herein by reference in their entirety for all purposes.

FIELD OF THE INVENTION

The present invention provides methods and compositions for using polymorphisms in genes involved in fatty acid metabolism, e.g., Stearoyl-CoA-Desaturase 5 (SCD5), Sterol regulatory element-binding protein-1 (SREBP1), SREBP cleavage-activating protein (SCAP), Insulin induced protein 1 (INSIG1), Insulin induced protein 2 (INSIG2) and Signal recognition particle receptor (SRPR), that are associated with economically important traits related to fatty acid composition and disposition in livestock carcasses.

BACKGROUND OF THE INVENTION

Molecular techniques can be employed to detect and map the chromosomal locations of genes contributing to variation in growth, feed intake, energetic efficiency, feeding behavior, and carcass merit. Several molecular tools and approaches, as well as statistical and computational techniques, are available that can be employed to quantify the number(s), location(s) and effect(s) of quantitative trait loci (QTL) through the use of genotypic information from genetic markers that are evenly spaced along chromosomes in the genome. A QTL is defined as the chromosomal location of individual or groups of genes, of unknown primary function, that show(s) significant association with a complex trait of interest (Lander and Kruglyuak, 1995, *Natural Genet* 11: 241-247). In beef cattle, QTL have been detected for disease tolerance (Hanotte et al., 2003, *PNAS Agricultural Sciences* 100:7443-7448), fertility and reproductive performance (Kirkpatrick et al., 2000, *Mammalian Genome* 11:136-139), body conformation (Grobet et al., 1998, *Mammalian Genome* 9: 210-213), birth weight and growth performance (Davis et al., 1998, *Proc. 6th World Congr. Genet. Appl. Livest. Prod.* 23: 441-444; Casas et al., 2003, *J. Anim. Sci.* 81, 2976-83; Li et al., 2002, *J. Anim. Sci.* 80:1187-1194; Kim et al., 2003, *J. Anim. Sci* 81, 1933-42), and carcass and meat quality (Keele et al., 1999, *J. Anim. Sci* 77. 1364-1371; Casas et al., 2000, *J. Anim. Sci.* 78:560-569; MacNeil and Grosz, 2002, *J. Anim. Sci.* 80:2316-2324; Casas et al., 2003; supra; Kim et al., 2003, supra: Moore et al., 2003, *J. Anim. Sci.* 81:1919-1925; and Li et al., 2004, *J. Anim Sci.* 2004 82: 967-972).

It is possible to search for and identify associations between polymorphisms in specific candidate genes and measures of variation in feed intake, feed efficiency and feeding behavior. A candidate gene may be selected based on previously known biochemical or physiological information or may be chosen because it maps to or close to the location of a QTL (positional candidate gene). Of interest among these candidates are genes shown to affect feed intake, behavior, energy balance, and body composition.

Several polymorphisms in candidate genes have been shown to be associated with economically relevant traits in beef cattle (e.g., Chrenek et al., 1998, *Czech Journal of Animal Science* 43, 541-544; Barendse et al., 2001, "The TG5 DNA marker test for marbling capacity in Australian feedlot cattle." on the worldwide web at beef.crc.org.au/Publications/MarblingSym/Day1/Tg5DNA: Ge et al., 2001, *J. Anim. Sci.* 79:1757-1762; Grisart et at, 2002. *Genome Research* 12:222-231; Buchanan et al., 2002; *Genet. Sel. Evol.* 34:105-116: Moore et al., 2003, *J. Anim. Sci.* 81:1919-1925; Li et al., 2004, supra; and Nkrumah et al., 2005, *J. Anim. Sci.* 83:20-28).

Likewise, several polymorphisms in candidate genes have been shown to be associated with economically relevant traits in dairy cattle (e.g., Blott, et al., (2003) *Genetics* 163:253-66; Cohen-Zinder, et al., (2005) *Genome Research* 15:936-44; Grisart, et al., (2004) *Proc Natl Acad Sci USA* 101:2398-403; Khatib, et al., (2007) *J Anim Breed Genet* 124:26-8; Khatib, et al., (2007) *J Dairy Sci* 90:2966-70; Khatkar, et al., (2004) *Genet Sel Evol* 36:163-90; Kubarsepp (2005) *Agronomy Research* 3:55-64; Olsen, et al., (2007) *BMC Genet* 8:32: Tsiaras, et al., (2005) *J Dairy Sci* 88:327-34; and Weikard, et al., (2005) *Physiol Genomics* 21:1-13).

Cattle are an important food source, both for their milk and meat. There is increasing interest in identifying the genetic basis for the fat content of milk from dairy cows and the marbling pattern of meat from dairy and beef cattle. The present invention meets these and other needs.

BRIEF SUMMARY OF THE INVENTION

In one aspect, the invention provides methods of selecting individual bovines with desirable traits based on the knowledge of the bovine's genotype in a gene involved in fatty acid metabolism. In some embodiments, the methods comprise the steps of: determining the alleles of the bovine at one or more SNP IDs selected from the group consisting of SREBP1-13636, SCAP-34632, INSIG1-3885, INSIG1-6082, INSIGI-12052, INSIG2-93277, INSIG2-93461. INSIG2-93867, SCD5-134718, SCD5-179412, SRPR-3064 and SRPR-4150; wherein the traits are indicative of the fatty acid disposition and composition in the bovine, wherein:

i) a "CC" genotype at SREBP1 SNP ID 13636 is correlated with the phenotype of increased predicted transmitting ability for fat (PTAF);

ii) a "TT" genotype at SCAP SNP ID 34632 is correlated with the phenotype of increased predicted transmitting ability for milk (PTAM), increased predicted transmitting ability for protein (PTAP), increased cheese dollars (CHEESD), increased net merit dollars (NMD) and increased net merit protein (NMP);

iii) a "TT" genotype at INSIG1 SNP ID 3885 is correlated with the phenotype of increased PTAF, increased CHEESD, increased NMD and increased NMP;

iv) a "GG" genotype at INSIG1 SNP ID 6082 is correlated with the phenotype of increased PTAM, increased PTAF, increased PTAP, increased CHEESD, increased NMD and increased NMP;

v) an "AA" genotype at INSIG1 SNP ID 12052 is correlated with the phenotype of increased PTAM, increased PTAF, increased PTAP, increased CHEESD, increased NMD and increased NMP;

vi) a "CC" genotype at INSIG2 SNP ID 93277 is correlated with the phenotype of increased predicted transmitting ability for fat percentage (PTAFP);

vii) a "CC" genotype at INSIG2 SNP ID 93461 is correlated with the phenotype of increased health index (HI) and decreased short chain fatty acids (FA);

viii) a "CC" genotype at INSIG2 SNP ID 93867 is correlated with the phenotype of decreased saturated fatty acids (SFA), increased polyunsaturated fatty acids (PUFA), increased C6 to C14 FA, increased C14:1/C14:0 ratio and increased CLA 9-11 content;

ix) a "CC" genotype at SCD5 SNP ID 134718 is correlated with the phenotype of increased HI, decreased SFA, increased monounsaturated fatty acids (MUFA), decreased C6 to C14 FA, and increased CLA 9-11 content;

x) a "TT" genotype at SCD5 SNP ID 179412 is correlated with the phenotype of decreased SFA, increased PUFA, increased C14:1/C14:0 ratio, increased C 16: I/C16:0 ratio, increased CLA 9-11 content, decreased PTAM decreased PTAP, decreased NMD and decreased NMP;

xi) an "AA" genotype at SRPR SNP ID 3064 is correlated with the phenotype of increased NMD. increased NMP and increased CHEESD; and xii) a "CC" genotype at SRPR SNP ID 4150 is correlated with the phenotype of increased HI, decreased SFA, increased MUFA, increased medium and long chain FA, increased PTAM, increased PTAF, increased CHEESD, increased NMD and increased NMP.

In another aspect, the invention provides methods for 17. A method for distinguishing bovines having a polymorphism in a gene involved in fatty acid metabolism. In some embodiments, the methods comprise:

a) amplifying one or more alleles of bovine genes involved in fatty acid metabolism using an oligonucleotide pair to form nucleic acid amplification products comprising amplified gene polymorphism sequences;

b) detecting one or more polymorphisms present in the bovine genes at one or more positions selected from the group consisting of SREBP1-13636, SCAP-34632, INSIG1-3885; INSIG1-6082, INSIG1-12052, INSIG2-93277, INSIG2-93461, INSIG2-93867, SCD5-134718; SCD5-179412, SRPR-3064 and SRPR-4150; and c) analyzing the one or more polymorphisms, wherein i) a "CC" genotype at SREBP1 SNP ID 13636 is correlated with the phenotype of increased predicted transmitting ability for fat (PTAF);

ii) a "TT" genotype at SCAP SNP ID 34632 is correlated with the phenotype of increased predicted transmitting ability for milk (PTAM), increased predicted transmitting ability for protein (PTAP), increased cheese dollars (CHEESD), increased net merit dollars (NMD) and increased net merit protein (NMP);

iii) a "TT" genotype at INSIG1 SNP ID 3885 is correlated with the phenotype of increased PTAF, increased CHEESD, increased NMD and increased NMP;

iv) a "GG" genotype at INSIG1 SNP ID 6082 is correlated with the phenotype of increased PTAM, increased PTAF, increased PTAP, increased CHEESD, increased NMD and increased NMP;

v) an "AA" genotype at INSIG1 SNP ID 12052 is correlated with the phenotype of increased PTAM, increased PTAF, increased PTAP, increased CHEESD, increased NMD and increased NMP;

vi) a "CC" genotype at INSIG2 SNP ID 93277 is correlated with the phenotype of increased predicted transmitting ability for fat percentage (PTAFP);

vii) a "CC" genotype at INSIG2 SNP ID 93461 is correlated with the phenotype of increased health index (HI) and decreased short chain fatty acids (FA);

viii) a "CC" genotype at INSIG2 SNP ID 93867 is correlated with the phenotype of decreased saturated fatty acids (SFA), increased polyunsaturated fatty acids (PUFA), increased C6 to C14 FA, increased C14:1/C14:0 ratio and increased CLA 9-11 content;

ix) a "CC" genotype at SCD5 SNP ID 134718 is correlated with the phenotype of increased HI, decreased SFA, increased monounsaturated fatty acids (MUFA), decreased C6 to C14 FA and increased CLA 9-11 content;

x) a "TT" genotype at SCD5 SNP ID 179412 is correlated with the phenotype of decreased SFA, increased PUFA, increased C14:1/C14:0 ratio, increased C16:1/C16:0 ratio, increased CLA 9-11 content, decreased PTAM, decreased PTAP, decreased NMD and decreased NMP;

xi) an "AA" genotype at SRPR SNP ID 3064 is correlated with the phenotype of increased NMD, increased NMP and increased CHEESD; and xii) a "CC" genotype at SRPR SNP ID 4150 is correlated with the phenotype of increased HI, decreased SFA, increased MUFA, increased medium and long chain FA, increased PTAM, increased PTAF, increased CHEESD, increased NMD and increased NMP.

With respect to the embodiments, in some embodiments, the alleles of two or more SNP IDs are determined. In some embodiments, the alleles of 3, 4, 5, 6, 7, 8, 9, 10, 11 or 12 SNP IDs are determined.

In some embodiments, the alleles of the SNP IDs for determining the phenotype of one or more particular traits of interest, e.g., PTAF, PTAM, PTAP, PTAFP, CHEESD, NMD, NMP, SFA, PUFA, MUFA, C14:1/C14:0 ratio, C16:1/C16:0 ratio, CLA 9-11 content, C6 to C14 FA, HI, short chain FA, medium chain FA and/or long chain FA, are determined.

In some embodiments, the bovine is a female, and the allele of one or more SNP IDs selected from the group consisting of INSIG2-93461, INSIG2-93867, SCD5-134718, SCD5-179412 and SRPR-4150 are determined.

In some embodiments, the bovine is a male, and the allele of one or more SNP IDs selected from the group consisting of SREBP1-13636, SCAP-34632, INSIG1-3885, INSIG1-6082, INSIG1-12052, INSIG2-93277, SCD5-179412, SRPR-3064 and SRPR-4150 are determined.

In some embodiments, the bovine is a *Bos*. In some embodiments, the bovine is a *Bos taurus*.

In some embodiments, the gene encoding bovine SREBP1 is SEQ ID NO:1 or a complement thereof. In some embodiments, the gene encoding bovine SREBP1 shares at least about 95%, 96%, 97%, 98% or 99% sequence identity with SEQ ID NO:1 or a complement thereof.

In some embodiments, the gene encoding bovine SCAP is SEQ ID NO:2 or a complement thereof. In some embodiments, the gene encoding bovine SCAP shares at least about 95%, 96%, 97%, 98% or 99% sequence identity with SEQ ID NO:2 or a complement thereof.

In some embodiments, the gene encoding bovine INSIG1 is SEQ ID NO:3 or a complement thereof. In some embodiments, the gene encoding bovine INSIG1 shares at least about 95%, 96%, 97%, 98% or 99% sequence identity with SEQ ID NO:3 or a complement thereof.

In some embodiments, the gene encoding bovine INSIG2 is SEQ ID NO:4 or a complement thereof. In some embodiments, the gene encoding bovine INSIG2 shares at least about 95%, 96%, 97%, 98% or 99% sequence identity with SEQ ID NO:4 or a complement thereof.

In some embodiments, the gene encoding bovine SCD5 is SEQ ID NO:5 or a complement thereof. In some embodiments, the gene encoding bovine SCD5 shares at least about 95%, 96%, 97%, 98% or 99% sequence identity with SEQ ID NO:5 or a complement thereof.

In some embodiments, the gene encoding bovine SRPR is SEQ ID NO:6 or a complement thereof. In some embodiments, the gene encoding bovine SRPR shares at least about 95%, 96%, 97%, 98% or 99% sequence identity with SEQ ID NO:6 or a complement thereof.

In some embodiments, the alleles are independently detected by one or more amplification reactions using polynucleotides that distinguish between alleles at positions SREBP1-13636, SCAP-34632, INSIG1-3885, INSIG1-6082, INSIG1-12052, INSIG2-93277, INSIG2-93461, INSIG2-93867, SCD5-134718, SCD5-179412, SRPR-3064 and SRPR-4150.

In some embodiments, the amplification reaction is selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

In some embodiments, the alleles are independently detected by hybridization using polynucleotides that distinguish between alleles at positions SREBP1-13636, SCAP-34632, INSIG1-3885, INSIG1-6082, INSIG1-12052, INSIG2-93277. INSIG2-93461, INSIG2-93867, SCD5-134718, SCD5-179412, SRPR-3064 and SRPR-4150.

In some embodiments, the alleles are independently detected by sequencing a subsequence of the gene encoding SREBP1-13636, SCAP-34632, INSIG1-3885, INSIG1-6082, INSIG1-12052, INSIG2-93277, INSIG2-93461, INSIG2-93867, SCD5-134718, SCD5-179412, SRPR-3064 or SRPR-4150.

In some embodiments, the SNP ID SREBP1-13636 is detected, wherein a "CC" genotype at SREBP1 SNP ID 13636 is correlated with the phenotype of increased predicted transmitting ability for fat (PTAF);

In some embodiments, the SNP ID SCAP-34632 is detected, wherein a "TT" genotype at SCAP SNP ID 34632 is correlated with the phenotype of increased predicted transmitting ability for milk (PTAM), increased predicted transmitting ability for protein (PTAP), increased cheese dollars (CHEESD), increased net merit dollars (NMD) and increased net merit protein (NMP);

In some embodiments, the SNP ID INSIG1 3885 is detected, wherein a "TT" genotype at INSIG1 SNP ID 3885 is correlated with the phenotype of increased PTAF, increased CHEESD, increased NMD and increased NMP;

In some embodiments, the SNP INSIG1-6082 is detected, wherein a "GG" genotype at INSIG1 SNP ID 6082 is correlated with the phenotype of increased PTAM, increased PTAF, increased PTAP, increased CHEESD, increased NMD and increased NMP;

In some embodiments, the SNP ID INSIG1-12052 is detected, wherein an "AA" genotype at INSIG1 SNP ID 12052 is correlated with the phenotype of increased PTAM, increased PTAF. increased PTAP, increased CHEESD, increased NMD and increased NMP;

In some embodiments, the SNP ID INSIG2-93277 is detected, wherein a "CC" genotype at INSIG2 SNP ID 93277 is correlated with the phenotype of increased predicted transmitting ability for fat percentage (PTAFP);

In some embodiments, the SNP ID INSIG2-93461 is detected, wherein a "CC" genotype at INSIG2 SNP ID 93461 is correlated with the phenotype of increased health index (HI) and decreased short chain fatty acids (FA);

In some embodiments, the SNP ID INSIG2-93867 is detected, wherein a "CC" genotype at INSIG2 SNP ID 93867 is correlated with the phenotype of decreased saturated fatty acids (SFA), increased polyunsaturated fatty acids (PUFA), increased C6 to C14 FA, increased C14: 1/C14:0 ratio and increased CLA 9-11 content;

In some embodiments, the SNP ID SCD5-134718 is detected, wherein a "CC" genotype at SCD5 SNP ID 134718 is correlated with the phenotype of increased HI, decreased SFA, increased monounsaturated fatty acids (MUFA), decreased C6 to C14 FA and increased CLA 9-11 content;

In some embodiments, the SNP ID SCD5-179412 is detected, wherein a "TT" genotype at SCD5 SNP ID 179412 is correlated with the phenotype of decreased SFA, increased PUFA, increased C 14:1/C14:0 ratio, increased C 16:1/C16:0 ratio, increased CLA 9-11 content, decreased PTAM, decreased PTAP, decreased NMD and decreased NMP;

In some embodiments, the SNP ID SRPR-3064 is detected, wherein an "AA" genotype at SRPR SNP ID 3064 is correlated with the phenotype of increased NMD, increased NMP and increased CHEESD; and In some embodiments, the SNP ID SRPR-4150 is detected, wherein a "CC" genotype at SRPR SNP ID 4150 is correlated with the phenotype of increased HI, decreased SFA, increased MUFA, increased medium and long chain FA, increased PTAM, increased PTAF, increased CHEESD, increased NMD and increased NMP.

In a related aspect, the invention provides methods of distinguishing a *Bos taurus* from a *Bos indicus* based on one or more polymorphisms in the bovine SREBP1 gene. In some embodiments, the methods comprise determining the SREBP1 alleles of a bovine at one or more positions selected from the group consisting of 1199, 12504 and 13508 of a bovine gene encoding SREBP1, wherein:

i) a "CC" genotype at position 1199 indicates that the bovine is a *Bos taurus*, and a "GG" genotype at position 1199 indicates that the bovine is a *Bos indicus*;

ii) a "TT" genotype at position 12504 indicates that the bovine is a *Bos taurus*, and a "CC" genotype at position 12504 indicates that the bovine is a *Bos indicus*; and iii) a "TT" genotype at position 13508 indicates that the bovine is a *Bos taurus*, and a "CC" genotype at position 13508 indicates that the bovine is a *Bos indicus*.

In another aspect, the invention provides methods of distinguishing a *Bos taurus* from a *Bos indicus* based on one or more polymorphisms in the bovine SREBP1 gene. In some embodiments, the methods comprise:

a) amplifying one or more alleles of the bovine SREBP1 gene using an oligonucleotide pair to form nucleic acid amplification products comprising amplified SREBP1 gene polymorphism sequences;

b) detecting one or more polymorphisms present in the bovine SREBP1 gene at a position selected from the group consisting of 1199, 12504 and 13508; and c) analyzing the one or more polymorphisms, wherein
  i) a "CC" genotype at position 1199 indicates that the bovine is a *Bos taurus*, and a "GG" genotype at position 1199 indicates that the bovine is a *Bos indicus*;
  ii) a "TT" genotype at position 12504 indicates that the bovine is a *Bos taurus*, and a "CC" genotype at position 12504 indicates that the bovine is a *Bos indicus*; and
  iii) a "TT" genotype at position 13508 indicates that the bovine is a *Bos taurus*, and a "CC" genotype at position 13508 indicates that the bovine is a *Bos indicus*.

In some embodiments, the polymorphism detected is a restriction fragment length polymorphism.

In some embodiments, the amplifying step is an amplification reaction selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

In some embodiments, the bovine SREBP1 gene is SEQ ID NO:1 or the complement thereof.

In some embodiments, the alleles of 1, 2 or 3 SNP IDs that distinguish a *Bos taurus* from a *Bos indicus* are determined.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, ed., Current Protocols in Molecular Biology, 1990-2008, John Wiley Interscience), which are provided throughout this document. The nomenclature used herein and the laboratory procedures in analytical chemistry, and organic synthetic described below are those well known and commonly employed in the art. Standard techniques, or modifications thereof are used for chemical syntheses and chemical analyses.

SREBP1, SCAP, INSIG1, INSIG2, SCD5 or SRPR refers to nucleic acids and polypeptide polymorphic variants (including single nucleotide polymorphisms involving displacement, insertion, or deletion of a single nucleotide that may or may not lead to a change in an encoded polypeptide sequence), alleles, mutants, and interspecies homologs that: (1) have an amino acid sequence that has greater than about 90% amino acid sequence identity, for example, greater than 91%, 92%, 93%, 94%, 95%, 96%, 97%, 98% or 99% amino acid sequence identity, preferably over a region of over a region of at least about 25, 50, 100, 200, 500, 1000, or more amino acids, to an amino acid sequence encoded by a SREBP1, SCAP, INSIG1, INSIG2, SCD5 or SRPR nucleic acid (see, e.g SEQ ID NOS: 1, 2, 3, 4, 5 or 6, respectively); (2) bind to antibodies, e.g., polyclonal antibodies, raised against an immunogen comprising an amino acid sequence of a SREBP1, SCAP, INSIG1, INSIG2, SCD5 or SRPR polypeptide (e.g., encoded by SEQ ID NOS: 1, 2, 3, 4, 5 or 6, respectively), and conservatively modified variants thereof; (3) specifically hybridize under stringent hybridization conditions to an anti-sense strand corresponding to a nucleic acid sequence encoding a SREBP1, SCAP, INSIG1, INSIG2, SCD5 or SRPR protein, and conservatively modified variants thereof, (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a SREBP1, SCAP, INSIG1, INSIG2, SCD5 or SRPR nucleic acid. SREBP1, SCAP, INSIG1, INSIG2, SCD5 or SRPR nucleic acids include polynucleotides comprising the SNPs described herein.

SNP positions within the SREBP1, SCAP, INSIG1, INSIG2, SCD5 or SRPR nucleic acids can be counted from nucleotide 1 of SEQ ID NO: 1, 2, 3, 4, 5 or 6, respectively, with reference to the genomic nucleic acid sequences annotated in the Figures, in reference to the adenosine nucleotide of the ATG start codon, or alternatively, in reference to the intron or exon in which the SNP resides. The polynucleotide or polypeptide sequences are typically from a domesticated livestock animal, for example, a bovine, ovine, equine, porcine or gallus. The nucleic acids and proteins of the invention include both naturally occurring and recombinantly produced molecules.

The term "livestock animal" refers to any breed or population of animal kept by humans for a useful, commercial purpose. As used herein, a livestock animal can be mammal or avian. Generally, the livestock animal is an agricultural mammal, for example, bovine, equine, ovine, porcine. Livestock animals raised for the production of meat find use with the present invention, for example, beef cattle, pigs, goats, sheep, bison, chickens, turkeys, etc. The livestock animals can be in all stages of development, including embryonic, fetal, neonate, yearling, juvenile and adult stages.

The term "bovine" refers to a domesticated (purebred or crossbreeds) or wild mammal that is a *Bovinae*, for example, of the genera *Bos* (e.g., cattle or oxen) or *Bison* (e.g., American buffalo). Exemplary mammals of the genus *Bos* include without limitation *Bos taurus*, *Bos Bovis*, *Bos frontalis* (gayal), *Bos gaurus* (gaur), *Bos grunniens* (domestic yak), *Bos grunniens×Bos taurus* (dzo), *Bos indicus* (zebu cattle), *Bos indicus gudali* (Gudali zebu), *Bos indicus×Bos taurus* (hybrid cattle), *Bos javanicus* (banteng), *Bos primigenius* (aurochs), and *Bos sauveli* (kouprey). *Bos* species for the production of meat products, e.g., beef cattle are of use in the present invention. Exemplary beef cattle breeds of *Bos* include without limitation Black Angus, Red Angus, Horned Hereford, Polled Hereford, Charolais, Simmental, Limousine, Chianina, Brahman, Santa Gertrudis, Texas Longhorn and Wagyu. Exemplary dairy cattle breeds of *Bos* include without limitation Ayrshire, Brown Swiss, Canadiennem, Dutch Belted, Guernsey, Holstein (Holstein-Friesian), Jersey, Kerry, Milking Devon, Milking Shorthorn and Norwegian Red.

The term "carcass traits" refers to traits of an animal's carcass determined after the animal has been slaughtered.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A "single nucleotide polymorphism" or "SNP" refers to polynucleotide that differs from another polynucleotide by a single nucleotide exchange. For example, without limitation, exchanging one A for one C. G or T in the entire sequence of polynucleotide constitutes a SNP. Of course, it is possible to have more than one SNP in a particular polynucleotide. For example, at one locus in a polynucleotide, a C may be exchanged for a T, at another locus a G may be exchanged for an A and so on. When referring to SNPs, the polynucleotide is most often DNA and the SNP is one that usually results in a change in the genotype that is associated with a corresponding change in phenotype of the organism in which the SNP occurs.

A "variant" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variant" are used interchangeably herein to describe such variants. As used herein, the term "variant" in the singular is to be construed to include multiple variances: i.e., two or more nucleotide additions, deletions and/or substitutions in the same polynucleotide. A "point mutation" refers to a single substitution of one nucleotide for another.

A nucleic acid "that distinguishes" as used herein refers to a polynucleotide(s) that (1) specifically hybridizes under stringent hybridization conditions to an anti-sense strand corresponding to a nucleic acid sequence encoding a SREBP1, SCAP, INSIG1, INSIG2, SCD5 or SRPR protein, and conservatively modified variants thereof; or (2) has a nucleic acid sequence that has greater than about 80%, 85%, 90%, 95%, preferably greater than about 96%, 97%, 98%, 99%, or higher nucleotide sequence identity, preferably over a region of at least about 25, 50, 100, 200, 500, 1000, or more nucleotides, to a SREBP1, SCAP, INSIG1, INSIG2, SCD5 or SRPR nucleic acid (e.g., a sequence as set forth in SEQ ID NOs:1, 2, 3, 4, 5 or 6, respectively, or complements or a subsequences thereof. A nucleic acid that distinguishes a first SREBP1, SCAP, INSIG1, INSIG2, SCD5 or SRPR polymorphism from a second SREBP1, SCAP, INSIG1, INSIG2, SCD5 or SRPR polymorphism at the same position in the SREBP1, SCAP, INSIG1, INSIG2, SCD5 or SRPR sequence, respectively, will allow for polynucleotide extension and amplification after annealing to a SREBP1, SCAP, INSIG1, INSIG2, SCD5 or SRPR polynucleotide comprising the first polymorphism, but will not allow for polynucleotide extension or amplification after annealing to a SREBP1, SCAP, INSIG1, INSIG2, SCD5 or SRPR polynucleotide comprising the second polymorphism. In other embodiments, a nucleic acid that distinguishes a first SREBP1, SCAP, INSIG1, INSIG2, SCD5 or SRPR polymorphism from a second SREBP1, SCAP, INSIG1, INSIG2, SCD5 or SRPR polymorphism at the same position in the SREBP1, SCAP, INSIG1, INSIG2, SCD5 or SRPR sequence will hybridize to a SREBP1, SCAP, INSIG1, INSIG2, SCD5 or SRPR polynucleotide comprising the first polymorphism but will not hybridize to a SREBP1, SCAP, INSIG1, INSIG2, SCD5 or SRPR polynucleotide comprising the second polymorphism.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point I for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC. and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated SREBP1, SCAP, INSIG1, INSIG2, SCD5 or SRPR nucleic acid is separated from open reading frames that flank the SREBP1, SCAP, INSIG1, INSIG2, SCD5 or SRPR gene and encode proteins other than SREBP1, SCAP, INSIG1, INSIG2, SCD5 or SRPR. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
 1) Alanine (A), Glycine (G);
 2) Aspartic acid (D), Glutamic acid (E);
 3) Asparagine (N), Glutamine (Q);
 4) Arginine I, Lysine (K);
 5) Isoleucine (I), Leucine (L), Methionine (M), Valine (V);
 6) Phenylalanine (F), Tyrosine (Y), Tryptophan (W);
 7) Serine (S), Threonine (T); and
 8) Cysteine (C), Methionine (M)
 (see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., SEQ ID NOs:1, 2, 3, 4, 5 or 6, or a polypeptide encoded by SEQ ID NOs:1, 2, 3, 4, 5 or 6), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50-100 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to SREBP1, SCAP, INSIG1, INSIG2, SCD5 or SRPR nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds., 1990-2008, Wiley Interscience)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

BRIEF DESCRIPTION OF THE DRAWINGS

In the annotated genomic sequences depicted in FIGS. 1-7, each exon is labeled with a letter "E" with the number of the exon, and is marked with a line above the corresponding sequence ("~~~~").

FIGS. 1A-G illustrate the annotated sequence of the bovine Sterol Regulatory Element-Binding Protein-1 ("SREBP1") (SEQ ID NO:1). The positions of SNP IDs 1199, 12504, 13508 and 13636 are identified.

Figure 2B:
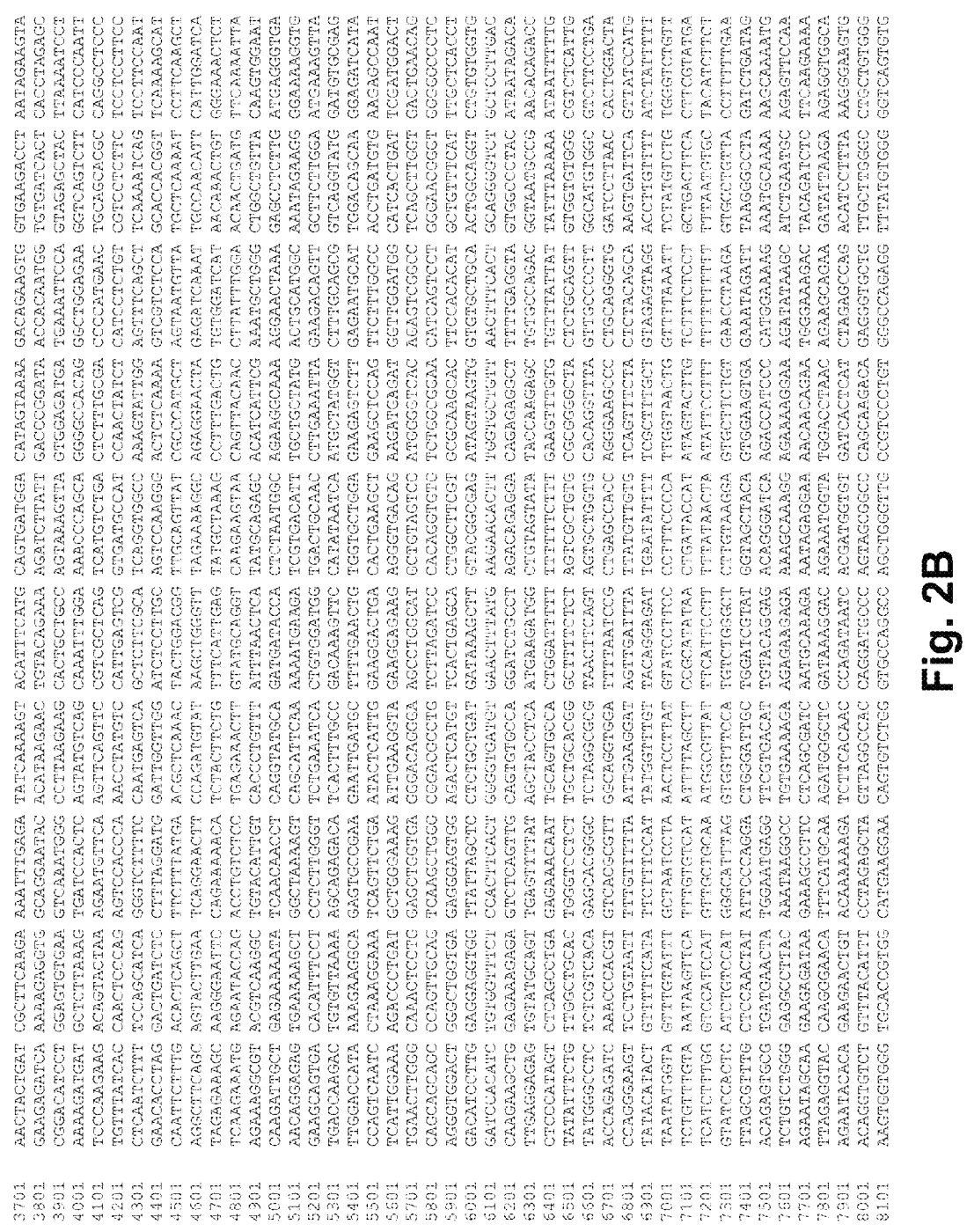
Figure 2C:
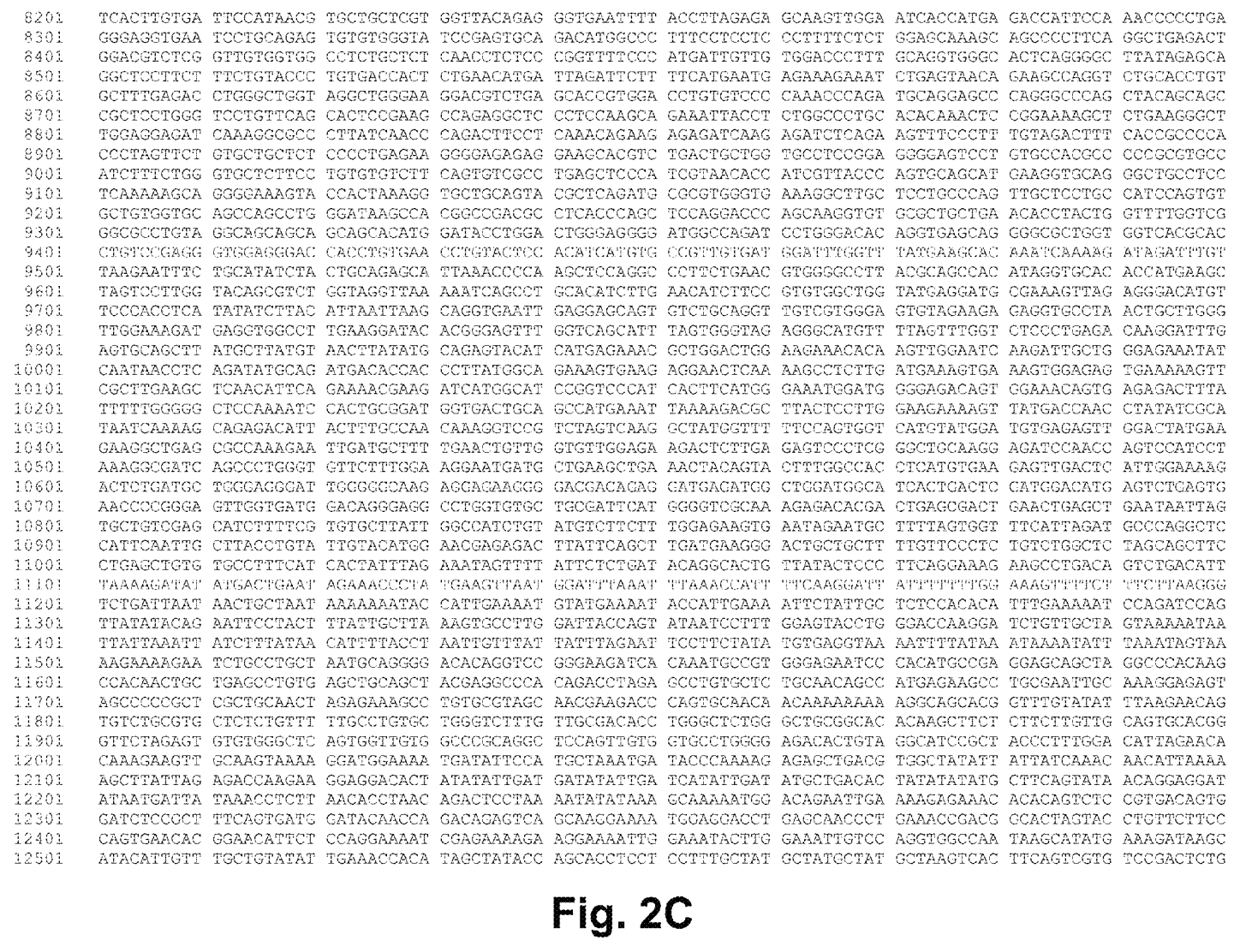
Figure 2D:
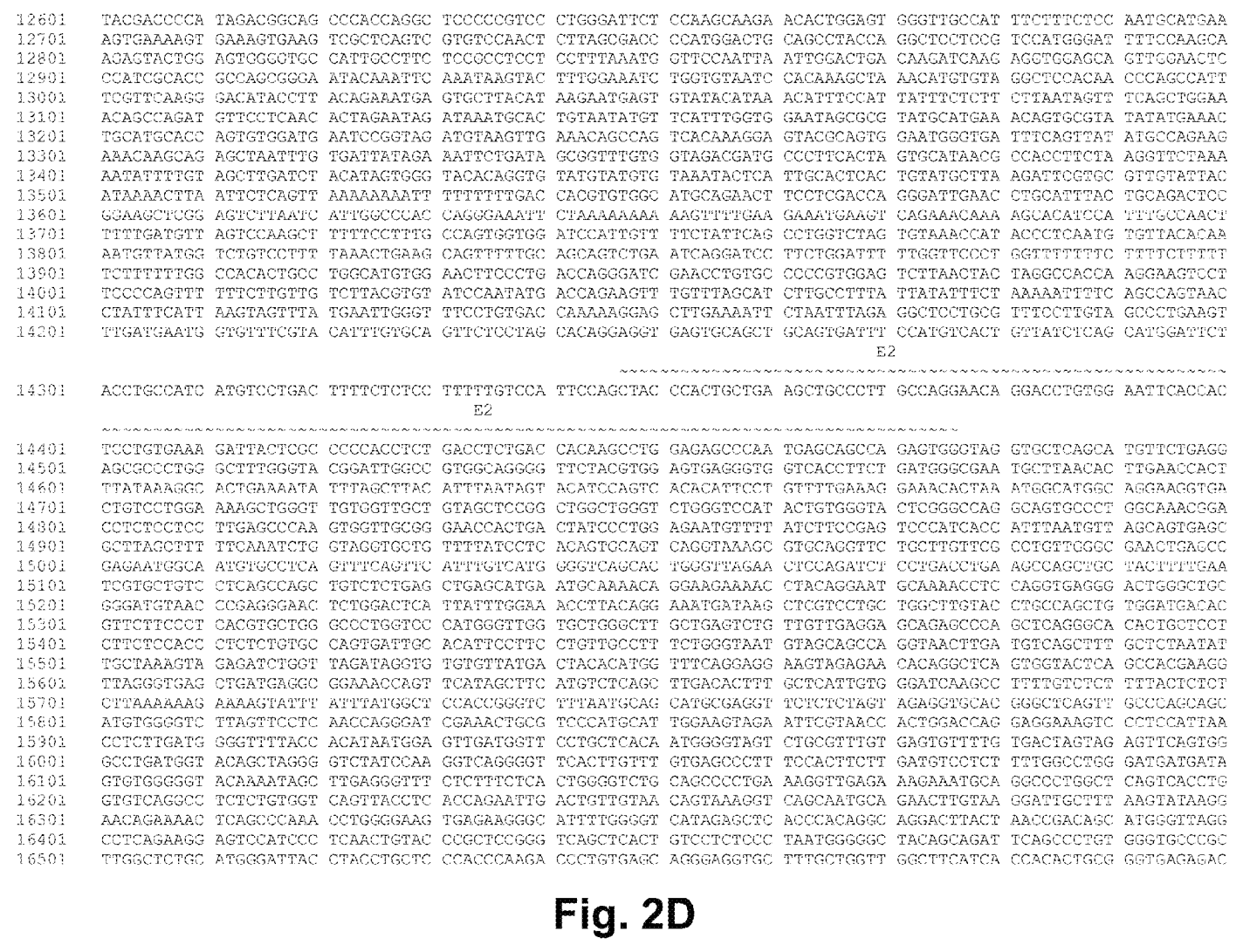
Figure 2E:
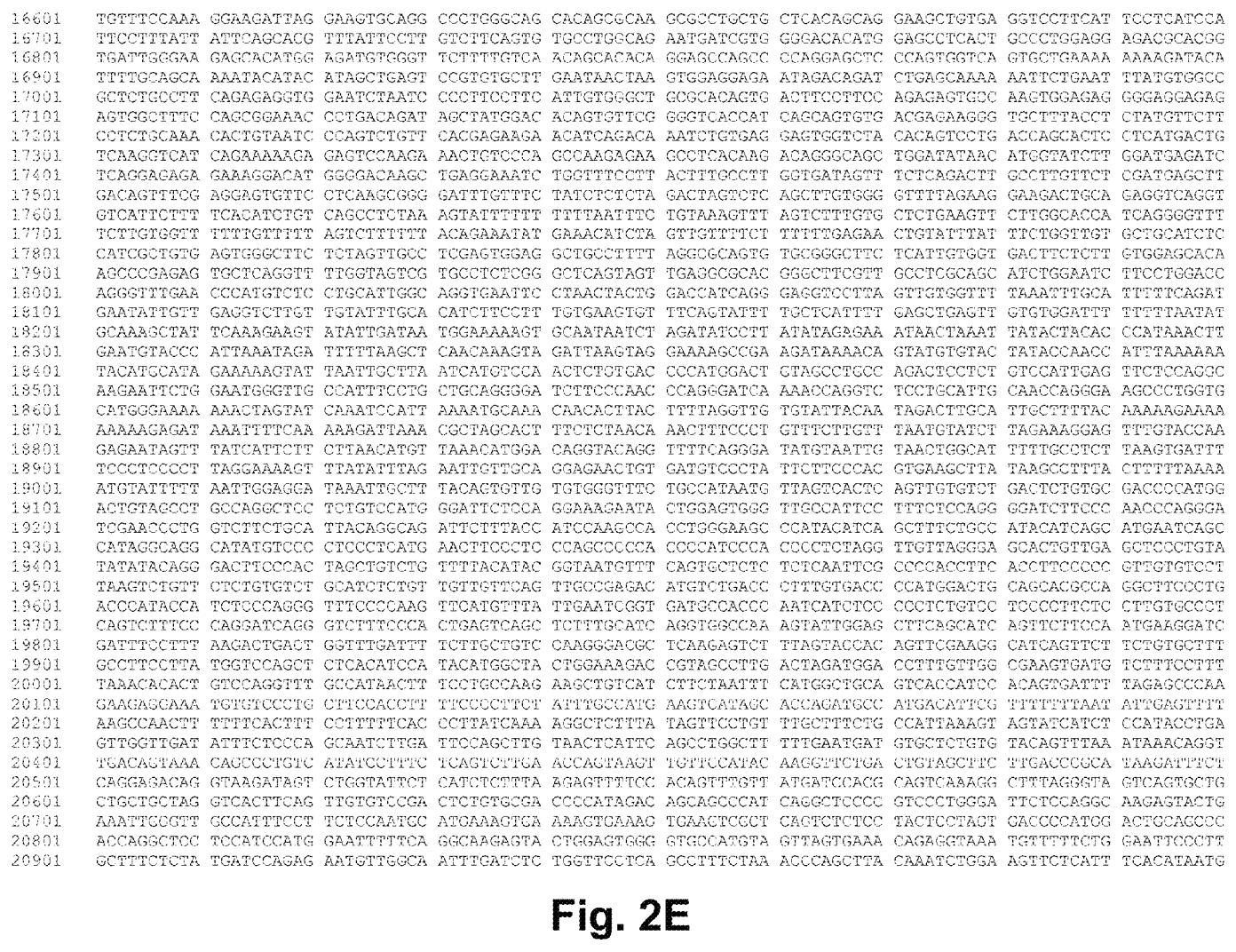
Figure 2F:
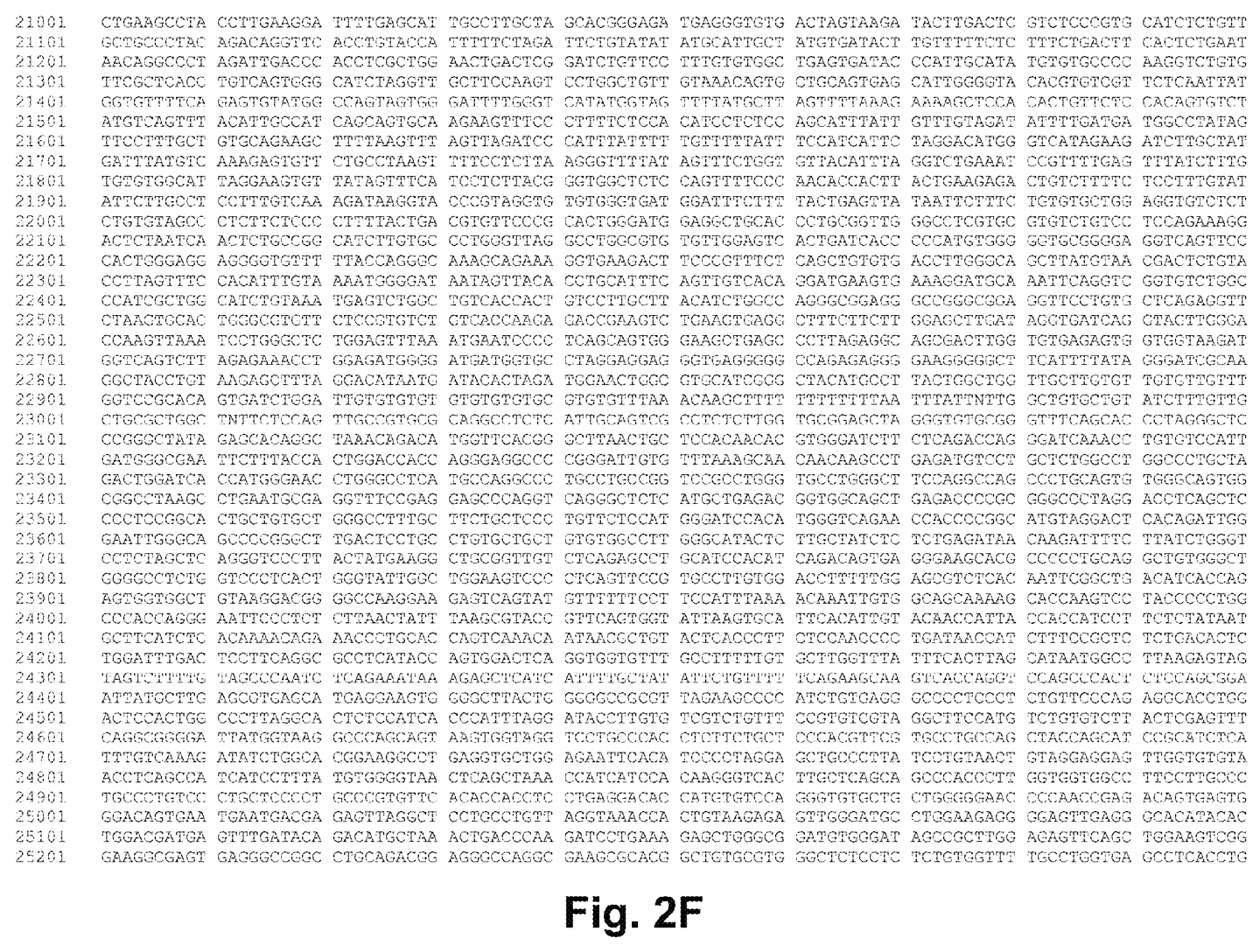
Figure 2I:
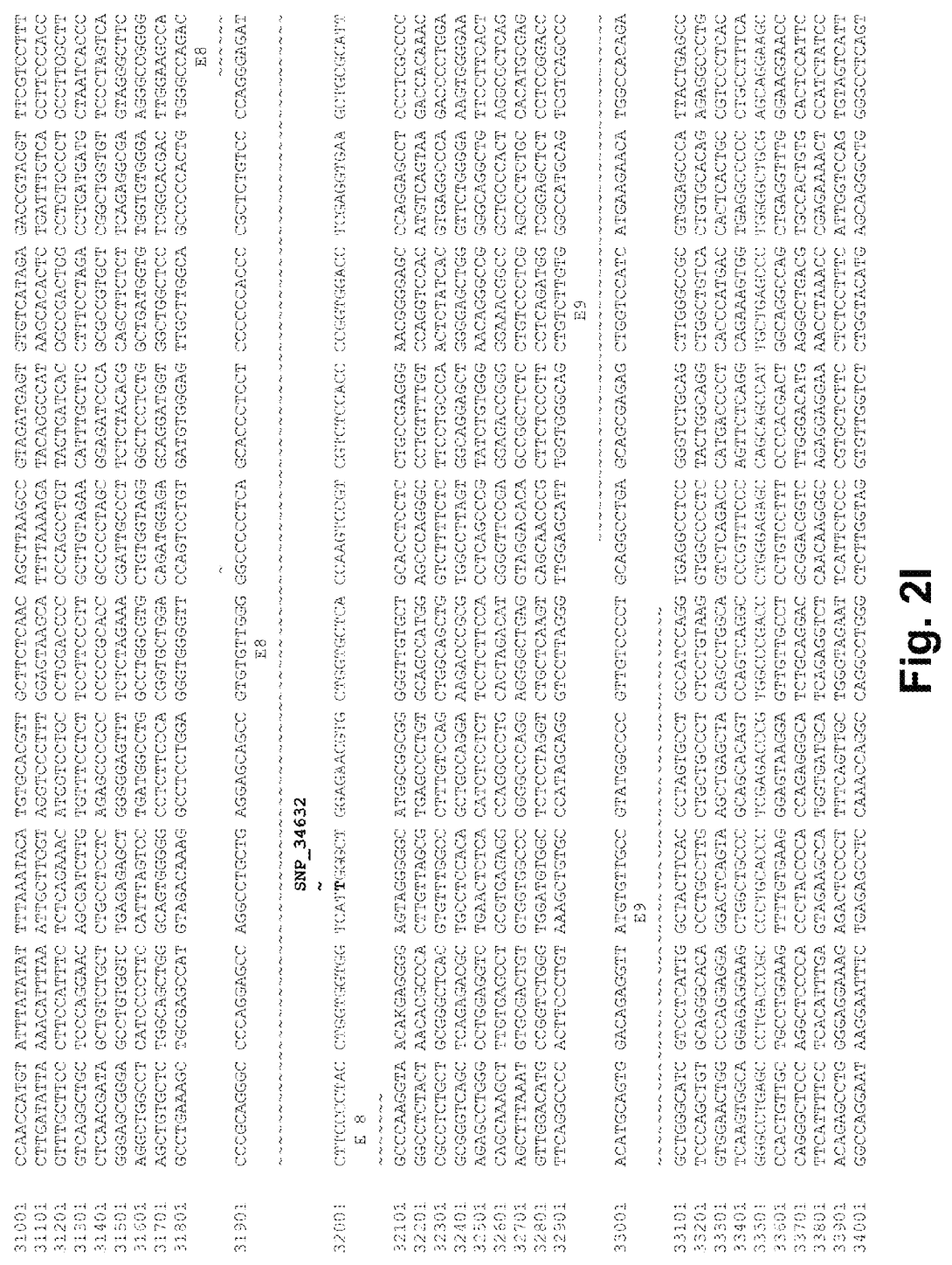
Figure 2L:
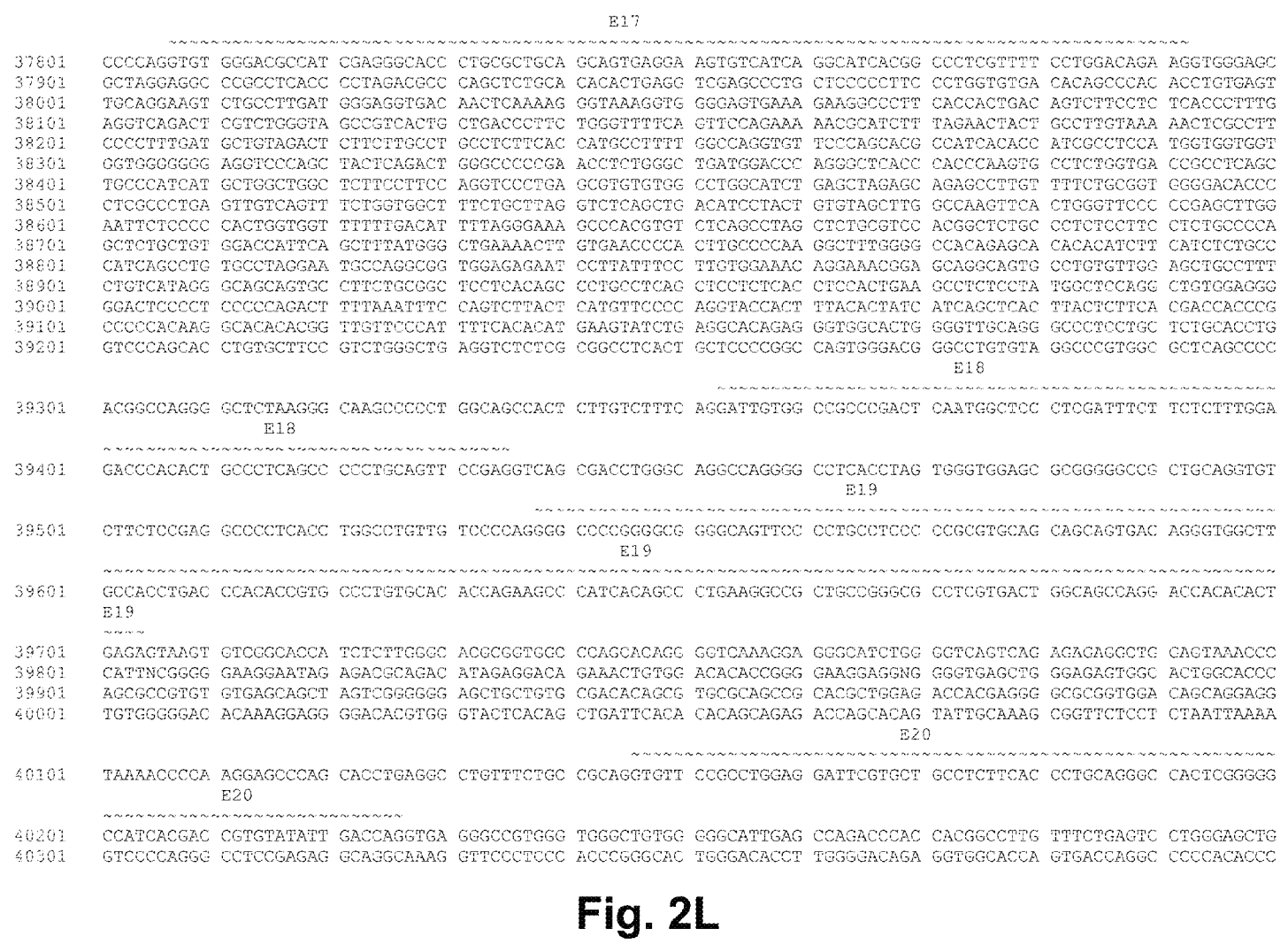

FIGS. 2A-M illustrate the annotated sequence of the bovine SREBP Cleavage-Activating Protein ("SCAP") (SEQ ID NO:2). The position of SNP ID 34632 is identified.

FIGS. 3A-D illustrate the annotated sequence of the bovine Insulin Induced Protein 1 ("INSIG1") (SEQ ID NO:3). The positions of SNP IDs 3885, 6082 and 12052 are identified.

FIGS. 4A-D illustrate the annotated sequence of the bovine Insulin Induced Protein 2 ("INSIG2") (SEQ ID NO:4). The positions of SNP IDs 93277, 93461 and 93867 are identified.

Figure 5B:
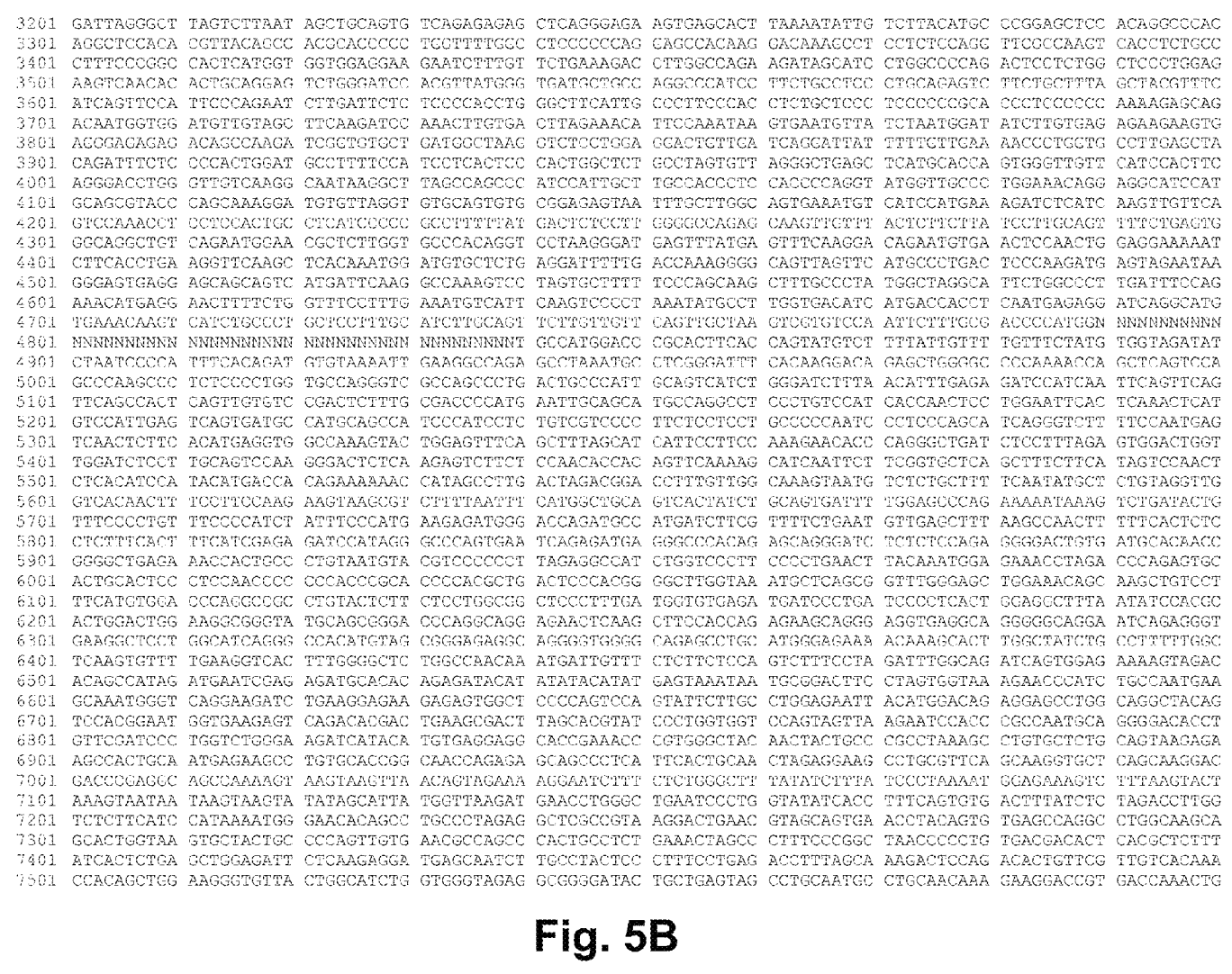
Figure 5D:
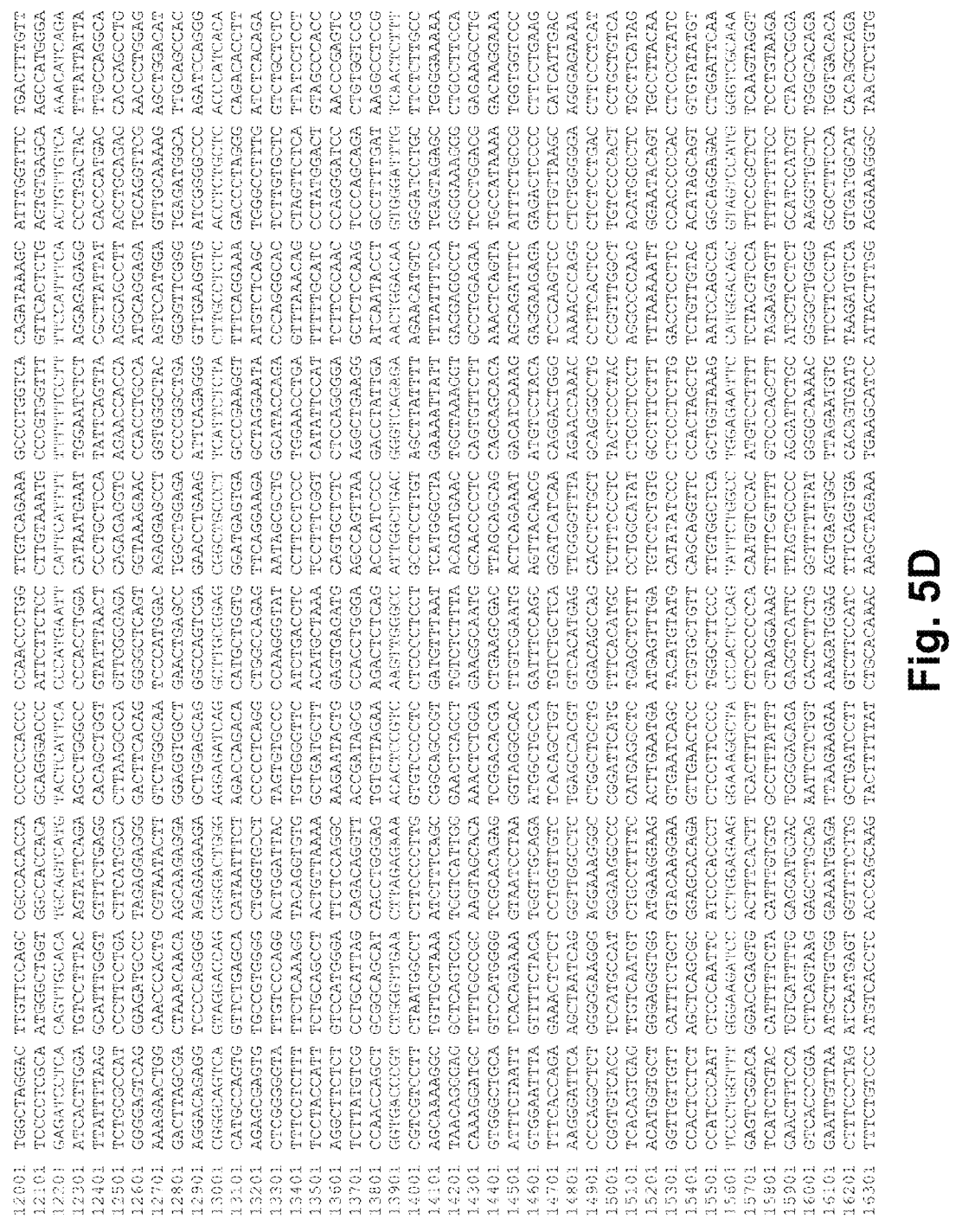
Figure 5E:
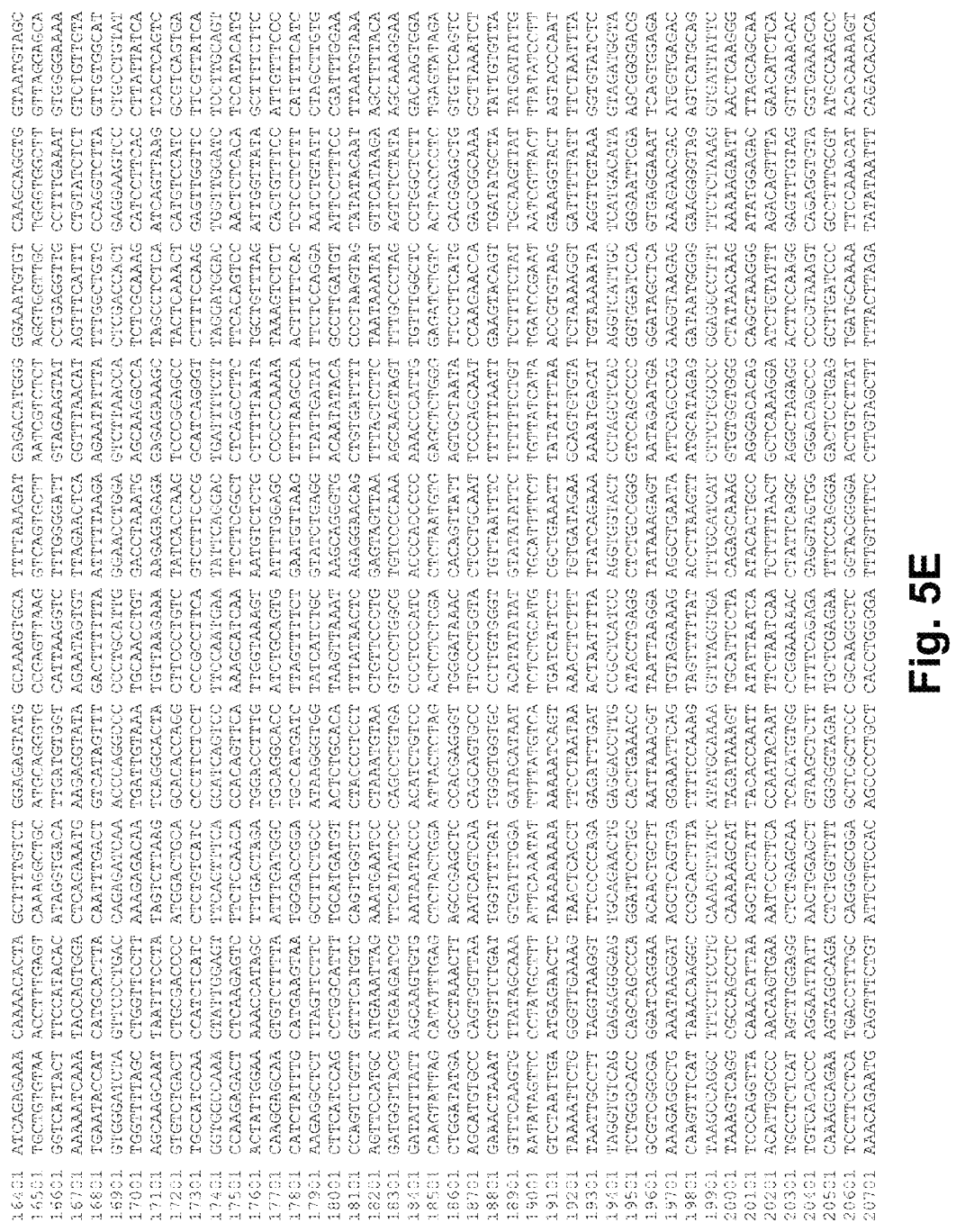
Figure 5F:
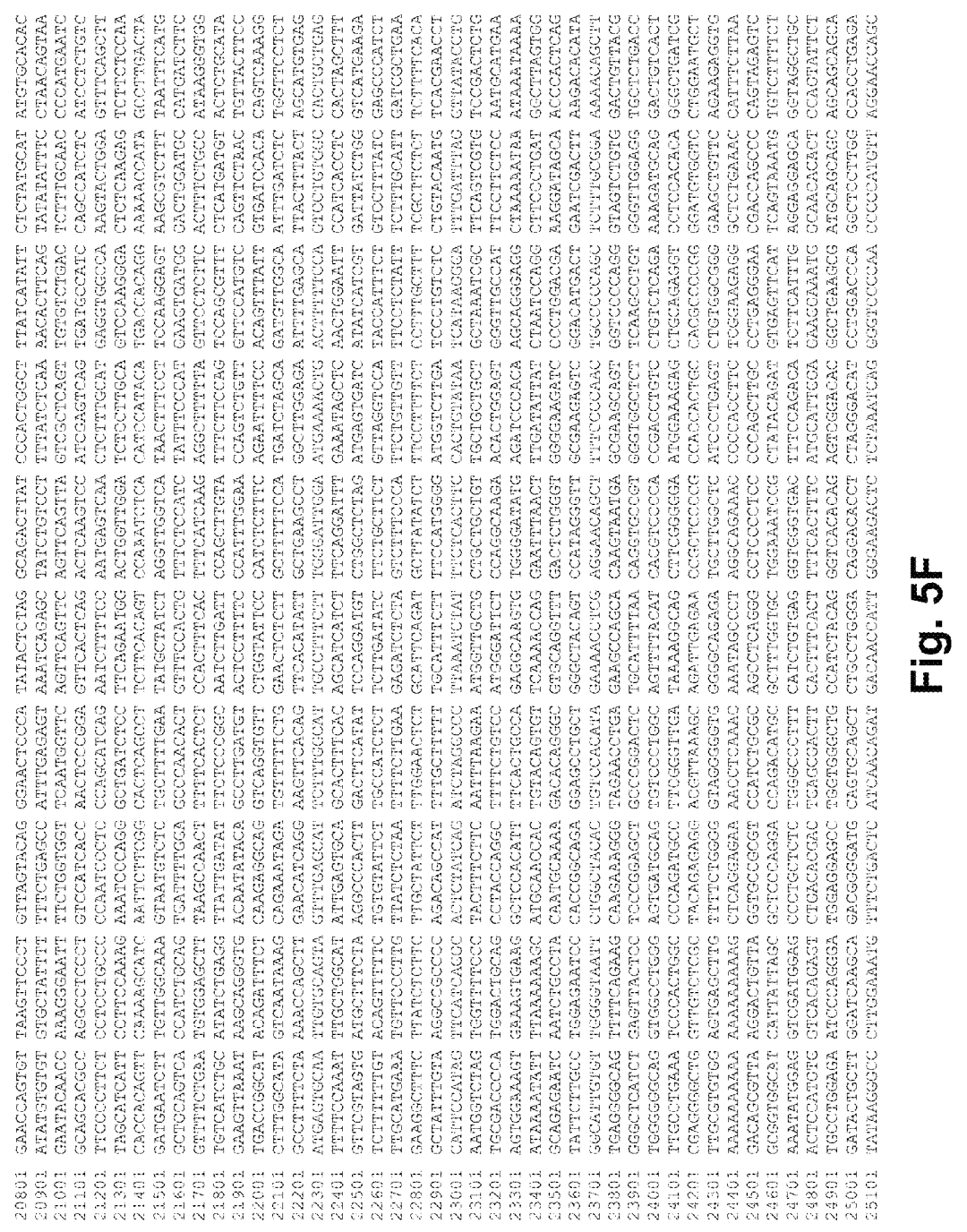
Figure 5G:
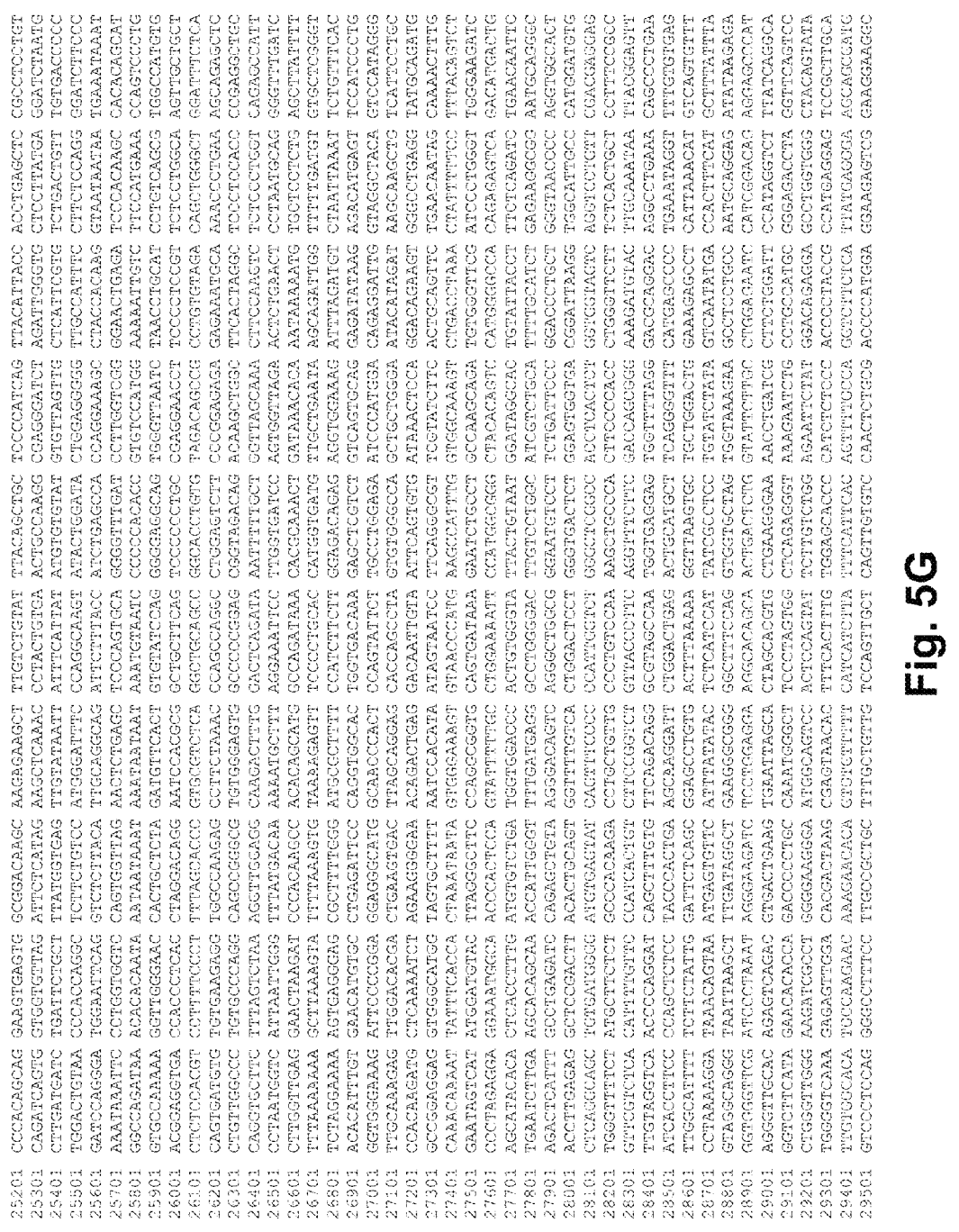
Figure 5I:
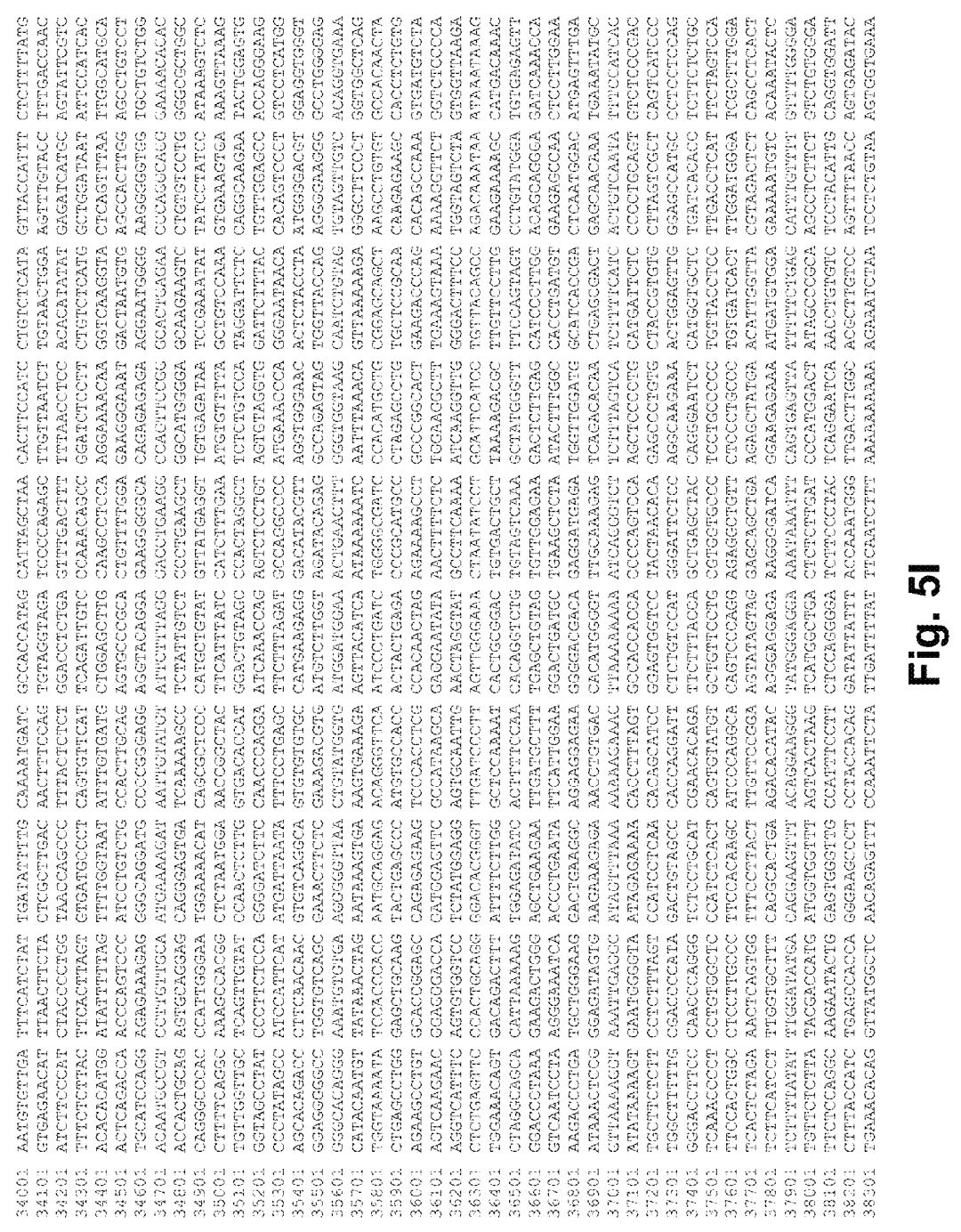
Figure 5J:
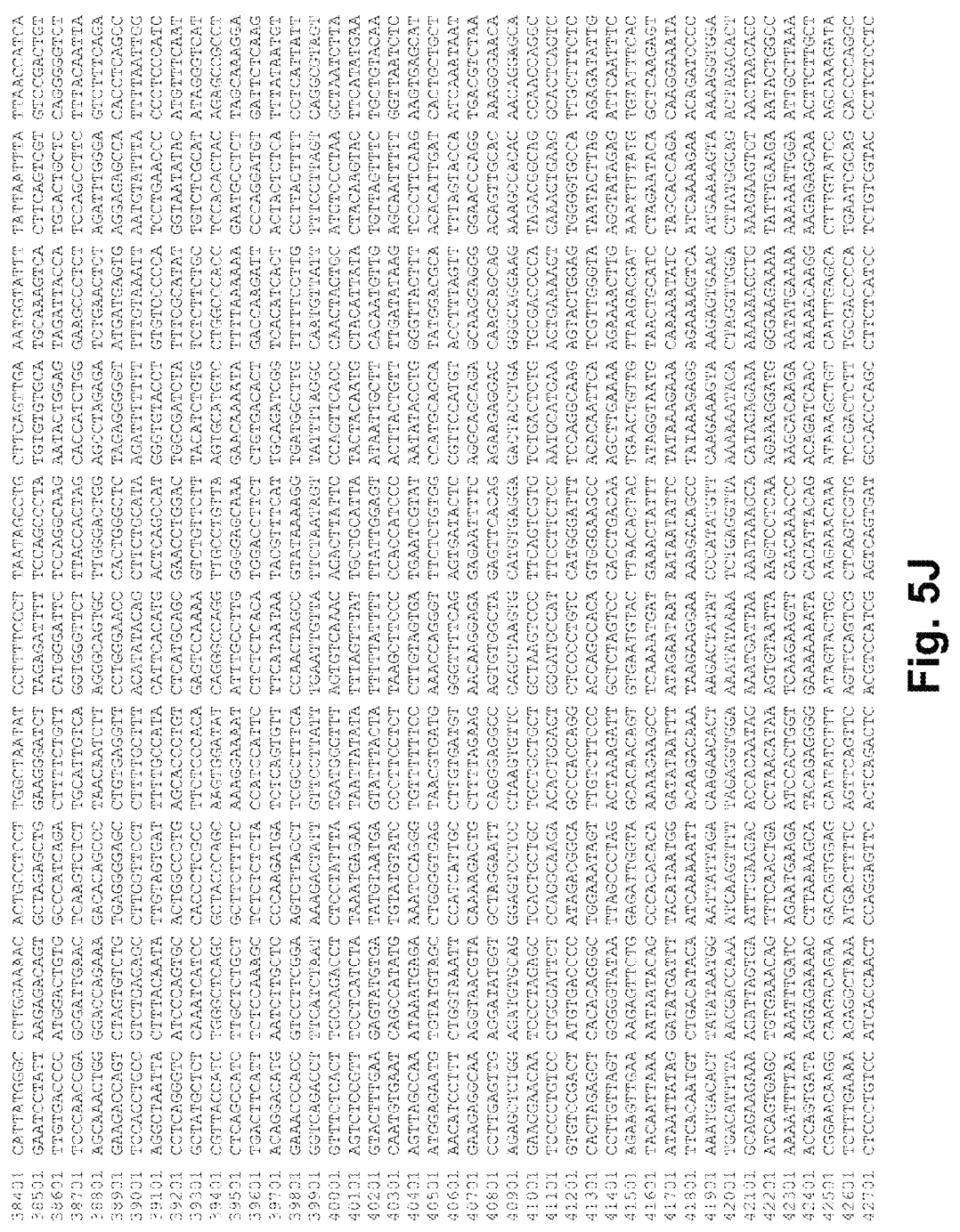
Figure 5K:
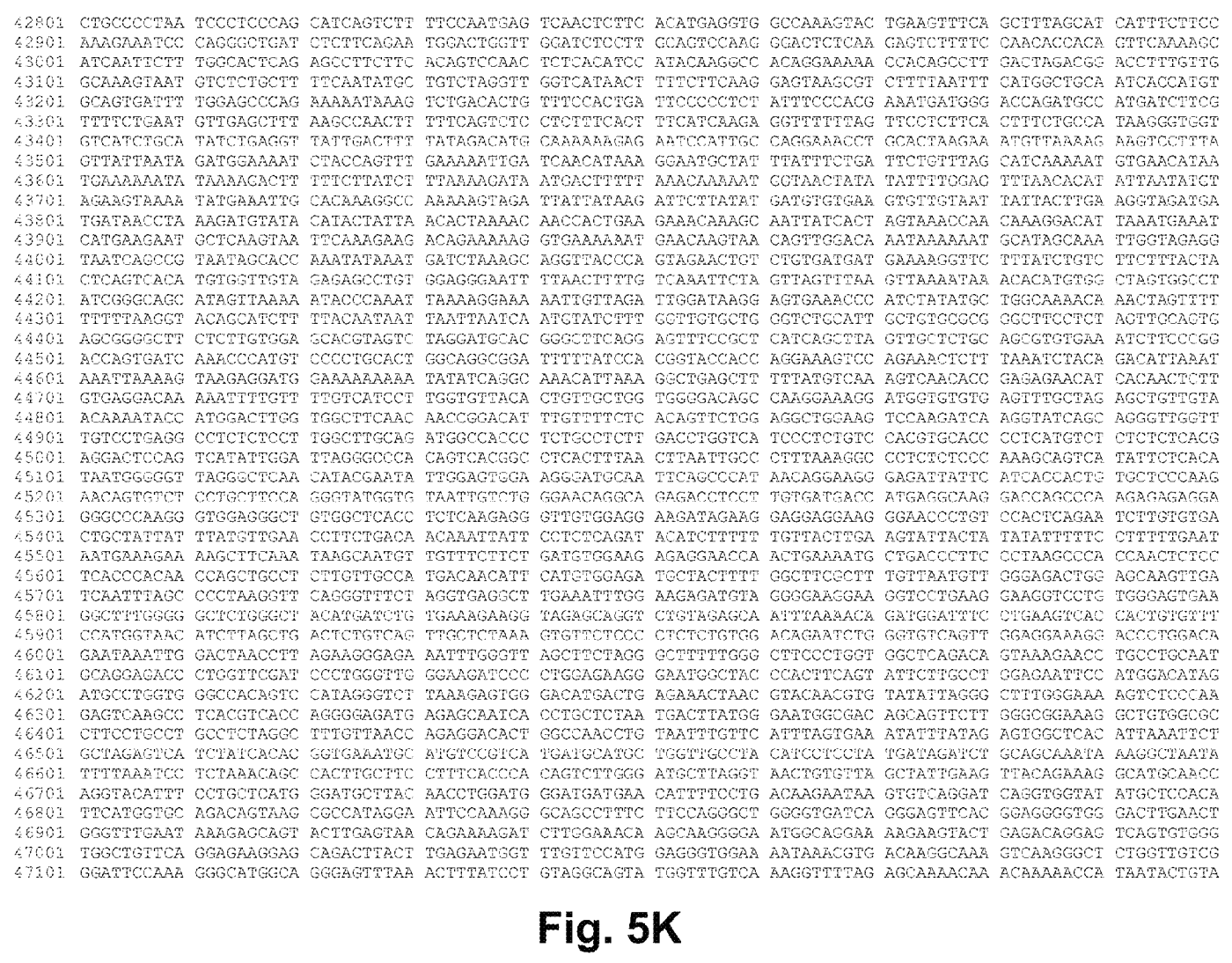
Figure 5M:
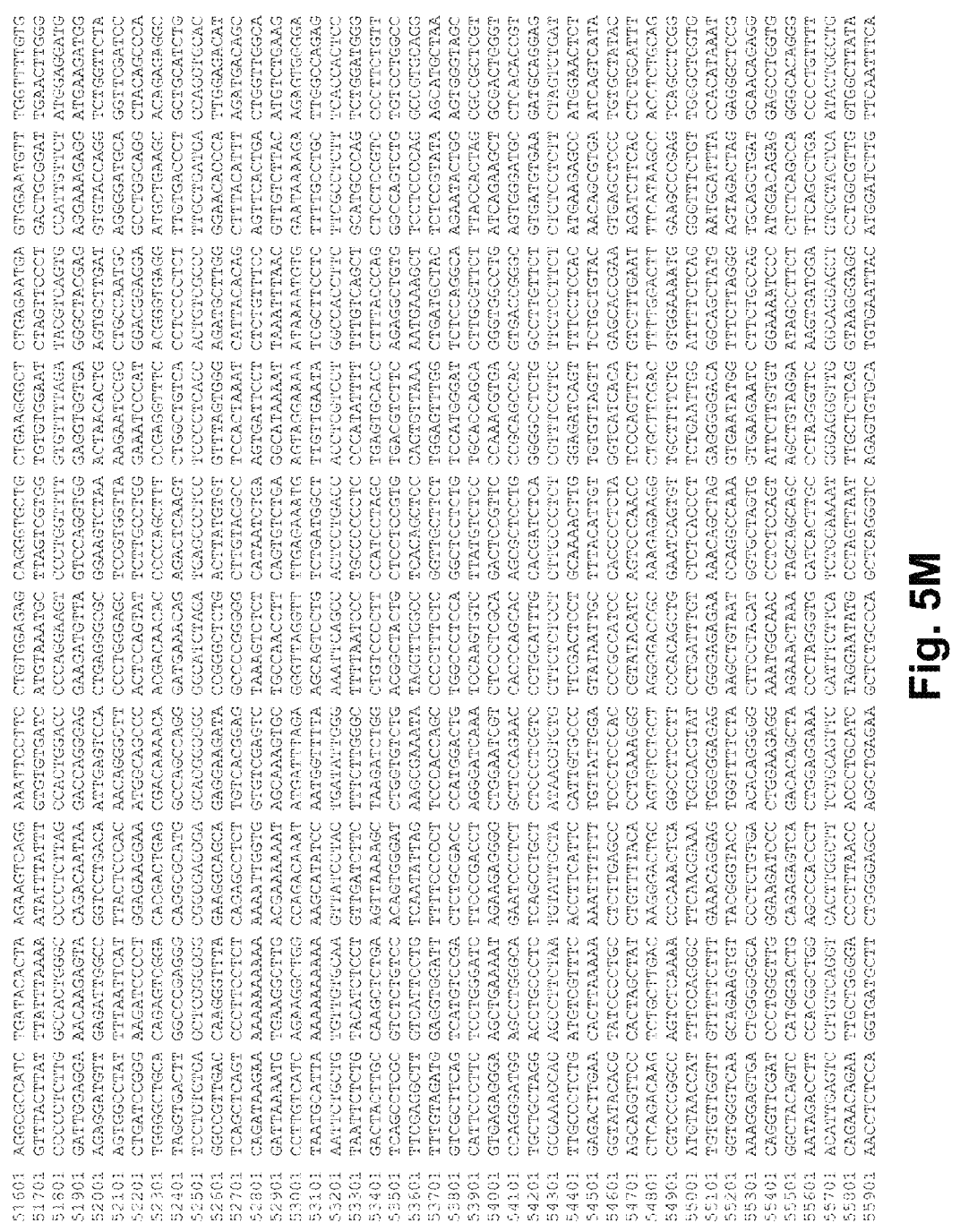
Figure 5Q:
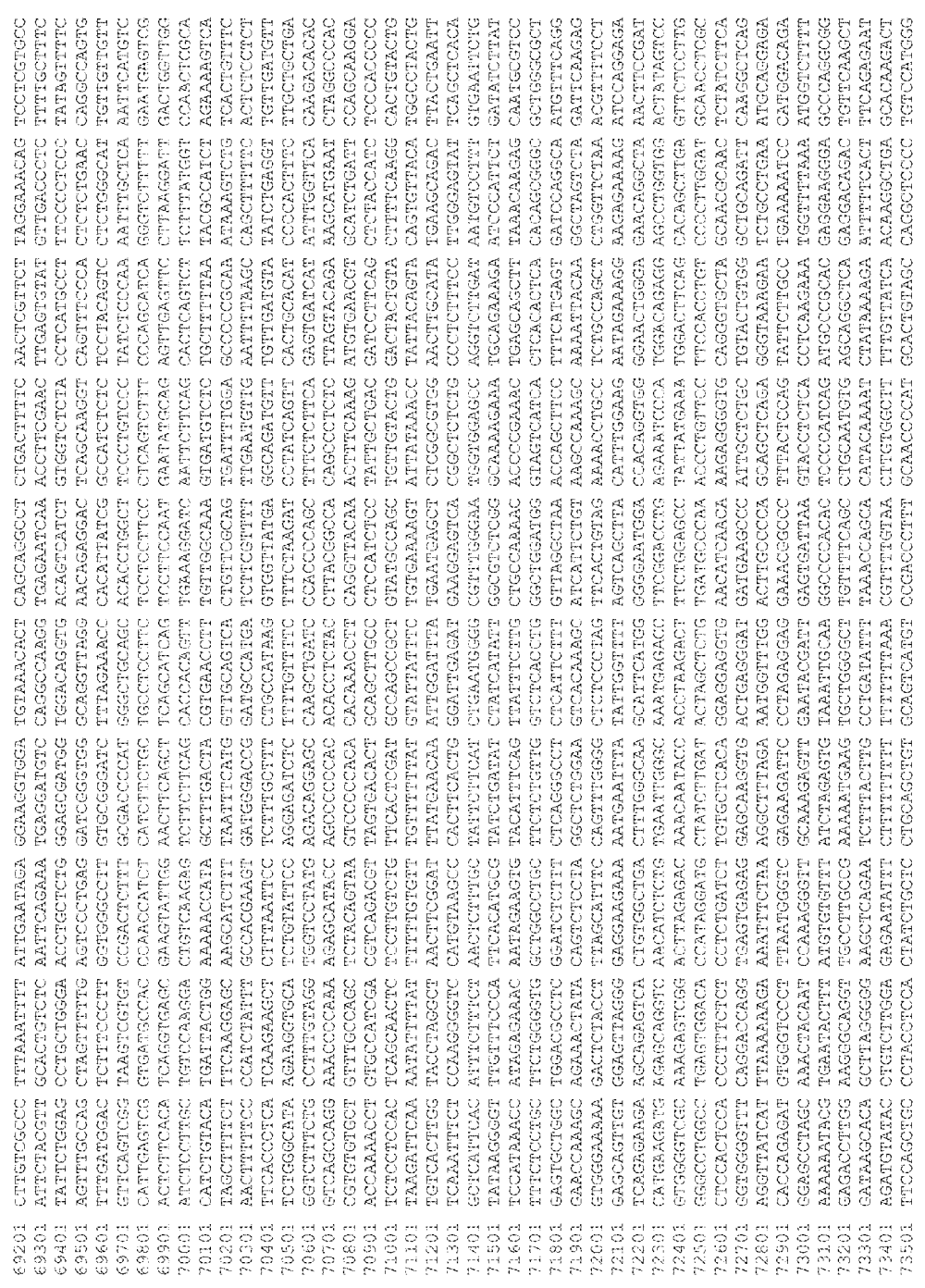
Figure 5R:
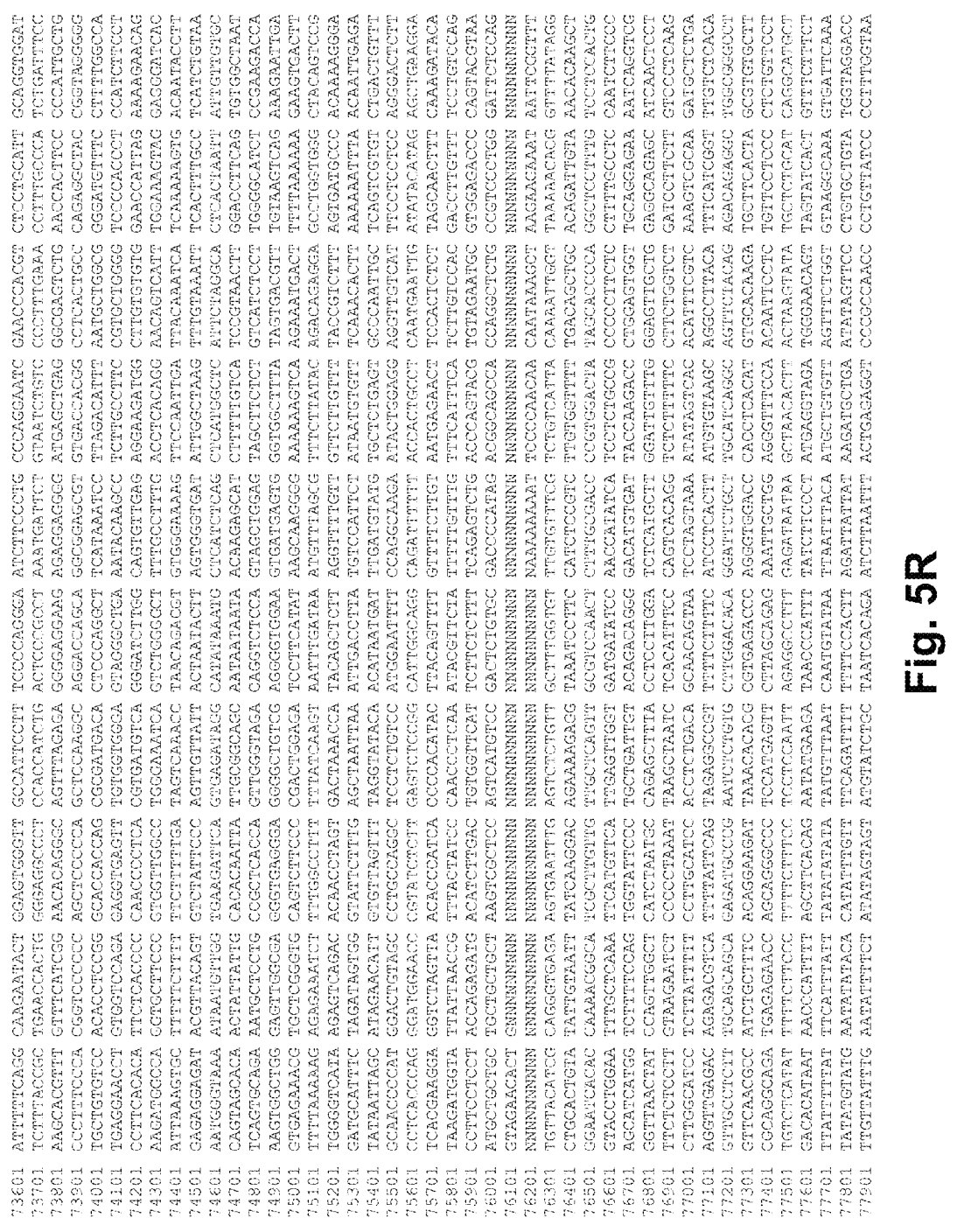
Figure 5S:
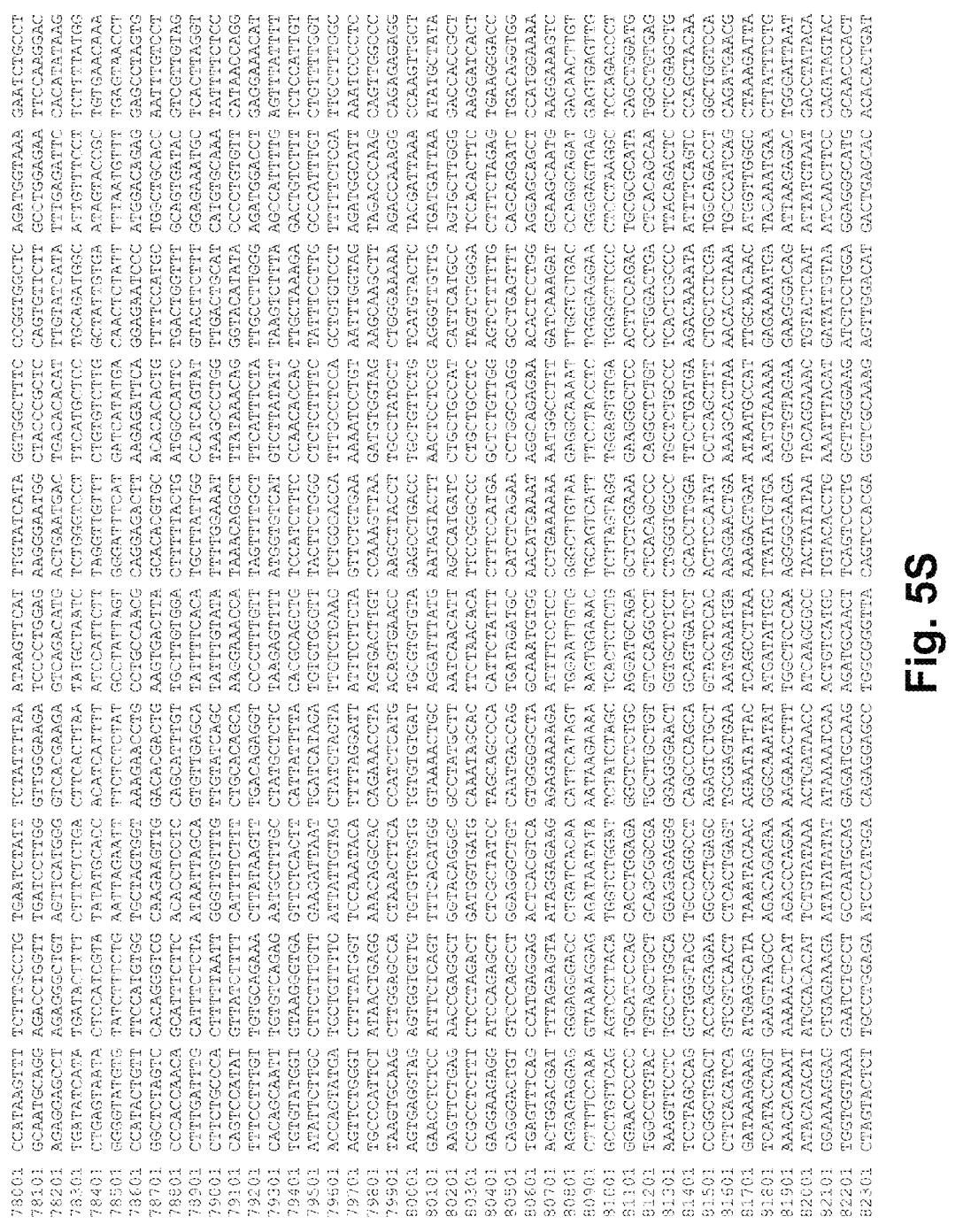
Figure 5T:
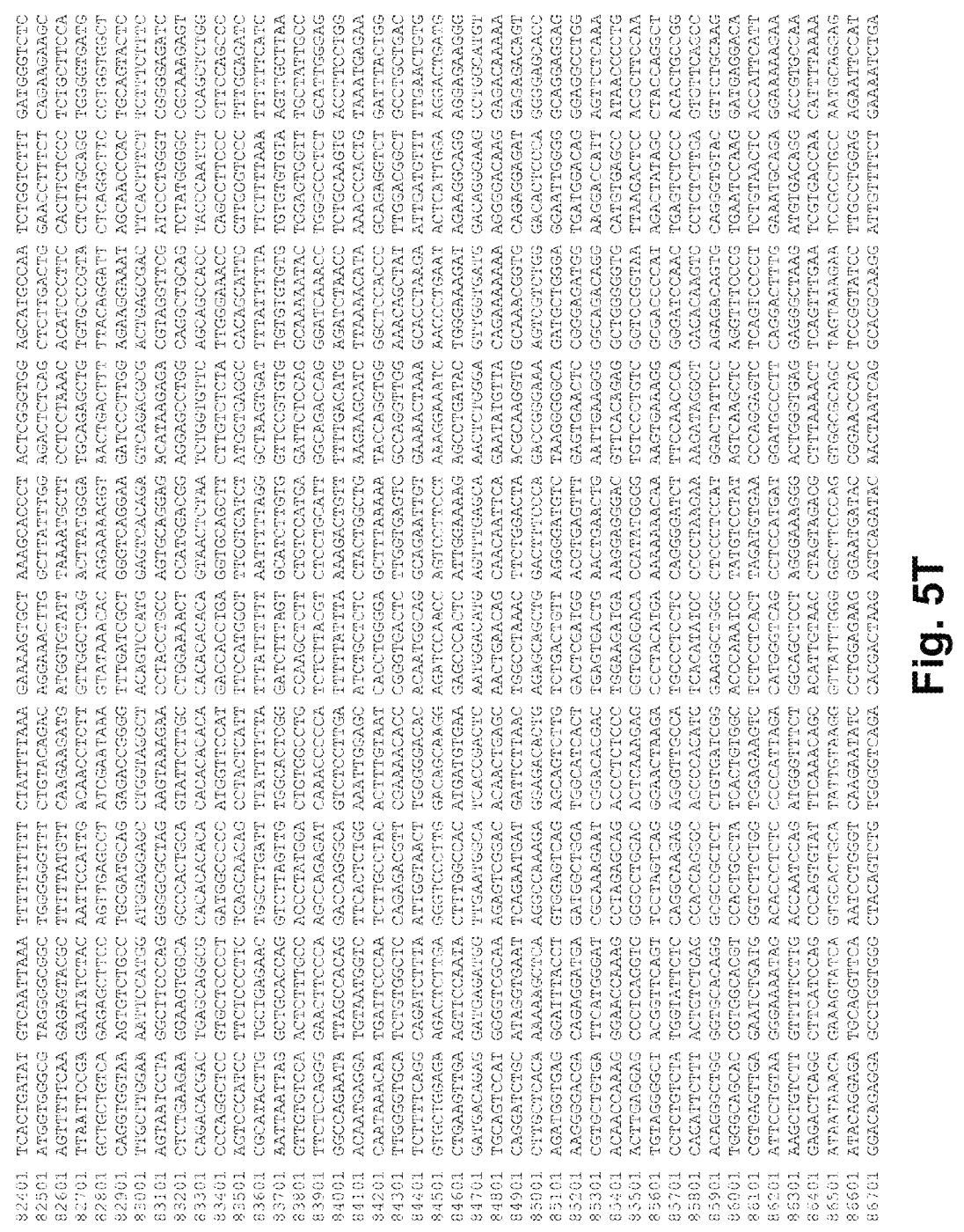
Figure 5U:
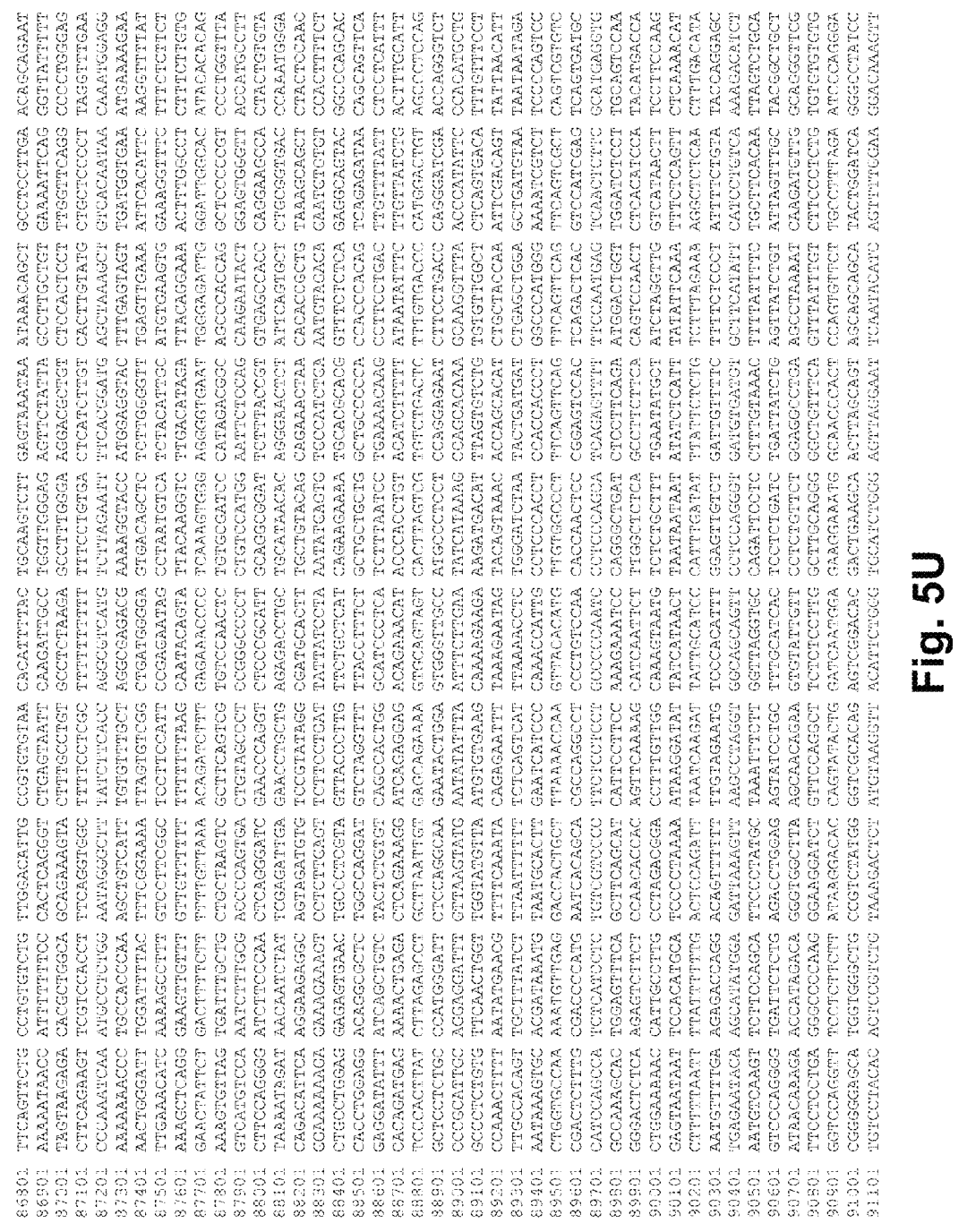
Figure 5W:
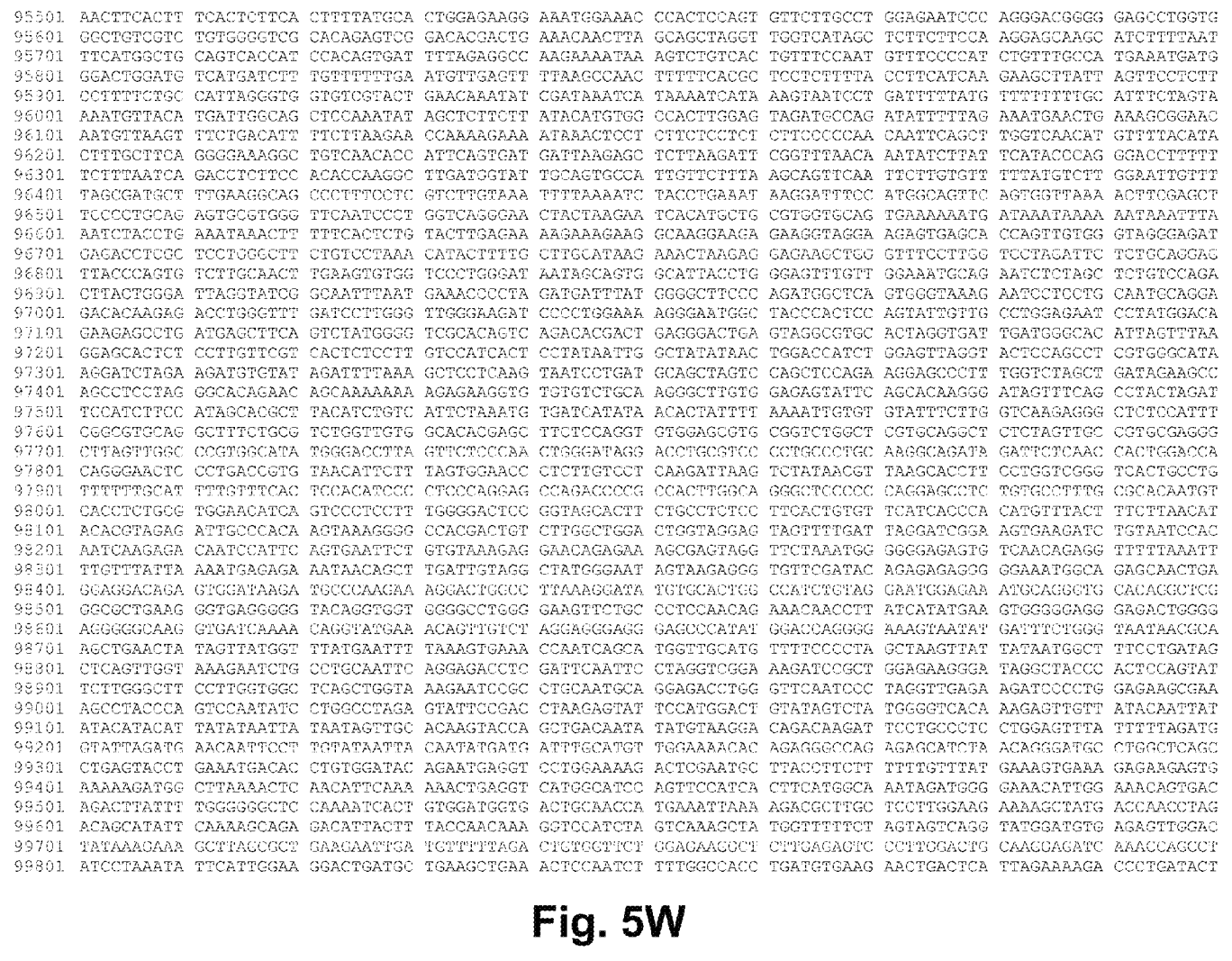
Figure 5X:
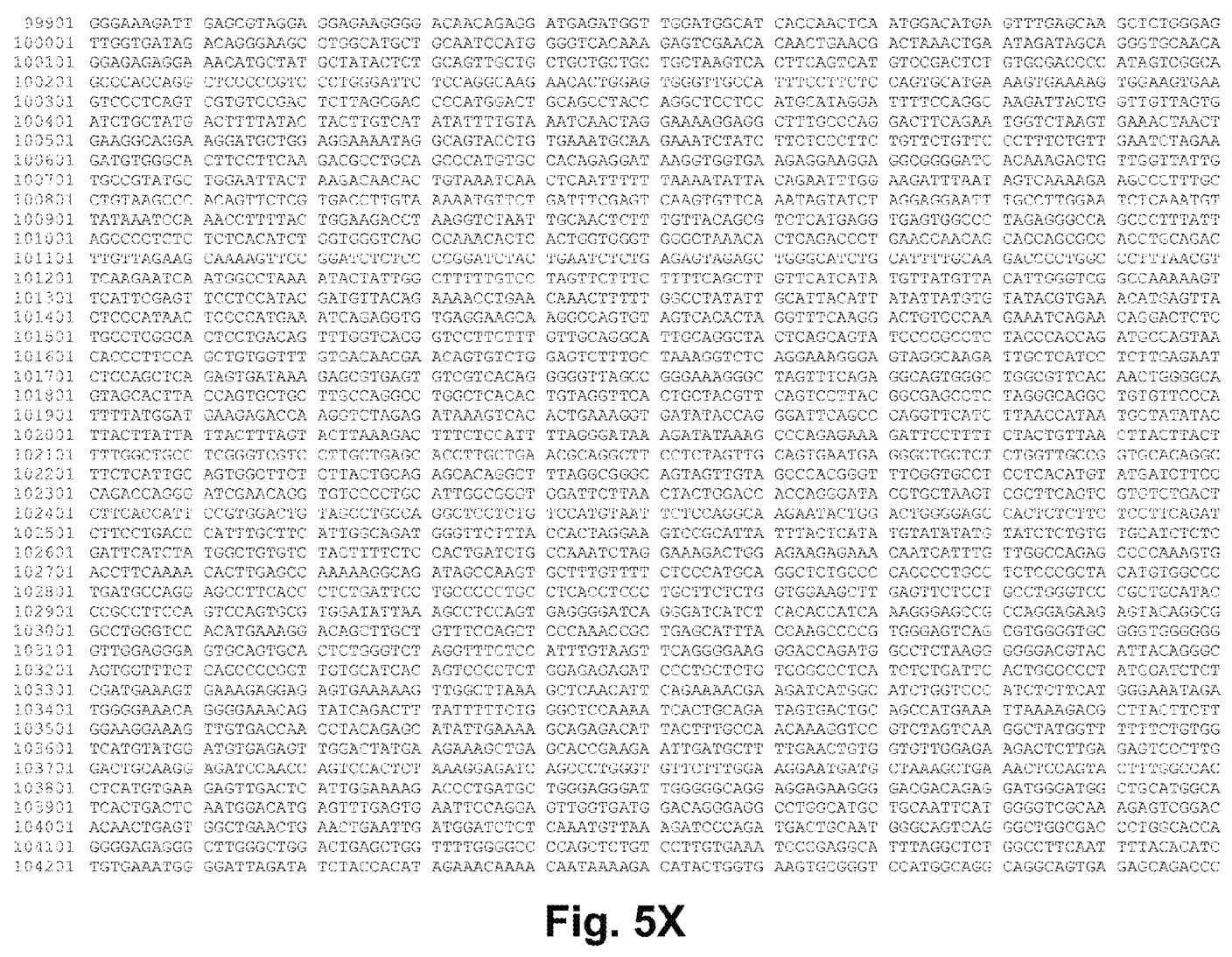
Figure 5Y:
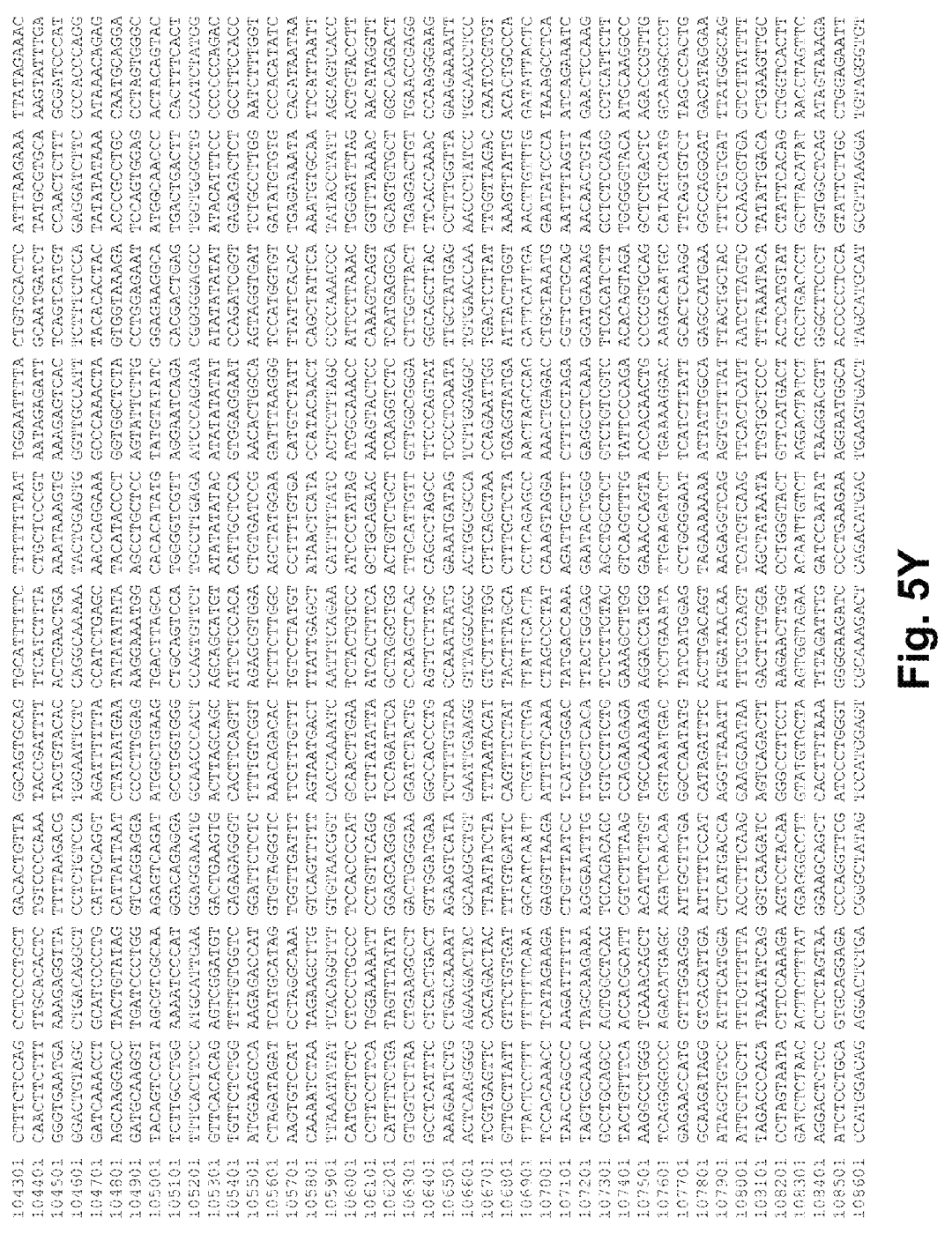
Figure 5Z:
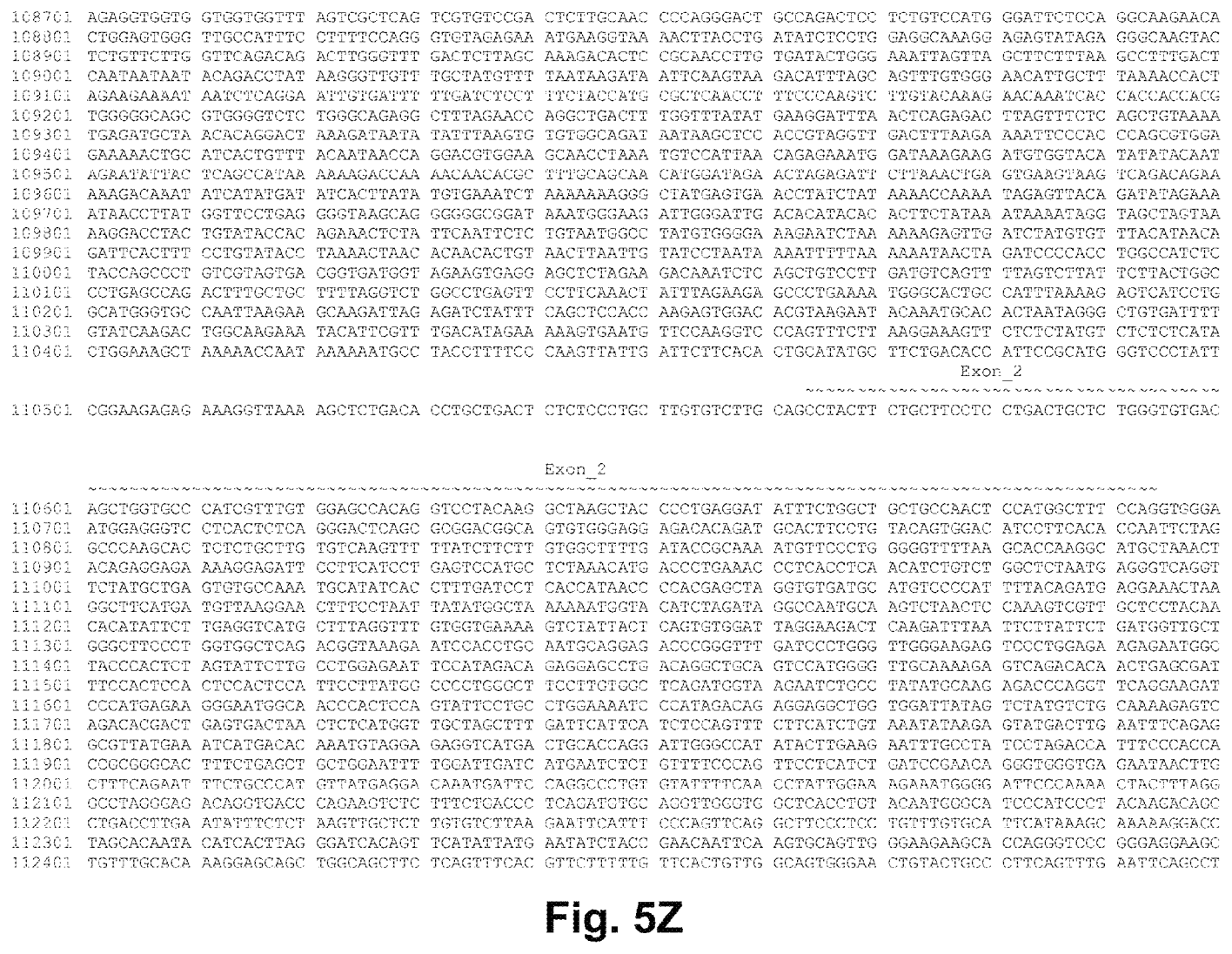

FIGS. 5A-QQ illustrate the annotated sequence of the bovine Stearoyl-CoA-Desaturase 5 ("SCD5") (SEQ ID NO:5). The positions of SNP IDs 134718 and 179412 are identified.

FIGS. 6A-C illustrate the annotated sequence of the bovine Signal Recognition Particle Receptor ("SRPR") (SEQ ID NO:6). The positions of SNP IDs 3064 and 4150 are identified.

DETAILED DESCRIPTION

1. Introduction

The present invention is based, in part, on the identification of single nucleotide polymorphisms (SNPs) in the bovine SREBP1 pathway genes (e.g., Stearoyl-CoA-Desaturase 5 (SCD5), Sterol regulatory element-binding protein-1 (SREBP1), SREBP cleavage-activating protein (SCAP), Insulin induced protein 1 (INSIG1), Insulin induced protein 2 (INSIG2) and Signal recognition particle receptor (SRPR)) that are associated with milk fat content (i.e., butterfat content) and carcass fatty acid composition (i.e., marbling) in cattle. The identified SNPs are useful as genetic markers for selection of breeding populations of cattle, including, e.g., dairy cattle and beef cattle.

2. Methods of Determining Desirable Fatty Acid Content and Disposition Traits a. Livestock Animals The present invention is useful for identifying desired phenotypes in a livestock animal based on its SREBP1, SCAP, INSIG1, INSIG2, SCD5 or SRPR genotype, for example, at SNP IDs SREBP1-13636, SCAP-34632, INSIG1-3885, INSIG1-6082, INSIG1-12052, INSIG2-93277, INSIG2-93461, INSIG2-93867, SCD5-134718, SCD5-179412, SRPR-3064 and SRPR-4150. The livestock animal can be any animal that is raised commercially for meat production or for dairy products, for example, beef, pork, mutton, lamb, goat or poultry. Oftentimes the livestock animal is a mammal. In some embodiments, the livestock animal is a bovine, ovine, equine, or porcine. In some embodiments, the livestock animal is a bovine, for example, of the genus Bos, for example, beef cattle or dairy cattle.

b. Biological Samples

The methods of the present invention involve taking a biological sample comprising genomic DNA from the animal to be tested. The biological sample can be from solid tissue or a biological fluid that contains a nucleic acid comprising a single nucleotide polymorphism (SNP) described herein, e.g., a nucleic acid comprising a SREBP1, SCAP, INSIG1, INSIG2, SCD5 or SRPR gene. The biological sample can be tested by the methods described herein and include body fluids including whole blood, serum, plasma, cerebrospinal fluid, urine, lymph fluids, semen, and various external secretions of the respiratory, intestinal and genitourinary tracts, tears, saliva, milk, white blood cells, myelomas, and the like; and biological fluids such as cell extracts, cell culture supernatants; fixed tissue specimens; and fixed cell specimens. Biological samples can also be from solid tissue, including hair bulb, skin, biopsy or autopsy samples or frozen sections taken for histologic purposes. These samples are well known in the art. A biological sample is obtained from any livestock animal to be tested for SREBP1, SCAP, INSIG1, INSIG2, SCD5 or SRPR SNPs as described herein, including, e.g., a beef or dairy cow. A biological sample can be suspended or dissolved in liquid materials such as buffers, extractants, solvents and the like.

c. SNPs in Fatty Acid Metabolism Genes Correlated with Desirable Traits

Livestock mammals, including bovines, ovines, equines and porcines, are diploid organisms possessing pairs of homologous chromosomes. Thus, at a typical genetic locus, an animal has three possible genotypes that can result from the combining of two different alleles (e.g. A and B). The animal may be homozygous for one or another allele, or heterozygous, possessing one of each of the two possible alleles (e.g. AA, BB or AB).

The SNP IDs statistically correlated with desirable fatty acid disposition and content phenotypes include SREBP1-13636, SCAP-34632, INSIG1-3885, INSIG1-6082, INSIG1-12052; INSIG2-93277, INSIG2-93461, INSIG2-93867, SCD5-134718, SCD5-179412, SRPR-3064 and SRPR-4150.

Figure 1B:
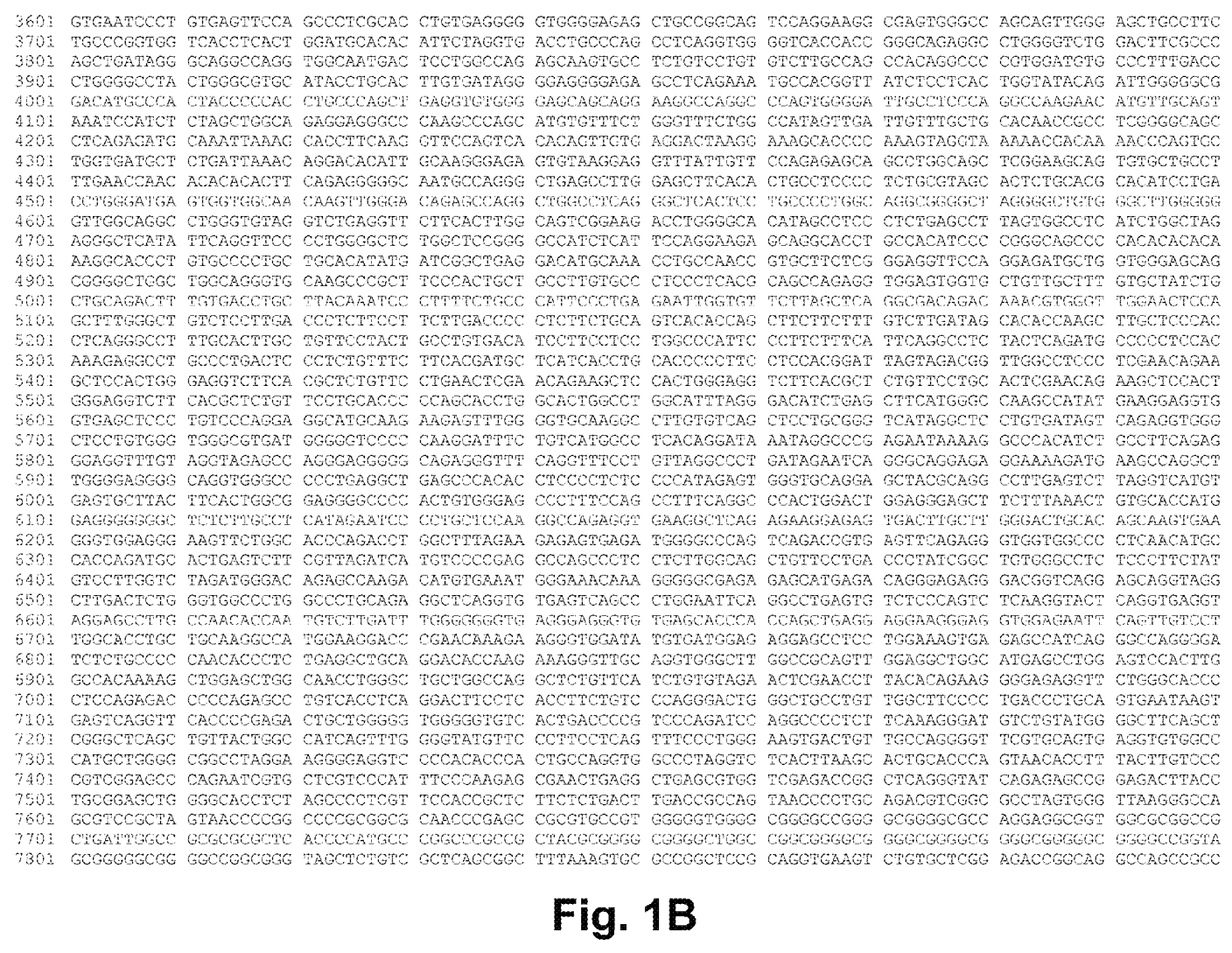
Figure 1C:
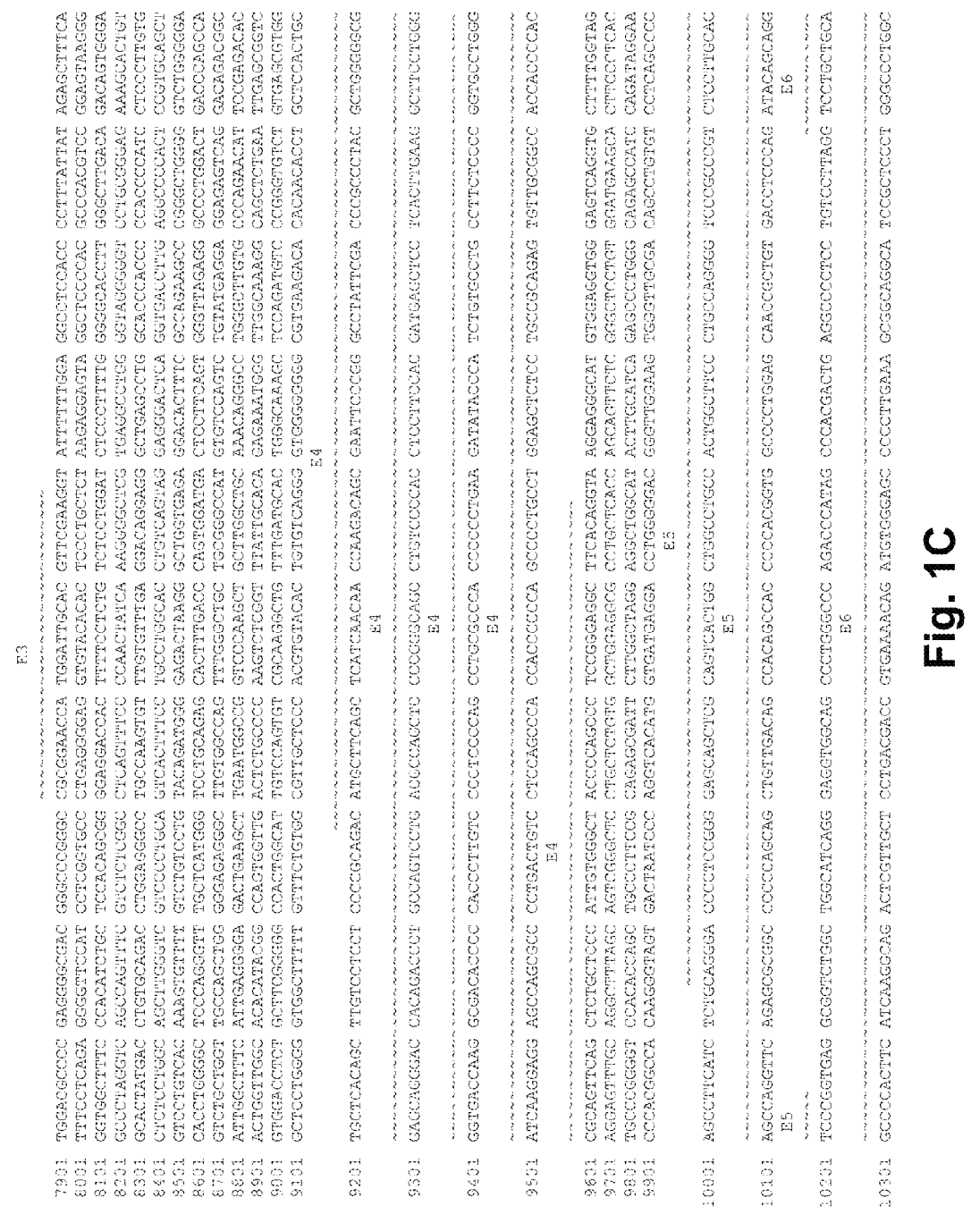
Figure 1D:
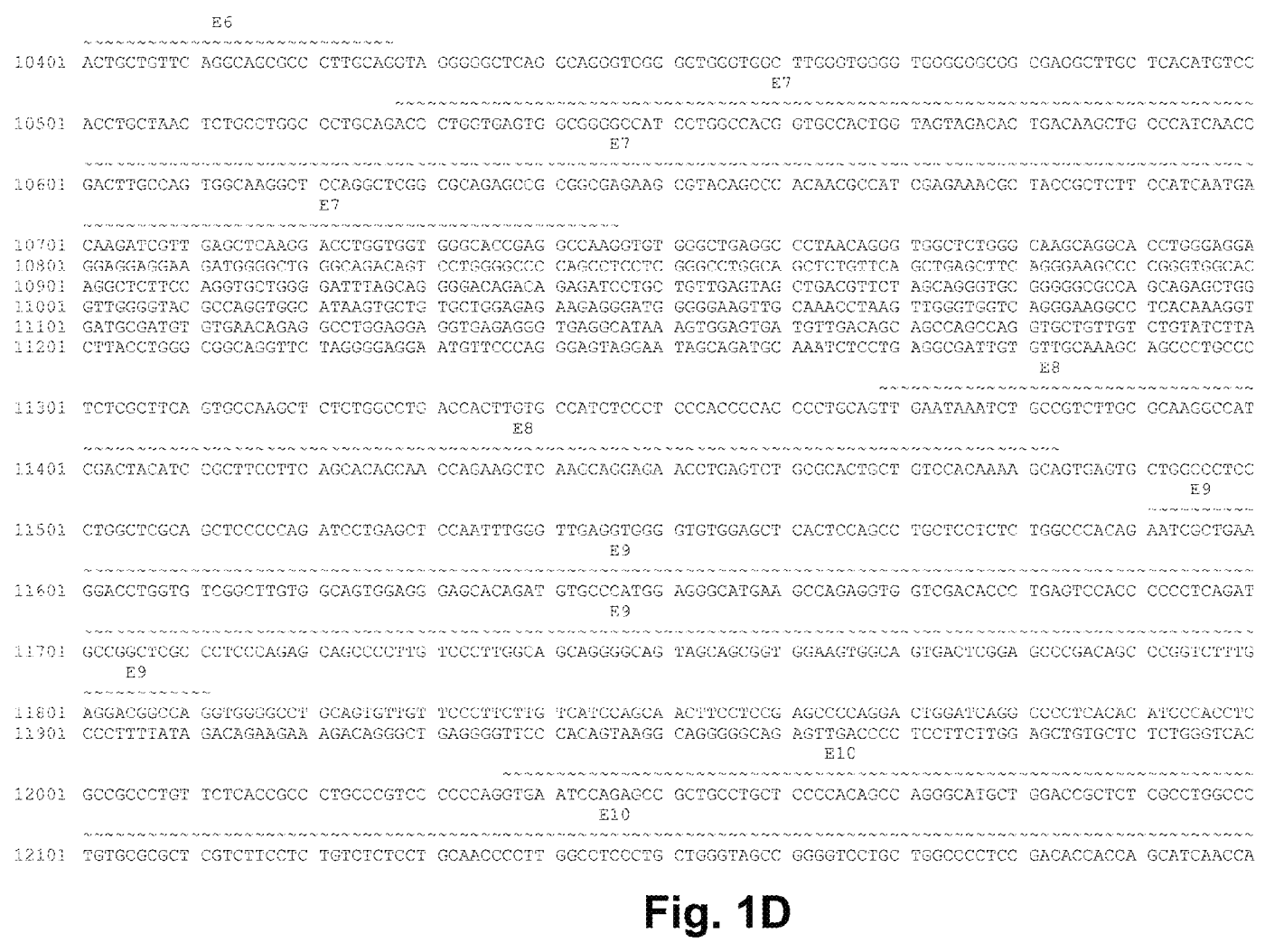

SREBP1 SNP ID 13636 is identified in FIG. 1. As shown in FIG. 1, SREBP1 SNP ID 13636 is positioned at nucleotide 14495 of the bovine genomic sequence of SREBP1 depicted in FIG. 1, or at position 14495 of SEQ ID NO:1. SREBP1 SNP ID 13636 is also positioned at nucleotide 66 of exon 16 of the SREBP1 sequence depicted in FIG. 1. A homozygous "TT" genotype at SREBP1 SNP ID 13636 is statistically correlated with the phenotype of decreased predicted transmitting ability for fat (PTAF). A homozygous "CC" genotype at SREBP1 SNP ID 13636 is statistically correlated with the phenotype of increased predicted transmitting ability for fat (PTAF). See, Table 2. The flanking sequences surrounding SREBP1 SNP ID 13636 are shown in Table 3.

SCAP SNP ID 34632 is identified in FIG. 2. As shown in FIG. 2, SCAP SNP ID 34632 is positioned at nucleotide 32025 of the bovine genomic sequence of SCAP depicted in FIG. 2, or at position 32025 of SEQ ID NO:2. SCAP SNP ID 34632 is also positioned at nucleotide 31 of exon 8 of the SCAP sequence depicted in FIG. 2. A homozygous "TT" genotype at SCAP SNP ID 34632 is statistically correlated with the phenotype of increased predicted transmitting ability for milk (PTAM), increased predicted transmitting ability for protein (PTAP), increased cheese dollars (CHEESD), increased net merit dollars (NMD) and increased net merit protein (NMP). A homozygous "CC" genotype at SCAP SNP ID 34632 is statistically correlated with the phenotype of decreased predicted transmitting ability for milk (PTAM), decreased predicted transmitting ability for protein (PTAP), decreased cheese dollars (CHEESD), decreased net merit dollars (NMD) and decreased net merit protein (NMP). See, Table 2. The flanking sequences surrounding SCAP SNP ID 34632 are shown in Table 3.

Figure 3B:
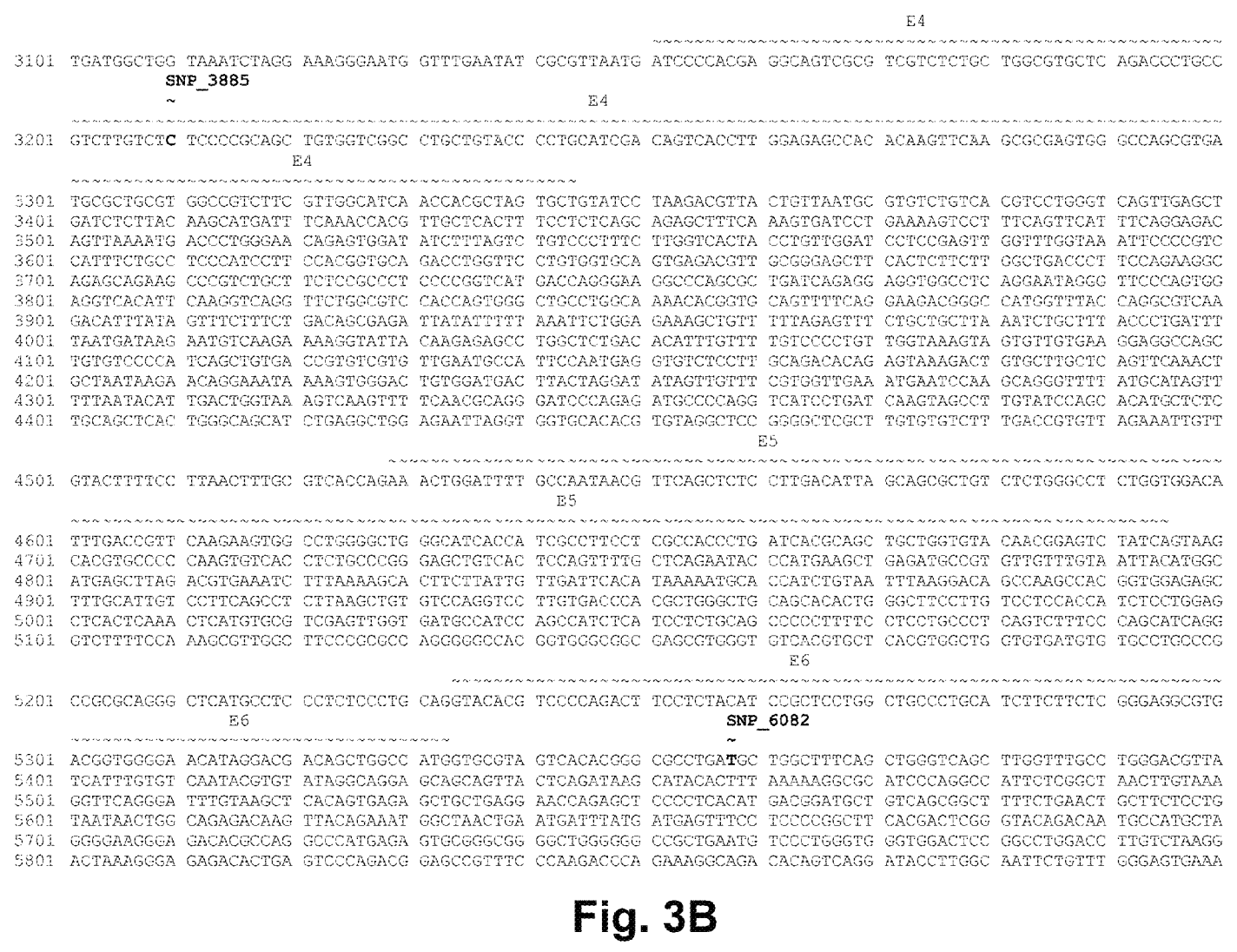
Figure 3C:
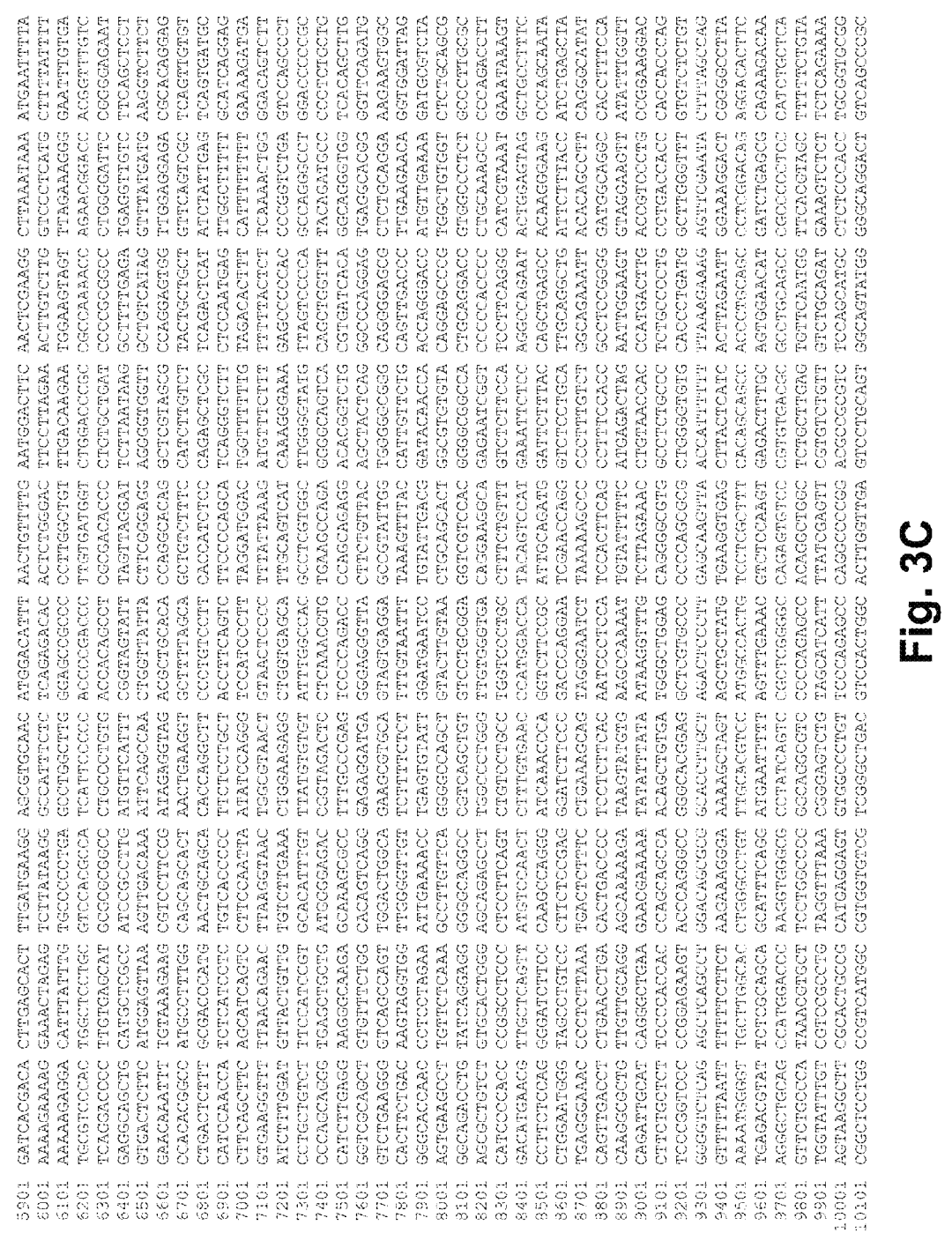

INSIG1 SNP ID 3885 is identified in FIG. 3. As shown in FIG. 3, INSIG1 SNP ID 3885 is positioned at nucleotide 3210 of the bovine genomic sequence of INSIG1 depicted in FIG. 3, or at position 3210 of SEQ ID NO:3. INSIG1 SNP ID 3885 is also positioned at nucleotide 60 of exon 4 of the INSIG1 sequence depicted in FIG. 3. A homozygous "TT" genotype at INSIG1 SNP ID 3885 is statistically correlated with the phenotype of increased predicted transmitting ability for fat (PTAF), increased cheese dollars (CHEESD), increased net merit dollars (NMD) and increased net merit protein (NMP). A homozygous "CC" genotype at INSIG1 SNP ID 3885 is statistically correlated with phenotype of decreased predicted transmitting ability for fat (PTAF), decreased cheese dollars (CHEESD), decreased net merit dollars (NMD) and decreased net merit protein (NMP). See, Table 2. The flanking sequences surrounding INSIG1 SNP ID 3885 are shown in Table 3.

INSIG1 SNP ID 6082 is identified in FIG. 3. As shown in FIG. 3, INSIG1 SNP ID 6082 is positioned at nucleotide 5358 of the bovine genomic sequence of INSIG1 depicted in FIG. 3, or at position 5358 of SEQ ID NO:3. INSG1 SNP ID 6082 is also positioned at nucleotide 25 of intron 6 of the INSIG1 sequence depicted in FIG. 3. A heterozygous "GT" and a homozygous "GG" genotype at INSIG1 SNP ID 6082 is statistically correlated with the phenotype of increased predicted transmitting ability for milk (PTAM), increased predicted transmitting ability for fat (PTAF), increased predicted transmitting ability for protein (PTAP), increased cheese dollars (CHEESD), increased net merit dollars (NMD) and increased net merit protein (NMP). A homozygous "TT" genotype at INSIG1 SNP ID 6082 is statistically correlated with phenotype of decreased predicted transmitting ability for milk (PTAM), decreased predicted transmitting ability for fat (PTAF), decreased predicted transmitting ability for protein (PTAP), decreased cheese dollars (CHEESD), decreased net merit dollars (NMD) and decreased net merit protein (NMP). See, Table 2. The flanking sequences surrounding INSIG1 SNP ID 6082 are shown in Table 3.

INSIG1 SNP ID 12052 is identified in FIG. 3. As shown in FIG. 3, INSIG1 SNP ID 12052 is positioned at nucleotide 11328 of the bovine genomic sequence of INSIG1 depicted in FIG. 3, or at position 11328 of SEQ ID NO:3. INSIG1 SNP ID 12052 is also positioned at nucleotide 492 of the 3' untranslated region (3' UTR) of the INSIG1 sequence depicted in FIG. 3. A homozygous "AA" genotype at INSIG1 SNP ID 12052 is statistically correlated with the phenotype of increased predicted transmitting ability for milk (PTAM), increased predicted transmitting ability for fat (PTAF), increased predicted transmitting ability for protein (PTAP), increased cheese dollars (CHEESD), increased net merit dollars (NMD) and increased net merit protein (NMP). A homozygous "GG" genotype at INSIG1 SNP ID 12052 is statistically correlated with phenotype of decreased predicted transmitting ability for milk (PTAM), decreased predicted transmitting ability for fat (PTAF), decreased predicted transmitting ability for protein (PTAP), decreased cheese dollars (CHEESD), decreased net merit dollars (NMD) and decreased net merit protein (NMP). See, Table 2. The flanking sequences surrounding INSIG1 SNP ID 12052 are shown in Table 3.

Figure 4C:
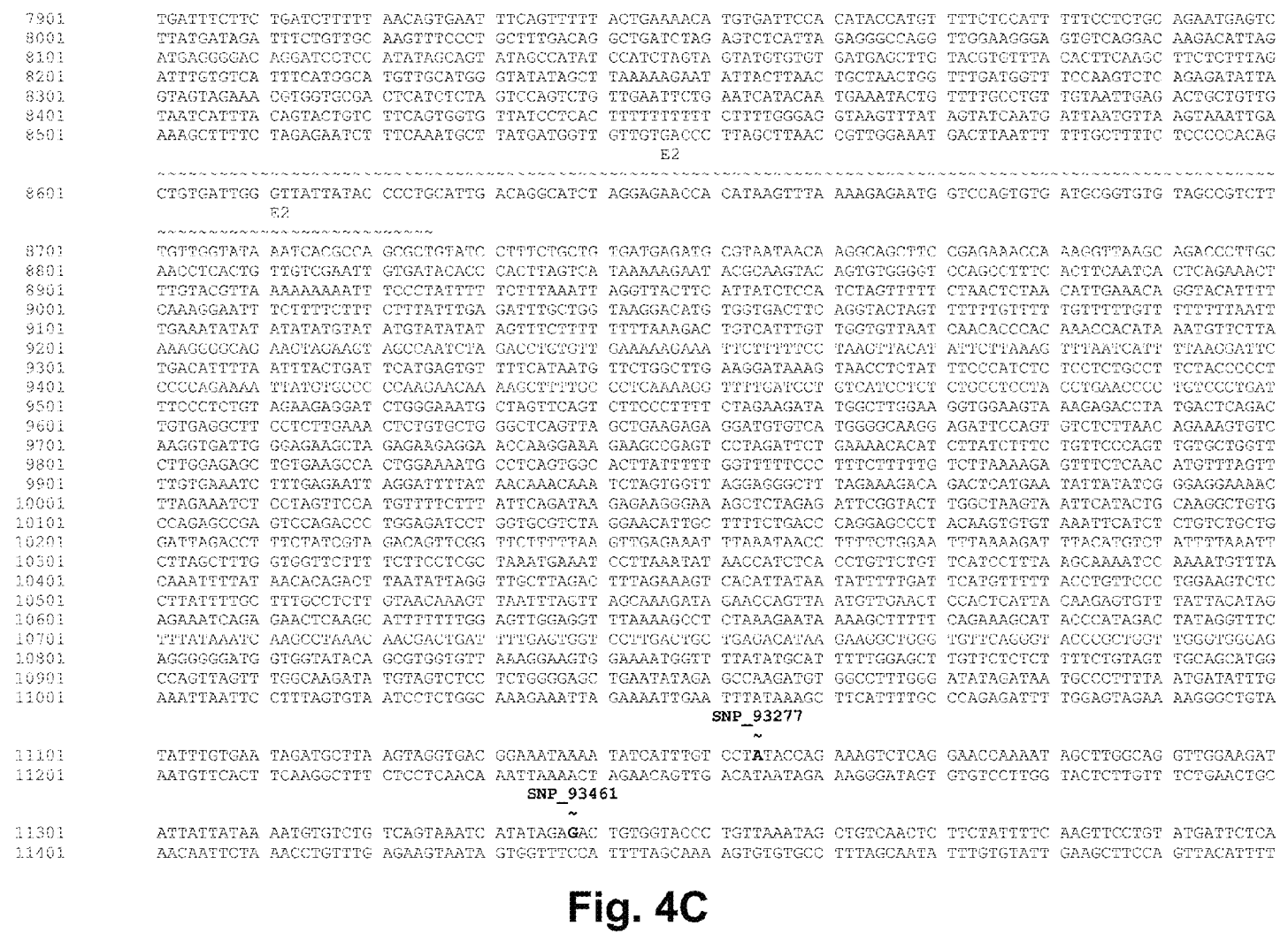
Figure 4D:
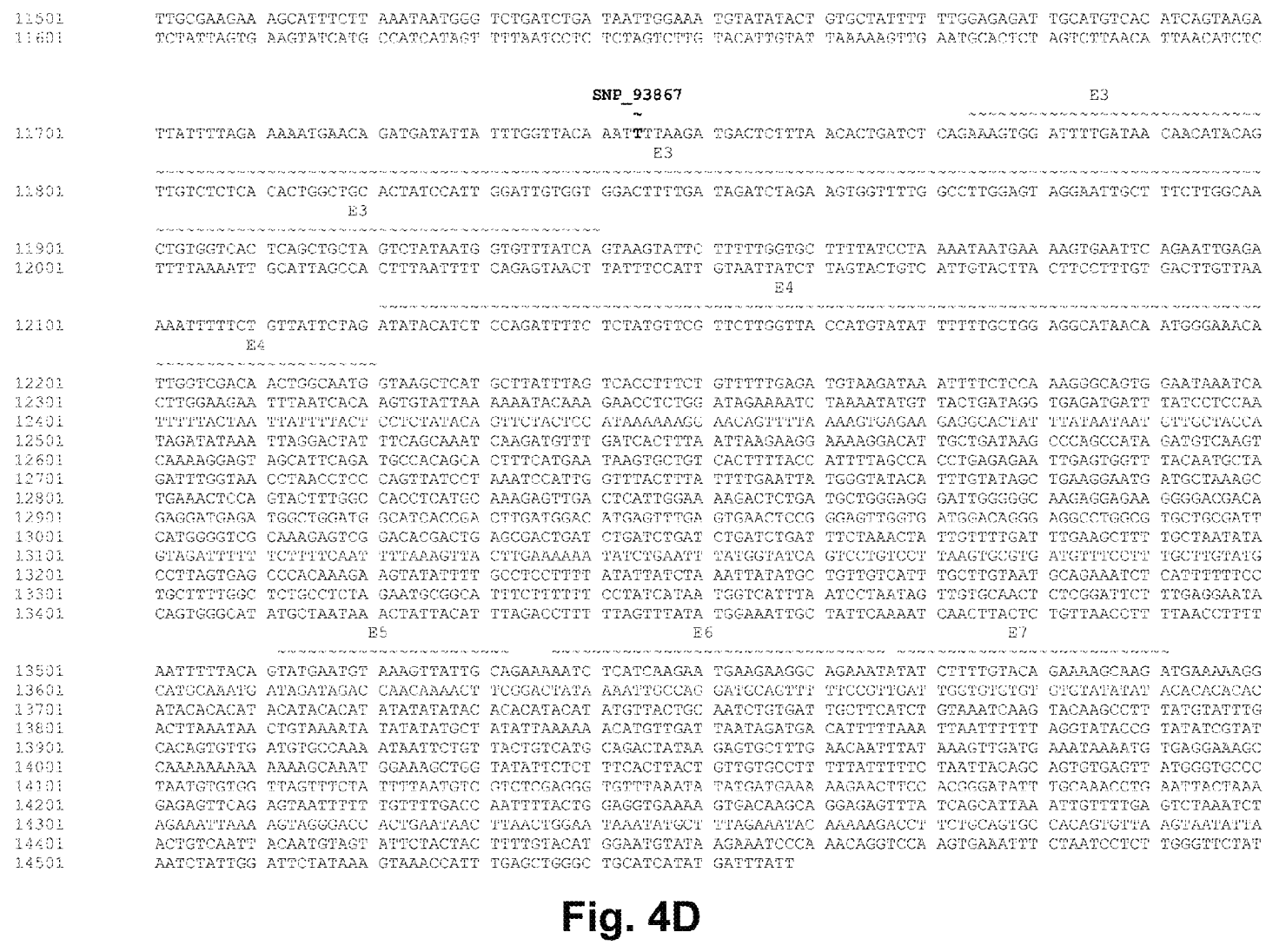

INSIG2 SNP ID 93277 is identified in FIG. 4. As shown in FIG. 4, INSIG2 SNP ID 93277 is positioned at nucleotide 11154 of the bovine genomic sequence of INSIG2 depicted in FIG. 4, or at position 11154 of SEQ ID NO:4. INSIG2 SNP ID 93277 is also positioned at nucleotide 2429 of intron 2 of the INSIG2 sequence depicted in FIG. 4. A homozygous "CC" genotype at INSIG2 SNP ID 93277 is statistically correlated with the phenotype of increased predicted transmitting ability for fat percentage (PTAFP). A homozygous "AA" genotype at INSIG2 SNP ID 93277 is statistically correlated with phenotype of decreased predicted transmitting ability for fat percentage (PTAFP). See, Table 2. The flanking sequences surrounding INSIG2 SNP ID 93277 are shown in Table 3.

INSIG2 SNP ID 93461 is identified in FIG. 4. As shown in FIG. 4, INSIG2 SNP ID 93461 is positioned at nucleotide 11338 of the bovine genomic sequence of INSIG2 depicted in FIG. 4, or at position 11338 of SEQ ID NO:4. INSIG2 SNP ID 93461 is also positioned at nucleotide 2613 of intron 2 of the INSIG2 sequence depicted in FIG. 4. A homozygous "CC" genotype at INSIG2 SNP ID 93461 is statistically correlated with the phenotype of increased health index and decreased short chain fatty acids. A homozygous "GG" genotype at INSIG2 SNP ID 93461 is statistically correlated with the phenotype of decreased health index and increased short chain fatty acids. See, Table 1. The flanking sequences surrounding INSIG2 SNP ID 93461 are shown in Table 3.

INSIG2 SNP ID 93867 is identified in FIG. 4. As shown in FIG. 4, INSIG2 SNP ID 93867 is positioned at nucleotide 11744 of the bovine genomic sequence of INSIG2 depicted in FIG. 4, or at position 11744 of SEQ ID NO:4. INSIG2 SNP ID 93867 is also positioned at nucleotide 3019 of intron 2 of the INSIG2 sequence depicted in FIG. 4. A homozygous "CC" genotype at INSIG2 SNP ID 93867 is statistically correlated with the phenotype of decreased saturated fatty acid, increased PUFA, increased C6 to C14 fatty acid, increased C14:1/C14:0 ratio and increased CLA 9-11 content. A homozygous "TT" genotype at INSIG2 SNP ID 93867 is statistically correlated with the phenotype of increased saturated fatty acid, decreased PUFA, decreased C6 to C14 fatty acid, decreased C14:1/C14:0 ratio and decreased CLA 9-11 content. See, Table 1. The flanking sequences surrounding INSIG2 SNP ID 93867 are shown in Table 3.

SCD5 SNP ID 134718 is identified in FIG. 5. As shown in FIG. 5, SCD5 SNP ID 134718 is positioned at nucleotide 134718 of the bovine genomic sequence of SCD5 depicted in FIG. 5, or at position 134718 of SEQ ID NO:5. SCD5 SNP ID 134718 is also positioned at nucleotide 165 of exon 3 of the SCD5 sequence depicted in FIG. 5. A homozygous "CC" genotype at SCD5 SNP ID 134718 is statistically correlated with the phenotype of increased health index, decreased saturated fatty acid, increased MUFA, decreased C6 to C14 fatty acid and increased CLA 9-11 content. A homozygous "TT" genotype at SCD5 SNP ID 134718 is statistically correlated with the phenotype of decreased health index, increased saturated fatty acid, decreased MUFA, increased C6 to C 14 fatty acid and decreased CLA 9-11 content. See, Table 1. The flanking sequences surrounding SCD5 SNP ID 134718 are shown in Table 3.

SCD5 SNP ID 179412 is identified in FIG. 5. As shown in FIG. 5, SCD5 SNP ID 179412 is positioned at nucleotide 179412 of the bovine genomic sequence of SCD5 depicted in FIG. 5, or at position 179412 of SEQ ID NO:5. SCD5 SNP ID 179412 is also positioned at nucleotide 770 of exon 5 of the SCD5 sequence depicted in FIG. 5. A homozygous "TT" genotype at SCD5 SNP ID 179412 is statistically correlated with the phenotype of decreased saturated fatty acid, increased PUFA, increased C14:1/C14:0 ratio, increased C16:1/C16:0 ratio, increased CLA 9-11, decreased predicted transmitting ability of milk (PTAM), decreased predicted transmitting ability of protein (PTAP), decreased net merit dollars (NMD) and decreased net merit protein (NMP). A homozygous "GG" genotype at SCD5 SNP ID 179412 is statistically correlated with the phenotype of increased saturated fatty acid, decreased PUFA, decreased C14:1/C14:0 ratio, decreased C16:1/C16:0 ratio, decreased CLA 9-11, increased predicted transmitting ability of milk (PTAM), increased predicted transmitting ability of protein (PTAP), increased net merit dollars (NMD) and increased net merit protein (NMP). See, Tables 1 and 2. The flanking sequences surrounding SCD5 SNP ID 179412 are shown in Table 3.

SRPR SNP ID 3064 is identified in FIG. 6. As shown in FIG. 6, SRPR SNP ID 3064 is positioned at nucleotide 3064 of the bovine genomic sequence of SRPR depicted in FIG. 6, or at position 3064 of SEQ ID NO:6. SRPR SNP ID 3064 is also positioned at nucleotide 214 of intron 4 of the SRPR sequence depicted in FIG. 6. A homozygous "AA" genotype at SRPR SNP ID 3064 is statistically correlated with the phenotype of increased net merit dollar (NMD), increased net merit protein (NMP) and increased cheese dollar (CHEESD). A homozygous "GG" genotype at SRPR SNP ID 3064 is statistically correlated with the phenotype of decreased net merit dollar (NMD), decreased net merit protein (NMP) and decreased cheese dollar (CHEESD). See, Table 2. The flanking sequences surrounding SRPR SNP ID 3064 are shown in Table 3.

SRPR SNP ID 4150 is identified in FIG. 6. As shown in FIG. 6, SRPR SNP ID 4150 is positioned at nucleotide 4150 of the bovine genomic sequence of SRPR depicted in FIG. 6, or at position 4150 of SEQ ID NO:6. SRPR SNP ID 4150 is also positioned at nucleotide 69 of intron 8 of the SRPR sequence depicted in FIG. 6. A homozygous "CC" genotype at SRPR SNP ID 4150 is statistically correlated with the phenotype of increased health index, decreased saturated fatty acid, increased MUFA, increased medium and long chain fatty acid, increased predicted transmitting ability of milk (PTAM), increased transmitting ability of fat (PTAF), increased cheese dollar (CHEESD), net merit dollar (NMD) and increased net merit protein (NMP). A homozygous "GG" genotype at SRPR SNP ID 4150 is statistically correlated with the phenotype of decreased health index, increased saturated fatty acid, decreased MUFA, decreased medium and long chain fatty acid, decreased predicted transmitting ability of milk (PTAM), decreased transmitting ability of fat (PTAF), decreased cheese dollar (CHEESD), decreased net merit dollar (NMD) and decreased net merit protein (NMP). See, Tables 1 and 2. The flanking sequences surrounding SRPR SNP ID 4150 are shown in Table 3.

d. Traits Measured in Cows

Fatty acid traits measured in cows or dams (i.e., female livestock) include Health Index (HI), Saturated Fatty Acid content (SFA), Monounsaturated Fatty Acid content (MUFA), Polyunsaturated Fatty Acid content (PUFA), C6-C14 content (C6-C14), Short Chain Fatty Acid content (e.g., C4, C6, C8), Medium Chain Fatty Acid content (e.g., C10:0, C12:0, C14:0, C14:1, C15:0, C16:0, C16:1), Long Chain Fatty Acid content (e.g., C18:0, C18:1,t4, C18:1,t5, C18:1,t6-8, C18:1,t9, C18:1,t10, C18:1,t11, C18:1,t12, C18:1,c9, C18:2,c9,c12, C20:0, C18:3), C14:1/C14:0 ratio, C16:1/C16:0, C18:1/C18:0, and CLA 9-11 content. Their analysis and measurement is described in detail in the Example section, below.

Health Index (HI) is the inverse of atherogenic index proposed by Ulbricht and Southgate (1991) *Lancet* 338, 985-92, as suggested by Zhang et al (2008) *Anim Genet* 39, 62-70.

$$HI = \frac{\Sigma MUFA + \Sigma PUFA}{4 \times C14:0 + C12:0 + C16:0}$$

Percentage of saturated FA ("SFA") (SFA=C4:0+C6:0+C8:0+C10:0+C12:0+C14:0+C15:0+C16:0+C18:0+C20:0).

Percentage of monounsaturated FA (MUFA=C12:1+C14:1+C16:1+C18:1(C18:1,t4; C18:1,t5; C18:1,t6-8; C18:1,t9; C18:1,t10; C18:1,t11;C18:1,t12; C18:1,c9)).

Percentage of polyunsaturated FA (PUFA=C18:2,c9,c12+C18:3).

Percentage of short chain FA (SCF), (SCF=C4:0+C6:0+C8:0).

Percentage of medium chain FA (MCF), (MCF=C10:0+C12:0+C14:0+C14:1+C15:0+C16:0+C16:1).

Percentage of long chain FA (LCF), (LCF=C17:0+C18:0+C18:1+18:2,c9,c12+C20:0+C18:3).

C6 to C 14=(C6:0+C8:0+C10:0+C12:0+C14:0).

The extent of FA desaturation was determined by calculating the ratio of (cis-9 unsaturated) to (cis-9 unsaturated+ saturated for a specific FA) (Palmquist et al. (2004) *J Nutr* 134, 2407-14; Mele et al. (2007) *J Dairy Sci* 90, 4458-65. The ratios are as follows:

Ratio of C14:1/C14:0
Ratio of C16:1/C16:0
Ratio of C18:1/C18:0 e. Traits Measured in Bulls

Traits measured in bulls (i.e., male livestock) include predicted transmitting ability for milk (PTAM), fat (PTAF), protein (PTAP), fat percentage (PTAFP) and protein percentage (PTAPP); Cheese dollars (CHEESD), Net Merit dollars (NMD), and Net merit protein (NMP).

Genetic merit of a trait in lactating cows and bulls with daughters is expressed as predicted transmitting ability (PTA). The PTA is half an animal's expected breeding value and is equivalent to the genetic worth that is expected to be transmitted to its offspring. Any offspring's breeding value for a trait will be, on average, the average of its parents' breeding values for that trait. Equivalently, the expected breeding value of a daughter is the sum of the PTAs of her sire and dam.

PTAs are expressed as differences from the breed base. The breed base is equivalent to the genetic merit of an average animal in the population and is occasionally recalculated by United States Department of Agriculture-Animal Improvement Programs Laboratory ("USDA-AIPL"). See, the worldwide web at aipl.arsusda.gov/eval.htm.

The PTA for milk production is divided in PTAs for milk yield, fat, and protein. All are measured in total pounds per 305-day lactation in a mature cow. Thus, a PTA milk of 1 implies one pound more milk in 305 days compared to the breed base.

Net Merit (NM) and Cheese Dollar (CHEESD) are indices that combine PTA values with economic values for several traits, so selection of animals can be performed simultaneously combining the effect of several traits weighted by genetic parameters and economic values. The 2006 revision of net merit (NM$) includes updated values of traits and the milk component prices were revised to make NM$ and cheese merit (CM$) useful for more producers. The indexes each estimate lifetime profit based on incomes and expenses obtained in cooperation with Project S-1008, Genetic Selection and Crossbreeding To Enhance Reproduction and Survival of Dairy Cattle, collaborative research of the Southern Association of Agricultural Experiment Station Directors. See, the worldwide web at aipl.arsusda.gov/reference/nmcalc.htm and at ans.iastate.edu/research/S1008/.

f. Detection of SNPs

The SREBP1, SCAP, INSIG1, INSIG2, SCD5 or SRPR SNPs can be detected using any methods known in art, including without limitation amplification, sequencing and hybridization techniques. Detection techniques for evaluating nucleic acids for the presence of a single base change involve procedures well known in the field of molecular genetics. Methods for amplifying nucleic acids find use in carrying out the present methods. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1990-2008, including supplemental updates; Sambrook & Russell, Molecular Cloning, A Laboratory Manual (3rd Ed, 2001).

According to one aspect of the present invention, there is provided a method for distinguishing livestock animals e.g., bovines having a SREBP1, SCAP, INSIG1, INSIG2, SCD5 or SRPR gene polymorphism. The method comprises the steps of first isolating a genomic DNA sample from a livestock animal, e.g., bovine, and then detecting, e.g., amplifying a region of the SREBP1, SCAP, INSIG1, INSIG2, SCD5 or SRPR gene using an oligonucleotide pair to form nucleic acid amplification products of SREBP1, SCAP, INSIG1, INSIG2, SCD5 or SRPR gene polymorphism sequences. Amplification can be by any of a number of methods known to those skilled in the art including PCR, and the invention is intended to encompass any suitable methods of DNA amplification. A number of DNA amplification techniques are suitable for use with the present invention. Conveniently such amplification techniques include methods such as polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification. The precise method of DNA amplification is not intended to be limiting, and other methods not listed here will be apparent to those skilled in the art and their use is within the scope of the invention.

In some embodiments, the polymerase chain reaction (PCR) process is used (see, e.g., U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest. Any type of PCR, including quantitative PCR, RT-PCR, hot start PCR, LA-PCR, multiplex PCR, touchdown PCR, finds use. In some embodiments, real-time PCR is used.

The amplification products are then analyzed in order to detect the presence or absence of at least one polymorphism in the SREBP1, SCAP, INSIG1, INSIG2, SCD5 or SRPR gene that is associated with the desired phenotypes, as discussed herein. By practicing the methods of the present invention and analyzing the amplification products it is possible to determine the genotype of individual animals with respect to the polymorphism.

In some embodiments, analysis may be made by restriction fragment length polymorphism (RFLP) analysis of a PCR amplicon produced by amplification of genomic DNA with the oligonucleotide pair. In order to simplify detection of the amplification products and the restriction fragments, those of skill will appreciate that the amplified DNA will further comprise labeled moieties to permit detection of relatively small amounts of product. A variety of moieties are well known to those skilled in the art and include such labeling tags as fluorescent, bioluminescent, chemiluminescent, and radioactive or colorigenic moieties.

A variety of methods of detecting the presence and restriction digestion properties of SREBP1, SCAP, INSIG1, INSIG2, SCD5 or SRPR gene amplification products are also suitable for use with the present invention. These can include methods such as gel electrophoresis, mass spectroscopy or the like. The present invention is also adapted to the use of single stranded DNA detection techniques such as fluorescence resonance energy transfer (FRET). For FRET analysis, hybridization anchor and detection probes may be used to hybridize to the amplification products. The probes sequences are selected such that in the presence of the SNP, for example, the resulting hybridization complex is more stable than if there is a G or C residue at a particular nucleotide position. By adjusting the hybridization conditions, it is therefore possible to distinguish between animals with the SNP and those without. A variety of parameters well known to those skilled in the art can be used to affect the ability of a hybridization complex to form. These include changes in temperature, ionic concentration, or the inclusion of chemical constituents like formamide that decrease complex stability. It is further possible to distinguish animals heterozygous for the SNP versus those that are homozygous for the same. The method of FRET analysis is well known to the art, and the conditions under which the presence or absence of the SNP would be detected by FRET are readily determinable.

Suitable sequence methods of detection also include e.g., dideoxy sequencing-based methods and Maxam and Gilbert sequence (see, e.g., Sambrook and Russell, supra). Suitable HPLC-based analyses include, e.g., denaturing HPLC (dH-PLC) as described in e.g., Premstaller and Oefner, LC-GC Europe 1-9 (July 2002); Bennet et al., BMC Genetics 2:17 (2001); Schrimi et al., Biotechniques 28(4):740 (2000); and Nairz et al., PNAS USA 99(16):10575-10580 (2002); and ion-pair reversed phase HPLC-electrospray ionization mass spectrometry (ICEMS) as described in e.g., Oberacher et al.; Hum. Mutat. 21(1):86 (2003). Other methods for characterizing single base changes in SREBP1, SCAP, INSIG1, INSIG2, SCD5 or SRPR alleles include, e.g., single base extensions (see, e.g., Kobayashi et al, Mol. Cell. Probes, 9:175-182, 1995); single-strand conformation polymorphism analysis, as described, e.g, in Orita et al., Proc. Nat. Acad. Sci. 86, 2766-2770 (1989), allele specific oligonucleotide hybridization (ASO) (e.g., Stoneking et al., Am. J. Hum. Genet. 48:70-382, 1991; Saiki et al., Nature 324, 163-166, 1986; EP 235,726; and WO 89/11548); and sequence-specific amplification or primer extension methods as described in, for example, WO 93/22456; U.S. Pat. Nos. 5,137,806; 5,595, 890; 5,639,611; and U.S. Pat. No. 4,851,331; 5'-nuclease assays, as described in U.S. Pat. Nos. 5,210,015; 5,487,972; and 5,804,375; and Holland et al.. 1988, Proc. Natl. Acad. Sci. USA 88:7276-7280.

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the SREBP1, SCAP, INSIG1, INSIG2, SCD5 or SRPR SNPs described herein.

For example FRET analysis can be used as a method of detection. Conveniently, hybridization probes comprising an anchor and detection probe, the design of which art is well known to those skilled in the art of FRET analysis, are labeled with a detectable moiety, and then under suitable conditions are hybridized a SREBP1, SCAP, INSIG1, INSIG2, SCD5 or SRPR amplification product containing the site of interest in order to form a hybridization complex. A variety of parameters well known to those skilled in the art can be used to affect the ability of a hybridization complex to form. These include changes in temperature, ionic concentration, or the inclusion of chemical constituents like formamide that decrease complex stability. The presence or absence of the SREBP1, SCAP, INSIG1, INSIG2, SCD5 or SRPR SNP is then determined by the stability of the hybridization complex. The parameters affecting hybridization and FRET analysis are well known to those skilled in the art. The amplification products and hybridization probes described herein are suitable for use with FRET analysis.

g. Selecting Livestock Animals with Desirable Traits

The present invention provides a method of selecting individual livestock animals based on the knowledge of an animal's SREBP1, SCAP, INSIG1, INSIG2, SCD5 or SRPR genotype. With respect to the SNPs described in the present invention, livestock animals with alleles at SNP IDs SREBP1-13636, SCAP-34632, INSIG1-3885, INSIG1-6082, INSIG1-12052, INSIG2-93277, INSIG2-93461, INSIG2-93867, SCD5-134718, SCD5-179412, SRPR-3064 and SRPR-4150 correlated with desirable fatty acid disposition and content traits can be selected.

According to the methods of the present invention, a livestock animal can be selected based on its genotype at SNP IDs SREBP1-13636, SCAP-34632, INSIG1-3885, INSIG1-6082, INSIG1-12052, INSIG2-93277, INSIG2-93461, INSIG2-93867, SCD5-134718, SCD5-179412, SRPR-3064 and SRPR-4150. With the knowledge of the animal's SREBP1, SCAP, INSIG1, INSIG2, SCD5 or SRPR genotype one can then identify and sort animals into groups of like phenotype(s), or otherwise use the knowledge of the genotype in order to predict which animals will have the desired phenotypes, for example, increased saturated fatty acids, increased predicted transmitting ability of milk and protein, increased net merit dollar and protein, increased cheese dollar. Knowledge of the animal's SREBP1, SCAP, INSIG1, INSIG2, SCD5 or SRPR genotype allows a breeder to encourage breeding between animals with a desired SREBP1, SCAP, INSIG1, INSIG2, SCD5 or SRPR genotype, and to discourage breeding between animals with an undesirable SREBP1, SCAP, INSIG1, INSIG2, SCD5 or SRPR genotype.

Selecting or sorting can be taken to mean placing animals in physical groupings such as pens, so that animals of like genotype are kept separate from animals of a different genotype. This would be a useful practice in the case of breeding programs where it would be desirable to produce animals of particular genotypes. On the other hand, it may also be desirable to decrease production of animals with an undesired SREBP1, SCAP, INSIG1, INSIG2, SCD5 or SRPR genotype. Separating out animals with the desired SREBP1, SCAP, INSIG1, INSIG2, SCD5 or SRPR genotype(s) would prevent animals with an undesired SREBP1, SCAP, INSIG1, INSIG2, SCD5 or SRPR genotype from breeding with animals possessing a desired SREBP1, SCAP, INSIG1, INSIG2, SCD5 or SRPR genotype, facilitating the reproduction of animals with an increased tendency to display the desired phenotypes associated with the SREBP1, SCAP, INSIG1, INSIG2, SCD5 or SRPR alleles. Furthermore, ensuring that at least one animal in a breeding pair possesses desired SREBP1, SCAP, INSIG 1, INSIG2, SCD5 or SRPR alleles allows for the frequency of the desired SREBP1, SCAP, INSIG1, INSIG2, SCD5 or SRPR alleles to be increased in the next, and subsequent generations. For example, a favorable breed of Bos may not have a desired SREBP1, SCAP, INSIG1, INSIG2, SCD5 or SRPR genotype, but the desired SREBP1, SCAP, INSIG1, INSIG2, SCD5 or SRPR genotype could be bred into the genepool of the favorable breed of *Bos*.

Sorting may also be of a "virtual" nature, such that an animal's genotype is recorded either in a notebook or computer database. In this case, animals could then be selected based on their known genotype without the need for physical separation. This would allow one to select for animals of desired phenotype where physical separation is not required.

In some embodiments, the genetic markers identified herein can be used for: 1) "Marker Assisted Selection", e.g., to select animals for breeding purposes to increase the frequency of desirable or advantageous genotypes in the population and/or 2) "Marker Assisted Mangement", e.g., to separate animals with desirable or advantageous genotypes to feed them or manage them in a certain way to enhance the quality of their products, or to directly harvest products of a desired quality. For example, to harvest milk with a lower concentration of saturated FA to make a softer and healthier butter, or to select or sort animals of a particular genotype to feed them or manage them in a way that enhances the desired phenotype.

3. Distinguishing *Bos taurus* from *Bos indicus* by Determining SREBP1 SNPs

In a related aspect, the invention provides a method for distinguishing bovines, in particular *Bos taurus* from *Bos indicus*, based on SREBP1 gene polymorphisms that are fixed in each species. The method comprises the steps of first isolating a genomic DNA sample from the bovine, and then detecting, e.g., amplifying a region of the SREBP1 gene using an oligonucleotide pair to form nucleic acid amplification products of SREBP1 gene polymorphism sequences. A biological sample comprising genomic DNA is taken from the bovine to be tested, as described above. The methods used to detect the SREBP1 polymorphism can be any means of SNP detection known in the art, as discussed above, including without limitation, amplification, sequencing and hybridization techniques. Amplification can be by any of a number of methods known to those skilled in the art, as discussed above. Upon determining the species of the bovine based on genotypic analysis, the bovine is selected or rejected, either physically or virtually, as described above.

a. SREBP1 SNPs Useful to Distinguish *Bos taurus* from *Bos indicus*

SREBP1 SNPs useful to distinguish *Bos taurus* from *Bos indicus* include SREBP1 SNP IDs 1199, 12504 and 13508.

SREBP1 SNP ID 1199 is identified in FIG. 1. As shown in FIG. 1, SREBP1 SNP ID 1199 is positioned at nucleotide 1198 of the sequence depicted in FIG. 1, or at position 1198 of SEQ ID NO:1. SREBP1 SNP ID 1199 is also positioned at nucleotide 107 within intron 1 of the SREBP1 sequence depicted in FIG. 1. A homozygous "CC" genotype at SREBP1 SNP ID 1199 indicates that the bovine is *Bos taurus*. A homozygous "GG" genotype at SREBP1 SNP ID 1199 indicates that the bovine is *Bos indicus*. See, Table 3.

SREBP1 SNP ID 12504 is identified in FIG. 1. As shown in FIG. 1, SREBP1 SNP ID 12504 is positioned at nucleotide 13363 of the sequence depicted in FIG. 1, or at position 13363 of SEQ ID NO:1. SREBP1 SNP ID 12504 is also positioned at nucleotide 86 of intron 13 of the SREBP1 sequence depicted in FIG. 1. A homozygous "TT" genotype at SREBP1 SNP ID 12504 indicates that the bovine is *Bos taurus*. A homozygous "CC" genotype at SREBP1 SNP ID 12504 indicates that the bovine is *Bos indicus*. See, Table 3.

SREBP1 SNP ID 13508 is identified in FIG. 1. As shown in FIG. 1, SREBP1 SNP ID 13508 is positioned at nucleotide 14367 of the sequence depicted in FIG. 1, or at position 14367 of SEQ ID NO:1. SREBP1 SNP ID 13508 is also positioned at nucleotide 177 of intron 15 of the SREBP1 sequence depicted in FIG. 1. A homozygous "TT" genotype at SREBP1 SNP ID 13508 indicates that the bovine is *Bos taurus*. A homozygous "CC" genotype at SREBP1 SNP ID 13508 indicates that the bovine is *Bos indicus*. See, Table 3.

In some embodiments, the amplicon produced can be further subjected to restriction endonuclease digestion.

2. Kits for Genotypic Analysis of Polymorphisms in Fatty Acid Metabolism Genes

The invention further provides diagnostic kits useful for determining the SREBP1, SCAP, INSIG1, INSIG2, SCD5 or SRPR genotypes of livestock animals, e.g., bovines. In general, each of the kits comprises one or more oligonucleotide primer pairs as described herein suitable to amplify the portions of the gene comprising the SNPs of the present invention, i.e., one or more of SNP IDs SREBP1-13636, SCAP-34632, INSIG1-3885, INSIG1-6082, INSIG1-12052, INSIG2-93277, INSIG2-93461, INSIG2-93867, SCD5-134718, SCD5-179412, SRPR-3064 and SRPR-4150. The kits comprise forward and reverse primers suitable for amplification of a genomic DNA sample taken from an animal. As described above, the biological sample can be from any tissue or fluid in which genomic DNA is present. Conveniently, the sample may be taken from blood, skin or a hair bulb.

The kits find use in determining the fatty acid composition traits of a livestock animal, e.g., a bovine. In some embodiments, the kits comprise polynucleotides for detecting one or more SNPs selected from the group consisting of INSIG2-93461, INSIG2-93867, SCD5-134718, SCD5-179412 and SRPR-4150. In some embodiments, the kits comprise polynucleotides for detecting one or more SNPs selected from the group consisting of SREBP1-13636, SCAP-34632, INSIG1-3885, INSIG1-6082, INSIG1-12052, INSIG2-93277, SCD5-179412, SRPR-3064 and SRPR-4150.

EXAMPLES

The following examples are offered to illustrate, but not to limit the claimed invention.

Example 1

Identification of and Sequencing of Candidate Genes in Cattle Associated with the Fatty Acid Composition of Animal Products Including Milk and Meat Using bioinformatics tools, we collected the available genomic information for each gene of interest (i.e., Stearoyl-CoA-Desaturase 5 (SCD5), Sterol regulatory element-binding protein-1 (SREBP1), SREBP cleavage-activating protein (SCAP), Insulin induced protein 1 (INSIG1), Insulin induced protein 2 (1NSIG2) and Signal recognition particle receptor (SRPR)). Sequences from bovine scaffolds, assembled traces, BACs, ESTs and all available bovine sequences from web browsers and databases such as NCBI Cow genome resources (on the worldwide web at ncbi.nlm.nih.gov/genome/guide/cow/index.html), Ensemble cattle server (on the worldwide web at ensembl.org/*Bos_taurus*/index.html) and DFCI cattle gene index (on the worldwide web at compbio.dfci.harvard.edu/tgi/cgibin/tgi/gimain.pl?gudb=cattle) were obtained. A number of gene sequences deposited in databases are not totally correct, so each sequence was manually assembled and curated in order to obtain a consensus sequence to confidently use for SNPs discovery. A consensus sequence for each gene was created and analyzed to define and confirm the gene structure and the reading frame, followed by VISTA sequence alignments using genomic information from different species to establish conserved noncoding regulatory regions.

Example 2

Sequencing of Candidate Genes to Identify Genetic Variation in Coding and Non-Coding Regions to Develop a Set of Tag SNPs for Use in Association Studies Once the complete gene sequence information was compiled, we proceeded with SNPs discovery analysis. The resequencing of candidate genes was performed in our UC Davis DNA resource population developed specifically for SNP discovery. To create a discovery panel of DNA samples, we searched multiple AI bull databases and the UC Davis dairy herd and selected a group of eight animals of each breed (8 Holstein, 8 Jersey and 8 Brown Swiss) that are representative of the major dairy lineages and that are unrelated at least three generations back in their pedigrees. Using the same approach, we also selected a group of six animals of each breed (6 Angus, 6 Simmental and 6 Brahman), representing diverse beef cattle breeds. The portions resequenced were as follows: 1000 or 500 bp of the 5' UTR, the entire coding region, 500 by of the 3' UTR and conserved noncoding regions of each gene.

DNA traces were analyzed using CodonCode aligner software (on the worldwide web at codoncode.com/aligner) to detect sequence polymorphisms among and within breeds. Gene sequences and polymorphisms were assembled and annotated using Vector NTI advance 10.1.1 software (Invitrogen Corporation). Each polymorphism identified in our SNP discovery analysis was compared to the bovine NCBI dbSNP database (on the worldwide web at ncbi.nlm.nih.gov/SNP/index.html) using BLAST (Basic Local Alignment Search Tool).

Haploview software (on the worldwide web at broad.mit.edu/mpg/haploview/) was used to identify linkage disequilibrium regions and to determine tag SNPs. The analysis of the total number of SNPs and their haplotypes allowed us to determine the LD structure needed for the choice of efficient tag SNPs. Haplotype blocks were defined based on estimates of confidence interval of D' for all pairwise combinations of SNPs within a chromosome. To select the tag SNPs in candidate genes, we used the Tagger tool for the selection and evaluation of tag SNPs from genotype data. This strategy allowed us to select a minimal set of markers (tag SNPS) such that all alleles captured are correlated at an $r^2$ greater than 0.8 and a LOD threshold of 3 with a marker in the set.

Variation in coding regions was analyzed using computational algorithms such as SIFT (Sorting Intolerant From Tolerant) (on the worldwide web at blocks.fhcrc.org/sift/SIFT.html) and Polyphen (Polymorphism Phenotyping) (on the worldwide web at coot.embl.de/PolyPhen/) to predict whether an amino acid substitution affects protein function and to prioritize amino acid substitutions for further study. Non synonymous SNPs were forced into the tag list created in Haploview.

A total of 96 SNPs were detected in the 6 target genes and 53 were identified as tag SNPs (i.e., SNPs useful for association studies and genotyping assays). Seventeen SNPs were located in exons, 13 were synonymous (i.e., caused an amino acid change) and 4 were non-synonymous (i.e. caused no amino acid change). SIFT and Polyphen analysis were performed in the non-synonymous SNPs and two of the SNPs turned out to be not tolerated, the first one is an amino acid change Pro/Ser in SCAP and the second one is an amino acid change Leu/Pro in the SREBP1 protein.

Detailed descriptions of the discovered sequence variation for each gene are summarized below.

A total of 19 SNPs were identified in the bovine SCAP gene, including two in the 5' UTR and five in the exons. Of the 19 SNPs, 9 are suitable for use as Tag SNPs.

A total of 17 SNPs were identified in the bovine INSIG1 gene, including two in the 5' UTR, five in the 3' UTR; and three in the exons. Of the 17 SNPs, nine are suitable for use as Tag SNPs.

A total of 17 SNPs were identified in the bovine INSIG2 gene, including three in the 5' UTR and one in the exons. Of the 12 SNPs, 11 are suitable for use as Tag SNPs.

A total of 10 SNPs were identified in the bovine SREBP1 gene, including four in the 5' UTR, one in the 3' UTR, and one in the exons. Of the 10 SNPs, 5 are suitable for use as Tag SNPs.

A total of 11 SNPs were identified in the bovine SCD5 gene, including one in the 3' UTR, and five in the exons. Of the 11 SNPs, 8 are suitable for use as Tag SNPs.

A total of 22 SNPs were identified in the bovine SRPR gene, and 11 are suitable for use as Tag SNPs.

The SNPs identified and set forth herein are useful as genetic markers that for genetic and metabolic directed selection.

Example 3

Association Analysis of SNP Variation in Relation to Cattle Milk Fatty Acid Composition SNPs Genotyped After resequencing the candidate genes (i.e., SCD5, SREBP1, SCAP, INSIG1, INSIG2 and SRPR) in the UCD SNP discovery population, we identified 58 Tag SNPs. Tag SNPs are a minimal information subset of SNPs that capture all the variation of a gene in defined populations. These SNPs were used to develop genotyping assay to perform association studies. The SNPs with associations with desirable traits are as follows:

INSIG1 gene: INSIG1 -3885, INSIG1-6082 and INSIG1-12052

INSIG2 gene: INSIG2-93277, INSIG2-93461 and INSIG2-93867

SCAP gene: SCAP-34632

SCD5 gene: SCD5-134718 and SCD5-179412

SREBP1 gene: SREBP1-13636

SRPR gene: SRPR-3064 and SRPR-4150

Traits

Samples: The samples used for the association study consisted of 882 Holstein bulls from the UC Davis archival collection and 315 Holstein cows. The UC Davis archival collection started in 1995 and consists of approximately 1100 bull DNA samples extracted from frozen semen straws sent by private companies to our Laboratory in the Animal Science Department at UC Davis. The cow samples were collected from 4 dairy farms in the California Central Valley. These were healthy cows in their 1st and 2nd lactation and at 100 to 150 days in milk with complete milk records. Milk samples were collected triplicates during the routine USDA/DHIA procedure and kept on ice until the composition analysis was performed. High quality DNA was extracted from semen and blood samples using the PureGene Genomic DNA Purification Kit from Gentra Systems (catalog number D-5500).

Bull phenotypes: Predicted transmitting ability for milk (PTAM), fat (PTAF), protein (PTAP), fat percentage (PTAFP) and protein percentage (PTAPP). Cheese dollars (CHEESD), Net Merit dollars (NMD), and Net merit protein (NMPR). These values used in the association analysis were downloaded from the USDA Animal Improvement Programs Laboratory database (Beltsville, Md.), on the worldwide web at aipl.arsusda.gov/eval.htm.

Cow phenotypes: One milk samples was sent to Silliker Laboratories (Modesto, Calif.) for the milk composition analysis, which included a profile for: Lactose, Somatic Cell Count (SCC), Milk Urea Nitrogen (MUN), fat percentage (FatP), protein percentage (ProtP), casein percentage (CasP) and total solids. Milk yield information was collected from the USDA/DHIA genetic evaluation procedure.

The second sample was sent to Dr. Dale Bauman's laboratory at Cornell University, for fatty acid analysis and the third sample is stored in our laboratory as a reference for future analysis.

The Fatty Acid analysis performed at the Bauman's laboratory included the profile for the following FA: C4:0; C6:0; C8:0; C10:0; C12:0; C14:0; C14:1; C15:0; C16:0; C16:1; C17:0; C18:0; C18:1,t4; C18:1,t5; C18:1,t6-8; C18:1,t9;C18:1,t10; C18:1,t11; C18:1,t12; C18:1;c9; C18:2,c9,c12; C20:0; C18:3; CLA, 9-11; CLA, 10-12.

Using the fatty acid profile we calculated various indices for each sample, as follows:

1) Health Index (HI) as the inverse of atherogenic index proposed by Ulbricht and Southgate (1991) *Lancet* 338, 985-92, as suggested by Zhang et al (2008) *Anim Genet* 39, 62-70.

$$HI = \frac{\Sigma MUFA + \Sigma PUFA}{4 \times C14:0 + C12:0 + C16:0}$$

The characterization of food in terms of their total fat content, saturated fat content, their Polyunsaturated FA (PUFA) to Saturated FA ratio (P/S ratio), the proportion of energy from fat, or their PUFA content alone can lead to misleading statements. To improve on the P/S ratio as a suitable measurement for atherogenicity or thrombogenicity of a diet or food, the Index of atherogenicity was created by Ulbricht and Southgate (1991), supra. Zhang et al. (2008), supra, suggested using the Health Index as the inverse of Atherogenic Index. HI is higher for the dietary components with less atherogenic properties.(Ulbricht & Southgate 1991; Zhang et al. 2008).

2) Percentage of saturated FA ("SFA") (SFA=C4:0+C6:0+C8:0+C10:0+C12:0+C14:0+C15:0+C16:0+C18:0+C20:0).

Typical milk fat of cows comprises 70% saturated, 25% monounsaturated and 5% polyunsaturated fatty acids. According to Bobe et al., (2007) *J Dairy Sci* 90, 3955-60, the proportion of total SFA in US Holstein cows is 67.18±4.2. Experimental evidence indicates that a diet high in SFA is associated with high levels of serum cholesterol which in turn arc related to high incidences of cardiovascular diseases. See, e.g., Bobe et al. 2007; Bobe et al., (2008) *J Dairy Sci* 91, 1209-13. SFA lauric acid (C12:0), myristic acid (C14:0) and palmitic acid (C 16:0) are considered to have the most harmful cardiovascular effects, and stearic acid (C18:0) is believed to be neutral (Bonanome & Grundy (1988) *N Engl J Med* 318, 1244-8.

3) Percentage of monounsaturated FA (MUFA=C12:1+C14:1+C16:1+C18:1(C18:1,t4; C18:1,t5; C18:1,t6-8; C18:1,t9; C18:1,t10; C18:1,t11; C18:1,t12, C18:1,c9)).

According to Bobe et al 2007, supra, the proportion of total MUFA in US Holstein cows is 29.67±3.9.

Unsaturated fatty acids, i.e., MUFA and PUFA increase hepatic low density lipoprotein (LDL) receptor activity, thereby decreasing the circulating concentration of LDL-cholesterol (Rudd et al. (1995) *Arterioscler Thromb Vase Biol* 15, 2101-10.

4) Percentage of polyunsaturated FA (PUFA=C18:2,c9, c12+C18:3).

According to Bobe et al 2007, supra, the proportion of total PUFA in US Holstein cows is 2.95±0.5.

MUFA and PUFA are protective against the formation of cholesterol promoted by SFA.

5) Percentage of short chain FA (SCF), (SCF=C4:0+C6:0+C8:0).

6) Percentage of medium chain FA (MCF), (MCF=C10:0+C12:0+C14:0+C14:1+C15:0+C16:0+C16:1).

7) Percentage of long chain FA (LCF), (LCF=C17:0+C18:0+C18:1+18:2,c9,c12+C20:0+C18:3).

8) Percentage of saturated FA synthesized de-novo in the mammary gland (Palmquist et al. (1993) *J Dairy Sci* 76, 1753-71. C6 to C 14=(C6:0+C8:0+C10:0+C12:0+C14:0).

Saturated FA have significant genetic variation and therefore have the potential to be altered by genetic selection. ($h^2$=0.30 r=0.40) (Bobe et al. 2008, supra).

9) The extent of FA desaturation was determined by calculating the ratio of (cis-9 unsaturated) to (cis-9 unsaturated+saturated for a specific FA) (Palmquist et al. (2004) *J Nutr* 134, 2407-14; Mele et al. (2007) *J Dairy Sci* 90, 4458-65. The ratios are as follows:

Ratio of C14:1/C14:0
Ratio of C16:1/C16:0
Ratio of C18:1/C18:0

Association Analysis

The association analysis was performed using the Golden Helix Genetic Association Test and Regression Module from Helixtree software to test allelic associations with phenotypic variables. The Genetic Association Test offered a straightforward way of testing for genetic associations against quantitative traits under additive and dominant genetic model assumptions. The Regression Module supports both linear and logistic regression. A stepwise regression was used to find confounding phenotypic variables, fix those regressors and then perform a search for significantly associated SNPs. This regression approach was particularly powerful for overcoming the difficult challenges of population stratification. The covariates in the cow analysis were: dairy, lactation number and milk yield.

Although the association analysis in this study was performed in relation to the FA composition of milk, it is likely that these SNPs will also be important in relation to the FA composition of other cattle tissues, like body fat or intramuscular fat. Association significance results of identified SNPs with the analyzed traits are shown in Tables 1 and 2. Nucleic acid sequences flanking the SNPs are shown in Table 3.

TABLE 1

Statistically significant association results in the cow population (P < 0.05)

| Genotypes | P-value | Additive Effect P-value | Dominace Effect P-value | Allele Subs. Effect |
|---|---|---|---|---|

Health Index

TABLE 1-continued

Statistically significant association results in the cow population (P < 0.05)

| | Genotypes | | | P-value | Additive Effect P-value | Dominance Effect P-value | Allele Subs. Effect |
|---|---|---|---|---|---|---|---|
| INSIG2-93461 | GG | CG | CC | 0.040 | 0.036 | 0.036 | 0.032 |
| | 0.51 ± 0.004 | 0.53 ± 0.01 | 0.54 ± 0.004 | | | | |
| SCD5-134718 | TT | CT | CC | 0.023 | 0.023 | 0.08 | 0.029 |
| | 0.48 ± 0.01 | 0.51 ± 0.006 | 0.52 ± 0.006 | | | | |
| SRPR-4150 | GG | CG | CC | 0.024 | 0.019 | 0.065 | 0.024 |
| | 0.50 ± 0.008 | 0.51 ± 0.008 | 0.53 ± 0.007 | | | | |

Sat FA

| | | | | | | | |
|---|---|---|---|---|---|---|---|
| INSIG2-93867 | CT | CC | TT | 0.003 | 9.49E−05 | 3.83E−05 | −1.46 |
| | 62 ± 0.3 | 62.2 ± 0.8 | 63.3 ± 0.2 | | | | |
| SCD5-134718 | CC | CT | TT | 0.022 | 0.0214 | 0.1003 | −1.19 |
| | 62.5 ± 0.2 | 62.9 ± 0.2 | 64.3 ± 0.6 | | | | |
| SCD5-179412 | TT | GT | GG | 0.024 | 0.0074 | 0.0445 | 1.1 |
| | 61.6 ± 0.5 | 62.7 ± 0.3 | 63.2 ± 0.2 | | | | |
| SRPR-4150 | CC | CG | GG | 0.041 | 0.0371 | 0.1747 | −0.88 |
| | 62.4 ± 0.3 | 62.7 ± 0.3 | 63.4 ± 0.3 | | | | |

MUFA

| | | | | | | | |
|---|---|---|---|---|---|---|---|
| SCD5-134718 | TT | CT | CC | 0.045 | 0.0471 | 0.1189 | 0.88 |
| | 29 ± 0.5 | 29.8 ± 0.3 | 30.1 ± 0.3 | | | | |
| SRPR-4150 | GG | CG | CC | 0.021 | 0.0235 | 0.0596 | 0.87 |
| | 29.4 ± 0.2 | 29.9 ± 0.2 | 30.3 ± 0.2 | | | | |

PUFA

| | | | | | | | |
|---|---|---|---|---|---|---|---|
| INSIG2-93867 | TT | CC | CT | 5.41E−12 | 2.85E−11 | 1.70E−12 | 1.02 |
| | 3.56 ± 0.05 | 4.0 ± 0.02 | 4.17 ± 0.06 | | | | |
| SCD5-179412 | GG | GT | TT | 0.033 | 0.0340 | 0.0312 | −0.27 |
| | 3.7 ± 0.06 | 3.87 ± 0.06 | 3.9 ± 0.1 | | | | |

C6-C14

| | | | | | | | |
|---|---|---|---|---|---|---|---|
| INSIG2-93867 | TT | CC | CT | 0.0011 | 0.0012 | 0.0007 | 1.31 |
| | 16.6 ± 0.1 | 17.3 ± 0.5 | 17.4 ± 0.2 | | | | |
| SCD5-134718 | CC | CT | TT | 0.015 | 0.01588 | 0.0215 | −0.87 |
| | 16.7 ± 0.2 | 17.1 ± 0.2 | 17.5 ± 0.4 | | | | |

Short FA

| | | | | | | | |
|---|---|---|---|---|---|---|---|
| INSIG2-93461 | CC | CG | GG | 0.029 | 0.0293 | 0.0951 | −0.38 |
| | 6.1 ± 0.5 | 6.7 ± 0.1 | 6.79 ± 0.04 | | | | |

Medium FA

| | | | | | | | |
|---|---|---|---|---|---|---|---|
| INSIG2-93867 | CC | CT | TT | 0.0056 | 0.0058 | 0.0092 | −1.73 |
| | 43 ± 0.9 | 44.2 ± 0.3 | 45 ± 0.2 | | | | |
| SRPR-4150 | GG | CG | CC | 0.023 | 0.0251 | 0.0829 | 1.07 |
| | 44.2 ± 0.3 | 44.6 ± 0.2 | 45.3 ± 0.4 | | | | |

Long FA

| | | | | | | | |
|---|---|---|---|---|---|---|---|
| INSIG1-3885 | TT | CT | CC | 0.027 | 0.0280 | 0.0281 | 1.11 |
| | 44.6 ± 0.3 | 45.3 ± 0.2 | 45.6 ± 0.4 | | | | |
| SRPR-4150 | GG | CG | CC | 0.023 | 0.0238 | 0.0561 | 1.07 |
| | 44.5 ± 0.4 | 45 ± 0.2 | 45.6 ± 0.3 | | | | |

C14:1/C14:0

| | | | | | | | |
|---|---|---|---|---|---|---|---|
| INSIG2-93867 | TT | CC | CT | 0.001 | 0.0014 | 0.0006 | 0.016 |
| | 0.068 ± 0.002 | 0.076 ± 0.007 | 0.078 ± 0.003 | | | | |
| SCD5-179412 | GG | GT | TT | 0.017 | 0.0173 | 0.2972 | −0.01 |
| | 0.071 ± 0.002 | 0.071 ± 0.002 | 0.086 ± 0.006 | | | | |

C16:1/C16:0

| | | | | | | | |
|---|---|---|---|---|---|---|---|
| SCD5-179412 | GG | GT | TT | 0.021 | 0.0216 | 0.2068 | −0.0049 |
| | 0.0401 ± 0.0009 | 0.040845 ± 0.0009 | 0.047 ± 0.00043 | | | | |

CLA 9-11

| | | | | | | | |
|---|---|---|---|---|---|---|---|
| INSIG2-93867 | TT | CC | CT | 8.40E−06 | 0.0002 | 4.70E−05 | 0.16 |
| | 0.53 ± 0.01 | 0.53 ± 0.04 | 0.60 ± 0.01 | | | | |
| SCD5-134718 | TT | CT | CC | 0.0004 | 0.0003 | 0.0035 | 0.1 |
| | 0.45 ± 0.04 | 0.54 ± 0.01 | 0.58 ± 0.01 | | | | |
| SCD5-179412 | GG | GT | TT | 0.006 | 0.006 | 0.0312 | −0.07 |
| | 0.53 ± 0.01 | 0.56 ± 0.01 | 0.62 ± 0.03 | | | | |

Fatty acid contents are expressed as g/100 g of total fatty acids.

INSIG2-93867 allele C is associated with a decrease in saturated FA, increase in PUFA, C6 to C14 FA, C 14:1/C14:0 ratio and CLA9-11 content.

SCD5-134718 allele C is associated with a high Health Index, decrease in saturated FA, increase in MUFA, decrease in C6 to C14 FA, C14:1/C14:0 ratio and increase in CLA9-11 content.

Haplotypes with INSIG2-93867/SCD5-134718 polymorphisms are also significantly associated (p<0.0001) with Health Index, Saturated fat, C6-C14 and CLA9-11.

SRPR-4150 allele C is associated with a high Health Index, decrease in saturated FA, increase in monounsaturated FA, and increase in medium and long chain FA.

SCD5-179412 allele T is associated with decrease saturated FA, increase polyunsaturated FA, increase in C14:1/C14:0 and C16:1/C16:0 ratio and CLA9-11.

INSIG2-93461 allele C is associated with a high Health Index and a decrease in short chain FA.

TABLE 2

Statistically significant association results in the bull population ($P < 0.05$)

| | Genotypes | | | P-value | Additive Effect P-value | Dominace Effect P-value | Allele Subs. Effect |
|---|---|---|---|---|---|---|---|
| PTA Milk (lb) | | | | | | | |
| INSIG1-12052 | GG | AG | AA | 0.006 | 0.006 | 0.009 | 196.1 |
| | 416 ± 42 | 530 ± 35 | 601 ± 54 | | | | |
| INSIG1-6082 | TT | GG | GT | 0.00084 | 0.00087 | 0.00032 | 393.5 |
| | 414 ± 33 | 454 ± 161 | 655 ± 53 | | | | |
| SCAP-34632 | CC | CT | TT | 0.0088 | 0.0089 | 0.019 | −254.67 |
| | 207 ± 181 | 415 ± 52 | 526 ± 28 | | | | |
| SCD5-179412 | TT | GT | GG | 0.033 | 0.033 | 0.19 | 154.6 |
| | 349 ± 69 | 501 ± 34 | 535 ± 40 | | | | |
| SRPR-4150 | GG | CG | CC | 0.026 | 0.026 | 0.0074 | 154.8 |
| | 453 ± 56 | 453 ± 36 | 601 ± 59 | | | | |
| PTA Fat (lb) | | | | | | | |
| INSIG1-12052 | GG | AG | AA | 0.0012 | 0.0013 | 0.26 | 8.21 |
| | 18 ± 1 | 20 ± 1 | 27 ± 2 | | | | |
| INSIG1-3885 | CC | CT | TT | 0.00027 | 0.00028 | 0.002 | −9.44 |
| | 13 ± 2 | 19 ± 1 | 24 ± 1 | | | | |
| INSIG1-6082 | TT | GG | GT | 8.30E−05 | 9.30E−05 | 5.40E−05 | 16.7 |
| | 16 ± 1 | 25 ± 4 | 26 ± 2 | | | | |
| SREBP1-13636 | TT | CT | CC | 0.035 | 0.035 | 0.1 | 5.26 |
| | 18 ± 1 | 20 ± 1 | 24 ± 2 | | | | |
| SRPR-4150 | GG | CG | CC | 0.04 | 0.043 | 0.07 | 4.99 |
| | 17 ± 2 | 19 ± 1 | 22 ± 2 | | | | |
| PTA fat percentage | | | | | | | |
| INSIG2-93277 | AC | AA | CC | 0.03 | 0.035 | 0.003 | −1.99 |
| | 0.0 ± 0.4 | 0.5 ± 0.7 | 2.4 ± 0.7 | | | | |
| PTA protein (lb) | | | | | | | |
| INSIG1-12052 | GG | AG | AA | 0.0022 | 0.0023 | 0.0026 | 5.9 |
| | 16 ± 1 | 19.6 ± 0.9 | 21 ± 2 | | | | |
| INSIG1-6082 | TT | GG | GT | 2.04E−05 | 2.29E−05 | 4.80E−06 | 13.6 |
| | 15.4 ± 0.9 | 18 ± 4 | 24 ± 1 | | | | |
| SCD5-179412 | TT | GT | GG | 0.0038 | 0.0039 | 0.008 | 5.7 |
| | 15 ± 2 | 17.5 ± 0.9 | 21 ± 1 | | | | |
| SCAP-34632 | CC | CT | TT | 0.005 | 0.0053 | 0.01 | −7.42 |
| | 9 ± 6 | 16 ± 1 | 19.3 ± 0.8 | | | | |
| Cheese dollars | | | | | | | |
| INSIG1-12052 | GG | AG | AA | 0.00024 | 0.00025 | 0.0021 | 69.01 |
| | 109 ± 11 | 140 ± 9 | 180 ± 14 | | | | |
| INSIG1-3885 | CC | CT | TT | 0.00053 | 0.00055 | 0.0088 | −66.6 |
| | 80 ± 19 | 130 ± 9 | 154 ± 10 | | | | |
| INSIG1-6082 | TT | GT | GG | 0.00035 | 0.00038 | 0.00061 | 110.1 |
| | 110 ± 9 | 164 ± 13 | 227 ± 30 | | | | |
| SCAP-34632 | CC | CT | TT | 0.0092 | 0.0093 | 0.021 | −66.9 |
| | 55 ± 50 | 114 ± 14 | 142 ± 7 | | | | |
| SRPR-4150 | GG | CG | CC | 0.004 | 0.0041 | 0.00068 | 52.76 |
| | 118 ± 14 | 120 ± 9 | 169 ± 12 | | | | |
| SRPR-3064 | GG | AG | AA | 0.0005 | 0.00052 | 0.00054 | 91.99 |
| | 74 ± 68 | 100 ± 13 | 148 ± 7 | | | | |
| NM dollars | | | | | | | |
| INSIG1-12052 | GG | AG | AA | 0.00017 | 0.00018 | 0.0017 | 69.2 |
| | 102 ± 11 | 133 ± 9 | 174 ± 14 | | | | |
| INSIG1-3885 | CC | CT | TT | 0.00047 | 0.00049 | 0.0082 | −65.7 |
| | 73 ± 19 | 123 ± 9 | 147 ± 10 | | | | |
| INSIG1-6082 | TT | GT | GG | 0.00042 | 0.00044 | 0.00077 | 106.7 |
| | 104 ± 9 | 156 ± 13 | 219 ± 30 | | | | |

TABLE 2-continued

Statistically significant association results in the bull population (P < 0.05)

| | Genotypes | | | P-value | Additive Effect P-value | Dominace Effect P-value | Allele Subs. Effect |
|---|---|---|---|---|---|---|---|
| SCD5-179412 | TT | GT | GG | 0.0016 | 0.0016 | 0.0083 | 59.3 |
| | 87 ± 19 | 121 ± 9 | 148 ± 10 | | | | |
| SCAP-34632 | CC | CT | TT | 0.0069 | 0.007 | 0.06 | −67.8 |
| | 49 ± 47 | 106 ± 13 | 135 ± 7 | | | | |
| SRPR-4150 | GG | CG | CC | 0.0028 | 0.0028 | 0.00057 | 53.7 |
| | 110 ± 14 | 114 ± 9 | 162 ± 12 | | | | |
| SRPR-3064 | GG | AG | AA | 0.00033 | 0.00034 | 0.00037 | 92.8 |
| | 66 ± 66 | 93 ± 13 | 142 ± 7 | | | | |
| NM protein (lb) | | | | | | | |
| INSIG1-12052 | GG | AG | AA | 0.0014 | 0.001 | 0.008 | 9.6 |
| | 29 ± 2 | 33 ± 2 | 39 ± 3 | | | | |
| INSIG1-3885 | CC | CT | TT | 0.0011 | 0.0011 | 0.011 | −10.09 |
| | 24 ± 3 | 31 ± 2 | 35 ± 2 | | | | |
| INSIG1-6082 | TT | GT | GG | 0.0051 | 0.0051 | 0.0079 | 13.7 |
| | 29 ± 1 | 36 ± 2 | 45 ± 7 | | | | |
| SCD5-179412 | TT | GT | GG | 0.004 | 0.004 | 0.0099 | 8.9 |
| | 27 ± 3 | 31 ± 1 | 36 ± 2 | | | | |
| SCAP-34632 | CC | CT | TT | 0.027 | 0.027 | 0.043 | −9.17 |
| | 22 ± 7 | 29 ± 2 | 33 ± 1 | | | | |
| SRPR-4150 | GG | CG | CC | 0.011 | 0.01 | 0.0024 | 7.45 |
| | 30 ± 2 | 30 ± 1 | 37 ± 2 | | | | |
| SRPR-3064 | AG | GG | AA | 0.0097 | 0.0098 | 0.0062 | 11.06 |
| | 27 ± 2 | 30 ± 10 | 34 ± 1 | | | | |

INSIG1-12052 allele A is associated with increased PTAM, PTAF, PTAP, CHEESD, NMD and NMP.

INSIG1-6082 allele G is associated with increased PTAM, PTAF, PTAP, CHEESD, NMD and NMP.

SCAP-34632 allele T is associated with increased PTAM, PTAP, CHEESD, NMD and NMP.

SCD5-179412 allele G is associated with increased PTAM, PTAP, NMD and NMP.

INSIG1-3885 allele T is associated with increased PTAF, CHEESD, NMD and NMP.

SRPR-4150 allele C is associated with increased PTAM, PTAF, CHEESD, NMD and NMP.

SRPR-3064 allele A is associated with increased NMD, NMP and CHEESD.

SREBP1-13636 allele C is only associated with PTAF.

INSIG2-93277 allele C is only associated with PTAFP.

TABLE 3

Sequences Flanking SNPs

| Locus | Poly ID | Context |
|---|---|---|
| SCD5 | 134718 | GTGGTCGAGGGACCACCGAGTCCATCACAAGTACTCGGAGACGGACGCTGACCCACACAATGCC<br>CGCCGGGGCTTCTTCTTCTCCCACATCGGCTGGCTGTTTGTCCGCAAGCATCGGGAYGTCATTGAG<br>AAGGGGAGGAAGCTTGACGT[T/C]ACCGACTTGCTGGCTGACCCYGTGGTCCRGTTCCAGAGAAA<br>GTAAGTGAGCAATCACCATTGATGTCCCTGAGGGACAGGACCCAGAGTCAGAGCCCAGTGGGGT<br>GTAATAATATCCCCAGGCAGTTCCCCTGCAGATTGGATCTTCTTA<br>(SEQ ID NO: 7) |
| SCD5 | 179412 | GGTGGAAGACAAAAGAGAGTCTAAGTAGTAAGGAAAGAATGTTTCTGCTTTGTAATTATTGTGTG<br>TGTGTGTTGTTGTTTTAAAGTAAGAAAATTGAAAATGTTAAAAAATGAGAATACAGGAAATGGCT<br>CTCTTATTTTTTTGCCCTGT[T/G]TCCAGCTTGTTAATGTTCCGCTTTCTTTGCTTCAAGGGGTCTGT<br>TCACTGCTCAGCTAGTTTTGTGTCCTGAGCTGTCCGTCCAGCTGACCCTATAATCAGTGCCTGTTTT<br>AAGTGTTTGATTTTGTTCTCTTTGCTATTGTCGTTTTAA<br>(SEQ ID NO: 8) |
| SREBP1 | 1199 | CGAGCCGTGCGAGCTGGACGCGGCGCTGCTGACCGACATAGAAGGTGCGTCAGGGCCACTGGRCT<br>CCGCGCACGGGCGGCGCCGGGCCGGGGGCGCGGAGGGCGTCGGGGCGCGGCCCGCGCCTCTGTG<br>CGGAGCGCTCCGCGTCTCTGC[C/G]CCGAGGGCTGCGGGCCTCGCGGTCCTGTCCCCGCGGAGCTG<br>CCCGTGCCCGCTGGGTCCTGTAGGAGGCTCGGCGCTGAGCACGTGCGCCTCTGGGCGCCCCGGCC<br>CGCACCCCGCGGCCACCGAGTCCTCAGTCGCGAGGCGGCGTTGG<br>(SEQ ID NO: 9) |
| SREBP1 | 12504 | AGATCTACGTGGCCGCCGCACTCAGGGTCAAGGCCAGTCTGCCCCGGGCCTTGCATTTTCTGACA<br>GTGAGTAGGTGGTGACCAGTGGGGGCTCTGTGGGTAGGTGAGGGCTGCACAGAAAGGCAYGTGG<br>TTATGGGGCCRGCTGTGGGCC[T/C]GCCGTGGTCTCGGCCAGGGTTCAGTTTGACGGCCCGTTCCT<br>TCCTCAACAGCGCTTCTTCCTGAGCAGTGCTCGCCAGGCCTGCCTGGCACAGAGCGGCTCAGTGC<br>CCCTTGCCATGCAGTGGCTCTGCCACCCTGTGGGCCACCGTTTC<br>(SEQ ID NO: 10) |
| SREBP1 | 13508 | GCCAGAGCCCCCTGTTCAGTGGAGCCTGTGGGTGGCCAGAGCTGGGCCACTGTGGCCTTAGGTGC<br>ATTTCGGTTCCTCTCTGGGCCTCAGTTTCCCACCGGCCCAGCACGAGGGGATGGAGGCTCTTGGAG |

TABLE 3-continued

Sequences Flanking SNPs

| Locus | Poly ID | Context |
|---|---|---|
| | | GAGCCAGGAGGCCAGGCTG[T/C]GCTGTGTGCAGAGGTGAGGACCCCTGCCAGCCATCCTGACCG<br>CCCRTCCTCTCCTGCCACAGGGAGTTCTCAGATGCCCTGGGGTACCTGCAGCTGCTGAACAGCTGT<br>TCGGACGTGGCCGGAGCTCYTACCTGCAGCTTCTCCATCAGC<br>(SEQ ID NO: 11) |
| SREBP1 | 13636 | GAGGAGCCAGGAGGCCAGGCTGYGCTGTGTGCAGAGGTGAGGACCCCTGCCAGCCATCCTGACC<br>GCCCGTCCTCTCCTGCCACAGGGAGTTCTCAGATGCCCTGGGGTACCTGCAGCTGCTGAACAGCTG<br>TTCGGACGTGGCCGGAGCTC[T/C]TACCTGCAGCTTCTCCATCAGCTCCAGCATGGCTGCCACCCC<br>CGGTGAGCCCCCCACCTGTGACGCCCTCAGCCCCAGCGCCAAGCAGCTCAGCTTCGGGTGCAGTG<br>TGGCTGAGTTTCTGCCTCCTGTGCCCCCTTTGCAGGCACAGAC<br>(SEQ ID NO: 12) |
| SCAP | 34632 | TTGGCAGCCCCCACTGTGGGCCAGACCCCGCAGGGCCCCAGGAGCCAGGCCTGCTGAGGAGCAG<br>CCGTGTGTTGGGGRCCCCCTCAGCACCCTCCTCCCCCCACCCCGCTCTGTCCCAGGGAGATCTTC<br>CCCTACCTGGTGGTGGTCAT[T/C]GGGCTGGAGAACGTGCTGGTGCTCACCAAGTCCGTCGTCTCC<br>ACCCCGGTGGACCTCGAGGTGAAGCTGCGCATTGCCCAAGGTAACAKGAGGGGAGTAGGGGGCA<br>TGGCGGCGGGGGTTGTGCTGCACCTCCTCCTGCYGAGGGAACGG<br>(SEQ ID NO: 13) |
| INSIG1 | 3885 | ATTAGTTTAAAAATAAAAGATGTAAAGTTAGTTTAAATATCTGATGGCTGGTAAATCTAGGAAAG<br>GGAATGGTTTGAATATCGMGTTAATGATCCCCACGAGGCAGTCGCGTCGTCTCTGCTGGCGTGCT<br>CAGACCCTGCCGTCTTGTCT[C/T]TCCCCGCAGCTGTGGTCGGCCTGCTGTACCCCTGCATCGACAG<br>TCACCTTGGAGAGCCACACAAGTTCAAGCGCGAGTGGGCCAGCGTGATGCGCTGCGTGGCCGTCT<br>TCGTYGGCATCAACCACGCTAGTGCTGTATCCTAAGACGTTA<br>(SEQ ID NO: 14) |
| INSIG1 | 6082 | GGCTCATGCCTCCCTCTCCCTGCAGGTACACGTCCCCAGACTTCCTCTACATCCGCTCCTGGCTGC<br>CCTGCATCTTCTTCTCRGGAGGCGTGACGGTGGGGAACATAGGACGACAGCTGGCCATGGTGCGT<br>AGTCMCACGGGCGCCTGA[T/G]GCTGGCTTTCAGCTGGGTCAGCTTGGTTTGCCTGGGACGTTATC<br>ATTTGTGTCAATACGTGTAYAGGCAGGAGCAGCAGTTACTCAGATAAGCATACACTTTAAAAAGG<br>CGCATCCCAGGCCATTCTCGGCTAACTTGTAAAGGTTCAGGG<br>(SEQ ID NO: 15) |
| INSIG1 | 12052 | CCCCGGGGACGGCTTGGTGGTGCTTACAAAGATGAAGTGTGGTGAGACAGGAATATCACTMATCC<br>AAAAGATTTTAAAAATAGGGCTGTGTTATGAAAAAGAAAAGGCGGGGGTGGCAGCAAGCGCAG<br>GGTGGCCGTGCCGGGCAGGC[G/A]GGCACGGCGTGCCCTCGGTGCCCGTGTAGGGTGCTACGCAG<br>ACAATCCTGCAGAGGAGGCAGTGAGTGGGAGGTTGTGGCTCTGCGCTGCAATGGGTTGGACTTTC<br>CACCCTGGTGTTCACGGAATCCGCACCGTCTCGAATGGGCGCCC<br>(SEQ ID NO: 16) |
| INSIG2 | 93277 | TTAATTCCTTTAGTGTAATCCTCTGGCAAAGAAATTAGAAAATTGAATTTATAAAGCTTCATTTTG<br>CCCAGAGATTTTGGAGTAGAAAAGGGCTGTATATTTGTGAATAGATGCTTAMGTAGGTAGCGGAA<br>ATAAAATATCATTTGTCCT[A/C]TACCAGAAAGTCTCAGGAACCAAAATAGCTTGGCAGGTTGGAA<br>GATAATGTTCACTTCAAGGCTTTCTCCTCAACAAATTAAAACTAGAACAGTTGACATAATAGAAA<br>GGGATAGTGTGTCCTTGGTACTCTTGTTTCTGAACTGCATTA<br>(SEQ ID NO: 17) |
| INSIG2 | 93461 | CAGGTTGGAAGATAATGTTCACTTCAAGGCTTTCTCCTCAACAAATTAAAACTAGAACAGTTGAC<br>ATAATAGAAAGGGATAGTGTGTCCTTGGTACTCTTGTTTCTGAACTGCATTATTATAAAATGTGTC<br>TGTCAGTAAATCATATAGA[G/C]ACTGTGGTACCCTGTTGAATAGCTGTCAACTCTTCTATTTTCAA<br>GTTCCTGTATGATTCTCAAACAATTCTAAACCTGTTTGAGAAGTAATAGTGGTTTCCATTTTAGCA<br>AAAGTGTGTGCCTTTAGCAATATTTGTGTATTGAAGCTTC<br>(SEQ ID NO: 18) |
| INSIG2 | 93867 | AGTAAGATCTATTAGTGAAGTATCATGCCATCATAGTTTTAATCCTCTCTAGTCTTGTACATTGTAT<br>TAAAAAGTTGAATGCACTCTAGTCTTAACATTAACATCTCTTATTTTAGAAAAATGAACAGATGAT<br>ATTATTTGGTTACAAAT[T/C]TTAAGATGACTCTTTAACACTGATCTCAGAAAGTGGATTTTGATAA<br>CAACATACAGTTGTCTCTCACACTGGCTGCACTRTCCATTGGATTGTGGTGGACTTTTGATAGATC<br>TAGAAGTGGTTTTGGCCTTGGAGTAGGAATTGCTTTCT<br>(SEQ ID NO: 19) |
| SRPR | 3064 | CCTTCCCTCTGTCGTCGTTTGCCTCCCTGGCTCAGGTGCCCACCACCCTSATTATTGTCCCCARTGT<br>CGGTGATCCCCAGGTGTTTCTTCACAGTTTTCTCTGAATGATCTGGGAGGGTTTCCCCATTTGTC<br>TATTTTGTTGGAATTC[A/G]GTCTTTTTTTTTCAGTGAGTTTTCTCCTTGACAGGTTCTGATGGCCC<br>TCTGGCTACTAGCAAAGCAGCCCCTGCAGAAAAGTCAGGTCTCCCAGTAGGACCTGAGAACGGGG<br>AGGAACTTTCCAAAGAGGAGCAGATCCGCAGGAAGCG<br>(SEQ ID NO: 20) |
| SRPR | 4150 | CTCAAGGGCCTTGTGGGTTCCAAGAGCTTGACTCGTGAAGACATGGARTCTGTGCTGGACAAGAT<br>GCGTGATCATCTCATTGGTGAGTCAGGACAGGGCAGACTCGTGTTTTKGGGCTAAGGATAGTGGG<br>GTAGAAGGGCTGTACCGTGG[G/C]GGTCGTTCACTCCTGCCAGGGCATTCACCCCACGTTTGTCCC<br>CCCTCCTTAGCTAAGAATGTGGCAGCAGACATTGCAGTCCAGCTCTGTGAATCCGTGGCCAACAA<br>GTTGGAAGGGAAGGTGATGGGGACGTTCAGCAGTAAGTATCTC<br>(SEQ ID NO: 21) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of selecting individual bovines comprising:
   a) detecting in a biological sample comprising genomic DNA the allele at SNP ID INSIG2 93867 in one or more bovines, wherein a "CC" genotype is detected in at least one bovine; and
   b) selecting the bovines with a "CC" genotype at SNP ID INSIG2 93867.

2. The method of claim 1, further comprising detecting in the biological sample from the one or more bovines the alleles at one or more SNP IDs selected from the group consisting of SREBP1-13636, SCAP-34632, INSIG1-3885, INSIG1-6082, INSIG1-12052, INSIG2-93277, INSIG2-93461, SCD5-134718, SCD5-179412, SRPR-3064 and SRPR-4150.

3. The method of claim 2, further comprising selecting one or more bovines having one or more genotypes selected from the group consisting of:
  i) a "CC" genotype at SREBP1 SNP ID 13636;
  ii) a "TT" genotype at SCAP SNP ID 34632;
  iii) a "TT" genotype at INSIG1 SNP ID 3885;
  iv) a "GG" genotype at INSIG1 SNP ID 6082;
  v) an "AA" genotype at INSIG1 SNP ID 12052;
  vi) a "CC" genotype at INSIG2 SNP ID 93277;
  vii) a "CC" genotype at INSIG2 SNP ID 93461;
  viii) a "CC" genotype at SCD5 SNP ID 134718;
  ix) a "TT" genotype at SCD5 SNP ID 179412;
  x) an "AA" genotype at SRPR SNP ID 3064; and
  xi) a "CC" genotype at SRPR SNP ID 4150.

4. The method of claim 1, further comprising detecting in the biological sample from the one or more bovines the alleles at one or more SNP IDs selected from the group consisting of INSIG2-93461, SCD5-134718, SCD5-179412 and SRPR-4150.

5. The method of claim 4, wherein the one or more bovines are female.

6. The method of claim 1, wherein the alleles of the one or more bovines are detected by one or more amplification reactions using polynucleotides which distinguish between alleles of the SNP.

7. The method of claim 6, wherein the one or more amplification reactions are selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

8. The method of claim 1, wherein the alleles of the one or more bovines are detected by hybridization using polynucleotides which distinguish between alleles of the SNP.

9. The method of claim 1, wherein the alleles of the one or more bovines are detected by sequencing a subsequence of the gene comprising the SNP.

10. The method of claim 1, wherein the one or more bovine is a *Bos*.

11. The method of claim 10, wherein the one or more bovine is a *Bos taurus*.

* * * * *

SEQUENCE LISTING

<160> NUMBER OF SEQ ID NOS: 21

<210> SEQ ID NO 1
<211> LENGTH: 17493
<212> TYPE: DNA
<213> ORGANISM: Bos taurus
<220> FEATURE:
<223> OTHER INFORMATION: sterol regulatory element-binding protein-1 (SREBP1)

<400> SEQUENCE: 1

```
attagtatct cagtccacct tattaggacc ctcccttggc acctagctct gcccccaacc      60
cacaggaccc agggtcctgg tccagctctc tccccagtct agctgtctcc tctgacctgc     120
ccgggcctgt cccgatccag ggcaagggg cccaggccca aagcacagac tgcccctacc     180
tcatcccagc tgctctgggg acggggtcca gtcctggtac agctccaggt ggctgtgtga     240
gcttgtgctg gtgagctcct aaactccggg tgcagaggcc agcccacctt cagcagccgg     300
actgggccca ctaaccccca gccttctgt cagtcccaca gctggatctg ggaggaaacc     360
agagtaagtc agagtgggaa attctagcct cttccagact cttcagaaga tctaaagaag     420
gaggggcagg ctcatctcac aggcccagcc ggccaccgtt actaacgtcc cagtcagcct     480
atgcggagac accatcaagc cccgttacag ctgaggaaac tgaggaacag tgtggtgagg     540
taactggcca gagggcacac agcaggtctt ggactagtct gtcttctaaa ggcccaaatc     600
tcagaatgaa gtttgtcggg tcacttcttg ccccaagttc agcgacatct gggacggacc     660
caacccgggg cttccactcg gcctccttgc tcagggcggg agaagccggg gcctgggagc     720
cccgcagcag tccgcgcagg gatggaacgc caggggggcg ggtgcgcagg ccagatcggg     780
gccgcctgac gctcctcagg ttgggcggga ccgtccaccc gggggcgggg ctcctgcaag     840
gctccgcccc gccccgcctg ccccgcagaa ccgccgccgg gaacccagtt tccgaggaac     900
ttttctcggg cgctgggcac caccgagttc cgggcgggac gcgaacgcgc ggagcggctg     960
cggcgggccc ggcggacctc cgagaggagg tgactgcgcc atggacgagc cacccttcaa    1020
cgaagcggcc ttggagctgg cgctggccga gccgtgcgag ctgacgcgg cgctgctgac    1080
cgacatagaa ggtgcgtcag ggccactggg ctccgcgcac gggcggcgcc gggccggggg    1140
cgcggagggc gtcgggggcgc ggcccgcgcc tctgtgcgga gcgctccgcg tctctgcccc    1200
gagggctgcg ggcctcgcgg tcctgtcccc gcggagctgc ccgtgcccgc tgggtcctgt    1260
aggaggctcg gcgctgagca cgtgcgcctc tgggcgcccc ggcccgcacc ccgcggccac    1320
cgagtcctca gtcgcgaggc ggcgttggcg agagccgggg accggcgtc gccgatgccc    1380
cgccccgccc cggccttgac gtcagcagga ggttactctc ggtcgttccc tccggccgga    1440
gagttcagct cggcgcccgc gctcctgcgc atgcgcgccg cggtcccgcg gaccctgaca    1500
gaccagggcc cggttctcct agctggctcc gggtatcggt tcggcacacg tttatcgagc    1560
gtctactgaa taccaggccc agttctaggc accagaggtt cacagacctg ggctccccct    1620
ttccttggaa gcacaaaccc accctaagga aacccataaa cggatactta tatctgtggt    1680
ggagctgggg cagggtgact gcttcgggta gggcggtggg gtgggacctg agctcagccc    1740
tgagaaggat gtcttcccg cagagggcac ggcgaggagt tggaggggca caggtgagac    1800
```

```
tgggcagatg ggtggaagag gacttggcag ggaaaggcgg gagcagcagc gcgggctctc      1860
ttacacacct agaaacactg ctctggttgt tctacaaaga gggtgttggg ggcgaagctg      1920
cagcggggcc agtcaggagg ctgttgccca cggagcacag agcacattcc agcctccgca      1980
ggttgcctcc gaggttccta tgcagtttca gccacgttgg ctaccttgca cttggttgat      2040
ggggaaaaca ggccctgagc acaggaccca aacctcccac agcctggatg gactcatcca      2100
tggagcctat ggccgcccta gggttagcaa aatggacaca actgagccaa cccctctttg      2160
gatggctctc tgggaaccca gctggtaggg cccaagagtt gccaggtccc ctggagggga      2220
gttgagagga gggccaggca gcgttgactc ggaggtgaga gctgaactgg atcccagagg      2280
cagtgggatg ttaagtgact tgtcccaggt cacacagcag agcatggtag agccagaatt      2340
caaacccagg gtgggagctc cagagcccac gctcttaaat gctggtctcc tattgtgaat      2400
gtgtgtatgt gtgtgacact gtagagcagg ggactcagga ggctgctcta tatggaggta      2460 tgctggggc ctgggagtgg gtcgaaacgg tcacaggtca cacggccacc tcatcctagc      2520
ccagagcctt tgactcatga gacggaggac tggcatcagg gagtctgccc atggccctga      2580
gccccaccca gcctgggcat gtgcctcggc cagactccgt catgtgacca gcgccctcac      2640
caggagcccc aagtcctgtg ctgcaggctg ggccctggct gcactgcacc acaactctgg      2700
gtagatccac ttgctcccag cctccttctc ccgttcttgt tttggggtcc cttgtgccca      2760
ttagagaggg tgtgtgggag ccgccttgca tgagtgctgg gattgtgttg atgccgtgga      2820
gggccttatc tccccactggt tcattcactg cactatgctg ctcagtgacg aagggggtgat     2880 tggaggacgc tgctggtcgg gtgggcctgg tcaaggggtg gcctgggcct ccagtgcata      2940
gctggaagtc acctctgcct gggcttccca gttcactcgt cttcgaagtc caggtgtctg      3000
ccttcgaccc agtccctaaa tcaaccacag ggacctggct tcctgggttc caggccagcc      3060
tgctcaaaga ggtacatggg ggccaacctg ccccccccagg cctctcccta cagtctctca      3120
tgcccaggtc tctccctggt gctgccaagc atgggccctc cttagaaaac aagctcaaga      3180
tggcttacag ccctgctctg gccacagcac atgcctgctc agctccctaa ccaccatggc      3240
tgcccagaac cccaagatac agtcccttgt ctcagtgtgg tgtttgagac ctgtcaggtg      3300
ggccgggccc gccctcccgt ggtgagtcct gtccctccag gccctcccca tgccctggac      3360
acactctgcc cccacatggc tctcctgcct catcctcacg tccagaggtc ctgagggcag      3420
agcctgggag aggcctctcc ccctggacat ggccctctc catccctctc ctgccttggg      3480
tgcctggccc atctgcccca ggtggcagga agcagaggcc ctcccggtgt ggctgtgtac      3540
tctctccagg ttgcagtggc tgccctgaaa agctggggtg aggccatagg tgggctgccc      3600
gtgaatccct gtgagttcca gccctcgcac ctgtgagggg gtggggagag ctgccggcag      3660
tccaggaagg cgagtgggcc agcagttggg agctgccttc tgcccggtgg tcacctcact      3720
ggatgcacac attctaggtg acctgcccag cctcaggtgg ggtcaccacc gggcagaggc      3780
ctggggtctg gacttcgccc agctgatagg gcaggccagg tggcaatgac tcctggccag      3840
agcaagtgcc tctgtcctgt gtcttgccag ccacaggccc cgtggatgtg cccttttgacc     3900 ctggggccta ctgggcgtgc atacctgcac ttgtgatagg ggaggggaga gcctcagaaa      3960
tgccacggtt atctcctcac tggtatacag attgggggcg gacatgccca ctaccccac      4020 ctgcccagct gaggtgtggg gagcagcagg aaggccaggc ccagtgggga ttgcctccca      4080
ggccaagaac atgttgcagt aaatccatct ctagctggca gaggagggcc caagcccagc      4140
atgtgtttct gggtttctgg ccatagttga ttgtttgctg cacaaccgcc tcggggcagc      4200
```

```
ctcagagatg caaattaaag caccttcaag gttccagtca cacagttgtg aggactaagg   4260
aaagcacccc aaagtaggta aaaacgacaa aacccagtgc tggtgatgct ctgattaaac   4320
aggacacatt gcaagggaga gtgtaaggag gtttattgtt ccagagagca gcctggcagc   4380
tcggaagcag tgtgctgcct ttgaaccaac acacacactt cagaggggc aatgccaggg    4440
ctgagccttg gagcttcaca ctgcctcccc tctgcgtagc actctgcacg cacatcctga   4500
cctgggatga gtggtggcaa caagttggga cagagccagg ctggcctcag ggctcactcc   4560
tgccctggc aggcggggct aggggctgtg ggcttggggg gttggcaggc ctgggtgtag    4620
gtctgaggtt cttcacttgg cagtcggaag acctggggca catagcctcc ctctgagcct   4680
tagtggcctc atctggctag agggctcata ttcaggttcc cctggggctc tggctccggg   4740
gccatctcat tccaggaaga gcaggcacct gccacatccc cgggcagccc cacacacaca   4800
aaggcaccct gtgccctgc tgcacatatg atcggctgag gacatgcaaa cctgccaacc    4860
gtgcttctcg ggaggttcca ggagatgctg gtgggagcag cggggctggc tggcagggtg   4920
caagcccgct tcccactgct gccttgtgcc ctccctcacg cagccagagg tggagtggtg   4980
ctgttgcttt gtgctatctg ctgcagactt tgtgacctgc ttacaaatcc cttttctgcc   5040
cattccctga gaattggtgt tcttagctca ggcgacagac aaacgtgggt tggaactcca   5100
gctttgggct gtctccttga ccctcttcct tcttgacccc ctcttctgca gtcacaccag   5160
cttcttcttt gtcttgatag cacaccaagc ttgctcccac ctcagggcct ttgcacttgc   5220
tgttcctact gcctgtgaca tccttcctcc tggcccattc ccttctttca ttcaggcctc   5280
tactcagatg ccccctccac aaagaggcct gccctgactc cctctgtttc ttcacgatgc   5340
tcatcacctg caccccttc ctccacggat tagtagacgt ttggcctccc tcgaacagaa    5400
gctccactgg gaggtcttca cgctctgttc ctgaactcga acagaagctc cactgggagg   5460
tcttcacgct ctgttcctgc actcgaacag aagctccact gggaggtctt cacgctctgt   5520
tcctgcaccc ccagcacctg gcactggcct ggcatttagg gacatctgag cttcatgggc   5580
caagccatat gaaggaggtg gtgagctccc tgtcccagga ggcatgcaag aagagtttgg   5640
ggtgcaaggc cttgtgtcag ctcctgcggg tcataggctc ctgtgatagt cagaggtggg   5700
ctcctgtggg tgggcgtgat gggggtcccc caaggatttc tgtcatggcc tcacaggata   5760
aataggcccg agaataaaag gcccacatct gccttcagag ggaggtttgt aggtagagcc   5820
agggaggggg cagagggttt caggtttcct gttaggccct gatagaatca gggcaggaga   5880
ggaaaagatg aagccaggct tggggagggg caggtgggcc ccctgaggct gagcccacac   5940
ctcccctctc cccatagagt gggtgcagga gctacgcagg ccttgagtct taggtcatgt   6000
gagtgcttac ttcactggcg gaggggcccc actgtgggag cccttccag cctttcaggc    6060
ccactggact ggagggagct tctttaaact gtgcaccatg gaggggggc tctcttgcct    6120
catagaatcc cctgctccaa ggccagaggt gaaggctcag agaaggagag tgacttgctt   6180
gggactgcac agcaagtgaa gggtggaggg aagttctggc acccagacct ggctttagaa   6240
gagagtgaga tggggcccag tcagaccgtg agttcagagg gtggtggccc ctcaacatgc   6300
caccagatgc actgagtctt cgttagatca tgtccccgag gccagccctc ctcttggcag   6360
ctgttcctga ccctatcggc tgtgggcctc tcccttctat gtccttggtc tagatgggac   6420
agagccaaga catgtgaaat gggaaacaaa gggggcgaga gagcatgaga cagggagagg   6480
gacggtcagg agcaggtagg cttgactctg ggtgccctg gccctgcaga ggctcaggtg    6540
tgagtcagcc ctggaattca ggcctgagtg tctcccagtc tcaaggtact caggtgaggt   6600
```

```
aggagccttg ccaacaccaa tgtcttgatt tggggggtg agggagggtg tgagcaccca      6660
ccagctgagg aggaagggag gtggagaatt cagttgtcct tggcacctgc tgcaaggcca      6720
tggaaggacc cgaacaaaga agggtggata tgtgatggag aggagcctcc tggaaagtga      6780
gagccatcag ggccagggga tctctgcccc caacaccctc tgaggctgca ggacaccaag      6840
aaagggttgc aggtgggctt ggccgcagtt ggaggctggc atgagcctgg agtccacttg      6900
gccacaaaag ctggagctgg caacctgggc tgctggccag gctctgttca tctgtgtaga      6960
actcgaacct tacacagaag gggagaggtt ctgggcaccc ctccagagac ccccagagcc      7020
tgtcacctca ggacttcctc accttctgtc ccagggactg ggctgcctgt tggcttcccc      7080
tgaccctgca gtaataagt gagtcaggtt caccccgaga ctgctggggg tggggtgtc      7140 actgaccccg tcccagatcc aggcccctct tcaaagggat gtctgtatgg ggcttcagct      7200
cgggctcagc tgttactggc catcagtttg gggtatgttc ccttcctcag tttccctggg      7260
aagtgactgt tgccaggggt tcgtgcagtg aggtgtggcc catgctgggg cggcctagga      7320
aggggaggtc cccacaccca ctgccaggtg cccctaggtc tcacttaagc actgcaccca      7380
gtaacacctt tacttgtccc cgtcggagcc cagaatcgtg ctcgtcccat ttcccaagag      7440
cgaactgagg ctgagcgtgg tcgagaccgg ctcagggtat cagagagccg gagacttacc      7500
tgcggagctg gggcacctct agccctcgt tccaccgctc ttctctgact tgaccgccag      7560 taaccctgc agacgtcggc gcctagtggg ttaagggcca gcgtccgcta gtaaccccgg      7620
ccccgcggcg caacccgagc cgcgtgccgt gggggtgggg cggggccggg gcggggcgcc      7680
aggaggcggt ggcgcggccg ctgattggcc gcgcgcgctc accccatgcc cggcccgccg      7740
ctacgcgggg cggggctggc cggcggggcg gggcggggcg gggcggggc ggggccggta      7800 gcggggcgg ggccggcggg tagctctgtc gctcagcggc tttaaagtgc gccggctccg      7860
caggtgaagt ctgtgctcgg agaccggcag gccagccgcc tggacgcccc gaggggcgac      7920
gggcccgggc cgcggaacca tggattgcac gttcgaaggt attttttgga ggcctccacc      7980
cctttattat agagctttca tttcctcaga ggggttccat cctcggtgcc ctgaggggag      8040
gtgtacacac tccctgctct aagaggagta ggctccccac gcccacgtcc ggagtaaggg      8100
ggtggctttc ccacatctgc tccacagcgg ggaggaccac ttttcctctg tctcctggat      8160
ctcccttttg ggggcacctt gggcttgaca gacagtggga gccctaggtc agccagtttc      8220
gtctctcggc ctcagtttcc ccaactatca aaggggctcg tgaggcctgg ggtaggggt      8280 cctgcgggag aaagcactgt gcactatgac ctgtgcagac ctggagggcc tgccaagtgt      8340
ttgtgtttga ggacaggagg gctgagcctg gcacccaccc ccaccccatc ctcccttgtg      8400
ctctcctggc agcttgggtc gtcccctgca gtcactttcc tgcctggcac ctgtcagtag      8460
gagggactca ggtgaccttg aggccccact ccgtgcagct gtcctgtcac aaagtgtttt      8520
gtctgtcctg tacagatggg gagactaagg gctggtgaga ggacactttc gccagaagcc      8580
cgggctgggg gtctggggga cacctggggc tcccagggtt tgctcatggg tcctgcagag      8640
cactttgacc cagtggatga ctccttcagt gggttagagg gccctggact gacccagcca      8700
gtctgctggt tgccagctgg gggagagggc ttgtggccag tttgggctgc tgcgggccat      8760
gtgtccagtc tgtatgagga ggagagtcag gacagacggg attggctttc attgagggga      8820
gactgaagct tgaatggccg gtcccaagct gcttggctgc aaacagggcc tgggcttgtg      8880
cccagaacat tccgagacac actggttggc acacatacgg ccagtggttg actctgcccc      8940
aagtctcggt ttattgcaca gagaaatggg ttggcaaagg cagctctgaa ttgagcggtc      9000
```

```
gtggacctct gcttcggggg ccactggcat tgtccagtgt cgcaaggctg tttgatgcac    9060
tgggcaaagc tccagatgtc ccgggtgtct gtgagcgtgg gctcctgggg gtggctttt     9120 gtttctgtgg cgttgctccc acgtgtacac tgtgtcaggg gtggggggg cgtgaagaca     9180 cacaacacct gctccactgc tgctcacagc ttgtcctcct ccccgcagac atgcttcagc    9240
tcatcaacaa ccaagacagc gaattcccgg gcctattcga cccgccctac gctggggcg     9300 gagcagggac cacagaccct gccagtcctg acgccagctc ccgggcagc ctgtccccac     9360 ctccttccac gatgagctcc tcacttgaag gcttcctggg ggtgaccaag gcgacacccc    9420 caccccttgtc ccctccccag cctgcgccca ccccctgaa gatatacccca tctgtgcctg   9480 ccttctcccc ggtgcctggg atcaaggagg agccagcgcc cctgactgtc ctccagccca   9540 ccaccccccca gcccctgcct ggagctctcc tgccgcagag tgttgcggcc accacccac    9600 cgcagttcag ctctgctccc attgtgggct acccagcc tccgggaggc ttcacaggta     9660
aggagggcat gtggaggtgg gagtcaggtg cttttggtag aggagtttgc aggctttagc    9720
agtcgggctc ctgctctgtg gctggaggcg cctgctcacc agcagttctc gggctcctgt    9780
ggatgaagca cttccctcac tgcccggggt ccacaccagc tgcccttccg cagagcgatt    9840
cttggctagg aggctggcat acttgcatca gagccctggg cagagccatc cagataggaa    9900
cccacggcca caagggtagt gactaatccc aggtcacatg gtgatgagga cctggggggac   9960 gggttggaag tgggttgcga cagcctgtgt cctcagcccc agccttcatc tctgcaggga   10020
cccctccggg gagcagctcg cagtcactgg ctggcctgcc actggcttcc ctgccagggg   10080
tcccgcccgt ctccttgcac agccaggttc agagcgcggc ccccagcag ctgttgacag    10140 ccacagccac ccccacggtg gccctggag caaccgctgt gacctcccag atacagcagg    10200
tcccggtgag gcggtctggc tggcatcagg gaggtggcag ccctgggccc agacccatag   10260
cccacgactg aggcccctcc tgtccttagg tcctgctgca gccccacttc atcaaggcag   10320
actcgttgct cctgacgacc gtgaaaacag atgtgggagc cccttgaaa gcggcaggca    10380 tccgctccct gggccctggc actgctgttc aggcagcgcc cttgcaggta gggggctcag   10440
gcagggtggg ggtgggtggc ttgggtgggg tgggggcgg cgaggcttgc tcacatgtcc    10500
acctgctaac tctgcctggc cctgcagacc ctggtgagtg gcggggccat cctggccacg   10560
gtgccactgg tagtagacac tgacaagctg cccatcaacc gacttgccag tggcaaggct   10620
ccaggctcgg cgcagagccg cggcgagaag cgtacagccc acaacgccat cgagaaacgc   10680
taccgctctt ccatcaatga caagatcgtt gagctcaagg acctggtggt gggcaccgag   10740
gccaaggtgt gggctgaggc cctaacaggg tggctctggg caagcaggca cctgggagga   10800
ggaggaggaa gatggggctg gcagacagt cctgggggccc cagcctcctc gggcctggca    10860
gctctgttca gctgagcttc agggaagccc cgggtggcac aggctcttcc aggtgctggg   10920
gatttagcag gggacagaca gagatcctgc tgttgagtag ctgacgttct agcagggtgc   10980
gggggcgcca gcagagctgg gttggggtac gccaggtggc ataagtgctg tgctggagag   11040
aagagggatg ggggaagttg caaacctaag ttgggtggtc agggaaggcc tcacaaaggt   11100
gatgcgatgt gtgaacagag gcctggagga ggtgagaggg tgaggcataa agtggagtga   11160
tgttgacagc agccagccag gtgctgttgt ctgtatctta cttacctggg cggcaggttc   11220
taggggagga atgttcccag ggagtaggaa tagcagatgc aaatctcctg aggcgattgt   11280
gttgcaaagc agccctgccc tctcgcttca gtgccaagct ctctggcctg accacttgtg   11340
ccatctccct cccacccccac ccctgcagtt gaataaatct gccgtcttgc gcaaggccat   11400
```

```
cgactacatc cgcttccttc agcacagcaa ccagaagctc aagcaggaga acctgagtct   11460
gcgcactgct gtccacaaaa gcagtgagtg ctggccctcc ctggctcgca gctccccag    11520 atcctgagct ccaatttggg ttgaggtggg gtgtggagct cactccagcc tgctcctctc   11580
tggcccacag aatcgctgaa ggacctggtg tcggcttgtg gcagtggagg gagcacagat   11640
gtgcccatgg agggcatgaa gccagaggtg gtcgacaccc tgagtccacc cccctcagat   11700
gccggctcgc cctcccagag cagccccttg tcccttggca gcaggggcag tagcagcggt   11760
ggaagtggca gtgactcgga gcccgacagc ccggtctttg aggacggcca ggtggggcct   11820
gcagtgttgt tcccttcttg tcatccagca acttcctccg agccccagga ctggatcagg   11880
cccctcacac atcccacctc ccctttata  gacagaagaa agacagggct gaggggttcc   11940
cacagtaagg caggggggcag agttgacccc tccttcttgg agctgtgctc tctgggtcac   12000
gccgccctgt tctcaccgcc ctgcccgtcc ccccaggtga atccagagcc gctgcctgct   12060
ccccacagcc agggcatgct ggaccgctct cgcctggccc tgtgcgcgct cgtcttcctc   12120
tgtctctcct gcaacccctt ggcctccctg ctgggtagcc ggggtcctgc tggcccctcc   12180
gacaccacca gcatcaacca cggtcccagg cgcagcatgc tgggtgctga gggcagaggt   12240
agggtggtag gaggggggct ctcgcagagg tggatcttgt cctgtgggct tggggctctg   12300
aatttcctgg gtgcccagcc tctgtgtccc cagcttctgt ctgcccctag atggtcctgg   12360
ctgggcccca tggctgctgc cccactggt ctggctgatg aatgggctgc tggtgctctt    12420
ctccttggca cttctctttg tctatggaga accagtcact cggccccact catgcccgc    12480 cgtgcacttc tggaggcatc gcaagcaggc tgacctggac ctggccaggg taagtggcca   12540
gaccctgggg gatgggatcc ggcaaggctg ggaccccgag cagtgtctgg gaaggtgctg   12600
ggcataccgt ggacctcccc tgttcttccc actcctgact accccctccga ctcctgtgga  12660 cccctagggg cccagcctgc gctgctggga tggtgtggtc ctcacgggag gcccaaggtg   12720
gaggagtagc acagccccac gtttcttacc tgaaaacccc tcaccccccag ggggactttg  12780 cccaggctgc ccagcagctg tggctggccc tgcgggcctt gggccggcct ctgcccacct   12840
cccacctgga cctggcctgc agcctgctct ggagcctcat ccgccacctg ctgcaacgtc   12900
tctgggtggg ccgctggctg gccggctggg cagggggcct acggagggac agggccctac   12960
aggcagatgc tcgcaccagt gcccgtgacg cagccctcgt ctaccacaag ctgcaccagc   13020
tgcacaccat gggtatgcga gcaagggctg ggccccgggg gtcctgctgc ctccacacca   13080
ctcttggcct cacgccctct tatcttccag gaaagtactc aggtgggcac ctcgctgctg   13140
ccaacctggc actgagtgcc ctgaacctgg ccgagtgcgc tggagatgct gtgtccgtgg   13200
ccacgctggc tgagatctac gtggccgccg cactcagggt caaggccagt ctgccccggg   13260
ccttgcattt tctgacagtg agtaggtggt gaccagtggg ggctctgtgg gtaggtgagg   13320
gctgcacaga aaggcacgtg gttatggggc cggctgtggg cctgccgtgg tctcggccag   13380
ggttcagttt gacggcccgt tccttcctca acagcgcttc ttcctgagca gtgctcgcca   13440
ggcctgcctg gcacagagcg gctcagtgcc ccttgccatg cagtggctct gccaccctgt   13500
gggccaccgt ttcttcgtgg atggcaactg ggccctgtgc agcgccccga gggacagctt   13560
gtacagcgtg gctgggaacc caggtgcctt ctctcccctgg gccttcccc gtgcccaccc   13620 ctttccccac agctggccgc ctcctctgtc cccgttccc attcctcatg cctttccctg   13680
gtcagtctct tgtcccctgc ctctctgctg tcccggccca cctgcctg ctgccctgcc    13740 atctggtgtg gctatgggga tgtgcagatg gggaggccaa cctgggtctg tctcagcggg   13800
```

```
ggctcttcag aggcaaacag gaagacgggg caggggggcca gggggctgat tcaagaggtg    13860
ctccagacaa catcaccatg cagtgaggag gtcgggaaag ggcgtgcatc ccaggtgggt    13920
tatcctgtcc acaggtggac ggagtgttta tccaccagct ttcaattgtc tcagagccag    13980
gccctcccgt gcccagaaaa gatccctagt gcagggaggt gcctgtgcac aggaggggtg    14040
gggccattct cgcccctcca ctcgcccact cttctccaca gtggatcccc tggcccaggt    14100
gactcaactg ttccgcgaac atctcttgga gcgagcactg aattgcgtgg cccagcccag    14160
ccccagtcct ggatcagccg aggggacaa gtgagtgtct ctgtgcacct cagcaggcca     14220 gagcccctg ttcagtggag cctgtgggtg gccagagctg ggccactgtg gccttaggtg     14280
catttcggtt cctctctggg cctcagtttc ccaccggccc agcacgaggg gatggaggct    14340
cttggaggag ccaggaggcc aggctgtgct gtgtgcagag gtgaggaccc ctgccagcca    14400
tcctgaccgc ccgtcctctc ctgccacagg gagttctcag atgccctggg gtacctgcag    14460
ctgctgaaca gctgttcgga cgtggccgga gctcttacct gcagcttctc catcagctcc    14520
agcatggctg ccaccccggg tgagcccccc acctgtgacg ccctcagccc cagcgccaag    14580
cagctcagct tcgggtgcag tgtggctgag tttctgcctc ctgtgccccc tttgcaggca    14640
cagacccggt ggccaagtgg tgggcctctc tgacagctgt ggtgacccac tggcttcggc    14700
gggatgagga ggcagccgag aggctgtacc cattggtgga gcacctgccc cgtgccctgc    14760
aggagtccga gtgagcacag gctgcatgct cgtgccccac cccaaccct gccccagct     14820 ttgttctatg tccttggggt ctcaccatgc tcttcccatg aagccagaac cagggcagag    14880
ggaggtccaa ccatgacact tctgccttgg ccccaacagg aaaccctac ccagggcggc     14940 tctgcactcc ttcaaggctg cccggaccat tctaggccgc gggaaggctg agtctggccc    15000
agccagcctg gcaatgtgtg agaaggccag tgggtacctg caggacagcc tggccaccac    15060
accagctgac agctccattg acaaggtaag ggctggggcc aggggcctgg cctgtctcag    15120
gggccttggc ctttccactc cctggatggt ccccttggg ctgcagaaga ctgcagggtc     15180
agcccaacag cacaggacgg gggacccagc cggccttgcc ttctggctaa ggcttgggtc    15240
caggggagaa tggctgctcc ctctggcctc aatgttgccc tcctaggagg agggtggggt    15300
gaacatgtgg cagggccctc cttggaggct gccgcgcagg ccggtggggg catggggggcc   15360 tggagagcgg gcggccccgc ggtgcattgc tgttgcattg catgtgtgag gcaggtgcag    15420
tgcctcggca gtgcagcccg gagccggccc ctggcaccgc gggcccccta gccttctctc    15480
ccacagccag aggccctgac ccctgccctg ccctacccac caccccagg ccttgcagct     15540 gctcctgtgt gacctgctcc ttgtggcgcg caccagcctc tggcagcggc agaagctgcc    15600
ggcacccacc caggcctcgc agggccctgg aggtggggcc caggcctctg ccctcgagct    15660
tcgtggtttc cagagggacc tgagtggcct gaggcgtctg gcacagaatg ttcggcctgc    15720
catgcggagg gtgagtgccc acagagtcct gacttgcgat ggggacagac atgaggtgtc    15780
tgaagggagt ggggcctgac ctgaacctct cctggttcct cctgcccagg tattcctaca    15840
tgaagccact gcccgactga tggcagggc cagcccagcc ggacacacc agcttctgga      15900 tcgcagcctg aggaggaggg tcggcccctg caaaggaggt gagaaggccg gctggcccag    15960
gtgggaaggg tcgcaggcca ggtgaaggct gcagaggag accataagac acacaggagc     16020
ctcgggactt cgaggtggcc cctgatggga gccctaacct gtgactcggg ggacgactgt    16080
cctttgtgga gcactcgctc tgtgctccag gggaagaagc ggaagggacc aagctgcatg    16140
gcagcccaaa accaaaggcg tgggggcgca ggctggacca ggcgacaggg gcggggccgg    16200
```

```
ggcctgagcc ccaccctggc gcagcccccg cccctgacgt gctcccgtgt gcgtgcgcag    16260
gtgcggtggc ggcggaactg gagtcccggc ccacgaggcg ggagcaggcc gaggctttgc    16320
tgctggcctc ttgctacctg ccgcccggct tcctatcggc gcccgggcag cgcgtgggca    16380
tgctggccga ggcggcgcgc acgctggaga agctcggtga ccgccggctg ctgcacgact    16440
gtcagcagat gctcatgcgc ctgggcggtg ggaccactgt gacctccagc tagactcctg    16500
ccggcgggcc tgccctagag cccggtctcc gtatcagcgg ccgagagcga cgccggagat    16560
ccggggctca cgcccagtcc acagactgcg cggcccctgg gcggctggag accctcagag    16620
acgtctgctc ttgacctgcg ggcctaccca gcccgctccc gcactcggcg cgcggtggcc    16680
aggatagtgc tggcccctgg tggccggctg gggaattacc ggggcctgcc gccgccgccg    16740
gatgtcacgt gctcccagtg acaccgctcc tgggtgtcat gggcccccag tccgcagctc    16800 tcccctccc tccagagaga agagagggggt gcatttcacc gaaccgaggg accctacccc    16860
ctgtgcctcc ctcccatcta gggagacctg tgcatagtgt agatcggagt gcaccagcct    16920
cctggcctcc aaggctcagg cgttactttg ccttttgcag actttatttt cataggttga    16980
gaagttttgt acagagaata aaaaatgaaa ttatttataa tctgggtttt gctcctttgg    17040
ggagaggcta accagagggg attctttggg ccttctgtcc ctctagcacc caggcaaagg    17100
cttcttgttg ccacctgccc ttctgtgttt gggaggcctg gctttattcc ctccagctga    17160
cctgggccct ggcgcgcgct ctcatctcct aacccttagg gcccttgtgg tctcagcttt    17220
tccttcttgc ttcccctccc agcttctgcc ccctttaggt ccaggaatga tatgttcttg    17280
ggaatctgtg gtgacgggag gaactacaac ctgggtcttc ctgtgtgtct gggtgtgtca    17340
cctgcctaac ccctgtcccc tcatctgagg ccacacagct gtggcagggc agcagggct    17400 tctctccctg acagcacatt cctgtcccag agcccgcccc taaagcctgg accctctccc    17460
aggaaaatct ggtcagaatc cacgggctgc aga                                17493
```

<210> SEQ ID NO 2
<211> LENGTH: 41379
<212> TYPE: DNA
<213> ORGANISM: Bos taurus
<220> FEATURE:
<223> OTHER INFORMATION: sterol regulatory element-binding protein
      (SREBP) cleavage-activating protein (SCAP)
<221> NAME/KEY: modified_base
<222> LOCATION: (1)...(41379)
<223> OTHER INFORMATION: n = a, g, c or t

<400> SEQUENCE: 2

```
aattctagat ctctggggct ttctgttaga attttatatt ctgatttttt ggggtgtaag      60
tttctctgtt gggaagcaag gcacagacaa aacagagatt taattggaag gatatgggat     120
ggccggaagg aagacctaat gagtcttcag aaaggactgg agccagagca gtgcaatgat     180
ctgggagctg gaacctctca gggaggattc agtaccgcca tgtccagttt tgcttctttt     240
tgtcagaagt caaagtccag agagacagac atgaccagcc tgatgggggt cagggagagg     300
accttaactg acagtccata cagggtggat cttgtgcaga aagctagtgt tctgagtcgc     360
gctgggcgct gtccctcaaa gaaggagaca gcttgggcag caggagcaga agggggccctc   420 tgccccacat gttcccagag caacggggga ccagaagcag agacttccac cttgcagtgc    480
aatttgtttt atgtcagggg cctaggcttt ttggtgtttt tacgttgagg gctgacctca    540
ctgaacgttc tttatcagtg aatcactgtt tgtgcaagaa atgtgttttt tgaggggtca    600
gtccttgaag gttttttccca aggatttctc ttggtctggc ctttgcacaa agaacagggg   660
```

-continued

```
ggagggtttc cagaaagtcc atttggctga gagcagctga aggtgctgtc gattacacag    720
gcatgctctc ctgtgccaca tatgagaaca atgccctctc gagggagtgg ccttttttaag   780 acagtgccta atgtggaaga tggttgagag tttgttacta gaactagagg ggcagttttt   840
tggtttcttt ggttagactt atttggacac tgcccacagt cactaggagc tgaccaagat   900
tatgcacgtg tgtatatgca tgtgtgggct ggacctttg  tctccagctc ttgcctgtaa    960
catcctgatt gggcctttac atccccgcca cctccctgg  gtgccctagt gttcacagcc   1020
aggtattctt tgctaatttg cttttctccc ttcttgccag gtgtctgcaa atggtgtaca   1080
ttgtcagttc catccagcgt gtgccaggct gatccatggt cactttccgg gatggcagca   1140
aggtgacttc agctgaggat gaccctgact gaaaggctgc gtgagaagat atcccaggcc   1200
ttctacaacc atgggctgtt ctgtgcgtcc taccccatcc ccatcattct cttcacgggg   1260
ctctgcatct tagcctgctg gtatgttttcc aagttgccct gtatgtggtg ggccagtcga   1320
cctcctaacc ctgactgttg tgtagcccctt ggactgggtc tttttacaca gtggaacttg   1380
aggctcatcc cggcccacca gcgggaagct ctagtcctgg ggtggaagcc actgcactag   1440
aacagtccag gctcgcccta atttagtaag tcgccagatt tgttcatatt attgagaatt   1500
tctcaaaata acgttgagat gtttcgaaga aactgcagga tgaataaaag tgtgatcttt   1560
taattttcct tctcagcagt ggtagcttcc ttttggtatc tggttaagag caggagcctt   1620
ggagtgttgc aagaacagtc cacttcaaca attcttggga taccatcagt gttgcaggct   1680
aatcccagga taggttttc  tacataggg  cctgtcattg cctctcgcgg gatcttttgt   1740
tgcatggact ctctagtgat gtgtgggccc agtacttgca gtgtgcgggc tctctggttg   1800
ttggacttag ttgtcttgca gtatgtgggg tcttaggtcc tggaccaggg atcataccgg   1860
tgtcttctgc attgcaaggt ggattcttaa ccactggatc accaggcacc tccctcttca   1920
gtcattttct tgtgttcctg gggagcctcc ttctgacctg gttggtccct gggcctgcca   1980
cactcaccag cactgagagc tgtgccgccc tctctccatg tctgttgtgc tgtcccaggg   2040
ccccggagaa ccctaagagc tgtggctgat gaagacactg tagaaggaga ggcttgatgt   2100
aaggtgataa ccaggggtcc cctttggctt gcaaacactg acaagaaaag agcccacctc   2160
gttgtccttg tctctgggaa gaattctggt ttccagattc attgcacatc taatgtttat   2220
agaagtttac attgctgtgc tggaagaaag atggttcggt tgttaatgat cccaagttct   2280
tccttaatta ggacaaggaa agatgagcat attcttgaga atttcctgct gggcgcttca   2340
gcaggtatat aattaaacgt ctcgttgatc ctcagaaaaa ccttgggaaa tggtccagtt   2400
atatttccat ttaaccaaag ggaggatgga ggtttaaagc ttgcctagtc tacacaacca   2460
atgagcaggg aaccgagttc agatccaggc cagggatcct ggtgcctgca cctgtggcac   2520
tgtgtccccc gctcttgtca ctctggttca gtgtatttgt ttaaactttg ttaatttgtg   2580
ttgtacatga taagatgctt gtggcttta  cctgcacatg atgaattagg agtgttctga   2640
gaacccagct cttggttttg cttgtattct ttccttaag  tcagtttaca catctctgtc   2700
tttgagaatc atccttttct aggtctggct catgtgcttg acagtgatt  cttaaagctg   2760 ctctagcatc agaatcacca ggagggccgg ttaaatgaaa ctgccgggct ctaccccaga   2820
gtttctcgtt cctcaggtct gagtgaagcc aagaatgtgc gtctctaaac aacttcccag   2880
gccaggggtc tacatgctga gaacactaga ctgtgtgtct gtcttgaaaa gttctaccac   2940
atctcagcta aaagtacttt ttattctgac ttctggagca gtggtttgtg gggacactcc   3000
tggtcgttat tgctcctgtc gccttctgta ggggtgggtg gtgcccagct cccctgtcct   3060
```

```
acatcctcac ttgtgtgata gcctctgtgc atgtgcctct gcacctggga gggcgctagg   3120
taaatctata atggatgagc accctgagtt cagcttgtct tctcagtggg cagttgaaga   3180
ggtagttgtg actcccttc cacaaggaca gctctagtaa cagaaaggaa aggatgtttc    3240
ttcttgccat tcacctttgg aggattgaat ttggccagcc gggtccagac agcttcccag   3300
acagggagtg tgtgatgggg gcagcagctg tgagtgtagc tgggtgcaac tgggatttat   3360 cttgaatga ataatttgat atcacacatg tgtttcaaaa caaattgtcc ttggatttat    3420 gatagggcc tctggtatga aaactttctg acctttgtgg ctaaggtctc aagtatggaa    3480
gatgccgtga ctcaaggtga atttgaatgg ggctggggat aggggaagag gcaaatgtga   3540
tagtatttag caaccagtgt agcccagttg cagaagaaaa gcaaaagca agggagagag    3600 ggaaaggtat gctcacctga atgcagagtt ccagagaata gcagagagag acaagaaggc   3660
ctttttcaaa agaaatagag gaaacaaca gaatgggaat aactactgat cgcttcaaga   3720
aaatttgaga tatcaaaagt acatttcatg cagtgatgga catagtaaaa gacagaagtg   3780
gtgaagacct aatagaagta gaagagatca aaagaggtg gcaggaatac acataagaac   3840
tgtacagaaa agatcttatt gacccggata accacaatgg tgtgatcact cacctagagc   3900
cggacatcct ggagtgtgaa gtcaaatggg ccttaagaag cactgctgcc agtaaagtta   3960
gtggagatga tgaaattcca gtagagctac ttaaaatcct aaaagatgat gctcttaaag   4020
tgatccactc agtatgtcag caaatttgga aacccagca ggggccacag ggctggagaa    4080
ggtcagtctt catcccaatt tcccaagaag acagtactaa agaatgttca agttcagttc   4140
cgtcgctcag tcatgtctga ctctttgcga ccccatgaac tgcagcacgc caggcctccc   4200
tgtttatcac caactcccag agtccaccca aacctatgtc cattgagtcg gtgatgccat   4260
ccaactatct catcctctgt cgtcctcttc tcctccttcc ctcaatcttt tccagcatca   4320
gggtcttttc caatgagtca gctcttcgca tcaggtggcc aaagtattgg agtttcagct   4380
tcaaaatcag tccttccaat gaacacctag gactgatctc ctttaggatg gattggttgg   4440
atctccttgc agtccaaggg actctcaaaa gtcgtctcca gcaccacggt tcaaaagcat   4500
caattctttg acactcagct ttctttatga acgctcaaac tactggacgg ttgcagttat   4560
cgcccatgct agtaatgtta tgctcaaaat ccttcaagct aggcttcagc agtacttgaa   4620
tcaggaactt ccagatgtat aagctgggtt tagaaaaggc agaggaacta gagatcaaat   4680
tgccaacatt cattggatca tagagaaagc aagggaattc cagaaaaaca tctacttctg   4740
tttcattgag tatgctaaag cctttgactg tgtggatcat aacaaactgt gggaaactct   4800
tcaagaaatg agaataccag acctgtctcc tgagaaactt gtatgcaggt caagaagtaa   4860
cagttacaac cttatttgga acaactgatg ttcaaaatta agaaaggcgt acgtcaaggc   4920
tgtacattgt caccctgttt atttaactca tatgcagagc acatcattcg aaatgctggg   4980
ctggctgtta caagtggaat caagattgct gagaaaaata tcaacaaccct caggtatgca   5040 gatgatacca ctctaatggc agaaggcaaa aggaactaaa gagcctcttg atgagggtga   5100
aacaggagag tgaaaaagct ggctaaaagt cagcattcaa aaaatgaaga tcgtgacatt   5160
tgctgctatg actgcatggc aaatagaagg ggaaaggtg gaagcagtga cacatttcct    5220
cctcttgggt tctgaaatca ctgtggatgg tgactgcaac cttgaaatta gaagacagtt    5280
gcttcttgga atgaaagtta tgaccaagac tgtgttaaaa agcagagaca tcactttgcc    5340
gacaaagttc catataatca atgctatggt ctttgcagcg gtcaggtatg gatgtgcgag   5400
ttggaccata aagaaggca gagtgccgaa gaattgatgc ttttgaactg tggtgctgga    5460
```

```
gaagagtctt gagaatgcat tggacagcaa ggagatcata ccagtcaatc ctaaaggaaa   5520
tcagttctga atactcattg gaaggactga cactgaagct gaagctccag ttctttggcc   5580
acctgatgtg aagagccaat tcattggaaa agaccctgat gctgggaaag attgaaggta   5640
gaaggagaag agggtgacag aagatgagat ggttggatgg catcactgat tcgatggact   5700
tgaacttggg caaactcctg gagctggtga gggacaggga agcctggcat gctgtagtcc   5760
atggggtcac agagtcggcc tcagcttggt gactgaacag cagcagcagc ccagttgcag   5820
tcaagctggg cggacgcctg tcttagatcc cacaggtgtg tctggcggaa catcagtcct   5880
gggaacgggt ggggccctc agggtggact gggctggtga gagggagtgg agactcatgt    5940
tcactgagca ctggcttcgt gcgcaagcac ttccacacat gctgtttcat ttgctcacct   6000
gacatccttg gaggaggtgg ttattagctc ctctgctgat gataaagctt gtacggcgag   6060
atagtaagtg gtgtgctgca actggcaggt ctgtgtggtg gatccacatc tgtggtttct   6120
ccacttcact ggggtgatgt gaactttatg aagaacactt tggtgctgtt aactttcact   6180 gcagggtct gctccttgac caagaagctg agaaagaga gtctcagttg cagtgtgcca     6240
ggatctgcct agacagagga cagagaggct ttttgaggta gtggccctac ataatagaca   6300
ttgaggagag tgtatgcagt tgagttttat agctacctca atgaagatgg ctgtagtata   6360
taccaagagc tgtgccagac ggtaatgccg aacacagacc ctcccatagt ctcagcctga   6420
gagaaacaat tgcagtgcca ctggattttt tttttctttt gaagtttgtg tgtttattat   6480
tatttaaaaa ataattttg tatatttctg ttggctgcac tgggtcctct tgctgcacgg    6540
gcttttctct agtcgctgtg cgcggggcta ctctgcagtt gtggtgtggg cgtctcattg   6600
tatgggcctc tctcgtcaca gagcacgggc tctaggcgcg taacttcagt agtgctggtg   6660
cacaggttta gttgccccctt ggcatgtggc gtcttcctga accagagatc aaacccacgt  6720
gtcacgcgtt ggcaggtgga ttttaatccg ctgagccacc agggaagccc ctgcagggtg   6780
gatccttaac cactggacta ccagggaagt tcctgtaatt tttgttttta attgaaggat   6840
agttgattta ttatgttgtg tcagtttcta ctctacagca aagtgattca gttatccatg   6900
tatacatact gttttttcata ttctttccat tatggtttgt tacaggagat tgaatatttt  6960
tcgctttgct gtagagtagg accttgtttt atctattttt taatatggta gtttgtatt    7020 gctaatccta aactccttat gtatccttcc cctttcccca ttggtaactg gttttaaatt   7080
tctatgtctg tgggtctgtt tctgtttgta ataagttca tttgtgtcat attttagctt    7140
ccgcatataa ctgataccat atagtacttg tctttctcct gctgacttca cttcgtatga   7200
tcatctttgg gtccatccat gttgctgcaa atggcgttat ttcattcctt tttataacta   7260
atattccttt ttttttttt tttaatgtgc tacatcttct gtatccactc atctgtccat    7320
gggcatttag gtgtttcca tgtctgggct cttgtaagga gtgcttctgt gaacctaaga    7380
gtgcctgtta ccttttgaa ttagcgtttg ctccaactat attcccagga ctgggattgc    7440
tggatcgtat ggtagctaca gtggaagtga gaaatagatt taagggccta gatctgatag   7500
acagagtgcg tgatgaacta tggaatgagg ttcgtgcat tgtacaggag acagggatca    7560
agaccatccc catggaaaag aaatgcaaaa agcaaaatg tctgtctggg gaggccttac    7620
aaataaggcc tgtgaaaaga agagaagaga aagcaaagg agaaaggaa agatataagc     7680 atctgaatgc agagttccaa agaatagcaa gaagagataa gaaagccttc ctcagcgatc   7740
aatgcaaaga aatagaggaa acaacagaa tgggaaagac tacagatctc ttcaagaaaa    7800
ttagaggtac caagggaaca tttcatgcaa agatgggctc gataaaggac agaaatggta   7860
```

```
tggacctaac agaagcagaa gatattaaga agaggtggca agaatacaca gaagaactgt   7920
acaaaaaaga tcttcacaac ccagataatc acgatggtgt gatcactcat ctagagccag   7980
acatccttta aagggaagtg acaggtgtct gtttacattt cctagagcta gttaggccac   8040
caggatgccc agtagcggcc cagcaagaca gagggtgctg ttgcttgggc ctgctgtggg   8100
aagtggtggg tgcaccgtgg catgaaggaa cagtgtctgg gtgccaggcc agctgggttg   8160
ccgtccctgt gggccagagg tttatgtggg ggtcagtgtg tcacttgtga ttccataacg   8220
tgctgctcgt ggttacagag ggtgaatttt accttagaga gcaagttgga atcaccatga   8280
gaccattcca aaccccctga gggaggtgaa tcctgcagag tgtgtgggta tccgagtgca   8340
gacatggccc tttcctcctc ccttttctct ggagcaaagc agcccttca ggctgagact    8400
ggacgtctcg gttgtggtgg cctctgctct caacctctcc cggttttccc atgattgttg   8460
tggacccttt gcaggtgggc actcagggc ttatagagca ggctccttct ttctgtaccc    8520
tgtgaccact ctgaacatga ttagattctt ttcatgaatg agaaagaaat ctgagtaaca   8580
gaagccaggt ctgcacctgt gctttgagac ctgggctggt aggctgggaa ggacgtctga   8640
gcaccgtgga cctgtgtccc caaacccaga tgcaggagcc cagggcccag ctacagcagc   8700
cgctcctggg tcctgttcag cactccgaag ccagaggctc cctccaagca gaaattacct   8760
ctggccctgc acacaaactc cggaaaagct ctgaagggct tggaggagat caaggcgcc   8820
cttatcaacc cagacttcct caaacagaag agagatcaag agatctcaga gtttcccttt   8880
tgtagacttt caccgcccca ccctagttct gtgctgctct cccctgagaa ggggagagag   8940
gaagcacgtc tgactgctgg tgcctccgga ggggagtcct gtgccacgcc ccgcgtgcc   9000
atctttctgg gtgctcttcc tgtgtgtctt cagtgtcgcc tgagctccca tcgtaacacc   9060
atcgttaccc agtgcagcat gaaggtgcag ggctgcctcc tcaaaaagca ggggaaagta   9120
ccactaaagg tgctgcagta cgctcagatg cgcgtgggtg aaaggcttgc tcctgcccag   9180
ttgctcctgc catccagtgt gctgtggtgc agccagcctg gataagcca cggccgacgc    9240
ctcacccagc tccaggaccc agcaaggtgt gcgctgctga acacctactg gttttggtcg   9300
ggcgcctgta ggcagcagca gcagcacatg gatacctgga ctgggagggg atggccagat   9360
cctgggacac aggtgagcag gggcgctggt ggtcacgcac ctgtccgagg gtggagggac   9420
cacctgtgaa cctgtactcc acatcatgtg ccgttgtgat ggatttggtt tatgaagcac   9480
aaatcaaaag atagatttgt taagaatttc tgcatatcta ctgcagagca ttaaacccca   9540
agctccaggc ccttctgaac gtggggcctt acgcagccac ataggtgcac accatgaagc   9600
tagtccttgg tacagcgtct ggtaggttaa aaatcagcct gcacatcttg aacatcttcc   9660
gtgtggctgg tatgaggatg cgaaagttag agggacatgt tcccacctca tatatcttac   9720
attaattaag caggtgaatt gaggagcagt gtctgcaggt tgtcgtggga gtgtagaaga   9780
gaggtgccta actgcttggg ttggaaagat gaggtggcct tgaaggatac acgggagttt   9840
ggtcagcatt tagtgggtag agggcatgtt ttagtttggt ctccctgaga caaggatttg   9900
agtgcagctt atgcttatgt aacttatatg cagagtacat catgagaaac gctggactgg   9960
aagaaacaca agttggaatc aagattgctg ggagaaatat caataacctc agatatgcag  10020
atgacaccac ccttatggca gaaagtgaag aggaactcaa aagcctcttg atgaaagtga  10080
aagtggagag tgaaaaagtt cgcttgaagc tcaacattca gaaaacgaag atcatggcat  10140
ccggtcccat cacttcatgg gaaatggatg gggagacagt ggaaacagtg agagacttta  10200
tttttggggg ctccaaaatc cactgcggat ggtgactgca gccatgaaat taaaagacgc  10260
```

```
ttactccttg gaagaaaagt tatgaccaac ctatatcgca taatcaaaag cagagacatt   10320
actttgccaa caaaggtccg tctagtcaag gctatggttt ttccagtggt catgtatgga   10380
tgtgagagtt ggactatgaa gaaggctgag cgccaaagaa ttgatgcttt tgaactgttg   10440
gtgttggaga agactcttga gagtccctcg ggctgcaagg agatccaacc agtccatcct   10500
aaaggcgatc agccctgggt gttctttgga aggaatgatg ctgaagctga aactacagta   10560
ctttggccac ctcatgtgaa gagttgactc attggaaaag actctgatgc tgggagggat   10620
tgggggcaag aggagaaggg gacgacagag gatgagatgg ctggatggca tcactgactc   10680
gatggacatg agtctgagtg aaccccggga gttggtgatg gacagggagg cctggtgtgc   10740
tgcgattcat ggggtcgcaa agagacacga ctgagcgact gaactgagct gaataattag   10800
tgctgtcgag catcttttcg tgtgcttatt ggccatctgt atgtcttctt tggagaagtg   10860
aatagaatgc ttttagtggt ttcattagat gcccaggctc cattcaattg cttacctgta   10920
ttgtacatgg aacgagagac ttattcagct tgatgaaggg actgctgctt tgttccctc    10980 tgtctggctc tagcagcttc ctgagctgtg tgcctttcat cactatttag aaatagtttt   11040
attctctgat acaggcactg ttatactccc ttcaggaaag aagcctgaca gtctgacatt   11100
taaaagatat atgactgaat agaaaccta tgaagttaat ggatttaaat ttaaaccatt   11160
ttcaaggatt attttttttgg aaagttttct ttcttaaggg tctgattaat aactgctaat   11220
aaaaaaatac cattgaaaat gtatgaaaat accattgaaa attctattgc tctccacaca   11280
tttgaaaaat ccagatccag ttatatacag aattcctact ttattgctta aagtgccttg   11340
gattaccagt ataatccttt ggagtacctg ggaccaagga tctgttgcta gtaaaaataa   11400
ttattaaatt atctttataa catttttacct aattgtttat tatttagaat tccttctata   11460
tgtgaggtaa aattttataa ataaaatatt taaatagtaa agaaaagaa tctgcctgct    11520 aatgcagggg acacaggtcc gggaagatca caaatgccgt gggagaatcc cacatgccga   11580
ggagcagcta ggcccacaag ccacaactgc tgagcctgtg agctgcagct acgaggccca   11640
cagacctaga gcctgtgctc tgcaacagcc atgagaagcc tgcgaattgc aaaggagagt   11700 agccccgct cgctgcaact agagaaagcc tgtgcgtagc aacgaagacc cagtgcaaca    11760
acaaaaaaaa aggcagcacg gtttgtatat ttaagaacag tgtctgcgtg ctctctgttt   11820
ttgcctgtgc tgggtctttg ttgcgacacc tgggctctgg gctgcggcac acaagcttct   11880
cttcttgttg cagtgcacgg gttctagagt gtgtgggctc agtggttgtg gcccgcaggc   11940
tccagttgtg gtgcctgggg agacactgta ggcatccgct acccttttgga cattagaaca   12000 caagaagtt gcaagtaaaa ggatggaaaa tgatattcca tgctaaatga tacccaaaag    12060
agagctgacg tggctatatt attatcaaac aacattaaaa agcttattag agaccaagaa   12120
ggaggacact atatattgat gatatattga tcatattgat atgctgacac tatatatatg   12180
cttcagtata acaggaggat ataatgatta taaacctctt aacacctaac agactcctaa   12240
aatatataaa gcaaaaatgg acagaattga aaagagaaac acacagtctc cgtgacagtg   12300
gatctccgct ttcagtgatg gatacaacca gacagagtca gcaaggaaaa tggaggacct   12360
gagcaaccct gaaaccgacg gcactagtac ctgttcttcc cagtgaacac ggaacattct   12420
ccaggaaaat cgagaaaaga aggaaaattg gaaatacttg gaaattgtcc aggtggccaa   12480
taagcatatg aaagataagc atacattgtt tgctgtatat tgaaaccaca tagctatacc   12540
agcacctcct ccttttgctat gctatgctat gctaagtcac ttcagtcgtg tccgactctg   12600 tacgaccca tagacggcag cccaccaggc tccccgtcc ctgggattct ccaagcaaga     12660
```

```
acactggagt gggttgccat ttctttctcc aatgcatgaa agtgaaaagt gaaagtgaag   12720
tcgctcagtc gtgtccaact cttagcgacc ccatggactg cagcctacca ggctcctccg   12780
tccatgggat tttccaagca agagtactgg agtggggtgc cattgccttc tccgcctcct   12840
cctttaaatg gttccaatta attggactga caagatcaag aggtggagca gttggaactc   12900
ccatcgcacc gccagcggga atacaaattc aaataagtac tttggaaatc tggtgtaatc   12960
cacaaagcta acatgtgta ggctccacaa cccagccatt tcgttcaagg gacatacctt    13020
acagaaatga gtgcttacat aagaatgagt gtatacataa acatttccat tatttctctt   13080
cttaatagtt tcagctggaa acagccagat gttcctcaac actagaatag ataaatgcac   13140
tgtaatatgt tcatttggtg gaatagcgcg tatgcatgaa acagtgcgta tatatgaaac   13200
tgcatgcacc agtgtggatg aatccggtag atgtaagttg aaacagccag tcacaaagga   13260
gtacgcagtg gaatgggtga tttcagttat atgccagaag aaacaagcag agctaatttg   13320
tgattataga aattctgata gcggtttgtg gtagacgatg cccttcacta gtgcataacg   13380
ccaccttcta aggttctaaa atattttgt agcttgatct acatagtggg tacacaggtg     13440
tatgtatgtg taaatactca ttgcactcac tgtatgctta agattcgtgc gttgtattac   13500
ataaaactta attctcagtt aaaaaaaatt ttttttgac cacgtgtggc atgcagaact    13560
tcctcgacca gggattgaac ctgcattac tgcagactcc ggaagctcgg agtcttaatc    13620
attggcccac cagggaaatt ctaaaaaaaa aagttttgaa gaaatgaagt cagaaacaaa   13680
agcacatcca ttgccaact ttttgatgtt agtccaagct ttttcctttg ccagtggtgg    13740
atccattgtt ttctattcag cctggtctag tgtaaaccat accctcaatg tgttacacaa   13800
aatgttatgg tctgtccttt taaactgaag cagttttgc agcagtctga atcaggatcc    13860
ttctggattt ttggttccct ggttttttc ttttctttt tcttttttgg ccacactgcc     13920
tggcatgtgg aacttccctg accagggatc gaacctgtgc ccccgtggag tcttaactac   13980
taggccacca aggaagtcct tccccagttt tttcttgttg tcttacgtgt atccaatatg   14040
accagaagtt tgtttagcat cttgccttta ttatatttct aaaaattttc agccagtaac   14100
ctatttcatt aagtagttta tgaattgggt ttcctgtgac caaaaaggag cttgaaaatt   14160
ctaatttaga ggctcctgcg tttccttgta gccctgaagt ttgatgaatg gtgtttcgta   14220
catttgtgca gttctcctag cacaggaggt gagtgcagct gcagtgattt ccatgtcact   14280
gttatctcag catggattct acctgccatc atgtcctgac ttttctctcc ttttgtcca   14340 ttccagctac ccactgctga agctgccctt gccaggaaca ggaccgtgtg aattcaccac   14400
tcctgtgaaa gattactcgc ccccacctct gacctctgac cacaagcctg gagagcccaa   14460
tgagcagcca gagtgggtag gtgctcagca tgttctgagg agcgccctgg gctttgggta   14520
cggattggcc gtggcagggg ttctacgtgg agtgagggtg gtcaccttct gatgggcgaa   14580
tgcttaacac ttgaaccact ttataaaggc actgaaaata tttagcttac atttaatagt   14640
acatccagtc acacattcct gttttgaaag gaaacactaa atggcatggc aggaaggtga   14700
ctgtcctgga aaagctgggt tgtggttgct gtagctccgg ctggctgggt ctgggtccat   14760
actgtgggta ctcgggccag gcagtgccct ggcaaacgga cctctcctcc ttgagcccaa   14820
gtggttgcgg gaaccactga ctatccctgg agaatgtttt atcttccgag tcccatcacc   14880
atttaatgtt agcagtgagc gcttagcttt ttcaaatctg gtaggtgctg ttttatcctc   14940
acagtgcagt caggtaaagc gtgcaggttc tgcttgttcg cctgttgggc gaactgagcc   15000
gagaatggca atgtgcctca gtttcagttc atttgtcatg gggtcagcac tgggttagaa   15060
```

```
ctccagatct cctgacctga agccagctgc tactttttgaa tcgtgctgtc ctcagccagc   15120
tgtctctgag ctgagcatga atgcaaaaca ggaagaaaac ctacaggaat gcaaaacctc   15180
caggtgaggg actgggctgc gggatgtaac ccgagggaac tctggactca ttatttggaa   15240
accttacagg aaatgataag ctcgtcctgc tggcttgtac ctgccagctg tggatgacac   15300
gttcttccct cacgtgctgg gccctggtcc catgggttgg tgctgggctt gctgagtctg   15360
ttgttgagga gcagagccca gctcagggca cactgctcct cttctccacc ctctctgtgc   15420
cagtgattgc acattccttc ctgttgcctt tctgggtaat gtagcagcca ggtaacttga   15480
tgtcagcttt gctctaatat tgctaaagta gagatctggt tagataggtg tgtgttatga   15540
ctacacatgg tttcaggagg aagtagagaa cacaggctca gtggtactca gccacgaagg   15600
ttagggtgag ctgatgaggc ggaaaccagt tcatagcttc atgtctcagc ttgacacttt   15660
gctcattgtg ggatcaagcc ttttgtctct tttactctct cttaaaaaag aaaagtattt   15720
atttatggct ccaccgggtc tttaatgcag catgcgaggt tctctctagt agaggtgcac   15780
gggctcagtt gcccagcagc atgtggggtc ttagttcctc aaccagggat cgaaactgcg   15840
tcccatgcat tggaagtaga attcgtaacc actggaccag gaggaaagtc cctccattaa   15900
cctcttgatg gggttttacc acataatgga gttgatggtt cctgctcaca atggggtagt   15960
ctgcgtttgt gagtgttttg tgactagtag agttcagtgg gcctgatggt acagctaggg   16020
gtctatccaa ggtcaggggt tcacttgttt gtgagcccctt tccacttctt gatgtcctct   16080
tttggcctgg gatgatgata gtgtggggt acaaaatagc ttgagggttt ctcttttctca   16140 ctggggtctg cagcccctga aaggttgaga agaaatgca ggccctggct cagtcacctg   16200
gtgtcaggcc tctctgtggt cagttacctc accagaattc actgttgtaa cagtaaaggt   16260
cagcaatgca gaacttgtaa ggattgcttt aagtataagg aacagaaaac tcagcccaaa   16320
cctggggaag tgagaagggc attttggggt catagagctc acccacaggc aggacttact   16380
aaccgacagc atgggttagg cctcagaagg agtccatccc tcaactgtac ccgctccggg   16440
tcagctcact gtcctctccc taatgggggc tacagcagat tcagccctgt gggtgcccgc   16500
ttggctctgc atgggattac ctacctgctc ccacccaaga ccctgtgagc agggaggtgc   16560 tttgcttggtt ggcttcatca ccacactgcg ggtgagagac tgtttccaaa ggaagattag   16620
gaagtgcagg ccctgggcag cacagcgcaa gcgcctgctg ctcacagcag gaagctgtga   16680
ggtccttcat tcctcatcca ttcctttatt attcagcacg tttattcctt gtcttcagtg   16740
tgcctggcag aatgatcgtg gggacacatg gagcctcact gccctggagg acgcacgg   16800 tgattgggaa gagcacatgg agatgtgggt tcttttgtca acagcacaca ggagccagcc   16860
ccaggagctc ccagtggtca gtgctgaaaa aaaagataca ttttgcagca aaatacatac   16920
atagctgagt ccgtgtgctt gaataactaa gtggaggaga atagacagat ctgagcaaaa   16980
aattctgaat ttatgtggcc gctctgcctt cagagaggtg gaatctaatc cccttccttc   17040
attgtgggct gcgcacagtg acttccttcc agagagtgcc aagtggagag gggaggagag   17100
agtggctttc cagcggaaac cctgacagat agctatggac acagtgttcg gggtcaccat   17160
cagcagtgtg acgagaaggg tgctttacct ctatgttctt cctctgcaaa cactgtaatc   17220
ccagtctgtt cacgagaaga acatcagaca aatctgtgag gagtggtcta cacagtcctg   17280
accagcactc ctcatgactg tcaaggtcat cagaaaaaga gagtccaaga aactgtccca   17340
gccaagagaa gcctcacaag acagggcagc tggatataac atggtatctt ggatgagatc   17400
tcaggagaga gaaaggacat ggggacaagc tgaggaaatc tggtttcctt actttgcctt   17460
```

```
ggtgatagtt tctcagactt gccttgttct cgatgagctt gacagtttcg aggagtgttc   17520
ctcaagcggg gatttgtttc tatctctcta gactagtctc agcttgtggg gttttagaag   17580
gaagactgca gaggtcaggt gtcattcttt tcacatctgt cagcctctaa agtattttt    17640 ttttaatttc tgtaaagttt agtctttgtg ctctgaagtt cttggcacca tcaggggttt   17700
tcttgtggtt ttttgttttt agtctttttt acagaaatat gaaacatcta gttgttttct   17760
tttttgagaa ctgtatttat ttctggttgt gctgcatctc catcgctgtg agtgggcttc   17820
tctagttgcc tcgagtggag gctgcctttt aggcgcagtg tgcgggcttc tcattgtggt   17880
gacttctctt gtggagcaca agcccgagag tgctcaggtt ttggtagtcg tgcctctcgg   17940
gctcagtagt tgaggcgcac gggcttcgtt gcctcgcagc atctggaatc ttcctggacc   18000 aggggtttgaa cccatgtctc ctgcattggc aggtgaattc ctaactactg gaccatcagg   18060 gaggtccttta gttgtggttt taaatttgca ttttttcagat gaatattgtt gaggtcttgt   18120
tgtatttgca catcttcctt tgtgaagtgt ttcagtattt tgctcatttt gagctgagtt   18180
gtgtggattt ttttaatat gcaaagctat tcaaagaagt atattgataa tggaaaaagt   18240
gcaataatct agatatcctt atatagagaa ataactaaat tatactacac ccataaactt   18300
gaatgtaccc attaaataga tttttaagct caacaaagta gattaagtag gaaaagccga   18360
agataaaaca gtatgtgtac tataccaacc atttaaaaaa tacatgcata gaaaaagtat   18420
taattgctta atcatgtcca actctgtgac cccatggact gtagcctgcc agactcctct   18480
gtccattgag ttctccaggc aagaattctg gaatgggttg ccatttcctg ctgcagggga   18540
tcttcccaac ccagggatca aaaccaggtc tcctgcattg caaccaggga agccctggtg   18600
catgggaaaa aaactagtat caaatccatt aaaatgcaaa caacacttac ttttaggttg   18660
tgtattacaa tagacttgca ttgcttttac aaaagaaaa aaaagagat aaattttcaa    18720 aaagattaaa cgctagcact ttctctaaca aactttccct gtttcttgtt taatgtatct   18780
tagaaaggag tttgtaccaa gagaatagtt tatcattctt cttaacatgt taaacatgga   18840
caggtacagg ttttcaggga tatgtaattg taactggcat ttttgcctct taagtgattt   18900
tccctcccct taggaaaagt ttatatttag aattgttgca ggagaactgt gatgtcccta   18960
ttcttcccac gtgaagctta taagccttta ctttttaaaa atgtattttt aattggagga   19020
taaattgctt tacagtgttg tgtgggtttc tgccataatg ttagtcactc agttgtgtct   19080
gactctgtgc gacccatgg actgtagcct gccaggctcc tctgtccatg ggattctcca   19140
ggaaagaata ctggagtggg ttgccattcc tttctccagg ggatcttccc aacccaggga   19200
tcgaaccctg gtcttctgca ttacaggcag attcttacc atccaagcca cctgggaagc   19260
ccatacatca gctttctgcc atacatcagc atgaatcagc cataggcagg catatgtccc   19320
ctccctcatg aacttccctc ccagccccca ccccatccca cccctctagg ttgttaggga   19380
gcactgttga gctccctgta tatatacagg gacttcccac tagctgtctg ttttacatac   19440
ggtaatgttt cagtgctctc tctcaattcg ccccaccttc accttccccc gttgtgtcct   19500
taagtctgtt ctctgtgtct gcatctctgt tgttgttcag ttgccgagac atgtctgacc   19560
ctttgtgacc ccatggactg cagcacgcca ggcttccctg acccatacca tctcccaggg   19620
tttccccaag ttcatgttta ttgaatcggt gatgccaccc aatcatctcc ccctctgtcc   19680
tccccttctc cttgtgccct cagtcttttcc caggatcagg gtctttccca ctgagtcagc   19740
tctttgcatc aggtggccaa agtattggag cttcagcatc agttcttcca atgaaggatc   19800
gatttccttt aagactgact ggtttgattt tcttgctgtc caagggacgc tcaagagtct   19860
```

```
ttagtaccac agttcgaagg catcagttct tctgtgcttt gccttcctta tggtccagct   19920
ctcacatcca tacatggcta ctggaaagac cgtagccttg actagatgga cctttgttgg   19980
cgaagtgatg tctttccttt taaacacact gtccaggttt gccataactt tcctgccaag   20040
aagctgtcat cttctaattt catggctgca gtcaccatcc acagtgattt tagagcccaa   20100
gaagaggaaa tgtgtccctg cttccacctt ttccccttct atttgccatg aagtcatagc   20160
accagatgcc atgacattcg ttttttttaat attgagtttt aagccaactt ttttcacttt   20220
ccttttttcac ccttatcaaa aggctcttta tagttcctgt ttgctttctg ccattaaagt   20280
agtatcatct ccatacctga gttggttgat atttctccca gcaatcttga ttccagcttg   20340
taactcattc agcctggctt tttgaatgat gtgctctgtg tacagtttaa ataaacaggt   20400
tgacagtaaa cagccctgtc atatcctttc tcagtcttga accagtaagt tgttccatac   20460
aaggttctga ctgtagcttc ttgacccgca taagatttct caggagacag gtaagatagt   20520
ctggtattct catctcttta agagttttcc acagtttgtt atgatccacg cagtcaaagg   20580
ctttagggta gtcagtgctg ctgctgctag gtcacttcag ttgtgtccga ctctgtgcga   20640
ccccatagac agcagcccat caggctcccc gtccctggga ttctccaggc aagagtactg   20700
aaattgggtt gccatttcct tctccaatgc atgaaagtga aaagtgaaag tgaagtcgct   20760
cagtctctcc tactcctagt gaccccatgg actgcagccc accaggctcc tccatccatg   20820
gaatttttca ggcaagagta ctggagtggg gtgccatgta gttagtgaaa cagaggtaaa   20880
tgtttttctg gaattccctt gctttctcta tgatccagag aatgttggca atttgatctc   20940
tggttcctca gcctttctaa acccagctta caaatctgga agttctcatt tcacataatg   21000
ctgaagccta ccttgaagga ttttgagcat tgccttgcta gcacgggaga tgagggtgtg   21060
actagtaaga tacttgactc gtctcccgtg catctctgtt gctgccctac agacaggttc   21120
acctgtacca ttttttctaga ttctgtatat atgcattgct atgtgatact tgttttttctc   21180
tttctgactt cactctgaat aacaggccct agattgaccc acctcgctgg aactgactcg   21240
gatctgttcc tttgtgtggc tgagtgatac ccattgcata tgtgtgcccc aaggtctgtg   21300
ttcgctcacc tgtcagtggg catctaggtt gcttccaagt cctggctgtt gtaaacagtg   21360
ctgcagtgag cattgggggta cacgtgtcgt tctcaattat ggtgttttca gagtgtatgg   21420
ccagtagtgg gattttgggt catatggtag ttttatgctt agttttaaag aaaagctcca   21480
cactgttctc cacagtgtct atgtcagttt acattgccat cagcagtgca agaagtttcc   21540
cttttctcca catcctctcc agcatttatt gtttgtagat atttttgatga tggcctatag   21600
ttcctttgct gtgcagaagc ttttaagttt agttagatcc catttatttt tgttttttatt   21660
tccatcattc taggacatgg gtcatagaag atcttgctat gatttatgtc aaagagtgtt   21720
ctgcctaagt tttcctctta agggttttat agttctggt gttacattta ggtctgaaat   21780
ccgttttgag tttatctttg tgtgtggcat taggaagtgt tatagtttca tcctcttacg   21840
ggtggctctc cagttttccc aacaccactt actgaagaga ctgtcttttc tcctttgtat   21900
attcttgcct cctttgtcaa agataaggta cccgtaggtg tgtgggtgat ggatttcttt   21960
tactgagtta taattcttc tgtgtgctgg aggtgtctct ctgtgtagcc ctcttctccc   22020
cttttactga cgtgttcccg cactgggatg gaggctgcac cctgcggttg ggcctcgtgc   22080
gtgtctgtcc tccagaaagg actctaatca actctgccgg catcttgtgc cctgggttag   22140
gcctggcgtg tgttggagtc actgatcacc cccatgtggg ggtgcgggga ggtcagttcc   22200
cactgggagg agggggtgttt ttaccagggc aaagcagaaa ggtgaagact tcccgtttct   22260
```

```
cagctgtgtg accttgggca gcttatgtaa cgactctgta ccttagtttc cacatttgta   22320
aaatggggat aatagttaca cctgcatttc agttgtcaca ggatgaagtg aaaggatgca   22380
aattcaggtc ggtgtctggc ccatcgctgg catctgtaaa tgagtctggc tgtcaccact   22440
gtccttgctt acatctggcc agggcggagg gccgggcgga ggttcctgtg ctcagaggtt   22500
ctaagtgcac tgggcgtgtt ctccgtgtct gtcaccaaga gaccgaagtc tgaagtgagg   22560
cttcttcttt ggagcttgat aggtgatcag gtagttggga ccaagttaaa tcctgggctc   22620
tggagtttaa atgaatcccc tcagcagtgg gaagctgagc ccttagaggc agcgacttgg   22680
tgtgagagtg gtggtaagat ggtcagtctt agagaaacct ggagatgggg atgatggtgc   22740
ctaggaggag ggtgaggggg ccagagaggg aagggggct tcattttata gggatcgcaa    22800
ggctacctgt aagagcttta ggacataatg atacactaga tggaactggc gtgcatcggg   22860
ctacatgcct tactgctggg ttgcttgtgt tgtgttgttt ggtccgcaca gtgatctgga   22920
ttgtgtgtgt gtgtgtgtgc gtgtgtttaa acaagctttt ttttttttaa tttattnttg   22980
gctgtgctgt atctttgttg ctgcgctggc tnttctccag ttgccgtgcg caggcctctc   23040
attgcagtcg cctctcttgg tgcggagcta gggtgtgcgg gtttcagcac cctagggctc   23100
ccgggctata gagcacaggc taaacagaca tggttcacgg gcttaactgc tccacaacac   23160
gtgggatctt ctcagaccag ggatcaaacc tgtgtccatt gatgggcgaa ttctttacca   23220
ctggaccacc agggaggccc cgggattgtg tttaaagcaa caacaagcct gagatgtcct   23280
gctctggcct ggccctgcta gactggatca ccatgggaac ctgggcctca tgccaggccc   23340
tgcctgccgg tccgcctggg tgcctgggct tccaggccag ccctgcagtg tgggcagtgg   23400
cggcctaagc ctgaatgcga ggtttccgag gagcccaggt cagggctctc atgctgagac   23460
ggtggcagct gagaccccgc gggccctagg acctcagctc ccctccggca ctgctgtgct   23520 gggccttttgc ttctgctccc tgttctccat gggatccaca tgggtcagaa ccaccccggc   23580
atgtaggact cacagattgg gaattgggca gccccgggct tgactcctgc ctgtgctgct   23640
gtgtggcctt gggcatactc ttgctatctc tctgagataa caagattttc ttatctgggt   23700
cctctagctc agggtccctt actatgaagg ctgcggttgt ctcagagcct gcatccacat   23760
cagacagtga gggaagcacg cccccctgcag gctgtgggct ggggcctctg gtccctcact   23820
gggtattggc tggaagtccc ctcagttccg tgccttgtgg acctttttgg agcgtctcac   23880
aattcggctg acatcaccag agtggtggct gtaaggacgg ggccaaggaa gagtcagtat   23940
gttttttcct tccatttaaa acaaattgtg gcagcaaaag caccaagtcc tacccctgg    24000 cccaccaggg aattccctct cttaactatt taagcgtacc gttcagtggt attaagtgca   24060
ttcacattgt acaaccatta ccaccatcct tctctataat gcttcatctc acaaaacaga   24120
aaccctgcac cagtcaaaca ataacgctgt actcaccctt ctccaacccc tgataaccat   24180 cttttccgctc tctgacactc tggatttgac tccttcaggc gcctcatacc agtggactca   24240
ggtggtgttt gccttttttgt gcttggttta tttcacttag cataatggcc ttaagagtag   24300
tagtcttttg tagcccaatc tcagaaataa agagctcatc attttgctat attctgtttt   24360
tcagaagcaa gtcaccaggt ccagcccact ctccagcgga attatgcttg agcgtgagca   24420
tgaggaagtg gggcttactg ggggccgcgt tagaagcccc atctgtgagg gccctccct    24480 ctgttcccag aggcacctgg actccactgg cccttaggca ctctccatca cccatttagg   24540
ataccttgtg tcgtctgttt ccgtgtcgta ggcttccatg tctgtgtctt actcgagttt   24600
caggcgggga ttatggtaag gcccagcagt aagtggtagg tcctgcccac ctcttctgct   24660
```

```
cccacgttcg tgcctgccag ctaccagcat ccgcatctca tttgtcaaag atatctggca   24720
cggaaggcct gaggtgctgg agaattcaca tcccctagga gctgccctta tcctgtaact   24780
gtaggaggag ttggtgtgta acctcagcca tcatccttta tgtggggtaa ctcagctaaa   24840
ccatcatcca caagggtcac ttgctcagca gcccacccct ggtggtggcc ttccttgccc   24900
tgccctgtcc ctgctcccct gcccgtgttc acaccacctc ctgaggacac catgtgtcca   24960
gggtgtgctg ctgggggaac cccaaccgag acagtgagtg ggacagtgaa tgaatgacga   25020
gagttaggct cctgcctgtt aggtaaacca ctgtaagaga gttgggatgc ctggaagagg   25080
ggagttgagg gcacatacac tggacgatga gtttgataca gacatgctaa actgacccaa   25140
gatcctgaaa gagctgggcg gatgtgggat agccgcttgg agagttcagc tggaagtcgg   25200
gaaggcgagt gagggccggc ctgcagacgg agggccaggc gaagcgcacg gctgtgcgtg   25260
ggctctcctc tctgtggttt tgcctggtga gcctcacctg ctgaggagtg ggagcagatg   25320
agcagggggg tttacctgag cagatggaag gtcaaaggag agagaggcgt gcggggccga   25380
gggggttcag attctgtgca gtctgaaagc cgtggatcct ctcccctaac aatgacgagg   25440
ttatgatagt agagacactt ctgagaagaa atgtgagttg tcagggtgc ttacagaact    25500 cctggggcca tcccaagagc cctgatggag agctctggtt ctgaagtaca ttctttgtta   25560
ctctgctgaa atggaggcct ggtggggtct gggtttggac tggagggcca gggagcagtc   25620
ctgcttggaa actgaagctt cagttgggcc ccggggttgag gggtggagga ggtggtctct   25680
gcggtcacag cctcgtgccc actgggaaca gtctggcggc tctaccgggc cagctgtccc   25740
tgggtgccat gccatgtcct tcgcggagat gctggagggt gctaaccca gtgtcgctct    25800 cccttttggag ctgcgagctg ggtcgagtcg aggagctcag gtggcgtccg ttctgtgcag   25860
gtccctctgc acctcctgac atcgtctgcc aggtctggtc tgtgcagaag gctaagctgg   25920
tgaggcttct atccccagcg cctgtcagaa atgcacattt caccaaggct caggtggtgc   25980
ctggggtgct ttgtatgatc agtatcttgg cccgtgctta tgctggagca ccgcgttgtt   26040
gctggtggat ggcatgctct cctcacaccc gcccttcaga gttcctgacg gccgcacagg   26100
tgtcaggacg tcccccatc cccaaccagg cccagctccc tccagccggc acctcacagc    26160
accccagggc tgcaggctgg ccttcctgt ctccgggtag atgatggtct aactttagtg    26220
ttccctggag cgctgcgttg taaggtcgcc cttccctctg agacagtcag ggcttttctt   26280
cgtcacctgg ttaaaaccca gacagttcag tcaggcgtca tcccgccccc ctcattgccc   26340
tgtgatttcc attactccca tcaggacacc cctgtgctgt ctgagctgcc cctgccccct   26400
cctgcccccc gcctcctgac cacccctccc gccccccac tacccctcc tcaccgcctc    26460 acctcccctc ccacccgccc actacccctc ccacctcaca gccccacgc agctcctccc    26520 ggccataacc ctgccgcggc cagtccagtc ttgttttggg gctgcttctc gacatgtcca   26580
ccgctgggag tcgttccttg cctgttatgt gtgtgtcact ttgtcactta agtgccttta   26640
aggatatatg gcaggttctg gtgagggag tggtgtgttt cagtgagatc tgggtaggaa    26700
tcctcacatc ctgctcaagt ccggagacct ggagtcactt tgcgtctcat aggagagtcg   26760
tgctggccag tgagaggaca cgccacacct gtgctcgctt acatgtccat ggacacttag   26820
tctctgcttg cactgtgtgt gtgcacacgc gtcctagtga tgctgcagtg tgaacgtcat   26880
tatccccatg tcacgctgaa gaaactgaaa tccagagacg tcaaagttat ttccaaggcc   26940
acacacttcg gagagcagag atttaagact gggtctgctg agctcaaaat ccactgacct   27000
gcaagtggca agaccagggt cagcacggtg ggttctgccc ttggggagct tgtggcctct   27060
```

```
tggcaggtcc tcaggcgttt ggcgtcaagg gctgggtgat acaggtcttg tgcaggcttt    27120
gagggtcact ctgcctgttg tgaactctca cctctcattg ttgtgtgaaa gcagaacagt    27180
gtggaatggg gtggctgtgg ctctgttcca ggaaaacttt ctttagtaaa acaggtgcca    27240
gactcagtta atggcctgtg gtcactgtcc tgttgagaaa taggtaggaa agtggtttat    27300
tcagtggtga gaaggccctt gtgaacgtct tcattattta aaaaaaaatt ttttttggtc    27360
accccacgca gcatgtggga tcttagttcc ctgaccaggg gtggaatcca cacccttgc    27420 ggtggaagga cagagtcttt ttttttaaa tacttatttt gctgtgccag gtctgaatgg    27480
tggcacgcgg gatcttccat ctttgtgggt atgcaggatc tttacttgtg gcatgtggga    27540
tccatttcct gaccagggat ccagcccgag tccccggctg tggaagctca gagtcttaac    27600
cactgggctg ccatgggagt ccctgggcgt cttcgtgttt gaagggctgt acggtgttgc    27660
ccatactggg tgctcagcca gtccttgccc aggaccggcc gtgcttctcc ctcttgtgct    27720
gagctatctt gctggtggtg gttcagtcac tcagtcgtgt ccgactcttt gcaaccccat    27780
ggactgtagc ccgcctggct cctctgtcca tgggactttc ccagcatgag tactgacctt    27840
tctaccatcc cccatctctt ccgcagtacg tgggggcccc ggtggcttat atccagcaga    27900
tatttgtgaa atcttccgtg tctccctggc acaagaacct cctagcagta gatgtgttcc    27960
gctcacctct gtcgagggca ttccagctgg tggaggagat tcggaaccac gtgctgaaag    28020
acaggtatcc atgccaggcc ccagcctccc cgacccagct ccacacctaa ggtggggcac    28080
agccctcagc ataaatctac cgagctggct agctctgcga gactaagagg gtgggtgagc    28140
tcgcttcgcc tttctcaggg gcgaaagtcc acacagctgc tgggtccact gcagctgtgt    28200
tcccctcaga cctgtgccga gagccctgag cgtcgtcccc aggcctcaca cagacagatc    28260
cactgggctg accctgggac aggctctccg agacccggtt gactggtggc cctgagggct    28320
cactgcccag agcttgtgag atgcgagtgt gatggtggcc aagctgacga gaagccagct    28380
gtgcccagag gtcccctcct ggagtcccag cccaccagtg cttctctggg gcgtgctgcc    28440
ctgcaggctg cctcagtgct agttgaggtt agctgagggc ttgggccaca cacagccct   28500 ggttttcatc ctgcctcctc tgcctgccga actgcagggg ttctagtgag ggagctgtgc    28560
tcactcccaa gcatgcctct cctcggaggg gctgggcttt ggggctccac gtgcacttgg    28620
aaggtcaggc tgcctccccg tgtggtggct gagcccctgg aagaacttcc ccggctgccc    28680
ttgtcctcgg ccctttgaga caccaggcac ctgggagctt cacgcgcggg gctgtgtggg    28740
gccggcagac tcggcagcgc ctcgtcctgt cccccgcaca gctccgggac caggagcctg    28800
gaggacgtgt gcctgcaggt gactgacctg ctgccaggcc tcaggaagct ccgcaacctc    28860
ctgcccgagc atggatgcct gctgctctcc cccgggaact tctggcagaa tgacagggag    28920
cgcttccacg cagatcccga catcatcagg accatccacc agcacgagcc caaaaccctg    28980
cagacctcgg ccacactcaa aggtgcccgg gcagtcccct gagagccatc gggggcctgt    29040
cagtcaccac atcctctttg gaggctgctc tggcagatct ggggttgccc tgagtttctc    29100
agggttgggt agaaaggggt ccttggtatc tctacgtagc tgccggtcct ttgtcagcac    29160
ctgttgccct ctgtctgcag acctgctgtt tggcgtccct gggaagtaca gcggggtgag    29220
cctgtacacc aggaagcggc tggtctcata ccatcaccc ctggtcttcc agcactacca    29280
cgccaagtaa ggctggcctg cggcacagca ggcagctttt ccatttggag tgtcaccagt    29340
gcccccggga gcttggagtt ctcaggcctt ctgctgaaag gttcatgtcc ctcagggtgc    29400
tgtctgctca cgcttgaggg gggccacctg acagctgact aagaacaatg gggaaggcag    29460
```

```
gcctggcaag ctcagggtcc tggtgccccc atggtctctc tggagccttg ggtggggtc    29520 cccagctggt gactgccaag ccccatgtga cttgggagag cgcagcagac agttctccaa    29580
ggggcgaggg cacggagggg gcccccgatg ggctgttctg ggcctgtggc agtcagagcg    29640
cagtgatagg ttgggagtgg ggtcctcagg ggcgttctga gacagctggg ccaaccccct    29700
caagactgga gggaaggtta gacaccgcga ggagggaatc cccagctgcc ttcttcaggg    29760
attgcctttg tcccccggac agagagggac aggccatctc ccaccccca cccaggttcc    29820 tgggcagcct gcgggcccgc ctgatgctcc tgcaccccag ccccaactgc agcctcgag    29880 cagagagcct ggtccatgtg cacttcaagg aggagattgg catcgctgag ctcatccccc    29940
tggtgaccac ctacatcatc ctgttcgcct acatctactt ctccacacgt aggtccacag    30000
cacagaggcc agggctttct cccagctaat tggggcgttt ccagatcact ccttccctgc    30060
ctcttcaggg gcccgggcag agatgtagaa tgtgccagct ggtcaccgaa gctgggcctt    30120 catccccag cggggcctga ggggcttggg taggtccagg gttcctccca ctactcacag    30180
agtcccttcc tgggaaggtt ttcaaggaca ctgtgccctg agactgggaa gggtacacat    30240
tctctgcgca aaccagggcc ttctcttcct cgaatgtcag gcacaccccc tcccagctcc    30300
caggatacag ggcccagtga gccaggctct ggggagaggc tgccctgatg tattctttgc    30360
cctccaggca agatcgacat ggtcaagtcc aagtggggc tggctctggc tgccgtcgtc    30420
acggtgctca gctcgctgct catgtctgtg gggctctgca cactcttcgg cctgacaccc    30480
acgctcaatg gcgggtaggt cccagcaggc tcccctgggg ggcagggtgg gcccgcaggc    30540
cggagcatca tgcacctctg ggtgcttggc ctgccctgcc ctcgacactt gctgttaccc    30600
tatattttca catggtaatt ttgacactta agagggatgt gtttttactt ttttgagtta    30660
cctggcttac gatcatacat atttatatac aaaccgtatg tatatttaca tataatacat    30720
ccataggtgt gtgtatgtgt gtgtatattc atgtgtatgt ttgtgtgtat atatgggta    30780 agtatttata tgtgtgtatg tatgtgttta cgcatatgtg tgggaatgta ttgtgtgcgt    30840
ctgtgtgtct gagggtgtat agatgtgtga attgttgttg ttcgttgctg agttgtgtct    30900
gactctgcaa ccccatggac tgcagcacgc cgggtttccc tgtccttcac tgtctcccag    30960
agtttgctca aactcgtgtc cactgagtcg gtgatgccat ccaaccatgt atttatatat    31020
tttaaataca tgtgcacgtt gcttctcaac agcttaagcc gtagatgagt gtgtcataga    31080
gaccgtacgt ttcgtccttt cttgatatta aaacatttaa attgcttggt aggtcccttt    31140
ggagtaagca ttttaaaaga tacaggccat aagcacactc tgatttgtca ccttcccacc    31200
gtttgcttcc cttccatttc tctcagaaac atggtcctgc cctggacccc gccagcctgt    31260
tagtgatcac ggccgactgg cctgtgccct gccttggctt gtcaggctgc tcccaggaac    31320
agcgatcttg tgtttcctct tccttccctt gcttgtagaa catttgcttc ctttcctaga    31380
cctgatgatg ctaatcaccc ctcaacgata gctgtctgct ctgcctcctc agagcccccc    31440 ccccgcacc gccccctagc ggagatccca gcgccgtgct cggctggtgt ccctagtca    31500 gggagcggga gcctgtggtc tgagagagct gggggagttt tctctagaaa cgattgccct    31560
tctctacacg cagcttctct tcagaggcga gtagggcttc aggctggcct catcccttc    31620 catttagtcc tgatggcctg gcctggcgtg ctgtggtagg ggctcctctg gctgatggtg    31680
tggtgtggga agggccgggg agctgtgctc tggcagctgg gcagtggggg cctcttccca    31740
cggtgctgga cagatggaga gcaggatggt ggctggctcc tcggcacgac ttggaagcca    31800
gcctgaaagc tgcgagccat gtagacaaag gcctcctgga gggtggggtt ccagtcctgt    31860
```

```
gatgtgggag ttgcttggca gcccccactg tgggccagac cccgcagggc cccaggagcc   31920
aggcctgctg aggagcagcc gtgtgttggg ggcccctca gcaccctcct cccccaccc    31980 cgctctgtcc ccagggagat cttcccctac ctggtggtgg tcattgggct ggagaacgtg   32040
ctggtgctca ccaagtccgt cgtctccacc ccggtggacc tcgaggtgaa gctgcgcatt   32100
gcccaaggta acakgagggg agtagggggc atggcggcgg gggttgtgct gcacctcctc   32160
ctgccgaggg aacgggagc ccaggagcct ccctcgcccc ggcctctact aacacgccca    32220
cttgttagcg tgagccctgt gcagccatgg agcccagggc cctgttttgt ccaggtccac   32280
atgtcagtaa gaccacaaac cgcctctgct gcgggctcac gtgtttggcc ctttgtccag   32340
ctggcagctg gtcttttctc ttcctgccca actctatcac gtgaggccca gaccctgga    32400 gcgggtcagc tcagagacgc tgcctccaca gctgccagga aagacccgcg tggccttagt   32460
ggcaggagct ggggagctgg gttctgggga aagtggggaa agagcctggg cctggaggtc   32520
tgaactctca catctcctct tcctcttcca cctcagcccg tatctgtggg aacagggccg   32580
gggcaggctg ttccttcact cagcaaagct ttgtgagcct gcgtgagagg ccaggccctg   32640
cactagacat ggggttccga ggagaccggg ggaaacggcc gctgcccact aggcgctcag   32700
agctttaaat gtgcgactgt gtggtggccc ggggcccagg aggggctgag gtaggacaca   32760
gccggctctc ctgtccctcg agccctctgc cacatgcgag gttggacatg ccggtctggg   32820
tggatgtggc tctcctaggt ctgctcaagt cagcaacccg cttctccctt cctcagatgg   32880
tcggagctct cctccggacc ttcaggcccc acttccctgt aaagctgtgc ccatagcagg   32940
gtccttaggg ttggagcatt tggtgggcag ctgtcttgtg ggccatgcag tcgtcagccc   33000
acatgcagtg gacagaggtt atgtgttgcc gtatggcccc gttgtcccct gcaggcctga   33060
gcagcgagag ctggtccatc atgaagaaca tggccacaga gctgggcatc gtcctcattg   33120
gctacttcac cctagtgcct gccatccagg tgaggcctcc gggtctgcag cttgggccgc   33180
gtggagccca ttactgagcc tcccagctgt gcagggcaca ccctgccttg ctgctgccct   33240
ctcctgtaag gtgcccctc tactggcagg ctggctgtca ctgtgcacag agaggccctg    33300
gtggaactgg cccaggagga ggactcagta agctgagcta cagcctggca gtctcagacc   33360 catgaccct cacccatgac cactcactgc cgtccctcac tcaagtggca ggagaggaag    33420
ctggctgccc gcagcacagt ccagtcaggc cccgtttccc agttctcagg cagaaagtgg   33480
tgaggccccc ctgcctttca gggcctgagc cctgacccgc ccctgcaccc tcgagacccg   33540
tggcccgacc ctgggagagc cagcagccat tgctgagccc tggggctgcg agcaggaagc   33600
ccactgttgc tgcctggaag ttttgtgaag ggagtaagga gttgttgcct cctgtccttt   33660
ccccacgact ggcaggccag ctgaggtttg ggaaggaacc cagggctccc aggctcccca   33720 ccctaccccca ccagagggca tctgcaggac gcggacggtc ttgggacatg agggctgacg  33780
tgccactgtg cactccattc ttcattttcc tcacatttga gtagaagcca tggtgatgca   33840
tcagaggtct caacaagggc agaggaggaa aacctaaacc cgagaaaact ccatctatcc   33900
acagagcctg gggaggaaag agactcccct tttcagttgc tgggtagaat tcattctccc   33960
cgtgctcttc ctctccttc attggtccag tgtagtcatt ggccaggaat aaggaatttc   34020
tgagagcctc caaaccaggc caggcctggg ctcttggtag gtgttggtct ctggtacatg   34080
agcagggctg gggcctcagt tagggagggc ttttggagta ctgcaggctg ttggggcatc   34140
agtgccaggg gtctctgctg cccctcatgg ggagggaggg agctgctgct gcatcctcct   34200
tggtggctcc tggatgtcaa agttccagca tctctcctcc ctgctgtgcc tcgcaagaaa   34260
```

```
ctgccctgca gcgtccaggg tgccagctgt ttggggtgca gtggtcaggg cccatgaggc  34320
tcccacatgg ggctgcggcc acagcaggca gggaactggt tctccagtgc tgggccctga  34380
ggtcagtgtc ctctcattgc cttttttcca ggagttctgt ctttttgccg tcgtggggct  34440
ggtgtctgac ttttccttc agatgctgtt tttcaccact gtcctgtcca ttgacattcg   34500
ccggatggag gtaggagtgg gctgagccct gccctaacca cctcctcctc agccctggct  34560
gtgctcaggg gtctctgggc aagagagggc agacctaggg cagggccgca gccccaagtg  34620
ggagcttctg gaccgcggct ccaggccctg accactgcac ccccaacagc tggcggacct  34680
gaacaagcgg ctgccccctg aggcctgcct gcccccagcc aagccggtgg ggcggccaac  34740
acgctttgag cggcagccga ctgtgcggcc atccatgccc cacaccatca cactgcagcc  34800
gtcctccttc cgcaacctgc gtctccccaa gcggctgcgt gtcatctact tcctggcccg  34860
aacccgcctg gcacagcgcc tcatcatggt acctgccacc cccacccgca ggcccgcact  34920
cacagtcctc ttgccgtttg catttgtctt gggggggtgc tccccaggcc ctcgtggccc  34980
ctggaagcct agctttggga agcctcccct tctcccctcc tgcccagacc ttgtggtttc  35040
tggggtgaga agcctgtctc tggagaagca gctggtgtca tcaggagag gagtctgccc    35100
agagtgacca ggacggatgc tctgggatgg aaccaggtgg ttccccaagt cagggttcac  35160
tgtgcaggca gcaggaaatg ctggctgggc agacggaaga aggagcaagg ttggctgaag  35220
tgagagggga gcggggctga ggccctctga ggactgagac ccgtggtgtc cctggagcag  35280
gtcaggcagc tggtccctgc ggctatgctg accatggggg cccaagctga gggagcggtt  35340
agggtgggaa agttctgtat caaacccagg gtgcctctct ctatttcggc caggagtctc  35400
aaacccgagc atggaaaggg agcttggtcc gtccagggg ggcagttggt cttagtcata   35460
gaggacttga ggcagaaggg aaggacaggt ggcctgtgtc ctctctctac cctctggcct  35520
gccgcttttcc agcgtgaggg ccgagtgtac agcggggtgaa ggctgcccct tcctccctgg 35580
ggtcctgctg agcccccact ccctgctgca ggctggcacg gtggtgtgga tcggcatcct  35640
tgtgtacacg gacccagctg ggctgcgcac ctacctggcc gcccaggtaa cggagcagag  35700
cccgctgggc gagggtgccc tggctcctct gcctgtgccc agtggtgtgc tgcctgccag  35760
ccacccggat cctgcctttt ccatcttccc gccggatgcc tccaagttac ccgagaacca  35820
gacgttgcca ggggagccgc ctgagcccgg gggtctcgcc gagggcgtcc atgacagccc  35880
ggccccagag gtcacctggg ggcccgagga cgaggagctc tggaggaaac tgtccttccg  35940
ccactggccc acgctcttca gctattacaa catcacactg gccaagaggt gggtgggctg  36000
agctgggtcc cccctcccac ctgttcgtgt cagctcactg cccccagagc accccttccc  36060
tcaggaggga gaccctgtggg tttgaattct gaattttctt tgaaataaac acccatcagg  36120
ttgtggggta ggaagcagtg ttctcagtag ccacaacctg agtccctggg ccccgctctg  36180
tgaggtcata ggtcgctgtc agctacttag ccaaaatgag atccacacct cacttccccc  36240
cactctgcca gaattggtga cagagggaca gtgattgcta gggtggtgga gtctgtgaca  36300
gggcaaggtt ggggtgccag agctggagcg ggggagccta ctgctgggaa gactgtcttg  36360
ggaggatgtt cttggagctt ggcagagcag gccgagtccc atggggagag tagagggggc  36420
cctgggcagc agcaggccct ccgagggcgt ctccgctgag gctgagcgct gcccggctca  36480
ggtacgtcag cctgctgcct gtcatccccg tcacgctccg cctgaacccg cgggaggctc  36540
tggagggccg gcacccctcag gacggccgca gcgcctggcc cccgccccgg cccggcagg   36600
gtgggctctg ggaggccggc cccaaggggc caggcacggc gcaggcgcag agagacctca  36660
```

```
ccctgtacaa gtaaggccca tgagtcgggg gtggggcggc cggcggggtc gcggggccgg    36720
ggcaggtctc accaggctct gcccgatgca gggtggcggc acttggcctg gcctcaggca    36780
tcgtgcttgt gctgctgctg ctctgcctgt accgtgtgct ctgcccgcgc aactacgggc    36840
agcccggcgc ggggcccggc cggcggcggc gggggagct gccctgcgac gattatggct     36900
acgcgccccc cgagacggag attgtgcccc tggtgctgcg cgggcacctc atggtgagtg    36960 gatgggccg ggggcgcggg gggccgagcc gcgccgccgc cagtgcccat gtgcatgccg     37020
cgctcccgca ggacatcgag tgtctggcca gcgacgggat gctactggtg agctgttgcc    37080
tggcaggcca cgtgtgtgta tgggacgcgc agaccggaga ctgcctcacc cgcatcccgc    37140
acccgggtag gtgctccgcc ctgcccttgg ccgnccctc cnttnnnnnn nnnnnnccc     37200 tagcaggcag cggcgggaca gcggtgttgg ccttgggctg gagactcagg agacctggga    37260
acggctgtcg gacggcggga agggtggccc ggaggagcct ggggacagcc ctccgctgcg    37320
gcaccggccc cggggccctc cacccctgc cctctttggg gaccagccag acctcacctg     37380
cttgattgac accaactttt cagcgcggcc acagctcccc gagccggctc agcccgagcc    37440
ccggtaccgg gcgggccgcc gtgctcaaga ctccgcaggc tacgacttca gccgcctggt    37500
gcagcgcgtg taccaggagg ggggcatggc tcccgtgcac acgccagccc tgcgcccacc    37560
ctctcccggg cccacgttcc ccctggcccc tgaggacgag gctggctttc ctcccgagaa    37620
gagctgcccg tccctcgcct gggcccccag cgcagatggc tccatctgga gtctggagtt    37680
gcagggcagc ctcatcgtgg tggggcgag cagtggccgg ctggaggtgg gcagcggggg     37740
ctggagggag gcagggggt cgtgggtgtt cccagttaca ggtgctcaca gcctctgggc     37800
ccccaggtgt gggacgccat cgagggcacc ctgcgctgca gcagtgagga agtgtcatca    37860
ggcatcacgg ccctcgtttt cctggacaga aggtgggagc gctaggaggc ccgcctcacc    37920
cctagacgcc cagctctgca cacactgagg tcgagccctg ctcccccttc cctggtgtga    37980
cacagcccac acctgtgagt tgcaggaagt ctgccttgat gggaggtgac aactcaaaag    38040
ggtaaaggtg gggagtgaaa gaaggccctt caccactgac agtcttcctc tcaccctttg    38100
aggtcagact cgtctgggta gccgtcactg ctgacccttc tgggttttca gttccagaaa    38160
aacgcatctt tagaactact gccttgtaaa aactcgcctt cccctttgat gctgtagact    38220
cttcttgcct gcctcttcac catgccttttt ggccaggtgt tccagcacg ccatcacacc    38280 atcgcctcca tggtggtggt ggtgggggg aggtcccagc tactcagact gggcccccga    38340
acctctgggc tgatggaccc agggctcacc cacccaagtg cctctggtga ccgcctcagc    38400
tgcccatcat gctggctggc tcttccttcc aggtccctga gcgtgtgtgg cctggcatct    38460
gagctagagc agagccttgt tttctgcggt ggggacaccc ctcgccctga gttgtcagtt    38520
tctggtggct ttctgcttag gtctcagctg acatcctact gtgtagcttg gccaagttca    38580
ctgggttccc ccgagcttgg aattctcccc cactggtggt tttttgacat tttagggaaa    38640
gcccacgtgt ctcagcctag ctctgcgtcc acggctctgc cctctccttc ctctgcccca    38700
gctctgctgt ggaccattca gctttatggg ctgaaaactt gtgaacccca cttgcccaa     38760 ggctttgggg ccacagagca cacacatctt catctctgcc catcagcctg tgcctaggaa    38820
tgccaggcgg tggagagaat ccttatttcc ttgtggaaac aggaaacgga gcaggcagtg    38880
cctgtgttgg agctgccttt ctgtcatagg gcagcagtgc cttctgcggc tcctcacagc    38940
cctgcctcag ctcctctcac ctccactgaa gcctctccta tggctccagg ctgtggaggg    39000
ggactcccct cccccagact tttaaatttc cagtcttact catgttcccc aggtaccact    39060
```

```
ttacactatc atcagctcac ttactcttca cgaccacccg cccccacaag gcacacacgg    39120
ttgttcccat tttcacacat gaagtatctg aggcacagag ggtggcactg gggttgcagg    39180
gccctcctgc tctgcacctg gtcccagcac ctgtgcttcc gtctgggctg aggtctctcg    39240
cggcctcact gctccccggc cagtgggacg ggcctgtgta ggcccgtggc gctcagcccc    39300
acggccaggg gctctaaggg caagcccect ggcagccact cttgtctttc aggattgtgg    39360
ccgcccgact caatggctcc ctcgatttct tctctttgga gacccacact gccctcagcc    39420
ccctgcagtt ccgaggtcag cgacctgggc aggccagggg cctcacctag tgggtggagc    39480
gcgggggccg ctgcaggtgt cttctccgag gcccctcacc tggcctgttg tccccagggg    39540
ccccggggcg gggcagttcc cctgcctccc ccgcgtgcag cagcagtgac agggtggctt    39600
gccacctgac ccacaccgtg ccctgtgcac accagaagcc catcacagcc ctgaaggccg    39660
ctgccgggcg cctcgtgact ggcagccagg accacacact gagagtaagt gtcggcacca    39720
tctcttgggc acgcggtggc ccagcacagg ggtcaaagga gggcatctgg ggtcagtcag    39780
agagaggctg gagtaaaccc cattncgggg gaaggaatag agacgcagac atagaggaca    39840
gaaactgtgg acacaccggg gaaggaggng gggtgagctg ggagagtggc actggcaccc    39900
agcgccgtgt gtgagcagct agtcgggggg agctgctgtg cgacacagcg tgcgcagccg    39960
cacgctggag accacgaggg gcgcggtgga cagcaggagg tgtgggggac acaaaggagg    40020
ggacacgtgg gtactcacag ctgattcaca cacagcagag accagcacag tattgcaaag    40080
cggttctcct ctaattaaaa taaaacccca aggagcccca cacctgaggc ctgtttctgc    40140
cgcaggtgtt ccgcctggag gattcgtgct gcctcttcac cctgcagggc cactcggggg    40200
ccatcacgac cgtgtatatt gaccaggtga gggccgtggg tgggctgtgg gggcattgag    40260
ccagacccac cacggccttg tttctgagtc ctgggagctg gtccccaggg cctccgagag    40320
gcaggcaaag gttccctccc acccgggcac tgggacacct tggggacaga ggtggcacca    40380
gtgaccaggc ccccacaccc actcctgcag accatggtgc tggccagcgg aggccaagac    40440
ggggccatct gcctgtggga cgtgctgacc ggcagccggg tcagccacat gttcgctcac    40500
cgtggggatg tcacctccct cacctgcacc acctcgtgcg tcatcagcag tggcctggac    40560
gacctcatca gcatctggga ccgcagcacg ggcatcaagc tctactccat ccagcaggta    40620
ggcgtggggg ccacggggcc tctggctgtc gggaagggct ccagaccccg agcccgtctt    40680
gtccttgtct ccaggacctg ggctgtggcg cgagcctggg tgtcatctca gacaacctgc    40740
tggtgaccgg cggccagggc tgtgtttcct tttgggaccct gaactacggg gacctgttac    40800
agacagtcta cctgggcaag aacagcgagg cccagccggc ccgccagatc ctggtgctgg    40860
acaacgctgc cattgtctgc aactttggca gcgagctcag cctggtgtac gtgccctctg    40920
tgctggagaa gctggactga gggtgggcct tccccaccec tctggctggg gcgctcggtt    40980
ggcaacgcat gggacctgga cgggggagt gctgagtctt gggaaagctg cttctgactg    41040
tcctgtcctg cctcatgact gtaatattaa atgtttttt aaatgacatc agccaggggc    41100
cttttgagcc acttggtgtc ttcccttgga cgggctctgc catcactcac accctccggt    41160
tgcccgaaaa tgcaaccctg gggtttaaac cctttgctca acctcaaaaa cggcttccct    41220
ggccaggaaa accccaattg aaaatccggg ggccaattta aaaaattttt ggggggggg    41280
gggggggggc aaacccggg gggcccccc ccctccttaa aaaaccccc tccctttttt    41340
gttaaaaata aaagcagggg gggggcggg ggagagaat                          41379
```

```
<210> SEQ ID NO 3
<211> LENGTH: 11836
<212> TYPE: DNA
<213> ORGANISM: Bos taurus
<220> FEATURE:
<223> OTHER INFORMATION: insulin induced protein 1 (INSIG1)

<400> SEQUENCE: 3
cggcgagccc gcaggcgggc gccccctcggc caggtacgcg gggcgcggcg agggcggcgg      60
ggtgggggct ccaaggcggg ccaggctggg atgtccgggt gccgacccct ccactccaga     120
gcctcccttc taggccgctt tcctttgggg gactctcggg cctgggcccc agccctgacc     180
ccagccccgg tccctgcgcg ggggcccagc accgcgacc cctgccggtg cgcctcccgg      240
gtcgggagga ccccagcaac ttgtcctggg acaacctgcc ccaggtcctg cctggctgag     300
tccatctcct gcagacggac ggggtctgga aaacttctgg actggacggg ccagaacttc     360
agggcttctg tggaggggcg tcgtggcggg agcgcaacgc tcagatgcac ctaacctgcc     420
tgcctcggaa agcagtcggt gcatctgcct ggccggggct gtgggcagga tccttgcagc     480
tgctcccaac tcctgcagct cctgcccggt gtgactaagt cccggagggc cttgggggtt     540
ttcctggacc tgctggtggt gaaccagagc agagccctcc ttgagtgggc ctccctggtc     600
ctgacctcct ttggaagtga acttgatctg gttccacct ccacgccccc ttttcgttct      660
aggaaagcct gcaggcgggt ggctcatgcc cagactggac gaccacctct ggagaggtcc     720
ctgtgccaag ggcacgaagc acagaagcca cccgagggcc agcgccagag ggctggtggc     780
caaagcggga gagatgatca actcctcggg gtcaggcccc tctctgctgg cagcccatgg     840
tgccctgggc actgaccccg ctcacgggcc tcagagcgct ggtgtagggg ccagggcag     900
cagcagccac gtcaacagct ggcatcacca cttggtgcag aggagcctgg tgctgttctc     960
ggtgggggtg gtcctggcct tggtgctcaa cctcctgcag gtccagagga acgtcaccct    1020
gttcccggac gaggtcatcg ccaccatctt ctcctccgcc tggtgggttc ctccgtgctg    1080
cgggacagca gcgggtgagt agacactgga gatgtctgtt gggttaggaa gtgtgttggg    1140
cctctgagaa ctgtttattt gagaatgaa ccatccacag aggggcggtg tgcctctcca     1200
gtgagcgtat ctagaggaga aggggcgaga ggcaggagcc cagatgccag gactctggat    1260
gctggtgatg gggaccaggc ggggcagtga ttggctgttc ctcgcccgtg ccaggctgac    1320
cgaggtcctt ccctctttct gatctggccc tgaggacagt gttgaggggc ccacagctgt    1380
taccccgagc aagccgcgcc attggccacc agcggaactg gtgagccgag gaactgccac    1440
gtgattggct ggccctggga acatgctacc agccgggcaa ccgaaaacaa accatcacgt    1500
gggcgagtgg gcagagctgc cccagtggct tcttgcactt cctttttcag gatggccctg    1560
tgaacgtgcc aaagccaggc ctttcccctg cccccctcca aaaaaaaaca ccggggtccc    1620
tggatgaagg aaaacaagtg tcttattcag agtttagctt ttagtgcacc tggccaaaga    1680
caaaacctga cccagagtct gcagtcttaa cagactaacc ggatggacta tacctctgag    1740
taaaatttct tggtcgtctg gctggttta ggtaaaaaca ctgaattgat ctcagcccag     1800
tagggcgctt aggacttctc tggtcaccca gcgtttgccg tggcctaagg tctgccggtg    1860
gttgaagtgc agcgagcagc ctgccctgg cgggcgtcct gggctagggg gcaggacagg     1920
tgtgacctg ggtgaccagg ccggctcctg gctgctccgt ggttggcatt tatgactgt      1980
ttgatatgtt ttgcttcccc tggtccttac gagactctgc cgcagctcca tttcacagcc    2040
gtgggaacca caaggggcca cgccgagtgg caggcccgcc gtccatagct gggtgtgtcc    2100
cctgcactgg gaacggtgcc tcgtcagcag cctcccttag agcaggggca ggccccaggc    2160
```

```
tggagtgggg accctcaggg gagggggtgct gtggggagaa ggttcgcacc gttctcagga    2220
aggtgggctc ctgctctgtt ttctaagccc tgccagcatg ccctttttggg cactaggccc    2280 agatgtgcac ttccgtcttc attctcatat gatacagtag ttttttttgac tgaaacagtt    2340 gatctcaaaa ccgtcgaacc atttggttta ggctttatttt gtaacagaag cttcaaggaa    2400
ttccagggat atctgtacgt gatgtctggt accctagctg cttttttttaa gccatcagtc    2460 aggagcataa agggaagatt ccatagtaca ttttcaccta ctcgaatctg aaaggtaacg    2520
ttaagatata gtgacttaag tgatagaact gttttgggttc cattttttcaa gactccagaa    2580 ttatgggaat tccctggcgg tctagtggtt aggactcagt gctttcactg tggttgtcca    2640
ggttcaatac ctggtcaggg aactaagatc ccacaatcta tgccatgtgg gtccccaccc    2700
ccctcaaaaa aaagtccaaa atcagaactg gataaaatgt attatgaaat tggaactatt    2760
tcatcgactc ttggcctgag gctgtgttgc ttgttcctct gtttgggacc tgaactgggc    2820
ccttctcgtg ggacaccagg ggtgccgtgc atgactctca agcctcagta cctggctgac    2880
tccacctggc ctgcctcccg ccagccacca gcaggagtgc gggggtgctt cccatgtgga    2940
taattaaacc cctggctcca ttccttctat aggtcaagcc aaacaacccc agttttattt    3000
aaaattgtac aaaatgatgt gggttttttg gtttgtattc aaggagaaca aagtgtaaca    3060 ttagttttaaa aataaaagat gtaaagttag tttaaatatc tgatggctgg taaatctagg    3120
aaagggaatg gtttgaatat cgcgttaatg atccccacga ggcagtcgcg tcgtctctgc    3180
tggcgtgctc agaccctgcc gtcttgtctc tccccgcagc tgtggtcggc ctgctgtacc    3240
cctgcatcga cagtcacctt ggagagccac acaagttcaa gcgcgagtgg gccagcgtga    3300
tgcgctgcgt ggccgtcttc gttggcatca accacgctag tgctgtatcc taagacgtta    3360
ctgttaatgc gtgtctgtca cgtcctgggt cagttgagct gatctcttac aagcatgatt    3420
tcaaaccacg ttgctcactt tcctctcagc agagcttttca aagtgatcct gaaagtcct    3480 ttcagttcat ttcaggagac agttaaaatg accctgggaa cagagtggat atctttagtc    3540
tgtccctttc ttggtcacta cctgttggat cctccgagtt ggtttggtaa attccccgtc    3600
catttctgcc tcccatcctt ccacggtgca gacctggttc ctgtggtgca gtgagacgtt    3660
gcgggagctt cactcttctt ggctgaccct tccagaaggc agagcagaag cccgtctgct    3720
tctccgccct ccccggtcat gaccagggaa ggcccagcgc tgatcagagg aggtggcctc    3780
aggaataggt ttcccagtgg aggtcacatt caaggtcagg ttctggcgtc caccagtggg    3840
ctgcctggca aaacacggtg cagttttcag gaagacgggc catggtttac caggcgtcaa    3900
gacatttata gtttctttct gacagcgaga ttatattttt aaattctgga gaaagctgtt    3960
tttagagttt ctgctgctta aatctgcttt accctgattt taatgataag aatgtcaaga    4020
aaaggtatta caagagagcc tggctctgac acatttgttt tgtcccctgt tggtaaagta    4080
gtgttgtgaa ggaggccagc tgtgtcccca tcagctgtga ccgtgtcgtg ttgaatgcca    4140
ttccaatgag gtgtctcctt gcagacacag agtaaagact gtgcttgctc agttcaaact    4200
gctaataaga acaggaaata aaagtgggac tgtggatgac ttactaggat atagttgttt    4260
cgtggttgaa atgaatccaa gcagggtttt atgcatagtt tttaatacat tgactggtaa    4320
agtcaagttt tcaacgcagg gatcccagag atgccccagg tcatcctgat caagtagcct    4380
tgtatccagc acatgctctc tgcagctcac tgggcagcat ctgaggctgg agaattaggt    4440
ggtgcacacg tgtaggctcc ggggctcgct tgtgtgtctt tgaccgtgtt agaaattgtt    4500
gtacttttcc ttaacttttgc gtcaccagaa actggatttt gccaataacg ttcagctctc    4560
```

```
cttgacatta gcagcgctgt ctctgggcct ctggtggaca tttgaccgtt caagaagtgg   4620
cctggggctg ggcatcacca tcgccttcct cgccaccctg atcacgcagc tgctggtgta   4680
caacggagtc tatcagtaag cacgtgcccc caagtgtcac ctctgcccgg agctgtcac    4740
tccagttttg ctcagaatac ccatgaagct gagatgccgt gttgtttgta attacatggc   4800
atgagcttag acgtgaaatc tttaaaagca cttcttattg ttgattcaca taaaaatgca   4860
ccatctgtaa tttaaggaca gccaagccac ggtggagagc tttgcattgt ccttcagcct   4920
cttaagctgt gtccaggtcc ttgtgaccca cgctgggctg cagcacactg gcttccttg    4980
tcctccacca tctcctggag ctcactcaaa ctcatgtgcg tcgagttggt gatgccatcc   5040
agccatctca tcctctgcag ccccctttc ctcctgccct cagtctttcc cagcatcagg    5100
gtcttttcca aagcgttggc ttcccgcgcc agggggccac ggtgggcggc gagcgtgggt   5160
gtcacgtgct cacgtggctg gtgtgatgtg tgcctgcccg ccgcgcaggg ctcatgcctc   5220
cctctccctg caggtacacg tccccagact tcctctacat ccgctcctgg ctgccctgca   5280
tcttcttctc gggaggcgtg acggtgggga acataggacg acagctggcc atggtgcgta   5340
gtcacacggg cgcctgatgc tggctttcag ctgggtcagc ttggtttgcc tgggacgtta   5400
tcatttgtgt caatacgtgt ataggcagga gcagcagtta ctcagataag catacacttt   5460
aaaaaggcgc atcccaggcc attctcggct aacttgtaaa ggttcaggga tttgtaagct   5520
cacagtgaga gctgctgagg aaccagagct cccctcacat gacggatgct gtcagcggct   5580
tttctgaact gcttctcctg taataactgg cagagacaag ttacagaaat ggctaactga   5640
atgatttatg atgagtttcc tccccggctt cacgactcgg gtacagacaa tgccatgcta   5700
ggggaaggga gacacgccag gcccatgaga gtgcgggcgg ggctgggggg ccgctgaatg   5760
tccctgggtg ggtggactcc ggcctggacc ttgtctaagg actaaaggga gagacactga   5820
gtcccagacg gagccgtttc ccaagaccca gaaaggcaga cacagtcagg ataccttggc   5880
aattctgttt gggagtgaaa gatcacgaca cttgagcact ttgatgaagg agcgtgcaac   5940
atggacattt aactgttttg aatggacttc aactcgaagg cttaaataaa atgaatttta   6000
aaagaaaag gaaactagag tcttataagg gccatttctc tcagagacac actctgggac    6060
ttccttagaa acttgtcttg gtccctcatg cttttatttt aaaaagagga catttatttg   6120
tgcccctga gcctggcttg ggagccgccc ccttggctgt ttgacaagaa tggaagtagt    6180
ttagaaaggg gaatttgtga tgcgtcccac tggctcctgc gtccacgcca tcattccccc   6240
accccgaccc ttgtgatggt ctggacccgc cgccaaaacc agaacggacc acggtttgtc   6300
tcaggacccc ttgtgagcat gcgcgcggcc ctgccctgtg accacagcct cgcgacaccc   6360
ctgtgctgat ccccgcggcc ctggggattc cggggagaat gaggcagctg catgctcgcc   6420
atccgccttg atgttcattt cggtagtatt tagttaggat tcttaataag gcttttgaga   6480
tgaggttgtc ttcagctcct gtgactcttc atggagttaa agttgacaaa attcagccaa   6540
ctggttatta cttcgggagg aggggtggtt gctgtcatag gtttatgatg aaggtcttct   6600
gaacaaattt tgtaaagaag cgtccttccg atagaggtag acgctgcaca ccaggcacag   6660
gctcgtagcg ccaggagtgg ttggaggaga cgcacaggag ccacgcggcc atgcctttgg   6720
cagcagcact aactgaaggt gcttttagca gctgtctttc catcttgtct tactgctgct   6780
gttcagtcgc tcagttgtgt ctgactcttt gcgacccatg aactgcagca caccaggctt   6840
ccctgtcctt caccatctcc cagagctcgc tcagactcat atctattgag tcagtgatgc   6900
catccaacca tctcatcctc tgtcaccccc ttctcctgct accttcagtc ttccccagca   6960
```

```
tcagggtctt ctccaatgag ttggcttttt gcatcaggag cttcagcttc agcatcagtc   7020
cttccaatta atatccaggg tccatccctt taggatggac tggttttttg tagacacttt   7080 cattttttt gaaaagatga gtgaaggttt ttaacagaac ttaaggtaac tggcgtaact    7140
gtaactcccc tttattaaag atgtttcttt tttttactct tcaaaactgg ggacagtctt   7200
atctttggat gttactgttg tgtcttgaaa ctggaagagg ctggtgagca ttgcagtcat   7260
caaagggaaa gagcccccac cccggtctga gtccagccct cctgctgtct ttccatccgt   7320
gcacatttgt ttatgtgtgt atttggccac gcctcgtggc ttggggtatg ttagtcccca   7380
gccagggcct ggaccccgc cccagcaggg tgagctgctg atgggagac cggtagactc      7440 ctcaaacgtg tgaagccaga ggggcagtca cagctggttt tacagatgcc ccctctgctg   7500
catcttgagg aagggcaaga gcaaagcgcc tttgcccgag tccccagacc ccagcagagg   7560
acacggtctg cgtgatcaca ggcagggtgg tcacagcttg ggtcgcagct gtgtttctgg   7620
cacagtcagg gagaggatga gggagggtta cttctgttac agctactcag ggcccaggag   7680
tgaggcacgg ggttcagatg gtctgaaggg gtcagccagt tggactggca gaagcgtgca   7740
gtagtgagga gccgtattgg tggggcggg caggggagc ctctgcagga aagaagtggc    7800
cacttctgac aagtaggtgg ttggggttgt tcttttctct tttgtaattt taaagtttac   7860
cattgttctg cagttgaccc ttgaagaaca ggtggattag gggcaccaac cctcctagaa   7920
attgaaaacc tgagtgtatt ggatgaatcc tgtattgacg gatacaacca accagggacc   7980
atgttgaaaa gatgcgtcta agtgaagcct tgttctcaaa gccttgttca ggggccagct   8040
gtacttgtaa ctgcagcact ggcgtgtgta caggagcccg tggctgtggt ctctgcagcg   8100
ggcagacctg tatcaggagg ggggcaggcc cgtcagctgt gtcctgcgga ggtcgtccac   8160
ggggcggcca ctgcaggacc gtggccctct gcccttgcgc agcgctgtct gtgcactggg   8220
agcagagcct tggccctggg ttgtgggtga caggaaggca gagaatcggt cccccacccc   8280
ctgcaaagcc cccagacctt catccccacc ccggcctccc ctccttcagt ctgtcctgcc   8340
tggtccctgc ctttctgttt gtctcttcca tccttcaggg catcgtaaat gaaataaagt   8400
gacatgaacg ttgctcagtt atgtccaact ctttgtgaac ccatggacca tacagtccat   8460
gaaattctcc aggccagaat actggagtag gctgcctttc ccttctccag gggatcttcc   8520
caagccaggg atcaaaccca ggtcttccgc attgcagatg gattctttac cagctgagcc   8580
acaagggaag cccagcaata ctggaatggg tagcctgtcc cttctccgag ggatcttccc   8640
gacccaggaa tcgaaccagg gtctcctgca ttgcaggctg attctttacc atctgagcta   8700
tgagggaaac ccctcttaaa tgactctttc ctgaaagcag tagggaatct taaaaagccc   8760 cccttttgtct ggcagaaatt acacagcctt cagggcatat cagttgacct ctgaacctga  8820
cactgacccc tcctcttcac aatccctcca tccacttcag cctttccacc gcctccgggg   8880
gatggcaggc caccttcca caaggcgctg ttgttgcagg agcaaaaaga taagtatgtg    8940
aagccaaaat tgtatttttc atgagactag aattggaagt gtaggaagtt atatttggtt   9000
cagattgcat cagggctgaa gaacgaaaaa tatatttata ataaggtttg tcttagaaac   9060
ctgtaaccac ccatgacttg accgtccctg ccggaaggac cttctgctct tccccaccac   9120
ccagcagcca acagctgtga tgggctggag caggggcgtg gcctctgccc tctgcccctg   9180
cctgaccacc caccacccag tcccggtccc ccggagaagt acccagggcc gggcacggag   9240
gctcgtgccc cccagcgcg ctggggtgtg caccctgatg gcttgggttt gtgtctctgt    9300
ggggtctcag agctcagcct ggacagcgcg gcaccttgct agactcccett gagcaagtta  9360
```

```
accattttttt ttaaagaaag agttcgaata ctttagccag gttttaatt tttttcttct    9420
aagaaaggga aaaagctagt agctgctatg tgaaggtgag cttactcatc acttagaatt    9480
ggaaaggact cggggcctta aaatgggt tgcttggcac ctgggcctgt ttgcacgtcc      9540
atggccactg tcctcgcttt cacagcagcc accctgcagc cctcggacag aggacacttc    9600
tgagacgtat tctcgcagca gcatttcagg atgaatttt agtttgaaac gtctccaagt     9660
gagactttgc agtggaacat gatctgagcg cagaagacaa agggctgcag ccatggaccc    9720
aaggtgggcg cctatcagtc cgctcggggc cagagtgtcc cgtgtgacgc gcctgcagcc    9780
cgcccctcc catctgctca gttctgccca taaacgtgct cctggcccg ggcaggcgtc      9840
ccccagagcc acaggctggc tctgcttgag tgttcaatgg ttcacgtagc ttttctgta     9900
tggtatttgt cgtccgcctg taggtttaaa cgggagtctg tagcatcatt ttatcgagtt    9960
cgtgtctgtt gtctgcagat gaaagtctct tctcagaaaa agtaaggctt cgcactgccg   10020
catgaggagt gtggccctgt tcccagagcc caggccccgg acgccgcgtc tccagcatgc   10080
ctctcccacc tgcggtgcgg cggctcctgg ccgtcatggc cgtggtgtcg tcgggctgac   10140
gtccactggc acttggttga gtcctgcagt ggcagtatgg gggcaggact gtcagcccgc   10200
tttggagatg gggttggag cccaggaggc tgagcgcctg gcgtctggtg cagagcgggc    10260
tggcccttgt ggctcgctca gcctctcagc agggtcagg gtggacacgc agggaccccg    10320
gctctggcag gaggcagggg gctctcctca cacagccccg tgacctcagg aaggtcagcc   10380
tctggtctcg gacctgctgc tccagtgggg tgtccatcct cggttgaggg ccaccaggcc   10440
aggcccagac accggccaca agtgtggggt gccctctctg ggtatctgtg ctgtccggcg   10500
acgagacgtg catagacaca gcttctgggc agcagtacca cctcctgtcc tgcctgctac   10560
accccgccc tgcctgagcg ggacagacca ggtctgctga gatgtgggct cccagctcag   10620
ggctccgagg gcatcgctgt ggggccgggg gagcctgtct gctgctccgt gattctggtc   10680
tccaccctcg cctctggcgc aaagggattc ttcatctctc actttgtagg gtccgcttaa   10740
attgctaagt aaaacacgca cacatacagc gctaacatcc ttttttttct ctgtttctcc   10800
acatagggtg tccccgaaaa gccacacagt gattgaatcc tcaggcgcac ggatcctgaa   10860
gagtggcaag gtttggggag aaagtccgcg atactgggta gtgacgagac tatctctttt   10920
cctcagtaac ctcttcagat ggggctgact gtaccagtga ctcctggaaa acacttcacc   10980
tgtttcagag cagccgagcg gtggatggcc gctggtggtg ggacggtgcc cctgcccgcg   11040
tccgctgggg gcaccacgag caggccggct gggcaccggg ccccgaggac tcagtttctc   11100
gtgttattaa atgccaagtt gccatatttg ctagcctcga actaaagcct gactgccagc   11160
tctggttccg tgtcagcgcc ccggggacgg cttggtggtg cttacaaaga tgaagtgtgg   11220
tgagacagga atatcactca tccaaaagat tttaaaaata gggctgtgtt atgaaaaaag   11280
aaaaggcggg ggtggcagca agcgcagggt ggccgtgccg ggcaggcggg cacggcgtgc   11340
cctcggtgcc cgtgtagggt gctacgcaga caatcctgca gaggaggcag tgagtgggag   11400
gttgtggctc tgcgctgcaa tgggttggac ttttccaccct ggtgttcacg gaatccgcac   11460
cgtctcgaat ggggcgcccg tcggccacac gtctccgtct tggcccaaac cttgcgtttt   11520
cttttgctact cggaagaaga gacggctttt tccccacagc cctatgggat ctgcaatctg   11580
tgattgcctt gtaaaagaa gagtgcgcac gtcactgcat cacattcggt gtctctaaac    11640
cctcaaagga cgcggtgagc acagtgtact cactcaatgg cacagcccac gttgggcccg   11700
gtgtgcaggt cctgggccctt cgacttcaag tgcaatgtat aggaacacca atctgagcct   11760
```

-continued

| | |
|---|---|
| tgtattctct ttaaatattt attattattt ttttaaacgt gtgagatgct aaagagggtt | 11820 |
| ctccatttca gtgctg | 11836 |

<210> SEQ ID NO 4
<211> LENGTH: 14558
<212> TYPE: DNA
<213> ORGANISM: Bos taurus
<220> FEATURE:
<223> OTHER INFORMATION: insulin induced protein 2 (INSIG2)

<400> SEQUENCE: 4

| | |
|---|---|
| acagtccatg gggtgcaaaa agttggacat gactgagcat gcatgcatgt tcttaaaact | 60 |
| cacttcttgg tacaaaggaa agaccacttt ggttggcaag ggcagggagt gatggtgagt | 120 |
| gaatacctag agtgactgta cttggaaagt tctaggtttt aggaatcaga cgccctgtgc | 180 |
| ctcgaactcc ttagaatcta gcccagaggt tattctttgt tttcttagct tcctttctta | 240 |
| cgcttcctgc tccagctttc tcacaatagc tctcatgatt gcaacaaagg tggactgggt | 300 |
| gacggcaggg gtggctcaca actctggacc tggggacaga gggtcaggtc tgatttctat | 360 |
| gcttgatgta cgtgttagtg aatgggtggt ggtctgtttt ttatagggca cttttgtgca | 420 |
| gaaattcaca tgtttaagca ttaaacatta aaagagtcat tttattcccc tatggagatc | 480 |
| gtcctccttg agcatgtcac atttgattga gaacagtaaa acactaacag tcagaatatg | 540 |
| ccgattttct gtaaagttct gtaaagtgta aaaatttctg tgtgaatctc caagcccttc | 600 |
| agttacatgg gcttggagat tgggtagaag aaacagaaac ctggagattt gatcttgtgg | 660 |
| tttctccaac agtaaaagtg tctcaggtag cctgagctgc ttttttcact gatgtggggc | 720 |
| aagcaaggtc actagttctg tcctagtaaa tataaattta gcacttcatg ttttattaca | 780 |
| atatgcatat aaaagtgctt tttacgtctt cttattccat aagtaactaa tttaaataag | 840 |
| catgtaaact tgtcatttca ttatttgttc tttaaaatga actagtattg aaatcaggaa | 900 |
| aactctagtc atttattagg catacattga ttgctttttt cttatctctt gcaggatttc | 960 |
| tggtaggtcc tgttttagga cgagatgcag tactgttgaa acgccagtct gctttggttc | 1020 |
| atacaatcag cttttttcagc tgggaaaccc tttcttgttc cttttttttt ttttttgccaa | 1080 |
| cttactgaac ttatgaaacc atggcagaag gagagacaga gtcacctggg cccaaaaagc | 1140 |
| gtggtccata tatctcatct gtcactagcc ggagtgtgaa cttgatgatt cgaggagtag | 1200 |
| tgctgttttt tattggagta tttcttgcat tagtgttaaa tttacttcag attcagagaa | 1260 |
| atgtgacact ctttccacct gatgtgattg caagcatctt ttcttcagca tggtgggtac | 1320 |
| cgccatgctg tggcacagca tcaggtatgt gaaggctgtt tctgtaatgc aaaagacatt | 1380 |
| aggataaatg actatggctg ttttctggga aatatttgaa aaagtcagct ctactgggtt | 1440 |
| gtagtttaaa tacagtacaa tggacctgtt ttaagtgatc agtttaatga gtttagatga | 1500 |
| atcatacatt catgtaacca cccccacagt tcagctatag aacatttctg ctgctaagtc | 1560 |
| gcttcagtcg tgtccgactc tgtgcgaccc tatagacagc agcccatcag gctccaccgt | 1620 |
| ccctgggatt ctccaggcaa gaacacagga gtgggttgcc atttccttct ccaatgcatg | 1680 |
| aaagtgaaaa gtgaaagtga agtcgctcag tcgtgtccga ctcttatcga ccccatggac | 1740 |
| tggagcctac caggctcctc cgtccatggg attttccagg caagagtact ggagtggggt | 1800 |
| gccattacct tctgcaatag aacatttctg ctgctgctgc tgctaagttg cttcagtcgt | 1860 |
| gtccgactct gggcgacccc atagacgaaa gcacaccagg ctcccctgtc cctgggattc | 1920 |
| tccaggcaag aactctggag tgcgttgcca tttccttctc cagtgcatga aagtgaaaag | 1980 |

```
tgaaagggaa atcactcagt cgtgtcctac tcttagcgac cctgtggact gcagcccacc   2040
aggctcctcc gcccatggga ttttccaggc atttctagta ccctctaaat tctcttgtgc   2100
ccttttgcag cctaccacca gcctcaggct gaatctggat tattttcacc tgttctagaa   2160
tttagtataa atggaatcat agagttctta ttcgtttgtg tctgatttct atgtgactga   2220
cccatatgac ctttaaaaat tcagtcctaa aaacagtctt gattctcttg aggatgaggc   2280
ttttaacctc ttaattttgt tctttcttca acccacctca tataaattta tttgaaatta   2340
ttttgatgac actggtttta aggttttgat gtatgttatc gtccagtttt taaagtaaat   2400
gaaaacttga aaaatggaag acagttgatc cttgaacagc acaagtgtga agggttatgt   2460
gtggggttgt ttttttttaa atgtgtatca cacagtctga gcttggttga atctgcaggt   2520
gcagaactgt gtatacagag ggcgaactgt aaagttacag gcgtattttc acttatacag   2580
agggttggtg cccttaagcc tcaatgttgt tcaagggttg actataattt tatacaaatt   2640
taaagcctca tgttatcttt tagatttttg tatgtttttt ctctttatat cttgttttta   2700
gatatacttt cagaataata aattcttaaa agagaagtaa ggcagattgt cttcgattaa   2760
aatcattatt ctattagttt agatctctct tcatgggcaa tgtatattgg ataaagtgga   2820
gcatttcaga atactgtatt gatgctgcac ttctataatg gatagctctt tggctttttc   2880
tagtgagacc aatagattat actactttat gtaataaagt aatagatgta gaagaaagcc   2940
acatgggtag aagagaattc attattttat gaatgtccgt ttggtatctc acacttaata   3000
tatatcacta cctttcaata taatgtagat cttccttgat ttatgtccta cagctagagg   3060
gccaagggtg aggagttagg tgtgagatat ttttaaaatg ctattgtgaa acttattgga   3120
catttacata atcccattgc gtggatggaa aggcattttt gtggtaaggt ttcagcatgg   3180
tttatatact gatgtctcac tattacagta tttaccttaa aagagaactt gtaaaggtta   3240
tgattcttca tttccccagg gctgctgcta ttctctgaga gaacagttga cagttcaaat   3300
agacaaagga aaaaagcata aattgtattt tattattctc tgttgtattc agtatctacc   3360
agtcctcatg tgttttcttt tctttcattt acattcagaa gaaaaaagtt ttcccaacaa   3420
ctttttctac ttctttattt tctcctgtag cagagctgct gtccctgtac agtagaagct   3480
tttcaggact tagaagagtg tgtctttcca gaatagacaa aggagcagcg gggggaggaaa   3540
acccttgttt tattgagtgt cttaatgttt tggtctgtcc cttaatcaca gggatctgta   3600
gggcaacctt gggaatgaga tgtttgcatt gtgcctattt tgaggggatg aagaaacagg   3660
agagggtatc agtgagctca gggttccaga gcagggagtg gtgtggccac atgacatcac   3720
atcatcacat gctggggaaa ggcacagagg gagccactct tcctcccctc tctgggtacc   3780
tctctgaact ttccagactc agtgcctggc ctgaaggtac agtggcctac agtacaccgg   3840
cctatgctgc accttctggg aaagggcagg agaaccggac tgaggttccg ttgcgcctcc   3900
cttactggga ggagcaggga gtacatctct ctctgtgatg tgggcacttt tgccacaaac   3960
tcacatttag gaaggaaaat ttctaatgtt aatgctacat ttcagtcacc ctgttcctac   4020
tttcctacct tttcccaacc actagcttgt cccagttgcc agcttaacct catatcattt   4080
catgtggagt atttacattt acacttcttg cttaagtgtt tcttctgaaa gtggtacatt   4140
ccatgaggtg cccaggcaaa tgaaaggaga gattccagtt aagtccacac ttgatggtgt   4200
tggttaagtc atggtgttta gtaggtaggg acaaggatat caggtgcgtg caagctgcca   4260
tagatggaaa atagattctt acgtaattgc tgcctccccc acaccccagc tccaatttta   4320
gggaaagtgt ttaaaaaagg taaatgctgt gagaaacagt gtgtacagtt tatgtgtata   4380
```

```
tatggtatgt atatgttttt gtgtatatat gttgctgtgc attttcaaag ttctcttggc    4440
tcttatcatc tcagatcaga aaaactgata attatccttt gattttctg tccaataaat    4500
atctgtagac tgagcagcta ccttctggag catctccaaa atcaccactt tgtacatgta    4560
aaccctgttc tgagaaattc actagtggtg cttcgggagg ggcagctagt agagaaccct    4620
ggtaaactcc tttggatccc attctccttt tcctggttct ctgttttcag tttaataatg    4680
ggcagtattt caagttggtt aacttttta acttgcacag agcgttagaa ttggagttaa    4740
gaacctcttg aatgtggttg agagctacaa aggagtattt ctgaagaaaa atagggaaaa    4800
aagattatgt ggctaaaata actggagaac ttgactgaca aatcattagt aactagactg    4860
tgtctgtgcc tatgaagtga atatctgatt taaaaatgca aaacaaacat cttttctgtt    4920
ggcccatgca gtcagtcacc cagttactgg agagccttac aaggctcctc ctttctctct    4980
catgacccac attgggtttc caagttttcc atctctccct tgcctcatct cggtctaggc    5040
cctcaaccgc tctgcttgga attttcagtc attttgtttt tctgccttgg attttgtctc    5100
cctcgtcccc ccaagcccct cctttcctgt cctgtgttag cccctcacta ctggaagaac    5160
gtttgtccct ctatctggca caagtgtgag ggtgttattt tcccagtgac tgtgggaaaa    5220
gtctctttgt atggcctgta tgctttccac aggctttcca ccacctgtgg cgctagtggt    5280
aaagaatctg cctaccagtg cagggacata agagacatgg gttccattcc tggattggga    5340
agatccccta aagggggta tggtaaccca ctccagtatt cttgcctgga gaatcccatg    5400
gactggcagg ctacagtcca tgagtcgcaa agagtcagac acgactaatg tgacttggca    5460
catggcccct gccagcttgt atccttctca gagaatttct ggactctaaa actctttctg    5520
cctaaagtta ccagtttcca gatgatacca ggaattttct gttgtctgtg cttttcctca    5580
gatgcttccc tttgattaga aagcccttta cagaccattc agccactgaa cactctgcct    5640
taagggtcac ctcttctgtg ttactctcct aacaggttta caccctcctc cccttggcat    5700
acgacaggaa agacgggacc tttgggccct gttagtgctg cccctcagag aaggcaatgg    5760
caccccactc cagtactctt gcctggaaaa tcccatgaat ggaggagcct ggtgggctgc    5820
agtccatgga gtcgctaaaa gtcagacacg acttcacttt cactttcact ttcatacatt    5880
ggagaaggaa atggcaaccc actccagtgt tcttgcctgg agaatcccag ggatggggga    5940
gcctggtggg ctgccatcta tggggttgca cagagttgga cacgactgaa gcaacttagc    6000
agcagcagca gcagtgctgc ccgtaacacg ttacttgatc aaattgtttc tgtggtcact    6060
ttgggactga gtcacgtctt actcgtttac ccttttaaa tgcccagcaa atatgaagaa    6120
ccagacacat tgtgggttct gcttcatctt gttagatgaa cacattgctc agcctgtcat    6180
agttcttcat gaaagtatat ctcattccat ggttgtgctt gttcagctcc ctttccttga    6240
aaaatgttta acttaacttt ttcttttagt ggagtgctgc attaaacaca ttaccatgaa    6300
aaataatgac ttgatgtttt acaaacttct cttgtttttg gtcttggtag cctacaatta    6360
gttactggga aataactgaa atatacctca agaaatgtga ttttgctgc agagaaccat    6420
ctgattaagc aggactgtgt tgcatatgg ttttacacag gcatgatttt tagtctctcg    6480
tgttaaaata agaaactgga ggaagaggac aagaagacca gacacattc tgatgagctc    6540
tcaacagtgc tgccttcctg cactgtagat tttgctctca gactctgcca agcctttatt    6600
taaaggaaag aaaaaagaca tttaatggga agtgacaagc tccctcgaat tctccctctc    6660
agtgagcatc caagaaccat gcagactcga tggatttgat tttattggc aaatcccaag    6720
gttggcagcg tggcagttta aatttctttt tatgtttttg ctttctctcc tcagttgtct    6780
```

```
ctcacttgtg agtctgacat cacatgcata aaaatatagt caattttact tatttatatc    6840
tttgcccaca catgtcagta ctctctatgt gataattctc tacctatggc atcagctgct    6900
gaggaaaatt gacttgaaat gcctgatctt agttgatatc ctcagcaaca ggcaaaggaa    6960
gggaagaggg agcaagagca aggaccgaca cattgagctg ctagtttcat gaccccttga    7020
gaacaaaaaa agaggtaata ttcattcaga tatatttcag ctgttaggca tgcttgttgc    7080
cactttaact ttgtagaaat ttggaaatgc tgtcaattag tctcacggga tattagagca    7140 gaaccttta  aataggaata taatttgaaa ctttaaaatt tactagtagt tgttggaact    7200
ctgcattggg gaaatgtgtt gctaatgtct tgatggtctg tgaaccatt  atcctcagca    7260 aaagcctaat cggaagagcc cattcagttt tgtggattag aaaatgtata tttcattgca    7320
acatctcaaa tccagatggc atggtggcca tatggcctgt ttgctatgct gttccatttg    7380
tctgctagct tgtgatttt  ttatattagt tgatttcatt tttctttgaa gatgaaatgc    7440
attgtttgtg agctagagct aaccagtacc agcccaggca agggcttcta acccttggt    7500 tacttaggtt tgggtaccat aatttcatga ttcattgtag gaaatactgg acattttaag    7560
catacttttc aaccagtgtg acagttgtgt ttttattacc aaatggcagc gtaaacattc    7620 tgttttagg  aagattatca aactaaagct acccagatat ttcctattaa atttagtctg    7680
tagaagtata ttttattcat aacttgttga aaaatgtttt ggttcatgaa atactctttt    7740
ttttttttta atgagtaatt tagcatttta aatcctctcc taccaaatga gtaaaatgtt    7800
gaggtttaac aaggatttaa gttaaaaatt gaattactca taattaattg cactgttagc    7860
tttcaatatg ttctttgcaa aatgaagaaa tattctaaaa tgatttcttc tgatctttt     7920 aacagtgaat ttcagttttt actgaaaaca tgtgattcca cataccatgt tttctccatt    7980
tttcctctgc agaatgagtc ttatgataga tttctgttgc aagtttccct gctttgacag    8040
gctgatctag agtctcatta gagggccagg ttggaaggga gtgtcaggac aagacattag    8100 atgagggac  aggatcctcc atatagcagt atagccatat ccatctagta gtatgtgtgt    8160
gatgagcttg tacgtgttta cacttcaagc ttctctttag atttgtgtca tttcatggca    8220
tgttgcatgg gtatatagct taaaaagaat attacttaac tgctaactgg tttgatggtt    8280
tccaagtctc agagatatta gtagtagaaa cgtggtgcga ctcatctcta gtccagtctg    8340
ttgaattctg aatcatacaa tgaaatactg ttttgcctgt tgtaattgag actgctgttg    8400
taatcattta cagtactgtc ttcagtggtg ttatcctcac ttttttttt  cttttgggag    8460 gtaagtttat agtatcaatg attaatgtta agtaaattga aaagcttttc tagagaatct    8520
ttcaaatgct tatgatggtt gttgtgaccc ttagcttaac cgttggaaat gacttaatt    8580 tttgcttttc tcccccacag ctgtgattgg gttattatac ccctgcattg acaggcatct    8640
aggagaacca cataagttta aaagagaatg gtccagtgtg atgcggtgtg tagccgtctt    8700
tgttggtata aatcacgcca gcgctgtatc ctttctgctg tgatgagatg cgtaataaca    8760
aggcagcttc cgagaaacca aaggttaagc agacccttgc aacctcactg ttgtcgaatt    8820
gtgatacacc cacttagtca taaaaagaat acgcaagtac agtgtggggt ccagcctttc    8880
acttcaatca ctcagaaact ttgtacgtta aaaaaaaatt tccctatttt tctttaaatt    8940
aggttacttc attatctcca tctagttttt ctaactctaa cattgaaaca ggtacatttt    9000
caaaggaatt tcttttcttt ctttatttga gatttgctgg taaggacatg tggtgacttc    9060
aggtactagt ttttgtttt  tgttttgtt  tttttaatt  tgaaatatat atatatgtat    9120
atgtatatat agtttctttt ttttaaagac tgtcatttgt tggtgttaat caacacccac    9180
```

```
aaaccacata aatgttctta aaaggggcag aagtagaagt agccaatcta gacctgtgtt    9240 gaaaagaaa  ttcttttttcc taagttacat attcttaaag tttaatcatt ttaaggattc    9300
tgacatttta atttactgat tcatgagtgt tttcataatg ttctggcttg aaggataaag    9360
taacctctat ttcccatctc tcctctgcct tctacccctt ccccagaaaa ttatgtgccc    9420
ccaagaacaa aagcttttgc cctcaaaagg ttttgatcct gtcatcctct ctgcctccta    9480
cctgaacccc tgtccctgat ttccctctgt agaagaggat ctgggaaatg ctagttcagt    9540 cttcccttt  ctagaagata tggcttggaa ggtggaagta aagagaccta tgactcagac    9600
tgtgaggctt cctcttgaaa ctctgtgctg ggctcagtta gctgaagaga ggatgtgtca    9660
tggggcaagg agattccagt gtctcttaac agaaagtgtc aaggtgattg ggagaagcta    9720
gagaagagga accaaggaaa gaagccgagt cctagattct gaaaacacat cttatctttc    9780
tgttcccagt tgtgctggtt cttggagagc tgtgaagcca ctggaaaatg cctcagtggc    9840 acttatttt  ggttttttccc tttcttttttg tcttaaaaga gtttctcaac atgtttagtt    9900
ttgtgaaatc tttgagaatt aggattttat aacaaacaaa tctagtggtt aggagggctt    9960
tagaaagaca gactcatgaa tattatatcg ggaggaaaac ttagaaatct cctagttcca   10020
tgttttcttt attcagataa gagaagggaa agctctagag attcggtact tggctaagta   10080
attcatactg caaggctgtg ccagagccga gtccagaccc tggagatcct ggtgcgtcta   10140
ggaacattgc tttctgacc  caggagccct acaagtgtgt aaattcatct ctgtctgctg   10200
gattagacct ttcatcgta  gacagttcgg ttctttttaa gttgagaaat ttaaataacc   10260
ttttctggaa tttaaaagat ttacatgtct atttttaaatt cttagctttg gtggttcttt   10320
tcttcctcgc taaatgaaat ccttaaatat aaccatctca cctgttctgt tcatccttta   10380
agcaaaatcc aaaatgttta caatttttat aacacagact taatattagg ttgcttagac   10440
tttagaaagt cacattataa tatttttgat tcatgttttt acctgttccc tggaagtctc   10500
cttattttgc tttgcctctt gtaacaaagt taatttagtt agcaaagata gaaccagtta   10560
atgttgaact ccactcatta caagagtgtt tattacatag agaaatcaga gaactcaagc   10620
atttttttgg agttggaggt ttaaaagcct ctaaagaata aaagcttttt cagaaagcat   10680
acccatagac tataggtttc tttataaatc aagcctaaac aacgactgat tttgagtggt   10740
ccttgactgc tgagacataa gaaggctggg tgttcagggt acccgctggt tgggtgggag   10800 agggggatg  gtggtataca gcgtggtgtt aaaggaagtg gaaaatggtt ttatatgcat   10860
ttttggagct tgttctctct tttctgtagt tgcagcatgg ccagttagtt tggcaagata   10920
tgtagtctcc tctggggagc tgaatataga gccaagatgt ggccttttggg atatagataa   10980 tgcccttta  atgatatttg aaattaattc ctttagtgta atcctctggc aaagaaatta   11040
gaaaattgaa tttataaagc ttcattttgc ccagagattt tggagtagaa aagggctgta   11100
tatttgtgaa tagatgctta agtaggtgac ggaaataaaa tatcatttgt cctataccag   11160
aaagtctcag gaaccaaaat agcttggcag gttggaagat aatgttcact tcaaggcttt   11220
ctcctcaaca aattaaaact agaacagttg acataataga aagggatagt gtgtccttgg   11280
tactcttgtt tctgaactgc attattataa aatgtgtctg tcagtaaatc atatagagac   11340
tgtggtaccc tgttaaatag ctgtcaactc ttctatttc  aagttcctgt atgattctca   11400
aacaattcta aacctgtttg agaagtaata gtggtttcca tttttagcaaa agtgtgtgcc   11460 tttagcaata tttgtgtatt gaagcttcca gttcactttt ttgcgaagaa agcatttctt   11520
aaataatggg tctgatctga taattggaaa tgtatatact gtgctatttt ttggagagat   11580
```

```
tgcatgtcac atcagtaaga tctattagtg aagtatcatg ccatcatagt tttaatcctc    11640
tctagtcttg tacattgtat taaaaagttg aatgcactct agtcttaaca ttaacatctc    11700 ttatttaga aaaatgaaca gatgatatta tttggttaca aatttaaga tgactcttta     11760 acactgatct cagaaagtgg attttgataa caacatacag ttgtctctca cactggctgc    11820
actatccatt ggattgtggt ggacttttga tagatctaga agtggttttg gccttggagt    11880
aggaattgct ttcttggcaa ctgtggtcac tcagctgcta gtctataatg gtgtttatca    11940
gtaagtattc tttttggtgc ttttatccta aaataatgaa aagtgaattc agaattgaga    12000
ttttaaaatt gcattagcca ctttaatttt cagagtaact tatttccatt gtaattatct    12060
tagtactgtc attgtactta cttcctttgt gacttgttaa aaattttct gttattctag     12120 atatacatct ccagattttc tctatgttcg ttcttggtta ccatgtatat tttttgctgg    12180
aggcataaca atgggaaaca ttggtcgaca actggcaatg gtaagctcat gcttatttag    12240
tcacctttct gtttttgaga tgtaagataa attttctcca aagggcagtg gaataaatca    12300
cttggaagaa tttaatcaca agtgtattaa aaaatacaaa gaacctctgg atagaaaatc    12360
taaaatatgt tactgatagg tgagatgatt tatcctccaa tttttactaa ttattttact    12420
cctctataca gttctactcc ataaaaaagg aacagtttta aaagtgagaa gaggcactat    12480
ttataataat gttgctacca tagatataaa ttaggactat ttcagcaaat caagatgttt    12540
gatcacttta attaagaagg aaaaggacat tgctgataag cccagccata gatgtcaagt    12600
caaaaggagt agcattcaga tgccacagca ctttcatgaa taagtgctgt cacttttacc    12660
attttagcca cctgagagaa ttgagtggtt tacaatgcta gatttggtaa cctaacctcc    12720
cagttatcct aaatccattg gtttacttta tttgaatta tgggtataca tttgtatagc     12780
tgaaggaatg atgctaaagc tgaaactcca gtactttggc cacctcatgc aaagagttga    12840
ctcattggaa aagactctga tgctgggagg gattgggggc aagaggagaa ggggacgaca    12900
gaggatgaga tggctggatg gcatcaccga cttgatggac atgagtttga gtgaactccg    12960
ggagttggtg atggacaggg aggcctggcg tgctgcgatt catggggtcg caaagagtcg    13020
gacacgactg agcgactgat ctgatctgat ctgatctgat ttctaaacta ttgttttgat    13080
ttgaagcttt tgctaatata gtagatttt tcttttcaat tttaaagtta cttgaaaaaa     13140
tatctgaatt tatggtatca gtcctgtcct taagtgcgtg atgtttcctt tgcttgtatg    13200
ccttagtgag cccacaaaga agtatatttt gcctcctttt atattatcta aattatatgc    13260
tgttgtcatt tgcttgtaat gcagaaatct catttttttcc tgcttttggc tctgcctcta    13320
gaatgcggca tttctttttt cctatcataa tggtcattta atcctaatag ttgtgcaact    13380
ctcggattct ttgaggaata cagtgggcat atgctaataa actattacat ttagaccttt    13440
ttagtttata tggaaattgc tattcaaaat caacttactc tgttaacctt ttaacctttt    13500 aattttaca gtatgaatgt aaagttattg cagaaaaatc tcatcaagaa tgaagaaggc     13560
agaaatatat cttttgtaca gaaaagcaag atgaaaaagg catgcaaatg atagatagac    13620
caacaaaact tcggactata aaattgccag gatgcagttt ttccgttgat tggtgtgtgt    13680
gtgtatatat acacacacac atacacacat acatacacat atatatatac acacatacat    13740
atgttactgc aatctgtgat tgcttcatct gtaaatcaag tacaagcctt tatgtatttg    13800
acttaaataa ctgtaaaata tatatatgct atattaaaaa acatgttgat taatagatga    13860
catttttaaa ttaatttttt aggtataccg tatatcgtat cacagtgttg atgtgccaaa    13920
ataattctgt tactgtcatg cagactataa gagtgctttg aacaatttat aaagttgatg    13980
```

```
aaataaaatg tgaggaaagc caaaaaaaaa aaaagcaaat ggaaagctgg tatattctct     14040
ttcacttact gttgtgcctt tttattttc taattacagc agtgtgagtt atgggtgccc      14100
taatgtgtgg ttagtttcta ttttaatgtc gtctcgaggg tgtttaaata tatgatgaaa    14160
aagaacttcc acgggatatt tgcaaacctg aattactaaa gagagttcag agtaattttt    14220
tgttttgacc aattttactg gaggtgaaaa gtgacaagca ggagagttta tcagcattaa    14280
attgttttga gtctaaatct agaaattaaa agtagggacc actgaataac ttaactggaa    14340
taaatatgct ttagaaatac aaaaagacct tctgcagtgc cacagtgtta agtaatatta    14400
actgtcaatt acaatgtagt attctactac ttttgtacat ggaatgtata agaaatccca    14460
aacaggtcca agtgaaattt ctaatcctct tgggttctat aatctattgg attctataaa    14520
gtaaaccatt tgagctgggc tgcatcatat gatttatt                            14558
```

<210> SEQ ID NO 5
<211> LENGTH: 181134
<212> TYPE: DNA
<213> ORGANISM: Bos taurus
<220> FEATURE:
<223> OTHER INFORMATION: stearoyl-CoA-desaturase 5 (SCD5)
<221> NAME/KEY: modified_base
<222> LOCATION: (1)...(181134)
<223> OTHER INFORMATION: n = a, g, c or t

<400> SEQUENCE: 5

```
cttccatacc tgggcctgtc tccttctgct cactgcaggt gcagccacgg ctgtttcagg       60
cacagccagc tgccccttct ctgcgctcct gtgccatcag ggtgctctct gaggagctct      120
aaattatctg cctagggggg aatgagcaga caagattttt tcttaggttc atttgccttg     180
gaacgttctg cgtgattttt tttttttttcc tgaagcccca ttctcaaccg gggctgactt    240
caaggctaag atagtccaga agcctactgg ccagaggaga atttgccacg aacagctgca    300
aggctgaggg gccgcgcaag tgggccgggc ccgactggat actaaccggc cccttgatcc    360
tttatcatct gacaggcgct atctgagcac cttctgcgtg tctggctgca gttgttcaaa    420
taagaaccga gcgagcggct gcctccatcc cctccacaca ggcccccagag ccataggagc   480 cgggagacac aggaacttct gatcgtcatc ccagatctgg ccttaacttg tgtgcaattt    540
gggaatagga ctgcaaattc tccagcctgt agcttcaaag aggggggtaaa aagaagtctt   600 tttcaatagg gaaaggtatt tcggggaact ggagaaacca ccgcagcagc agcacaagtg    660
gtttggaggc tctgcgggct ccctgacctt gcagccacag cctcctcgac ccactccccc    720
gcgctccgcc cccggcggag gctgcccact gccctgcgga ctgccccgtc cggccccggg    780
gagcccgggc agccgaggcc aaggggggcgc ctttctcttt aagagcctca agggcgaccc    840
tgattggctg tagctatgca ggtctttctt ccccgctccc tccgagcagt ccctccccccg    900 ccgcgctctc agctctttcc acacccccctc ccctccccccg gcgccccctc cctccccgcg    960
cgctcgcccc ctcttcctcg ccgccgccga gttcttctcc ggcagccgag cgggtgatgc   1020
gccagcaaca gatgccgggc accaagattg gcatccttag gccacgctga acgcctgaag   1080
aagcgagaag gaagcagagc agggccggga aggcggggac aggaggtgcc ggagatcccc   1140
ctcacccaat cccctcaaaa aaaggcagaa gccgccgccc ccaccggaga gctccgctcc   1200
tcggagatcg ccggctcgct gccactgccg cgggcgccta ggtctcccca gccatgccag   1260
gcccggccgt ggacgcggag aagtccccct tccgcagcgc caaggaggag atccgtgcgg   1320
gggtaggggt cgagggctcg gagggcggcg gcggcggcgg cggccgggag aggcccggcg   1380
```

-continued

```
cgcgcgggca ccggcaggac atcgtctgga ggaacgtgtt cctgatgagc ctgctccact    1440
tggcggccgt gtactccctg gtgctcatcc ccaaagccca gccgctcact ctgctctggg    1500
gtgagtactc tgcccgcgcc ccctgcgcc ccgggcacc gaggcgcgag gcgcggcaag      1560
gccggcggcg ccggggcgcg cgagatcgcg ggtcgccgct ggctgcgggc cgtgcggagc    1620
ctccgcggct ctcggttcgc cttctctcct gctccccct ctcctccccc ccgcccccca    1680
cccccaggcc tgtagttgtc cggccttggg gacgggaagg tatttctatc caggtatttt    1740
caacttctgc ccctccgct gtctccttga gtaggcgcct ttggcgaccc ctggatggag     1800
agcgagaggg actcggggtc ctgcggcgcc agcgccgtgc gcagaggcgc gcgaaggggg    1860
atgctaagcc cgggctccag ggcggggaga ccaacgcggt gactgtatag cccctgcgcg    1920 tcccagggg gctgctatcg gccgcctttc cgcgtctcag tctcctccgt gggccacgga     1980
ccttgaggcc gagtgaagga ctagaaaggg agttgtagcg ggggttggag agaccaccgg    2040
caccggttca gcgttgattt tcgcgcagga gatggaagaa gccagttctc ttcctgcgcc    2100
tgtaaggccc ctgtccctgc cctctcgggg atctcttgtg cccagttgga gttttccggt    2160
cccagaagtt tctcggcgag ctctggccca gcacaaagct ccgaggtggc tgtgtagacc    2220
cttccaggcc tgtccccttc tgaccaggtg ccagtctgtc accgcacctg tagcgctccc    2280
tcgcgccacc cactttccta gcaaaaccac tcctgcagc atgggaggga acccgggtgc     2340
ccactccccc tccaaccccc ccccccccc acagctcctg gggccggggg gcttcagagc     2400
ctgccctgca tgactccagt tgctgactca gaaccacttc caaaccccct tctctagtaa    2460
ctggttttgg cctcagtcac tatagtggcc accttagccg ggacaaaaag gcgcctgccc    2520 ggggcttgc tatcctgggt tgagaactgg caaagtaatc caaaaagccc tttcaggtct     2580
cctgtccgaa atcggcaagg aacagggtag caggagaaac ataacctcct tttatttcca    2640
gaggggaaga ggaaggaaga aaatatgaag acctctttcg gcaaagcttc cgacttggca    2700
tagtgccagc tccaagtgcc ggggttcaga atggggccac tcggttttaa gctttcccctt   2760 gaaactctgc agtctctgct cttggaagca gacccttcca gaagatgggt gcctcttggg    2820
gagggtgtgt ggctgagcag agttgaggaa tgttgggagg ggcaggggtc tttgggaatc    2880
tgtgaagcct ttgaaagtcc cctgaaagct ttgagtaacc tctcccaacg tcagtacact    2940
tcctcaattc agtgttcttt tctccatctt ttttgttatg tattgatttc attctcctat    3000
cttctttctt cctttacctc tagatgatta gatcataaga tgctcagcca ttgcttccta    3060
gacacacttc ctccaccagc caaccaaagc tcttattgcc ctgtatcccc tagaagggat    3120
ccctctgcac ccctcctctc ccccatgccc ccaggggcag gactgtgcct ttggacttta    3180
gagccctcct ggcaccagga gattaggct tagtcttaat agctgcagtg tcagagagag     3240
ctcagggaga agtgagcact taaaatattg tcttacatgc ccggagctcc acaggcccac    3300
aggctccaca cgttacagcc acgcaccccc tggttttggc ctcccccag gagccacaag     3360 gacaaagcct cctctccagg ttcgccaagt cacctctgcc cttttccggc cactcatggt    3420
ggtggaggaa gaatctttgt tctgaaagac cttggccaga agatagcatc ctggcccag     3480 actcctctgg ctccctggag aagtcaacac actgcaggag tctgggatcc acgttatggg    3540
tgatgctgcc aggcccatcc ttctgcctcc ctgcagagtc ttctgcttta gctacgtttc    3600
atcagttcca ttcccagaat cttgattctc tccccacctg ggcttcattg cccttcccac    3660
ctctgctccc tccccccgca ccctcccccc aaaagagcag acaatggtgg atgttgtagc    3720
ttcaagatcc aaacttgtga cttagaaaca ttccaaataa gtgaatgtta tctaatggat    3780
```

```
atcttgtgag agaagaagtg agggagagag acagccaaga tcggtgtgct gatggctaag    3840
gtctcctgga ggactgttga tcaggattat ttttgttgaa accctggtg ccttgagcta    3900 cagatttctc cccactggat gccttttcca tcctcactcc cactggctct gcctagtgtt    3960
agggctgagc tcatgcacca gtgggttgtt catccacttc agggacctgg gttgtcaagg    4020
caataaggct tagccagccc atccattgct tgccaccctc caccccaggt atggttgccc    4080
tggaaacagg aggcatccat gcagcgtacc cagcaaagga tgtgttaggt gtgcagtgtg    4140
cggagagtaa tttgcttggc agtgaaatgt catccatgaa agatctcatc aagttgttca    4200
gtccaaacct cctccactgc ctcatccccc gcctttttat gactctcctt ggggccagag    4260
caagttgttt actcttctta tccttgcagt tttctgagtg ggcaggctgt cagaatggaa    4320
cgctcttggt gcccacaggt cctaagggat gagtttatga gtttcaagga cagaatgtga    4380
actccaactg gaggaaaaat cttcacctga aggttcaagc tcacaaatgg atgtgctctg    4440 aggattttg accaaagggg cagttagttc atgccctgac tccaagatg agtagaataa    4500 gggagtgagg agcagcagtc atgattcaag gccaaagtcc tagtgctttt tcccagcaag    4560 cttttgcccta tggctaggca ttctggccct tgatttccag aaacatgagg aacttttctg    4620 gtttccttg aaatgtcatt caagtcccct aaatatgcct tggtgacatc atgaccacct    4680
caatgagagg atcaggcatg tgaaacaagt catctgcccc gctcctttgc atcttgcagt    4740
tcttgttgtt cagttgctaa gtcgtgtcca attctttgcg accccatggn nnnnnnnnn    4800 nnnnnnnnnn nnnnnnnnnn nnnnnnnnnn nnnnnnnnnt gccatggacc cgcacttcac    4860
cagtatgtct tttattgttt tgtttctatg tggtagatat ctaatcccca tttcacagat    4920
gtgtaaaatt gaaggccaga gcctaaatgc ctcgggattt cacaaggaca gagctggggc    4980
cccaaaacca gctcagtcca gcccaagccc tctccctgg tgccagggtc gccagccctg    5040
actgcccatt gcagtcatct gggatcttta acatttgaga gatccatcaa ttcagttcag    5100
ttcagccact cagttgtgtc cgactctttg cgaccccatg aattgcagca tgccaggcct    5160
ccctgtccat caccaactcc tggaattcac tcaaactcat gtccattgag tcagtgatgc    5220
catgcagcca tcccatcctc tgtcgtcccc ttctcctcct gcccccaatc cctcccagca    5280
tcagggtctt ttccaatgag tcaactcttc acatgaggtg gccaaagtac tggagtttca    5340
gctttagcat cattccttcc aaagaacacc cagggctgat ctcctttaga gtggactggt    5400
tggatctcct tgcagtccaa gggactctca agagtcttct ccaacaccac agttcaaaag    5460
catcaattct tcggtgctca gctttcttca tagtccaact ctcacatcca tacatgacca    5520
cagaaaaaac catagccttg actagacgga cctttgttgg caaagtaatg tctctgcttt    5580
tcaatatgct ctgtaggttg gtcacaactt ccttccaag aagtaagcgt ctttttaattt    5640 catggctgca gtcactatct gcagtgattt tggagcccag aaaaataaag tctgatactg    5700 tttccctgt ttccccatct atttcccatg aagagatggg accagatgcc atgatcttcg    5760
ttttctgaat gttgagcttt aagccaactt tttcactctc ctctttcact ttcatcgaga    5820
gatccatagg gcccagtgaa tcagagatga gggcccacag agcagggatc tctctccaga    5880
ggggactgtg atgcacaacc ggggctgaga aaccactgcc ctgtaatgta cgtcccccct    5940
tagaggccat ctggtccctt ccctgaact tacaaatgga gaaacctaga cccagagtgc    6000
actgcactcc ctccaacccc cccacccgca ccccacgctg actcccacgg ggcttggtaa    6060
atgctcagcg gtttgggagc tggaaacagc aagctgtcct tcatgtggaa cccaggccgc    6120
ctgtactctt ctcctggcgg ctccctttga tggtgtgaga tgatccctga tcccctcact    6180
```

```
ggaggcttta atatccacgc actggactgg aaggcgggta tgcagcggga cccaggcagg    6240
agaactcaag cttccaccag agaagcaggg aggtgaggca gggggcagga atcagagggt    6300
gaaggctcct ggcatcaggg ccacatgtag cgggagaggc aggggtgggg cagagcctgc    6360
atgggagaaa acaaagcact tggctatctg ccttttggc tcaagtgttt tgaaggtcac     6420
tttggggctc tggccaacaa atgattgttt ctcttctcca gtctttccta gatttggcag    6480
atcagtggag aaaagtagac acagccatag atgaatcgag agatgcacac agagatacat    6540
atatacatat gagtaaataa tgcggacttc ctagtggtaa agaacccatc tgccaatgaa    6600
gcaaatgggt caggaagatc tgaaggagaa gagagtggct ccccagtcca gtattcttgc    6660
ctggagaatt acatggacag aggagcctgg caggctacag tccacggaat ggtgaagagt    6720
cagacacgac tgaagcgact tagcacgtat ccctggtggt ccagtagtta agaatccacc    6780
cgccaatgca ggggacacct gttcgatccc tggtctggga agatcataca tgtgaggagg    6840
caccgaaacc cgtgggctac aactactgcc cgcctaaagc ctgtgctctg cagtaagaga    6900
agccactgca atgagaagcc tgtgcaccgg caaccagaga gcagccctca ttcactgcaa    6960
ctagaggaag cctgcgttca gcaaggtgct cagcaaggac gacccgaggc agccaaaagt    7020
aagtaagtta acagtagaaa aggaatcttt ctctgggctt tatatcttta tccctaaaat    7080
ggagaaagtc tttaagtact aaagtaataa taagtaagta tatagcatta tggttaagat    7140
gaacctgggc tgaatccctg gtatatcacc tttcagtgtg actttatctc tagaccttgg    7200
tctcttcatc cataaaatgg gaacacagcc tgccctagag gctcgccgta aggactgaac    7260
gtagcagtga acctacagtg tgagccaggc ctggcaagca gcactggtaa gtgctactgc    7320
cccagttgtg aacgccagcc cactgcctct gaaactagcc cttcccggc taacccctg     7380 tgacgacact cacgctcttt atcactctga gctggagatt ctcaagagga tgagcaatct    7440
tgcctactcc ctttcctgag acctttagca aagactccag acactgttcg ttgtcacaaa    7500
ccacagctgg aagggtgtta ctggcatctg gtgggtagag gcggggatac tgctgagtag    7560
cctgcaatgc ctgcaacaaa gaaggaccgt gaccaaactg tcaggagtgc cgaggcagag    7620
agtcctgttc tgatttcttg ggacagtcct tgaaacctag tgtgactaca ctggccttgc    7680
ttcctcacac ctctgatttc atggggagtt atgggagtaa ctcatgtttc acgtatacac    7740
ataatataat gtaatgcaat ataggccaaa aagtttgttc aggttttctg taacatcgta    7800
tggaggaact cgaatgaact ttttggccga cccaatgtaa cataacatat gatgaacaag    7860
ctgaaaagaa agaactagga caaaagcca atagtatttt aggccattga ttcttgaacg    7920
ttaaagggcc aggggtcttg caaaatgcag atgcccagct ctactctcag agattcagta    7980
gatccgggga gagatccgga acttttgctt ctaacaagtc tgcaggtggc gctggtgctg    8040
ttggttcagg gtctgagtgt ttagcccacc caccagtgag tgtttggctg acccaccaga    8100
tgtgagagag aggggctaat aaagggctgg ccctctaggg ccactcacct catgagacgc    8160
tgtaacaaag agttgcaatt agaccttagg tcttccagta aaaggtttgg atttataaca    8220
tttgagattc caaggcaaat tcctcctaga tactatttga acacttgact cgaaatcaga    8280
acatttttac aaggtcacga gaactgtggg cttacaggca aagggcttct tttgactatt    8340
aaatcttcca aattctgtaa tattttaaaa aattgagttg atttacagtg ttgtcttagt    8400
aattccagca tacggcacaa taaccaacag tctttgtgat ccccgcctcc ttcctcttca    8460
ccaccttatc ctctgtggca catgggctgc aggcgtcttg aaggaagtgc ccacatcttc    8520
tagattcaac agaaagggaa cagaacagaa gggagaagat agatttcttg catttcacag    8580
```

```
gtactgccta ttttcctcca gcatccttcc tgccttcagt tagtttcact tagaccattc   8640
tgaagtcctg ggcaaagcct ccttttccta gttgatttac aaaatatatg acaagtagta   8700
taaaagtcat agcagatcac taacaaccag taatcttgcc tggaaaatcc tatgcatgga   8760
ggagcctggt aggctgcagt ccatggggtc gctaagagtc ggacacgact gagggacttc   8820
acttccactt ttcactttca tgcactggag aaggaaatgg caacccactc cagtgttctt   8880
gcctggagaa tcccagggac gggggagcct ggtgggctgc cgactatggg gtcgcacaga   8940
gtcggacatg actgaagtga cttagcagca gcagcagcag caactgcaga gtatagcata   9000
gcatgtttcc tctctcctgt tgcaccctgc tatctattca gtttagtcgt tcagttgtgt   9060
tcgactcttt gtgaccccat ggattgcagc atgccaggct ccctgtctca tcaccaactc   9120
ccagagcttg ctcaaactca gtccattga gttggtgatg ccatccaacc atctcatcct   9180
ctgttgtccc cttctcctac gctcaatctt tcccagtatc agggtctttt ctaatgagtc   9240
agttcttcac atcaggtggc caaaagattg gagtttcagc ttcagcatca gtccttccaa   9300
tgaatatttg gggttgattt cctttaggat tgtctggttt gatctccttg cagtccatgg   9360
gactctcaaa agtcttcacc aggatcacag tttgaaaaca tcagttctca gccttccatc   9420
ttgccccagg ccaaatgtgt ccattgctga agtagataca ggattctctg gtgctctttt   9480
ggtggctaga acccagccta tgggaggaag ctgagacatg gcagaggtgg ataaggcagt   9540
ctggcaggag cttgggtcag gagaggcagg gtttggaacc tgctggtcca ccagtcaaat   9600
tctgtccaat cctgtgagct gcccaaggat gagctatttt ctgtcagaca ctgggtagcc   9660
tgaatccaca ccttcgatgg tcctaacgtc tttgttgagt tgtgcttctt tttttctgtc   9720
aaatccctaa tattgttgag gagctccaag aatgcgtggc catggacttc tgtttcacct   9780
ccgggttttt tagggtgaaa gtgaaagtga aatcgctcag tcgtgtccga ctccttgcga   9840 cccctagac tgtagcctac catagactgt agcctacagg gttctccatc cacaggattt   9900
tccaggcaag agtactggag tgggttgcca tttccttctc caggggatct tcccaaccca   9960
gggatcgaac cagggtctcc cacattgcag gcagacactt taccctctga gccaccaggg   10020
aagcccacag ctcaaaagag aaacagctct caatgtgaat ccctgctctt ctacgtgttc   10080
accaactgca tagcctgatg ggacaaataa acatctccag acctcaactt tctcacctgt   10140
aaaatggata gatccgtact tcttgctcat gaggttgtga gaaataaatt cgataatagg   10200
tgtaaattac ttggcacagt agctggccct tggctgatgt ccataattg ttagctgctc   10260 tcattattcc tggtcctgat actgcctttg ttttctttag tagaaggaaa aaaggccctc   10320
ttgcagcaca atcagttcta caaagctggc atacaacgtg gcatcgttgc ctcttgcatg   10380
gaaaagattg ctttggtttg ggaaacaagg gttctttctc aaagtctcca aagagaaatg   10440
aacacaaata gccctgttcc tcctccctcc cccatcccct tctctttcat cctctcttcc   10500 tcccctttc ctctaaaaag tcactatttt gtaaataagt atcttttgt tcagctggac   10560 aactcacctg gtctctagtg ttttctttgg ggttttttga gcggagccag ttgcagtcgc   10620
tgttaaaaca gggcttaatc atttctctaa atgtcttagg ttctcagtgt tgaattttc   10680 ccgcatttgt cttcttgagt catcttttta aaaaacaaa actttaatgt tcaaactact   10740
aaaaaaactg aaaaacatca atgagacttt tcttaaagt ctgtaattcc cagcccattg   10800
ttgcaactct tccatttta ataccgggc aagcactaag ggccacgccc caggctgggt   10860
ggagtacaga gaaacccggg agaatggagc gtggcttcat agtctcaaca agtataaata   10920
taggttgaga ttaacattat taacttggtt cttttttct tctaaaactg gtcaaggtca   10980
```

```
ctgccaactg cactgtgatc ctaaaatgta aagtcctgca gagtaggaac cagggctgag    11040
atcccagcct tgcctcttgg ttcagcttca ggcaagtctc tttccagtgt gagagccttg    11100
ggctcctggt ctctgagctg gaagctcctt taagcatcag ggcaaatgtc aaagtggagc    11160
cgcagggtag agttctctct actgcttcta acccccaccg cggggcggc atcaggaaat     11220 tcacagggct tcagtgtctg tctgggacct ggagttcttg gggctccaat ataatgcaca    11280
cacaatgttt aaatccgaat aaaacatcat gacctttctt gtgtaacatt tagttctcat    11340
cttgtcctga cttgtgtatt gtagaaaatt ataatatttg ctttaaaaag ccggtgataa    11400
atttacacaa cggtgacaca atgtgaaagt gttagttgct cagttgtgtc tgactctttg    11460 tgacccatg gactgttgcc caccaggctc ctctgtccat gaaattctcc aggcaagaat     11520
actggtgtgg gtagccattc ccttcccca gggatcttcc caactcaggg gttgaacccc     11580
gggctcctgc attacaggca gattatttac catttgagcc accagaaatt ttctataaaa    11640
ggcaccatta tctttggccg gcattcttct gttgagcatc tattttgatg tcctgtcttc    11700
tccggtgtca gtctccccat ccctctgctg tgtcgtgacc cgttttgtg gaagtggcac     11760 catcctgggg ttgagagtat aggcgttgga gtctgagtgt ctggattcaa agcctagccc    11820
cccaggtaca gccttgggca gatcaatcgc cctctccagc ttcggcgtcc ccagttgccc    11880
agtgagaatg acagctcagc cagcgtcact tcgcagctgg agtgaaatga acaagtcag     11940 taaagaactt gaccccttgct acttcccttc actccttccc ttccttcagc tcctccttgg    12000
tggctaggac ttgttccagc cgccacacca ccccccaccc ccaaccctgg ttgtcagaaa    12060
gccctggtca cagataaagc atttggtttc tgactttgtt tcccctcgca atgggctggt    12120
ggccaccaca gcagggaccc attcttctcc cttgtaaatg cccgtggttt gttcactctg    12180
agtgtgagca agccatggga gagatcctca cagttgcaca tgcagtcatg tactcattca    12240
cccatgaatt cattcatttt ttttttcctt ttccatttca actgttgtca aaacatcaga    12300
atcacttgga tgtcctttac agtattcaga agcctgggcc cccacctgga cataatgaat    12360
tggaatctct aggagagagg ccctgactac tttattatta ttattttaag gcatttgggt    12420
gtttctgagg cacagctggt gtatttaact ccctgctcca tattcagtta cgcttattat    12480
cacccatgac ttgccaggca tctgcgccat cccttcctga cttcatggca cttaaggcca    12540
gttggggaga cagagaggtg agaaccacca aggcagcctt agctgcagag caccagcctg    12600
ggggagtcag ggagatgccc tagaggaggg gacttcacag ggggctcagt ggtaaagaac    12660
ccacctgcca atgcaggaga tgcaggttcg aaccctggag aaagaactgg caacccactg    12720
cgtaatactt gtctgggcaa tcccatggac agaggagcct ggtgggctac agtccatgga    12780
gttgcaaaag agctggacat gacttagcga ctaaacaaca agcaagagga ggaggtggct    12840
gaactgagcc tggctggaga cccggctga ggggttcggg tgagatggca ttgcagccac      12900
aggacagagg tccccagggg agagagaaga gctggagcag ggccagtcga aacctgaag     12960 attcagaggg gttgaaggtg atcggggccc agatccaggg cgggcagtca gtaggaccag    13020
cgggactggg aggagatcag gcttgcggag cggctgccct tcattctcta cttgcctctc    13080
acctctgctc acccatcaca catgccagtg gttctgagca cataatttct agaccagaca    13140
catgctggtg ggatgagtga gcccgaaggt tttcaggaaa gaccctaggg cagacacctt    13200
agagcgagtg tgccgtgggg ctgggtgcct cccctcagg ctggcagag ttcaggaaga      13260 gctaggaata atgtctcagc tgggccttg atctcacaga ctcggggta ttgtcccagg      13320 actggattac tagtgtgccc ccaagggtat aatagcgctg gcataccaga cccagggcac    13380
```

```
tcttgtgctc gtctgctctc tttcctcttt ttctcaaagg tacaggtgtg tgtggggttc      13440
atctgacctc ccttcctccc tggaacctga gtttaaacag ctagttctca ttatcctcct      13500
tcctaccatt tctgcagcct actgttaaaa gctgatgctt acatgctaaa tcctttcggt      13560
catattccat tttttgcatc cctatggact gtagcccacc aggcttctct gtccatggga      13620
ttctccaggc aagaatactg gagtgagatg cagtgctctc ctcagggga tcttcccaac       13680 ccagggatcc aacccgagtc tcttatgtcg cctgcattag cagacaggtt accgatagcg      13740
ccacctggga agccagttaa aggctgaagg gctctccaag tcccagcaga ctgtggtccg      13800
ccaaccagct gcggcagcat cacctgggag tgtgttagaa agactctcag acccatcccc      13860
gacctattga atcaatacct gccttttgat aaggcctccg ggtgacccgt ctgggttgaa      13920
cttagagaaa acactccgtc aagttgggcc attggctgac gggtcagaga actggacaa      13980 gtgggatttg tcaactcttt cgtcgtcctt ctaatggcct cttccccttg gtgtcccctc      14040
ctcccctcct gcctccttgt agcttatttt agaacatgtc gggatcctgc ttctcttgcc      14100
agcaaaaggc tgttgctaaa atctttcagc cggcagccgt gatgtttaat tcatgggcta      14160
gaaaattatt tttattttca tgagtagagc tggggaaaaa taacagggag gctcagtgca      14220
tggtcattgg gaactcagct tgtctcttta acagatgaac tggtaaaggt gaggaggcct      14280
ggggaaaggg ctgccttcca caaggatgc ttttggccgc aagtagcaca aaactctgga       14340
gaaggcaatg gcaaccctc cagtgttctt gcctggagaa tccctggacg gagaagcctg       14400
gtgggctgca gtccatgggg tcgcacagag tcggacacga ctgaagcgac ttagcagcag      14460
cagcagcaca aaactcagta tgccataaaa gacaaggaaa atttctaatt tcacagaaaa      14520
gtaatcctaa ggtagggcac ttgtcgaatg actcagaaat gacatcaaag agcagatttc      14580
atttctgccg tggtggtccc gtggaattta gttttctaca tggttgcaga atggctgcca      14640
gatttccagc agttacaacg atgtcctaca gaggaagaga gagactcccc cttcctgaag      14700
tttcaccaga gaaactctct cctggttgtc tcacagctgt tgtctgctca ggatcatcaa      14760
caggactggg tcccaagtcc cttgttaagc catcattgac aagggattca agctaatcag      14820
ggttggcctc tgagccacgt gtcacatgag ttgggggttta agaaccaaac aaaacccagg     14880
ctctggggga agggagaaaa cccaggctct gggggaaggg aggaaagggc ctggctgctg      14940
ggacagccag cacctctgct gcagggcctg ccttcactcc ctctcctgac cttccctcat      15000
cggtgtcacc tccatgccat gggaaggccc cggattcatg tttcacatgc tctttccctc      15060
tactccctac ccgtttggct tgtccccact cctgctgtca tcacagtgag ttgtcaatgt      15120
ctgccttttc catgaggctc tgagctcttt cctggcatat ctgcctccct aggccccaac      15180
acatggcctc tgcttcatag acatggtgct gggagggtgg atgaaggaag acttgaatga      15240
atgagtttga tgtctctgtg gcctttcttt tttaaaaatt ggaatacagt tgccttacaa      15300
ggttgttgtt catttctgct gtacaaggaa gtgaatcagc tacatgtatg catatatccc      15360
ctccctcttg gacctccttc ccaccccac ctcccctatc ccactcctct agctcagcgc       15420
ggagcacaga gttgaactcc ctgtgctgtt cagcaggttc ccactagctg tctgttgtac      15480
acatagcagt gtgtatatgt ccatcccaat ctcccaattc atcccaccct ctccttcccc      15540
tgggcttccc ttgtggctca gctggtaaag aatccagcca ggcaggagac ctggattcaa      15600
tccctggttt gggaagatcc cctggagaag ggaaaggcta cccactccag tattctggcc      15660
tggagaattc catggacagc gtagtccatg gggtcgcaaa gagtcggaca ggaccgagtg      15720
actttcactt tcactttctt ctccccccca caatgtccac atgtcctttt tctacgtcca      15780
```

```
ttcccgctct tcaagtaggt tcatctgtac cattttctta catttgtgtg gcctttattt    15840
ctaaggaaag ttttcgtttt gtcccagctt tagaagtgtt ttttttttcc tcctgtaaga    15900
gaactttcca tgtgattttg gaggatggac tggggagaga gaggtcattc ttagtgcccc    15960
aggattctgc atgctcctct gcatccatgt ctacccggga gtcacccgga cttcagtaag    16020
gagcttgcag aattctctgt cactcttctg gttttttat ggggcaaaac ggggctgggg    16080
aaggttgctc tgggcacaga gaattgttaa atgcttgtgg gaaaatgaga ttaagaagaa    16140
aaagatggag agtgagtggc ttagaatgtg ttcttcccta gcgctttcca tggtgacaca    16200
ctttccctag atcaatgagt ggttttcttg gctgatcctt gtcttccatc tttcaggtga    16260
cacagtgatg taagatgtca gtgatggcat cacagccaga tttctgtccc atgtcacctc    16320
acccagcaag tacttttat ctgcacaaac aagctagaaa tgaagcatcc attactttgg    16380
aggaaagggc taactctgtg atcagagaaa caaaacacta gcttttgtct ggagagtatg    16440
gcaaagtgca ttttaaagat gagacatggg ggaaatgtgt caagcaggtg gtaatgtagc    16500
tgctgtgtaa acctttgagt caaaggctgc atgcagggtg ccgagttaag gtcagtgctt    16560
aatcgtctct aggtggttgc tgggtggctt gttaggagca ggtcattact ttccatacac    16620
ataggtgaca ttgatgtggt cattaaggtc tttggggatt gtagaagtat cctgaggttg    16680
cctttgaaat gtggggaaaa aaaaatcaaa taccagtgga ctcagaaatg aagaggtata    16740
agaatagtgt ttagaactca ggtttaacat agtttcattt ctgtatctct gtctgttgta    16800
tgaataccat catgcactta caatttgact gtcatagttt gactttttta attttaaga    16860 agaatattta tttggctgtg ccaggtctta gttgtggcat gtgggatcta gttccctgac    16920
cagagatcaa acccaggccc ccctgcattg ggaacctgga gtcttaacca ctcgaccact    16980
gaggaagtcc ctgcctgtat tggttttagc ctggttcctt aaagagacaa tgattgtaaa    17040
tgcaacctgt gacctaaatg agcaaggcca tctcgcaaag catccttcac cttattatca    17100
agcaagcaat taatttccta tagtcttaag tcaggcacta tgttaagaaa aagagagaga    17160
gagagaaagc tagcctctca atcagttaag tcactcagtc gtgtctgact ctgcgacccc    17220
atggactgca gcacaccagg cttccctgtc tatcaccaag tcccggagcc tactcaaact    17280
catgtccatc gcgtcagtga tgccatccaa ccatctcatc ctctgtcatc cccttctcct    17340
cccgccttca gtctttcccg gcatcagggt cttttccaag gagttggttc ttcgttatca    17400
ggtggccaaa gtattggagt ttcagtttca gcatcagtcc ttccaatgaa tattcaggac    17460
tgattttctt taggatggac tggttggatc tccttgcagt ccaagagact ctcaagagtc    17520
ttctccaaca ccacagttca aaagcatcaa ttcttcggct ctcagccttc ttcacagtcc    17580
aactctcaca tccatacatg actattggaa aaaccatagc tttgactaga tggacctttg    17640
ttggtaaagt aatgtctctg cttttttaata tgctgtttag attggttata gcttttcttc    17700
caaggagcaa gtgtctttta atttgatggc tgcaggcacc atctgcagtg attttggagc    17760
ccccccaaaa taaagtctct cactgttttcc attgtttccc catctatttg catgaagtaa    17820
tgggaccgga tgccatgatc ttagtttttct gaatgttaag ttttaagcca acttttttcac    17880 tctcctcttt cattttcatc aagaggctct ttagttcttc gctttctgcc ataagggtgg    17940
tatcatctgc gtatctgagg ttattgatat ttctccagga aatctgtatt ctagcttgtg    18000
cttcatccag cctggcattt tgcatgatgt actctgcaca taagttaaat aagcagggtg    18060
acaatataca gccttgatgt attccttttcc cgatttggaa ccagtctgtt gtttcatgtc    18120
cagttggtct ctaccctcct tttataactc agaggaacag ctgtgatttt ccctaagtag    18180
```

```
tatatacaat ttaatgtaaa agttccatgc atgaaattag aaatgaatcc ctaaatgtaa   18240
ctgttccctg gagtagttaa tttactcttc taataaatat gttcataaga agcttttaca   18300
gatggttacg atgaagatcg ttcatattcc cagcctgtga gtccctggcg tgtccccaaa   18360
agcaagtagt tttgccctag agtctctata agcaaaggaa gatatttatt agcaagtgtg   18420 aataatacccc acatctgtcc ccctcccatc acccaccccc aaacccattg tgtttggctc   18480
cctggctctt gacaagtgga caagtattag catatttgag ctctactgga attactctag   18540
actctctcga ctctaatgtg gagctctggg gagatctgtc actacccctc tgagtataga   18600
ctggatatga gcctaaactt agccgagctc ccacgagggt tgggataaac cacagttatt   18660
agtgctaata ttccttcatg cacggagctg gtgttcagtc agcatgtgcc cagtggttaa   18720
aatcagtcaa cagcagtgcc ttccctggta ctcctgcaat tcccagcaat ccaagaacca   18780
gagcggcaaa gcttaaatct gaaactaaat ctgttctgat tggttttgat tgggtggtgc   18840
ccttgtgggt tgttaatttc ttttttaatt gaagtacagt tgatatgcta tattgtgtta   18900
gtttcaagtg ttatagcaaa gtgatttgga gatacataat acatatatat gtatatattc   18960
ttttttctgt tctttttctat tgcaagttat tatgatattg aatatagttc cctatgcttt   19020
attcaaatat ttttatgtca tctctgcatg tgcattttct tgttatcata tgatccgaat   19080
aatcgttact ttatatccttt gtctaattga atgagaactc taaaaaaaaa aaaaatcagt   19140
tgatcattct cgctgaaatt tatattttaa accgtgtaag gaaaggtact agtacccaat   19200
taaaattctg gggttgaaag taactcacct ttcctaataa aaacttcttt tgtgatagaa   19260
gcagtgtgta tctaaaaggt gattttttatt ttctaattta taattgcctt taggtaaggt   19320
ttcccccaga gagatttgat actaatttta ttatcagaaa aaaatgacat tgtaaaaata   19380
aggttgtaaa ggtgtatctc taggtgtcag gagagggag tgcagaactg gaggaccttg   19440
ccgctcatcc aggtggtact cctagctcac aggtcattgc tcatgacata gtagatggta   19500
tctgggcacc cagcagccca ggattcctgc cactgaaacc atacctgagg ctctgccggg   19560
gtccagcccc ggtggatcca gggaattcga agcggggacg gcgtcggcga ggatcaggaa   19620
acaactgctt aattaaacgt taattaagga tataagagt aatagaatga ggatagctca   19680
gtgaggaaat tcagtggaga aaagaggctg aaataaggat agctcagtga ggaaattcag   19740
tgtagaaaag aggctgaata attcagccag aaggtaagag aaagaacgac atggtgagac   19800
caagtttcat taaacaaggc ccgcacttta ttttccaaag tagtttttat accttaagtt   19860
atgcatagag gataatgggg gaaggggtag agtcatgcag taagccaggc tttcttcctg   19920
caaacttatc atatgcaaaa gtttaggtga tttgcatcat cttctggccc ggaggccttt   19980
ttctctaaag gtgattattc taaagtcagg cgccagcctc caaaaagcat tagataaagt   20040
tgcattccta cagagcaaag gtgtggtggg ctataacaag aaaaagaatt aactcaaggg   20100
tcccaggtta caaacattaa agctactatt tacaccaatt atattaatca atacactgcc   20160
agggacacag caggtaaggg atatggagac ttagcagcaa acattggccc aacaagtgaa   20220
aatcccttca ccaatacaat ttctaatcaa tcttttaact gctcaaagga atctgtattt   20280
agacagttta gaacatctca tgcctctcat agtttggagg ctctgagcaa tcacatgtgg   20340
ccggaaaaac ctattcaggc aggctagagg acttccaagg gagtttgtag gttgaaacac   20400
tgtcacaccc aggaattatt aactggagct gtaagctctt ttttcagaga gaggtagtgg   20460
gggacagccc cccgtaaagt cagaggtgta ggtgaaagca caaagcagaa agtaggcaga   20520
ctctggtttt gggggtagat tgctcgagaa tttccaggga gactcctgag gcttgatccc   20580
```

```
gcctttgcgt atgccaagcc tccttcctca tgacctttgc caggggcgga gctcgctccc   20640
cgcaaggctc ggtacgggga actgtcttat tgatgcaaaa ttccaaacat acacaaaagt   20700
aaacagaatg cagtttctgt attcttccac agcccctgct cacctgggga tttgttttc    20760 cttgtagctt tttacttaga tatataattt cagacacaca gaaccagtgt taagttccct   20820
gttagtacag ggaactccca tatactctag gcagacttat cccactggct ttatcatatt   20880
ctctatgcat atgtgcacac atatgtgtgt gtgctatttt tttctgagcc atttgagagt   20940
aaatcagagc tatctgtcct tttatctcaa aacacttcag tatatatttc ctaacagtaa   21000
gaatacaacc aaagggaatt ttctggtggt tcaatggttc agttcagttc agttcagtta   21060
gtcgctcagt tgtgtctgac tctttgcaac cccatgaatc gcagcacgcc aggcctccct   21120
gtccatcacc aactcccgga gttcactcag actcaagtcc atcgagtcag tgatgccatc   21180
cagccatctc atcctctgtc ttccccttct cctcctgccc ccaatccctc ccagcatcag   21240
aatcttttcc aatgagtcaa ctctttgcat gaggtggcca aagtactgga gtttcagctt   21300
tagcatcatt ccttccaaag aaatcccagg gctgatctcc ttcagaatgg actggttgga   21360
tctccttgca gtccaaggga ctctcaagag tcttctccaa caccacagtt caaaagcatc   21420
aattcttcgg cactcagcct tcttcacagt ccaaatctca catccataca tgaccacagg   21480
aaaaaccata gccttgacta gatgaatctt tgttggcaaa gtaatgtctc tgcttttgaa   21540
tatgctatct aggttggtca taactttcct tccaaggagt aagcgtcttt taatttcatg   21600
gctgcagtca ccatctgcag tgattttgga gcccaacact gtttccactg tttctccatc   21660
tatttcccat gaagtgatgg gactggatgc catgatcttc gttttctgaa tgtggagctt   21720
taagccaact ttttcactct ccactttcac tttcatcaag aggcttttta gttcctcttc   21780
actttctgcc ataagggtgg tgtcatctgc atatctgagg ttattgatat ttctcccggc   21840
aatcttgatt ccagcttgta tttcttccag tccagcgttt ctcatgatgt actctgcata   21900
gaagttaaat aagcagggtg acaatataca gccttgatgt actccttttc ccatttggaa   21960
ccagtctgtt gttccatgtc cagttctaac tgttacttcc tgaccggcat acagatttct   22020
caagaggcag gtcaggtgtt ctggtattcc catctctttc agaattttcc acagtttatt   22080
gtgatccaca cagtcaaagg ctttggcata gtcaataaag cagaaataga tgttttctg    22140 gaactctctt gcttttcca tgatctagca gatgttggca atttgatctc tggttcctct    22200
gccttttcta aaaccagctt gaacatcagg aagttcacag ttcacatatt gctgaagcct   22260
ggcttggaga attttgagca ttactttact agcatgtgag atgagtgcaa ttgtgcagta   22320
gtttgagcat tctttggcat tgcctttctt tgggattgga atgaaaactg acttttcca    22380 gtcctgtggc cactgctgag ttttccaaat ttgctggcat attgagtgca gcactttcac   22440
agcatcatct ttcaggattt gaaatagctc aactggaatt ccatcacctc cactagcttt   22500
gttcgtagtg atgctttcta aggcccactt gacttcatat tccaggatgt ctggctctag   22560
atgagtgatc atatcatcgt gattatctgg gtcatgaaga tctttttgt acagttttc     22620 tgtgtattct tgccatctct tcttgatatc ttctgcttct gttaggtcca taccatttct   22680
gtcctttatc gagcccatct ttgcatgaaa tgttcccttg ttatctctaa ttttcttgaa   22740
gagatctcta gtcttttccca ttctgttgtt ttcctctatt tctttgcatt gatcgctgaa   22800
gaaggctttc ttatctcttc ttgctattct ttggaactct gcattcagat gcttatatct   22860
ttcctttctt cctttgcttt tcgcttctct tcttttcaca gctatttgta aggccgcccc   22920
agacagccat tttgcttttt tgcatttctt ttccatgggg atggtcttga tccctgtctc   22980
```

```
ctgtacaatg tcacgaacct cattccatag ttcatcaggc actctatcag atctaggccc    23040
ttaaatctat ttctcacttc cactgtataa tcataaggga tttgatttag gttatacctg    23100
aatggtctag tggttttccc tactttcttc aatttaagaa atggttgctg ctgctgctgt    23160
tgctgctgct gctaaatcgc ttcagtcgtg tccgactctg tgcgacccca tggactgcag    23220
cctaccaggc ttttctgtcc atgggattct ccaggcaaga acactggagt gggttgccat    23280
ttccttctcc aatgcatgaa agtggaaagt gaaagtgaag gctccacatt ttcactgcca    23340
gaggcaagtg tggggatatg agatcccaca agcagggagg ctaaaaataa ataaataaaa    23400
ataaaatatt ttaaaaaagc atgcaaccac tgtacagtgt tcaaaaccag gaatttaact    23460
ttgatattat ctaatccagg cttccctgat ggcttagtgg gcagagaatc aatctgccta    23520
caatgcaaaa gacacagggc gtgcaggttt gactctgggt ggggaagatc ccctggacga    23580
aaggatagca acccactcag tattcttgcc tggagaatcc caccggcaga ggagcctgct    23640
gggctacagt ccatagggtt gcgaagagtc ggacatgact gaatcgactt aagacacata    23700
ggcattgtgt tggggtaatt ctggctacac tgtccacata gaaaacctcg aggaacagct    23760
tttccccaac tgcccccagc tctttgcgga aaaacagctt tgaggggcag ttttcagaag    23820
caagaaaggg tagaacctga gaagccagca caagtaatga gcgaagcagt ggtccccagg    23880
gtagtctgtg gactgttacg gggctcatct gagttactcc tcccggagct gcccggactc    23940
tgcattttaa caggtgccgt gggtggctct tcaagcctgt gggttggagg tgctctgacc    24000 tgggggggcag gtgcctggg agtgatgcag tgtccctggc agttttacat cacgtcccca    24060
ccgacctgtc ctgtctcaga aaagatgcag gactgtcact ttgcctgaaa tcccactggc    24120
cccagatgcc ttcgggttga taaaaggcag cttcggggga atggaaagag ctgcagaggt    24180
cctccacaca gggctgatcg cgaggggctg gttgtctcgc tacagagagg acgttaaagc    24240
agattgagaa ccgctccccg ccaccactgc cacgccccgg ggatgtggtc ctggaatgct    24300
ttgcgtgtgg agtgagcttg ttttctgggg gtaggggggtg ggggcagaga tgcttggctc    24360
atccctgagt ctgtggcggg gaagctgttc agaagaggtg aaaaaaaaaa aaaaaaaag    24420 ctcaggagaa aacctcaaac aaatagccct aggcagaaac ccccaccttc tcggaagagg    24480
gctctgaaac catttcttaa gacagcgtta aggactgtta ggtgccgcgt ccatctgcgc    24540
agcctcaggg cctcccctcc cccagcttgc cctgagggaa cgaccagccc cagtagagtc    24600
gcggtggcat cattattagc gctcccagga ccagacatgc gctttggtgc tggaaatccg    24660
ctatacagat gtgagttcat tcagtaaatg tgtcttttct aaatatggag gtcgatggag    24720
ccctgctctc tgggcccttt catctgtgag ggtgggtgac tttccagaca tcttcatttg    24780
aggaggagca ggtaggctgc actccatgtg gtcacagagt ctgacacgac tgagcgactt    24840
cactttcact tttcactttc atgcattgga gaaggaaatg gcaacacact ccagtattct    24900
tgcctggaga atcccaggga tggaggagcc tggtgggctg ccatctacag ggtcacacag    24960
agtcggacac ggctgaagcg atgcagcagc agcagcagca gatactgctt ggatcaagca    25020
gacggggatg cagtgcagct ctgcctggga caggacacct ctagggacat cctggaccca    25080
ggctccttgg ccacctgaga tataagggcc cttggaaatg tttctgactc atcaacagat    25140
gacaaccatt gggaagactc tctaaatcag gggtccccaa cccccatgtt aggaaccagc    25200
cccacagcag gaagtgagtg gcggacaagc aagagaagct ttgtctgtat ttacagctgc    25260
tccccatcag ttacattacc acctgagctc cgcctcctgt cagatcagtg gtggtgttag    25320
attctcatag aagctcaaac cctactgtga actgccaagg cgagggatct agattgggtg    25380
```

```
ctccttatga ggatctaatg cttgatgatc tgattctgct ttatggtgag ttgtataatt   25440
atttcattat atgtgtgtat gtgttagttg ctcattcgtg tctgactgtt tgtgaccccc   25500
tggactgtaa cccaccaggc tcttctgtcc atgggatttc ccaggcaagt atactggata   25560
ctggaggggg ttgccatttc cttctccagg ggatcttccc gatccaggga tggaattcag   25620
gtctcttaca ttgcaggcag attctttacc atctgagcca ccaggaaagc ctaccacaag   25680
gtaataataa tgaaataaat aaataaattc cctggtggtc cagtggttag aactctgagc   25740
tcccagtgca ggggtttgat ccttggtcgg ggaactgaga tcccacaagc cacacagcat   25800
ggccagataa acacacaata aataataaat aaataataat aaatgtaatc cccccacacc   25860
gtgtccatgg aaaaattgtc ttccatgaaa ccagtccctg gtgccaaaaa ggttgggaac   25920
cactgctcta gatgttcact gtgtatccag ggggaggcag tgggttaatc taacctgcat   25980
cctgtcagcg tggccatgtg acggaggtga ccaccctcac ctaggacagg aatccacgcg   26040
gctgcttcag tccccctgc cgaggaacct tccctccgt tctcctggca agttgctgct    26100
ctctccacgt cctttcctt ttagcaccc gtgcgtctca ggctgcagcc ggcacctgtg    26160
tagacagccg cctgtgtaga cagctgggct ggatttctca cagtgatgtg tgtgaagagg   26220
tggccaagag ccttctaaac ccagccaggc ctggagtctt cccggagaga gagaaatgca   26280
aaaccctgaa agcagagctc ctgttggccc tgtgccagg cagccgggcg tgtgggagtg    26340
gcccccggag cggtagacag acaagctggc ttcactaggc tccctccacc ccgaggctgc   26400
caggtgcttc tttagtctaa aggttggagg caagactttg gactcagata aattttttgct  26460
ggttagcaaa cttccaagtc tctccctggt cagagccatt cctaatggtc attaattggg   26520
tttatgacaa aaaatgcttt aggaaattcc ttggtgatcc agtggttaga actctgaact   26580
cctaatgcag gggtttgatc cttggttgag gaactaagat cccacaagcc acacagcatg   26640
gccagataaa cacgcaaact gataaacaca aataaaaatg tgctcctctg agcttatttt   26700
tttaaaaaaa gcttaaagta ttttaaagtg taaaagagtt tcccctgcac catggtgatg   26760
ttgctgaata agcagattgg ttttttgatgt gtgctcgggt tctaggaaaa agtgagggag   26820
cgcttttggg atgcgctttt ccatcttctt ggagacagag aggtggaaag atttagatgt   26880
ctaattaaat tctgtttcac acacatttgt gaacatgtgc ctgagattcc caggtggcac   26940
tggtgacaaa gagctcgtct gtcagtgcag gagatataag agacatgagt tccatccctg   27000
ggtgggaaag attccccgga ggagggcatg gcaacccact ccagtattct tgcctggaga   27060
atcccatgga cagaggattg gtaggctaca gtccataggg ttgcaaagag ttggacacga   27120
ctgaagtgac ttagcaggag caccagccta gtgtgggcca gctgctggga atacatagat   27180
aagcaagctg tcattcctgc ccacaagatg ctcaaaatct agaaggggaa acagactgag   27240
gacaattgta attcagtgtg ataaactcca ggacagaagt gggcctgagg tatgcagatg   27300
gccggaggag gtgggcatgg tagtgctttt aatccacata atagtaatcc ttcagggcgt   27360
tcgtatcttc actgcagttc tgaacaatag caaaactttg caaacaaaat tatttcacca   27420
ctaaataata gtgggaaagt gtaacccatg aagccatttg gtggcaaagt ctgacctaaa   27480
ctatttttcc tttacagtct gaatagtcat atggatgtac ttagggcttc ccaggcggtg   27540
cagtgataaa gaatctgcct gccaagcaga tgtgggttcg atccctgggt tgggaagatc   27600
ccctagagga ggaaatggca acccactcca gtatttttgc ctggaaaatt ccatggcggg   27660
ctacacagtc catggggcca cagagagtca gacatgactg agcatacaca ctcacctttg   27720
atgtgtctga tggtggaccc actgtgggta ttactgtaat ggataggcac tgtattacct   27780
```

```
ttctcagatc tgaacaattc tgaatcttga agcacagcaa accattgggt tttgatgagg    27840
gcctggggac ttgtcctggc atcgtctgca ttttgcatct gagaaggcgg aatgcagggc    27900
agactcattt gcctgagatc cagagctgta agggacagtc agggctggcg ggaatgtcct    27960
tctgattccc ggaccctgct gggtaacccc aggtggcact accttgagag gctccgactt    28020
acactgcagt ggttttgtca ctggactcct gggtgactct ggagtggtga cggattaagg    28080
tggcattgcc catggatgtg ctcaggcagc tgtgatgggg atgtgagtat cagtttcccc    28140
ccattggtct gggctcggcc acctcactct ggtggtagtc aggtcctgtt cgacgaggag    28200
tgggttttct atgcttctct gcccacaaga cctgctgttg ccctgtccaa aagctgccca    28260
cttccccacc ctgggttctt tctcactgct cctttccgcc gttcgtctca cattttgttc    28320
ccatcactgt cttccggtct gttacccttc aggtttcttc gaccagcggg aaagatgtac    28380
ttgcaaataa ttacggagtt ttgtaggtca accccaggat cagctttgtg ttcagacagg    28440
gcgtagccaa tggtgaggag tggttttagg gacgcaggac aggcctgaaa cagccctgaa    28500
atcaccttcc ccagctctcc tacccactga agcaaggatt ctggactgag actgcatgct    28560
tcaggggttt catgagcccc tgaaataggt tttgtgtgag ttggcatttt tcttctattg    28620
gattctcagc ggagcctgtg actttaaaaa ggttaagtgc tgctggactg gaaagagcct    28680
cattaaacat gtcagtgttt cctaaaagga taaacagtaa atgagtgttc atttatatac    28740
tctcatccat tatcgcctcc tgtatctata gtcaatatga ccactttcat gctttattta    28800
gtaggcaggg taattaagct ttgataggct gaagggcggg ggctttccag gtggtgctag    28860
tggtaaagaa gcctcctgcc aatgcaggag atataagaga ggtgggttcg atccctaaat    28920
agggaagatc tcctggagga aggcacagca actgactctg gtattcttgc ctggagaatc    28980
catcggacag aggagcccat agggttgcac agagtcagac gtgactgaag tgaattagca    29040
ctagcacgtg ctgaagggaa aacctgatcg cttctggatt ccataggtct ttatcaggca    29100
ggtcttcata gaacacacca gaccccctgc caaatgggct tccctagtgg ctcagagggt    29160
aaagaatctg cctgccatgc gggagaccta ggttcagtcc ctgggttggg aagatcgcct    29220
ggggaaggga atggcagtcc actccagtat tcttgtctgg agaattctat ggacagagga    29280
gcctggtggg ctacagtata tggggtcaaa gagagttgga cacgactaag cgagtaacac    29340
tttcactttg tggagcaccc catctctccc accctaccg ccatgaggag tccgcttgca    29400
ttgtggcaca tgccaagaac aaagaacaca gtgtgttttt catcatctta tttcattcac    29460
agttttgcca ggtcttctca ttatgaggga agcagcgatg gtccctccag gggcctttcc    29520
ttgccgctgc tttgctgttg tccagttgct cagttgtgtc caactctgcg accccatgga    29580
ggaagagtcg gaaggaaggc ttctctgtcc ttccaccatct tccggagttt gcgcaaactc    29640
atgttcatca agtcaatgat gccatccaac catcctctgt cgtcccttc tcctcctgcc    29700
ttcagtcttt cccagcatca ggatcttttc caatgagttg gcccttcgca tcaggtgacc    29760
caagtattgg agcttcagct tcagcatcag tccttccaat gaatattcag gattaaagtc    29820
tctgcttatc tctgcttatt gaaacactc tggcatcatc atcgtgaaac tcataataat    29880
tattgtacaa aagccctgta ttttcattgt acactcagtc ctgtatttca ttgtacactc    29940
agtcctgtaa atcatgtagc tggtcctgat actgggaaag tttcttggtc accttctccc    30000
ttccttccct gtccccagcc tcagggcttc ttgcagggcc aggactgcac accatcacaa    30060
caaagggtat gttcccagaa cttccctggt ggtccagcag ttaagactct gcacttccag    30120
tgcggaagcc acaggttcga ttcctggtta gggaactaag attccccata tagcatagta    30180
```

```
tggcaaagtt aaaaaatgaa tttttaaaaa tgtcccttttt tggtgatggc agagtattta   30240
gccagacttg gggcccttct acggcattgc gttctcaccc tggtcgtaca ccatgaagcg   30300
tgaagaggcc actgcccagg ataacgttca tggtgtgtgt ccttggcgcc ctctgatatc   30360
acaagggatg tttcaggatt gtttcccaga gaactgccaa gaccatgggc cttggccctg   30420
aggacttact ttcttatcac agaacttgtc ttggttgcac tggataaata gaataatgat   30480
gccgcttgac aggcactttg ctctgtttgg caggaatcca cattccagga gcaggaaggg   30540
agagggctgt gaggaaaaga aacttgggat gcttggagct tcccgttccg atagcgtgac   30600
cttggacaag caccagagat tctccccatc ccagttcttc gtctataagg ttactgactc   30660
caaagtgact tcgtgaggct ggttggttaa ggggctctga gaggggccag gactgtggct   30720
ggcgtgtagg gccaccagct cccctaccca tccaacaggt ctctggccag aacaaatggc   30780
cacagagtct gcagatgagt gtgggcacag tctctgagga ccagcctcat tcagtgtggc   30840
tgacctgatg tgcttgtccc cctgctcccc tttacctgcc ctcagcacac ctacacccac   30900 accccacac ctgtggaggt gctttcctct gcaggaccgg gagctgctga tctgagcttc   30960
cccagcccca gcctgcccag aagccttcca gcctgaagca gatatctgag gaagactcgg   31020
gatggacagg ggagggaaac cgcgagggag gaaggagacc cttgtggtcc aatgaatggg   31080
ggatgactgg agactcatct ccatagactc atccccacca gcacttgctg catctttccc   31140
agcagctggt tcatgggcac tgttgggaga ggcagaagcg aaggctagta tgtcgtctcc   31200
cccacccacc cggctctggc cgagcccggg gggctaatca gccgtgcaga ggcaggctgt   31260
acaagggagg gggtgcctag aggatctgga atgtgcccaa ggagatatcc ctgctgcagg   31320
gagtggaccg tggagagcct ggggcagcca ggcctggctg gggcagttag tacatctctg   31380
aagctctcct ggtggttgag tggccagtgc atctcttctc ccagctgata ccctcgcttt   31440
taaggggcat cctgggagga cagggtgggt ggaacagtga gcagggttgg agagacgcag   31500
aaggggaaga cttcggatct ggttaacagc tttcttcaag caacacagtc ctttcaccaa   31560
ataggaggag caaagagtgg gagtggggtg gggctggaga cccgaggctt ctcatttttct   31620 ctctgaagaa tcttatttta catctttgtt gttgttttag cacatattta ctttattatt   31680
tatttatgtt taaaattaat ttttcttgga gcatagttgc tttgcaacgt tacgctggtt   31740 tcttttgttgt tcagtcgcta agtcacgtgc agcttttttgc gacgccatgg actgcagcat   31800
gccaggcttc cctgtccttc atcatctcct tgagcttact caaattcatg tccattgagt   31860
tggttatgcc atccagcctt ctcgttctct gctgtcccct tcttctcctg ccttcaatct   31920
ttcccagcat caaggtcttt tctaattagt caacttttttg catcaggtgg ccaaagtatt   31980
agagctttgg cttttagcatc agtcctttttt atgaatagtc agggttgatt tccttttagga   32040 ttgactggtt tgatcttgct gtccaaggga ctctcaagag tattctccaa tgcctcagtt   32100
agaaagcatc agttcttcag tgctcagcct gctctaaggt tcaaccctca cttccgtaca   32160
tgacaactgg aaaaaccata gctttgacta gctggacctt tgttggcaaa gtgatgtctc   32220 tgcttttttaa tactctgtct tggttagtca tagcttttct tccaaggagc aggggtcttt   32280
taatttcgtg gctgcagtca ccatcctcag tgattctgga gcccaagaaa ataaaagtat   32340
ctcactgttt ccactgtttc cccatctatt tgccatgaag tgaccggact ggatgccatg   32400
atctttgttt tttgaatgtt gaattttaag ccagcttttt cattctcctc tttcaccttc   32460
accaagaggc tctttagttc ctctttgctt tctgccacaa gggtggtatt atctgcatat   32520
ctgaggttat tgatatctct cccagcaatc ttgattccag cttgtgcttc attcagtgtt   32580
```

```
gttagtttct gctgtacagc aaagtgaatt ggccatacgt gtacgtatat cccctctctt   32640
ttggatttcc ttcccattta ggtcaccaca gaacactgag tagggttccc ttattttata   32700
tcttataaat acttattcct tgtagacagc ctaggaaaat gcaggcatgc caaagtaaaa   32760
aaaatatctc cccatctgag agatgccatt tccttctcta ggggatcttc cagacccagg   32820
gatcgaactc gtgtctcctg catttcaggc agattcttta ccatcggagc caccatggaa   32880
gcccacattg ctaacatttg gggctatgtc cttctggaca ttttttctcta tgcataaacg   32940
aaatttcact ctctgcgttt acactacagt gctgttttgt tatcagcttt tgtcccttgt   33000
tgccacatca gagacttatt tcatgcccat agatgtggat cgtggaattt ttaaaatggc   33060
agtggggttt tgcaaagttt gggtgggctt attccctct tgttggaaat ttaggtggtc    33120
cttttcctgc tcttgttact catgtcaaca gcactgtgtc ctggtagctt catcttcata   33180
tgtgtcctta attgtttcct cagaagatat tttgataagc tttccataat atatatttca   33240
ttctaaactt attttttttt aaattgaagt acaattgatt tgtaatacag tgttagtttc   33300
agatgtaccg cagagtgatt cacatatata tatgtatgta tattttcaga ttcttttcca   33360
ctataggtta ttacaaggca ttgaatatag ttccctgtgc tatacaacaa atctttgttg   33420
tttatctact ttatatatag tagtttgtat atgttcatcc catattccta atttatccct   33480
cccctctcc ataggataca tttctgtggg cattttaaa gctttagatg agtggttctc     33540
cagctccctg gcaaggggca tttggcaatg tatagagact atgcaggaga cccgagttgg   33600
atccccaggt caggaagatc cctggagggg agcttggcag cccactccag tgttctttcc   33660
tggagaattc catggacaga ggagcctgat gggctgtagt ccatggggtc tcaaaagagt   33720
cagacatgac tgagtgacca acacttgcac tttcagagac acttttgtct gtcacagcta   33780
gaggtgaggt tgctgccagg atctagtggt aaggaagcat gatgctgcta aacatgcagc   33840
aattacagga cagctctcac atcaaagaat tatcaagttc agaatgttaa cgagcaccaa   33900
cgttgagaaa ctctgctgtg aacacatgaa ttccacttct ctccaccgag ctttattaag   33960
atataattga cacataacat tgtataagtt taagatgtat aatgtgttga tttcatctat   34020
tgatattttg caaaatgatc gccaccatag cattagctaa cacttccatc ctgtctcata   34080
gttaccattt ctcttttatg gtgagaacat ttaacttcta ctcgcttgac aactttccag   34140
tgtaggtaga tccccagagc ttgttaatct tgtaactgga agtttgtacc tttgaccaac   34200
atcttcccat ctacccctgg taaccagccc tttactctct ggacctctga gtttgacttt   34260
tttaacctcc acacatatat gagatcatgc agtattcgtc tttctcttac ttcacttagt   34320
gtgatgccct cagtgttcat tcagattgtc ccaaacagcc ggatctcctt ctgtctcatg   34380
gctggataat attccatcac acacacatgg atattttag ttttggtaat atttgtgatg    34440
ctggagcttg caagcctcca aggaaaacaa ggtcaaggta ctcagtttaa ttggcatgca   34500
actcagacca acccagtccc atcctgtctg ccacttgcag agtgcccgca ctgttttgga   34560
gaagggaaat gactaatgtg agccacttgg agcctgtcct tgcatccagg agagaaagag   34620
gggcaggatg ccccgggagg aggtacagga gaaggggca cagagagaga aggaatgggg    34680
aagggggtgg tgctgtctgg acaatgccgt ccttgttgca atgaaaagat aattgtatgt   34740
attctttagg gacctgaagg ccagttccgg gcactgagaa cccaggcagg gaaaacacac   34800
accactgcag agtgcaggag cagggagtga tcaaaaagcc tctattgtct ccctgaagct   34860
ggcatgggga gcaagaagtc ctgtgtcctg gggcgctggc cagggcccac ccattgggaa   34920
tggaaaacat cagcgctccc catgctgtat gttatgaggt tgtgagataa tccgaaatat   34980
```

```
tatcctatcc ataaagtctc cttttcaggc aaagccacgg ctctaatgga aaccggctac    35040
ttcatttatc catctttgaa atgtgtttta gctgtccaaa gtgaaagtga aaagttaaag    35100
tgttggttgc tcagttgtat ccaactcttg gtgacaccat ggactgtagc ccactaggct    35160
tctctgtcca taggattctc caggcaagaa tactggagtg ggtagcctat cccttctcca    35220
ggggatcttc caacccagga atcaaaccag agtctcctgt agtgtaggtg gattctttac    35280
tgttggagcc accagggaag ccctatagcc atccattcat atgattaata tttcctgagc    35340
ttctttagat gccaggcccc atgaaaccca gggaataaca cacagtccct gtcctcatgg    35400
agcacagacc cttcaacaac gtgtcaggca gtgtgtgtgc catgaagagg gacatacgtt    35460
aggtgggaac actctaccta atggggacgt ggaggtgggt ggaggggggcc tggtgtcagc    35520 gaaacttctc gaaagacgtg atgtcttggt agatacagag gccagagtag tggttaccag    35580
aggggaaggg gcctggggag gggcacaggg aaatgtgtga aggggttaa ctgtatggtg    35640 atggatggaa actgaacttt gggtggtaag caatctgtag tgtagttgtc acaggtgaaa    35700
catacaatgt tataaactag aataaagtga aagtgaaaga agttacatca ataaaaaatc    35760
aatttaaaca gttaaaaaga gggcttccct ggtggctcag tggtaaaata tccacccacc    35820
aatgcaggag acagggttca atccctgatc tgggcgatc ccacatgctg cggagcagct    35880
aagcctgtgt gccacaacta ctgagcctgg gagctgcaag tactgagccc atgtgccacc    35940
actactgaga cccgcatgcc ctagagcctg tgctccgcaa caagagaagc cacctctgtg    36000
agaagcctgt gcaccggagc cagagagaag tcccacctcg ccacaactag agaaaagcct    36060
gcccggcact gaagacccag cacagccaaa gtgatgtcta agtcaagaac ggagggacca    36120
gatggagttc gccataagca gaggaatata aacttttctc tggaaggctt tgaaagtaaa    36180
aaaaggttct ggtctcccca aggtcatttc agtgtggtcc tctatggagg agtgcaattg    36240
aactaggtat gccttcaaaa atcaaggttg gggactttcc tggtagtcta gtggttaaga    36300
ctctgagttc ccactgcagg ggacacgggt ttgatccctt agttgggaaa ctaatatcct    36360
gcattcatcc tgttacagcc agacaaataa ataaataaag tggaaacagt gacagacttt    36420 atttcttgg gctccaaaat cactgcggac tgtgactgct taaaagacgc ttgttccttg     36480
gaagaaaagc catgacaaac ctaggcagca cattaaaaag tggagatatc acttttccaa    36540
cacaggtctg tgtagtcaaa gctatgggtt ttccagtagt cctgtatgga tgtgagagtt    36600
ggaccctaaa gaagactggg agctgaagaa ttgatgcttt tgagctgtag tgttggagaa    36660
gactcttgag catcccttgg acagcaggga gatcaaacca gtcaatccta agggaaatca    36720
accctgaata ttcattggaa ggactgatgc tgaagctcta atactttggc cacctgatgt    36780
gaagagccaa ctccttggaa aagaccctga tgctgggaag gactgaaggc aggaggagaa    36840
ggggacgaca gaggatgaga tggttggatg gcatcaccga ctcaatggac atgagtttga    36900
ataaactccg ggagatagtg aagaaagaga aacctgtgac cacatggggt ttgcaaagag    36960
tcagacacaa ctgagcgact gagcaacaaa tgaaatatgc gttaaaaggt aaattgaggc    37020
atagtttaaa aaaagaaac ttaaaaaaaa atcagggtct tctttagtca tcttttcatc    37080
actgtcaata tttccatcac atataaaagt gaatgggta atagagaaaa cacctttagt    37140
gccaccacca ccccagtcca agctcccctg catgattctc cccctgcagt gtctcccgac    37200
tgcttctctt cctctttagt ccatcctcaa cacagcatcc ggagtggtcc tactaacaca    37260
gagccctgtg ctaccgtgtg cttagtcgct cagtcatccc tggcttttg cgaccccata    37320 gactgtagcc caccaggatt ctctgtccat gggattctcc aggcaagaaa actggagttg    37380
```

```
ggagccatgc cctcctccag gggaccttcc caacccaggg tctcctgcat cgaacacaga    37440
ttctttacca gctgagctac cagggaatct catggtgctc tgatcacacc tcttctctgc    37500
tcaaacccct cctgtggctc ccatctcact cagtgtatgt gctgttcctg cgtggtgccc    37560
tcctgccccc tgttacctcc ttgacctcat ttctagtcca ttccactggc ctccttgccc    37620
ttccacaagc atcccaggca cagtcccagg agaggctgtt ctccctgccc tgtgatcact    37680
ttggatggga tcgctttgga tcactctaga aactcagtgg tttccttact tgttccgga    37740 agtatagtag gagcagctga agagctatga acattggtta cgtagactct cagcctcact    37800
tcttcatcct ttggtgcttt caggcactga agacacatac agggaggaga aaggggatca    37860
ggaagagaaa atgatgtgga gaaaaatgtc acaaatactc tcttttatat ttggatatga    37920
caggaagttt acaggaaggg tatgggagga aaataaattt cagtgagtta tttttctgag    37980
catttgtttt gttttgggga tgttctctta tacgaccatg atggtggttt agtcactaag    38040
tcatggctga ctctcttgat cccatggact atagcccgca agcctcttct gtctgtggga    38100
ttctccaggc aagaatactg gagtgggttg ccatttcctt ctccagggga tcttccctac    38160
tcaggaatca aacctgtgtc tcctacattg caggtggatt ctttaccatc tgagccacca    38220
gggaagccct cctaccacag gatattattt accaaatggg ttgacttggc acgcttgtcc    38280
agttttaacc agtgagatac tgaaacacag gttatggctc aacagagttt ccaaattcta    38340
ttgattttat ttcaatcttt aaaaaaaaaa agaaatctaa tcctctgtaa agtggtgaaa    38400
cattatgggc cttggaaaac actgcctcct tggctaatat ccttttccct taatagcctg    38460
cttcagttga aatggtattt tattaattta ttaaccatca gaatcctatt aagagacagt    38520
gctagagctg gaagggatct tagagatttt tccagcccta tgtgtgtgca tgcaaagtca    38580
cttcagtcgt gtccgactgt ttgtgacccc atggactgtg gcccatcaga cttttctgtt    38640
catgggattc tccaggcaag aatactggag tagattacca tgcactgctc caggggtct    38700 tcccaaccga gggattgaac tcaagtctct tgcattgtca ggtgggttct ttaccactag    38760
caccatctgg gaagccctct tccagccttc tttacaatta agcaaactgg ggaccagaaa    38820
gacacagccc taacaatctt agggcagtgc ttgggactgg agcctagaga tctgaactct    38880
agatttggga gtctttcaga gaagaccagt ctagtgtctg tgaggggagc ctgtgaggtt    38940
cctgggaacc cactgggctc tagaggggt atgatgagtg aggagagcca cacctcagcc    39000
tccagctgcc gtctgagagc cttggttcct cttttgcttt acatatacag cttctgcata    39060 agatttttt tttgtaaatt aatgtattta ttttaattgg aggctaatta ctttacaata    39120
ttgtagtgat ttttgccata cattcacatg actcagccat gggtgtacct gtgtccccca    39180
tcctgaaccc cctcccatc cctcagggtc atcccagtgc actggccctg agcaccctgt    39240
ctcatgcagc gaacctggac tggcgatcta tttcgcatat ggtaatatac atgtttcaat    39300
gctatgctct caaatcatcc caccctcgcc ttctcccaca gagtccaaaa gtctgttctt    39360
tacatctgtg tctcttctgc tgtctcgcat atagggtcat cgttaccatc tgggctcagc    39420
gctacccagc aagtggatat cagggccagg ttgcctgtta agtgcatgtc ctggcccacc    39480
tccacactac agagccgcct ctcagccatc ttgctctgct gcttcttttc aaaggaaaat    39540
atttgccttg ggggagcaaa gaacaaaata ttttaaaaaa gaatgcctct tagcaaagga    39600
tgacttcatt tctccaaagc tctctctcta ccatccattc ctctctcaca tggaccttct    39660
ctgtgacact gaccaagatt cccaggatgt gattctcaag acaggacatg aatcttgctc    39720
cccaagatga tctcagtgtt ttcataataa tacgtttcat tgcagatcgg tcacatcact    39780
```

```
actactctca tttataatgt gaaacccacc gtccttcgga agtcttacct tcgcctttca   39840
ccaactagcc gtataaaagg tgatggcttg ttttccttg ccttactttt cctcattatt    39900
ggtcagacct ttcatctaat aaagactatt gttccttatt tgaattgtta ttctaatagt   39960
tattttaggc caatgttatt tttccttagt caggcgtagt gtttctcact tgccagacct   40020
ctcctattta tgatgggttt agtgtcaaac agacttattc ccagttcacc caactagtgc   40080
atgtccctaa gctaatctta agtctccgtt tcctcatcta taaatgagaa taattatata   40140
tttagtttat tgctgcatta tactacaatg ctacattata ctacaagtac ttcatatgaa   40200
gtactttgaa gagtatgtga tatgtaatga gtatttacta tttttatttt ttattggagt   40260
ataattgctt cacaatgttg tgttagtttc tgctgtacaa caatgtgaat cagccatatg   40320
tgtatgtatc cccttcctct taagcttccc ccaccatccc acttactgtt ttgatataag   40380
agcaattttt ggttaatctc agttagccaa ataaatgaga aaatccaggg tgttttttcc   40440
cttgtagtga tgaatcgtat aatatacctg gggttacttt tcccttcaag aagtgagcat   40500
atggagaatg tgtatgtagc ctggggtgag taacgtgatg aaaccagggt ttctctgtgg   40560
ccatgcagca tatggacgca acacattgat cactgctgct aacatccttt ctggtaaatt   40620
ccatcattgc cttgtgatgt gggttttcag agtgatactc cgttccatgt acctttagtt   40680
tttagtacca atcaaataat gaagaggcaa aggtaacgta caaaagactg cttttagaag   40740
aacaaggaga gagaattttc aggcagcaga gcaaggaggg ggaacccagg tgacgtctaa   40800
ccttgagttg aggatatggt gctaggaatt cagggaggcc agtgtggcta gagttcacag   40860
agaagaggac caagcagcag acagttgcac aaagggaaca agagctctgg agatgtgcag   40920
ggagtcctcc ctaagtgttc cagctaagtg catgtgagga gactacctga gggcaggaag   40980
aaagccacac aacaggagca gaaggaacaa tccctagagc tcactgctgc tgctgctgct   41040
gctaagtccc ttcagtcgtg tctgactctg tgcgacccca tagacggcag ccaaccaggc   41100
tcccctgtcc ctgggattct ccaggcaaga acactggagt gggatgccat ttccttctcc   41160
aatgcatgaa agtgaaaagt gaagtgaag gcactcagtc gtgtccgact atgtgacccc    41220
atagacggca gcccaccagg ctcccctgtc catgggattt tccaggcaag agtactggag   41280
tggggtgcca ttgctttctc cactagagct cacacagggc tggaaatagt ttgtcttccc   41340
accagccaca gtgggaagcc acacaattca tcgttgggta taatacttag agagatattg   41400
ccttgttagt gggggtataa ttagccctag actaaagatt gctctagtcc cacctgacaa   41460
agcttgaaaa agaaaacttg aggtatagag attcaatttc agaagttgaa aagagttctg   41520
gagattggta gcacaacagt gtgaatgtac ttaacactac tgaactgttg ttaagacgat   41580
aaattttatg tgtatttcac tacaattaaa aataatacag cccacacaca aaagaagcc    41640 tcaaaatgat gaaactattt ataggtaatg taactgcatc ctagaataca gctcaagagt   41700
ataattatag gatatgattt tacataatgg gatataattt atagaataat aataatattc   41760
tataaagaaa caaaaatatc tagcaccaga caaggaaata ttcacaatgt ctgacataca   41820
atcaaaaatt acaagacaaa taagaaggaa aaagacagcc tataaagagg agaaaagtca   41880
atcaaaagaa acagatcccc aaatgacact tatataatgg aattattaga caagaacact   41940
aagactatat cccatatgtt caagaaagta aagagtgaac atgaaaagta aaaggtgga   42000 tgacatttta aacgaccaaa atcaagtttt tagaggtgga aaatataaaa tctgaggtta   42060
aaaaaataca ctaggttgga cttatggcag actagacact gcagaagaaa agattagtga   42120
atttgaagac accacaatag aaatgattaa aaataaagca catagagaaa aaaaaagctg   42180
```

```
aaagaagtgt aactaacagc atcagtgagc tgtgaaacag tttcaactga cctaacataa    42240
agtgtaatta aagtcctcaa agaaaggatg gggaagaaaa tatttgaaga aatactggcc    42300
aaaattttaa aaatttgatc agaatgaaga atccactggt tcaagaagtt caacaaaccc    42360
aagcacaaga aatatgaaaa aaaaattgga attgcttaaa accagtgata aggagaaaac    42420
cttaaaagca tacagagggg gaaaaaaata cacattacag acagatcaac aaaaacaagg    42480
aagagagcaa acttcttgct cggaacaagg caagacagaa gacagtggag caatatcttt    42540
atagtactgc aagaaacaaa ataaagctgt caattgagca ctttgtatcc agcaaagata    42600
tctttgaaaa agaggctaaa atgacttttc agttcagttc agttcagtcg ctcagtcgtg    42660
tccgactctt tgcgacccca tgaatcgcag cacccaggc ctccctgtcc atcaccaact    42720
ccaggagttc actcagactc acgtccatcg agtcagtgat gccacccagc cttctcatcc    42780
tctgtcgtac ccttctcctc ctgcccctaa tccctcccag catcagtctt ttccaatgag    42840
tcaactcttc acatgaggtg gccaaagtac tgaagtttca gctttagcat catttcttcc    42900
aaagaaatcc cagggctgat ctcttcagaa tggactggtt ggatctcctt gcagtccaag    42960
ggactctcaa gagtcttttc caacaccaca gttcaaaagc atcaattctt tggcactcag    43020
agccttcttc acagtccaac tctcacatcc atacaaggcc acaggaaaaa ccacagcctt    43080
gactagacgg acctttgttg gcaaagtaat gtctctgctt ttcaatatgc tgtctaggtt    43140
ggtcataact tttcttcaag gagtaagcgt cttttaattt catggctgca atcaccatgt    43200
gcagtgattt tggagcccag aaaaataaag tctgacactg tttccactga ttcccccctct    43260 atttcccacg aaatgatggg accagatgcc atgatcttcg ttttctgaat gttgagcttt    43320
aagccaactt tttcagtctc ctctttcact ttcatcaaga ggttttttag ttcctcttca    43380
ctttctgcca taagggtggt gtcatctgca tatctgaggt tattgacttt tatagacatg    43440
caaaaaagag aatccattgc caggaaacct gcactaagaa atgttaaaag aagtcctta    43500 gttattaata gatggaaaat ctaccagttt gaaaaattga tcaacataaa ggaatgctat    43560
ttatttctga ttctgtttag catcaaaaat gtgaacataa tgaaaaaata taaaagactt    43620
tttcttatct ttaaaagata atgactttt aaacaaaaat ggtaactata tattttggag    43680
tttaacacat attaatatgt agaagtaaaa tatgaaattg cacaaaggcc aaaaagtaga    43740
ttattataag attcttatat gatgtgtgaa gtgttgtaat tattacttga aggtagatga    43800
tgataaccta aagatgtata catactatta acactaaaac aaccactgaa gaaacaaagc    43860
aattatcact agtaaaccaa caaaggacat taaatgaaat catgaagaat gctcaagtaa    43920
ttcaaagaag acagaaaaag gtgaaaaaat gaacaagtaa cagttggaca ataaaaaat    43980 gcatagcaaa ttggtagagg taatcagccg taatagcacc aaatataaat gatctaaagc    44040
aggttaccca gtagaactgt ctgtgatgat gaaaaggttc tttatctgtc ttctttacta    44100
ctcagtcaca tgtggttgta gagagcctgt ggagggaatt ttaacttttg tcaaattcta    44160
gttagtttaa gttaaaataa acacatgtgg ctagtggcct atcgggcagc atagttaaaa    44220
atacccaaat taaaaggaaa aattgttaga ttggataagg agtgaaaccc atctatatgc    44280
tggcaaaaca aactagtttt tttttaaggt acagcatctt ttacaataat taattaatca    44340
atgtatcttt ggttgtgctg ggtctgcatt gctgtgcgcg ggcttcctct agttgcagtg    44400
agcggggctt ctcttgtgga gcacgtagtc taggatgcac gggcttcagg agtttccgct    44460
catcagctta gttgctctgc agcgtgtgaa atcttcccgg accagtgatc aaacccatgt    44520
cccctgcact ggcaggcgga tttttatcca cggtaccacc aggaaagtcc agaaactctt    44580
```

```
taaatctaca gacattaaat aaattaaaag taagaggatg gaaaaaaaaa tatatcaggc   44640
aaacattaaa ggctgagctt tttatgtcaa agtcaacacc gagagaacat cacaactctt   44700
gtgaggacaa aaattttgtt ttgtcatcct tggtgttaca ctgttgctgg tggggacagc   44760
caaggaaagg atggtgtgtg agtttgctag agctgttgta acaaaatacc atggacttgg   44820
tggcttcaac aaccggacat ttgtttctc acagttctgg aggctggaag tccaagatca    44880
aggtatcagc agggttggtt tgtcctgagg cctctctcct tggcttgcag atggccaccc   44940
tctgcctctt gacctggtca tccctctgtc cacgtgcacc cctcatgtct ctctctcacg   45000
aggactccag tcatattgga ttagggccca cagtcacggc ctcactttaa cttaattgcc   45060
ctttaaaggc cctctctccc aaagcagtca tattctcaca taatgggggt tagggctcaa   45120
catacgaata ttggagtgga agggatgcaa ttcagcccat aacaggaagg gagattattc   45180
atcaccactg tgctcccaag aacagtgtct cctgcttcca gggtatggtg taattgtctg   45240
ggaacaggca gagacctcct tgtgatgacc atgaggcaag gaccagccca agagagagga   45300
gggcccaagg gtggagggct gtggctcacc tctcaagagg gttgtggagg aagatagaag   45360
gaggaggaag ggaaccctgt ccactcagaa tcttgtgtga ctgctattat ttatgttgaa   45420
ccttctgaca acaaattatt cctctcagat acatcttttt tgttacttga agtattacta   45480 tatattttc cttttgaat aatgaaagaa aagcttcaaa taagcaatgt tgtttcttct    45540
gatgtggaag agaggaacca actgaaaatg ctgacccttc cctaagccca ccaactctcc   45600
tcacccacaa ccagctgcct cttgttgcca tgacaacatt catgtggaga tgctactttt   45660
ggcttcgctt tgttaatgtt gggagactgg agcaagttga tcaatttagc ccctaaggtt   45720
cagggtttct aggtgaggct tgaaatttgg aagagatgta ggggaaggaa ggtcctgaag   45780
gaaggtcctg tgggagtgaa ggctttgggg gctctgggct acatgatctg tgaaagaagg   45840
tagagcaggt ctgtagagca atttaaaaca gatggatttc ctgaagtcac cactgtgttt   45900
ccatggtaac atcttagctg actctgtcag ttgctctaaa gtgttctccc ctctctgtgg   45960
acagaatctg ggtgtcagtt ggaggaaagg accctggaca gaataaattg gactaacctt   46020
agaagggaga aatttgggtt agcttctagg gcttttttggg cttccctggt ggctcagaca   46080
gtaaagaacc tgcctgcaat gcaggagacc ctggttcgat ccctgggttg gaagatccc    46140 ctggagaagg gaatggctac ccacttcagt attcttgcct ggagaattcc atggacatag   46200
atgcctggtg ggccacagtc catagggtct taaagagtgg gacatgactg agaaactaac   46260
gtacaacgtg tatattaggg ctttgggaaa agtctcccaa gagtcaagcc tcacgtcacc   46320
aggggagatg agagcaatca cctgctctaa tgacttatgg gaatggcgac agcagttctt   46380
gggcggaaag gctgtggcgc cttcctgcct gcctctaggc tttgttaacc agaggacact   46440
ggccaacctg taatttgttc atttagtgaa atatttatag agtggctcac attaaattct   46500
gctagagtca tctatcacac ggtgaaatgc atgtccgtca tgatgcatgc tggttgccta   46560
catcctccta tgatagatct gcagcaaata aaggctaata ttttaaatcc tctaaacagc   46620
cacttgcttc ctttcaccca cagtcttggg atgcttaggt aactgtgtta gctattgaag   46680
ttacagaaag gcatgcaacc aggtacattt cctgctcatg ggatgcttac aacctggatg   46740
ggatgatgaa catttttcctg acaagaataa gtgtcaggat caggtggtat atgctccaca   46800
ttcatggtgc agacagtaag cgccatagga attccaaagg gcagcctttc ttccagggct   46860
ggggtgatca gggagttcac ggaggggtgg gacttgaact gggtttgaat aaagagcagt   46920
acttgagtaa cagaaaagat cttggaaaca agcaagggga atggcaggaa aagaagtact   46980
```

```
gagacaggag tcagtgtggg tggctgttca ggagaaggag cagacttact tgagaatggt   47040
ttgttccatg gagggtggaa aataaacgtg acaaggcaaa gtcaagggct ctggttgtcg   47100
ggattccaaa gggcatggca gggagtttaa actttatcct gtaggcagta tggtttgtca   47160
aaggttttag agcaaaacaa acaaaaacca taatactgta gtagggtgct taatctgta   47220 gctgtgcata ggattgaagg agggaagaaa gagccagaaa ggttgaatgg aaaactgatt   47280
gaagggttgg atggtggttg aggaaatgga aagaggaatg cttgggtgca tggatggact   47340
gaatggatgg gaaggaggga ccccagggat actgagaagg aatagactgt aactgattgg   47400
atacagcaga acaggtgagg ggaactgtaa tgtttgagct ttggtgagta gcaaagcagt   47460
tcataacttt aaagaaaggg tgcttatgaa accttgtgtt aatcaaaaaa cacaagagga   47520
aaattcttgc ctttaagtaa ctcacagcca agtacgagga gaccactgtg attagagatg   47580
ccaggacaga agcatgtgca gagtccaggg aagggctcac aggaaggagt ggtcctccat   47640
tctggggaag aggcggattg tcaggaagag gtttataaga gatgcgcttg aactgaatgc   47700
tgagggacag cttatttgag gaagaaatat gatgtgactt cagagttgac ttggaggtga   47760
aacagaacat ctaagtggaa gcattcattc gttccattca ttgttacaga gggacttctg   47820
tgtgagtctg cccttgggca ggaatgaaga gatgagtgag gctcgctccc caccgtggag   47880
gaactgcccg tccagtgcgg ggaggaacat tcactgtatc cttcaaaggt ctgtttagag   47940
acctacaacc aaccatgtgc tgcgggggggc actggatcac aggagtgaac agaacggacc   48000
agattcctcc tctcacagag gccatctgct agttaagaac tttctcacca acaggcagaa   48060
ttaggctagg taagaaagga caggttgaag gggagtgcca aggatgcaaa gaaaaggagt   48120
agtgaattct tcgcagacca tctccatcac cagcagtgtc agggtatgag ggccacctgg   48180
tgagtggttt catttacctc gcttggagcc agccgtctgt ctgtaggggc tggggttggg   48240
gtgagaatga agtggctctg agggatgaag tccagtgttg tatgtgcccc ctgattgtga   48300
gatgagaggc ttgttccttt gagaaggcac ctttgtggct ggcaccctga gcctggcgtg   48360
cacgccctgg gtgttttgtg caccagggcg gtgcaccacc acccatgagc agtgtgttca   48420
cctgctccat gtccatggag ccctggcact gacaccaacg tctgtcacaa gacccaaggc   48480
tcatgtcctg gttacagagt ggtctctgga gagtggatgt tatgggctga attgtaatcc   48540
cacctcccat ttataggtta aagtcttaac cctctgaacc tcagaaggtg gctgtgtttg   48600
agataggtct ttacaaggta atcaaactaa aatgaagtca ttagctatgg ttttccatc   48660 catgtacgga tgtgagagtt ggactggctg agcactgaag aattgatgcc tttaaactgg   48720
tgctggggaa gactcgtgag agtcccttgg acagcaagaa gatcaaacca gtcaatccta   48780
aaggaaatca accctaaata ttcattggaa ggattgctgc tgactctgaa gctccaatac   48840
tttggccacc tgatgtgaag agctgactca ttgggaaaga ccctgatgct gggaaagact   48900
gaaggcagaa ggagaagggg cgacagagaa tgagatggtt ggatggcatc atcagctcag   48960
tggacatgag tttgagcaag ctctgggagg tggtgaaaga caggaagcc tggcctgctg   49020 cagtccatga ggttgcaaag agtcggatac aactaagcga ctaaacagca acaagggtgg   49080
atcctattca agtagaactg atgtccttat aaagaggaaa gctgggcgta gatgtgctca   49140
cagggagatg ccaggtgaag atgaaggcag aggtgaggag tgatgggagc tgagactgaa   49200
gaacatcaga ggtcgcccac aaaccagttt tgaggggagc ggccgggcga tgaacctccc   49260
tccaggttct cagcaggaag gttacttgcc cacaccttga tttcgggctt ccagcctcca   49320
gagctgtgag aggaaatgtc gtgcagccac ccagactgcg gggcctgcta tggctgctct   49380
```

```
cgtagactca gacagagagt caggctttca ggagcctgtg ggccccgaga ccacggtgac   49440
atggtccctg agggcccttc cccatactgt ggaaatccgt gttttccttg caggcttgga   49500
gagtctcagt cagaagtttt gctgtgactg gccggccctc agctccttca gagaagctgt   49560
tggcagctgt gaggggcctg cctttcctgc ttgtttattt tttcgggatt gttgctgttg   49620
ctcagttgca cagtcgtatc cgactcttca gggctgattt cctttaggat tgactggttt   49680
gatcttgcag tccaagaggc tctcaagagt cttctccagt gcctaactac agcagaacct   49740
atgcaaatgc tctgctggac aggtgttaga tttgtgagta ggcaagttag caagaaaaa    49800 aatttcatac atgcttgtgg tggcgttcgg caagattttc tccgttatgt agcattttaa   49860
tgaactgaga gtatttccac tccaggtcct ggcatgaagg ccagggaatc atttctgatc   49920
atcttcaccc gccgctgact ctgctggggc tggaggtgta aggaagttat ggaaacagag   49980
attggttaag aaggtcctct ggacaaagta tggatctgtt acccattgtt agagttttgg   50040
caaagcttag ctctggggaa ggcttccctg gtggctccga cagttaagaa tctgcctgca   50100
acgcaggaga cctgagttca accctgggt tgggaagatc ccctggaaaa gaacccactc    50160
cagtattctt acctgggaag tcccaggac  agaggagtct ggcaggctgc aatccatggg   50220
attgtaaaga gtcggacatg actgagtgag taacactcta gctctgtaga gttaatctgc   50280
tcttgtacag actagcagga gggtccaggg atctgttgcc caccacctgc tgggggtgag   50340
cagcttgctc tgggctcact gttgtcctcc ggaactctcc aggatgtgtt ccctggctcc   50400
tcacagggac tgctctcagt aacccagtct ctggggaatg gagcgtaatc actccacctg   50460
ctgattcagc ccctttctct cgctgacttt ttggaagtct cagaagcagc caaatgaaca   50520
tcatatccaa gattatcttg gcatagccgt ttgtgagttc tgcctataaa actaaagcta   50580
gtggccatcc ttttttttt ttttttaattt gcattctatt gctattttc atttgtcaca    50640 atttccccca cacccttgaa gtttatatat gagcttaggc tgtgccaggc accaggctaa   50700
agactctgtg ttaaattaac cttgttgttt cttcacaata cgtctgtgaa ggaggtactg   50760
cagtcatctc cgttttacag atggggcttc acaaggtcag tgacacgata aaggtcgtag   50820
agccagtaaa tgctggatat gtgcccagca cgtggattcc agagtccatg tccttaaccc   50880
ttgcatcaca tggtcatctg tttgggtctg aatatattag agttgtaaag gtgcttggaa   50940
tgagtcccgc tctccagttt cagtcttact tggtggatgt ggagcaggag aaacacacgg   51000
agctttggga acccagagga agagtttgcc cagggttggg attctggaag tgaaaatgtt   51060
agtctctcag ttgtgtttga ctctttgaga tgctaggac  tgtagcccct agctaccagg   51120
cacctctatc catgggattc tccaggcaag aatactggag tcaccatttc cttctccagg   51180
ggatcttcct ggaccaggaa ttgaacctgt gtctcctgcg ttggcaggtg ggttctatcc   51240
aggcgcctct atccacagga ttctccaggc aagaatactg aagtcactat ttccttctcc   51300
aggggatctt cctggaccag gaattgaacc tgtgttccct gcgttggcag gtgggttttt   51360
taccactgag ccacaaggga gttctggag  gctctctgaa ggtgatgatg actaaattgg    51420
gagctggaga acttttccat agagaaatca cgcaaactaa ggcttggagg ctggactcca   51480
caagacgggg ggtgaacagc agctcagagt agcagggcag caggggcaca gagaggaaag   51540
ggggagagag aggaggtggc agaattggag atggcgagaa gggggagggc aggctgggga   51600
aggcgccatc tgatacacta agaagtcagg aaattccttc ctgtggagag cagggtgctg   51660
ctgaagggct ctgagaatga gtggaatgtt tggttttgtg gtttactat  ttatttaaaa   51720 atatttattt gtgtgtgatc atgtaaatgc ttagtcgtgg tgtgtggaat ctagttccct   51780
```

```
gactgcggat tgaacttggg cccctcttg gccactgggc ccctcttag ccactggacc    51840 cccaggaagt ccctggtttt gtgttttaga tacgtcagtg ccattgttct atggaggatg    51900
gattggagga aacaagagta cagacaataa gaccagggag gaagatgtta gtccaggtgg    51960
gaggtggtga gggctacgag aggaaagagg atgaagatgg agaggatgtt gagattggcc    52020
ggtcctgaca attgagtcca ctgagggcgc ggaagtctaa actaacactg agtgcttgat    52080
gtgtaccagg tctggttcta agtggcctat tttaattcat ttactcccac aacagggctt    52140
ccctgggagc tccgtggtta aagaatccgc ctgccaatgc aggggatgca ggttcgatcc    52200
ctgatccggg aagatcccct ggagaaggaa atggcagccc actccagtat tcttgcctgg    52260
gaaatcccat ggacggagga gcctggcagg ctacagccca tggggctgca cagagtcgga    52320
cacgactgag cgacaaaaca acgacaacac ccccagcttt ccgaggtttc acgggtgagg    52380
atgctgaagc acagagaggc taggtgactt ggcccgaggg caggcgcatg gccagccagg    52440
gatgaaacag agactcaagt ctggctgtca cctcccctct ttgtgaccct gctgcatctg    52500
tcctgtgtga gctcgggggg cggggaggga gcagggggc ggcatctaga tgagccctcc    52560
tcccctcacc actgtcgccc ttgctgatga ccaggtgcac ggccgttgac caagggttta    52620
gaaggcagca gaggaagata ccgggctctg acttatgtgt gtttagtggg agatgcttgg    52680
ggaacaccca ttggagacat tcagctcagt cccttcctct cagagcctct tgtcacggag    52740
gccccggggg cttgtacgcc tccactaaat cattacacag ctttacattt agatgacagc    52800
cagataagaa aaaaaaaaa aaattggtg gtgtcgagtc taaagtctct cataatctga    52860
agtgattcct ctctgtttcc agttcactga ctggttggca gattaaaatg tgaaggcttg    52920
acgaaaaaat agcaaagtgc tgccaacctt cagtgtctga ggcataaaat taaatttaac    52980
gttgtcttac atgtctgaag ccttgtcatc agaaggctgg ccagacaaat atgatttaga    53040
gggttaggtt ttgagaaatg agtaggaaaa ataaaatgtg gaataaaaga agagtgggga    53100
taatgcatta aaaaaaaaaa aagcatatcc aatggtttta agcagtcctg tctgatggct    53160
ttgttgaata tcgcttcctc ttttgcctgc ttggccagag aattctgctg tgttgtgcaa    53220
gttatcctac tgatattggg aaattcagcc actcctgacc acctcgtcct ggccaccttc    53280
ttcgcctctt tcaccactcc taattctctg tacatctcct gttgatcttc tttcttgggc    53340
ttttaatccc tgcccccctc cccatatttt tttgtcagct gcatgcccag tctggatggg    53400
gactacttgc caagctctga agttaaaagc taagatctgg ctgtccccctt ccatcctagc    53460 tgagtgcacc ctttacccag ctcctccgtc cccttctgtt tcagcctcgc gtctctgtcc    53520
acagtgggat ctggtgtctg acggctactg ctcctccgtg tgacgtcttc agaggctgtg    53580
ggccagtctg tgtcctggcc ttcgaggctt gtcattcctg tcaatattag aagcgaaata    53640
taggttggcc tcacagctcc cagtgttaaa aatgaaagct tcctccccag gccgtgcagg    53700
tttgtagatg gaggtggatt ttttcccct tcccaccagc cccttttctc ggttgcttct    53760
tggagtttgg ctgatgctac tctccgtata agcatgctaa gtcgcttcag tcatgtccga    53820
ctctgcgacc ccatggactg tggccctcca ggctcctctg tccatgggat tctccaggca    53880
agaatactgg agtgggtagc cattcccttc tcctgggatc ttcccgacct agggatcaaa    53940
tccaagtgtc ttatgtctcc tgcaccagca cttgcgttct ttaccactag cgccgctcgt    54000
gtgagaggga agctgaaaat agaagagggg ctggaatcgt ctccctcgca gactccgttc    54060
ccaaacgtga gggtggcctg atcagaagct gcgactgggt ccaggdatgg agcctgggca    54120
gaatccctct gctccagaac cacccagcac agcgctcctg ccgcagccac gtgaccgggc    54180
```

```
agtgggatgc ctcacaccgt tgctgctagg acctgccctc tcagcctgct ctccctcgtc    54240
cctgcatttg cacgatctca gggggcctctg gccttgttct gtgatgtgaa gatgcaggag   54300
gcgaaagcag agccttctaa tgtattgcta ataacgtgtg cttctctcct cttgccctct    54360
cgtttccttc ttctccttct ctctcctctt ctagtctgat tgccctctg atgtcgtttc     54420
accttcattc cattgtgccc ttcgactcct gcaaaacttg ggagatcagt tttcctccac    54480
atgaagagcc atggaactct gagacttgaa cacttaaaaa aaattttttt tgttattgga    54540
gtataattgc tttacattgt tgtgttagtt tctgctgtac aacagcgtga atcagtcata    54600
ggtatacacg tatcccctgc ctcttgagcc tccctcccac cccgccatcc caccccctcta   54660
ggtcatcaca gagcaccgaa gtgagctccc tgtgctatac agcaggttcc cactagctat    54720
ctgttttaca cctgaaaggg cgtatacatc agtcccaacc tcccagttct gtctttgaat    54780
agatcttcac ctctgcatt ctcagacaag tctgcttgac aagggactgc agtgtctgct      54840
aggggaccgc aaagagaagg ctgcttcgac ttttggactt tcataagcc acctctgcag     54900
cgtcccggcc agtctcaaaa cccaaactca ggccttcctt cccacagctg gaatcagtgt    54960
tgcttttctg gtgaaaatg gaagcccgag tcagcctcgg atgtaaccat tttccagggc     55020
ttcaaggaaa tggcacgtat cctgatttgt ctctcaccct tctgaattgg attttctcag    55080
gggtttctgt tgggctggtg tgtgttggtt gttttctttt gaaacaggag tgggggagag    55140
ggggagagaa aaacagctag gaggggggaca ggcagctatg aatgcattta ccacataaat   55200
ggtgggtcaa gcagaagtgt tacgggtacc tggttttcta aagctgtaat ccaggccaaa    55260
gtgaatatgg tttcttaggg agtagactag gagggctccg aaaggagtga ctgggggggca   55320
ccctctgtga acacgggggg cttcctacat ggtgctagtg gtgaagaatc cttctgccag    55380
tgcagctgat gcaacagagg caggttcgat ccctgggttg ggaagatccc ctggaagagg    55440
aaatggcaac cctctccagt attcttgtgt ggaaaatccc atggacagag gagcctggtg    55500
ggctacagtc catgggactg cagagagtca gacacagcta agaaactaaa tagcagcagc    55560
agctgtagga atagccttct ctctcagcca gggcacaggg aatagacctt ccacggctgg    55620
agcccaccct ctggaggaaa ccctagggtg catcacttgc cctagggttc aagtgatgga    55680
ttcagcctga cccctgtttt acattgagtc cttgtcaggt cacttggctt tctgcagttc    55740
catttcttca tctggaaaat gggagggttg ggcaggagct gtgctactca atactggctg    55800
cagaacagaa ttgctgggga ccctttaacc accctgcatc taggaatatg cctagttaat    55860
ttgctctcag gtaagggagg cctggcgttg gtggcttata aacctctcca ggtgatgctt    55920
ctggggagcc aggctgagaa gctctgccca gctcagggtc agagtgtgca tgtgaattac    55980
atggatcttt ttcaatttca gactctactt ccgcgagttc ctggggagcc agaggttctg    56040
tccttccagc aggcttctgg aaaggctggt cctcagactg tgctctgagc agcaaaggcg    56100
gggatagtct tcaagatctt tgcagctctg atattctaca cttccttaat tattttctcg    56160
gcagggagag ggcagggagt gagtgaaaga dcattattt taatggtgta gtgggagtaa     56220
gttcccgttc atcactggag cgaaatgatg tctatgggaa aatgtgacag tatttggcgg    56280
gtagggttca gtttgtatct gatttcaata ttgaactcgg tttaattagg gagaaaaagg    56340
aaaacagata catctgtatg tgcatgcgtg ttgggatgtg tgtgtgtgtg tgtgtgtgtg    56400
atagagagag agagaaatag aacttgcata cgtgcatgtg tgtgttcagt cgtgtctgac    56460
tctttgcaac cccatggact gtagcccgat tctttgcagt cccatagact gtagcccgcc    56520
aggctcctct gtccatggga tcttccaagt caagaatgct ggagcgggtt gccatttcct    56580
```

```
tctccagggg atcttcctga cccagggatc gaaccacatc tcctgtgttt cctgcattgg   56640
aaggtggatt ctgtaccact gagccatctg ggaagcctga gaaatacaga gacaatgaaa   56700
gggggcaatg agtgaatgta tgagtgttcc tagggtgaat gttctgaata aatgaatttt   56760 aagagggat caaagggcat gtgtagcttc tccaggccca gttgtggtga ggagactaga   56820 gaagagggc aggttttatt cagctgggat tgaaggtgga gctctcgctc ctagagcagt   56880
tcagagggca ggagactcca tctcctcagc actgtctcat ccctgtgcta agcagctctt   56940
tgcttaattt attcctgaaa ttctaaggac agctttgggc ttatcagaac ttcccatcat   57000
ttgaacctag gagtagacgt gagattgtgc ctttcttggt cagaaaattt cagctggctg   57060
ctttcaaaag gctctctcct tgtatctccc cagcccttca gcctaaccat gagccacgga   57120
cactatcttg aaatgtgaag acttagtcca acttatgcac aattaaatat atattttaaa   57180
gtgaaggtca gccttagaga tgttgcctgc attttttgcct tctgcttttc ctcatcttga   57240
tagaagtacg gattcctata catgaatgaa ttccccccgg tttaaaatta tatttaattc   57300
agattaaaca cttcagactt tgtgatagtg gttctgccca cataattatg aggatttgtt   57360
ttgctttagc acaggtatca tgcagagcag tatttcttgc tagaattcac aattcaggat   57420
tttgtcactg tcctattttc agagattcct ccaacttgtg gttaaaggga gaagaatgtt   57480
tttgtgataa agatatttc cagtctttaa aaaggcaatt tatcttctc cgtgacatca    57540 ttttcatccc ctcccctcca taagaaggat tcctcatagc ctcactttac acatctgtct   57600
aatgggagta ccagttctac cctgcgtctt gtgcggatca gctgaggtaa aagtcctgaa   57660
agcaaggcta aggcatcaag tattagtcac atctattcct cccccttcct ttcctccaat   57720
tcttatttct tcctctgcct caaatgcatt agctcctggc ctccttggca cttttgatcag   57780 tcgttaggtc attcaagaaa cattctccaa gcacttatga gaccggcctt gtgccaggca   57840
cccagaatgg agctgaaaga ccacctctgt cctcaaggag gacatagaag gaggtgacca   57900
ggatattaaa tacaggatag cagattggat tataagaag gggcacctaa ctcagcctgg    57960
ctgaggatgg aaggaggtgg gagtagaggg cccgggtgtt tggggaaggc ttacagagaa   58020
gaatgataag tgagagttag ccagacagaa cgaacaggga agtgaaagaa cacgtgattt   58080
ccgcaaactg aaaatagttc cgatggttct tgtggggacc aagcaatcaa taataagatt   58140
ccctgaaggt taggattgag tttaggggct tccccagtgg ctcagtggta aagaatctgc   58200
tggccaatgc aggagactgg ggttccatcc ctgggtcatg aagatcccct ggagaaggaa   58260 atgcaaccc actccagtat tcttgcctgg gaaatcctat ggacagagga acctggcagg   58320
ccacagttta tggggtcaca gagagccaga catgactgag ggagcatgca tgcacacagg   58380
actgagtttg tcttttcacat ggtatgagtg atttctgacc tcttgtggaa aaatgagtat   58440
tttgacttat tcttttttgta agaataaaga atctgctcgt tcccaaggat gtgccccact   58500
gccaggaggt agccatccac gtgtagctcc aagagcagga ctgatggacc ttggtaggga   58560
gtgaggcctt gaccatggtt ccactagtcc agtgctctgt ccgactgaga aaactcatgc   58620
aggctcctcg tagtattggc cctgaccttc gaattgggaa tttgcagacg taacccttta   58680
tagcaagacc tttcaaactg caggttgcaa gccatatttc atgttatgta ggttagaaaa   58740
tcaataggtt gcaaccagca ttttaaacaa tgaagtagaa gagaatagaa tatcagaatg   58800
ctgctgctgc cgctgctaag tcgcttcagt cgtgtccaac tctgtgcgac cccatagacg   58860
gcagcccacc aggctccccc gtccctggga tgctccaggc aagaacactg gagtgggttg   58920
ccatttcctt ctccaatgca ggaaagtgaa agtgaagtcg ctcagtcgtg tccgactctt   58980
```

```
agcgacccca tggactgcag cctcccaggc tcctctgtcc atgggatttt ccaggcaaga   59040
gtattggagt ggggtgccat tgccttctcc agaatatcag aatacagccc acaaataagg   59100
actagtattc tttactgaaa cctgtgctaa tacttgatgc aaaatgcctt tattattggc   59160
tgtaccagat cttaggggc ccaggattga acctgggaga ggttgggaga ggttgggaga   59220
ggttgctgtc attgggagag tagagtttta gccattggac caccagggaa gtccccagaa   59280
tgccttgttt tactgaggct catggaaaag aaaatttgaa gtacactaga ctgtatactg   59340
ctaggtcaag gaggctaaga tatttcctct tgtttcctaa cttcagttga ttcctcatgg   59400
ctggctgggg gactggattg aaaacagttc agaggtggtg cctagactca gcagaaaagt   59460
gcatcacgga ttagcagtgc ttaacgtggc ctcacagcag cggccaggga ccacagggcc   59520
tgtgcatttg ccctccttgt tgaaggctct atacaggtta aaagtagttg ctagggcctt   59580
ccctggtggt ccatcattta aggggcttcc caggtggcac agtggtaaag aacccacctg   59640
ccaatgcagg agccacagga gatgcaggtt ccatatttgg ggttgggacg atcccctggg   59700
ggaggaaatg gctacccact ccagtattct tgcctgaaga atccgataaa cagagaagtc   59760
tggtgggcta cagtccatag ggtcaaaaag agttggacaa gaccgaagca acttagcatg   59820
cacacacggt gcacacacac acatatgtag ttacatgtat atgtacacat acatacacag   59880
atagctacac atacttcatt gtagttttca ttaataagaa acctcattat aacaaagaat   59940
ttaaatggct attatttgct aatgagatag cttaaaacat ttcagcctgt taaatagttt   60000
ggaaagatac ttttagggct catctagttg atttccattt agaaagggaa agattacaaa   60060
gactgacttg attaacccat gtgctctgag acagacattt gtattaataa cttgaaattt   60120
tcatgtatta ggaagctact gcccagactg gcagagaagg caatggcacc ccactccagt   60180
actcttgcct ggaatatccc atggatggag gagcctggtg ggctgcagtc catggggtcg   60240 ctggagtcg gacacgactg agcgacttca ctttcacttt tcactttcct gcattggaga   60300
aggaaatggc aacccactcc agtgttcttg cctggagaat cccagggaca ggggagcctg   60360
gtgggttgcc atccatgggg tcgcacagag tcggacacga ttaaagtgat tgagcagcag   60420
cagcggccca gtttggtgtt cacaggggct gggttttctc agtcatttga gaccaaaagg   60480
cttagtgaaa cataaaatgt ttcaagtcgt accaacaatg gcccatataa caaagaacca   60540
agttatctgg tcctcctgac tctgctctcc agcacttgtt cagtggctcg ttcatttatt   60600
ccacaaatat ttatggtgga cccagtgttc acttgatgct gtgctcacag agctctttgc   60660
taagcacttg agatacagca gaaaccaaaa gcaggcttgg cccaagttct cctgaagtct   60720
gaaggtagtg agagagacaa gcagagatag aggagaatgc aggtgtgcga tgtgaggaag   60780
gaacacaggt ctctgagcgt agagcagagg ttcccactta gactgttttt ctccagtcca   60840
gggcctctgg ggaaggcaca ttctttggga tttgctgcag aatttgagag aactttgta   60900 cacagagccc tcagcaaaca atttccagtt gacccttaag catgaactta atgcatgtga   60960
tcttcaatat atgcaaatca atcaatgtgg tacactatat taaggaggga gcctacttca   61020
acataataaa ggccatatac aacaaacccg tgtgtgtgtg tgtgtgtgtg tgtgtgtgcg   61080
tgtgtgtgtg tgcacacgca tgctaagtca cttcagtcgt gtccgactct ttgcaacccc   61140
atggactgta gcctgccagg ctcctgtgtc catgggattc tccaggcacg aatactagtg   61200
tgggttgcca tgccctcttc caggggatct tttcaaccca gggatcaaac cagcgtctct   61260
tacgtctcct gcataggcag gcgggttctt taccactagt gccaccgggg agcccacaac   61320
aaagccacag caaacattat tttcaatgga gaaaactga ttttctctaa aatcaagaat   61380
```

-continued

```
aagataaggg tgtccattct caccactatt attcagcgta gccttggaag tccttgccat    61440
ggcaatcaga gaagaaaaag aaataacact gcatgtgaaa taggcttcca aaccctcccc    61500
tcctggtcaa ccctcagacc ttttaatcag agctttctct tcttccctc aatacctct     61560 cttaaagcag acataattac ctgccttttg atcccacaac tctttttttg ctaccagcag    61620
ctctctggtt gcaggcagaa atacagctgt attctctgag actcaaaagg ctcttcacaa    61680
cttccctgaa tctttaagaa cattttctg gaagcagttt tattagcctt gaagcatcct     61740
ctcatccatt gtccctatca ccctctttta tcaaaatttt ataatgtggg atttaagtat    61800
ttttgaatgt ttttaaaaat tttttattgg agtatagttg atttacaatc ttatgttagt    61860
ttctagtgta gagcaaagtg attcagtcat acatatacat cgcagtctta ctcttttcaa    61920
agtgtgctta tttctaactt cagatttctt tttatcacct cttgcgtgtg tggaccaata    61980 attcatttt taatcaatat tttttattga agtatagttg atttacaata ttgtattaat    62040
ttctgctgta caacagtgtg atgcagttat atttatatac attctttctt aaagtattct    62100
tttaaagtat tattatggtt tatcatagat attgaacatg gttctctgtg ctatatggta    62160
ggaccttgtg gtttatctac tctatatata aaagcttaca tctgctaatc ccaacttctc    62220
attccatccc tcccccaact cctcccgctt ggtaggagtt accaccagtc tgttctctgt    62280
tggcccagta attcttaagc agacacatcg gatgtgatat ttccccacgt gttgctcgcg    62340
cagactgtta cgtgcctctt ccctgtctct agtctgtgcg ctcacctgcc tttacacact    62400
gagaatgggg aggtgggtct ccgagtcacc agtgcaggag acccttggct gtgcagtgcc    62460
ctggcccctg ccgatggcca tctcacacca gctctggctc ttagccacct tgttgaaaat    62520
agtcatgaaa gcagatattt ttgtggacta tgctgtccac tgagctgtgt actttatcac    62580
tgtgtattcc tcaccatgat tttatgaggc aaatctttta ttctcactta caaatgagaa    62640
aaccaaggct tagaagaatt aagtaacctg cctcaattac acagctgaaa agtgtagaaa    62700
tggtatttga acccaggaaa tctgttccat agtccttact cctagctact aatttatatt    62760
gccctcacaa ataaatataa aatatcgtta ggagtgtaaa gcctatagtc atttcagata    62820
aataactcca aaatcagcat gaggctaaaa ctgaccattt taaacaggac ataaggcgat    62880
ttttttttta atgtatttt gactgccctg ggtcttcgtt gctgcacagg ctttctcta    62940 gtcgtggtga gcaggggcta ttcatggtgg tggcttctct tgttttgaag catgggcatt    63000
agagaatgtg ggcttcggta attttcctga gtcatgtaga atcttcccag accagggatc    63060
aaacccacgt cccctgtatt ggcagaaact ttcttaacca ttggagcacc aaagaagtcc    63120
aaggcagtgt tttgaacgac tcctcgggca gtgattcttc atgtctcagt ctcacaggtc    63180
tccttgaaat gtgagtccgt ggtgtagttg gatgaattgg agtgaaactg tatggtgttg    63240
gcacttaggg ctcttcctct ctagaattgt ggtgtggctt ctgcaagatg gatatgtttt    63300
tgtaatctgg agacactcag cagtttccaa ggatgataca tttcccattt gacccagttt    63360
gtatcgttct ttattttttc tgtttatgta cacgctttgt ttccttaaat aagaccctaa    63420
gcttcttgac aacaatgtcc ttgaatgact cacacattgt ggtgaatggt gcttattgat    63480
ggtggttcta acagcagcag ctactgccgt ctcctcccac tggcctttcc cactgaaggg    63540
tgttgttctc tgagtccgtg actggctgcc tgctaacgca acccagttct gcagcatctg    63600
atgataaacc gagcacgctg aatcctgttt cttcccattt tgtgttcttc ttccctaacc    63660
tctgtaaatt cacttgcact gtttcttggg tctcagagtt gtttggaatc tgctacagta    63720
gggtccaggg cttccctggt ggctcagtgg taaagaatcc gcctgccagt gcagaagagt    63780
```

```
caggttcagt ctctggtctg ggaatatccc ttggagaagg aaatggcaac ccactcccgt    63840
attcttgcct gggaaattcc atggacaagg ggcctggcag gctataaatc catggaattg    63900
caagagagtt ggacacgact tagtgactaa acagcaataa cacagtaggg tccagactat    63960
atattatatc ccagcatctg tggactcaac aacagatttt aaaattgcac ttagttggaa    64020
tgataaagag gctttgcaag cttttttgcct ctgtagctca gagattgtgg cagttgtggt    64080
catcctcagc catgcaggtg ttaaaagtaa atgtcactcc caatgaattg ttccaattta    64140
aatttaaaat cctggcatct ttagcctggc aattagaagt gcacacagct gaatttgatg    64200
tcctcttcta ggtgtgtctg tgtgtgtgga ataaccgtt cactcctgtg tctctccctc    64260
ctccgactcc ctccgctgtg ccctgtgctg actgagttaa attcactctt agacctgagc    64320
ctggtaaatt ctcccttctg gagaaaggtt tatttaggtc ttctgcccat tttttgattg    64380
agttgtttgt tttgatgata tcaagcctca tgaaatgttt gtattactga attttggaga    64440
ctaatccctt gtcagtcaca tcacttgcaa atattttcgg gagaaaattg tcttttcgtt    64500
ttgctgtgca aaagcttttt gagtttaatt aggtaaattc tcccttctgg tttctggaca    64560
gtgcatgggc ccgcctcacc tttttttccct tctcctagtt tggctctgtc taaattctgg    64620 ttcctatttta agtctttgaa aattaaaatcc atctccttga ggttagaaca gggctcagga    64680
aaatgattaa attcttccca accctaaatc ctcggctctt ctgtggggtt acctcttcgt    64740
gcagcaaaat gagccaaagc ctccactcaa atccccaagt aattcttcct gccttctgca    64800
gtttattgaa ttcatccttc ttgagactga ttcggctgtg gtctcaaaca tcagctctgc    64860 cttctgtct tcccagctcc ataggcctga gctaaaacct ttcaggagtg ctggtttcct    64920
tattttaccc tgcttctcca tgcttttgcc ctcactgatg tctggttttc tcctaatgcc    64980
aggggcagga gtgcagtgcc atggaaaatg ccctttaaaa acaattttt tttttttttt    65040 tggctatgcc aggtctttgt tgaacttgga cacttgcatt gggagcacag agtcccaacc    65100 actgaccac cagggaagtc ccagacccctt atcttctaag tatcactttc cttacttttc    65160
attgtaatta aggtcatctg tctgtaagag gctctgtgaa aatcgtgaag tgcttagcac    65220
tatgcctggt gcatggtaag tattcagtct atgtgtatgg tcaatgttat aattacgtta    65280
acttctgttt gaatgttatc aaatctctcc catttacttg atcatttctt tggagaagat    65340
gttttagttt agcaaacatg atttagtctc ttgcctttac cttatcagtt cagttcagtc    65400
gctcagtcga gtccgactct ttgtgatccc atgaattgca gcacgccagg cctccctgtc    65460
cgtcaccaac tccagagtt cactcaaact cacgtccatc gagtcggtga tgccatccag    65520
ccatctcatc ctctgtcgtc cctttctcct cctgcccgca atccctccca gcatcagagt    65580
cttttccaat gagtcaactc ttcgcatgag gtggccaaag tactggagtt tcagctttag    65640
catcattcct tccaaagaac atgcaggact gatctccttt agaatggact ggttggatct    65700
ccttgcagtc caaccagtca ccttctattt gtccagattt tcagggaacg tgtaacatgt    65760
ttgaaagaag gacttgttgt atgggatgga atagtcaatt gataatagct gatactattc    65820
aaattgagat gagaacctgc ctgatctgaa cagaggaatt ttataagttc aagtttaaac    65880
ttgatgaacc attctagcac atcaaaatat gtcatcatgg tctcagaaga aagccaaaaa    65940
gaaagaaaaa aggcaaaatg tacatcgagag aatgagaatt ctctccagga aagagagatt    66000
tacagcaact catttaaaca acatctttt ttttttttt taattacttg ctttgcagtg    66060
ttgtgttagt ttcactgtac cagcaaagtg aatcagctac tcatatacac atatcccttc    66120 tttttttgcat tccttttccca tttgggaaag aagtcaccac agtgcattca gtagtgttcc    66180
```

```
tggtgctata cagcgtgttc ccattagtta tctatttac  acataccatc aataatgtat  66240
atgtgtcaat tccactttca tcttccttca ctgaaaagca ttcctcaact tctgagggct  66300
caagccgggt cacctgggat gtccttttgg gtaatttcct ccgctttccc gttttcctgc  66360
agcctggtcc tgcttccata attctctaat acaaatacaa tggaaaccac ccttcagata  66420
caagggaaac tgctgtccct ctcagcatgt ctgactccag ttgtcatagg aactcaactc  66480
cggtatctct ggtgtgggta atagttccac aaagcaattc ttcctaataa tggaagctta  66540
tacagtcctt tttgggagcc aggcatagtt ctctgccctt tagaggcatt aaggcatgta  66600
attttcacag ccagcttggg ggtaagtcct attacattcc cattttttgca aacaaagaaa  66660
ctgaggtata gattcaataa cctactcagg gttgtacacc tggtatttgg gcaagccagc  66720
gtgtgatcct ctggagcctg ccttgagtgt ctgtgctttt caccacccct ctttactgcc  66780
ccttatctct cttaattaca tgcagtgcac tttgatactt tctactgtat agtgttttt   66840
tttttacata tttgaattgt ttatttga  ttatgctta  caatgttgtg ttagtttctg   66900
ctgtacagca aagtgattca gttatgtgta tacataccc  ccctcgtttt tggatttcct  66960
tcccctttaa gtcaccacga gcattgagca gagttccctg agtgatacaa tgtgttctca  67020
ttagttatct atttatatca cagcatcagt agtgtatgta tgtcaatccc aatccctaa   67080
tcatctcac  cgccccttt  ccccacttgt tgaccatacg tttgttctct atgtctgtct  67140
ctatttttgc tttgcaaata aggccatcta taccatttt  ctggattcca catatatgtg  67200
ttaatatgtg atattattat ttaatggtgt ctcagtgtga cttgagaaat gatctcacag  67260
ctctaatgat actggcacga agcttgcaaa ccattggcca gaccctctgt attgggaaag  67320
gacctgccag gctgccttag tccagtgcct gaaacattcc aatcgtgtct tgttcagaag  67380
ccacactcac ccagcaacgc ggggcttaga atttggtctc ccatagaggt ctgcctgcag  67440
ggaaagaact aatgttatat ggacttcaag tatccctgtg aattaataga ttgtccctct  67500
ggttcaggct ctgaggctgg aagatgtgac tctgtcccca ggaaatggat tttttgagga  67560
atggagtcat cagatcagac ttcagtgccc aggaggctga aggccgcacc ctggaccttg  67620
tcagaatctt caagatccac cctgagatgt ctttcgtagg acagcctgca agattctt    67680
ctggggtggc aattcccagc attgaggagg ggctgcagga gcatgattta tgtttccaca  67740
gcactgagca tcatttgttc cgcagtcaga aacagagctc tgcgcccttg ttcctcgtct  67800
aatatatatc ctcattgact cacatagctt tccacagaaa agaaatggat gctcctttcc  67860
cacctgagcg ttattatgcg gcatgaataa atgtaacaca taacctgcaa ataattgatt  67920
gaaatgccat ccccctttc  ctctcacgcc agcaatatct ctctcggaag atggtctcca  67980
gtgaggccag gtctgcatgc attatgcatc tctatgatta tgcattaaat tctggagaac  68040
tagcaagtga tacctaaatt cttcaagcat gtttggttat gctaaataat tgatggcatc  68100
ttttattat  aaaaatttac ctgctggaat ttcagaacca gaggttctgc caacccatct  68160
tctctattag atttcagctt cctggcatga agtccaaaac ctcacccaca gatctcaatc  68220
tttgaaagct cttaggctgg tcgccaggat gaagtcctgc atttccagac aagtgagacg  68280
gatggacctg aagccaacac ctgttctgac ctcttcccac ggtcgtgggg acaaagctta  68340
agaccttcag cacctgggga acttaacttc caagtttata gcctcagtag ctctaagatc  68400
ctaaatggtg aacagcgagg ggctttctgg atttggacaa atgtaatcat gtagtgagat  68460
aagttataag cccacctagt ttgtctgatg ctgggaggga ttggggcag  gaggagaaag  68520
ggacaacaga ggatgagatg gctggatggc atcaccgact cgatggacgt gagtttgagt  68580
```

```
gaactccagg agttggtgac agacagggag gcctggcatg ctgcgattca tggggtcgca    68640
aagagtcgga cacaactgag agacaactga actgagtttg tctgaaggga aggatcacgt    68700
gagcaaagag aaatatgagt aactgtcttg ggaaaagag aattgaacaa agaggatgtt    68760
ttttgtcttg aaaagtatat tctgcagggg tagggttggg aggaattggg agtttgggat    68820
cgacatatat gtactattga tactatgcag aaaataggta actaatgata acttactgta    68880
tagcacagag aactctactc agtgatccgt ggtgacctag atgggaagga aatccaaaaa    68940 gggggggatat atgaatacat ataaatggct acccattcca gtattcttgc ctggagaatt    69000
ccatggacag aggagcctgg caggctatag tccatgggt ggcagaatca gacacgactg    69060
actgactaac actttcactt tcaaagaagt tgatgcaaaa aagaaaaaa gtatattctg    69120 gagaaatggt gaatagaata aatgtaacca gcacgcccaa cagacacaat tagtggtgtc    69180
atcaaaatat tgctttttg cttgtcgccc tttaaatttt attgaataga ggaaggtgga    69240
tgtaaacact cagcaggcct ctgacttttc aactcgttct taggaaacag tcctcgtgcc    69300
attctacgtt gcactgtctc aattcagaaa tgaggatgtc caggccaagg tgagaatcaa    69360
accttcgaac ttgagtgtat gttgacctc ttttgctttc tattctggag cctgctggga    69420
acctgctctg ggagcgatgg tggacaggtg acagtcatct gtggtctcta cctcatgcct    69480 ttccctccc tatagttttc agtttgccag ctagttttg agtccctgag gatcgggtgg    69540
gcaggttagg aacagaggac tcagcaaggt cagtttccca ctctctgaac caggccagtg    69600
tttgatggac tctttccctt ggtgggcctt gtgcgggatc tttagaaacc cacattatcg    69660
gccatctctc tcctacagtc ctctgggcat tgttgttgtt gttcagtcgg taagtcgtgt    69720
ccgactcttt gcgaccccat gggctgcagc acacctggct tccctgtccc tatctcccaa    69780
aatttgctca aattcatgtc cattgagtcg gtgatgccac ccaaccatct catcttctgc    69840
tgcctccttc tcctccttcc ctcagtcttt cccagcatca gggtcttttt gaatgagtcg    69900
actcttcaca tcaggtgagc gaagtattgg aacttcagct tcagcatcag tccttccaat    69960
gaatatgcag agttgagttc cttaaggatt gactggttgg atctccttgc tgtccaagga    70020
ctgtcaagag tcttcttcag caccacagtt tgaaaggatc aattcttcag cactcagtct    70080
tctttatggt ccaactcgca catctgtaca tgattactgg aaaaaccata gctttgacta    70140
cgtgaacctt tgttggcaaa gtgatgtctc tgcttttaa tacgccatct agaaaagtca    70200
tagcttttct ttcaaggagc aagcatcttt taatttcatg gttgcagtca ctgttcgcag    70260
tgattttgga gccccgcaa ataaagtctg tcactgtttc aacttttcc ccatctattt    70320 gccacgaagt gatgggaccg gatgccatga tcttcgtttt ttgaatgttg aattttaagc    70380 cagcttttc actctcctct ttcaccctca tcaagaagct cttaattcc tctttgcttt    70440 ctgccataag gtggttatga ggcagatgtt tgttgatgta tatctgaggt tgttgatgtt    70500
tctgggcata agaaggtgca tctgtattcc aggagatctc ttttgttttc tttctaagat    70560
cctatcagtt cactgcacat ccccactttc ttgctgctga ggtctttctg cctttgtagg    70620
tggtcctatg agacaggagc caagctgatc ccaccccagc tttctcttca gagtgatcat    70680
atttggttca caagacacac gtcagccagg aaaccccaaa agagcatacc agccccccac    70740
acacctctac cttacggcca cagccctctc ttagtacaga aagcatgaat ctaggccac    70800 cgtgtgtgct gttttgccagc tctacagtaa gtccccaca cacaaacctt caggttacaa    70860
actttcaaag atgtgaacgt gcatctgatt ccagcaagga accaaaacct gtgccatcga    70920
cgtcagacgt tagtgacact gcagcttgcc ctccatctcc tattgctgac gatccttcag    70980
```

-continued

| | |
|---|---|
| ctctaccatc tcccaccccc tctcctccac tcagcaactc tccttgtctg ttcactcgat | 71040 |
| gccagccgct gtatgccagc tgttgtactg gactactgta cttttcaagg cactgtactg | 71100 |
| taagattcaa aatatttttat tttttgtgtt tgttttttat gtattatttc tgtgaaaagt | 71160 |
| attataaacc tattacagta cagtgttaca tggcctactg tgtcacttgg tacctaggct | 71220 |
| aacttcggat ttatgaacaa attggattta tgaatgagct ctcggcgtgg aacttgcata | 71280 |
| tgaagcagac ttactgaatt tcaaatttct ccaaggggtc catgtaagcc cacttcactg | 71340 |
| ggattgagat gaaggagtca cggctctctg ccctctttcc ttgggagtat tcagctcaca | 71400 |
| gctcattcac atttctttct aactctttgc tattcttcat ctgaatgggg cgtttgggaa | 71460 |
| tggtggagcc aggtcttgat aatgtccttt gtgaattctg tataaggggt ttgtttccca | 71520 |
| ttcacatgcg tatctgatat ctatcatatt ggcgtctcgg gcaaaagaaa tgcagaaaga | 71580 |
| atcccattct gatatcttat tccataaacc atagagaaac aatagaagtg tacatttcag | 71640 |
| ttatttcttg ctgccaaaac accccgaaac tgagcagctt taaacaagag caatgcgtcc | 71700 |
| tttctcctgc ttctggggtg gctggcctgc ttctctgttg gtctcacctg gctggatgg | 71760 |
| gtagtcatca ctcacactca cacagcgggc gctgggcgct gagtgctggc tggacgcctc | 71820 |
| ggatctcttt ctcagggcct ctcattcttt gttaggctaa accagcttcc tttcatgagt | 71880 |
| gatccaggca atgtttcagg gaaccaaagc agaaactata cagtctccta ggctctggaa | 71940 |
| gtcacaaagc atcattctgt aagccaaagc aaaattacaa ggctagtcta gattcaagag | 72000 |
| gtgggaaaaa gactctacct ttagcatttc cagtttgggg ctctccctag ttcactgtag | 72060 |
| aaaacctgcc tctgccagct ctggttctaa acgttttcct gagcagttgt ggagttaggg | 72120 |
| gaggaagaaa aatgaattta tattggtttt agtcagctta catttggaag aatagaaagg | 72180 |
| aagagaaaag atccaggaga tcagaagga agcagagtca ctgtggctga ctttgggcaa | 72240 |
| gcattcatgg ggggaatgga ccacaggtgg ggaactggga gaacaggcta aacttccgat | 72300 |
| catgaagatg agagcaggtc aacatctctg tgaattgggc aaatgagacc ttcggacctg | 72360 |
| agaaatccca tggacagagg agcctggtgg actatagtcc gtggggtcgc aaagagtcgg | 72420 |
| acttagagac aaacaatacc acctaagact ttctggagcc tattatgaaa tggacttcag | 72480 |
| cacagcttga gttctccttg gggcctggcc tgagtggaca ccataggatg ctatcttgat | 72540 |
| actagctctg tgatgcccaa accctgttcc ttccacctgt cccttggat gcaacctcgc | 72600 |
| ctccactcca cccttctct cctctgatct tgtgctcaca ggaggaggtg aacatcaaca | 72660 |
| aagagggggtg cagggtgcta gcaacgcaac tctatcttca ggtggggttt caggaccagg | 72720 |
| tgagtgagag gagcaaggtg actgagggat gatgaagccc attgctctgc tgtactgtgg | 72780 |
| gctgcagatt caaggctcag aggttatcat ttaaaaaaga aaatttctaa aggctttaga | 72840 |
| aatggtttgg acttgcccca gcagctcaga gggtaaagaa tctgcctgaa atgcaggaga | 72900 |
| caccagagat gtgggtccct ttaatgggtc gagaagattc cctagaggag gaaacggccc | 72960 |
| tttactccag tattcttgcc tgaaaaatcc catggacaga ggagcctagc aaactacaat | 73020 |
| ccaaagggtt gcaaagagtt gaatacgatt gagtgattaa gtacctctca cctcaagaaa | 73080 |
| tggttttaaa atggtctttt aaaaaatacg tgaatacttt atgtgtgttt atctagagtg | 73140 |
| taaattgcaa ggccccacac tccccatcag atgcccgcac gaggaaggga gcccaggcgg | 73200 |
| gagaccttgg aagggcaggt tgccttgccg aaaaatgaag tgctggggct tgttttcagc | 73260 |
| ctgcaatgtg agcaggctca gaggacagac tgttcaagct gataagcaca gcttaggggg | 73320 |
| aagctcagaa tctttacttg cctgatattt taaaccagca catacaaaat ctataaaaga | 73380 |

```
atttttcact ttcagagaat agatgtatac ctgtcttgga gagaatattt cttttttttt   73440 ttttttaaa  cgttttgtaa cttgtggctt tttgttatca acaaggctga gcacaagact   73500
ttccagctgc cctacctcca ctatctgctc ctgcagctgt gcagtcatgt ccgacccttt   73560
gcaaccccat gcactgtagc caggctcccc tgtccatggg attttttcagg caagaatact   73620 ggagtgggtt gccattcctt tccccaggga atcttccctg cccaggaatc gaacccacgt   73680
ctcctgcatt gcaggtggat tctttaccgc tgaaccactg gggaggccct ccaccatctg   73740
actcccgcct aaatgattct gtaatctgtc cccttttgaaa cctttgccca tctgatttcc   73800
aagcacgttt gtttcatcgg aacacagggc agtttagaga ggggaggaag agaggagggg   73860
atgagctgag ggcgagtctg aaccacttcc cccattgctg cccttttccca cggtcccccc   73920 agctccccca gctccaaggc aggaccagca ggcggagcgt gtgaccacgg cctcactgcc   73980
cagaggctac cggtaggggg tgctgtgtcc acacctccgg gcaccaccag cgcgatgaca   74040
ctcccaggct tcataaatcc ttagacattt aatgctggcg gggatgtttc cttttggcca   74100
tgaggaacct gtggtccaga gaggtgagtt tgtggtggga gtagggctga aatacaagcc   74160
tcttgccttc cgtgctgggg tccccaccct ccatcttcct ccttcacaca ttctcacccc   74220
caacccctca cgtgatgtca gggatcttgg cagtgttgag aggaagatgg cttgtgtgtg   74280
gaaccattag aaaagaacag aagatggcca ggtgcttccc gtggttggcc tgggaaatca   74340
gtctggggct tttgccttttg acctcacagg aacagtcatt tggaaagtag gagggatcac   74400
attaaagtgc ttttctttt tcttttttga tagtcaaacc taacagacgt gtgggaaaag   74460
ttccaattga ttacaaatca tcaaaaagtg acaataccct gagaggagat acgttacagt   74520
gtctattccc agttgttatt actaatactt agtgggtgat attggctaag tttgtaaatt   74580
tcactttgcc tcatctgtaa aatgggtaaa ataatgttgg tgaagattca gtgagatagg   74640
catataaatg ctcatctcag ctcatggctc attctaggca ctcactaatt attgttgtgc   74700
cagtagcaca actattattg cacacaatta ttgcggcagc aataataata acaagagcat   74760 cttttttgtca tccgtaactt ggaccttcag tgtggctaat tcagtgcaga aatgctcctg   74820
ccgctcacca gttgggtaga caggtctcca gtagctggag tagcttctct gtcatctcct   74880
tggggcatct ccgaagacca aagtggctgg gagttggcga gggtgaggga ggggctgtcg   74940
aggggtggaa gtgatgagtg ggtggcttta tagtgacgtt tgtaagtcag aaagaattga   75000
gtgagaaacg tgctcgggtg cagtcttccc cgactggaga tccttcatat aagcaagggg   75060
aaaaaagtca agaaatgact ttttaaaaaa gaagtgactt ttttaaaaag agagaaatct   75120
tttggccttt tttatcaagt aatttgataa atgtttagcg tttcttatac agacagagga   75180
gcctggtggg ctacagtccg tggggtcata agagtcagac acaacctagt gactaaacca   75240
tacagctctt aggttttgtt gttcttgttt taccgtcttt agtgatgccc acaaaaggga   75300
gatgcatttc tagatagtgg gtattctttg agctaattaa attgacctta tgtccattct   75360
ataatgtgtt tcaaacactt aaaaaattta acaattgaga tataattagc atagaacatt   75420
gtgttagttt taggtataca acataatgat ttgatgtatg tgctctgagt gcccaattgc   75480
tcagtcgtgt ctgactgttt gcaaccccat ggactgtagc cctgccaggc tcctctgtcc   75540
atggaatttt ccaggcaaga atactggagg aggttgtcat ttcctcctcc agggactctt   75600
cctcacccag ggatggaacc cgtatctctt gagtctccgg cattggcagg cagattttttt   75660 accactgcct caatgaattg atatacatag agctgaagga tcacgaagga ggtctagtta   75720
acacccatca ccccacatac ttacagtttt gtttttcttgt aatgagaact tccactctct   75780
```

```
tagcaacttt caaagataca taagatggta ttattaaccg tttactatcc caaccctcaa    75840
atacgttcta ttttgtttg tttcatttca tcttgtccac gaccttgttt tcctgtccag    75900
ccttcctcct accagagatg acatcttgac tgtggttcat tcttctcttt tcagagtctg    75960
acccagtacg tgtagaatgc gtggagaccc cagtacgtaa atgctgctgc tgctgctgct    76020
aagtcgctcc agtcatgtcc gactctgtgc gaccccatag acggcagcca ccaggctctg    76080
ccgtccctgg gattctccag gtagaacact gnnnnnnnnn nnnnnnnnnn nnnnnnnnnn    76140
nnnnnnnnnn nnnnnnnnnn nnnnnnnnnn nnnnnnnnnn nnnnnnnnnn nnnnnnnnnn    76200
nnnnnnnnnn nnnnnnnnnn nnnnnnnnnn nnnnnnnnnn nnnnnnnnnn naaaaaaaat    76260
tccccaacaa caataaagct aagaagaaat aattcggttt tgttacatcg cagggtgaga    76320
agtgaatttg agtctctgtt gctttggtgt ttgtgtttcg tctgtcatta caaaattggt    76380
taaaaacacg gttttatagg ctgcactgta tattgtaatt tatcaaggac agaaaagagg    76440
taaatccttc catctccgtc ttgtggtttt tgacagctgc acagattgta aacacaagct    76500
ggaatcacac caaaacggca tcgcttgttg ttgctcagtt gcgtccaact cttttgcgacc   76560
ccgtggacta tagcacccca ggctcctttg tcctccactg gtacctggaa tttgctcaaa    76620
ttcatgttca ttgagttggt gatgatatcc aaccatatca tcctctgccg cccccttctc    76680
cttttgcctc caatcttccc agcatcatgg tcttttccag tggtattccc tgctgattgt    76740
acagacaggg gacatgtgat taccaagacc ctggagtggt tgcaggagaa aatcaggtcg    76800
ggttaactat ccagttggct catctaatgc cagagcttta cctccttgga tctcatgctt    76860
ggattgtttg ggagttgctg gaggcagagc atcaactcct ttctctcctt gtaagaatct    76920
cccccctaaa taagctaatc tcacatttcc cagtcacagg tctcttttc cttctggtct    76980
gatccttctt gtccctcaag cttggcatcc tcttatttt ccttgcatcc acctctgaca    77040
gcaacagtaa tcctagtaaa atatagtcac acatttcgtc aaagtcgcaa gatgctctga    77100
aggttgagac agagacgtca ttttattcag tagaggccgt tttctttc atcctcactt     77160
atgtgtaagc aggccttaca tttcatcggt ttgtctcaca gttgcctctt tgcagcagca    77220
gagatgcccg aatctctgtg cttggacaca ggattctgct tgcatcaggc agttctacag    77280
agacagaggc tggcgggcct gttcaacgcc atctgctttc acaggaagat taaacacacg    77340
cgtgagaccc agggtggacc cacctcacat gtgcacaaga tgcttcacta gcgtgtgctt    77400
cgcaggcaga tgagagaacc agcagggccc tccatgagtt cttagcagag aaattgctgg    77460
aggggtttcca acaattcctc tgttcctccc ctctgttcct tgtctcatat ttttcttccc    77520
tttctttcc tcctccaatt agaggccttt gagataataa gctaacactt actaagtata    77580
tgctctgcat caggcatgct gacacataat aacccatttt agcttcacag aatatgaaga    77640
taacccattt tatcttccct atgaggtaga tgggaacagt tagtatcact gtttctttct    77700
ttatttttat ttcatttatt tatatatata tatgtttaat caatgtataa ttaatttaca    77760
atgctgtgtt agtttctggt gtaaggcaaa gtgattcaaa tatatgtatg aatatataca    77820
catatttgtt ttcagattt ttttccactt agattattat aagatgctga atatagttcc     77880
ctgtgctgta tggtaggacc ttgttatttg aatatttct atatagtagt atgtatctgc     77940
taatcacaga atcttaattt actgagaggt cccgccaacc cctgttatcc cctttggtaa    78000
ccataagttt tctttgcctg tgaatctatt tctatttaa ataagttcat ttgtatcata     78060
ggtggctttc ccggtggctc agatggtaaa gaatctgcct gcaatgcagg agacctggtt    78120
tgatccttgg gttgggaaga tcccctggag aagggaatgg ctaccgctc cagtgttctt     78180
```

```
gcctggagaa ttccaaggac agaggagcct agagggctgt agttcatggg gtcacgaaga   78240
gtcagacatg actgaatgac tgacacacat ttgtatcata tttgagattc cacatataag   78300
tgatatcata tgatactttt ctttctctga cttcacttaa tatgctaatc tctgggtcct   78360
ttcatgctcc tgcagatggc attgtttcct tcttttatgg ctgagtaata ctccatcgta   78420
tatatgcacc acatcatttt atccattctt taggttgttt ctgtgtcttg gctattgtga   78480
atagtaccgc tgtgaacaaa ggggtatgtg tatctttctg aattagaatt ttctctctat   78540
gcctattagt gggatttcat gatcatatga caactctatt tttaatgttt tgagtaacct   78600
ccatactgtt ttccatgtgg tgctagtggt aaagaacctg cctgccaacg caggagactt   78660
aagagattca ggagaatccc atggacagag agcctagtg ggctctagtc cacagggtcg    78720
caagaagttg gacacgactg aagtgactta gcacacgtgc acacacactg ttttccatgc   78780
tggctgcacc aatttgtcct cccaccaaca gcatttcttc cacctcctc cagcatttgt    78840
tgcttgtgga cttttactg atggccattc tgactggttt gcagtgatac gtcgttgtag    78900
ctttgatttg catttctcta ataattagca gtgttgagca tattttcaca tgcttattgg   78960
ccatcagtat gtacttcttt ggagaaatgc tcacttaggt cttctgccca cttttaatt    79020
gggttgtttg ttgtatcagc tatttgtata ttttggaaat taagccctgg ttgactgcat   79080
catgtgcaaa tattttctcc cagtccatat gttatctttt catttctttt ctgcacagca   79140
aaggaaacca taaacaggct ttataaacag ggtacatata cccctgtgtt cataaccagg   79200
tttcctttgt tgtgcagaaa cttataagtt tgacagaggt ccccttttgtt tagttttgct   79260
ttcatttcta ttgccttggg agatggacct gaggaaacat cacagcaatt tgtgtcagag   79320
aatgctttgc ctatgctctc taagagtttt atggtgtcat gtcttatatt taagtctttta  79380
agccatttg agtttatttt tgtgtatggt gtaagggtga gttctcactt cattattta    79440
cacgcagctg tccatctttc ccaacaccac ttgctaaaga gactgtcttt tctccattgt   79500
atattcttgc cttctttgtt gaagattaat tgatcataga tgtgtgggtt tacttctggg   79560
ctctctttc tatttccttg gcccatttgt ctgttttggt accagtatga tgctgttttg    79620
attattgtag ctatgtagta ttgtctgaag tctgggagca tttgcctcca gctgtgtcct   79680
tttttctcga ttgctttggc agttctgggt cttttatggt tccaaataca ttttaggatt   79740
atttcttcta gttctgtgaa aaatcctgt aatttggtag agatggcatt aaatcccctc    79800
tgcccattct ataactgagg aaacaggcac cagaaaccta agtgacttgt ccaaagttaa   79860
gatgtggtag aagcaagctt tagacccaag cagttggccc taagtgcaag cttggagcca   79920
ctaaacttca ccatctcatg acagtgaacc aagcttacct tgcctatgct ctgggaaaaa   79980
agaccaaagg cagagagagg agtgaggtag agtggtgttg tgtgtgtgtg tgtgtgtgat   80040
tgcgtgtgta gagcctgacc tgctgttctg tcatgtactc tacgattaaa ccaagttgct   80100
gaacctctcc atttctcagt tttcacatgg gtaaaactgc aggattttatg aatagtactt  80160
aactcctccg agggttgttg tgatgattaa atatgctata aagttctgag aaccgaggct   80220
ggtacagggc gcctatgctt aatcaacatt agccatgatc ctgctgccat cattcatgcc   80280
agtgcttggg gaccaccgct ccgcctcttt ctcctagact gatggtgatg caaatagcac   80340
ttctaacaca ttccgggccc ctgctgcctc tagtctggga tccacacttc aaggatcact   80400
gaggaagagg atccagagct ctcgctatcc tagcagccca cattctattt ctttccatga   80460
gctctgttgg agtcttttg ctttctagag tgaagggacc cagggactgt gtcccagcct    80520
ggagggctgt caatgaccag tgatagatgc catctcagaa cctggccagg gcctgagttt   80580
```

```
cagcaggatc tgacaggtgg tgagtttcag ccatgaggag actcacgtca gtgggggcta    80640
gcaaatgtgg aacatgaaat aggcagagaa acactcctgg aggagcagct ccatggaaaa    80700
actggacgat tttagaagta ataggagaag agagaaaaga attttcctcc cctgaaaaaa    80760
aatggccttt gatcaaagat gcaagcaatg aaggaaagtc aggagaggag gggagggacc    80820
ctgatcacaa cattcatagt tggaattgtg gggcttgtaa gaggcaaaat ttggtctgac    80880
ccaggcagat gacaacttgt cttttccaaa gtaaaaggag agataatata aataagaaaa    80940
aagtggaaac tgcagtcatt ttcctacctc tggggaggaa ggggagtgag gagtgagttg    81000
gcctgttcag agtccttaca tggtctggat tctatctagc tcactctctg tcttagtagg    81060
tggagtgtga tggggttccc ctcctaaggc tccagaccct ggaaccccCC tgcatcccag    81120
cacctggaga ggctctctgc aggatgcaga gctctggaaa aagggctcc  acttccagac    81180 tgcgcgcata cagctggatg tggcctgtac tgtagctgct gcagcggcga tgcttgctgt    81240
gtccaggcct ctcacagccc caggctctgt cctggactga ctcacagcaa tggctgtgag    81300
aaagttcctc tgccttggca ggagagaggg ggagggaact ggtgctctct ctgggtggcc    81360
tgctctgccc tcactcgccc ttacagactc ctcggagctg tcctagccag gctgggtacg    81420
tgccaggcct cagcccagca gcagtgatct gcaccttgga ttcctgatga agacaaaata    81480
attttcagtc ccagctacaa ccggctgact accaggagaa ggcgctgagc agagtctgct    81540
gtacctccac acttccatat cctcagcttt ctgctctcga tggcagacct ggctggtcca    81600
cttcacatca gtcgtcaact ctcactgagt tgcgagtgaa aatgaaatga aaggaactga    81660
aaagcactaa aacacctaaa tgcccatcag cagatgaacg gataaagaag atgaggcata    81720
taaatacaac agaatattac tcagccttaa aaagagtgat ataatgccat ttgcaacaac    81780
atggttgggc ctaaagatta tcataccagt gaagtaagcc agacagagaa gggcaaatat    81840
atgatattgc ttatatgtga aatgtaaaaa gagaaaatga tacaaatgaa cttatttctg    81900
aaacacaaat aaaaactcat agacccagaa aagaaacttt tggctcccaa aggggaaga    81960 gggtgtagaa gaagggacag attaagagac tgggattaat atacacacat atgcacacat    82020
tgtgtataaa actgataacc atcaagggcg tactatataa tacaggaaac tgtactcaat    82080
attatgtaat gacctataca ggaaaaggag ctgagaaaga atatatatat ataaaatcaa    82140
actgtcatgc tgtacacctg aaatttacat gatattgtaa atcaacttcc cagatagtac    82200
tggtggtaaa gaatctgcct gccaatgcag gagatgcaag agatgcaact tcagtccctg    82260
ggttgggaag atctcctgga ggagggcatg gcaacccact ctagtactct tgcctggaga    82320
atcccatgga cagaggagcc tggcgggtta cagtccacga ggtcgcaaag agttggacat    82380
gactgagcac acacactgat tcactgatat gtcaattaaa ttttttttt  ctattttaaa    82440 gaaaagtgct aaagcaccct actcgggtgg agcatgccaa tctggtcttt gatgggtctc    82500
atggtgggcg tagggcggc  tggggggttt ctgtacagac aggaaacttg gcttatttgg    82560
agactctcag ctcttgactg gaacctttct cagaagaagc agttttcaa  gagagtacgc    82620 tttttatgtt caagaagatg atggtgtatt taaaatgctt cctcctaaac acatcccttc    82680
cacttctccc tctgcttcca ttaattccga gaatatctac aattccattg acaacctctt    82740
gttggctcag acttatggga tgcagagctg tgtgcccgta ctcttgcagg tggggtgatg    82800
gctgctgtca gagagcttcc agttgagcct atcgaataaa gtataaacac aggaaaaggt    82860
aactgacttt ttacaggatt ctcaggcttc cctggtggct caggtggtaa agtgtctgcc    82920
tgcgatgcag gagaccgggg tttgatcgct gggtcaggaa gatcccttgg agaaggaaat    82980
```

```
agcaacccac tgcagtactc ttgcttggaa aattccatgg atggaggagc ctggtaggct   83040
acagtccatg gagtcacaga gtcagacgcg actgagcgac ttcactttct tctttctttc   83100
agtaatccta ggcttcccag ggggcgctag aagtaaagaa cctacctgcc agtgcaggag   83160
acataagaga cgtaggttcg atccctgggt cggggagatc ctctgaagaa ggaagtggca   83220
gcccactgca gtattcttgc ctggaaaact ccatggacgg aggagcctgg caggctgcag   83280
tctatggggc cgcaaagagt cagacacgac tgagcaggcg cacacacaca cacacacaca   83340
cacacacaca gtaactctaa tctggtgttc agcagccacc tacccaatct ccagctctgg   83400
cccaggctcc gtgctcccct gatggccccc atggttccat gaccacctga ggtgcagctt   83460
cttgtctcta ttgggaaacc cagccttccc cttccagccc agtcccatcc ttctcccttc   83520
tgagcaacag cctactcatt ttccatgggt ttggtgatct atggtgaggc cacagcattg   83580
gttgggtccc tttggagatc cgcatacttg tgctgagaac tggcttgatt ttattttta   83640
tttatttttt aattttagg gctaagtgat tttattttta ttcttttaaa tttttcatc   83700
aattaattag gctgcaccag gtcttagttg tggcactcgg gatctttagt gcatcttgtg   83760
gttccgtgtg tgtgtgtgtg tgtgtgtgta agttgcttaa gttgtgtcca actctttgcc   83820
accctatgga ctgtggcctg ccaagctctt ctgtccatga gattctccag gcaaaaatac   83880
tggagtggtt tgctattgcc ttctccaggg gaacttccca agccagagat caaacccccca  83940
tctcttacgt ctcctgcatt ggcagaccag ggatcaaacc tgggccctct gcattgggag   84000
ggccagaata ttagccacag gaccagggca gtctccttga tttttattta aaagactgtt   84060
ttttgacatg agatctaacc tctgcaagtg accttcctgg acaatgagga tgtaatggtc   84120
ttcactctgg aaattggagc atctgctctc ctactggctg aagaagcatc ttaaaacata   84180
aaacccactg taaatgagaa caataaacaa tgattcccaa tcttgcctac actttgtaat   84240
cacctgggga gctttaaaaa taccaggtgg ggctccaccc gcagaggtct gatttactgg   84300
ttggggtgca tctgtggctc cagagacgtt cgaaaacacc cgggtgactc ttggtgagtc   84360
gccaggttgg aaacagctat ttggacggct gcctgctgac tcttttcagg cagatcttta   84420
attggtaact tgggggacac acaatggcag gcagaattgt gaaaactaaa gcacctaaga   84480
attgatgttt ttgaactgtg gtgctggaga agactcttga gggtcccttg gacagcaagg   84540
agatccaacc agtccttcct aaaggaaatc aaccctgaat actcattgga aggactgatg   84600
ctgaagttga agttccaata ctttggccac atgatgtgaa gagcccactc attggaaaag   84660
agcctgatac tgggaaagat agaaggcagg aggagaaggg gatgacagag gatgagatgg   84720
ttgaatggca tcaccgactc aatggacatg agtttgagca aactctggga gttggtgatg   84780
gacagggaag cctggcatgt tgcagtccat ggggtcgcaa agagtcggac acaactgagc   84840
aactgaacag caacaattca gaatatgtta cagaaaaaaa aggggacaag gagacaaaaa   84900
caggatctgc ataggtgaat tcagaatgat gattcttaac tggcctaaac ttctggacta   84960
acgcaaggtg gcaaacggtg cagaggagat gagagacagt cttgctcaca aaaaagctca   85020
aggccaaaga ggagacactg agagcagctg actttcccca gaccgggaaa agtcgtctgg   85080
gacactccca ggggagcacc agatggtgag ggatttacct gtggagtcag agcagtcttg   85140
tctgactgtt aggggatgtc taaggggca gatgctggga ggaattgggg gcaggaggag   85200
aagggggacga cagaggatga gatggctgga tggcatcact gactcgatgg acgtgagttt   85260
gagtgaactc cggggagatgg tgatggacag ggaggcctgg cgtgctgtga ttcatgggat   85320
cgcaaagaat cggacacgac tgagtgactg aactgaactg aattgaaggg ggcagacagg   85380
```

```
aaggaccatt agttctcaaa acaaccaaag ggaaccaaag cctagagcag accctctccc   85440
tggaagatga aaggagggac gttcacagag gctgggggtg catgtgagcc ataacccctg   85500
acttgaggag ccctcaggtg gggcctggac actcaaagag ggtgaggaca ccatatgggg   85560
tgtccctgtc ggtccggtaa ttaagactcc acgcttccaa tgtaggggct acggttcagt   85620
tcctagtcag ggaactaaga ccctacatga aaaaaaacaa aagtgaaagg gcgaccccat   85680
agactatagc ctaccaggct cctctgtcta tggtattctc caggcaagag agggttgcca   85740
tgccctcctc caggggatct ttccaaccca gggatccaac tgagtctccc acactgccgg   85800
cagattcttt actgtctgag ccaccagggc agcccagatg tcacatatgc cccctaagaa   85860
aagatagggt gagacaagtg cctctcttga gtgttcagcc acagggctgg ggtgcacagg   85920
gcgccgctct ctgtgatcgg gaaggctggc ctccctccat ggactattcc agagacagtg   85980
cagggtgtac gttctgcaag tgggcagcac cgtggcacgt ccactgccta tcactgtggc   86040
acccaaatcc tatgtcctat agtcaagctc aggtttcccg tgaatccaag gatgaggaca   86100
cgtgagttga gaatctgatg ggtcttctgg tggagaagtc tctcctcact tagatgtgaa   86160
cccaggagtc tcagtcccct tctgtaactc accattcatt attcctgtaa gggaaaatag   86220
acaccctctc ccccattaga catgggtcag cctccatgat ggatgccctt caggactttg   86280
gaaatgcaga ggaaaaagaa aagctgtctt gttttcttg accaatccag atgggtttct   86340
ggcagctcct agggaaaggg actgggtgag gagggctaag atgtgacagg accgtgccaa   86400
gagactcagg cttcatccag cccagtgtat ttcaaacagc acattgtaac ctagtagacg   86460 cttaaaact tcagtttgaa tcgtgaccaa cattttaaaa ataataaaca gaaagtatca   86520
gtgcactgca tattgtaagg gttatttggg ggcttcccag gtggcgcagc tagtaaagaa   86580
tccgcctgcc aatgcaggag atacaggaga tgcaggttca atcctgggt caagaatatc   86640 cctggagaag ggaatgatac cggaacccac tccggtatcc ttgcctggag agaattccat   86700
ggacagagga gcctggtggg ctacagtctg tggggtcaga cacgactaag agtcagatac   86760
aactaatcag gcacgcaagg attgttttct gaaaatctga ttcagttctg cctgtgtctg   86820
ttggacattg ccgtgtgtaa cacattttac tgcaagtctt gagtaaataa ataaacagct   86880
gcctccttga acagcagaat aaaaataacc atttttttcc cactcagggg ctgagtaatt   86940
caagattgcc tggttgggag agttctatta gccttgctgt gaaaattcag ggttattttt   87000
tagtaagaga cacgctggca gcagaaagta ctttgcctgt gcctctaaga gcctttggga   87060
aggacgctgt ctccactcct ttggttcagg cccctgggag cttcagaagt tcgtccacct   87120
ttcaggtggc ttttcctcgc tttttttttt tttcctgtga ctcatcttgt cacttgtatg   87180
ctgctcccct taggtttgaa cccaaatcaa atgcctctgg aatagggctt tatcttcacc   87240
aggcgtcatg tcttagaatt ttcacggatg agctaaagct gtcacaataa caaatggagg   87300
aaaaaaaccc tgccacccaa agctgtcatt tgtgtttgct aggcgagacg aaaaggtacc   87360
atggaggtac tttgagtagt tgatggtgaa atgaaaagaa aactgggatt tggattttac   87420
tttcggaaaa ttagtgtcgg ctgatgggga gtgacagctc tcttggggtt tgagttgaaa   87480
attcacattc aaggttttat ttgaaacatc aaaagccttt gtccttcggc tccttccatt   87540
ccgagaatag cctaatgtca tctacattgc atgtgaagtg gaaaggtttc tttctcttct   87600
aaagctcagg gaagttgttt gttgtttttt ttttttttaag caatacagta ttacaaggtc   87660
ttgacataga ttacaggaaa actttggcct ctttcttgtg gaactattct gacttttctt   87720 tttttgttaaa acagatcttt gagaaacccc tcaaagtggg aggggtgaat tgggagattg   87780
```

```
ggattggcac atacacacag aaagtgttag tgatttgctg ctgctaagtc gcttcagtcg    87840
tgtccaactc tgtgcgatcc catagacggc agcccaccag gctcccccgt ccctggttta    87900
gtcatgtcca aatctttgcg accccagtga ctgtagccct ccgggcccct ctgtccatgg    87960
aattctccag caagaatact ggagtgggtt accatgcctt cttccagggg atcttcccaa    88020
ctcagggatc gaacccaggt ctcccgcatt gcaggcggat tctttaccgt gtgagccacc    88080
caggaagcca ctactgtgta taaaatagat aacaatctat tcgagattga aacctgctg     88140
agagacctgc tgcataacac agggaactct attcagtgct ctgcggtgac ccaaatggga    88200
cagacattca aggaagaggc agtagatgtg tccgtatagg cgatgcactt tgctgtacag    88260
cagaaactaa cacaccgctg taaagcagct ctactccaac ggaaaaaaga gaaagaaagt    88320
cctcttgagt tcttcctgat tattatccta aatatgagtg tgccatctga aatgtagaca    88380
gaatgtgtgt ccacttttct ctgcctggag gagagtgaac tgccctcgta gttacccttg    88440
ttctgctcat cagaagaaaa tgcacgcacg gtttctctca gaggcagtac ggcccagcac    88500
cacctggagg acaggcgctc tggccaggat gtctaggttt ttacctttct gctgctgctg    88560
gctgccccca ccacccacag tcagagataa cagcagttca gaggatattt atcagctgtc    88620
tactctgtgt cagccactgg gcatccctca tctttaatcc tgaaaacaag ccttcctgac    88680
ttgtttattt ctcctcattt cacagatgag aaaactgaga ctcagaaagg atcagaggag    88740
acagaaacat acccacctgt acatcttttt ataatatttc ttgttatctg actttgcatt    88800
tcccacttat cttagagcct gcttaattgt gagcagaaaa gtgcagtagt cacttagtcg    88860
tgtctgactc tttgtgaccc catggactgt agccctccag gctcctctgc ccatgggatt    88920
ctccaggcaa gaatactgga gtgggttgcc atgccctcct ccaggagaat cttcctgacc    88980
cagggatcga accagggtct cccgcattgc aggaggattt gttaagtatg aatatattta    89040
atttcttgaa tcataaaag ccagcacaaa gcaaggttta acccatattc ccacatgctg     89100
gccctctgtg ttcaactggt tggtatgtta atgtgtgaag caaagaagaa aagatgacat    89160
ttagtgtctg tgtgttggct ctcagtgaca tttgtttcct ccaaactttt aatatgaacg    89220
ttttcaaata cagagaattt taagaatag tacagtaaac accagcacat ctgctaccaa     89280
attcgacagt tattaacatt ttgccacagt tgctttatct ttaatttttt tctcagtcat    89340
ttaaaacctc tgggatctaa tactgatgat ctgagctgga gctgatgtaa taataataga    89400
aataaagtgc acgataaatg taatgcactt gaatcatccc caaaccattg cctcccacct    89460
ccaccaccct ggcccatggg aaaatcgtct tccccagtcc ctggtgccaa aaatgttgag    89520
gaccactgct ttaaaaccaa gttacacatg ttgtggccct ttcagttcag ttcagttcag    89580
ttcagtcgct cagtcgtgtc cgactctttg cgacccatg aatcacagca cgccaggcct      89640
ccctgtccaa caccaactcc cggagtccac tcagactcac gtccatcgag tcagtgatgc    89700
catccagcca tctcatcctc tgtcgtcccc ttctcctcct gccccaatc cctcccagca     89760
tcagagtttt ttccaatgag tcaactcttc gcatgaggtg gccaaagcac tggagtttca    89820
gcttcagcat cattccttcc aaagaaatcc cagggctgat ctccttcaga atggactggt    89880
tggatctcct tgcagtccaa gggactctca agagtcttct ccaacaccac agttcaaaag    89940
catcaattct ttggctctca gccttcttca cagtccaact ctcacatcca tacatgacca    90000
ctggaaaaac cattgccttg cctagacgga cctttgttgg caaagtaatg tctctgcttt    90060
tgaatatgct atctaggttg gtcataactt tccttccaag gagtaataat tccacatgca    90120
tccccctaaaa ataaggatat tatcataact taataataat atatctcatt tatattcaaa   90180
```

```
tttctcagtt ctcaaaacat cttttaatt ttattttg actccagatt taatcaagat    90240
tattgcatcc catttgatat ttattctctg tcttagaaa aggctctcaa ctttgacata    90300
aatgttttga agagaccagg acagtttttt ttgtagaatg tcccacattt ggagttgtct    90360
gattgttttc ttttctccct attttctgta taccaggagc tgagaataca agcatatgga    90420
gattaaagtt aagcctaggt ggcagcagtt cctccagggt gatgtgatgt gcttcatatt    90480
catcctgtca aaagacatct aatgtcaagt tcttccagca ttccctatgc taaatttctt    90540
ggttaggtgc cagattcctc ctttgtaaac ttttatttc tgcttcacaa ttagtctgca    90600
gtcccagggg tgattctctg agacctggag agtatcctgc tttgcatcac tcctctgatc    90660
tgattatctg agttatctgt attagtttgc tacggctgct ataacaaaga accatagaca    90720
gggtggctta agcaacagaa gtgtattgtt cctctgttct ggaggcctga agcctaaaat    90780
caagatgttg gcagggttcg ttcctcctga gggcccaag ggaaggatct gttccaggct     90840
tctctccttg gcttgcaggg ggctgtttca gtttatttgt cttccctctg tgtgtgtgtg    90900
ggtccaggtt tcctcttctt ataaggacac cagtatactg gatcaatgga gaaggaaatg    90960
gcaacccact ccagtgttct tgcctttaga atcccaggga cgggggagca tggtgggctg    91020
ccgtctatgg ggtcgcacag agtcggacac gactgaagca acttagcagt agcagcagca    91080
tactggatca gggcctatcc tgtcctacac actccgtctg taaagactct atgtaaggtt    91140
acattctggg tgcatctggg agttaggaat tcaatacatc agttttggaa ggacaaagtt    91200
caactcataa caacatccat tgatgattct tgccagaatc cattacttat tgggatctca    91260
ggttgggttc tttgggaaac agattttgag atgcagactc aaaatctgtt tattgggggg    91320
ggtatatcag ggactgggct tggttatgac ttttgctgtt atgggcccct tctgccatca    91380
ggaaaattag aaattatatt ttataaccgt tgatataaag acacatataa cctaggctgg    91440
atttgttatt atatatttac tgttatgttt gttttccttc tgaagaaaat atactgtgga    91500
cttcagagc tgtatcttct gtgcctaata gataaggcct cggccctgct ccagatcaga     91560
ggctgggcgg gtgataagcg aagagggttg accctagagt gtccttgtgt atggggttag    91620
tggggcagc gtcagaaggg aagggccatt tagctcctga tgtttccagc tctctctatt     91680
tttcagaaga aggtagaaac tgaaatttta aattttgaat cagcagaaac taacacaaca    91740
ttgtaaagca attatcctcc aattaaaaaa aatcctatga ttaaaaaaaa ctatatataa    91800
aataatccac aaggatattg cttctaggcc ttttggctaa gatcaagggg acaagcatat    91860
attgtatagc aacggggaat acagccaatg tattatgata agtataaatg gaatatagcc    91920
tttaaatttt ttaatcacta tgctgtacgc ctgatgtgtg ttagtcgctc agtcgtgtca    91980
gactctttgt gaccccatgg actgtagccc tccagnnnnn nnnnnnnnnn nnnnnnnnnn    92040
nnnnnnnnnn nnnnnnnnnn nnnnggatc aaaacctggg tctcccacat tgcaggcaga     92100
ctctttactc tgagccacca tggaagcgcc tgaaactaat ataatattgt gtatcaacta    92160
tacttcaata aaaataatcc taataaatgg gcttcccagg tggttcgttg gtaaagaatc    92220
tgcctgcaat gcaggaaaca ccagatcgat ccctgggcct ggaagagtcc ctggagaagg    92280
gaatggcaac ccactccagt attcttgtct ggaaaatccc atggaacctg ccaggctaca    92340
gccatggggt gacaaaagag tcagacacga cttagcaact gaacaacaac aacaaataaa    92400
taaataaaat ttgaaatctt ttttttgggg ggggccacat cactggacat gtgcgatttt    92460
agttccccaa tcagggatgg aacccatgct tcttgcaagg gaagcagaga gtcctaattg    92520
ctggaccacc caggaatttc ctgaaatcct gtattttaa ttttcacttt tgtttttttt     92580
```

```
aaatctgtgg gcggattgta gcctgagggc tgccagtttg aggagctgtc ctgccatcag   92640
tctcctgggg gacagctatt gaccatttcc gtgctgagta ccttctagac agccgggcac   92700
acggaaggca ttggtgtgtg cttgtcgagg aagggaagaa ccaaatattt tgctaaggca   92760
acttataaaa tcaggttaga cttttgctt cagaacctgt gacgatcaga aaagcaggcc   92820
```

```
actcatgtct gttgagtcag tgatgccgtc taaccatctc aatctctgtt gcccccttct   95040
cctgccttca attttcccca gcatcagggc cttttctaat gagttggctc tttgcatcag   95100
gtggtcaaag gattggagct tcagcttcag catcagtcct tccaatgaat agtcaggact   95160
gatttccttt aggatggact ggttggatct ccttgcagtc caagggactc tcaagagtct   95220
tctctaacac cacagtttga aggcatcaat tcttcggcgc tcagccctttt ttattgccca   95280 actctcacat ctctgtgtga ctattggaaa aaccatagct tttgactata cacaccactg   95340
tcggcaaagt aatgtctctg cttttaata tcctgtctag gttggtcacg gagaaggcaa   95400
tggcacccca ctccagtact cttgcctgga aaatcccatg gatggaggag cctggtaggc   95460
tgcagtccgt ggggtcgcta ggagtcggac acgactgagc aacttcactt tcactcttca   95520
cttttatgca ctggagaagg aaatggaaac ccactccagt gttcttgcct ggagaatccc   95580
agggacgggg gagcctggtg ggctgtcgtc tgtggggtcg cacagagtcg gacacgactg   95640
aaacaactta gcagctaggt tggtcatagc tcttcttcca aggagcaagc atctttaat   95700 ttcatggctg cagtcaccat ccacagtgat tttagaggcc aagaaaataa agtctgtcac   95760
tgtttccaat gtttccccat ctgttgcca tgaaatgatg ggactggatg tcatgatctt   95820
tgttttttga atgttgagtt ttaagccaac ttttcacgc tcctctttta ccttcatcaa   95880
gaagcttatt agttcctctt ccttttctgc cattagggtg gtgtcgtact gaacaaatat   95940
cgataaatca taaaatcata aagtaatcct gattttatg tttttttgc atttctagta   96000 aaatgttaca tgattggcag ctccaaatat agctcttctt atacatgtgg ccacttggag   96060
tagatgccag atattttag aaatgaactg aaagcggaac aatgttaagt ttctgacatt   96120
ttcttaagaa ccaaaagaaa ataaactcct cttctcctct cttcccccaa caattcagct   96180
tggtcaacat gttttacata ctttgcttca ggggaaaggc tgtcaacacc attcagtgat   96240
gattaagagc tcttaagatt cggtttaaca aatatcttat tcatcccag ggaccttttt   96300 tctttaatca gacctcttcc acaccaaggc ttgatggtat tgcagtgcca ttgttcttta   96360
agcagttcaa ttcttgtgtt tttatgtctt ggaattgttt tagcgatgct ttgaaggcag   96420 cccttttcctc gtcttgtaaa ttttaaaatc tacctgaaat aaggatttcc atggcagttc   96480
agtggttaaa acttcgagct tcccctgcag agtgcgtggg ttcaatccct ggtcagggaa   96540
ctactaagaa tcacatgctg cgtggtgcag tgaaaaaatg ataaataaaa aataaattta   96600
aatctacctg aaataaactt tttcactctg tacttgagaa agaaagaag gcaaggaaga   96660 gaaggtagga agagtgagca ccagttgtgg gtagggagat gagacctcgc tcctgggctt   96720
ctgtcctaaa catacttttg cttgcataag aaactaagag gagaagctgg gtttccttgg   96780
tcctagattc tctgcaggag ttacccagtg tcttgcaact tgaagtgtgg tccctgggat   96840
aatagcagtg gcattacctg ggagtttgtt ggaaatgcag aatctctagc tctgtccaga   96900
cttactggga ttaggtatcg gcaatttaat gaaacccta gatgatttat ggggcttccc   96960
agatggctca gtgggtaaag aatcctcctg caatgcagga gacacaagag acctgggttt   97020
gatccttggg ttgggaagat ccctggaaa agggaatggc tacccactcc agtattgttg   97080
cctggagaat cctatggaca gaagagcctg atgagcttca gtctatgggg tcgcacagtc   97140
agacacgact gagggactga gtaggcgtgc actaggtgat tgatgggcac attagtttaa   97200
ggagcactct ccttgttcgt cactctcctt gtccatcact cctataattg gctatataac   97260
tggaccatct ggagttaggt actccagcct cgtgggcata aggatctaga agatgtgtat   97320
agattttaaa gctcctcaag taatcctgat gcagctagtc cagctccaga aggagccctt   97380
```

```
tggtctagct gatagaagcc agcctcctag ggcacagaac agcaaaaaaa agagaaggtg    97440
tgtgtctgca agggcttgtg gagagtattc agcacaaggg atagtttcag cctactagat    97500
tccatcttcc atagcacgct tacatctgtc attctaaatg tgatcatata acactatttt    97560
aaaattgtgt gtatttcttg gtcaagaggg ctctccattt cggcgtgcag gctttctgcg    97620
tctggttgtg gcacacgagc ttctccaggt gtggagcgtg cggtctggct cgtgcaggct    97680
ctctagttgc cgtgcgaggg cttagttggc ccgtggcata tgggacctta gttctcccaa    97740
ctgggatagg acctgcgtcc cctgccctgc aaggcagata gattctcaac cactggacca    97800
cagggaactc cctgaccgtg taacattctt tagtggaacc ctcttgtcct caagattaag    97860
tctataacgt taagcacctt cctggtcggg tcactgcctg ttttttgcat tttgtttcac    97920
tccacatccc ctcccaggag ccagaccccg ccacttggca gggctccccc caggagcctc    97980
tgtgcctttg cgcacaatgt cacctctgcg tggaacatca gtccctcctt tggggactcc    98040
ggtagcactt ctgcctctcc ttcactgtgt tcatcaccca catgtttact ttcttaacat    98100
acacgtagag attgcccaca agtaaagggg ccacgactgt cttggctgga ctggtaggag    98160
tagttttgat taggatcgga agtgaagatc tgtaatccac aatcaagaga caatccattc    98220
agtgaattct gtgtaaagag gaacagagaa agcgagtagg ttctaaatgg ggggagagtg    98280
tcaacagagg tttttaaatt ttgtttatta aaatgagaga aataacagct tgattgtagg    98340
ctatgggaat agtaagaggg tgttcgatac agagagaggg ggaaatggca gagcaactga    98400
ggaggacaga gtggataaga tgcccaagaa aggactggcc ttaaaggata tgtgcactgg    98460
ccatctgtag gaatggagaa atgcagggtg cacaggctcg ggcgctgaag ggtgaggggg    98520
tacaggtggt ggggcctggg gaagttctgc cctccaacag aaacaaccct atcatatgaa    98580
gtgggggagg gagactgggg aggggcaagg gtgatcaaaa caggtatgaa acagttgtct    98640
aggagggagg gagcccatat ggaccagggg aaagtaatat gatttctggg taataacgca    98700
agctgaacta tagttatggt ttatgaattt taaagtgaaa ccaatcagca tggttgcatg    98760
ttttccccta gctaagttat tataatggct ttcctgatag ctcagttggt aaagaatctg    98820
cctgcaattc aggagacctc gattcaattc ctaggtcgga aagatccgct ggagaaggga    98880
taggctaccc actccagtat tcttgggctt ccttggtggc tcagctggta aagaatccgc    98940
ctgcaatgca ggagacctgg gttcaatccc taggttgaga agatcccctg gagaagcgaa    99000
agcctaccca gtccaatatc ctggcctaga gtattccgac ctaagagtat tccatggact    99060
gtatagtcta tggggtcaca aagagttgtt atacaattat atacatacat tatataatta    99120
taatagttgc acaagtacca gctgacaata tatgtaagga cagacaagat tcctgccctc    99180
ctggagttta ttttttagatg gtattagatg aacaattcct tgtataatta caatatgatg    99240
atttgcatgt tggaaaacac agagggccag agagcatcta acagggatgc ctggctcagc    99300
ctgagtacct gaaatgacac ctgtggatac agaatgaggt cctggaaaag actcgaatgc    99360
ttaccttctt ttttgtttat gaaagtgaaa gagaagagtg aaaaagatgg cttaaaactc    99420
aacattcaaa aaactgaggt catggcatcc agttccatca cttcatggca aatagatggg    99480
gaaacattgg aaacagtgac agacttattt tgggggctc caaaatcact gtggatggtg     99540
actgcaacca tgaaattaaa agacgcttgc tccttggaag aaaagctatg accaacctag    99600
acagcatatt caaaagcaga gacattactt taccaacaaa ggtccatcta gtcaaagcta    99660 tggttttttct agtagtcagg tatggatgtg agagttggac tataaagaaa gcttagcgct    99720
gaagaattga tgttttttaga ctgtggttct ggagaaggct cttgagagtc ccttggactg    99780
```

```
caaggagatc aaaccagcct atcctaaata ttcattggaa ggactgatgc tgaagctgaa    99840
actccaatct tttggccacc tgatgtgaag aactgactca ttagaaaaga ccctgatact    99900
gggaaagatt gagcgtagga ggagaagggg acaacagagg atgagatggt tggatggcat    99960
caccaactca atggacatga gtttgagcaa gctctggagg ttggtgatag acagggaagc   100020
ctggcatgct gcaatccatg gggtcacaaa gagtcgaaca caactgaacg actaaactga   100080
atagatagca gggtgcaaca ggagagagga acatgctat gctatactct gcagttgctg    100140
ctgctgctgc tgctaagtca cttcagtcat gtccgactct gtgcgacccc atagtcggca   100200
gcccaccagg ctcccccgtc cctgggattc tccaggcaag aacactggag tgggttgcca   100260
tttccttctc cagtgcatga aagtgaaaag tggaagtgaa gtccctcagt cgtgtccgac   100320
tcttagcgac cccatggact gcagcctacc aggctcctcc atgcatagga ttttccaggc   100380
aagattactg gttgttagtg atctgctatg acttttatac tacttgtcat atattttgta   100440
aatcaactag gaaaaggagg ctttgcccag gacttcagaa tggtctaagt gaaactaact   100500
gaaggcagga aggatgctgg aggaaaatag gcagtacctg tgaaatgcaa gaaatctatc   100560
ttctcccttc tgttctgttc cctttctgtt gaatctagaa gatgtgggca cttccttcaa   100620
gacgcctgca gcccatgtgc cacagaggat aaggtggtga agaggaagga ggcggggatc   100680
acaaagactg ttggttattg tgccgtatgc tggaattact aagacaacac tgtaaatcaa   100740
ctcaattttt taaaatatta cagaatttgg aagatttaat agtcaaaaga agcccttgc    100800 ctgtaagccc acagttctcg tgaccttgta aaaatgttct gatttcgagt caagtgttca   100860
aatagtatct aggaggaatt tgccttggaa tctcaaatgt tataaatcca aacctttac    100920 tggaagacct aaggtctaat tgcaactctt tgttacagcg tctcatgagg tgagtggccc   100980
tagagggcca gcccttttatt agcccctctc tctcacatct ggtgggtcag ccaaacactc   101040
actggtgggg gggctaaaca ctcagaccct gaaccaacag caccagcgcc acctgcagac   101100
ttgttagaag caaaagttcc ggatctctcc ccggatctac tgaatctctg agagtagagc   101160
tgggcatctg cattttgcaa gaccccctggc ccttttaacgt tcaagaatca atggcctaaa   101220
atactattgg ctttttgtcc tagttctttc ttttcagctt gttcatcata tgttatgtta   101280
cattgggtcg gccaaaaagt tcattcgagt tcctccatac gatgttacag aaaacctgaa   101340
caaacttttt ggcctatatt gcattacatt atattatgtg tatacgtgaa acatgagtta   101400
ctcccataac tccccatgaa atcagaggtg tgaggaagca aggccagtgt agtcacacta   101460
ggtttcaagg actgtcccaa gaaatcagaa caggactctc tgcctcggca ctcctgacag   101520
tttggtcacg gtccttcttt gttgcaggca ttgcaggcta ctcagcagta tccccgcctc   101580
tacccaccag atgccagtaa cacccttcca gctgtggttt tgtgacaacga acagtgtctg   101640 gagtctttgc taaaggtctc aggaaaggga gtaggcaaga ttgctcatcc tcttgagaat   101700
ctccagctca gagtgataaa gagcgtgagt gtcgtcacag ggggttagcc gggaaagggc   101760
tagtttcaga ggcagtgggc tggcgttcac aactggggca gtagcactta ccagtgctgc   101820
ttgccaggcc tggctcacac tgtaggttca ctgctacgtt cagtccttac ggcgagcctc   101880
tagggcaggc tgtgttccca ttttatggat gaagagacca aggtctagag ataaagtcac   101940
actgaaaggt gatataccag ggattcagcc caggttcatc ttaaccataa tgctatatac   102000
ttacttatta ttactttagt acttaaagac tttctccatt ttagggataa agatataaag   102060
cccagagaaa gattccttt ctactgttaa cttacttact tttggctgcc tcgggtcgtc    102120
cttgctgagc accttgctga acgcaggctt cctctagttg cagtgaatga gggctgctct   102180
```

```
ctggttgccg gtgcacaggc ttctcattgc agtggcttct cttactgcag agcacaggct  102240
ttaggcgggc agtagttgta gcccacgggt ttcggtgcct cctcacatgt atgatcttcc  102300
cagaccaggg atcgaacagg tgtccctgc attggcgggt ggattcttaa ctactggacc  102360
accagggata cgtgctaagt cgcttcagtc gtgtctgact cttcaccatt ccgtggactg  102420
tagcctgcca ggctcctctg tccatgtaat ctccaggca agaatactgg actggggagc  102480
cactctcttc tccttcagat cttcctgacc catttgcttc attggcagat gggttcttta  102540
ccactaggaa gtccgcatta tttactcata tgtatatatg tatctctgtg tgcatctctc  102600
gattcatcta tggctgtgtc tacttttctc cactgatctg ccaaatctag gaaagactgg  102660
agaagagaaa caatcatttg ttggccagag ccccaaagtg accttcaaaa cacttgagcc  102720
aaaaaggcag atagccaagt gctttgtttt ctcccatgca ggctctgccc caccctgcc  102780 tctcccgcta catgtggccc tgatgccagg agccttcacc ctctgattcc tgcccctgc  102840 ctcacctccc tgcttctctg gtggaagctt gagttctcct gctgggtcc cgctgcatac  102900 ccgccttcca gtccagtgcg tggatattaa agcctccagt gagggatca gggatcatct  102960 cacaccatca aagggagccg ccaggagaag agtacaggcg gcctgggtcc acatgaaagg  103020
acagcttgct gtttccagct cccaaaccgc tgagcattta ccaagccccg tgggagtcag  103080
cgtggggtgc gggtggggg gttggaggga gtgcagtgca ctctgggtct aggtttctcc  103140
atttgtaagt tcaggggaag ggaccagatg gcctctaagg ggggacgtac attacagggc  103200
agtggtttct cagccccggt tgtgcatcac agtcccctct ggagagagat ccctgctctg  103260
tgggccctca tctctgattc actgggccct atggatctct cgatgaaagt gaaagaggag  103320
agtgaaaaag ttggcttaaa gctcaacatt cagaaaacga agatcatggc atctggtccc  103380
atctcttcat gggaaataga tggggaaaca ggggaaacag tatcagactt tattttctg  103440 ggctccaaaa tcactgcaga tagtgactgc agccatgaaa ttaaaagacg cttacttctt  103500
ggaaggaaag ttgtgaccaa cctacagagc atattgaaaa gcagagacat tactttgcca  103560
acaaaggtcc gtctagtcaa ggctatggtt ttttctgtgg tcatgtatgg atgtgagagt  103620
tggactatga agaaagctga gcaccgaaga attgatgctt tgaactgtg gtgttggaga  103680 agactcttga gagtcccttg gactgcaagg agatccaacc agtccactct aaaggagatc  103740
agccctgggt gttctttgga aggaatgatg ctaaagctga aactccagta ctttggccac  103800
ctcatgtgaa gagttgactc attggaaaag accctgatgc tgggagggat tggggcagg  103860 aggagaaggg gacgacagag gatgggatgg ctgcatggca tcactgactc aatgacatg  103920 agtttgagtg aattccagga gttggtgatg gacagggagg cctggcatgc tgcaattcat  103980
ggggtcgcaa agagtcggac acaactgagt ggctgaactg aactgaattg atggatctct  104040
caaatgttaa agatcccaga tgactgcaat gggcagtcag ggctggcgac cctggcacca  104100
ggggagaggg cttgggctgg actgagctgg ttttggggcc ccagctctgt ccttgtgaaa  104160
tcccgaggca tttaggctct ggccttcaat tttacacatc tgtgaaatgg ggattagata  104220
tctaccacat agaaacaaaa caataaaaga catactggtg aagtgcgggt ccatggcagg  104280
caggcagtga gagcagaccc ctttctccag cctccctgct gacactgtta ggcagtgcag  104340
tgcatttttc tttttttaat tggaatttta ctgtgcactc atttaagaaa ttatagaaac  104400
caacttcttt ttgcacactc tgtccccaaa taccgatttt ttcatctta ctgctcccgt  104460 aatagagatt gcaatgatct tatgcgtgca aagtatttga gggtgaatga aaagaggtta  104520
ttttaagacg tactgtacac actgaactga aaataaagtg aaagagtcac tcagtcatgt  104580
```

```
ccaactctttt gcgatcccat ggactgtagc ctgacaggct cctctgtcca tggaattctc    104640
caggcaaaaa tactggagtg ggttgccatt tctttctcca gaggatcttc cccacccagg    104700
gatcaaacct gcatcccctg cattgcaggt agatttttta ccatctgagc aaccaggaaa    104760
gcccaaacta tacacactac tatatataaa ataaacagag agcaaggacc tactgtatag    104820
cattattaat ctataatgaa tatatatata tacataccct ggtggctcta gtggtaaaga    104880
acccgcctgc caatgcagga gatgcaaggt tgatccctgg gtcaggagga cccctiggag    104940 aaggaaatgg agcctgctcc agtattcttg cctggagaat tccagtggag cctagtgggc    105000
tacagtccat agcgtcgcaa agagtcagat atggctgaag tgacttagca cacacatatg    105060
tatgtatatc ggagaaggca atggcaaccc actacagtac tcttgcctgg aaaatcccat    105120
ggacagagga gcctggtggg ctgcagtcca tggggtcgtt aggaatcaga cacgactgag    105180
tgactgactt cactttcact tttcacttcc atgcattgaa ggaggaaatg gcaacccact    105240
ccagtgttct tgccttgaga atcccaggaa cgggggagcc tggtgggctg ccatctatgg    105300
gttcacacag agtcggatgt gactgaagtg acttagcagc agcagcatgt atatatatac    105360
atatatatat atatatatat atacatttcc ccccccagac tgttctctgg ttttgtggtc    105420
cagagagggt cacttcagtt attctccaca cattgctcca gtggaggaat ccagatcggt    105480
gagagactct gccttccacc atggaagcca aagagaccat ggattctctc ttttgtcggt    105540
agagcgtgga ctgtgatccg aacactggca agtaggtgat tctgccttgg aatctttggt    105600
ctagatagat tcatgcatag gtgtagggtc aaacagacac tcttcttggc agctatgaaa    105660
gatttaaggg tccatggtgt gatatgtgtg cccacatatc aagtgtccat cctaggcaaa    105720
tggttgattt ttcttttgttt tgtcctatgt ccttttgtga catgtctatt ttattccacac   105780 tgagaaaata cacataataa caaaatctaa tagaagcttg gtcagttttt agtaatgact    105840
ttattgagct ataactcata ccatacaact cagctattca aaatgtgcaa ttcattaatt    105900
ttaaatatat tcacaggttt gtgtaacggt caccaaaatc aatttcagaa cattttatc    105960 actctttagc ccccaaaccc tatacctatt agcagtcacc catgcttctc ctccctgccc    106020
tccaccccat gcaacttgaa tctactgtcc atccctatag atggcaaacc attcttaaac    106080
tgggatttag actgtacctt ccttccttca tggaaaaatt cctgttcagg tcttatatta    106140
atcactttca gctgcagaac aaagtactcc caaagtcagt ggtttaaaac aacataggtt    106200
cattttctga tagtttatat ggagcaggga tccagattca gctaggctgg actgtctgct    106260
tcaaggtctc tcatgaggca gcagtgtgct ggccaggact gtggtcttaa ctgaaggcct    106320
gactggggaa ggatctactg ccaagctcac ttgcattgtt gttggcggga cttggttact    106380
tgaggactgt tgaaccgagg gcctcatttc ctcactgact gttggatgaa ggccaccctg    106440
agttctttgc cagcctagcc ttcccagtat ggcagcttac ttcaccaaac ccaagggaag    106500
aaagaatctg ctgacaaaat agaagtcata tcttttgtaa ccaaataatg gaatgatag    106560 tccctcaata ttgctatgag cctttggtta aagaaaatt actcaagggg agaagactac    106620
gcaaggctgt gaattgaagg gttaggcagc actggcgcca tcttggaggc tgtgaaccaa    106680
aaccctatcc tgcaacctcc tcgtgagttc cacagactac ttaatatcta tttaatacat    106740 gtcttttgg cttcagctaa ccagaattgg tgactcttat ttggttagac caatccgtgt    106800
gttgcttatt gttctgtgat tttgtgattc cagtttctat tactttagca ctttgctcta    106860 tgaggtgatga attacttggt aaagttattg acactgccca ttactccttt ttttttcaaa    106920
ggcatcaatt ctgtatctga ttattcacta cctcagagcc aactagccag cattcattga    106980
```

```
aacttgtttg gatattactc tccacaaacc tcatagaaga gaggttaaga atttctcaaa  107040
ctagccctat caaagtagga aaactgagac ctgctaaatg gaatatccca taaagcctca  107100
taaccagccc aagatttttt ctgtttatcc tcatttggac tatgaccaaa agattgcttt  107160
ctttcctaga cgttctgcag aattttagtt atcagaaatc tagtgcaaac tagcaagaaa  107220
agggaatttg ttggctcaca ttactgggag gaatactggg gaggctcaaa ggatgaaaag  107280
aacaactgta gaactccaag gcctgcagcc agtggctcag tgcagacagc tgtccttctg  107340
tctcttgtag agctggctct gtctgtcgtc ttcacatctt gctctccagg cctcattctt  107400
tactgtttca accacgcatt cgtctttaag ccagaagaga gaaagcttgg gtcaggtttg  107460
tattcccaga acacagtaga tgggggtaca atgcaaggcc aaggcctggg tcaaacagct  107520
acattcttgt tgccaaaaga aggaccatgg gaaaccagta accacaactg ccccgtgcag  107580
gctctgactc agacccgttg tcaggggccc agacatgagc agatcaacaa ggtaaatgac  107640
tcctgaaata ttgaagatct tgaaaaggac aagacaatgc catagtcatg gcaaggccct  107700
gagaaccatg gtttggaggg attgctttga ggccaatatg tatcatggag cctggggaat  107760
tcatcttatt gcactcaagg ttcagtgtct tagcccactg gcaagatagg gtcacattga  107820
atttttccat catagatttc acttgacagt tagaaaaaaa attattggca gagccatgaa  107880
ggccagggat gacataggaa atagctgtcc atttcatgga ctcatgacca aggttaaatt  107940
atgataacaa aagaggtcag agtgttttat ttactgctac tttctgtgat ttatgggcag  108000
attgttgctt tttgttttta acctttcaag gaaggaataa tttgtcaagt tcatgtcaag  108060
ttcactcatt aatcttagtg ccaagggtga gtcttatttt tagacccaca taaatatcag  108120
ggtcaagatc agtcagactt gacttttgga agctataata ttgtgctccc tttaaataca  108180
tatattgaca ctgaagttgc cctagtaata cttccaaaga agtcctacaa gggccttcct  108240
aagaacttgg cctgggtact gttcatgact actcatgtat ctattcacag ctggtcactt  108300
gatctctaac acttctttat ggagggcctt gtatgtgcta agtggtagaa acaattgtct  108360
aggactatct gcctgaccct gcttacatat aacctagttc aggactctcc cctctagtaa  108420
ggaagcagct cactttaaa tttagatttg gatccaatat taaggacgtt gggcttccct  108480
ggtggctcag atagtaaaga atctcctgca gtgcaggaga cccaggttcg atccctgggt  108540
ggggaagatc ccctgaagaa aggaatggca accccctcca gtattcttgc ctggagaatt  108600
ccatggacag aggactctga cgggctatag tccatggagt cgcaaagact cagacatgac  108660
tgaagtgact tagcatgcat gcgttaagga tgtagggtgt agaggtggtg gtggtggttt  108720
agtcgctcag tcgtgtccga ctcttgcaac cccagggact gccagactcc tctgtccatg  108780
ggattctcca gcaagaaca ctggagtggg ttgccatttc cttttccagg gtgtagaaa  108840
atgaaggtaa aacttacctg atatctcctg gaggcaaagg agagtataga gggcaagtac  108900
tctgttcttg gttcagacag acttgggttt gactcttagc aaagacactc cgcaaccttg  108960
tgatactggg aaattagtta gcttctttaa gcctttgact caataataat acagacctat  109020
aagggttgtt tgctatgttt taataagata attcaagtaa gacatttagc agtttgtggg  109080
aacattgctt taaaccact agaagaaaat aatctcagga attgtgattt tgatctcct  109140
ttctaccatg cgctcaacct ttcccaagtc ttgtacaaag aacaaatcac caccaccacg  109200
tgggggcagc gtgggtctc tgggcagagg ctttagaacc aggctgactt tggttatat  109260
gaaggattta actcagagac ttagtttctc agctgtaaaa tgagatgcta acacaggact  109320
aaagataata tatttaagtg tgtggcagat aataagctcc accgtaggtt gactttaaga  109380
```

```
aaattcccac ccagcgtgga gaaaaactgc atcactgttt acaataacca ggacgtggaa    109440
gcaacctaaa tgtccattaa cagagaaatg gataaagaag atgtggtaca tatatacaat    109500
agaatattac tcagccataa aaaagaccaa aacaacacgc tttgcagcaa catggataga    109560
actagagatt cttaaactga gtgaagtaag tcagacagaa aaagacaaat atcatatgat    109620
atcacttata tgtgaaatct aaaaaaaggg ctatgagtga acctatctat aaaaccaaaa    109680
tagagttaca gatatagaaa ataaccttat ggttcctgag gggtaagcag gggggcggat    109740
aaatgggaag attgggattg acacatacac acttctataa ataaaatagg tagctagtaa    109800
aaggacctac tgtataccac agaaactcta ttcaattctc tgtaatggcc tatgtgggga    109860
aagaatctaa aaaagagttg atctatgtgt ttacataaca gattcacttt cctgtatacc    109920
taaaactaac acaacactgt aacttaattg tatcctaata aaattttttaa aaataacta    109980 gatccccacc tggccatctc taccagccct gtcgtagtga cggtgatggt agaagtgagg    110040
agctctagaa gacaaatctc agctgtcctt gatgtcagtt ttagtcttat tcttactggc    110100
cctgagccag actttgctgc ttttaggtct ggcctgagtt ccttcaaact atttagaaga    110160
gccctgaaaa tgggcactgc catttaaaag agtcatcctg gcatgggtgc caattaagaa    110220
gcaagattag agatctattt cagctccacc aagagtggac acgtaagaat acaaatgcac    110280
actaataggc ctgtgatttt gtatcaagac tggcaagaaa tacattcgtt tgacatagaa    110340
aaagtgaatg ttccaaggtc ccagtttctt aaggaaagtt ctctctatgt ctctctcata    110400
ctggaaagct aaaaaccaat aaaaaatgcc tacctttttcc caagttattg attcttcaca    110460
ctgcatatgc ttctgacacc attccgcatg ggtccctatt cggaagagag aaaggttaaa    110520
agctctgaca cctgctgact ctctccctgc ttgtgtcttg cagcctactt ctgcttcctc    110580
ctgactgctc tgggtgtgac agctggtgcc catcgtttgt ggagccacag gtcctacaag    110640
gctaagctac ccctgaggat attctggct gctgccaact ccatggcttt ccaggtggga    110700
atggagggtc ctcactctca gggactcagc gcggacggca gtgtgggagg agacacagat    110760
gcacttcctg tacagtggac atccttcaca ccaattctag gcccaagcac tctctgcttg    110820
tgtcaagttt ttatcttctt gtggcttttg ataccgcaaa atgttccctg gggttttaa    110880 gcaccaaggc atgctaaact acagaggaga aaaggagatt ccttcatcct gagtccatgc    110940
tctaaacatg accctgaaac cctcacctca acatctgtct ggctctaatg agggtcaggt    111000
tctatgctga gtgtgccaaa tgcatatcac ctttgatcct caccataacc ccacgagcta    111060
ggtgtgatgc atgtccccat tttacagatg aggaaactaa ggcttcatga tgttaaggaa    111120 cttttcctaat tatatggcta aaaaatggta catctagata ggccaatgca agtctaactc    111180
caaagtcgtt gctcctacaa cacatattct tgaggtcatg ctttaggttt gtggtgaaaa    111240
gtctattact cagtgtggat taggaagact caagatttaa ttcttattct gatggttgct    111300
gggcttccct ggtggctcag acggtaaaga atccacctgc aatgcaggag acccgggttt    111360
gatccctggg ttgggaagag tccctggaga agagaatggc tacccactct agtattcttg    111420
cctggagaat tccatagaca gaggagcctg acaggctgca gtccatgggg ttgcaaaaga    111480
gtcagacaca actgagcgat ttccactcca ctccactcca ttccttatgg cccctgggct    111540
tccttgtggc tcagatggta agaatctgcc tatatgcaag agacccaggt tcaggaagat    111600
cccatgagaa gggaatggca acccactcca gtattcctgc ctggaaaatc ccatagacag    111660
aggaggctgc tggattatag tctatgtctg caaaagagtc agacacgact gagtgactaa    111720
ctctcatggt tgctagcttt gattcattca tctccagttt cttcatctgt aaatataaga    111780
```

```
gtatgacttg aatttcagag gcgttatgaa atcatgacac aaatgtagga gaggtcatga    111840
ctgcaccagg attgggccat atacttgaag aatttgccta tcctagacca tttcccacca    111900
ccgcgggcac tttctgagct gctggaattt tggattgatc atgaatctct gttttcccag    111960
ttcctcatct gatccgaaca gggtgggtga gaataacttg ctttcagaat ttctgcccat    112020
gttatgagga caaatgattc caggccctgt gtattttcaa cctattggaa agaaatgggg    112080
attcccaaaa ctactttagg gcctaggag acaggtgacc cagaagtctc tttctgaccc    112140
tcagatgtgc aggttgggtg gctcacctgt acaatgggca tcccatccct acaagacagc    112200
ctgaccttga atatttctct aagttgctct tgtgtcttaa gaattcattt cccagttcag    112260
gcttccctcc tgtttgtgca ttcataaagc aaaaggacc tagcacaata catcacttag    112320
ggatcacagt tcatattatg aatatctacc gaacaattca agtgcagttg ggaagaagca    112380
ccagggtccc gggaggaagc tgtttgcaca aaggagcagc tggcagcttc tcagtttcac    112440 gttcttttg ttcactgttg gcagtgggaa ctgtactgcc cttcagtttg aattcagcct    112500
tcttagttca gtattgtgct gtctttaccc taacaatgag ttacgataat tataatttag    112560
aaactcactg atttaggtct tagatgctat tcaggactta actcagtaat tttcatttat    112620
tttgttcaag caatttatta ttttttagcct tcaactacat gaagccttca tgtagttatg    112680
aagtgaagtg aaattgctca gtcgtgtccg actctttgca accccatgga ctgtagacta    112740
tcaggctcct ccatccatgg gattttccag gcaagagtgc tggagtggat tgccataaag    112800 ctccctatt actggaatgt tttccaacat aaatgacttg aagttgagag cctaaaccta    112860
tttttctaaa taaaacttgg aaaacttgtt tgtaactcag ttttttaaaa cttaagtttc    112920
cttaacaaaa catcacatag agaacatcac actgtgattt taaatttact ttgaagagaa    112980
aatatattgt caaaggaagt atccaggtca ttgaaaaaat tcttggcttt gccatttgct    113040
gaatgtaggc tttggttccc gcctctgttc cttcatctgc aaaaggtgag tcaggggtgt    113100
aatgatattt acctcacaca gttattggga ggatgaaata atgaataata agtgccaagc    113160
ttatagtagc actcagtgaa tattgttccc gtcttctttt tgagaattgg caaccatctt    113220
actcatttct gtatttagt acctatcaca cagaaaatac tcagtgactg ttaaattaaa    113280
taatagatga gggtaaaaga ggagagtgaa aaagctggct taaaactcaa cattcaaaaa    113340
actaagatca gggcatccag tcccatcact tcatggcaaa tagaagggga aaagtggaag    113400
caaggacaga ttttattttc ttgggctcca aaatcgctga agattgtggc tgcagccatg    113460
aaattaaaag atgcttgctc cttaaaagga aagctatgac aaacctagac agcatgttaa    113520
aaagcagaga catcattttg ctgacaaagg tccatatagt caaagctatg gttttttccag   113580 tagtcatgta caggtatgag agttggacca taaagcaggc tgagcactga agagttgatg    113640
tttttgaact gtggtgctgc agaagactct tgagagtccc ttggacacat ggtggtcaag    113700
tcagtaaatc ctaaaggaaa tcagtcctga atattcattg gaaagactga tgctgaagct    113760
aaaactccag tactttggcc acctgatgca aagagccgac tctgatgctg ggaagattg    113820 agggcaggag gagaagggg tgacagagga tgagatggtt ggatggcatc accaactcaa    113880
tggacatgaa tttgggcaaa ctccaggaga cagtgaaaga caggggatcc tggcatgctg    113940
cagtccacgg ggttgcagag tcagacacga cttagcaact gaacagcaac aaagtatttt    114000
tagaaatcat caaatttgaa ctaagcatgc ttcttccagg cccgcatctg tagtggattt    114060
cttcattaat tcagcaccta cttactggca cccactatgt gacaggcact gaactagtca    114120
cactggctac agtgatttgc aaacatagtt acaaatcttg cctttatgta ggcttccagc    114180
```

```
tgatgagctg tttcccagtg ggaaatgtag gtgttttttgg cgtctgcagt tttttaacaa   114240
tggcacttca acctagatga gcggtgtctt ccataagatc agcaagggc caggggtccat   114300 ataatgcctg agtcagagga aagaatgcag ttgattcagg ccacttaacc ttaggaagag   114360
aaccacctgg gaaagtaaaa aagtatactg tgatctgcca gtctagggca ttgacctaca   114420
actttaactt aatgcagcat cattgattca gtttcccttt gatgtcccct tgcactttaa   114480
aagatcattt caaaggttct cttctgcttt tttccataag aatagtcatg cctttggcca   114540
aaatagacaa gtcatgccat ggttatctct gtttgaggat aaacagggct tttgctagag   114600
gctgctaaca agatcttgat cattaagaac aatcttaaaa atatgactga aacgttcaaa   114660
atttcttttt ctctttctgc ttcagaggat ctgggtatgg gggagagggc agtagtggga   114720
aagctgagtc ttaaaagatg atgatgggca aggaatgcca gataaggagc tgtaataatc   114780
ctctgttccg tccatgccct tccattcagc aaagacccca tgaattcctc tctggcttgt   114840
tctccttcct tcagttcagt cgctcagtca tttccaactg gtttgatctc cttgcagtcc   114900
aagggactct ccttccttac cagtaggcta taagtcactc aaaagtttgc ttgtgaacgt   114960
cttataattt tctctagtca actatgaacc tgggtgaggg attcctgcca tccagtggtc   115020
tccaagagtt tggttttcac agagtaccta aactttgga tttgggctgt cgtgttcatg   115080
cacacacacc cttgctggct gcagctgggt ctgttgtgac ctcaatccaa ccaaaagcac   115140
ctgtaggtgc tttagtcccc tcccttactg tccacattta ctcatcagac cctagtagag   115200
aggcactgga tttcaatctg taagggaact acagggattt ggcctaggtc ctcctatttt   115260
acggaaagat aaagagaggc agtgggtgtg gggtttgatt ctaaacccaa ttttgccctg   115320
catactgtct tgttgatgca cttccctcat atctcagttg gtaaagaatc tgctgcaatg   115380
caggagaccc tggttcgatt cctgggacgg gaagatccac tggagaaggg ataggctacc   115440
cagtccagta ttattgggct tcccttgtgg ctcagctaat aaagaatccg cctgcaatgc   115500
gggagacctg ggtttcatcc ctgggttggg aagatcccct ggagaaggga aaggtaccc   115560 actccactat tctggcctgg agaattccct ggactaagtc catggggtca caaagagtta   115620
gacacgactg agcgactttc actttcactg tcttgttggg gcttatcctt tgtccttgga   115680
cgtggggtct cttttttttgg tgggatccaa cttttctcctg ttgatggttg ttcagcagtg   115740
agttgcaatt tcggagttct caaagaagat gagcgcacat ccttcttctc catcattttg   115800
tgtaggggaa aaaaaaaaa gctatagtta aagctgtggt ttttccagta gtcatgtttg   115860
gatgtgagag ctggaccata aagaaagctg ggtgccaaag aattgatgct tttgaactgt   115920
gatgctgaag agtgccttgg acagcaagga gatcaaacca gtcaatccta aaggaaatca   115980
gtcctgaata ttcattggaa ggactgatgc tgaagctgaa gctccaatac tttggccacc   116040
tggtttgaag aactgactct ttggaaaaga ccctgatgct ggaaaagatt gaaggcagga   116100
ggagaaggcg atgacagagg atgaggtggt tggatggcat caccaagtca atggacctga   116160
gtttgagtaa gctctgggag ttggtgatgg acaggaagcc tggcctgctg cagtccatgg   116220
ggtcgcaaag agtcggacat gactgagcag ctgaactgaa cttaaagaat atcagggact   116280
tgttgaaggt cacaaactag ttagtggata gaccagactg aaactcaagt ctcctgaccc   116340
ttggcttaca cacggatgtt cttttgtgat gctcaacagt gtgacttgta aacaacttt   116400 agttggatat tgttctttta cccacccaa cagtccctgt cttttgattg gtgtatgtag   116460
accattcaca ctcaaagtga ttattaatat gtgtgagtta atatctgctg tatttctgct   116520
tgctattcat tgcccctgtt ctttgtgtct ttcttttgtt ttccagtcat ttttctgtct   116580
```

```
tccctgattt tatttgaaca ttttacaaga ttgtattttc tttcctctct tgacatgtca  116640
attatacttc ttttcaaatt cttttagtca ttgctctaga gtttgcaaaa tacacttaaa  116700
ggtaatctga gtccactttc agataacact gtactatttc atggtactgt gctaatattc  116760
ccacttactc ctccttgtcc cttatgacat cactgtcatt catttcatac ctccataagc  116820
tataatcacc aattttattt ttgctattat tattgcaagt caattgttgt ctattagatc  116880
aattaggaat aataaaagtt gaaggtttta ttttaccttc atttattcat tctctaatat  116940
tctttctttg tgtagatctg agtttccaac ctgtgccatt ttccttctcc gtaaagcatt  117000
tctgtcattt cttgccaggc agatctaccg gtgacaaatt tcttcaattt ttgttttgtct 117060
aagaaagtct ttatttcccc ttcacttttt tttttatttt attttaaac tttacataat   117120
tgtattagtt ttgccaatat caaaatgaat ccgccacagg tatacatgtg ttccccatcc  117180
tgaaccctcc tccctcctcc atcccatac catccctctg ggtcgtccca gcgccctagc   117240
cccaagcatc cagtatcgtg catcgaacct ggactggcgt ctcgtttcat acatgatatt  117300
ttacatgagt acagaattca agtctgtgga ttttctttc aacatttatg atagtttact   117360
ccactttctt cttgctgatg tgtttcttaa gaggaaaccc cgtatacctg gtgtgattcc  117420
tatcctcact tctctacagg taaggttttt tttttcccct cactctttgg ttgctttcaa  117480
gattttcgtt ttgtctttga tttttttcca ggtgaatatg atacgctcaa caacagattt  117540
tttgctattt atcctgctta gtgcttgctc tctgaacttc ctagatcagt ggttgggtgt  117600
ctgtctttaa ttttagaaac atctctttca gtcattattt cttcacatat ttctactgtt  117660
tgttccttct tctctcctgc ctaccctctt ttgctctttc ccgccttccc tccttttctct 117720
ccttccttct ccttttggta tcccattac acacaactta caccatttat aattgtccca   117780
cagttcccag atactctgtt gcaatctttt cacatttcag ttcggggaga ctgccatcaa  117840
tatgtcttaa agttcagtga ttcttttcctt agccatgtcc agtctagtga tgagccaatc  117900
aaaggcattc ttcatctgtt acagtgtttc tgacttccct ctgtttcttc tcattctttc  117960
ttagacttcc catctctctg cttataacat ccctatgttc ttgcatgttg tttacttttt  118020
ctattcaagt ccttagcaca tcaattgtaa ttattttaaa tagccagtct gataactcca  118080
acatctctct catatctgag tctggttctg atgcttgctt tttcttttaa gatggtattt  118140
tttgcttttt tgacatattc cataattttt tgttgagagg tggacatgat gtactgggta  118200
acaggaactg aggaaatagg gttttagtgt gagattttt tgtttatctg gctaggaatt   118260
aggctgtgtt actgtgtgca gtatctgtac tgtagtatcc agtgaccttc tttttgtccc  118320
tgagtggctg gcttttccta gagacttctt aaacaggagt taaggctttc agttctttca  118380
gttgaatccc ctgttgtaca aaatcctttg aagggacgcc tcctccatcc catgattagg  118440
tctcagtctt ccattgacct ggagctgagt atttccctcc cccgccccca gattagtcag  118500
gctttggtaa aatccccatt gattaagctc tgctgaaata atttctctta agaacagatc  118560
ttgctaaggg gaacagagag ctctgtcttg tatttcaaaa tgtttacttt tctcctcctg  118620
ctggaagagc aagggggattt ttcttggttg atcatcgcga gaacctggca ggcctcctgg  118680
agggaagatt catgaaagtg tgggggcgcc tagactggac cgctaagagt ttttcacttt  118740
cacgctcgcc cacactaaac ctccagcaat tcatcaatta cagcttagag tattgctgcc  118800
acgctactgc cagctgcagg cttttcctcc tggcctctgc tcctgctggt ctgtgattct  118860
gtctgtccat ctaggctgtg attctgtctg tctgtctctc tagcttttgg tgcagcaatt  118920
tgccttgtga cctcaattct ctgatagatc taagaagact tgttgatttt cagtttactg  118980
```

```
ggcttttatc tttcttgttc caaaagatga gagtaaatac ttccaagctc tttacatgtc   119040
agaccagaaa gtggaagttg cagtgtgatt cataaataca gtcaagtgaa tctcagagtc   119100
atgggccatg aactttggca attatataac aacaaaagaa caacagttac tgagcactga   119160
ctacatacca gcacttcatt tagtatttta gtcatctgac aatacccgta caaagatact   119220
gttcttttcc tcgtttgaca gttgaaaaca ttgaatcttt ccaaggacat acagatttaa   119280
gtaacagaag gggaatgcac atgcaggcac cttaactcta gaggtcaccc tctcattgca   119340
atgccctcat gcctctccca gcattcaagt gtctgtttat ctttcatttg gcagatacat   119400
gtgccaaacg tcatttccag cactggagaa gaaaaggcca aggtctctgt tctcatgaac   119460
atgtatattc cagtgggaga gaaagcaaat gaacaagaag tgaataaata agcttattca   119520
gaaagagatg gaattctcta ggccagaata ctggagtgcc tttcccttct ccaggggata   119580
tttccaaccc agggatcgaa cccaggtctc ccacatttca ggtggattct ttaccagctg   119640
agccacaagg aaagcccaac aagtaatgaa tagacaagtt tatttagaaa gagagaagag   119700
ctgaagaatt gaaacacagt gtatgataaa aaatgccagg gagggcgatt cctttagaga   119760
gaatggttag agaaattgtc acttagggcg tggcctgaga actgaggcgt gagggaagga   119820
acaggtaggg gaagagcatt ccagatagaa ggaggagtca gaagtgggaa catgtaatgc   119880
aggttcaagg aggagcaaga tggcccgtgt gactaggcca cgtgagtgag ggagaaagtg   119940
gtcataggag aggccagaga ggagggctgg gccacaccgg tgcagggctc tgccaggagt   120000
ggcagggagt ttggatattc ttctaaaagc cctgggggca cttccctgtt ggtccagtag   120060
ctgagactct gtgcttccaa tgcaggggc atgggttcaa tccctggtcg gggaacttag    120120
atgctacctg ccatgtgatg tagccaaaaa ataaaaataa agccccagga aggcactgca   120180
agcttttagg cagtggagtg acatgcctca tgcatttcga tggcacatat gagcctcaga   120240
cctcagacca ccgtcatgag accccagaga tgttgtacca gattcaggat cggggaccca   120300 cccccctaagg ctgggtctct ctggggtgtg cattcaagga gggagactgc atgtgaggca   120360
gtgcccttga ggacagcttg gggtgttagc agcagcatgg agtgaccgtt ggttagaagg   120420
agaagaaaac cccagaacat gccacaggct taagaatcct gaagcttacg tggttcttgg   120480
gtcctgactc tcagtgcaga gctcctctgt caggttctac cgccttccct aacagctacc   120540
ctagtttcag atgtacagcc tttcttccac atggcagaaa catgttctcc ttctgttgag   120600
atgggtggat gtggctggtt tcctcccact gtgtcaacag ccagcacaga agtggtcctg   120660 acccccagtgc ccagagaaga cttcccgata tggttttgga agatgacttg catgcctgcc   120720
tcacaccgtc tccttcttga agggcatctt gccctcctgg tcacctctgg tatcaagtag   120780
aaatagggct tcccaggtgg ctgccaatac aggaatagca ggagacgcgg gttcaatccc   120840
tgggtcagga agatccccta gaggaggaaa tggcagttgt ctctggtgac atatggattc   120900
atcaaagcat tgttaaatac atgctgcttt gtgactccat caggattgag agacactccg   120960
agagatgacg gggaggaggt gggaggcagg aaagagaaga aattctccca gggctactgc   121020
atagggccca gcattgtcct tccttctggt aggataaact acatatttcc tgccgagaaa   121080
aatgtaccat ttaaggtaga gattaagatg actctacccg cctaagatgc ttcacctcct   121140
tctttgttat ggatctaggt cagtggaaac aggtgacgtg agggaaactg tctcaaggga   121200
aggaaaaggt gatcgactga ggtggcctga aagagagag taactgtaga tggacatgcc    121260
aaccaataag actagtctgg tctctcgtgt tactcttccc aaatatagca gaggctttt    121320 ataaaatctt accctctttg taccacagat gtattcttaa gcatttcaag gtgattaaat   121380
```

```
tttgtaagca aataatgaca gactttcaag gcatacagag agttttttatt gaaagaaaca   121440
cttggtaaag ttgagggtat ttttgcaaac aaatagccac cagattttta ccgatacatg   121500
tgaatttggc tccacacctc tattgaaaga tattttaaga tgaatattaa atgaatacc    121560
tctattttaa gatgaatttc acatgcagtt ctgtccattt ggaatctgtc ttgaaacata   121620
ttttcaagct aaatgtttct ttctcccttc ttttcacacc taagatgttt aaaagtgcag   121680
agacagggca tcttaagagt attctgtccc taccctctct tcacctctct ccccacctcc   121740
actccccccc gccagtcttt tctgaaacca caaaagtttg aagctgaggg acattaaaaa   121800
ctaagtccta tcccttttct aacaactgaa aagtgctgag tcgctcagtt gtgtccgact   121860
cttttgcaacc ctgtggatgg tcgtctgtca ggctcctctg tccatgggga ttctccaggc  121920
aagagcactg gggtgggttg ccatgtcctc caacaactga aaaatgaagg ccaaatatc   121980
atacttattt ttgtttattt tttccacatt ttctccaaaa aatgctggtg ggcgttgaag   122040
gagactgtgt catggtgcaa gtcccttaca agccttttct ctctgtacct gccaccaagc   122100
gttggggcgg agccaccagg ttgtcaccgc tcattcttca ttccactgct ctcctgccag   122160
acgctcttct gttgctgctt tctaggtttc ccaacccact gattattttg catttttggat  122220
gatttctctc ccagctgcct tcatttgcat tttgcctaaa tcaaatctca ttgtgataat   122280
ttctcttcct atttctaacc tctttagatc catctgtgtt attctctgt ccctcaatga    122340
tgtctgcagc accccctaat ttggcaccaa ccaaaaatgt tattaaatgt gtacggcttg   122400
ttcctagtca ttaatgaaga tgctaaataa agctagagct aacagctact ttggagcctt   122460
cctttagctg catcccccac ccgatcccca tagactctga gctgttttt atctctggtt    122520
cttgtttatt aaagttcagg cttttcaatc atactgttct agttccttcc agtgccaacc   122580
agagctcttg tcacaggaat gtttcaagga tgctgtttta tatgctttat taagctccag   122640
aggtacaata gctacagaag tcattgaatc aagaattta attaacagta aaatttatag    122700
tttcatatgc cggaggaaat ttttcgcctt ttaaaaactc ttttgcaagg caaacacatt   122760
tgattaccct ttatcttctc ctatttattc tttagagctt tttatgtaaa tctgctagtt   122820
aattctcttt gaattaaag gtgcataaac cattatgcgc tggtgaagaa cacaggctat    122880
gaaaatgaaa tggcccttgt catgagaaac ttatgatctg ctagagcagg ctagattcat   122940
gtataatgaa gaaggactct atccagatga tgtggcatta aattgcttga agcttcaaa    123000
ctgactctta gggctgcaaa aatagaagta tgggttaggg tattaggata aagcctaatg   123060
cagaaggaaa ttttgagct gaaaactcaa aaggtgaaaa ggatttgcat tggcaaggaa    123120
gaagggaag atagggaaac atttgagcaa caagggcacc ccactccagt actcttgcct    123180
ggaaaatccc atggacagag gagcctggtg ggctgtagtc catggggttg cgaagagtcg   123240
gacacgactg atcgacttca cttttcacttt tcactttcat gcattggaga aggaaatggc   123300
aacccactcc agtgttcttg tctggagaat cccaggacg ggagagcctg gtgggctgcc    123360
gtctgtggga tcacacaggg tcagacacga ttgaagcaac ctagcagcag cagcagcagc   123420
agagagaagg acttctcagg tggtgctagt ggtaaagaac ctaactttca aagggagata   123480
taagagaggt agatttgatc cctgggttgg gcttctcttg tggctcagct ggtaaagaat   123540
ctgcctgcaa tgtgggagat ctgggttcaa tctctgggtt gggaagatcc cctgagaag    123600
ggaaaggtac ccagtccagt attctggcct ggagaattcc atgggcttgt ccatgggatt   123660
gaaaagagtc aggcacaact gagagacttt cacttcactc actttgggaa gatccctgg   123720
agaagggcat ggcaacccac tctagtattt ttgcctggaa aacttccacg gactcaggag   123780
```

-continued

```
cctggcaggc tgctgaccat agcgtcacag agtctgacat gacagaagtg acctagcaca 123840
gcatagcact gagagagaga aatgattgtg acatactgca tcgagtccct gagtagtaga 123900
acatcggtct gattggagaa aaaactggcg tggcgcattg cagatgtacg gcatctctca 123960
ccggactgta tggcatctct caccagatgt gtctgaggca tcttaaaacc agtgtgcctt 124020
gaatcaaagt tgttactcca tcctctcccc gaaaccactt ctctcctagt tttgcctgtc 124080
agaaatctgg atgtcttcca tgatttctct agctccccaa tcatccctca cccaatattt 124140
tagcccatct ctttaggttc tgctgcacag ttgtatctgc atgcttctca tttttgccac 124200
tctctagtct tagcctggac tactgcaaaa accccacaca cgtgtcttcc tcctccagca 124260
gttgcccttc tccataccac agccacacag aacttactga aaatgaaacc actctctaac 124320
aagaaaagaa aatatttgag tgactgagca gtccctttga agtgaaatcc aaccttgtta 124380
tcatgacata gatagcctgg tatggtcagg ctattacata ccagtgcttt ttccacgcca 124440
tgtgggtgca cttcaatatg attctaatta accactcaca ttggcttcag atacacaagg 124500
aaagacacca ctttgctggc aaaggtccgt ctagtcgaag ctatggtttt tccagtagtc 124560
gtgtacggtg agagctggac cttaaagaag gctgaacacc aaagagttga tgcttttgaa 124620
ttgtagtgct ggagaagact cttgacagtc ccttgaacag caagggatc aaaccagtca 124680 atcctaaaaa aatcaatcct gagtattcat tggaaggact gatgctaaaa ctgaagctcc 124740
aatactttgg ccatctgatg caaagagctg actcattgga aaagaccttg atgctgggaa 124800
agattgaggg caggaggaga agcggggggca gaggatgaga tggttggatg gcatcaccga 124860
ctcaatggac gtgagtttga gcaaactctg ggagatagtg aaggacaggg aagcctgatg 124920
tactgaagtc tgtggggtca caaagggtca gacacgactt agtaacttat tcaaaaaaca 124980
atgcaaggga aagcccctcc gtatgggcac ccctacttca tatgccagcc acaagcagga 125040
gtctccaggc ccctcatacc tacagattca ggagttccca caattccctc agtttaataa 125100
tttgctagaa caactcacag aactagagaa agcgctatac ttactcttac agttttatta 125160
taaagggtac aaatcagaac caaccaaatg gaatagacac acagtgggag gtctgggagg 125220
attcctcatg cagagcttcc tcgcctctcc ccatgaagtc agggggcctca ctttgcctgc 125280 ctatctgtgg gttcaccagc cagggagttc ctctgaacct cagcatccag agcttttact 125340
ggagtttcat tacaaaggct gggttgatta aatccttggc catgttacca agctcgatct 125400
ccagtcccct tctcctccca aagtgccagc actctaatca tatgtttgat ctttctggtg 125460
accagcccca atcctgaagc tatccagtgg tctgtactga gtcatctaat taatgcagta 125520
aagtcacttc tatcatttag gaaattccaa cagattttga agctctctgc caggaaccac 125580
tggggacagg tatatcttta ttgtatcaca atacttctca gatctcatct tacaccactc 125640
ttgcacccca cccacgagac atgctggtct tctcttaact cctggactgt gccaactcct 125700
ttcctctccc tgagacaatt ccttcttccc tatttcagtc ctgctctacc tcccccagcc 125760
taagaatata tgtccagtac aatggacatg aacttgggca aactttggga gatggtgagg 125820
gacagggagg cctggcaagc tgcagtccat ggggtcgcaa agagtcggac accactgggc 125880
gactgaacaa caacaacaag attatctgat tagaaagcct ttgcctgtct caatgtcatc 125940
cttttatctc tccatactta tctgcttcat gggactaatt ccaatctgaa atgatttgat 126000
ttatgtttat gcctccataa aatgtaaaca gccttgattg tcttgttcct tctttatctt 126060
ctagcacata ccaacattca gtaaatattt atcaaactaa agcaagtggg aaagtgggaa 126120
agataataat caggccagtt gaagctattt gattgctaag aagaagtgtt taggcttgat 126180
```

```
gagaaaagtg atatggtgaa gttgtcagat cagaagcaag agaatgatag atatttgggg   126240
agaatgagta tgtgaagtgt gatcacagtt tatcaattgt attgtggaag ggaaaggact   126300
agaggcaggg ggcccttcca ggagcccagg taaactgatg gaagtcggaa caagggtggt   126360
ggagtacgaa tggagtcaac gggggaaact gaggttttta agaaagatgc ccttgacatt   126420
tttttctttt aggtttaact tttttatttg aaataatttc aaactgacaa aaaagttgca   126480
aaaacattat gaaggactcc tgtgtacctg tcacccagat tcactcattg ttaatatgtt   126540
gcttcatttg ctttattatt ctctttcttt gtgtgtagag tatgcattct tttgtgttat   126600
tttttcatga atcctttgca aataagctat caacttcatg cctcttcatc cctaaacact   126660
ttagtgtgca tttcctaatg ggaaagacat ttcacagtga cacaatgctt gtaccaacgc   126720
cagggaattt aatgttgata cagtactgta tccagggtcc tagcccagga accagctcaa   126780
gatcctgcat aacagtgagt tgacctgtcc ctttagtcct tttttatttgg aatagttcct   126840 tggtctttga aggtagacat ttttgaagta tgcatgccaa ttatttttgca caatactcct   126900 cattttttggt ttgctcaagt ttcctcataa cttcactcag attgggcact tggggcagga   126960
atgctacatt aatgatcttg tgtcctagca tcagacaaga ggcccatgat atcactttgt   127020
catattattc atggtatgaa cataaatcgc ttagctaagg tagtgtccac cctgtttctc   127080
caaggtaaga ttactatgtt tccattggta attaatgagt aatttatgct gagatcctat   127140
gagccgatgt aatatgtttt ttattttaat caacctttttg attttagtaa ttttagcaca   127200
cattggtgag tcttgcctga atcagttatt gccaagacac ctgcaaaatg gtgattttttc   127260 tagctccatt attttttcta catttgttgg ttgacatttt acttcttaat tatttattgt   127320
gggttcatgg gttcttattt tattaatcca ttcctgttag tgttcatctt aacacaccca   127380
cattattcat cagagtaccc cagtgtgttc aatgggagca ctgcagatgg gctcctgggt   127440 cctttttgaca ggtccccatc gtattttgga gcaattcctt actttctcct gtaacaaaat   127500
ataccaagtt cctcttgtgc ttttcctgcc tttgtcctgg caccagccat tacactgaag   127560
agttctgatt ccttttcagt ggggaatgta tttaaaaacc gagatctggg agtgaggtgt   127620
atctgtggtc actggactgt cattgttttc caggtccttt cttccctgaa gttttgactc   127680
attgagtgag agagatctag gttaggagac taaacagtgg tcacctcaca gaccaaaatc   127740
atccaaaacc caaactggaa agattcacag aaggcaaacg agtgaaccaa ggtgctggtg   127800
ctaagtctga ctctttgcga ccgcatggac tgtagcccac caggcttctc tgtccatggg   127860
attctctagc caagaatcct ggagtgggtt tccatgcccc cctccagggg atcttcccaa   127920
cccagggatg gaacccacgt ctcttatgtt gccttgatgg caggcgagtt ctttaccatt   127980
gagctaccag acaagtctac caagaggact gcccaagcca tcttaaaaat gtgtcttaaa   128040
aatatcttac acaaatatat tctttgtgta agaatttaag tagtggagga ataaaagaaa   128100
acatgactca cccctgcagt ctttacgttt tgtcagcaaa cacttttaa atgctaaaac    128160 tggtttttca atgttcaccg gcttccgaaa cttccccagg ccagacggca ggtggggact   128220
tgttctgtcg aagctgccat ttgccaggtg gtgaaggctg acgccaggcc ttcttgggga   128280
ctttctgggc ccttcttaca gattgtcagt gttatctgga gggaaatcaa tactgacctg   128340
gtatcaactg tggggaaagc accgaacgtc cttcactgtt tgaatagcgc agtgttgtca   128400
tctgaactgg gggagatgag attcagactt ggagacagag ataaagtctg tttcgaatga   128460
gccttcgggt ccctgaagag tggcggccac agcgtctttc cctgttttgac ccccttgata   128520 aaatgactcc tttctcagac aggatgccgt tactcacaaa agactcacat acacagacac   128580
```

```
tctaatctaa aacttgccag ttcaaagctg acatgttggc cctggtttct ttttcactgc    128640
tgactggaaa cgaaggtgta ttacgaatac aagttggaat tacctggggg tgtgttttga    128700
gaccacctgg tagacgttcc cttttggaat tgtaagcagc tgcacaattg aattagggga    128760
tggaacagcc acacgggtgt ctggtcaaaa gcaagcatct gtttgcagta cctctagggg    128820
aaaggcagcc agtgatgcca gtctcagcaa ggaactctgc tcaatgttat gtggccgcct    128880
ggatggcggg gtggtggag tttggggag aatggatacg tgtatatgta tggctaagtc    128940
cctttgctgt ccacctgaag ctatcacact gttcatcgac tgtactccca tacaaaatga    129000
aaagttaaaa aaaatgattc tggtcttaga tctgttgact gggacaagcc cagtgctgtt    129060
catacttggc cttcatctta ttacccagag caaatgaggt gggccttaaa agacaggttc    129120
ccctactgcc atttagagga ttagactcaa gaatttattt tcaatataaa aggagattgg    129180
gagaaaagta gttctgattc agcaggttct tcctaatctg cttcagtaga gcttttgaga    129240
ttgattactc aagtcccaga gaacacgcaa aggctgagct tatggagtaa tatcacatac    129300
ttgatcacag gatcaatttc catttctaca gtctcagcag ggacccggtt agggacatta    129360
tctatgatgg agtgacgtga taaaggtaca ggacccaggg tgggtttcag cgagggcact    129420
gtccctgtac ttgagttggg ataggttgat cagtgctcat aagaatagag atcaaagaag    129480
cgtggtataa acatgcatca ctgactgcct tgctaggtga gtattattgc ctcatcattt    129540
tttcctaaca tggggctggt ggcagaagct gattgttttg attcaggcat atagaaactt    129600
aaaaatactt tgttaccctc atattacaga agaaaaactt gattatttta aaatgtaga    129660
aaatacaaca aacaaagaaa aaagttaaaa gtcatccact gccccacttt ctagggagaa    129720
cagctataaa tagattgaca tatacttgaa tgttttttcta cgcttaaata catattttta    129780
tcaagaatcc attcattcct gcgttcacgc tctttcgtgt ctgactcttt gcgaccctat    129840
ggactgcagc ccacccggct tctctgtcca tgggattctc taggcaagaa cactggagtg    129900
gggcaccatt tcctcctgca ggggatcttc ctgacccggg ggccaaaccc gtgtctcctg    129960
catctcctgc actggtaggt ggattcttta cctgtgagcc accagggaag cccaatcaat    130020
gcattcatca ctctatcacg tactttgtct ttcacttaac tactttccag ctcacctctc    130080
catgtcaata ctgcagtatc cttttttttt gtcagttttt taaaaagatt ttttggtgt    130140
ggaccatttt taaagtcttt attgaatttg ttacaatatt gcttctattt tatgtttggg    130200
tttttatttt tggccctgag gcatggggat tcttagttca cctgccaggg atcaaaccca    130260
caccccctg cattagaagg tgaagtctta accactggac caccagggaa gtcccttttt    130320
gctagtttga aatacaaaac caacagatgc tcttgttaaa aatttctgag tatagaatag    130380
aaagtatttc tcctacctcc cagtcttcct tccttcctgt aaccctaaga ctgtgtactt    130440
catgtttctc tccagaaaat ttctatggac acacacacaa atagtattca attaatgaat    130500
gtatcacaag gtagtaagta aaatcctgtt atgtggaaaa tcagggtttt tccaagttca    130560
gtgaacatct ttgtgattaa gcatttgcac acagccgtga ttatttccct gagataaact    130620
ccagaaaaca aatcgcacca ttttagtacg tctgatatgt gcagtgcatt cgcctttcat    130680
ttgatttatg ccagtttctc actgtcatcc ataagcaact ttgactttt aaaaatcttt    130740
aaagtataa cacatataga aaagagccca agtcatgggt taaacctgcc ctgtccaata    130800
tggtcagcac cagccacacg tggcagctga agtgtgtaac actagaaatg tggatggtcc    130860
aaactgaggt atgctggaag tgtaaaatac ccagtttcaa agaactggtc cagaaaaaag    130920
tcctgggaaa tatttcgtta atgattttat gctaataata tattgaatga cattttggat    130980
```

```
gtagtctgtt tagtaaagat atatgagtaa aattgatttc actggtctaa tttcactgtt   131040
ttagtgcagt tactagggaa atgcaagtca cacgtgtggc ttgcactgta tgtgtcgtgt   131100
acagcacaga gtaggacccc gtacagaccc tcagataata aacccgccac cgagggatgc   131160
actcctgata ggctctcttc ctctcccgct cctcccgccc cacgcccacc tgtgcctcag   131220
ttacagccag cgctcttaga actaatgtag ccccccttcac caccaccaat cctctgtcgg   131280
gttcaggtaa gccgctcagt catatcgaca aattactaga atgaagaagc agaccccatg   131340
gactgcagca tgccaggctt tcctgtccat aaccaactcc cggagcttgc tcaaaactca   131400
tgtccgtcga gtcggtgatg ccatccaacc atctcatcct ctgtcttccc tctcctcctg   131460
ccttcaatct tttcctctgt caggaatgat cagtaaacac gtggtgaatg cccacttttg   131520
aaggtaatgg ggtactaaga ccgtaatcta ccagaaccga ccaggagtac aagctctaag   131580
ttgcatcatt tttaattgat tggtgagaaa gtgtatgtat ttcgacttca gaaattgctg   131640
ctggagtcaa catcatgttt ctgctgaaat gtgcacacag agaatgggca gacggaatat   131700
gcaggcttga cggacagttc attgacggaa ggctgccatc tcttatcagc cctccgcttt   131760
cacttcctta cttattaatt gtaccagaca caccctggt gcacacacct tttcatcaaa    131820
cacgaatgct gttcccatat tggcttccac acccaacctg aagtgtggaa acaaaatgca   131880
gagaagtagg aagaaaaaaa ccctagggat tagcgtgtga ctcttgcttc ctttctgtcc   131940
tattgttggc ttatgtcttg ttctttgagt cactttttca ttggactcaa ttttagagta   132000
aaaaataaat aaaagatttt tcaaagtaca tcataaagta tttgggctcg attgtatgct   132060
caattatttg gaatgtggcc aaaatccttg cttcattcca ttgcttcact cagagtagct   132120
tctgtaggga aggtctccaa ggtgagagaa attaaagaaa catctctgct gcaacttgtc   132180
ctcattttca ctcttttgtt gttgttatat catgcttaat tttataagaa taatgtttct   132240 agcccttttag agctctccac ttagttttta taaaattgca ttttaataaa ttcaagagtc   132300
aacataacct tttaacaaga aaaatgagac ttctctttca aagattccct ctcccctgaa   132360
cttgaaggat aagggaaata tcttgttgaa atgaatgtga actaagaacg gtaagagctc   132420
catctttgtt ccgtgattaa acttactaga tgaacttgaa tacatatctt ctaagcctta   132480
attttgccat ctatgaactg gggacagagt gttccccctt cttcctatgt tcagatgggt   132540
ttgcaataaa agcaatacat tggatgaaaa agtaataaat tattccccag gctgcagtga   132600
tcttgacatt tgcaattcct tcctgactcg attctgtgat tataagtaat gaatgctttc   132660
actctttcca accactgtgt ttcaacacac tggtaaaatt taaagacctc tttcttatca   132720
cagtaagcca agctataatt ttcaccttac acagacttct aagcacctt ttttcctgtt     132780 tgtattcaaa gctgagcata tccttcttaa ggtctttcta cttctccctct ttgtcccatt   132840 accaaagtgt taagcaaatt tttaaagtta taagttaaac aagattgaat caccttccac   132900
cagcactggg taagccagag acacacacac atacaaaact ccataaatcc ttttctgatt   132960
aaaagaactg ttaaaacttt gagaataaag cagttctctc tcttctcatc attaggaaga   133020
aaccaatatc tgtgcaatga cagattccta atgaaagcat gactcagtac tgaataatac   133080
agtataaaac attattacct cttttttaaaa ggcttataca cgatatacat ttatttttat   133140
tttcagatta tagttgaccc ctgaacaact cagatgttaa gccacctata atttttcgtt   133200
gccttttcct atctgtggtt cctttacatc ctcagagtca accaacctca aaccatgaag   133260
tactatagca tttcctattg aaagatatct gtgtataagt ggacctgtgc aattcaaacc   133320
catgttgttc gagggtcagc tgcaatttc ctatcaaaaa tgctacttcc tgacttaatt    133380
```

-continued

```
tgccattctc aaagttttga aagcattatc aaataaaagc aaaacagagt ataagctgaa    133440
aaaatttata gatctctctg gcccatggct atagctgttt cattaacagt ttcagctgaa    133500
atacttcctc agatagctca cctacgacct ccggaccctg acactgtctc ccatcatgag    133560
gtcaacagct gatcccccat gtgtgcctga gccccgccct atctgtgggt ttggcagaat    133620
ctcctggact ccgacgtgtc tgcttctctg ggcaccagag tctctcctgg gattccagtg    133680
agtgccgcct gcctctccac atgggatgct gccaagcaga ccagattcct caaagagcca    133740
agtcccctcc ttcctgtctg tgacacactg ttagagcagt cctcagacaa tattatttgt    133800
gccttggcat tttgcagaga tttggtcaag cagctctttg ggttttttact tactgacttc    133860 ctcttctctg gtgtgttggg caggaagccc attgaagaga aggacgaagg acagagagag    133920
tcaggccaag aactaatccc cttctatact cagggttgcc cctttccttg aggatgaatg    133980
tctcttttct ggacatgaat gatctcccag tgggcttcag tagtccccac cagaactttc    134040
ttctggcttc cttactagtt cactcaacaa gccagaacct cctacagtgg gcacatccta    134100
attccctcgt ggctcagtca ataaagaatc tgcctgcaat gcaggaaacc tgggttcagt    134160
ccctgggtgg agaagatccc ctggaggagg gcatggcaac ccactccagt attcttgcct    134220
ggagaatccc acgcacagag gagcctggcg ggctgcagtc cataaggtct cacagagtta    134280
aacatgactg aagtgactta gcacacatgc aaggatgagc taagatgcct actaagtgag    134340
gatgtgtttc tgtttgggtg aaaaccaccc caaaccaacc cccggggatt gaacttgagg    134400
ttgagagact gtgagctgag gatgggagca agtctgccag tggtgaggat ggaagtgggg    134460
gtgggagtag gcagggggtg ggggaaattg gggaacttttc aggaaacacc ggggtgcttg    134520
atcccttcac tcaggtctgc cttctccctg cagaatgaca tcttcgagtg gtcgagggac    134580
caccgagtcc atcacaagta ctcggagacg gacgctgacc cacacaatgc ccgccggggc    134640
ttcttcttct cccacatcgg ctggctgttt gtccgcaagc atcgggacgt cattgagaag    134700
gggaggaagc ttgacgttac cgacttgctg gctgacccctg tggtccggtt ccagagaaag    134760
taagtgagca atcaccattg atgtccctga gggacaggac ccagagtcag agcccagtgg    134820
ggtgtaataa tatccccagg cagttcccct gcagattgga tcttcttagg gtcgctctct    134880
gttgattcat tccctttttga tcatgatgtt tttctctgtt cacacatttg ttttgaattt    134940
gaccttgatt ttgaaatgga gttcctgtaa gcccacttgt cgtttctttc cgacccatct    135000
gcgtgactga tttcatggaa tgtttctgtt gttttcctca ctcgctcgtc catgttttcc    135060
tgggctggcg aggagggcag agaggatttg ctttatttta gtgacacact ggactccagc    135120
gggactggcc tccctcgagg tccctgctg tgtgctccgg gaattctccc ctcccccact     135180
cctggaaatg gtaacaccgg aaggtttctg tgcagagaaa acatgcccgg gtaacaaaga    135240
gcctcagagt gcttgtgtgc acgcacggtg tcagctgagc ggtttcagcc catcagcgtt    135300
tacagggtga atctcctttc agcaacccgc cggtgatagc ctgcctgtca ctgtgcggca    135360
agtggggagc atccaaggtt cacatttcca ctaggaagcc ggcttggaga tctgcagagt    135420
tggcaacaat gtgttcatgt tagttgctcc atcatgtccg actctctgcg cccctgtgga    135480
ctgcagccca ccaggctcct ctgtgcatgg gattctccag aatactggag tgggttgcca    135540
ttgccctctc caggggatct acctgaccca gagatcgaac ccaggtctca ggcactgtag    135600
gcagattctt taccatctga gccaccaggg aagctcatgt tggtttaaat cagcagagtt    135660
ggccacgatg agagcactta taatagatt ccttgccccc aaaacaatgg atttatgtgc    135720
acagagagat gatttgagga cagcattcta gtgagatcct tgagttggta tggtggacaa    135780
```

```
atggtccctg gataccatct ccactgacag gcaggaatca tttgaagcgt tctctcaaac   135840
agaatctcct gataatggaa atggagtctg tacctttgac gcaaagttcc ttgcgtgaga   135900
ggaagtatgg cttagaaatg tgcccctttg atccttagcc tctcttctca catcgaagat   135960
ggtggtgaga aagggaggg tggaagagag attgcacagg cctgcacttg agcacctcca   136020
cagccttgca aaagagttga ctgctctcag ggctcagttt tggctgtaag atgggggtaa   136080
cagtagtacc tgtctcttac agcttttgtg aggacataat gaaacaaaa aggatggaa    136140
atgcctggca catagtatag attcatgatg actcacgccc taggcaggag ctactccagt   136200
ccacccctg ctttcttttt tttaaggtgt gctgggtctt tgctgtggtg ggctcaggaa   136260
ttgtgatgcc tgagattagt tgccagcatg tgggacgacc ttagttcccc aaccagggat   136320
cagacatttt gtccccagca ttagaaggag gattcttaat cacaggacca ccagggaagt   136380
ctgcgaacct ttgcttctgt tggcttcatc acaggctgtt ctttgtctcc tccatacagt   136440
tctttcaggc ggatgcaaca agttatcgat agccaaaagt tttatagcag aaataataa    136500
gatgcttgca attaaatgac ttcttgattc taatttttt atcatgaggg taaaatagaa    136560
caatctgcag aattcggaga agtagaaaga aaatcaccca ccgttctaac acgtaaacac   136620
aaccgcagtt tagattctat aatatcttct acatttatgc atacatttga catattttta   136680
catgatgaaa gtcatactgc ttatgtaatt ttatgtcttg ccttttaact tcagattatg   136740
ttaggcacca ttatcaaagg ctgcatgggt tcactgagtg tcagagttta tttaaccatc   136800
actccgcgac aggatatgta tgtcgtttcc aattttgtga tataaatgat gttgctatac   136860
aattagtaat gctttgggac aatcagacct tagattaatt tgaagagctc agatgagaag   136920
gcagaggatc ttctatttta ttcatgagaa gtgagccgag tataatagtg tggtttctct   136980
gagcataaaa atagaaaatt ttttcaagt tttcccttt aaacaatgtg gtaatatgat    137040
tcattaggtg tatactcgtg gtacgtatgt ccaaagacta tctctaaagg caggcagaag   137100
aacaaagact gtttcagcat gttccctgaa tagatgtctg agaacatcta tcattaccag   137160
ttcagtgacc gaaggattgc agtatcagaa atcattcatt cacagtatca tttcatgtat   137220
cattgagctc ctgctggaag tcagagccga ggatacagtc ttaaagattg gtctcagttc   137280
ccccagagtt tgcagactag cagggaaccc acaaattaac ttacagataa ttatattcta   137340
cagggaggag actgatatat aatagggtag agtaaggcac catgggaaca cagagagggg   137400
tctcctagcc caccctgcag gctggaagga actaactccc aagccacgac ctgaaggatg   137460
aaaagttaga taaggacggg ggcaagaata tttattatgc ctgtcacttc atagacatct   137520
atcgagccct tgagtttggg agcttttac aaatcagtta acccatgcct tccattttcc    137580
ctatgagaaa acaaataaac aaaatgtaaa tagaaagttg ggaatagaag tactgtcagt   137640
ctgtttgcac tactataaca aaaatactga tgaccaggtg gcttacgcaa cagacattta   137700
cttctcacag ttttggaggc tgggaagccc aagatcaagg cactggaaga tttggtgtct   137760
gatgagagcc tgcttcctgg ttcctagata gttgtcttct tgtattctca cagggcagaa   137820
ggggcaagag agctctctgg ggtctctctc ataagagccc taattctctt catgagggct   137880
tctcttttgt gacttactca cctcccgaag cccttcatta ccttgaggat tagatttcaa   137940
catatgaagt ttgttgttca gccgctcagt cttgtccaac tctttgcaac cccatggact   138000
gaagcccgcc aggctcctct atccatggga ttctccaggc aagagtactg gaatgggtag   138060
ccatgccctc ctccagggca tcttcctgac ccagagattg aacatgcatc tcctgcaatg   138120
caagtgggct ctttaacact gaaccaccag ggaagcccta agacccgatg cagcctctca   138180
```

```
aataaataat aataataaaa gaatcactga actacaggaa gagagctaca ttcatgaagc   138240
cagctttacc catcctgtca ttcaggcccc atagaggagg cacattcctt aaggaacaag   138300
tccttgctca tagagacggg agctggagca gtgggtccca tcacgggtgg cactgccaca   138360
tcgggtctca gaccttgctg ttctgtgcca agtgggaggg gcatcttgaa aaacagaaga   138420
agatgctcac tcagagccca gtcttgtgcc atttcagcag cactccttag agagtccctc   138480
tcctggatgg aattcccatc ccctctgtgg tcctctgagg acaacagtcc ttgttccatt   138540
tttagtggct gggtttgcc actgattcca ctacctcccg gagagcaatg tttgtgcaaa   138600
gaaacccaga gttttctcaa acaggcaatt gtgtaaatga cgagacccaa gatttagaga   138660
ctcctccttc agtcagaagg ttgcccaggt ggcacaatag taaagaatcc acctgtcgag   138720
caggagaccc gtattcagtc cctgggttgg aaagattccc tggaggggga aatggcaacc   138780
cactccttat tcttgcctgg agaatcccat ggacagagga gcctggtggg ctacagtcca   138840
tgtcgtccca aagagtcaga caccttcaat cagaacacaa gcactgatca ttttatttta   138900
tttatttttt tggccactgt gtgtggcatg tgggaatctt agttccgcaa ccagggattg   138960
aaccaatacc tcctgcagtg gaaatgtggc atcttaacca ctggaccacg agggacgtcc   139020
cctagcacta atattacagt tgatggattc actgtgcttg gtcatcctaa tgacaaccca   139080
tcaaaagaaa agcttgcctg acagccaagc ttgctcagct ttccattata cagtctaata   139140
aaagagagaa aatagtggcc ttaagggtaa tagggctttc cttgtgactc agctggtaaa   139200
gaatctgcct gcaatgtggg agacctgggt tcgatccctg ggttgggaag atcccctgga   139260
gaagggaaag gctacccact ctggtattct tgcctggaca attccatgga ctctatagtc   139320
catggggtcg caaagagtcg gacacgactg agcaacttcc acttaagggt aataggaaag   139380
tggcacagtt cagttttagt tccagacttt tcctctaaga ggtcactcta ccaaggtgat   139440
tacaagcagg tacctggaca gcttcaggtt ttgctctgtt aagttgtgaa cgctgaaacg   139500
gcaggcatta ggagatgaga gggctagaag ccagtggggt cacatttaga ccatggtggt   139560
tcgggtccct gcctggctcc tgtgccttca agagctgtgt ttgtcctcgc agggcaagaa   139620
gatcacagag cacaaaggct tgccacctgg aacctccttc cacttctaga ccttgcctta   139680
gggtcctagg atcctggaat gccctgccca agtgtctctg agctcacttt cagagtctgc   139740
accagcttct cccaggctct gtcctcctga agggaagtgc atgagcccta gaccaagagt   139800
cgccatgttg gtgtggggag gagcttagac gcctgggcct ggatttccac acaaagaaga   139860
cagacgtggg aagagaaggg gttaggccac agctaagggg ccctacctct tctcttggcc   139920
tggaccctga aaatgttggg agtgagccta aaggggcta ctcataaggt tgacagtggg   139980
tctattaggt gggaattgtg tttatcttaa gaaagaagtt catttctctc acatatgaaa   140040
gaattgtaca ggtccaggtt atggcagcat gagagccagg agaggactgg attctttcat   140100
ctttctgctc cgtccttagc atatgacttt ctgtgtttca ttctatggtc caaggttacc   140160
actaacgttc cacccaaagg aaggtggcgg gggggtgggg gggtggggg gttctgctgt   140220 gtgtgtttag tccctcagtc cctgactctc tgtggcccca tgaactgtag cccatcaagc   140280
tcctccatcc gtgggatttt ccaggcaaga atactagagt gggttgctat ttcctcctcc   140340
aggagatctt tccgacccag ggatcaaacc agcatctctt gtagtctcct gcattggcaa   140400
gtgggttctt taccactgag ccacgtggga agcccttaga agagatgaaa atgtgtaaat   140460
cttgccattt caggaagaaa ggcatttgaa tggctagaat tgttttgagg tcgatttac    140520 ctcactttgt ctcctaattt gttatcgttt gtcttctttt cttttccttt attaaggaca   140580
```

```
ccaaatctct cggtgatacc ttccttctta tgactttgtt ttagtccttt ctgtgtaaac   140640
cccaagtgta tttctctgtt ggtaacatca cataaccaag acagagcagt caaacaacga   140700
gtctacaatt gactcatctt cacttctcta tcgtcgcagc ttcctcttcc acttggggga   140760
ttccttaggt gggtgggatg aatcacctgg gaatttacaa acaagttggc tccgtctctg   140820
ttgaccaaat ccattgctct ttggttctgg ctccatgctg ggtcttgagg agtctctctc   140880
caccctgagt tcttttgcct tgcggcccta ctctaactgt tgctagagtg agacaacaat   140940
tcttgtctag aatttagtga cttgaatgg ctgagcacat tggttggcta attgtgtctt   141000
gtggaaaatt ctatagaaat aaccccccaaa ggagagattc taaataatga gacattcaaa   141060
catccaaaca tgtggatgag atgttgggga cagagccttt caagcataaa caccctctgt   141120
agctcccttg ctcatcagtc acttgtggtt tgaccactgc ctgtctcact tgggtccttg   141180
atcatcttgc aagagcagaa tcaaactgtc cccagggtga gcatcactca ggcatgctgt   141240
atgcagagcc cagctcttgg gcatcatctc tgcccactca catctcaatc atgaaagtct   141300
gtgaatgtcc cctgtggttc agtggctaag actttgcact cccaatgcag ggggccagg   141360 tttgatccca ggtcagagaa ctagatcctg catgctgcag ctaagagtcc aaacacaact   141420
aaaagatccc acatgcctca gggaagattg aagatcccga gtgccacagc taagacctgg   141480
cacagccaaa taaagatata ttaaaaaata atggaagcca tgaggcacat gggcttccct   141540
cgtggctcag atggtaaaga atctgcctgc aattctggag aacctgggtt caatccctgg   141600
gttgggaaga tccctggag aagggaatgg caacccactc cagtattctt gcctggagaa   141660
tcccatggac agaggagcct ggcgggctgc agttcatacg gtggaaaaga gttggacacg   141720
actgaagcga ctgataccca cttgagacac atggctaggg catccagcct ccttttcgtt   141780
tctacgtgta tcacttgtca ttcaacactg tgttttgaat atttgctgca taccaggctc   141840
tgctctagat gctggcaatg gaacaggac aagagaacca gattctggac agaacttgct   141900 cttctctgtct agagcccgat ttggatttgg gaaagtgaga aaggaagcct cgccagacat   141960
ccacctgtgg cctgactggg tgtctctctc catggatgcc ttggctgctc tctgttccac   142020
ctcttctgtt tctcagtcct gtctcctgaa gctgtttcca gctcatgcca tcttgttgat   142080
gggcctctta ccatcttggc tatctttgtc tctttccctg ccagagggct tgttccttg   142140 gtgcccttct ctgcacgagg acattttccc ctcctctgtc acacagcatt ctcccttctt   142200
ttgatgttcc ccatgttttc ctctcctcca gcctcttgag agaataaaag ccattcagcc   142260
tattgctcag gcattttgtt ttgatggcgc gagggttttg tcctcttgta acctctcctt   142320
gctccattgt cttgcccagg tttattcttt tcacacattc tttgtaaacg ttccttctcc   142380
ttgaatcttt tcttccactt gagcgctcag tcgtgtccga ctccttctga ccccgcgac   142440 tgtcgcccac caggatcctc catccatgga attttcctgg caagaatact agagtgggtg   142500
gccatttcct cctccaggga atcttcccaa ctcaggatc aaaccacat cttttgggtt   142560 tcctgtacgg gcaggtgaat tctttaccac tagcaccacc tgggaagccc tgtgagagac   142620
agcctgtctc tggttaacag cttgggcct ggaatcttct ctcccactct gtcctcactt   142680
taaaactgtc gcatcttatc cgggctctgt aaaactttta agaatgaaat aatttatttc   142740
tttgaataac tttctttata tccagctgtc gttgacggga gttaaaattg tgaatttctg   142800
aggtccaagg acttgataaa aatcagtgga agaagtttga gctgtattca gtcagatccc   142860
ttttgttaaa agtcaataag gaagaggtgg aacaatccca agccaaactt ctggcctttc   142920
ctttaaaaac attttttattg gggtattgtt gccttacaat gttgtttttg gcctttctaa   142980
```

```
agagactctg ctgtggtcaa acacctggat gatactctgg aatacaggac agagatgatt   143040
caatattgag gtggcagaac caacaaagtt tccctgtttt agtggctaaa aatttggaca   143100
ggggagaaac catgtggccc atagttcaag aactcatttt gacttttta aaatttccaa   143160 gtgaaaatgt ctatttgttt gcctctataa gaggtacttt tcctactaga actttgggag   143220
aacttgcgtg tgtgtgtgtg tgtgtgtgtg tgtgaataca cacatcaacc gcgttagtat   143280
catttttctt tccccacact gaccatccat gtctatgtgt gaaattcccc tgcaagatga   143340
agagacagtg tctcgaacgt catctgaata ttccagtcac gagcatgtta gacatattaa   143400
tcagtaggtg tcaatagatt tttgaactgc tgtttgtaaa gtgttatctt tgcttcattg   143460
ctgatggcaa taaggcatct tcttgcatct tcgagtcagt tcaataggca ataatagctg   143520
ctgtttatcc tagtggctca aatggtgaag atctgcctgc aatgcaggag acccgggttc   143580
aatccttggg tctggaagat cccctggaga agggaatggt tacccactcc aggattctag   143640
cctggagaat tccatggaca gagggctaca gtccatgagg tcgaaaagag ttggacacag   143700
ctgagcaacc aacactttca ccaactgcct actgtctgct tacatcatgt ctttgttatt   143760
gttgttcagt ctatttctga tcctttcaat aactctgtca tgtaaacgat gatacctgga   143820
ttctgttctt gaattctaaa gattcaggct ccccatggct ttgattaacc atgtcgaaag   143880
agaagagcac agtaaaaatt cttcaaaata aaagaacgaa aaagaagaac agcccatata   143940
tctgcacaaa attattcttt caaatcact gtggacggtg actgcagcca tgaaattaaa   144000
agatgcttgc tccttggaag aaaaactatg acaaacctag acagtgtatt aaaatgcaga   144060
gacatcactt tgctgataaa ggtccatcta gtcaaattta tagatttcc agtagttatg   144120 tactggtgta agagttggac cataaagaaa gctgagcacc aaagaactga tgcttttgaa   144180
ctgtggtgct ggagaaggct cttgagagtc ccttggactg caaggagatc caaccagtcc   144240
attctaaagg agatcagtcc tgggtgttct ttggaaggaa tgatgctaaa gctgaaactc   144300
cagtactttg gccacctcat gtgaagagtt gactcattgg gaaagactct gatgctggga   144360
gggattgggg gcaggaggag aaggggacga cagaggatga gatggctgga tgcatcatg   144420 aactcgatgg acacgggttt gagcaaactc cgggagatga tgagggacag ggaaacctgg   144480
catgcttcag tccacagggt cacaaagagt tggacttgac ttagcgactg aaccacaaat   144540
aaaatattaa tatgctcagt tatgtcagac tctgcaacct catggactgt agcccaccgg   144600
gctcctctgt ccatggaatt ttccaggcaa gaatactgga gtgggtgggc atttccttct   144660
ccaggggatc actccaacct agcgattgaa cccatgtctc ttatatctcc tgcattgaca   144720
ggcagaatct tttaccactg caccacctgg gaatctacca aaactaaaaa gtcttagtta   144780
gttttcaaat gtaaatgtaa attttgaata attacagaga tgtcaaagca aaattagaat   144840
gacatttgaa agattgacaa aatgaaagac attttggtgc aagtagataa cattctcact   144900
aatatttaga cattatcaat ttctggctct cttttctagac catgtagaga ttaatctttt   144960
aatatttcct tggaataaac aaccttcaa gtcatgtata tggctccagt cccaaagttt   145020
cagcctgcag agagaacatc cacagccttt ctaagaggct tctagttaat ccttatttat   145080
tatctagaaa cttaacttta ttactattgg cttatgcatc agagaggccc ttttgccttt   145140
tctttgcctc ttctttccca tatagtaggg gaaaaagtg gggaaagttt tcataacag   145200 aaaattcatt tcctagttat tatttcttct aacagttaac ttagaaaatt tctccaactt   145260
ctgagctctt gaaatctgca cattgtcttt aaagatatt tttagcacaa aatgtaatat   145320
aaattcaatg caaaaaattc agaaaatgca aatacatttt gtaaaaaata aataatatg   145380
```

```
tagtccttcc actcagaaaa acttagttga aattttgctg tatagccttc taaagtttat   145440
ttaaagcaca ttatgctgtt ctttctacaa aatatatcca tactctatat actacttaaa   145500
agtgattaaa ataagaaaaa tatatttaat atttccgtta attatttcct ttccagccta   145560
tttactgtgt gtgtatccta atttccattt gatatcatcc ttctacccaa agaactttct   145620
ttactatttc ttgtagcaca gttttattgg caataaattc tcaacttttg tttgtctaga   145680
ggtctttatt ttaattccat ctttgaaaga tattttact gaacataaaa ctcagaagta   145740
acacaatgtt aaagcagact ttccaaacaa caagatgtca gtcttgcctt gtacagcatc   145800
tgggaagtct gcaggaattc ttagcattat tcctgatcta gctccctgac caggattaga   145860
tccgggccgc ttgcactggg aacgcagagt cttagccatt gaaccaccag aggtccataa   145920
gcaagctcca gtgttagtca ctcagtcgtg tgcgactttt tgtgatccca tagattttag   145980
ccctccaggc tcctctgtcc actgaattct ccaggcaaga attctggagt ggattgccat   146040
ttccttgtcc gggaatcttc ccgacccagg aatcaaatcc gtgtctcctg tattgcaggc   146100
aaattcttta ccttctgacc caggtcctca tgtaatgttt ttcttgctgc cttcaagatt   146160
tcttttgtct ttggtttaag catttttgact ctgctgtgtc taggtttggt tttgttttat   146220
ttttttgagt aagggcagag caggagagtg ctatcctgct tgagagtctt tgagcttcct   146280
ggaactgtgg cttgttgtct ttcattaact tttttaattc atttttttatt gaaatatatt   146340
tgaatcacaa taccgtttat tataggatac tgagtatagt ttcctgtagt gggagcttgt   146400
tgtttatcca ttccagatat accagtttgc atctgctaat cccagattcc cactcctacc   146460
ctctttcatc cccccaagcc cttggcaacc actactctct cgtcccctaa ttctgtttca   146520
ttttcataga taggtttgtt tgtgtcctat tttagattcc acatgtaagt catactgtct   146580
ggtatttgtc tttctctttc tgactcactt cattagtgtg ataatctcta gttgcatccg   146640
tgttgctgca gatggcatca tttttctact ttcttatggc tgaatgtgaa atgtaccaca   146700
tcttcttaat ccagtcccct gtcgatggcc atttgtttcc atgtcctggc tacagtgaat   146760
agtgctgata tgaacatagg gatgcaagta tcttttttgaa ttattgtctg gatatatgcc   146820
tagcaggggg attcctgaat catatggtaa ttctagtttt agttttttct gaggaacctc   146880
catactgttt tccacagtgg ctgcaccaat ttacgttccc accaactgtg taggagggtt   146940
gcctttcttc cacgccctct ccagaatttg ttagacttaa ttaatgatgg ctgttctgac   147000
cagcatgagg tggtatctgt tctgaccagc gtgaggtggt atctcattgt agttttgatt   147060
tgcatttctc taataattta agaggttgag catcttttca tgtgcctgtt ggccaccgt   147120
atttcttctt ttggagaaat gtctctttat gtccattttt catttgggtt gttttttgtt   147180
gttgttgagt tgtatgagct gttttgtatat tatttcatta attttttaaa attcctggtc   147240
attatatctt cagattattt ttgaccttgt tttctatctt tgtctttttc taggactcta   147300
attacacaga tgtcttactg tttcatgttc cacaactctt gaaagtgctg tcctgtttaa   147360
ttcaactcct ttttatcttt atatttcagt ttgaataatt tctgttgaca tatcttcaag   147420
ttcatgaatt cttctctcag ctgtgcccta acaatactcc catcaaagaa attcatctct   147480
gatactgctt tttatgtaca acatttgcat ttgacacttt tgtactttct atctctttgc   147540
tgaaatttcc cgtctgttca tgcatattgt ccatctttc cactagatcc ctttaacatg   147600
ttaattatag ttatcttaaa gtccctatcg gattgataca acatctggat catccttgag   147660
tctggttcta tttattactt atctcttgat cattttttttt tcttgtgctt ttgtgtgatt   147720
cataattttt aattatatgc tagacatcat gcctggaaga acagagagac tgaggtaaat   147780
```

```
accatttatt attgagaatg ggcatactta ttctttcaag ctgtcagtgt tgggggtgtg    147840
tggcagaggg tggaggctga gtgagtgaat caagaggtga gctggatttg ggtctcgttg    147900
ttgctatggt tacagttagt gcaccacaga tttcaatggg tggttgctgt tactgtgtgt    147960
gtgtggagtg gaacctgggg tgcgagagga gttttctaag catttattct ttaccctcag    148020
cgttcagctg tctctgcaca cctgcacaca gagtagatct ctctcgtact cttgtcctca    148080
ccccagtgat tggaggacag gagcgctcac ttctgttgtt tgtctctctg ggcatggctt    148140
gttgtagagg taatggggtt tctttgttgt ccgggccctg catcagtctt aggcaagcct    148200
gaaccttggg gttaaggctt tctaagcatt ccggcctttc tctgcagtga cacctgct     148260 ttggagcagt gcataagcca atggacagaa gattttgct tccacctttc gctaagctgc     148320
agtggctctt tgattacgtc tgggggagag agactccttc tcctccctta gagaaaagca    148380
agttttgctt ttattcttct cccagaagca atggacttct gcctggtcct agaggccaga    148440
gggttttctg ccctccccac aggagcttga gattttgct ttgcaagaga aggctctggg    148500
aaagaagatg aagctagctt gtctcccagc agctgtttgt ctgtgtcacc tcctgcatgt    148560
ctgtgaagtg gagggggccc cgcgccagtg tcctcctctg cctctaacct ttcttatgaa    148620
cacccagtga cggtctgtag aaaagagctt gagagtaagt gcgagctccc tcttgtcaga    148680
gactctaagc tattccacat tgacacacta acccacccctg ggcctttaag ttgaatgttt    148740
agctaattac atggtgacca cctcctgtgc ttgtgctcag ccaaaagtga ggcggttcat    148800
ggatggactt ctcttcttgg ttgccttgtg acctcaactc tctgatgggc tcgagagaag    148860
ttattatttt gtaaattact cagcttttc tcatcattca gatggaaaca acattttctt    148920
aggactttcc acattgtaaa tagaagcaga actcagcatc ctactttata atctgcagtt    148980
ttctcttaac agaatactgt gaagtctttc cagttttaat tttttttaat ttatttttta    149040
aattggagta taattgcttt acaatgtttt gtcagtttct gctgtacaac agcatgaatg    149100
tattcccctc cctcttggac cttcctccca ccccccatcc cacagctcta ggtcatcata    149160
gagcactgag ttgagctccc tgtgctatac agcagattct cactagctat ctacttaata    149220
catgacagtg tattatgtt aatgctgttc tttccttcat tccaccctct ttcccaccct    149280
gtgtccacaa gtctggtctc tacatctgca tctctattca tgccctgcaa ataacttcat    149340
cagtaccatt tttctagatt ccatatatat gtgttagtaa gtgatatttg tttttctctt    149400
tctgacttac tttgctttgt atgacagatt ctagggtcat ccacatcact acaaatgacc    149460
caaattttgt ttcttttat ggctgagtaa tattccattg tgtgtatgta ccatatcttc    149520
ttcatcgttc ctctgttggg ggacgtttag gttgcttgca tgtcctggct cttataaaca    149580
gtgctgtgat gaacattggg gtagtctttc cagttgtaat ccctgcttag tatctcattg    149640
tgaagatcta ttgtaattat ttctgatgaa taatgaggga ttgccaccct tttaaattcc    149700
caccatgctc cacagctaga gaactaagcc tgtgctctac aaccagagaa ctaagcccgt    149760
gcaccacagc tagagaacta agcccatgct ccacaaccag agaactaagc ccgtgcacca    149820
cagctagaga actaagccca tgctccacaa gtaaagaact aagcctgtgc tccgcagcta    149880
gagaactaag ctagtaaccc acagccagag aactaagccc atgctccaca accagagaac    149940
tgagcccatg cgccacaacc agagaactaa gcccatgctc cgcagctaga gaactaagcc    150000
catgctccac aaccagagaa ctaagcccat gcaccacagc tagagaactg agcccatgct    150060
ccacaaccag agaactaagc cgtgcaccac agctagagaa ctaagcccat gctccacaa     150120 ctaaagaact aagcccatgc tccgcagcta gagaactaag ccagtaaccc acagctagag    150180
```

```
aactaagcct gtgctccaca accaaagaac tgagcccatg caccacaacc agagaactaa 150240
gcccatgctc tgcagctaga gaactaagcc tgtgcaccac agctagagaa ctaagcctat 150300
gatctgcagc cagagaacta agcccatgct ccacagccag agaactaagc ccatgatccg 150360
cagctagaga actaagcctg tgcccaacag ctagagaact aagccggtaa cccacagcta 150420
gagaagtctg catggcccag cgaagaccca gcagagccaa aaagtaaata aactgcaaat 150480
gcaagaattt catcttgttt ttttaaaaaa gagatactgt ctcttcatct ctcttccttt 150540
gttttttgttg ttaaagagag agatctgaga aagtgaggtg acaatgccta cttttttttc 150600
taatgatttt atttattcat ggctgtgtag gatcctcatt gctgcctggg cctttctcta 150660
gttgtggcaa gcaggggcca ctctctggtt ggggggcacag gcttctcatt gtggtggctt 150720
ctcttgttgc agagcacggg ctttgtgccc acagacttca ggagttgcag ctcccgtgtc 150780
ctagagcaca ggctcagtag ttgtggcacg agcttagctg ctccgtgcca tgtgggatct 150840
tcccgggatg gaactcgcat ctcctgcatt ggaaggtaag gatcctttac cactgagaca 150900
ccaggaaagc cctcaggaat attttagatt ctagttttcc acactcgtat ctggtgagag 150960
aggccaggat gaagaggcct gggagctggg agtcttcagc cacagttctg gctctgccat 151020
caaaagctct ggggcctctg gcgagcgcct gctgcttcct cagtcacgtc caattctttg 151080
caacccatg gactggagcc cctgaggctc ctctgtccgt ggaatttccc aggcaagact 151140
gctggagttg gttgccactt cctctccaa agcctacttt ttttttatcca gaatcctgcc 151200
tgtcatggga caagaaggta gaacaatcac aagtgcatct gatgtctaga taggcaaatt 151260
cacccatggg gtatgttaca catgtcttgt tcatcccact tcagtggtct gagctgggat 151320
atgttaacac aggtaatgag tcattttagt gctgttttc ttcctgcaag actctctcct 151380
gttccagctc ctctccacat ctatctggag ggaactacta agctagaaag agagcgacaa 151440
agaagatgtt taaacagagg catctgaaac caccagtgca tacacttagc gaagtagact 151500
agttaaccag aaacagatcc gttacttatc atacaaccat agttcttgct gtgaaatgat 151560
ttgcaaagtt tatgtcattg tgacagctgt tttgtgaaaa ttttgaatga ggctgactct 151620
gttttttgaaa ccgaaagagt gtgatgccta cgtatttgtg aaattcaagt atgttttgct 151680
ctcttattga tgcagactgc tgattggtaa tgtattatgg agcccccttg tccattgaca 151740
gttgaagcga aaatattatc ttaagtgata aatttattgg tagctgttcc attacccaaa 151800
atgaatgttt agattactcg tgagagtctg tcatgtcaga gctaccagtg agcttttcct 151860
gtgacacaat ttattctaat tcctaagtcc ccgcctcacc atgttatagc ctattaaatg 151920
tgtcatagaa tgattaggta gagagatatg agattttgtt attaacacaa tttacacagg 151980
agcactggaa aaatgaaacc cctgctgaac aaacttgggt tgattgtctc tgttttatc 152040
tgtacaaagg atgtccagag acaaatcagg attctcaacc atgaggatgc actacgaggt 152100
gctctgtgaa ttgcatcaag gatggatatt gaaaagtaac cctcatggct ttattatgga 152160
tttcttgaaa ccactccaaa tggtgcttct tgatacccgc tcccatgccc cttctaacat 152220
ccctggaggt atttgaaggt cagaagagag acagaatatg ggacttgtgg cattacataa 152280
tgtaacgttg gtggtgtata tattacatgt attgataaca ttatatacaa caatagacgt 152340
gcattcagaa accaagccat ttttaaaact gtgtgaagca tagagagaat tatgatctgt 152400
gttagcactc ggtcattcat tcattcattt agttgaccca aagaggtagt tttggagagg 152460
ttaaatacag tcttggaatc aaaagatctg acttttttcat tctctgagat tctgtttctt 152520
ccacacccat aaaatgatga tagtgatatc tacctgacaa agttattggg tgaataaatt 152580
```

```
aatttatatg aaaatgtgag gatatatgca gtaaacattt gtgtaattaa ttatgcatcc   152640
agcactccag gaaagccata ctgtttgtga agaccttagg gttttttag tattctagtt   152700 attttgttgt ttatttattt tttggctgct ctgggtcttc attgctgtag atgagctttc   152760
tctggtctcg gcgagtaggg gctactgtta ttacagcgca tgggcttctc actgcagtgg   152820
agtgcaggct ctaggcacat gggcttcagc atttgcagta cttgggctca gtagttgtgg   152880
cacatgggcg agctgccccg cagcaagggg attcttaacc actggaccat cagggaagtc   152940 caaaaccttta ggttttttcgt ttgcccagtt tttgcataaa tccaaagcga ctgaggtttt   153000
atatctccat aaataaaaac ataagtgatc cttccacttc aaagctttaa aaccagagta   153060
tgcttctctt tcttgcattt gatccaacat aaccccccag atgtggacct cccagagctt   153120
gctcggactc atgtccattg agttggtgat gccatccaac catctcatcc tctgtcgtcc   153180
ccttctcctc ctgccttcag tctttcccag catcaggatc ttttcccccc agatgtgggc   153240 cttattttt ttggctccaa aaccactgta gatggtgact acagctatga aattaaaaga   153300
cgcttgctcc ttgggaaaaa gctatgacca acctagacag catattaaaa agagacgtta   153360 cttttgccaac aaaggtccgt ctagtcaaag ctatagtttt tccaatagtc atgtatggat   153420
gtgagaattg gactataaac tgagcactaa agaattgacg cttttgaact gtggtattgg   153480
agaagactct tgagagtccc ttggattgca aggagatcca accagtcaat cctaaaggaa   153540
atcagtcctg aatattcatt ggaaggactg atgctgaagc tgaaactcca atactttggc   153600
cacctgatgc gaacagccga ctcgttggaa aagaccctga tactgggaaa aattgaaggc   153660
aggaggagaa ggggacgaca gaggatgaga tggttggatg gcatcaccga ctcgatagac   153720
atgagtttga gcaaactcca ggggttggtg atggacagga agctcgggtg tgctacagtc   153780
catggggttg caaagatttg gacacgactg aacgactgaa ctgaactgaa ttgaacagaa   153840
ctgaaaagag acagtccttg ttttttattta tcttatcatt taagtagaga agactcttca   153900
gaatccttgg acaacaagga tcaaaccagt caatcttaaa gaaaatcaac cccgaatatt   153960
cattagaagg actgatgctg aagctgaaac tctaatactt gggccacctg atgtgaagag   154020
ctgacttatt agaaaagatc ctgatgctgg gaaagcttga gtgcaggagg agaagggac   154080 gacagtggat gagatggtta aatgagatgg tatcactgat tcaacagaca tgagtttgag   154140
caaactttgg gagatagtga aggacaggga agcctggtgt actgcagtcc atggaatctc   154200
aaagagttgg acaggacttg gtgactgaac aacaaaatca tttaattgag aaaacactca   154260
tgaaatcgcc agagacctcc aagtccatgt atgaaagtaa cactagtaga tgattatatc   154320
atgaactgag aaaatccaga ataaagtagg gaagaaagaa cagggtcctt gaagtctgca   154380
tgaaagtgat ggttctttat acctggtggg gtgagggcat tctcctgagt ctctttgtcc   154440
aggaacagag ttgattcctt tgtcatactg tccttcagta aatgttcata gttttctaaa   154500
tatagacctt gtttcttatt tggttcattc ctaggcattc tataattttt gttattgtta   154560
acagcatcat taagtttgta tcccagggac agggagtgga tgcccagacc ttagcttatt   154620
gcccttggta tcttaggtaa atgacaggaa ctggtgagtt actaggaaat ggtgagttac   154680
ccggactttt cacaaaatac ctctgaggct cataccgta gagaatgtgg aggttgttgc   154740
cccaaggggt gctggcagga ggcatgtgtg catgctcagt cattgcagcc tcatggactg   154800
tagcctgcca gcctcctctg tccatgggat catcccaggc aaaattacta gagtgggttg   154860
ccatttgctt ctccagggga tcttcccgac ccagcaattg aacctgtgtc ttttgcatct   154920
catacattgg caggctgatt cttaccact gagccacctg ggaagcccct ctggctagag   154980
```

```
gcagagggca ccaacccaga accaccatca agacaggtag ggtagcttcc ccagctttag   155040
aaattaaaaa ttcacctcct tccctctttg ctttctttca agagatgctt ttgtggattc   155100
agagattctt gaatgaatgg agacctccct ggcggtcctg ggactaagac tctgcgttct   155160
aaatgcaggg ggcccgggtt ccatccctgg tcagggaact atatctcact tgccacagct   155220
aagacctgtt gaagccaaat aattaagtat taaaataata aaataaataa agtaaaatag   155280
agcacaggct aattctccct ttgtgggaag ttcaagagc ttatggcaag gatgttctaa    155340
gagccaagtt cttctcgtag aactgaaatt acaaagatta agaaagatga attcccagtg   155400
attagaaaga cccaggaaat caccatcagc cccctaactg aggaaagcct tgtcagaaat   155460
cggctttgaa ctgtctccct gtccaagtca cttatttctc ctcacactgc ctattttcat   155520
atagaacaat aagaaatcag tcacacggat acaaagactc gtagtgcagg ataatgtgg    155580 tttgtccaga cgtgctcatt gacgactcag ctgaagtgag ctatctcttc tgacatttgg   155640 cttctctca  taaacctcct cttatcttgt ctttcttttc aaagtaaaga aaacaattc    155700 ctcagatgtc ctaactatca agagatttag accaacccca tatatgtctt tcttcaaga   155760 taaataaata tgcttttcaag ttctgccaaa ctaagaatct gttttaggg taatgaaaac   155820 tttcatttac agtcagacgg ccaatggttg ctctaatgga gtgagaaggc gacacatcgt   155880
atgtgactgc aataactcac acttcaagcc aggaatgagg tattaagagt ctcagaatcc   155940
caggtagtgc caagggaatt tctggatcct gcaagccaaa cgttatagag aaagaggact   156000
agaaggacct actgtgagtg ctcaggcaga gagagagctt ttaaacctgt ggtggctgta   156060
tttcacatcc ataaatttt cctctgtgcc cttgtatctt tgcccattat tatctgccat    156120
tatcagatca gatcagatca gtcgctcagt cgtgtccaac tctttgctac cccatgaatc   156180
gcagcacgcc aggcctccct gtccatcacc aactcccaga gttcactcaa actcatgtcc   156240
atcgagtcaa tgatgccatc cagccatctc atcctctgtc gtccccttct cctcctaccc   156300
ccaatccctc ccagcatcag agtctttcc aataagtcaa ctcttcgcat gaggtggcca    156360
aagtactgga gtttcagctt tagcatcagt ccttccaaag aaatcccagg gctgatctcc   156420
ttcagagtgg actggttgta tctccttgca gtccaaggga ctcaagag tcttctccaa    156480 caccacagtt caaaagcatc aattcttcgg cgctcagcct tcttcacagt ccaaatctca   156540
catccataca tgaccacagg aaaaaccata gccttggcta ggtgaacctt tgttggcaaa   156600
gtaatgtctc tgcttttgaa tatgctatct aggttggtca taactttcct tccaaggagt   156660
aagtgtcttt taatttcatg gctacagtca ccatctgtag tgattttgga gcccagaaaa   156720
ataaagtctg acactgtttc cactgtttcc ccatctattt cccatgaagt gatgggaccg   156780
gatgccatga tcttcatttt ctgaatgttg agctttaagc ccactttttc actctcctct   156840
ttcactttca tcaagaggct ttttagttcc tcttcacttt ctgccatatg ggtggtgtca   156900
tctgcatatc tgaggttatt gatatttctc ccggcaatct tgattccagc ttgtgtttct   156960
tccagtccag cgtttctcat gatgtactct gcatataagt taaataagca gggtgacaat   157020
atacagcctt gacgaactcc tttcctatt tggaaccagt ctgttgttcc atgtccagtt    157080
ctaactgttg cttcctgacc tgcatacaga tttctcaaga ggcagatcag gtggtctggt   157140
attcccatct cttgaagaat tttccacagt ttattctgat ccacatagtg aaaggctttg   157200
gcatagtcaa taaagcagaa atagatgttt ttatggaact ctcttgcttt ttctatgatc   157260
cagcggatgt tggcaatttg gtctctggtt cctctgcctt ttctaaaacc agcttgaaca   157320
tcaggaagtt cacagttcac atattgctga agcctggctt ggagaatttt gagcattact   157380
```

```
ttactagcgt gtgagatgag tgcaattgtg ccatagtttg agcattcttt ggcattgcct    157440
ttctttggga ttggaatgaa aactgacctt ttccagtcct gtggccactg ccgagttttc    157500
caaatttgct ggcatattga gtgcagcact ttcacagcat caactttcag gatttggaat    157560
agctcaactg gaattccatc acctccacta actttgttcg tagtgatgct ttctatggcc    157620
tcttgacttc acattccagg atgtctggct ctagggcttt ataaccacca ggaaactaga    157680 aggggaaaa atctaggat ttaaacccctt caaattttgt attggaactt tgggtccaag     157740
ttgtattaga aaagaattag cttgaggcct gaggcccttc tcttctgatt gccaccagaa    157800
tctaatgtct gtctccttt ccattattt tgatttgatt tgatttttt tttcagccac       157860 gtcttgaggc atgcagaact tcccagatca gggatcgaac ccatgtcccc tgcagtggaa    157920
acgcagattc tttttttttt ttaatttaaa tttatttatt ttaattggag ctaattact    157980 ttacagtatg gtattggttt tgccatacat caacatgaat cagccacagg tatacacgtg    158040
ctccccatcc tgaacccccc ttccacctcc ctccctgtac catctctctg ggtcatccca    158100
gtgcaccagc cccaaccatc ctgtatcctg catcgaacct ggactggcaa ctcgtttcat    158160
atatgatatt atacatgttt caatgccatt ctcccaaatc atcccaccct ctccctctcc    158220
cacagagtcc aaaagactgg gtctatacgt ctgtgtctct tttgctgtct cgcatacacg    158280
gttatcgtta ccatctttct aaattccatg gatatgcgtt agtatactgt attggtgttt    158340
ttctttctgg cttacttcac tctgtataat aggctccagt ttcatccacc tcattagaac    158400
tgattcaaat gtattctttt taatggctga gtaaactcc attgtgtata tgtaccacag     158460
ctttcttatc cattcatctg ctgatggaca tctaggttgc ttccatgtcc tggctattat    158520
aaacagtgct gcaatgaaca ttgggtacac gtgtctcttt caattctggt ttcctcgctg    158580
tgtatgccca gcagtgggat tgctgggtca taaggcagtt ctatttccag ttttttaagg    158640
aatctccaca ctggtctccc tagtggctgt actagtctgc attcccaaca gtgtaagagg    158700
gttccctttt ctccacaccc tctccagcag attcttaacc cttggaccac cagggaagtc    158760
cccctcctcc attactaagg atgactatga gctgacactg cctggcatat cagtaggaaa    158820
acatttactt ttaggtgatt cccctctgtt cttcattctg aatgttttg ctcttgaaaa     158880 aaacaaaacc cttaagctcc attgtcttgt ttcatgcttt catctaatgt taaaataaca    158940
gcaataactt ccagttttta tctttaaaat tatctctata acattcttta ttgtattcat    159000
ttcagtgttt tgagtaccta ctatgcacca gactcatttc tctgtgcata taattcatat    159060 ctcttaccc ggcatgggat ctgaagctct gaaacgttga ctcagtagca ttttgatctt     159120
agccgaaagg ccgggaagcg attcagtaac gttttgaaga gggcaaagtt ggaatttaga    159180
caaactcaat cctcatccaa agcacatgtt cttcccaata aactctgttg taataatatc    159240
cacggagaat attagcttcc tccacttcat ccttgtcgtg cttactttgc tcgtatgttt    159300
tatttcagtt ttgagttatt tgttgttctt cagttgccaa gttgcgaccc catggactga    159360
agcacgccag gcttccctgt ccttcaccat ctcccggagt tgttcaaac tcaggtccac     159420 tgagtcagtg aagccattca accatctcat ccctgatact tcttgtgagc cagacttgtc    159480
tcctgcctaa gacctttca tggcttcccc gtggaaaaag ttaccactgt catctccgag    159540
accaggcctg cttccctcat ctctggaact gccctccttg tactcttctc tctagtcatg    159600
ctattccctt gcactttagc ctgctccctg acactttgcc ttcgattcct gctttttttc    159660
tggcttagat ttatgctact caaactgcag ttctggggac catcagtatc acttgggagc    159720
ttgttagaga ggcagaattc cagctgcacc cccagatccc aggtgattag gatgtgcagt    159780
```

```
gattgtttgg gaagcacaga cctagaaatg aaggagggca cggcagccca ctccagtatt   159840
cttgcctgga gaatcccacg gacagaggag cctggtgggc tacagtccat ggggtcgcac   159900
agagtcggac acgactgaag cgacttagca cgcacgcatg acctagaatg ttcttgttgt   159960
gtttttcacc ttgacaactc tcacttattc ttcaaaaact tacctttgga gagctgaggt   160020
cagttttcaa ggtccgtctg ggtgagaggt ccccaagcgt acaagtttta tatgtagcat   160080
ataagctctt gcctcttagg gaggggggtg tctgtgagct tctcctgtga ctaagcacag   160140
agatatgtaa ggcagctttt cttcagagac gtcaaacaaa acagtatatt acagcggact   160200
gactgcaggc acagatatgt caatccagct gcctctatta agccagacat taaagagagt   160260
tgcaattatg taaaatgagg ccattcttca cactgaaact cgttttttgt tttggaaaat   160320
agttatttt catcaacata tttatgctaa cacgtaatag gttattgtt atttttaatga    160380
actgatcaat ttaatattcc tgtatgacat gaacaaacat atttatttac tttataagca   160440
atcttgtatt attgataaat attaacattt agtattgatt caatcaagga gatattttta   160500
atttccctta tagttaatgt tgggcttccc aagtggctca gtggtaaaga atctgcctgc   160560
caatgcagga gacgaaagag acaggggttc tatccctcag tagggatgat cccctgagaa   160620
aggaaatggc taccgggtaa ccagttccag tgttcttgcg gggcccacct gtatagttct   160680
ctcattagat cctaagctcc ttgaggacta tgactatgac caattcatct ctcttattta   160740
ttgagactaa agaaacatgt agcatcctcc cagaatactc tggggactaa ggagtatgtt   160800
tactctccag tttatagaga gagccctggg cagcctacac ccaagaagcg gcttcagggg   160860
tgatgatttg tatatgatgc tctatccctc agttgctaaa gtgagtgaca catgggcatc   160920
accaccagcc ctgggggtcc tctgctccat gttgcagctg cctggagtcc cacctccgca   160980
ggaggtaggg gagttccatg agcagcagcg cccatttgtg cccggcatca tcacaccagc   161040
agtcatcttc ccctgtgtcc gtggctctct aacccgtaaa ggtacagtga gaggactcag   161100
ttcagtctca gttcagttgc tcagtcgtgt cttactcttt gcgaccccat gaattgcagc   161160
acaccaggcc tccctgtcca tcaccaactc ccagagttca ttcaaactca tgtccatcga   161220
gtcaatgatg ccatccagcc atctcatcct ctgtcgtccc cttctcctcc tgcccccaat   161280
ccctcccagc atcagaatct tttgcaatga gtcaactctt cgcatgaggt ggccaaagta   161340
ctggagtttc agctttacca tcattccttc caaagaaatc ccagggctga tctccttcag   161400
aatggactgg ttggatcttc ttgcagtcca agggactctc aagagtcttc tccaacacca   161460
cagttcaaaa gcatcaattc ttctgcgctc agccttcttc acagtccaac tctcacatcc   161520
atacatgacc acaggaaaaa ccatagcctt gactagacgg acctttcttg gcaaagtaat   161580
gtctctgctt ttgaatatgc tatctaggtt ggtcataact ttccttccaa ggagtaagtg   161640
tcttttaatt tcatggctgc aatcaccatc tgcagtgatt ttggagccca gaaaaataaa   161700
atctgacact gtttctactg tttccccatc tatttctcat gaagtgatgg gaccggatgc   161760
catgatcttc attttctgaa cattgagcct taagccaact ttttcactct cctctttcac   161820
tttcatcaag aggcttttta gttcctcttc gctttctgcc ataagggtgg tgtcatctgc   161880
atatctgagg ttattgatat ttctcccggc aatcttgatt ccagcttgtg tttcttccag   161940
tccagcgttt ctcatgatgt actctgcata taagttaaat aagcagggtg acaatataca   162000
gccttgacga actccttttc ctatttggaa ccagtctgtt gttccatgtc cagttctaac   162060
tgttgcttcc tgacctgcat acaaatttct caagaggcag atcaggtggt ctggtattcc   162120
catctcttga agaatttttcc acagtttatt gtgatccaca cagtcagagg ctttggcata   162180
```

```
gtcaataaag cagaaataga tgttttctg gaactctctt gctttttcca tgatccagcg    162240
gatgttggca atttgatctc tggttcctct gccttttcta aaaccagctt gaacatcagg    162300
aagttcacag ttcacatatt gctgaagccc ggcttgcaga attttgatca ttactttact    162360
agcatgtgag atgagtgcaa tcgtgtggta gtttgagcat tctttggcat tgcctttctt    162420
tgggattgga atgaaaactg acctttccca gtcctgtggc cactgctgag ttttccaaat    162480
ttgctggcat attgagtgca gcactttcac agcatcatct ttcaggattt ggaatagctc    162540
aactggaatt ccatcacctc cactagcttt gttcatagtg atgctttcta aggcccactt    162600
gacttcacat tccaggatgt ctagctctag gtcagtgatc acaccatagt gattatctgg    162660
gtcatgaaga tctttttgt acagttcttc tgtgtattct tgccacctct tcttgatatc    162720
ttctgcttct gttaggtcca taccattct gtcgtttagc gagcccatct ttgcatgaaa    162780
tgttcccttg gtgtctctaa ttttcttgaa gagatctgta gtctttccca ttctgttgtt    162840
ttcctctatt tctatgcatt gatcgctgag gaaggctaga tggtgccaca ggagactcgt    162900
ttggccatgt atgctgggaa ctgactttgg ccaactccag tgtgagagga ggaagaagcc    162960
catgggaata gaatcccaca tcacactaaa ttctaccgct attagggaca aaaccgcca     163020 tataccacat ctgcaagctt catgaatccc tgatccctac cattgaaaaa aattttttaa    163080
aattttgtat tgaagtgtat ctgattaaca atgttgtgat agtttcaggt gaacagcaaa    163140
gggacgcagc cacacgtata ctgtatccat tctccctgca aactcctctc ccatccaggc    163200
tgccacataa gcagagttcc ctgtgctatg cactaggtcc ttattggcta tccgttttaa    163260
atgtagcagt gtgtagatgt ccatcccaaa ctccttaact atccctttcc cctatccttc    163320
cccccgcacc cccagggcaa ccataagttc attctccaag tttgtgagtc tgtttctgtt    163380
ttgcaagtaa gttcatttgt atttcttttc agtctgca tagaatgcat gtcctttgct      163440
atttcccctc ctctgtctgg cttgctccac tcagcatgac aatctctaga cccatgcgtg    163500
ttgctgcaaa tgactttatt tcattttttt aaccctgctt cctgccctt tggatgccac      163560 aacaagcccc ttgcatggaa gccatgatgc agtcgtatcc tcttcctgtt ggaatccagc    163620
aacagaattc tgtcagtggc tggacacagg gtggaacaaa agcttaggtg ataccactct    163680
gatcctgaga ggtacctatc tagtatttct agccgaccca catgttttga ccactcattt    163740
tatcagtgaa atttatttc cttatcgtaa ttgcaaactc tttagggctg gttggagata    163800
acagtagttg aactctagac agacgtctgg tttatgaact atgagagttt gtcaaaagct    163860
aactaatgaa gtgtgggttc ctgatgaggg tacttcagat gttaatggac atccctagg     163920 gtgcagaata aagtgtgcac acacacacac atacacacac ccctgtctca cactgtttat    163980
gttgaagtat cttcaagtaa gtcacaggca gtataacaat atcattaagt tcaaatacac    164040
acaatatagt gaaaactaaa tatggtagag tctcatttat ctgaaattca gctatgccat    164100
catttcattt aactggaata aaaccaagaa cctgtgaata aacaggatca tcacagtaga    164160
tgctcagtac cgattcacca tatttcacgg aatcctctaa cctccaaaat acatgtcccc    164220
ctctttgccc ccatagaaag agatcttga ataaatgtca cactcctagt aattctgcat      164280
tttcagtctc agccctggtt accctctttg gccctggctc agagcctgtg tgttctccat    164340
ctgcatgcaa acacaacttc aactctctag gttttcgga cccttcgcag attaagagga      164400
gcaagttaga aggagacagg gaagctgctg caggtaggaa aactgacaaa cggaaacggc    164460
agcttttcag tgtacctgaa aataaaggtg gaatcggcaa aatttaataa gtcaatataa    164520
gaactcagtt cttataatga ctgagtcata tagtaagtca gttacttgag gccaagagct    164580
```

```
cttcatacct taacagaccc tgtgggaaaa acagagtcta aggctcacgc tcattgtatc   164640
agacacctgt ttggcaacat tacagaaatc tggacctcct ctttcctgag gctgaggccc   164700
ctcattctcg gcagttctct gcgctccagc tggtttccgg caggttcatc ctgacagcgc   164760
tatccttatg cccgagcctc ctgcacgggg gcgtctctct tggtgctgga gcccgtgaca   164820
cctctcagca cccatgttga caatccagaa gtttctgtgt ggtggtagtg gggatgtggg   164880
caatgtaggg cagctggtag atgcactctt ccccactctt cctcccagag ggattgttcc   164940
aagtctcgtc acccatctca gccaccaggt tgaggggtca agcagtggcc agctcaggtc   165000 agcccccctga ccttccctgc cgcccacatt ctgtcttccc gggactgagc tctccatata   165060
gagtaattca tagaagcttt ggcttaagac ttgccttttg agaaacccag gccaaaatac   165120
tcatcaccat catagaaggt caagttattt caaaaaattg atggtaaaga acctgcctgc   165180
attcagggag acctaggttc gatccctggg ttgggaagat cccctggaga agggaacagc   165240
tacccactcc agtattcttg cctggagaat cccatggaca gaggagccta gcagctacaa   165300
gtccatgggg tcgcaaagag ttggacatga ctgagcaact ttcactgatt aagagggacc   165360
aaaaaatggg cacagatttc cacatactat ttatttggca catagaaatt cccattaaaa   165420 tttttttattg tttatttttat ttattttttgg ttgcactggg tcttggtggc tttgctaagg   165480 cttttctctag ttgtggcaaa cagggattac tcttttttttt taatttattt attttaattg   165540
gaggctaatt actttacaat attgtagtgg tttttgccat acattgacat gaatcagcca   165600
tgggtgtgca tgtgttcccc atcctgaacc tccctcctgc ctccgtcccc atcccatcgc   165660
tctgggtcat cccagtgcac cagccctgag cacctggtct catgcatcga acctggactg   165720 gcgatcttttt tcatatatga taatatacat gtttcagtgc tattctctca gatcatccca   165780
ccttcacctt ctcccacaga gttcaaaaga ctgttctata catctgtgtc tcttttgctg   165840
tctcacatat agggtttttca ttaccatctt tctgaattcc atatatatgc gttagtatac   165900
ggtattggtg tttttctttc tgacttactt cactctgtat aataggctcc agtttcatcc   165960
acctcattag aactgattca aatgtattct ttttaatggc tgagtaatac tccattgtgt   166020
ctatgtacca cagcttttctt atccatttgt ctgctgatgg acatctaggt tgcttccatg   166080
tcctggctgg gggttactct tcattgcagt attctggctt ctcattgagg tggcttctct   166140
cattttgaag catgggctct agggctctag ggctcaggct cagcagtcat ggtgcacagg   166200
ctaaggttct ccatgagctt aggtgctcca cgggtttgtc tgctccacag catgtggaat   166260
cttcctggac cagggatcga acccatgtcc cctgcattgg caggtggatt tttaatccac   166320
tctgccacca gggaagtcca gaaatacccca tctttaatga ggtataattg acataacgtt   166380
atattagttt caggtgaaca acatgcttca gtatctgtag atactacaga atgatcacca   166440
cagtaagtcc agttaacatg cctcaccata catagttaca aatctttgtc tcatgatgag   166500
aaattctaag atccattccc ctaggtactt tcgagcatac aacacaggta tgtaacacag   166560
ttttattaac tatagtcacc atgcacatta tagacccagg acttactaat tataactgga   166620
aatgtgtgtc ttttgtccccc tttcatgtag aaatttccat tttgattcag attccatctg   166680
atggaactcc atcttatcct ttgccacaaa caatttaaaa gaaagtaggg gtaattaaac   166740 atttatacctt tcagctagca agaaaaactca gctgtctaaa gtagttgtct tcttgagtct   166800
tgacagcaca gttgtactga ggggtattgg aaaacgcaat cagcagagtt gggaggagat   166860
ttaccagaat aggctttctt tcttttttgt atttatttac ttttggctgc attgggtctt   166920
agttgtggct agcgggcttg gttaccccac cgcttgtggg atcttagttc ctcaaacagg   166980
```

```
aatcaaaccg acatcccctg cactggaagg tggcttctta acacctggac cgccagggaa   167040
gtcccaggat aggctttctg cagcaaatca gacttcagct gagttctgaa ggcctggaga   167100
cctttggaag gatggttcaa cttgagttta ggaatggaaa ccacgggcta gaaagcatgc   167160
attgtgcgca agggtgatac ttcttccacg tggaatggaa aaaccgtgt tttgtcagcc     167220 tgttcttttt tgcgtgcaac aaggaactta gtcagcccac ctaaatcagt tcatctgtag   167280
cagttgatat tgatcatgca aatagccaaa attactccag tggcttcttt cttgtgcaga   167340
aaccagctac tggtgagtaa cttatcattg atagagtttg ggaatcaacc ttgctccctt   167400
gggtggggca agaggattgt agtcttgtca cttggctatt gtccttttcag cacaagatcc   167460 atgtgtgagc acacacacac acacacacac acacacacac acacacacac acacagagtg   167520
ctatctactg tcaccaattc tataaaaaat tttactgtta aatagagaag ggaggataat   167580
ctcatatttt aaaggaccac tcttaaaaac attttttttac tacatcaaag gaccactctt   167640
taaaatgaat taaattttc ttacttaaat cttaggccag atcctaaagg aaacagaaa     167700 aataagactt aaataacaac agcatgatca aagcaaaaag tagtaaccta acatattggg   167760 cttttcattct tttgggaatt gaatatctct ttgagaattt gatgaaagct gtggaccttg   167820
aaccccagaa aaatgggaat acaaaaaaa agtttgcata taatttcatg ggtcccagat     167880
taaagaaaat ggttatgtct tcccctgtga tgttcagttt atctcagata gcaagagtcg   167940
aggtggaatg cagttttaag ggtgcagtct taagagagaa agtagatgtg cagtgacttt   168000
gttttaaagt tattttgtaa ataattgtaa ttgttcatct tagtcatcgt attctgttac   168060
catcaggagt taatctgtta ttcttataat ttattgagaa tgattggtaa ctaattagga   168120
agggagggag tagagttggg ggaaggaagg acagagacaa aaaatcctca agagagacac   168180
agattgacat agtgtctaat caacttaaat ttctaaagga gactggagaa accctaaata   168240
tcaaacaact gagggtgaac tgacttaatt ttttttggcc aaagacaggt ggattcctgt   168300
catgcaagtc aacaattcag ctacttattg ggcacctgct gtgttaacca gcattttgtg   168360
ttcaaggaac tacaaatgat gtgaattaga tcaagacaaa gcctaacctc aaagaattca   168420
tcctgcgctc attatgatgg aatcaaagct ttgaaaaggg aaaagtcctt ttaaccttcc   168480
ttccatggtc ttagcaatca atatgtctgg gcattttttct tcaagtcctt cattgttaat   168540
gaggtagggt taatgctctt ttgtgttaaa attctgcagt gatggtgttt atcttttgaa   168600
acgctgctta gtgagctcat gcaagctgtt tgtacaaaga caaattaaaa tcaagtagat   168660
ggatgcaact agcctccaca ttcagacctc aaaagcaaat aaagctgtag tcggagaaa     168720 aataaaaata tgtctttttt cccacacgtt gcaagtttcc gacagagatg ctttcgtgga   168780
gaggctggtt gctatctttg gttcctccat gggaggaatt atccaggata tgggaattat   168840
gcatctaggt agtctagtta aaggttttct tctaaagtga aagagtctag ttaaaggttt   168900
tcttctaagg gaatgcttat tgtgaagtag cacagagaaa gtgatgtcaa gactaactga   168960
gggtcacaaa caaatctgga gtgattaaaa ctttctgaaa atacttcaaa tgcagccatc   169020
atgaaacact ctcatttaaa gacactgaag catctgagaa gcaggctcca gggtacagcg   169080
gtgaagcctc ttttcaactt aattcagaga gtctggaaga ttttctgaaa cccatcaatg   169140
ggcttctgtc ttcagatctg cctccaaaca atcacatatt ccacctcctg gtggtcgata   169200
acagaggaga caaaggaagg agggaatggt ccgttcattt aaccagctgc cagggcagaa   169260
catctgtcct cagaataaat gtttgttgta agcacccaga tgattttgcc tggtccccta   169320
caagatgcga aaattgcagg gaagatgaat ttctgacttg gccgtaagtg gaatcacaga   169380
```

```
agcaaacatg tttaatcaag atgccagtga cggctcatcc ctcatcatta cgatacattt   169440
gaggactgta atttatctct catccgttat atttgcttct tttcacattt cctgagctga   169500
ctctgtttgg aagtcagcag gtcatttccc cttctttcat gctctaatag atttcactct   169560
caagatctca cacccccagca gcaccggact gctgtgcaag agttactcaa ggaacaagaa   169620
atgcttgcag agaacagcaa tttcgttttc atctgaagaa aaatgagagt tttaagatgt   169680
ttatcacacc cagatttgaa tatatatata tatatata tatatatata tatatatata   169740
tataagaatc cctgattctt ctccatagaa aaaactttg gtctcaaagc ctttaatgtt   169800
tcaattctta ttgtgatcca gtttattgga ataaggatat tcttcaaagc attgaaaggt   169860
tagggcctgt gtcaatatct gtgtcctgta atcaaagcct ccttggatgg tagtgttgtg   169920
gcgtgatggc atttgatgta tgaaaatgga ctgcacgtgc gtgcttggtc acttcagttg   169980
tgtctgactc tgcaactcca tggactgtag cccaccaggc tcctctgtcc gtgggattct   170040
ccaagcaaga atactggagt gggttgccat gccctcctct aggggttctg ccccacccag   170100
ggatcgaaac tgcacctctt aaagcctcct gcattggcag gtgagttttt tgttgttgct   170160 gttttacca ctaacgctac ctggaaagcc cagtggactg catatcttgg gctaaatgct   170220
gaaaaccatc tccccacttt gatagtggtg tcatgagcaa ctgtgagatg ggaactgaaa   170280
ggtttccaac atctattgtg ggcctggaaa agaaaacaac ggtctcaaag gctcttgctg   170340
aatcatctaa ctttggggaa aacaaaactg aactttaagt cctgtcctga tgctccgggc   170400
cggttgcatc tacctgggac ttctcacccc ctgcccagaa acctcccacc gcctacatct   170460
gcccgggaat tactgccccc tgcccagggg acttatcacc cctgcccaa aatctcccac   170520 cccctgttca actacaaatg ccatctcaac taaagattac ccaaaatgcc ccgcctgact   170580
aacgcttccc ttatcgcttc cacaaacctc cctttaaata tgaagcctcc ctgatccctc   170640
gcacgctcag cctggttggt aggtcgactg ttgcccctcc ttgcctgaat acaggtaacc   170700
tacctccatt gaggtcgtct ctcctttct gccttggccc gaactatatc ttacatccta   170760
cctccagttt aatgagtgat atctgagcat aagcttctag gtcattctct gagctgccaa   170820
atatgctaca tttttggcaa catttaagat taacagccag tctaacaggt ttggtctttt   170880
cttggaaatg tgactgactt cctccctgtc tctctgtgaa cacttacaag ctgtcatctt   170940
aaagctccag gacacacctc ccgagttact gtaaggtgag ctgagtgctt tgacttttgt   171000
gattttggct taaacgtgtg agtctctggt ttcggatcta taaggagag ctactcttct   171060 gtgggtcatt ctcagattca taccgcccct tctctctttc ttcaccccctt tctttttctt   171120 tctcccttga tgattttaga aggcttctcc tatctccttt cttttcctat cagataactc   171180
ccatctgagt gttcacactg gtttctgcta tacagcgaag tgaaccagct atgtgtacac   171240
atatatcccc tccctcttga acctccctcc catctcactc ccatcccagc cctctaggtc   171300
atcacagagc cccgagctga gctccccgtg ctggcattaa tatttgcttc tcacaagaac   171360
cgcatgtggt attgtaattc ctgcttgtgt tggacacctc ttgtgcccac ctcacactcc   171420
cagcccacct tttcactcct gcagctacct gtggcacaag tgtaactcac cagcaacgtg   171480
cccagccata ctgcctactt cctgccctgg cttctctgcc gccccacct ggatgcccgt   171540 gactacactc agccattcag acccaagcaa acctggaact gtgagagagc tgacatccca   171600
cgtagaccct ttgaccaaag aggaactgga gccaacggga aaatagtccc cttttcattc   171660
ctagagagaa ttctgagcta tcatgtgtcc catggaggtc ccgcagcagt gggcacccac   171720
agcttgactc tcccctcctt tcatttccct cttcccagct gcccactcct gttactcgag   171780
```

```
gtcacttccc caaatgaact acccgcatat aagcccttgc ctcatgctct gtttggggaa   171840
ccatctcact gtgtacacaa agactggaag aacaaagaga ggcttgtttt ccgtgaagag   171900
tcagacctgg actcaggtca gatttcttcc acctcccaca tctcatttcc tcaagctgcg   171960
ccccatccag gttcatacat gcgccttta acggaggcct cccatgagct gggtcagccg   172020
aaggaaaatc gaggagaaaa cggctgtgac caggcagctt tgttttgttt tgttgttttg   172080
gagtggggca ggggttggtt tattttttag ccaaaccgca cagcctgtgg gatcttagtt   172140
ccttgaccaa ggatcgaaac tgtggcccct gcagtggaag cgtggagtct taaccactgg   172200
acctccaggg aagttctgaa acaggcagct ttgaacattt tcatttcaca gcccttcat   172260 gtccctgcta agagcctgtg ccacacagcc aaaggtttca cacaaccgga gcagggactc   172320
ttgtcaaatt tgtcttggta ccactagccc ttggggcctg gtatacagga ggtgctcagg   172380
aaacacttgc tgggtactca agtccagcaa gcaaactatt gatggtttat ttttaatctt   172440
tgctttatac gtggccgtgt tgttcatat atttgtttat ttttatgctg gtttggaacg   172500
taattgctga tggacagaga gtgagagggt aacaggcagg aaggccaggg gtctcctaaa   172560
ggaggaaata gcctgcaagt gtcagacatt tttctctctc ttaaggggca agaggaaaca   172620
aactagcgat attttttcct tctctataca aatttaaaag gagggtttctc ttaaaatact   172680 gtgttgccat aatgacacct ggtttcacct gaagttaact attctcaaac ctagagatga   172740
ccaatgcatt tctcttatgg aaatgtttgt cttaagctat gctaacatgc tatgcattta   172800
ccccagactc tgtcttcaag tcggttcagc ctcttggctc agaacctact tgacaaaccg   172860
gtatgttata ttcagatagt gttcccctaa tctatgtaaa cgaaactatt tgtatggtga   172920
tctgcccttc ttcaagattc aagttaatca ttttatggcc caggatgaac catttggtgc   172980
caagattatc ccaaaatgca tcttatggct gaggggcctg gtgccattct gagttttaag   173040
gcattccttt cttacattaa cagacggcta ctcactatat aacatccagc tgaagactag   173100 cagggagta ctctttctgc acccttctga tgcctatgtc agaagctttc tctatctcct   173160
ttatacttta ataaaacctt attacgcaaa agctctgagc gatcaagcct cgtctctggc   173220
cccggattga attctcctct gggggccaag aattccggcg tcttttttca ttcaacgacc   173280
tttcaagaac atttaaggaa gggttgttta cctttttccc aagctacatt aaaacagatt   173340
cacatgcctg caaagtattc aaagaatatt agatatttct tgaaattatg gttaaaaaaa   173400
aacacaactg tttgtcgggt tgactgactg gtgaaagaaa tagaaaccat caaactgtgg   173460
cttgtaggac acacgctctg agatgcgtgg gtttcacctg tactgattgt ttaatacttg   173520
aaattctgaa gtttgcagca ggtcctacca cttcctataa cttctgcctt ccctaattct   173580
caagttggta ttacctgcct agccctggta ggtgatggg tttgtgaccc ccacacagag   173640
acacacatca ggctccaaga gcctggcatc attcctgact cccctgcag cttgctcact   173700 accccccacc accgtcaaca ggtgccccgt ggcagcgtga ccccctcctc tttccaggta   173760
ctacaagatc accgtggtgc tcatgtgctt cgtagtcccc acgctggtgc cctggtacat   173820
ctggggagaa agcctgtgga actcctactt cctgcctcc atcctccgct acaccatctc   173880
actcaacgtc acctggctgg tgaacagtgt cgctcacatg tacggaaacc ggccctatga   173940
caagcacatc agccctcggc agaacccgct cgtcaccctg ggtgccattg gtgagtgtcg   174000
ggtgggaacc cctggggaca gtgggtgttc agaccttctt ggcttctcgg gggttttgtg   174060
ggacgtgtca ggagaggcaa ttgaatggat aggactggaa tgaacttggg ctttggcgtt   174120
agaatcctgg ctcgtggaca agcctcttac tctctggttt acagctttat tatttgtgaa   174180
```

```
atggaaacag gaatacctgc ttcataaggg tgttacgggt ttgatccctg ggttgggaag    174240
atgtcctgga gaaggaagga aatagcaacc cactccagtg ttcttgccta gagaatcccc    174300
atagacagag gagcttgggg ggctacagtc catggggtcg caaagagtca gatccgactg    174360
agggactcac actttcaagg gtgttacgag aattaaataa gatactgtat atcatctgct    174420
tagtatggta cctggcacat agtaggtaat cagtaattag cagctattta ttttttacgct    174480 agccatttcc ctactaaagg aggagtagca gttgatgtcg ctctcaaact gcctgaccac    174540
tcttagcctc agctgtccag catttggctg accatttaaa aaggccctca acagaggga    174600 tggagagaaa cgggaccttg acaatctcat gggtccgcaa aatggttaag agtcagtctg    174660
acaggcttag ttgaggcttg gttcctctgc tcaatctctg ggcaagttat ctggctcctc    174720
cccaccttgt gttctcatct gtaaagtggg gataagagta gcgttgacct tcacctgggg    174780
tcaccatagg gttaggttac ctagtgtttg cagcagggct tagcaggaaa caaaccttca    174840
gggatgttgt tttccttact agcctaatgg tcttaggcaa gtaacttgtc ccttctgtgc    174900
acttccatcc tcattttaaa gtagggttaa tcacagcagc tagctgagtg atgtgaggat    174960
tataagcatt aaaaccttt gaagaatgca gccctgtgat tggcacacaa taaatgatta    175020
ataaatgtta ccaggacttc cctggtagct tagctggtaa agaatcctcc tgcaatgcag    175080
gagacccagg ttcaattcct ggattgggaa gatccctgg agaagggta ggctacccac    175140 tcgagtattc ttgggcttcc ctggtggctc agtttgtaaa gaatctgcct gcaatgcggg    175200
agacctgggt tcggtccctg ggttgggaag atcctctgga gagggcatg gcaaaccact    175260 ccagtattct tgcctggaga atccccatgg acagaggagc ctggcgggct gcagtccttg    175320
gcgttgcaaa gagttggaca tgactgagtg actaagcaca gctgtgtctt gatagaagca    175380
tttcgggctt ctgtataagc tgagcttgag ctcaagacca aacccaggaa ggaagtttcc    175440
tgctgttaag tataaacagt ctctgcatca ctctgcaatg aatttctgcc atcatggtgt    175500
aagggtcacc cattcattaa gaccctaggg atcttgtgtt gacaagagca atgtaagttg    175560
aatcaacacc agatttagct ttgggaataa cttgataagc agagagaaaa gtgtgagctt    175620
cctgacccct cctattgttt tctcttcatc tcactctttg tcctcaataa gaattgtggt    175680
gagggaagcc acatccagtg tggctctgag agtggacgag agtgggcacc atgcatctgt    175740
taccaccttc catgggggat gctgggccag ggaaccaagg aacgtggcta tgacgcaggt    175800
cctgaaaaac tgggtgttgg cttgaaggct ctcaaggtct acactgagct ctcagtcagc    175860
tttcctgata aaggtcatta gaagactctt attcatcag ccatatggga gactgggaa    175920 tatgttcaca gttctttgaa cagtgcctgt ttctgaaaaa tatgggaaa ctctacaact    175980 ctagtccaag aatgatgaac gtggagggac agggtagaaa agacctaaat taaaagaaa    176040 atcacagacc acagactgat ccatctgatg gactcatcat acagcagaat cttccaaatg    176100
tggtcaatag aagaactgta tgatgaccag tagccactta agaagtaaag gaggaatctg    176160
gtggttcctc aaatggttaa aaatagttac tataggatac agcaactcca ctcctaaatt    176220 tatacccctag agaaaagatg gtgtatgtcc acataaaac ttgtatatga gtgttcatag    176280
cagcattatt cataatagct ataaagtaga aatataccag atgtcactca cctgatgaat    176340
ggatgaatgc aatgtggtat atatatcccc taccatagaa ttctcttcag caataaaaac    176400
agatgaagta ctgatacctg ctacaacctt gaaaacagta tactgagtga aagaagctag    176460
ttgcaaaaga ctgcatatta tttgatttca tttacataaa atgttcagaa taagccaatc    176520
tatggagact gtattagtaa agattctcca ggcaagtgaa tgtaaaattt gctcagtcaa    176580
```

```
gtccgactct tgtgacagt atatatgtgt gtgtatatat ataagaagaa aatggcaacc   176640
cactccagta tccttgcctg ggaaatccca tggacagagg agcctggcgg gctatggtcc   176700
tggggtcaca aagagtcaga gattatatat atatatatac acacatggta gtttagttgc   176760
taagttgtct ccaactctta gctcctctgt ctgtggaatt tcccaggcaa ggatactgga   176820
atatatatat gcaattttat atatatatat atatatatat ataaaatatt gcttataata   176880
agtctctctc tacctatata ttgggtatat tctgtaagat catatggaaa cctgactgaa   176940 cttttttggcc aacccaatgt atatccatat agaaacagta ggatttctaa atctatataa   177000
aggtagatat attctgtttc tgtgtgtatt tacgggaaca gggcagggaa aggaggagag   177060
atttaggatg aggaactggc tggtgagatt acagaggctg agtcccactg tctgccatcc   177120
gaaagcggga gaccctggaa agccagtggt ataattaaat ctgagtacaa aggcctgaga   177180
actaggggag ctgatgatgc agatcccagt ctgagggcag gagaagatga aatagacatt   177240
caatcagtgt gtctggaaaa caggggggcaa ttcctcctcc aaggctttaa gggactgaaa   177300
gaaagtgaat tcgctcagtc atgtccgact ttttttcaacc tcatggactg tagcctacca   177360
agctcctctg ccgtgggatt ttccaggcaa taatactgga gtggattgcc atttccttct   177420
taagggactg gctgatgcca actcacatgg aggaggacca tctactttac tgactccatt   177480
gcttcaaatg ctaatctcat ccagaaacac cttcacagac acccagaaat aagggttaat   177540
ctgcgcactc cttggccagt taggttaaca tgcaaaatta accatcacag aggaagaaag   177600
taggactgga aggatggggg gatggatggg gctcaacatc catccatcct tggggagtgg   177660
ggtttctttt taggtagtga aaacgttgta aagatcgttg tggggatgcc tgcacaactc   177720
tgcaaatata ctgagagcca ttaacttgga tactttaaat gggtgaattg tgtggtgaat   177780
tacatctcaa taaagctgtt tgagaaaaat gaaaaaagat gtgagactcc tcctgaaaac   177840
accccggggg aggggcagta agggaggaaa agttactcac tgcgaaggga agagtaatat   177900
ataggaagat tttggatatt taaagatcca actccttaat tcacttactt atgggaacga   177960
ttatcattta tctcttccga gctttcccaa gaagtcttcc tttaatccct tcagtcgaca   178020 gaggctatt ttctttcgtg aacatacatc aaaatgatga tctgttatca gctattcggc   178080
atttagcttc cgaagtacag ctctaaagtc atgggagcat gtcaccagtt catgggaaaa   178140
ttcatcttga gactttatgc tgataacttt attgttattt ttctgttcct atcatttgtc   178200
tagccaattc agtgaatgct gcctaagggc agacggcaag tacagtaagt cccctacata   178260
cgaacacgtt cgattctgag accaagttcg gaagtccggt ttgttcagaa atccaacaaa   178320
gttagcctag gtagccatct aacacaattg gctatataat actgaactgt aataggtctc   178380
taatactttt cacatagata atacatacat aaaaagcaaa caaaaaataa agcatctcta   178440
atcttacagt ccagtaccttt gaaatgcatg cacagtacaa cagatggcat acaacacgtc   178500
tttgcaggtt tgtacatagg ggactttctg taagttttttt gtaccccatg gagcctaaca   178560
cagggtcttg caatctcgtg gcatttcaaa gctctgcaga gaggtgccga tagtgttatt   178620
tcaagccttc tttgtcttcc aggtgaaggt ttccataact accatcacac ctttccctt   178680 gactactctg cgagtgaatt tggcttaaat ttcaacccaa ccacctggtt cattgacttc   178740
atgtgttggc tggggctagc cactgaccgc aaacgggcaa ccaagcagat gatcgaagcc   178800
cggaaagccc ggactggaga cgggagcgcc tgactctgga tcctccatct gcgcccgctg   178860
tcaacgacgc ctccgttcat ggccttttgtt actacacttc tcttgttcat tggatcgtgg   178920
gagggggcgc aagctgggga gagaacagaa tccacgcagt ttgggggttt ttttcgttgg   178980
```

```
tctcaaaata atgtcaagat acaaactatc aatgaaaaga atttttttaaa agtcagtgta 179040
actatgcttt aacactagaa cgcggacatg tgatttaatc tctgtagcta caacatgtca 179100
ttcaaacata catcgtcatg tgctggtact tgtacgtgat gttaaccctg acaggatgaa 179160
ggaatttcat attctttcag tgtgattcag gagagccttt gttttctgtt ttaaacccaa 179220
ccttatttt aaacagacta tctgaaggag cagagaggca gggtggaaga caaaagagag 179280
tctaagtagt aaggaaagaa tgtttctgct ttgtaattat tgtgtgtgtg tgttgttgtt 179340
ttaaagtaag aaaattgaaa atgttaaaaa atgagaatac aggaaatggc tctcttattt 179400
ttttgccctg tttccagctt gttaatgttc cgctttcttt gcttcaaggg gtctgttcac 179460
tgctcagcta gttttgtgtc ctgagctgtc cgtccagctg accctataat cagtgcctgt 179520
tttaagtgtt tgattttgtt ctcttttgcta ttgtcgtttt aaggtgtaga actcagaagt 179580
gccagacatc aagtgaagct caaaggaagc tctcatttca atgtttagac acctaattta 179640
tattctaatt gatcctagcc actggtgcat gtactttacc tactcctgct aaataagcat 179700
attaattttc cacaccaggt catcagatct gaataaccaa cagttatcta gaactcagtg 179760
tctacaaatg tttcacctgc atgcggcctt cattgatttt gcagcaagac ataaagtgat 179820
cattatgtag cctctggatt ttaaaaaaat ctgtgtgtta agttgccttg taaagagcat 179880
gtcgaattaa tgggacagcg tgcccctttgt gttagatgtt agagcaaaag agagcctctat 179940
agtttggcat cagagcactt cgaagatagt gctgcaaaga tagggaagag taggatttaa 180000
ttttacattt ttgaaagaag tgacgccggt aggaaatgtc ataataaagt tcttcatcca 180060
gcaggtgttt aacggtgtta ttttgccatt aatatgtgta aactatgagt gatcacaata 180120
aatgattatg aattcgttgg tgttcctgac tgatacttaa acccagtttg aatgtccctc 180180
aagggtgcct tatgctttgt gatgaccaca taatgcacat ttgatttggg ctctgggcta 180240
acaacagccc ctaagatggg acctctccta tcccatcagt cttacgcata accagaggga 180300
aaatcagcag gttttatttg gactgtagag cagcagtccc caaccttttgg caccggggac 180360
tggttttgtg aaagacggtt ttttcacaga cttggggggg gggtgtgttt tggggggggt 180420
ggtttcggaa tgattcaaat gcattacaat tattgtgcac tttattgcat cagctctacc 180480
tcaggtcatc aggcattaga tcccgagttt ggggacccct gctgcccag tggtgtcact 180540
tctcactcag caacacctct gcttgtactg cttcgagctg acacgtggaa acccaactcc 180600
tacatgtcat caaaacatca tgaagcatcc cttcctcccc acagccctgc cgaggtgggc 180660
agatggactc aactctcact ccagccctgc ctctcagctc tgccccatgc catgctcctc 180720
actctctgcc catcttttgc cccaaagcag tgccctggcc atcagctgtc aacgtcctag 180780
cctgcctgca gttgagtggg aggccagctc tcggtgggg ccagactgga tttcattcct 180840
aaggactcta acgaggcatt gttcagctgc tttgtaccct aaagatatgt tgctaagacc 180900
ttgaatgcag tgttggtaga atgtagatat agtccaagac gaatctatat ccacctgaac 180960
taaaataacc ctgattggcc atatttctgt gaacttttga ccccctcaaag tactaaactt 181020
atttgcttgt ctattaatag aaaagattac acttggaatc tttgtaatct tctcacaaaa 181080
ggaagctgtt tcacagctaa tccaagtaaa tccagaacct ctggatttac actc       181134
```

<210> SEQ ID NO 6
<211> LENGTH: 6211
<212> TYPE: DNA
<213> ORGANISM: Bos taurus
<220> FEATURE:
<223> OTHER INFORMATION: signal recognition particle receptor (SRPR)

```
<400> SEQUENCE: 6
caaggctgat ctcagttccc agccgttcca tgtatggcta ccaacactac ctactggcag      60
tgcaggacat cgtcctagtt ggcttctctt cagttttcaa ctggtctacg aagccttccc     120
tctccagcta cacctcagac acctccagga cgtgtatcga atcctctctc ttctttcctc     180
ctcacggcca caaaacagca tcctgcgtgc aagcacgact tcattaattt ctgtgcaacc     240
aaagaatcag cccggctgca attttggtgg caaactcagg cacagaatca tctgggatat     300
gtcacctgag aaaggcaact ctgggatcca taccctgtc caggctctac aagctccggc      360
aggcaaggtt accccctact ccgagggacc cactgtcttc ccagcgtgag cttggattct     420
gagtcctgaa ggtcacaagg ctggagactg ggacacccc agaaccacga taccctccgc      480
tgccctcaac tttacccaga gtagagcctc ttctgtatgt gcctagcccc cgtccggaga     540
ggcacgggcc caggcggagc cgcagcgccc tccgaagcat ggccctgctg ttgctggccg     600
ctaggagagc agcaccctac ccgggtacag tcccagcctg cagtcactac tacgcgacgc     660
cagtcgttca ttcgagcact cccattgcca gcgacgccac ggggtcctgc ctcgcccccc     720
cccccccgcc accccatagg cggtcggtcc ctcccaggac atgctgagag gcccgccgag     780
gcccgccccc accctccatt ggccagctgg gcgtctacgt cagtcctgcg cgcccgtggg     840
cggagccggg gagggatccg ggcggcgctg agcggaagtg cggctgcgcc ggtttccggg     900
gccgctggtg tgacgtgtcc cgcgcttggc gcagcaggaa gcagcggcga tcgaggcctg     960
agttcccggc gccggcccg gctccttttcc cgctgccgcc atgctcgact tcttcaccat    1020
ttttttccaaa ggcgggctcg ttctctggtg ctttcagggc gtgagcgact catgcaccgg    1080
gcctgttaac gcgttaattc gttccgtgct gctgcaggta ccgcccccgc gggatcagaa    1140
ctccgggctc gtcccctcc ccctgaccc gaccctagt cccctttgac tgatcccggg       1200
cctccctctc accctgtctg cccacctcaa actggccact cgcttgtagc cagaactccg    1260
cttctttctc ccgctcctat cagaccatcc ctcaactttg tgatgtcccc tcccccctcc    1320
gctttctggg actctggcag gattcggtag tccattgaga cctcccttcg ttccccagtt    1380
tcactgccag cggcttgctt ttctgttgtc gcaaaggctg gatgagataa aggatgaaag    1440
aacgtctttt aagaagtgta gatagtgtcc ggctgccggt aaacctgatt gtttacatga    1500
ggactcttct cgctggcaca tgtcggtgcc tcccacctt ccctccttc ccccaccccc      1560
ccagctgggt gtctacactt ttctcccagg tgtaatgctg gagagcagtg ccctgaatct    1620
tttggccctg gaggacaggt ttgagtttag gggaatgtct ggttccttcc cgaaggtagt    1680
gctggagggg cccagctcca ggtgtttgag gggacagtct gaattctgag atacactctt    1740
tttccaggag agaggaggta acaactcctt cacccatgag gcactcactc tcaagtataa    1800
actggacaac cagtttgagt tggtgtttgt ggtaagtgag ggtattttag aggggtaacg    1860
attacactga caggcagtcc tgatgattca gaaaatcctg attaattgcg cccagtgtct    1920
acgatgaagt aactgagaaa acaaggaggg tggaggggaa aagggaagcc gctcttgggc    1980
ccagtcagag ggcttggctg ctcctcaggt cagggaaacc ggccagggc tgagccagtc     2040
cctggaggcc tgggtcaagt tggcttccct ctgttctggg ccggcatgta agcagatctg    2100
ctggctctgt tcctttccct gaacaggtag gttttcagaa gatcctaaca ctgacgtatg    2160
tggacaagtt gatagacgac gttcaccggc tgtttcgaga caagtaccgc actgagatcc    2220
aacagcagag tgccttaagt ctattgaatg gcactttcga tttccagaat gactttctgc    2280
ggctccttcg gtgagaggcc tcccctctgc aaaatcaatt tctgagactt gatgagttcc    2340
```

```
tttccttccc aagagggcat agtacactgt gggttgaaag gggctcctga gttggcttcc    2400
cagttctgat tgcctgcttg gtgtgagggc ccttcccctg gatttagact gtcaacctttt   2460
tctctttggg cttccctggt ggctcagatg gtaaagaata cctgcaatgt gggaaaccca    2520
ggtttgatcc ctggcttggg aagatcccct ggagaaggaa gtgtcaaccc actctagaat    2580
tcttgactgg agaatccaat cctggcccac caggctcctc tgtccataga atcgcagagt    2640
cagacacgac tgaagcgact tagtatgaac ttttctcttt agtgaagcag aggagagcag    2700
taagatccgt gctcccacta ccatgaagaa atttgaagat tctgagaagg cgaagaaacc    2760
tgtgagatcc atgattgaga cacggggtga aaagcctaag gaaaaagcca agaataacaa    2820
aaaaaacaag ggggccaaga aggaaggtga gtttgaactt ggacatccag gggcatgaga    2880
cgttgttcag gtggcactga agcggctccc tgtccttccc tctgtcgtcg tttgcctccc    2940
tggctcaggt gcccaccacc ctgattattg tccccaatgt cggtgatccc ccaggtgttt    3000
cttcacagtt ttctctgaat gatctgggag ggttttcccc atttgtctat tttgttggaa    3060
ttcggtcttt tttttttcag tgagttttct ccttgacagg ttctgatggc cctctggcta    3120
ctagcaaagc agcccctgca gaaaagtcag gtctcccagt aggacctgag aacgggagg     3180
aacttttccaa agaggagcag atccgcagga agcgggaaga gttcattcag aagcatggga    3240
ggggtatgga gaagtccagg tgagcagccc agctttgccc tcagcttttg ctatccagac    3300
acgttagggg tgagggagtc cttgtctctg aggtggatgc tgcctctcct gctgctccac    3360
cataaccctc tctactgtaa cccttcacag caagtccagt aagtcagatg ctcccaagga    3420
gaaaggcaaa aaggcacccc gggtgtgggc actgggaggc tctgctaaca aggaagttct    3480
ggactacagc actcccacca ccaacgagc cccggaagcg gccccgcctg aggacatcaa     3540
cttggtaaga ggtagcaggg gccagagtga gggttaatgg taataagcag caggggggaag   3600
gagagatgag gagggcagtc cccttcattg cttggagcca gagggtgggt tacatttgga    3660
gcttctggag tcaaggggc agagcagtgt gggacagggt cactccaggc ttccctcccc     3720
accagctcat ggtttcctga tcccttcttc ctctccccac accctccaga ttcgagggac    3780
tgggcctggg aggcagcttc aggatctgga ctgcagcagc tcagatgatg aaggagctgc    3840
tcagaactcc accaaaccta ggtacgggat ttggtggcgg gtggtgggta tggctccaaa    3900
ggcacaggac ttgctggctg cctgctggct ttctgtgcat ctgtggtttt ctgtgcctgc    3960
agtgctacca aggggactct gggtggcatg tttgggatgc tcaagggcct tgtgggttcc    4020
aagagcttga ctcgtgaaga catggaatct gtgctgacag agatgcgtga tcatctcatt    4080
ggtgagtcag acagggcag actcgtgttt tggggctaag gatagtgggg tagaagggct     4140
gtaccgtggg ggtcgttcac tcctgccagg gcattcaccc cacgtttgtc cccctcctt    4200
agctaagaat gtggcagcag acattgcagt ccagctctgt gaatccgtgg ccaacaagtt    4260
ggaagggaag gtgatgggga cgttcagcag taagtatctc cccagaccta gaagtgcttg    4320
ggtggaggtt atgaagtcac caccattctt attagatgcg tgacttttga caaactgtaa    4380
tctctaaatc tatgttgttt cacttagact tcaggtgttc atgacatcta acttaagaag    4440
atttgaatca attacttgtc aggtgcttag ggctgtcaga tatggtgtgg attcctgggc    4500
aggatcctag ttccctttag ctcagcaaga tgccaggtgt tcggagcacc tgacttgggc    4560
ttcatgggta tacctccctg ccccacccc agcggtgact tccacggtca agcaagctct    4620
gcaggagtcc ttggtgcaga ttctacagcc gcagcgccgc gtagacatgc tccgggacat    4680
catggatgcc cagcgtcatc agcgcccgta cgtggtcact ttctgtggtg tgaacggcgt    4740
```

```
ggggaagtct accaaccttg ccaaggtggg tgctgttcac caggctgagt ctgacattgt   4800
ttctgctgct ttttccgtct ctgccactgt ggggctggct gacagttctg cctcttttgc   4860
agatctcctt ctggctgtta gagaacggct tcagtgtcct catcgctgcc tgcgacacat   4920
ttcgtgccgg ggctgtggaa cagctgcgga cgcacacccg cgtctgagc gccctgcacc    4980 cccccgagaa gcacggcggc cggaccatgg tgcagctgtt cgagaagggc tacggcaagg   5040
atgctgctgg cattgccatg gaggccattg cctttggtac ggtgcacagc aagtgtgggg   5100
cttgtgcggg cccctctgct ccggggcttc tcttggaact gcagaggac cagggttacc    5160 ctaccaccaa ctttctgctc agtagcagct cagaattagt gatgtgccat gccatgctcc   5220
actttggggt gacgtgtagt tgcaggcaaa cctcatatat tcgttttgtt acctcaatat   5280
ttggtcacct ttatcctcct gctagggctt ccgggtgtg gctcagtggt aaagaatctg    5340
cctgccaatg caggagacaa aatagataca ggttccagcc ctgggtcggg aagatcccct   5400
gcaggaggaa atggaaccca ctccagtatt cttgcctggg aaattcatgg acagaggagc   5460
ctggcgggct acagtccaca gagttgcaga gagtcaggca cactgagtgt acacacacac   5520
ccacctgctc tcctttccct aaatatgctt catgacagcg tgtggaaact gtttcttaca   5580
tcaccttcta acttgattcg aacctaagga aataaacagg cagacttcta atagggccag   5640
tttaggacct gttgagagga agctggaaat gagtgttaac agtccaggag ttttgagttg    5700 accactttt tctttctagc acgtaaccaa ggctttgatg tggtgctggt ggacacagct     5760
ggccgcatgc aagacaacgc tccctgatg actgccctgg ccaagctcat cactgtcaac    5820
acacctgacc tggtgctgtt tgtggggag gccttagtag caacgaggc cgtggaccag      5880 ctggtgaggg ctcgggcctg gttctcttcc caacctcagc tctggccagt taggtatgtt   5940
atatttatat catgtttctc ctttcaggtc aagttcaaca gagccttggc tgaccattct   6000
atgcccagaa caccccggct tattgatggc attgtcctta ccaaatttga taccattgat   6060
gacaaggtaa acatgggcga gacagggcag agtgggacca ggaggggagt ggctgtcctt   6120 cacagggag cggagcctcc cgtcgctgag ggagtgcaaa ggcagggtcc agaaatgact     6180
gggtatcctg tctctgcctc aagtgggagc t                                   6211
```

<210> SEQ ID NO 7
<211> LENGTH: 301
<212> TYPE: DNA
<213> ORGANISM: Bos taurus
<220> FEATURE:
<223> OTHER INFORMATION: sequence flanking SCD5 SNP ID 134718

<400> SEQUENCE: 7

```
gtggtcgagg gaccaccgag tccatcacaa gtactcggag acggacgctg acccacacaa    60
tgcccgccgg ggcttcttct tctcccacat cggctggctg tttgtccgca agcatcggga   120
ygtcattgag aaggggagga agcttgacgt yaccgacttg ctggctgacc cygtggtccr   180
gttccagaga aagtaagtga gcaatcacca ttgatgtccc tgagggacag gacccagagt   240
cagagcccag tgggtgtaa taatatcccc aggcagttcc cctgcagatt ggatcttctt    300
a                                                                    301
```

<210> SEQ ID NO 8
<211> LENGTH: 301
<212> TYPE: DNA
<213> ORGANISM: Bos taurus
<220> FEATURE:
<223> OTHER INFORMATION: sequence flanking SCD5 SNP ID 179412

<400> SEQUENCE: 8

```
ggtggaagac aaaagagagt ctaagtagta aggaaagaat gtttctgctt tgtaattatt    60
gtgtgtgtgt gttgttgttt taaagtaaga aaattgaaaa tgttaaaaaa tgagaataca   120
ggaaatggct ctcttatttt tttgccctgt ktccagcttg ttaatgttcc gctttctttg   180
cttcaagggg tctgttcact gctcagctag ttttgtgtcc tgagctgtcc gtccagctga   240
ccctataatc agtgcctgtt ttaagtgttt gattttgttc tctttgctat tgtcgtttta   300
a                                                                   301
```

<210> SEQ ID NO 9
<211> LENGTH: 301
<212> TYPE: DNA
<213> ORGANISM: Bos taurus or Bos indicus
<220> FEATURE:
<223> OTHER INFORMATION: sequence flanking SREBP1 SNP ID 1199
<221> NAME/KEY: variation
<222> LOCATION: (151)...(151)
<223> OTHER INFORMATION: c indicates Bos taurus, g indicates Bos indicus

<400> SEQUENCE: 9

```
cgagccgtgc gagctggacg cggcgctgct gaccgacata aaggtgcgt cagggccact    60
ggrctccgcg cacgggcggc gccgggccgg gggcgcggag ggcgtcgggg cgcggcccgc   120
gcctctgtgc ggagcgctcc gcgtctctgc sccgagggct gcgggcctcg cggtcctgtc   180
cccgcggagc tgcccgtgcc cgctgggtcc tgtaggaggc tcggcgctga gcacgtgcgc   240
ctctgggcgc cccggcccgc accccgcggc caccgagtcc tcagtcgcga ggcggcgttg   300
g                                                                   301
```

<210> SEQ ID NO 10
<211> LENGTH: 301
<212> TYPE: DNA
<213> ORGANISM: Bos taurus or Bos indicus
<220> FEATURE:
<223> OTHER INFORMATION: sequence flanking SREBP1 SNP ID 12504
<221> NAME/KEY: variation
<222> LOCATION: (151)...(151)
<223> OTHER INFORMATION: t indicates Bos taurus, c indicates Bos indicus

<400> SEQUENCE: 10

```
agatctacgt ggccgccgca ctcagggtca aggccagtct gccccgggcc ttgcattttc    60
tgacagtgag taggtggtga ccagtggggg ctctgtgggt aggtgagggc tgcacagaaa   120
ggcaygtggt tatggggccr gctgtgggcc ygccgtggtc tcggccaggg ttcagtttga   180
cggcccgttc cttcctcaac agcgcttctt cctgagcagt gctcgccagg cctgcctggc   240
acagagcggc tcagtgcccc ttgccatgca gtggctctgc caccctgtgg gccaccgttt   300
c                                                                   301
```

<210> SEQ ID NO 11
<211> LENGTH: 301
<212> TYPE: DNA
<213> ORGANISM: Bos taurus or Bos indicus
<220> FEATURE:
<223> OTHER INFORMATION: sequence flanking SREBP1 SNP ID 13508
<221> NAME/KEY: variation
<222> LOCATION: (151)...(151)
<223> OTHER INFORMATION: t indicates Bos taurus, c indicates Bos indicus

<400> SEQUENCE: 11

```
gccagagccc cctgttcagt ggagcctgtg ggtggccaga gctgggccac tgtggcctta    60
ggtgcatttc ggttcctctc tgggcctcag tttcccaccg gccagcacg aggggatgga   120
```

```
ggctcttgga ggagccagga ggccaggctg ygctgtgtgc agaggtgagg acccctgcca    180
gccatcctga ccgcccrtcc tctcctgcca cagggagttc tcagatgccc tggggtacct    240
gcagctgctg aacagctgtt cggacgtggc cggagctcyt acctgcagct tctccatcag    300
c                                                                    301

<210> SEQ ID NO 12
<211> LENGTH: 301
<212> TYPE: DNA
<213> ORGANISM: Bos taurus
<220> FEATURE:
<223> OTHER INFORMATION: sequence flanking SREBP1 SNP ID 13636

<400> SEQUENCE: 12
gaggagccag gaggccaggc tgygctgtgt gcagaggtga ggacccctgc cagccatcct     60
gaccgcccgt cctctcctgc cacagggagt tctcagatgc cctggggtac ctgcagctgc    120
tgaacagctg ttcggacgtg gccggagctc ytacctgcag cttctccatc agctccagca    180
tggctgccac ccccggtgag cccccacct gtgacgccct cagccccagc gccaagcagc     240
tcagcttcgg gtgcagtgtg gctgagtttc tgcctcctgt gccccctttg caggcacaga    300
c                                                                    301

<210> SEQ ID NO 13
<211> LENGTH: 301
<212> TYPE: DNA
<213> ORGANISM: Bos taurus
<220> FEATURE:
<223> OTHER INFORMATION: sequence flanking SCAP SNP ID 34632

<400> SEQUENCE: 13
ttggcagccc ccactgtggg ccagaccccg cagggcccca ggagccaggc ctgctgagga     60
gcagccgtgt gttggggrcc ccctcagcac cctcctcccc ccaccccgct ctgtcccag    120 ggagatcttc ccctacctgg tggtggtcat ygggctggag aacgtgctgg tgctcaccaa    180
gtccgtcgtc tccaccccgg tggacctcga ggtgaagctg cgcattgccc aaggtaacak    240
gaggggagta gggggcatgg cggcggggt tgtgctgcac ctcctcctgc ygagggaacg    300
g                                                                    301

<210> SEQ ID NO 14
<211> LENGTH: 301
<212> TYPE: DNA
<213> ORGANISM: Bos taurus
<220> FEATURE:
<223> OTHER INFORMATION: sequence flanking INSIG1 SNP ID 3885

<400> SEQUENCE: 14
attagtttaa aaataaaaga tgtaaagtta gtttaaatat ctgatggctg gtaaatctag     60
gaaagggaat ggtttgaata tcgmgttaat gatccccacg aggcagtcgc gtcgtctctg    120
ctggcgtgct cagaccctgc cgtcttgtct ytccccgcag ctgtggtcgg cctgctgtac    180
ccctgcatcg acagtcacct tggagagcca cacaagttca agcgcgagtg ggccagcgtg    240
atgcgctgcg tggccgtctt cgtyggcatc aaccacgcta gtgctgtatc ctaagacgtt    300
a                                                                    301

<210> SEQ ID NO 15
<211> LENGTH: 301
<212> TYPE: DNA
<213> ORGANISM: Bos taurus
```

<220> FEATURE:
<223> OTHER INFORMATION: sequence flanking INSIG1 SNP ID 6082

<400> SEQUENCE: 15

```
ggctcatgcc tccctctccc tgcaggtaca cgtccccaga cttcctctac atccgctcct    60
ggctgccctg catcttcttc tcrggaggcg tgacggtggg aacatagga cgacagctgg   120
ccatggtgcg tagtcmcacg ggcgcctgak gctggctttc agctgggtca gcttggtttg   180
cctgggacgt tatcatttgt gtcaatacgt gtayaggcag gagcagcagt tactcagata   240
agcatacact ttaaaaaggc gcatcccagg ccattctcgg ctaacttgta aaggttcagg   300
g                                                                   301
```

<210> SEQ ID NO 16
<211> LENGTH: 301
<212> TYPE: DNA
<213> ORGANISM: Bos taurus
<220> FEATURE:
<223> OTHER INFORMATION: sequence flanking INSIG1 SNP ID 12052

<400> SEQUENCE: 16

```
ccccggggac ggcttggtgg tgcttacaaa gatgaagtgt ggtgagacag gaatatcact    60
matccaaaag attttaaaaa tagggctgtg ttatgaaaaa agaaaaggcg ggggtggcag   120
caagcgcagg gtggccgtgc cgggcaggcr ggcacggcgt gccctcggtg cccgtgtagg   180
gtgctacgca gacaatcctg cagaggaggc agtgagtggg aggttgtggc tctgcgctgc   240
aatgggttgg actttccacc ctggtgttca cggaatccgc accgtctcga atggggcgcc   300
c                                                                   301
```

<210> SEQ ID NO 17
<211> LENGTH: 301
<212> TYPE: DNA
<213> ORGANISM: Bos taurus
<220> FEATURE:
<223> OTHER INFORMATION: sequence flanking INSIG2 SNP ID 93277

<400> SEQUENCE: 17

```
ttaattcctt tagtgtaatc ctctggcaaa gaaattagaa aattgaattt ataaagcttc    60
attttgccca gagattttgg agtagaaaag ggctgtatat ttgtgaatag atgcttamgt   120
aggtgacgga aataaaatat catttgtcct mtaccagaaa gtctcaggaa ccaaaatagc   180
ttggcaggtt ggaagataat gttcacttca aggctttctc ctcaacaaat taaaactaga   240
acagttgaca taatagaaag ggatagtgtg tccttggtac tcttgtttct gaactgcatt   300
a                                                                   301
```

<210> SEQ ID NO 18
<211> LENGTH: 301
<212> TYPE: DNA
<213> ORGANISM: Bos taurus
<220> FEATURE:
<223> OTHER INFORMATION: sequence flanking INSIG2 SNP ID 93461

<400> SEQUENCE: 18

```
caggttggaa gataatgttc acttcaaggc tttctcctca acaaattaaa actagaacag    60
ttgacataat agaaagggat agtgtgtcct tggtactctt gtttctgaac tgcattatta   120
taaaatgtgt ctgtcagtaa atcatataga sactgtggta ccctgttaaa tagctgtcaa   180
ctcttctatt ttcaagttcc tgtatgattc tcaaacaatt ctaaacctgt ttgagaagta   240
atagtggttt ccattttagc aaaagtgtgt gcctttagca atatttgtgt attgaagctt   300
```

```
c                                                                           301

<210> SEQ ID NO 19
<211> LENGTH: 301
<212> TYPE: DNA
<213> ORGANISM: Bos taurus
<220> FEATURE:
<223> OTHER INFORMATION: sequence flanking INSIG2 SNP ID 93867

<400> SEQUENCE: 19
agtaagatct attagtgaag tatcatgcca tcatagtttt aatcctctct agtcttgtac    60
attgtattaa aaagttgaat gcactctagt cttaacatta acatctctta ttttagaaaa   120
atgaacagat gatattattt ggttacaaat yttaagatga ctctttaaca ctgatctcag   180
aaagtggatt ttgataacaa catacagttg tctctcacac tggctgcact rtccattgga   240
ttgtggtgga cttttgatag atctagaagt ggttttggcc ttggagtagg aattgctttc   300
t                                                                           301

<210> SEQ ID NO 20
<211> LENGTH: 301
<212> TYPE: DNA
<213> ORGANISM: Bos taurus
<220> FEATURE:
<223> OTHER INFORMATION: sequence flanking SRPR SNP ID 3064

<400> SEQUENCE: 20
ccttccctct gtcgtcgttt gcctccctgg ctcaggtgcc caccaccctg attattgtcc    60
ccartgtcgg tgatccccca ggtgtttctt cacagttttc tctgaatgat ctgggagggt   120
tttccccatt tgtctatttt gttggaattc rgtctttttt ttttcagtga gttttctcct   180
tgacaggttc tgatggccct ctggctacta gcaaagcagc ccctgcagaa aagtcaggtc   240
tcccagtagg acctgagaac ggggaggaac tttccaaaga ggagcagatc cgcaggaagc   300
g                                                                           301

<210> SEQ ID NO 21
<211> LENGTH: 301
<212> TYPE: DNA
<213> ORGANISM: Bos taurus
<220> FEATURE:
<223> OTHER INFORMATION: sequence flanking SRPR SNP ID 4150

<400> SEQUENCE: 21
ctcaagggcc ttgtgggttc caagagcttg actcgtgaag acatggartc tgtgctggac    60
aagatgcgtg atcatctcat tggtgagtca ggacagggca gactcgtgtt ttkgggctaa   120
ggatagtggg gtagaagggc tgtaccgtgg sggtcgttca ctcctgccag ggcattcacc   180
ccacgtttgt ccccctcct tagctaagaa tgtggcagca gacattgcag tccagctctg   240
tgaatccgtg gccaacaagt tggaagggaa ggtgatgggg acgttcagca gtaagtatct   300
c                                                                           301
```